US012788397B2

(12) United States Patent
Shelton, IV et al.

(10) Patent No.: US 12,788,397 B2
(45) Date of Patent: Nov. 10, 2026

(54) METHODS OF OPERATING A ROBOTIC SURGICAL STAPLER

(71) Applicant: Cilag GmbH International, Zug (CH)

(72) Inventors: Frederick E. Shelton, IV, Hillsboro, OH (US); Kevin M. Fiebig, Cincinnati, OH (US); Shane R. Adams, Lebanon, OH (US); Adam D. Hensel, Cincinnati, OH (US); Matthew D. Cowperthwait, Cincinnati, OH (US); Nicholas J. Ross, Franklin, OH (US); Curtis A. Maples, Cincinnati, OH (US); Gregory J. Bakos, Liberty Township, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/619,814

(22) Filed: Mar. 28, 2024

(65) Prior Publication Data

US 2024/0252167 A1 Aug. 1, 2024

Related U.S. Application Data

(63) Continuation of application No. 17/402,674, filed on Aug. 16, 2021, now Pat. No. 12,102,321.

(51) Int. Cl.
*A61B 17/072* (2006.01)
*A61B 17/068* (2006.01)
(Continued)

(52) U.S. Cl.
CPC ........ *A61B 17/0686* (2013.01); *A61B 17/072* (2013.01); *A61B 34/30* (2016.02);
(Continued)

(58) Field of Classification Search
CPC ............ A61B 17/07207; A61B 17/072; A61B 2017/00398; A61B 2017/00734;
(Continued)

(56) References Cited

U.S. PATENT DOCUMENTS 5,129,570 A 7/1992 Schulze et al.
7,183,737 B2 2/2007 Kitagawa
(Continued)

FOREIGN PATENT DOCUMENTS

EP 3225190 A2 10/2017
EP 3231374 A1 10/2017
(Continued)

OTHER PUBLICATIONS

International Search Report and Written Opinion dated Dec. 12, 2022, for International Application No. PCT/IB2022/057611, 16 pages.

(Continued)

*Primary Examiner* — Andrew M Tecco
(74) *Attorney, Agent, or Firm* — FBT Gibbons LLP

(57) ABSTRACT

A method of operating a robotically controlled surgical instrument that includes an end effector, a driving assembly, and a lockout, the method includes inhibiting actuation of the driving assembly when the lockout is in a locked configuration in response to an unspent staple cartridge being absent from a first jaw of the end effector. The method also includes inserting the unspent staple cartridge into the first jaw of the end effector to switch the lockout to an unlocked configuration. The method also includes actuating the driving assembly to pivot the first jaw, which includes the staple cartridge, toward a second jaw of the end effector to at least one of staple or cut tissue with the end effector when the lockout is in the unlocked configuration.

17 Claims, 150 Drawing Sheets

(51) Int. Cl.
*A61B 34/30* (2016.01)
*A61B 17/00* (2006.01)

(52) U.S. Cl.
CPC ............... *A61B 2017/00141* (2013.01); *A61B 2017/00154* (2013.01); *A61B 2017/07257* (2013.01); *A61B 2017/07271* (2013.01); *A61B 2017/07285* (2013.01); *A61B 2560/0266* (2013.01)

(58) Field of Classification Search
CPC ........... A61B 2017/00017; A61B 2017/00154; A61B 34/30; A61B 2090/064
See application file for complete search history.

(56) References Cited

U.S. PATENT DOCUMENTS 7,404,508 B2 7/2008 Smith et al.
7,434,715 B2 10/2008 Shelton, IV et al.
7,644,848 B2 1/2010 Swayze et al.
7,721,930 B2 5/2010 McKenna et al.
7,770,775 B2 8/2010 Shelton, IV et al.
7,810,692 B2 10/2010 Hall et al.
7,832,408 B2 11/2010 Shelton, IV et al.
7,845,537 B2 12/2010 Shelton, IV et al.
8,028,885 B2 10/2011 Smith et al.
8,083,120 B2 12/2011 Shelton, IV et al.
8,210,411 B2 * 7/2012 Yates ................. A61B 17/3205 227/19
8,408,439 B2 4/2013 Huang et al.
8,453,914 B2 6/2013 Laurent et al.
8,459,520 B2 6/2013 Giordano et al.
8,523,043 B2 9/2013 Ullrich et al.
8,708,213 B2 4/2014 Shelton, IV et al.
9,060,770 B2 6/2015 Shelton, IV et al.
9,186,142 B2 11/2015 Fanelli et al.
9,517,065 B2 12/2016 Simms et al.
9,615,888 B2 4/2017 Manzo et al.
9,622,746 B2 4/2017 Simms et al.
9,717,497 B2 8/2017 Zerkle et al.
9,795,379 B2 10/2017 Leimbach et al.
9,808,248 B2 11/2017 Hoffman
9,839,487 B2 12/2017 Dachs, II
10,011,018 B2 7/2018 McGrogan et al.
10,092,292 B2 10/2018 Boudreaux et al.
10,201,349 B2 2/2019 Leimbach et al.
10,238,386 B2 3/2019 Overmyer et al.
10,271,847 B2 4/2019 Racenet et al.
10,307,170 B2 6/2019 Parfett et al.
10,441,279 B2 * 10/2019 Shelton, IV ......... A61B 17/295
10,485,621 B2 11/2019 Morrissette et al.
10,498,269 B2 * 12/2019 Zemlok ..................... H02P 7/29
10,537,400 B2 1/2020 Dachs, II et al.
10,610,313 B2 4/2020 Bailey et al.
10,667,809 B2 6/2020 Bakos et al.
10,758,230 B2 9/2020 Shelton, IV et al.
10,806,530 B2 10/2020 Liao et al.
10,828,028 B2 11/2020 Harris et al.
10,863,988 B2 12/2020 Patel et al.
10,888,321 B2 1/2021 Shelton, IV et al.
11,002,634 B2 5/2021 Fayfield et al.
11,020,138 B2 6/2021 Ragosta
11,026,755 B2 6/2021 Weir et al.
11,076,926 B2 8/2021 Ragosta et al.
11,090,046 B2 8/2021 Shelton, IV et al.
11,096,687 B2 8/2021 Flanagan et al.
11,147,552 B2 10/2021 Burbank et al.
11,166,773 B2 11/2021 Ragosta et al.
11,234,700 B2 2/2022 Ragosta et al.
11,259,884 B2 3/2022 Burbank
11,523,826 B2 12/2022 Viola et al.
11,540,826 B2 1/2023 Nalagatla et al.
11,617,575 B2 * 4/2023 Yates ................. A61B 17/3205 227/181.1
11,779,332 B2 10/2023 Shelton, IV et al.
11,944,297 B2 * 4/2024 Shelton, IV ........... A61B 34/30
12,053,179 B2 * 8/2024 Weir ................ A61B 17/00234
12,102,321 B2 10/2024 Shelton, IV et al.
12,193,662 B2 1/2025 Paulowski et al.
12,622,695 B2 5/2026 Paulowski et al.
2003/0073981 A1 4/2003 Whitman et al.
2006/0185682 A1 8/2006 Marczyk
2007/0175956 A1 * 8/2007 Swayze .................. A61B 34/76 227/19
2007/0270790 A1 11/2007 Smith et al.
2007/0270884 A1 11/2007 Smith et al.
2008/0056865 A1 3/2008 Laing et al.
2009/0090763 A1 4/2009 Zemlok et al.
2010/0276471 A1 11/2010 Whitman
2011/0006103 A1 1/2011 Laurent et al.
2011/0022032 A1 1/2011 Zemlok et al.
2011/0295295 A1 12/2011 Shelton, IV et al.
2012/0205421 A1 8/2012 Shelton, IV
2012/0209314 A1 8/2012 Weir et al.
2013/0168431 A1 7/2013 Zemlok et al.
2013/0206814 A1 8/2013 Morgan et al.
2014/0175150 A1 6/2014 Shelton, IV et al.
2014/0305994 A1 10/2014 Parihar et al.
2015/0272572 A1 10/2015 Overmyer et al.
2015/0272575 A1 10/2015 Leimbach et al.
2015/0297228 A1 10/2015 Huitema et al.
2015/0374369 A1 * 12/2015 Yates ...................... G16Z 99/00 227/181.1
2016/0066916 A1 3/2016 Overmyer et al.
2016/0256185 A1 * 9/2016 Shelton, IV ......... A61B 17/295
2016/0361126 A1 12/2016 Schena et al.
2017/0020617 A1 1/2017 Weir et al.
2017/0245854 A1 * 8/2017 Zemlok ............ A61B 17/07207
2017/0258469 A1 9/2017 Shelton, IV et al.
2017/0265865 A1 9/2017 Burbank
2017/0265954 A1 9/2017 Burbank et al.
2017/0281188 A1 10/2017 Shelton, IV et al.
2017/0333037 A1 11/2017 Wellman et al.
2018/0168622 A1 6/2018 Shelton, IV et al.
2018/0168756 A1 6/2018 Liao et al.
2018/0271608 A1 9/2018 Ragosta et al.
2018/0310935 A1 11/2018 Wixey
2018/0325517 A1 11/2018 Wingardner et al.
2018/0325606 A1 11/2018 Weir et al.
2018/0344419 A1 12/2018 Dachs, II et al.
2018/0360445 A1 12/2018 Shelton, IV et al.
2018/0360446 A1 12/2018 Shelton, IV et al.
2018/0360455 A1 12/2018 Shelton, IV et al.
2019/0038371 A1 * 2/2019 Wixey ............ A61B 17/00234
2019/0059889 A1 2/2019 Shelton, IV et al.
2019/0076142 A1 3/2019 Wixey
2019/0076143 A1 3/2019 Smith
2019/0167266 A1 6/2019 Patel et al.
2019/0175174 A1 6/2019 Flanagan et al.
2019/0192158 A1 6/2019 Scott et al.
2019/0200989 A1 7/2019 Burbank et al.
2019/0201023 A1 * 7/2019 Shelton, IV ........... A61B 18/14
2019/0201046 A1 7/2019 Shelton, IV et al.
2019/0206565 A1 7/2019 Shelton, IV et al.
2019/0239967 A1 8/2019 Ragosta et al.
2019/0262088 A1 8/2019 Burbank
2019/0290265 A1 9/2019 Shelton, IV et al.
2019/0298355 A1 10/2019 Shelton, IV et al.
2020/0093487 A1 3/2020 Baber et al.
2020/0093506 A1 3/2020 Leimbach et al.
2020/0138529 A1 5/2020 Ragosta et al.
2020/0305862 A1 * 10/2020 Yates ...................... G16Z 99/00
2020/0305863 A1 * 10/2020 Yates ..................... A61B 17/32
2020/0397430 A1 12/2020 Patel et al.
2020/0405301 A1 12/2020 Shelton, IV et al.
2020/0405403 A1 12/2020 Shelton, IV et al.
2021/0353292 A1 11/2021 Flanagan et al.
2021/0393340 A1 12/2021 Beckman et al.
2021/0401433 A1 12/2021 Freidel et al.
2023/0045893 A1 2/2023 Shelton, IV et al.
2023/0045998 A1 2/2023 Shelton, IV et al.
2023/0048444 A1 2/2023 Shelton, IV et al.
2023/0049736 A1 2/2023 Shelton, IV et al.
2023/0050358 A1 2/2023 Shelton, IV et al.

(56) References Cited

U.S. PATENT DOCUMENTS

| | | | |
|---|---|---|---|
| 2023/0050707 A1 | 2/2023 | Shelton, IV et al. |
| 2023/0051105 A1 | 2/2023 | Shelton, IV et al. |
| 2023/0051222 A1 | 2/2023 | Shelton, IV et al. |
| 2023/0051271 A1 | 2/2023 | Shelton, IV et al. |
| 2023/0051361 A1 | 2/2023 | Shelton, IV et al. |
| 2023/0051938 A1 | 2/2023 | Shelton, IV et al. |
| 2023/0052307 A1 | 2/2023 | Shelton, IV et al. |
| 2024/0108334 A1 | 4/2024 | Shelton, IV et al. |

FOREIGN PATENT DOCUMENTS

| | | |
|---|---|---|
| EP | 3235444 A2 | 10/2017 |
| EP | 3338657 A1 | 6/2018 |
| EP | 3545881 A1 | 10/2019 |
| WO | WO 2015/153642 A1 | 10/2015 |
| WO | WO 2017/083125 A1 | 5/2017 |
| WO | WO 2017/083129 A1 | 5/2017 |
| WO | WO 2018/049198 A1 | 3/2018 |
| WO | WO 2018/049206 A1 | 3/2018 |
| WO | WO 2018/049211 A1 | 3/2018 |
| WO | WO 2018/049217 A1 | 3/2018 |
| WO | WO 2018/052806 A1 | 3/2018 |
| WO | WO 2018/052810 A1 | 3/2018 |
| WO | WO 2018/071497 A1 | 4/2018 |
| WO | WO 2018/071763 A1 | 4/2018 |
| WO | WO 2018/085529 A2 | 5/2018 |
| WO | WO 2018/175467 A1 | 9/2018 |
| WO | WO 2019/165403 A1 | 8/2019 |
| WO | WO 2020/131290 A1 | 6/2020 |

OTHER PUBLICATIONS

International Search Report and Written Opinion dated Dec. 13, 2022, for International Application No. PCT/IB2022/057614, 17 pages.

International Search Report and Written Opinion dated Dec. 6, 2022, for International Application No. PCT/IB2022/057617, 12 pages.

US Non-Final Office Action dated Oct. 2, 2025, for U.S. Appl. No. 19/002,948, 6 pages.

US Notice of Allowance dated Jan. 16, 2026, for U.S. Appl. No. 19/002,948, 8 pages.

* cited by examiner

1540

| | | Cycle Operation Counts | | | | | Event Count | |
|---|---|---|---|---|---|---|---|---|
| Device Cycle/Usage | Max Motor Power Limit | Motor Current Limit Exceeded | Motor Temperature Limit Exceeded | Impact/Bumping Forward Cycles | Impact/Bumping Reverse Cycles | Wait Period | Recoverable | Sum of Non-Recoverable |
| 1 | 100% | 1 | -- | 1 | 1 | 1 | -- | 4 |
| 2 | 93% | 1 | -- | -- | -- | -- | 1 | 4 |
| 3 | 91% | 1 | -- | -- | -- | 1 | -- | 6 |
| 4 | 86% | 2 | 1 | 1 | 1 | -- | -- | 11 |
| 5 | 80% | -- | -- | -- | -- | -- | -- | 11 |
| 6 | 79% | 2 | -- | -- | -- | -- | 2 | 11 |
| 7 | 77% | 3 | 2 | 2 | 2 | 2 | 1 | 21 |
| 8 | 65% | -- | -- | -- | -- | -- | -- | 21 |
| 9 | 64% | 1 | 2 | 1 | -- | 2 | -- | 27 |
| 10 | 55% | X | X | X | X | X | X | X |
| 11 | X | X | X | X | X | X | X | X |
| 12 | X | X | X | X | X | X | X | X |
| 13 | X | X | X | X | X | X | X | X |
| 14 | X | X | X | X | X | X | X | X |
| 15 | X | X | X | X | X | X | X | X |

FIG. 36

| TIME | OPERATION/ FUNCTION | IMAGE |
|---|---|---|
| $t_0$ | NO TISSUE CONTACT | 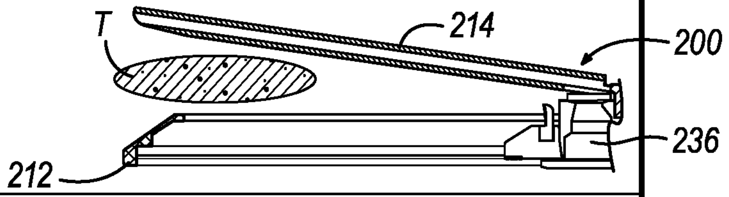  |
| $t_1$ | TISSUE CONTACT/ JAW CLOSURE | 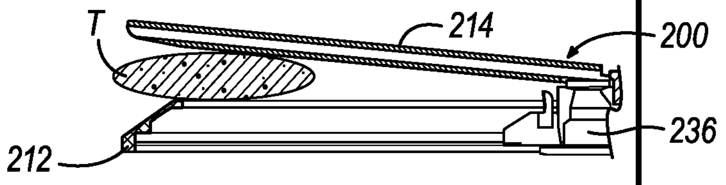  |
| $t_2$ | JAW CLOSED/ TISSUE COMPRESSION/ START FIRING I-BEAM | 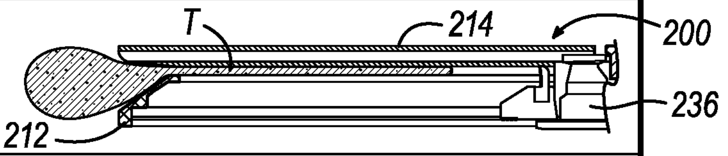  |
| $t_3$ | STOP FIRING I-BEAM/ ENGAGE JAW MOTOR TO INCREASE CLAMP FORCE | 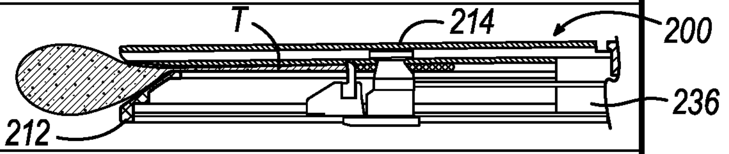  |
| $t_4$ | ENGAGE FIRING I-BEAM | 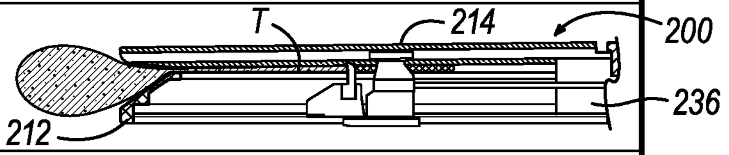  |
| $t_5$ | STOP FIRING I-BEAM/ ENGAGE JAW MOTOR TO INCREASE CLAMP FORCE | 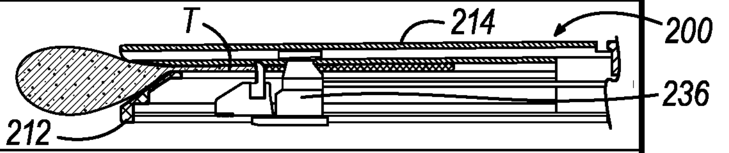  |
| $t_6$ | ENGAGE FIRING I-BEAM | 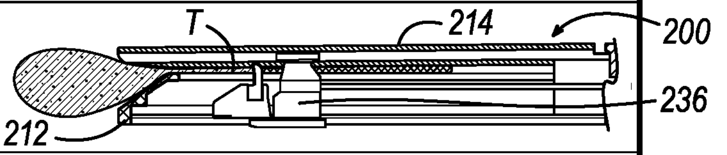  |
| $t_7$ | STOP FIRING I-BEAM/ MAX TRAVEL DISTANCE COMPOETED | 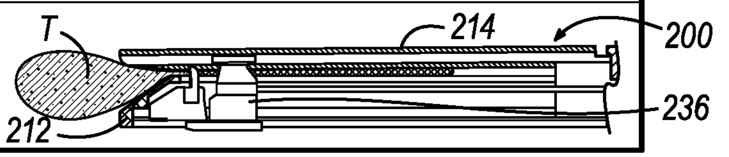  |

FIG. 51

METHODS OF OPERATING A ROBOTIC SURGICAL STAPLER

PRIORITY

This application is a continuation of U.S. patent application Ser. No. 17/402,674, entitled "Methods of Operating A Robotic Surgical Stapler," filed Aug. 16, 2021, published as U.S. Pat. Pub. No. 2023/0051361 on Feb. 16, 2023, issued as U.S. Pat. No. 12,102,321 on Oct. 1, 2024.

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically surgical systems. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probe, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. Patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 36 depicts an exemplary data table that may be utilized in conjunction with the end-of-life algorithm of FIG. 35;

FIG. 51 depicts a table showing an exemplary use of the motor control algorithm of FIG. 50;

FIG. 88 depicts a schematic view of a first exemplary firing circuit adapted for receiving signals from a plurality of lockout monitoring features and selectively powering an end effector;

FIG. 89 depicts a schematic view of a second exemplary firing circuit adapted for receiving signals from a plurality of lockout monitoring features and selectively powering an end effector;

FIG. 90 depicts a partial exploded perspective view of a driving assembly similar to FIG. 8 and an exemplary lockout member of an exemplary firing lockout assembly;

FIG. 91A depicts a perspective view of the driving assembly and the lockout member of FIG. 12 firing lockout assembly in a locked configuration;

FIG. 91B depicts a perspective view of the driving assembly and the distal portion of the firing lockout assembly of FIG. 1, but with the firing lockout assembly in an unlocked configuration in the presence of the staple cartridge of FIG. 6;

FIG. 92A depicts a schematic cross-sectional view of the firing lockout assembly disposed proximal to the end effector of FIG. 6, where the firing lockout assembly is in the locked configuration of FIG. 91A;

FIG. 92B depicts a schematic cross-sectional view of the firing lockout assembly and the end effector of FIG. 92A, but with the firing lockout assembly being moved to the unlocked configuration of FIG. 91B;

FIG. 92C depicts a schematic cross-sectional view of the firing lockout assembly and disposed proximal to the end effector of FIG. 92B, but with the driving assembly being driven distally to actuate the staple cartridge after the firing lockout assembly is moved to the unlocked configuration;

FIG. 93A depicts a side cross-sectional view of a proximal portion of another exemplary end effector for use with the robotic surgical system of FIG. 1, showing an exemplary lockout lever in a fully locked state for preventing firing of the end effector in the absence of a staple cartridge;

FIG. 93B depicts a side cross-sectional view of the proximal portion of the end effector of FIG. 93A, showing the lockout lever rotated to a partially locked state for preventing firing of the end effector with a spent staple cartridge;

FIG. 93C depicts a side cross-sectional view of the proximal portion of the end effector of FIG. 93A, showing the lockout lever rotated to an unlocked state for allowing firing of the end effector with a full staple cartridge;

Figure 1:
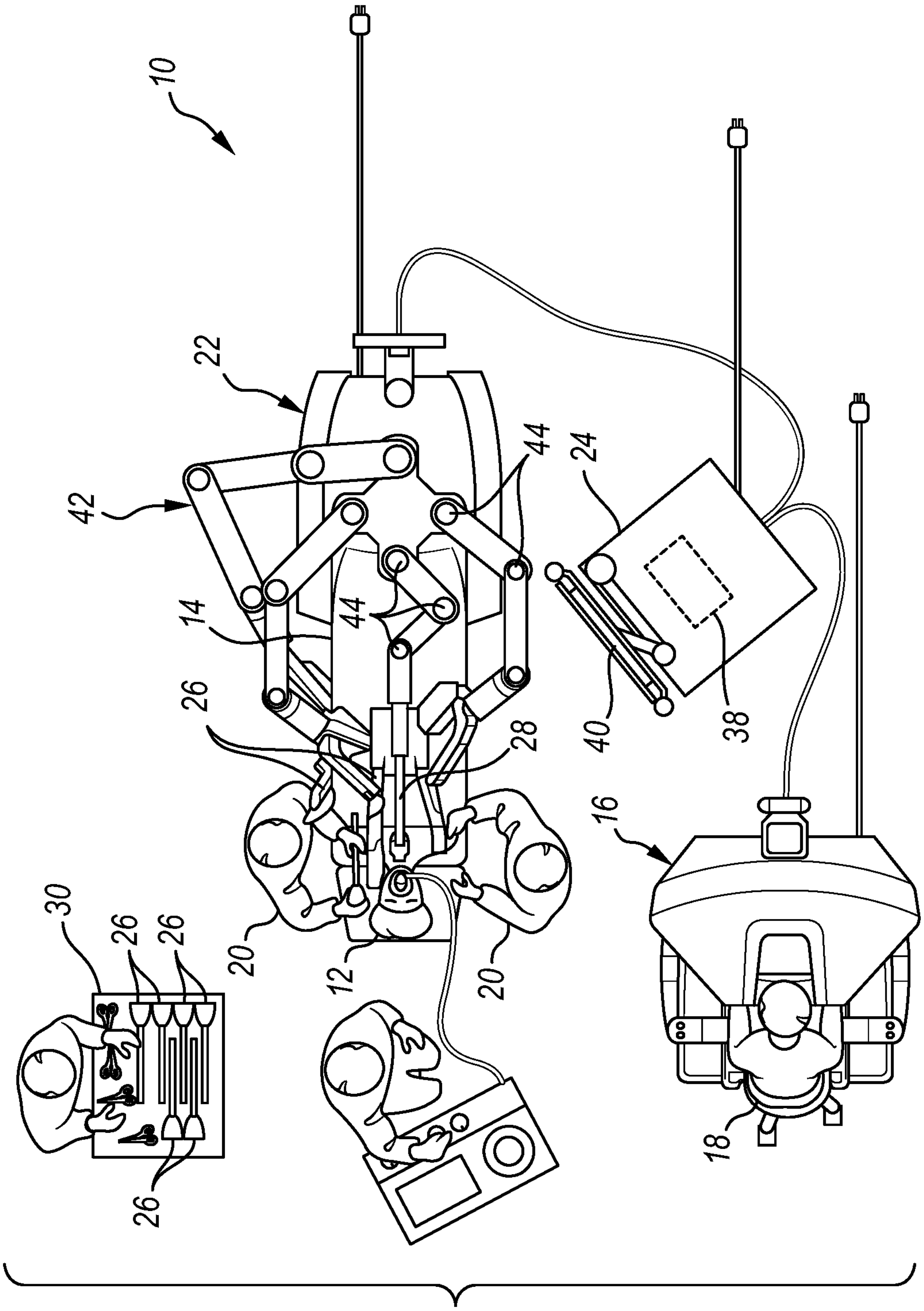
FIG. 1 depicts a top plan view of a robotic surgical system being used to perform a surgical procedure.
Figure 4:
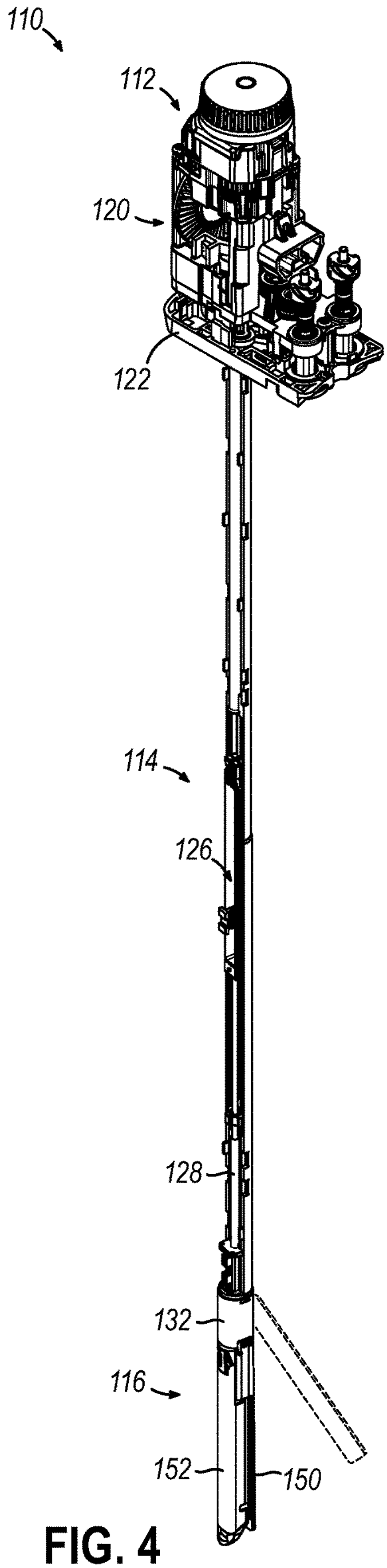
FIG. 4 depicts a perspective view of an exemplary surgical instrument that may be used with the robotic surgical system of FIG. 1, where the surgical instrument includes an instrument base, an elongate shaft, and an end effector, with select portions of the surgical instrument omitted to reveal internal features.
Figure 8:
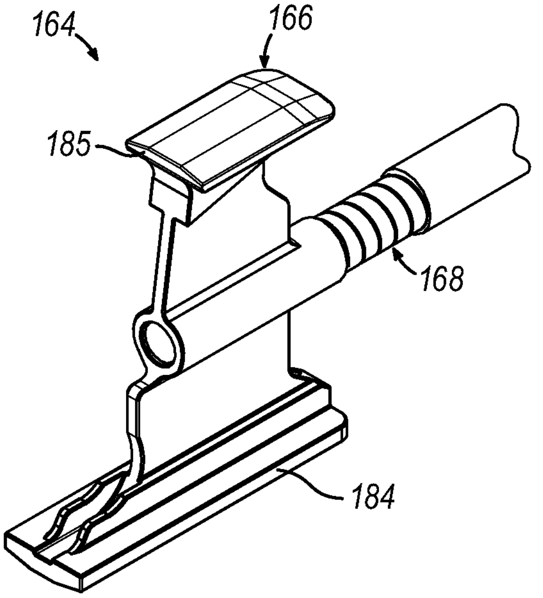
FIG. 8 depicts a driving assembly configured for use with the staple cartridge of FIG. 7.
Figure 12:
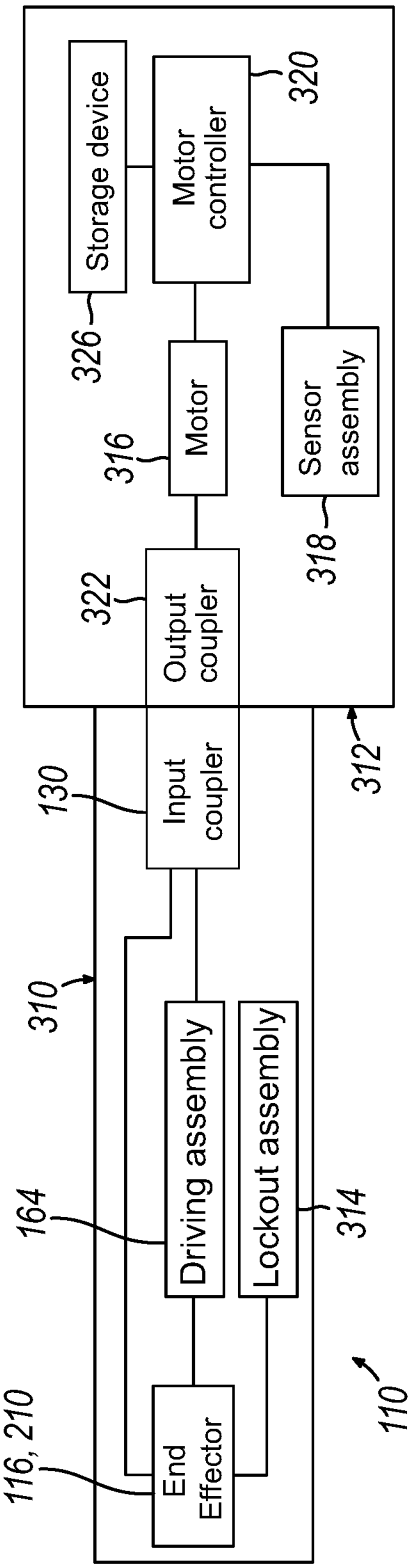
FIG. 12 depicts a schematic view of another exemplary robotic surgical system similar to the robotic surgical system of FIG. 1.
Figure 14:
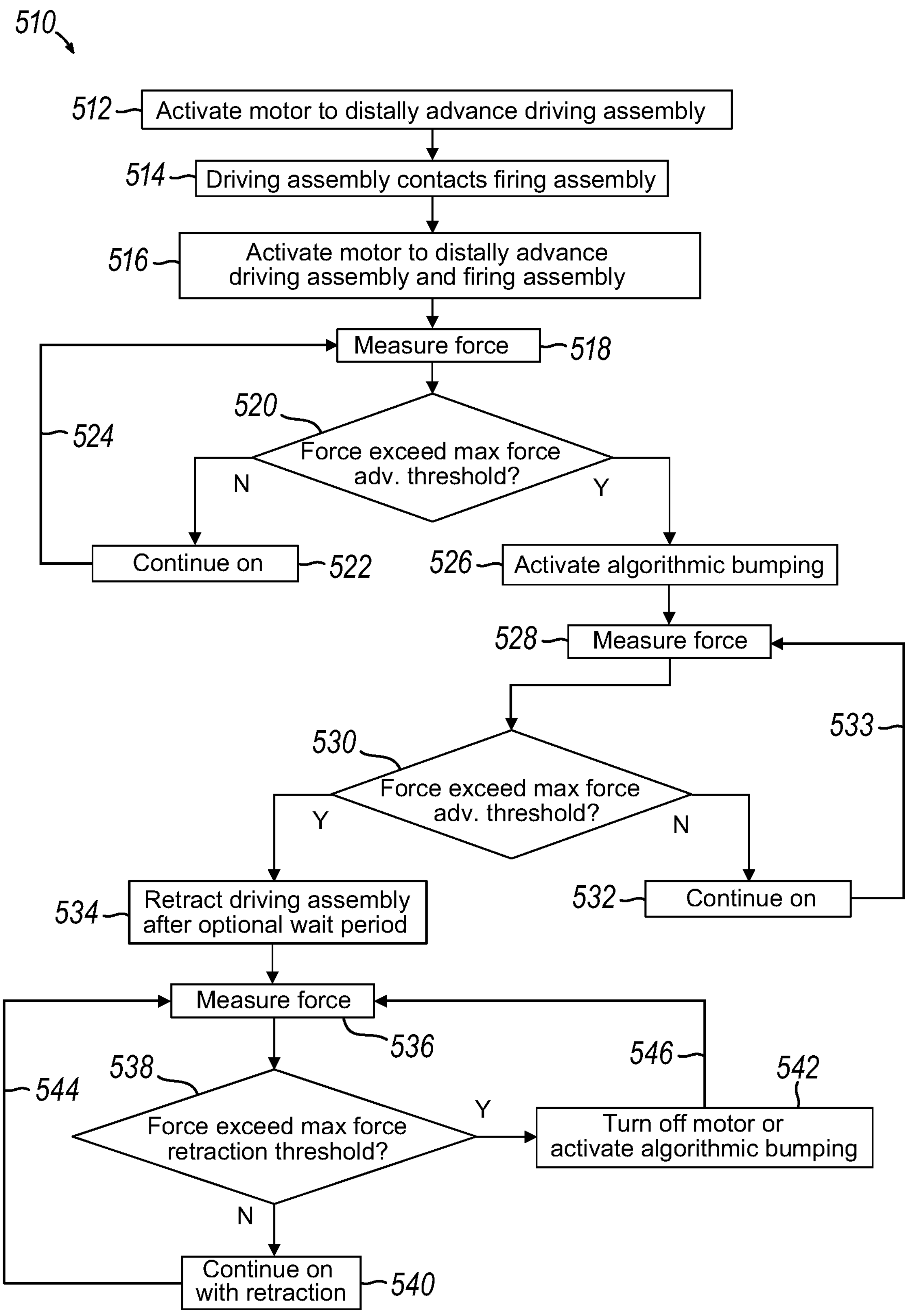
FIG. 14 depicts a block diagram of a second exemplary motor control algorithm that may be used by the robotic arm and surgical instrument shown in FIG. 12.
Figure 30:
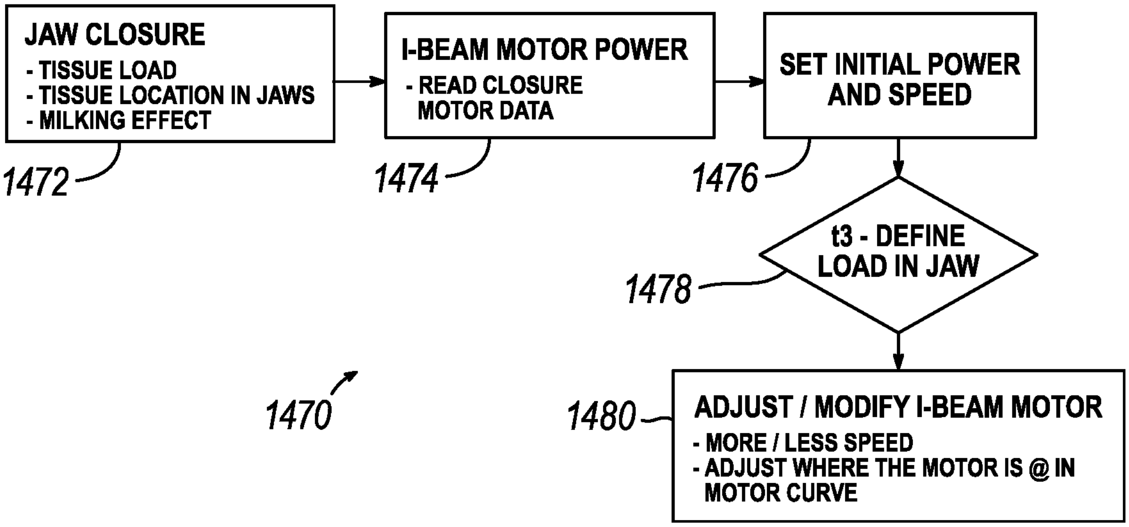
FIG. 30 depicts a block diagram of an exemplary motor control algorithm that may be used by the robotic arm and surgical instrument shown in FIG. 23.
Figure 94A:
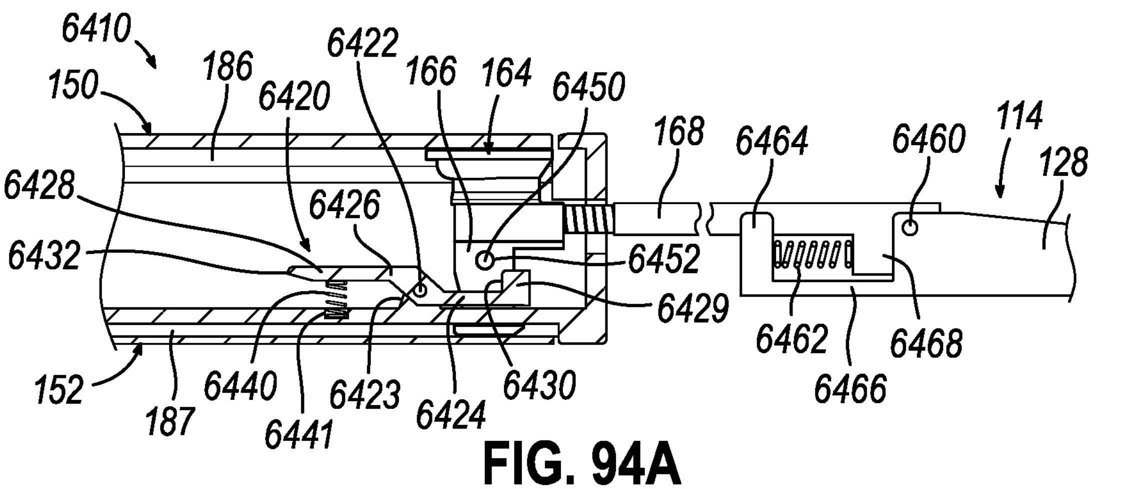
Figure 94B:
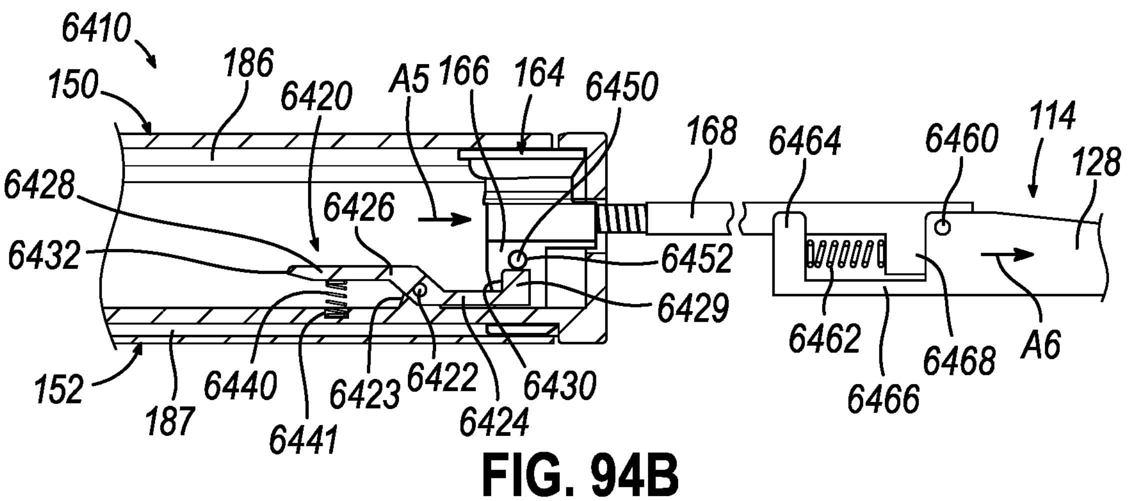
Figure 94C:
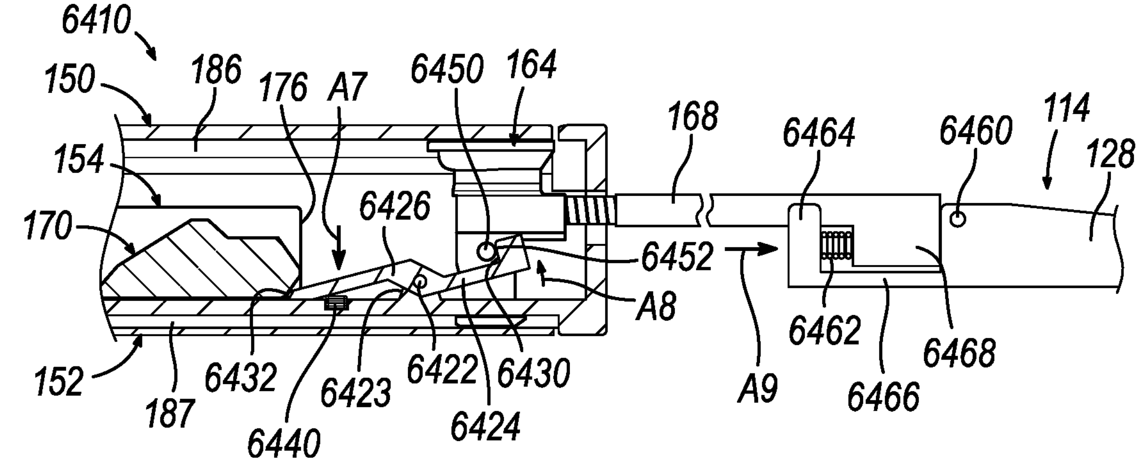
Figure 95:
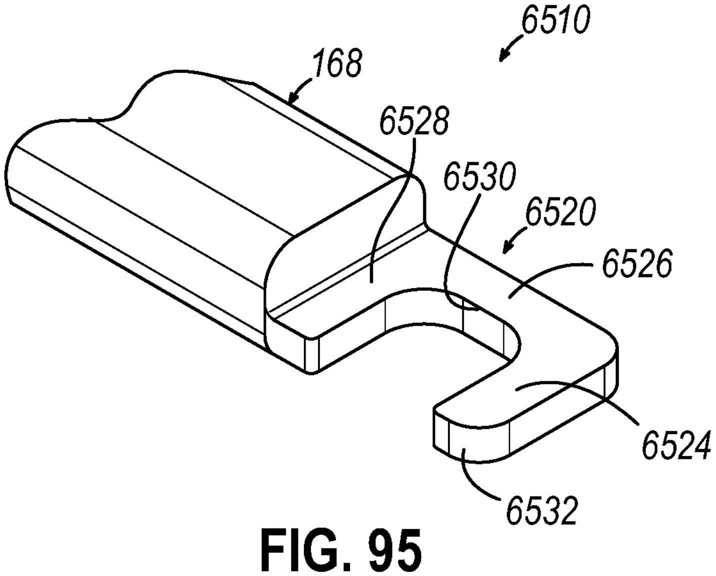
Figure 96A:
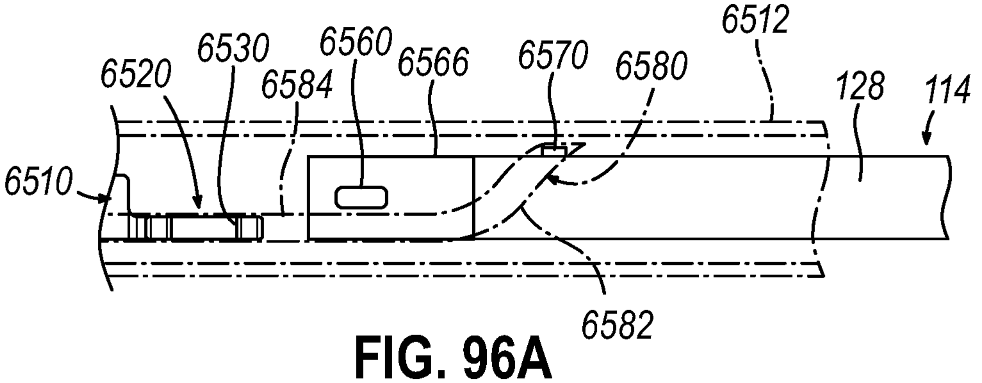
Figure 96B:
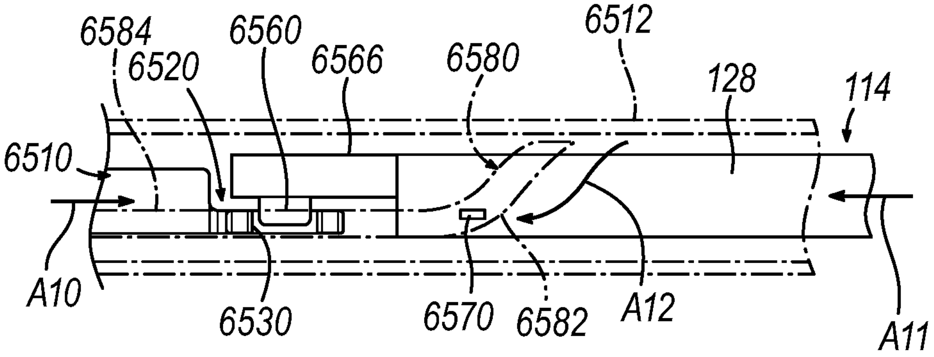
Figure 97:
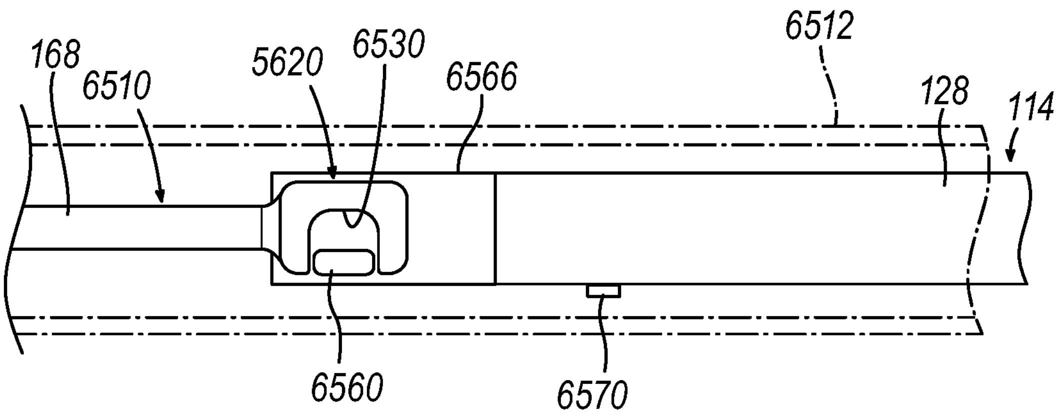
Figure 98:
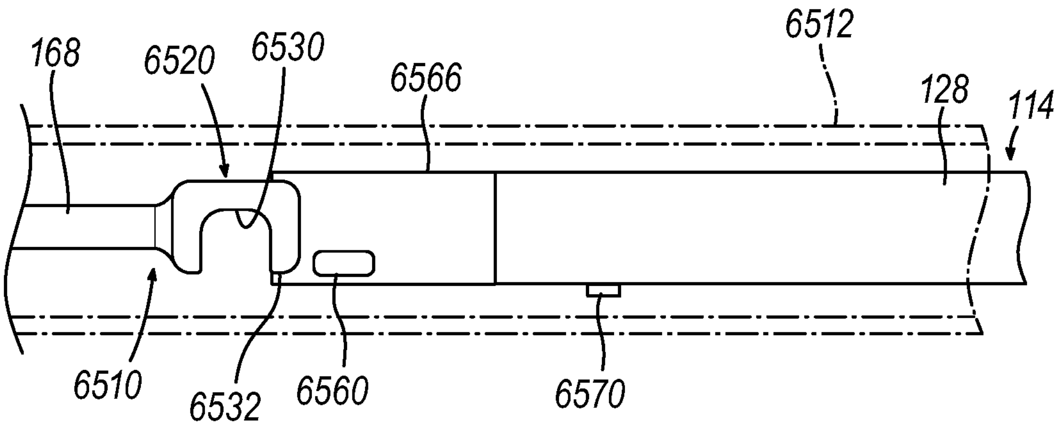
Figure 99:
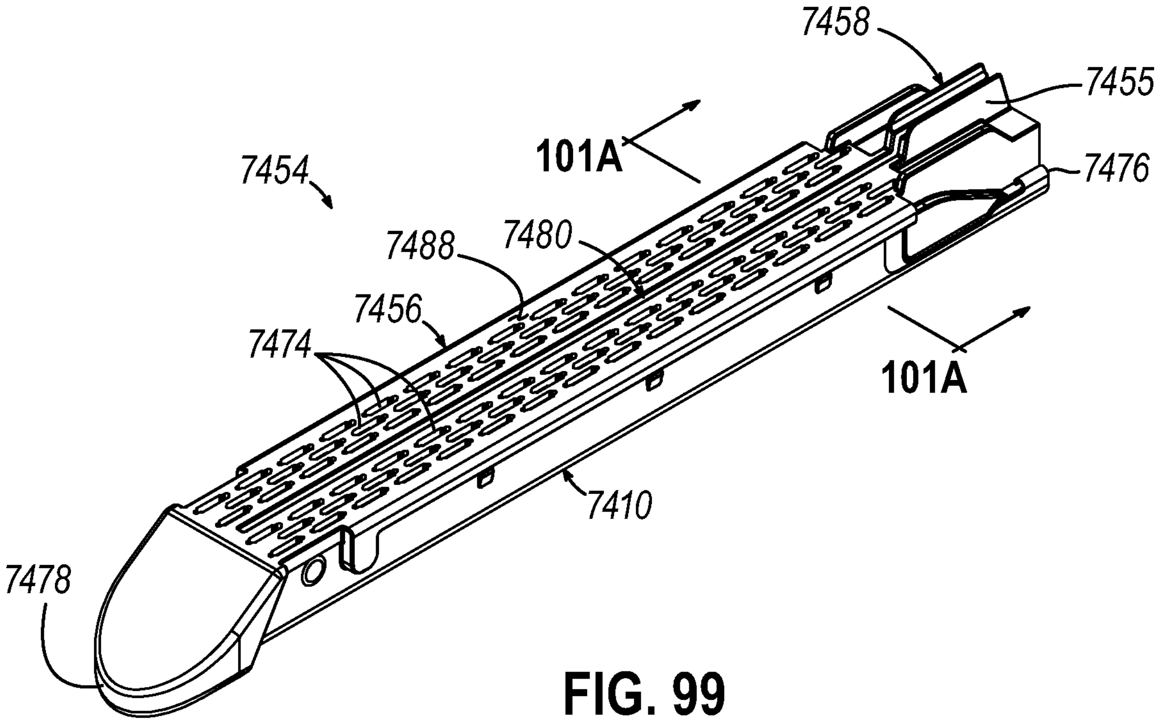
Figure 100:
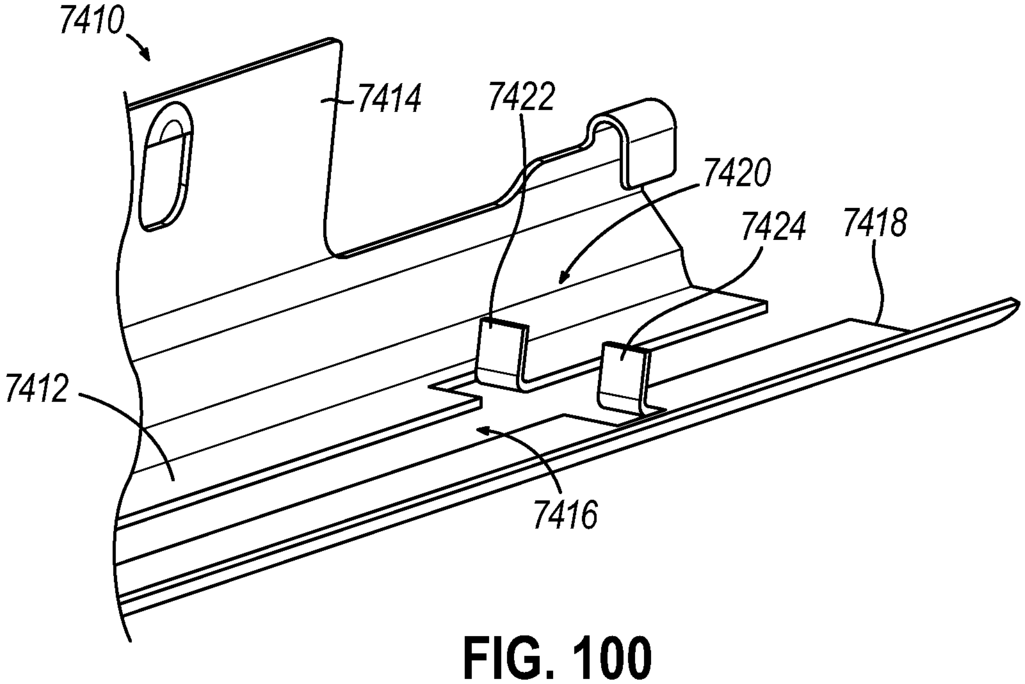
Figure 101A:
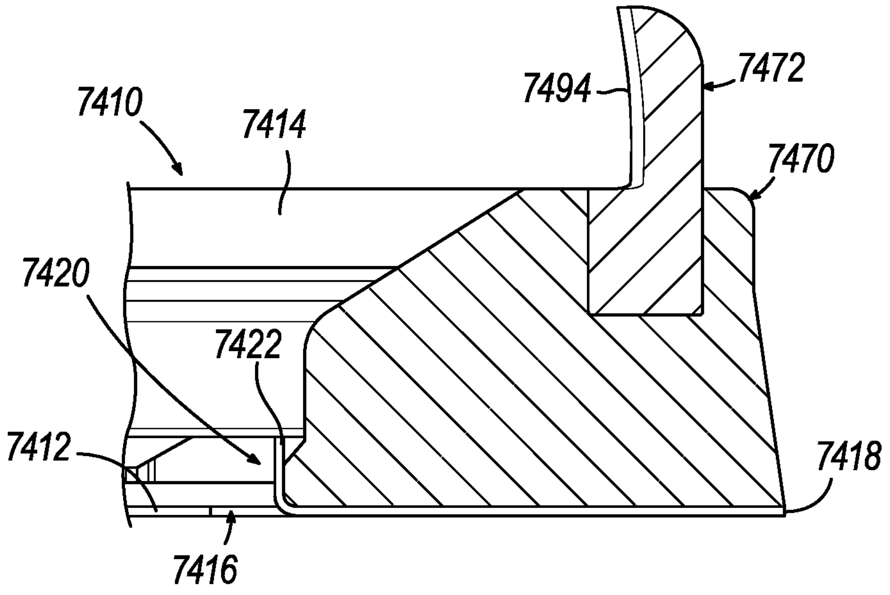
Figure 101B:
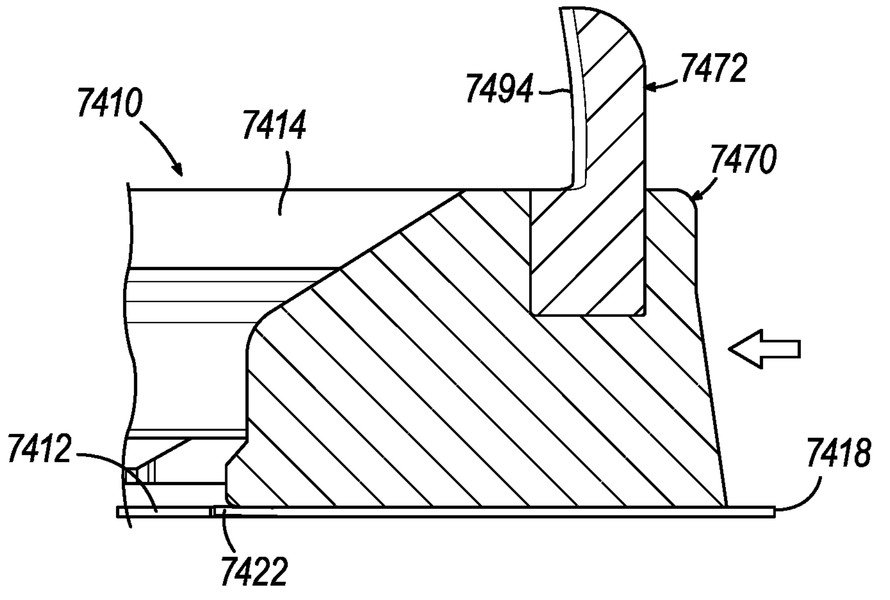
Figure 102:
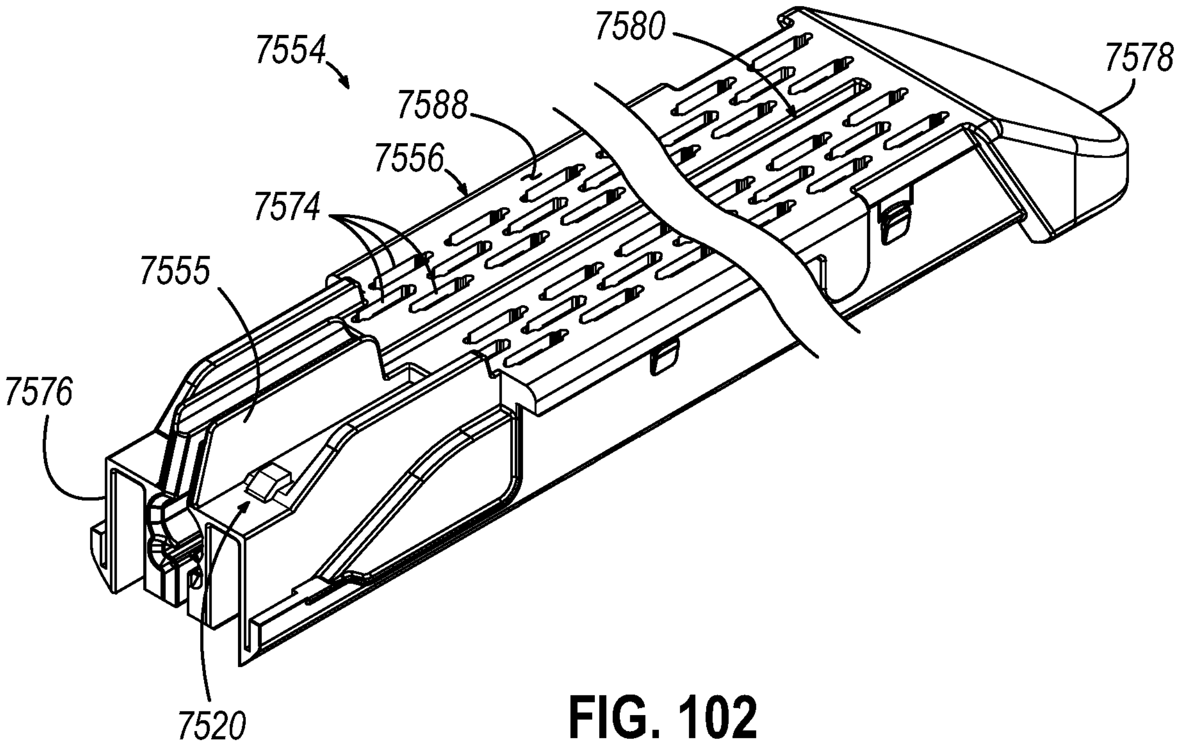
Figure 103:
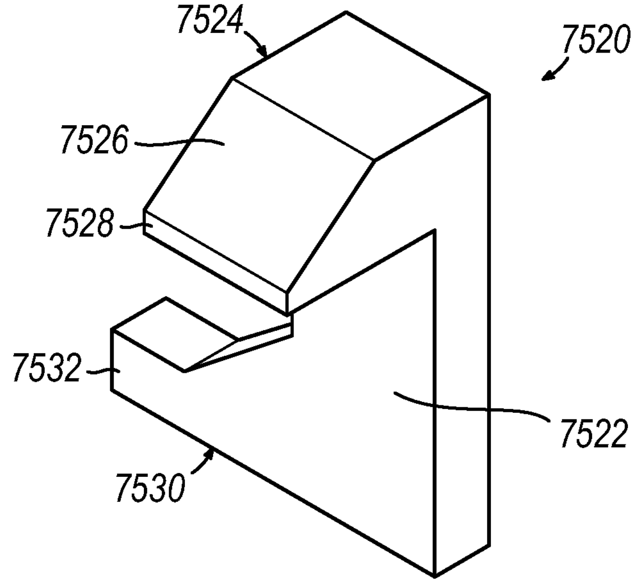
Figure 104:
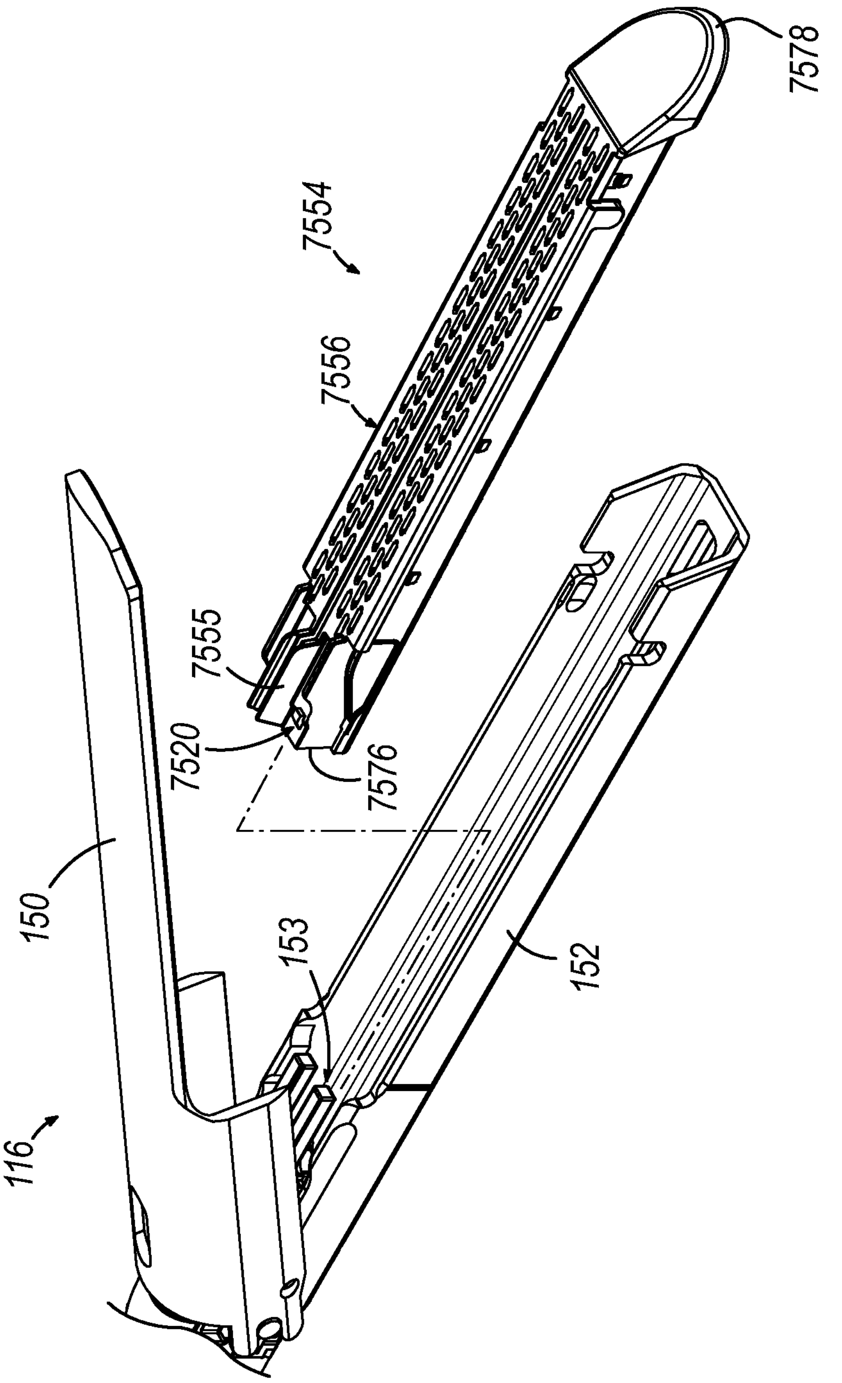
Figure 105A:
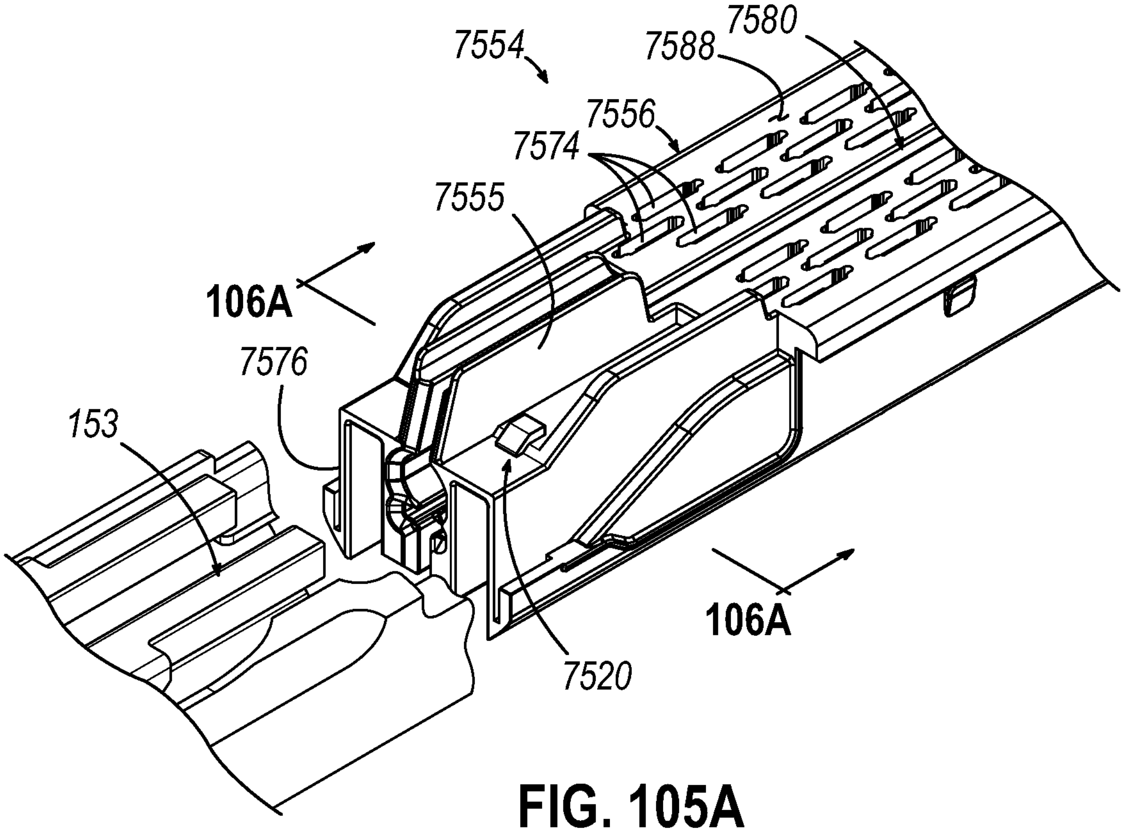
Figure 105B:
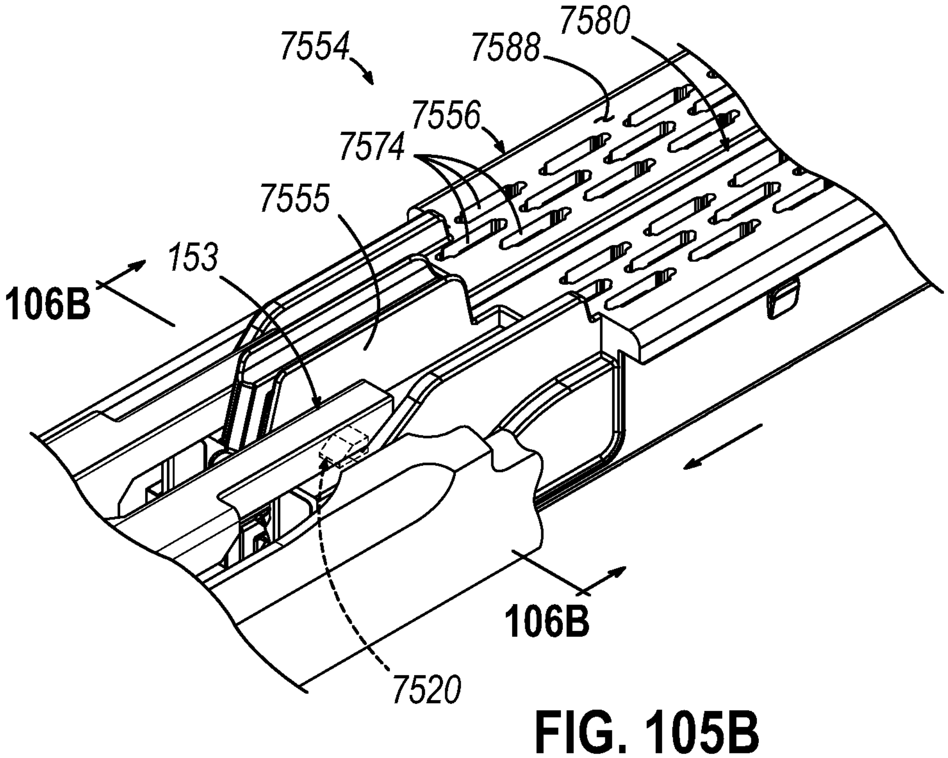
Figure 106A:
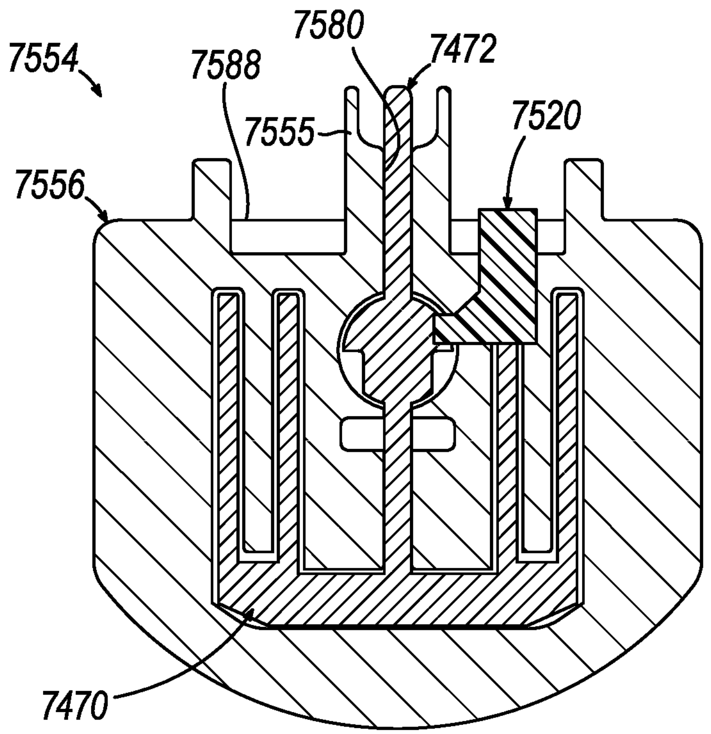
Figure 106B:
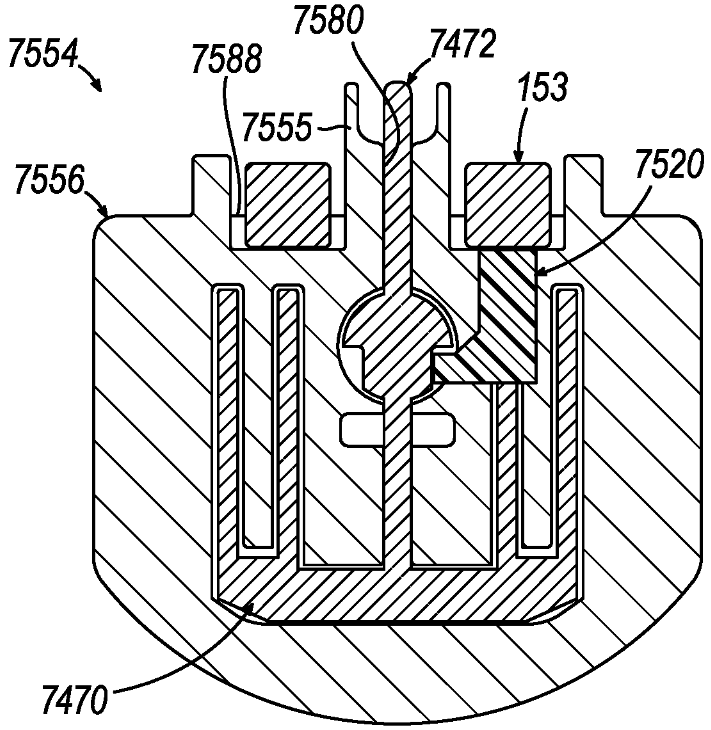
Figure 107:
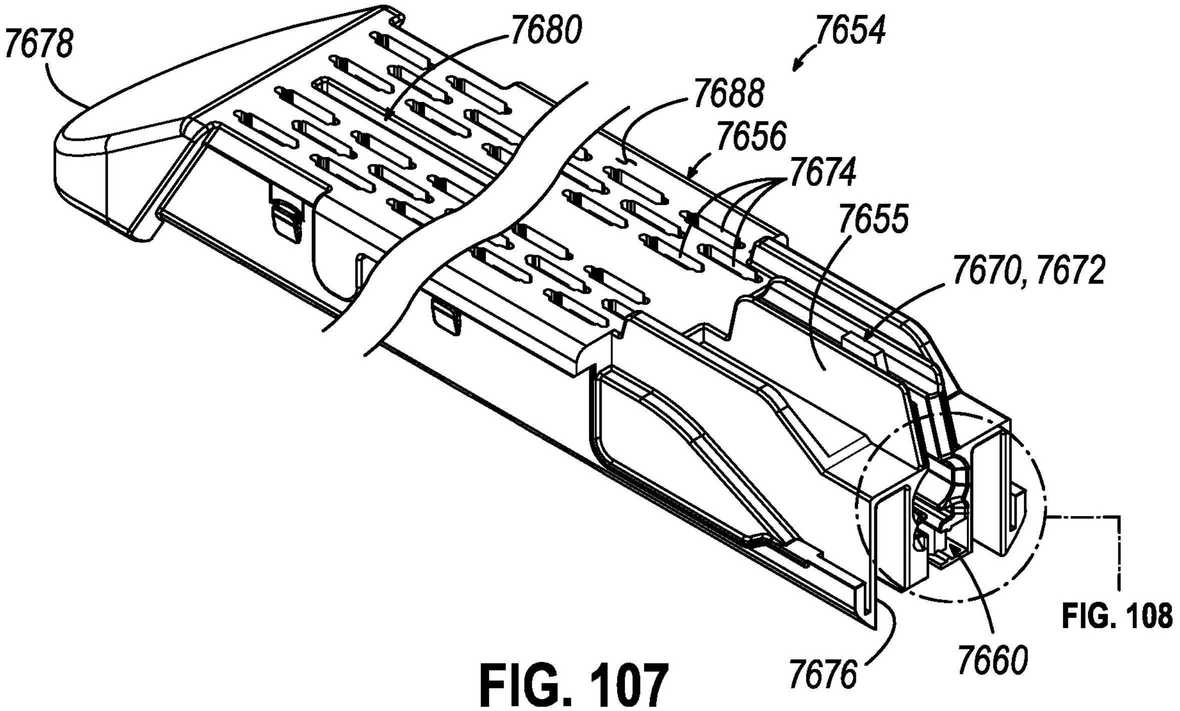
Figure 108:
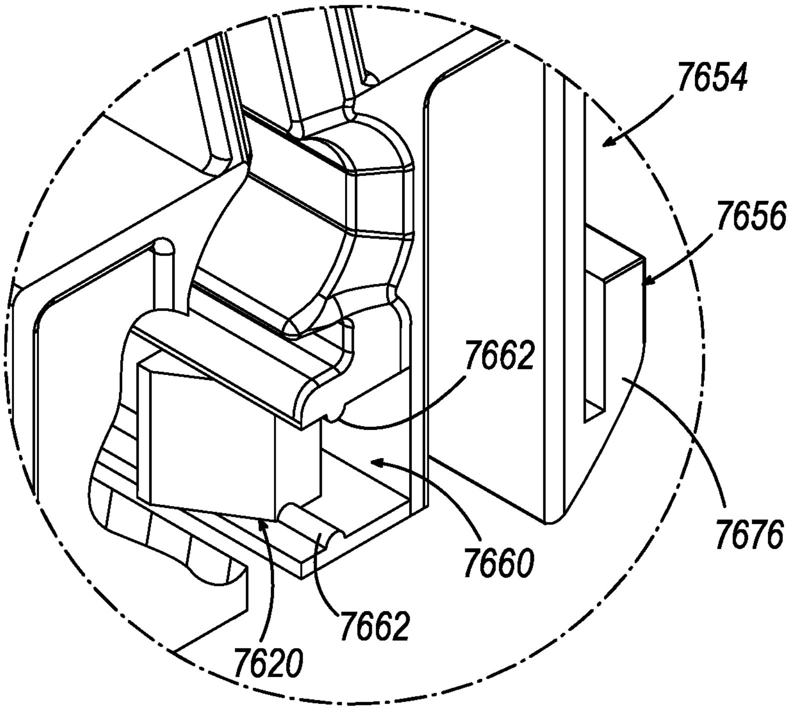
Figure 109:
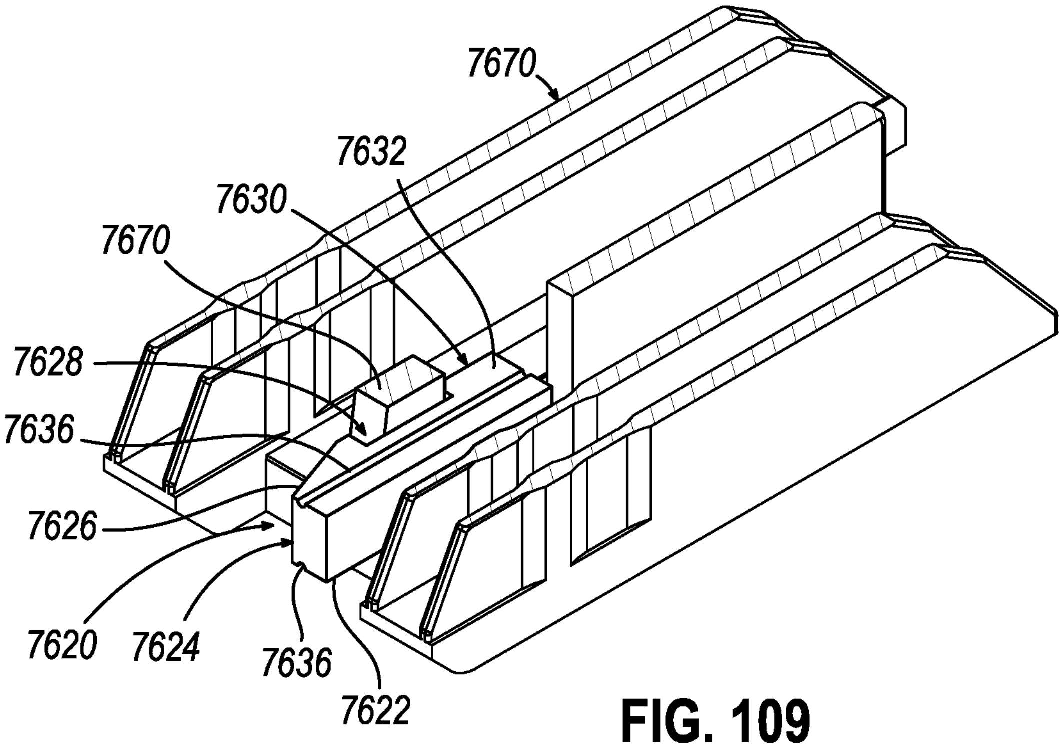
Figure 110:
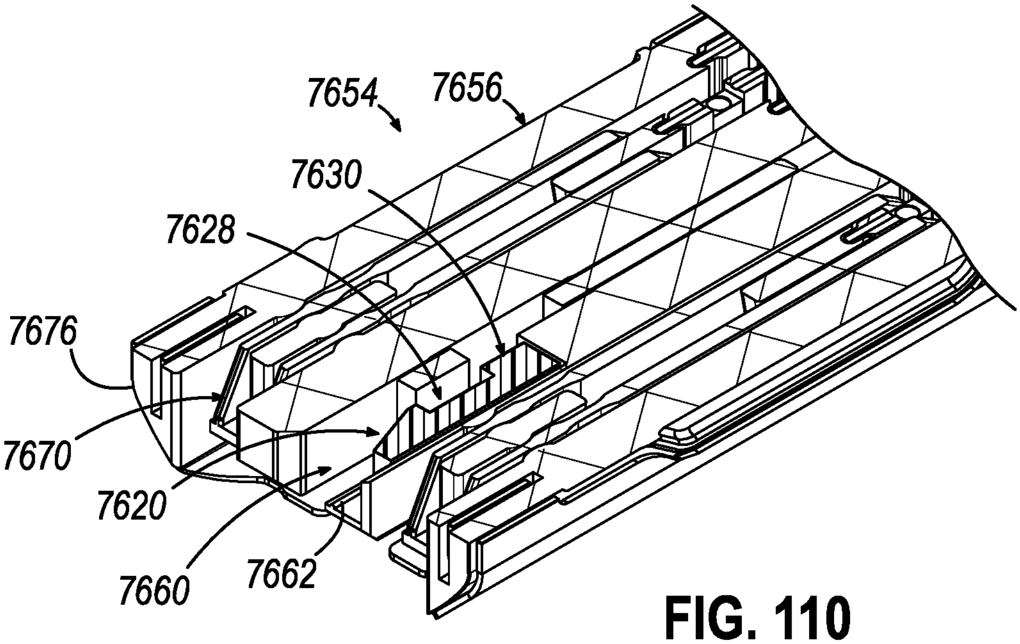
Figure 111A:
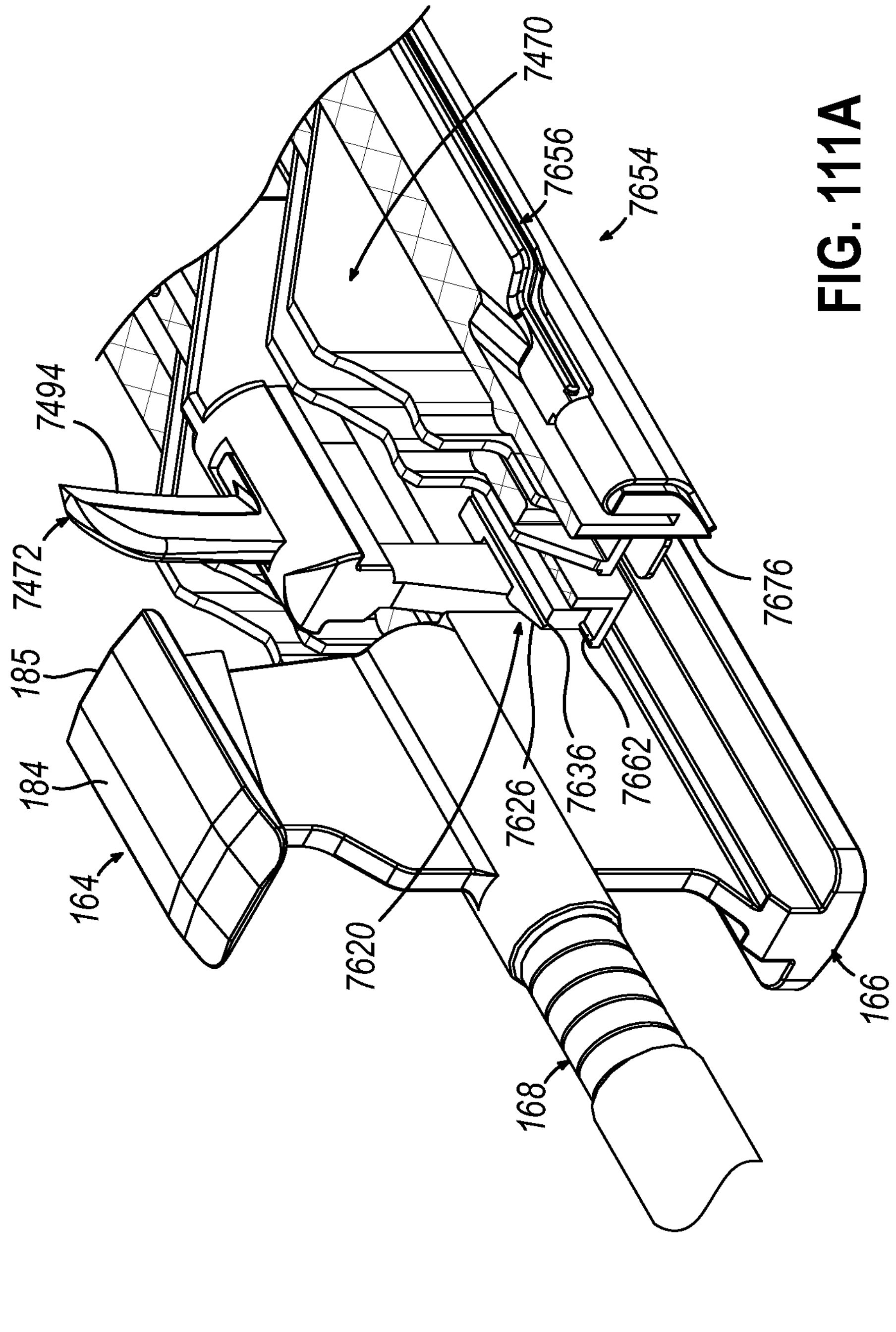
Figure 111B:
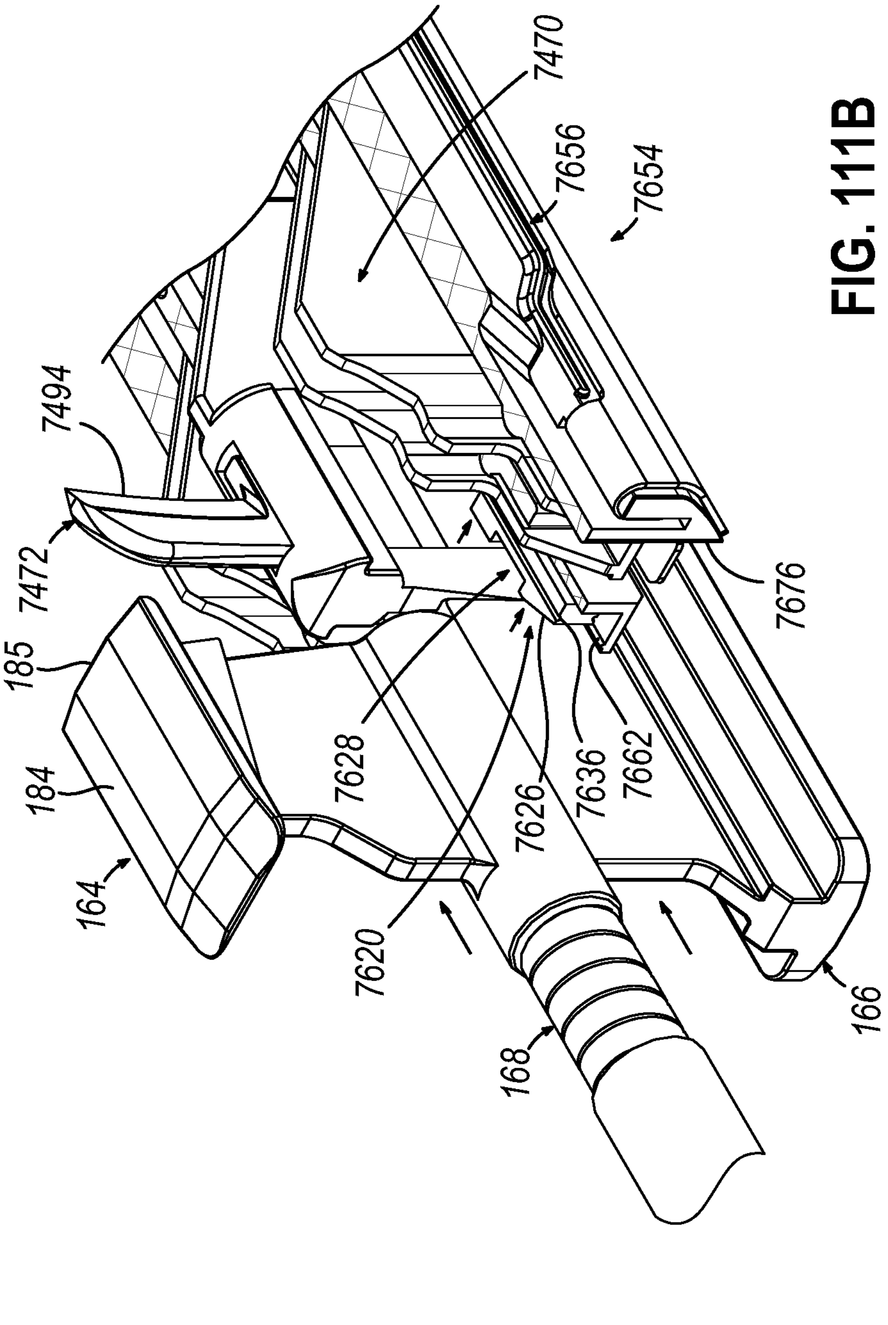
Figure 112:
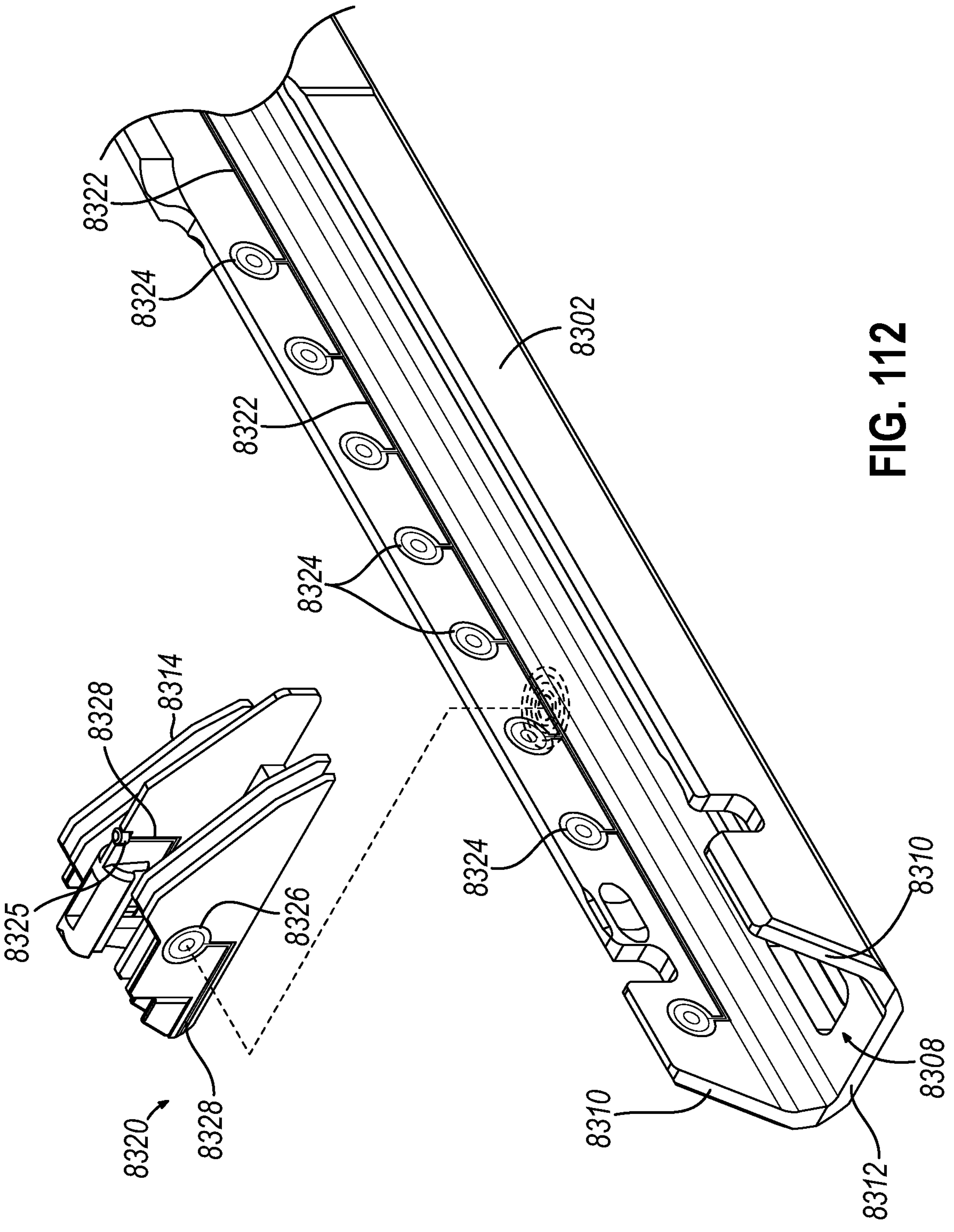
Figure 113:
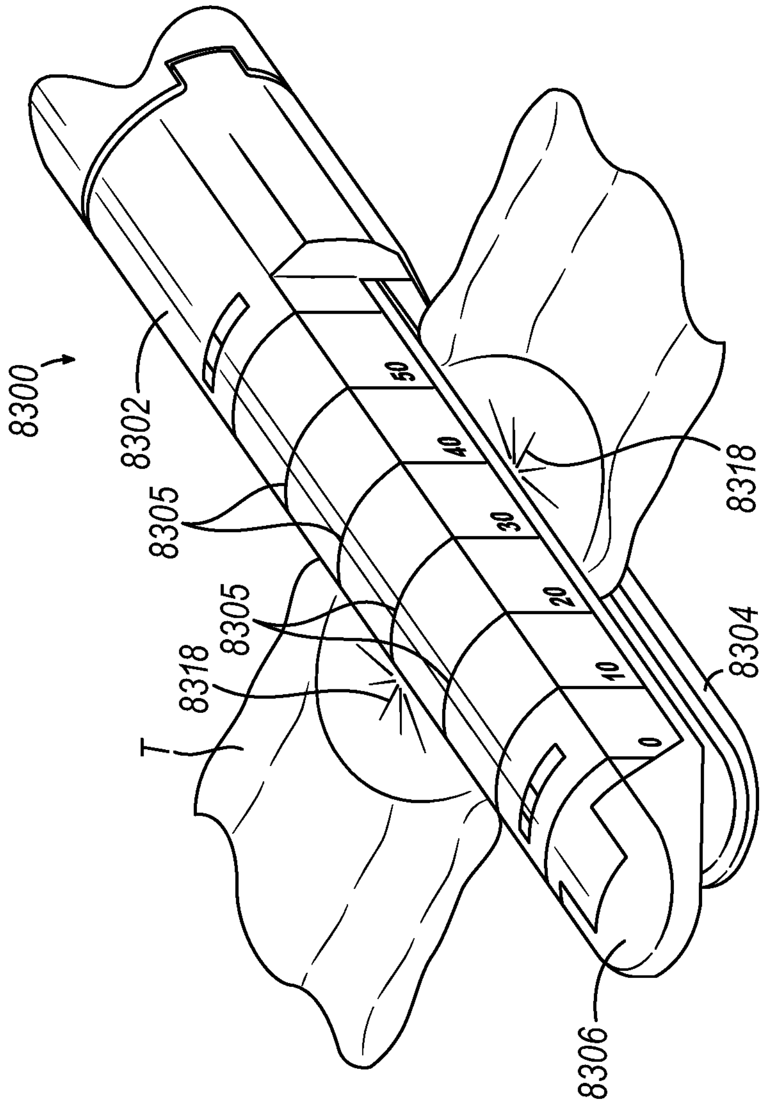
Figure 114:
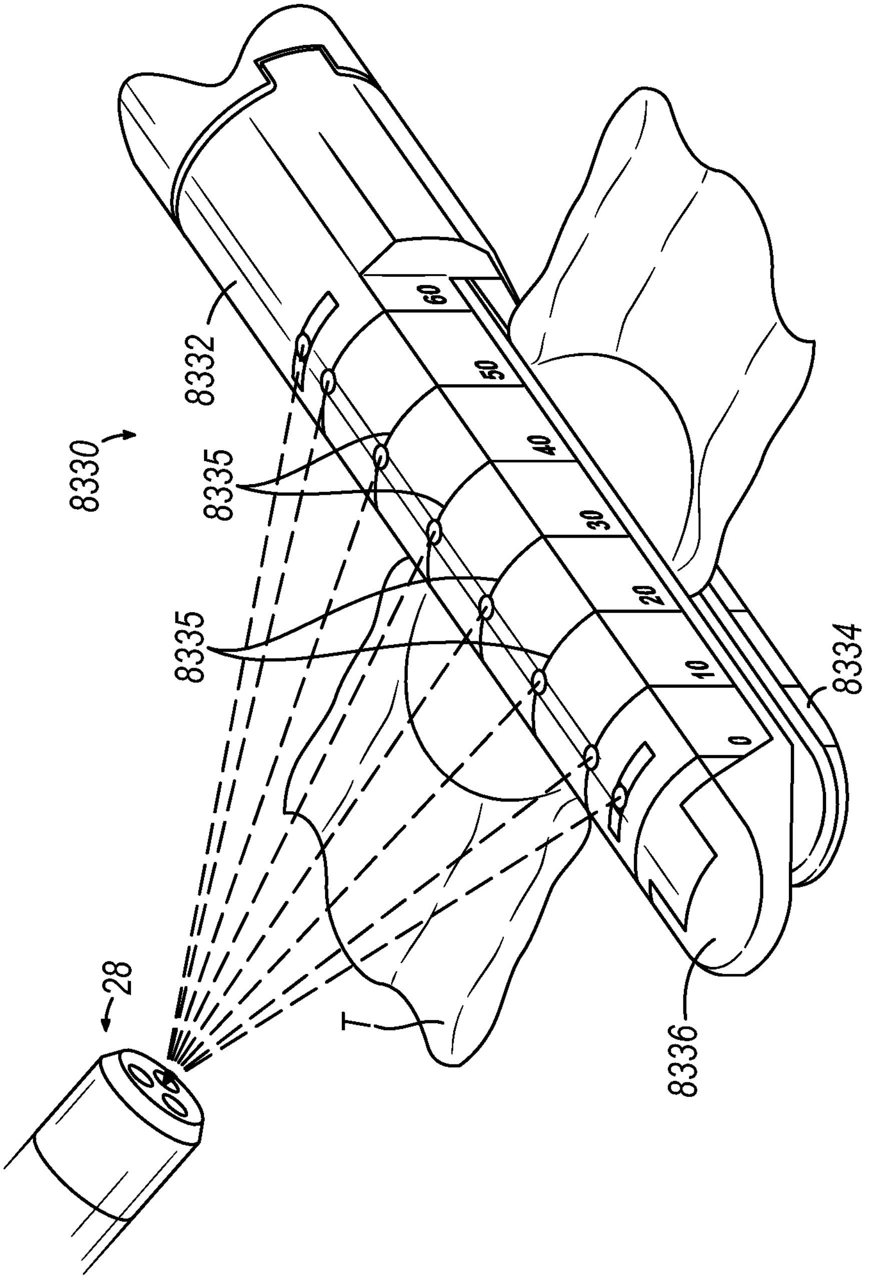
Figure 115:
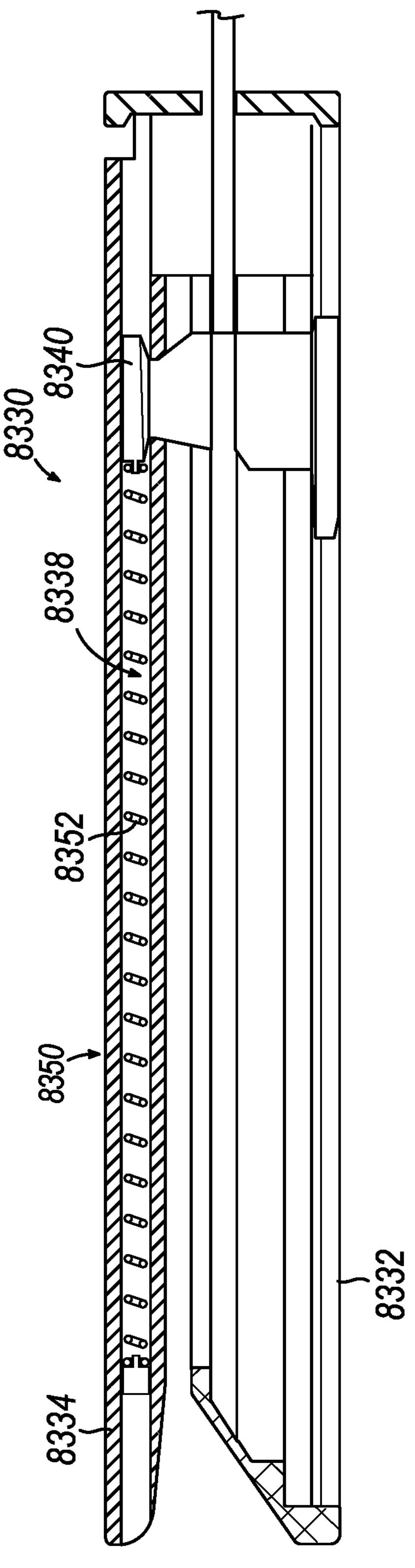
Figure 116:
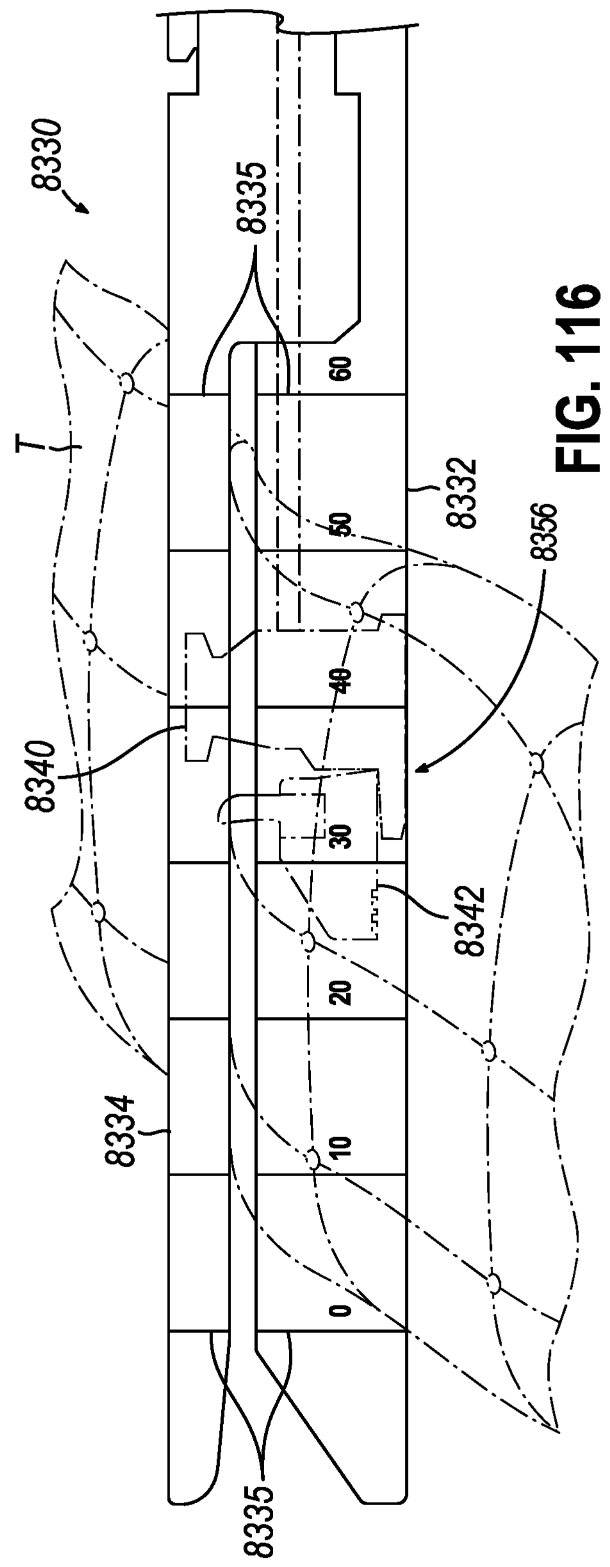
Figure 117A:
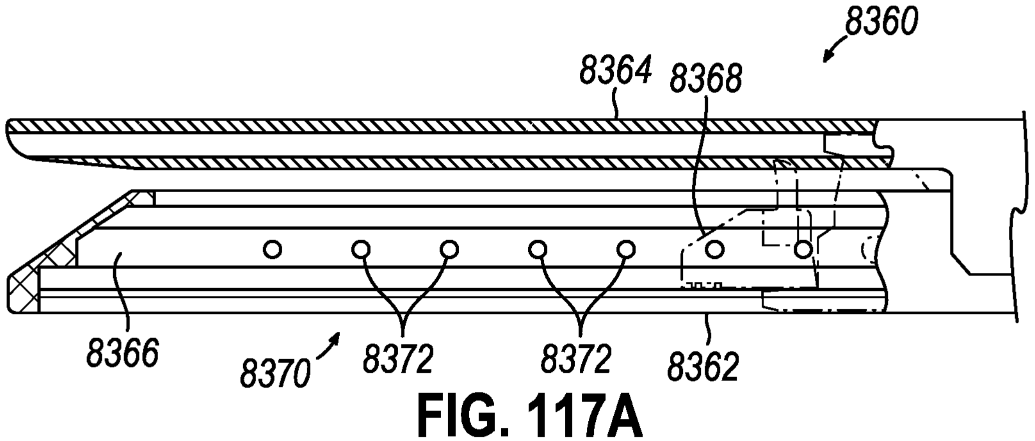
Figure 117B:
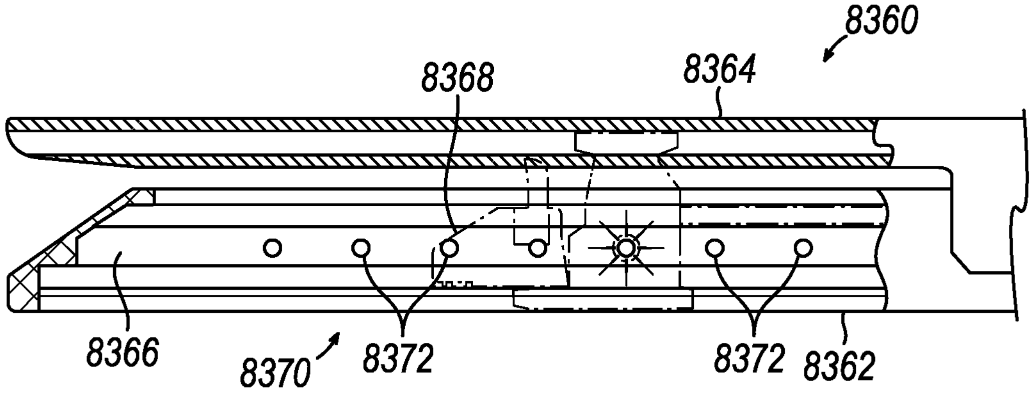
Figure 117C:
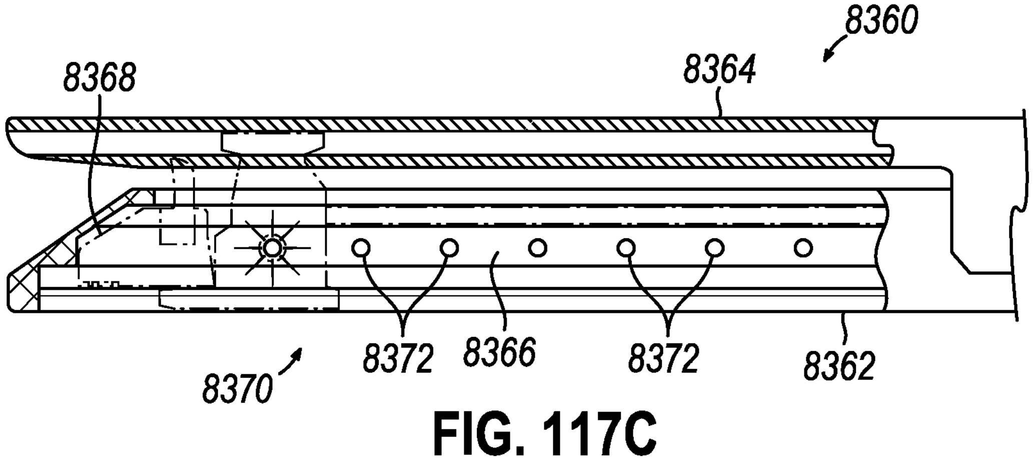
Figure 118:
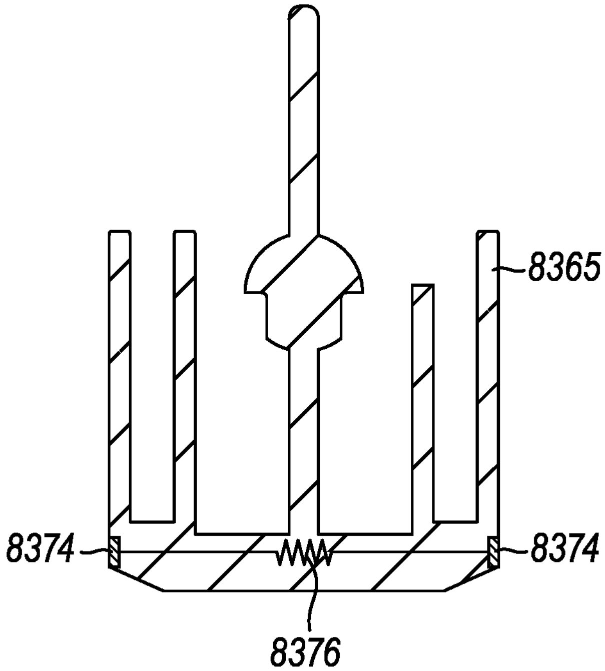
Figure 119:
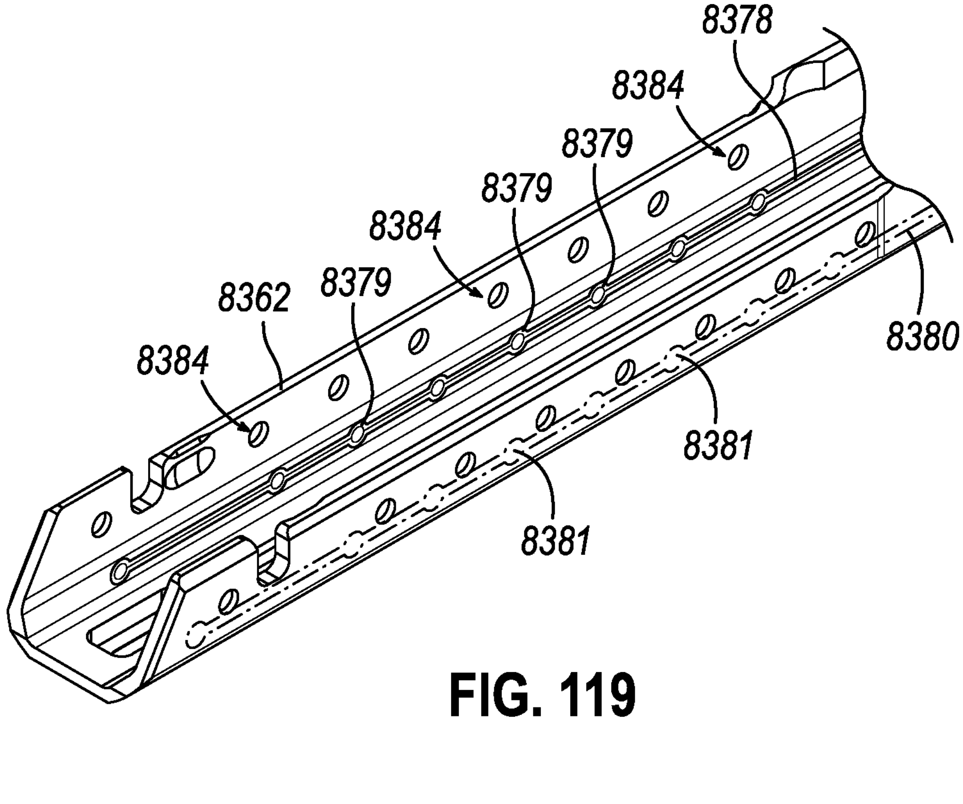
Figure 120:
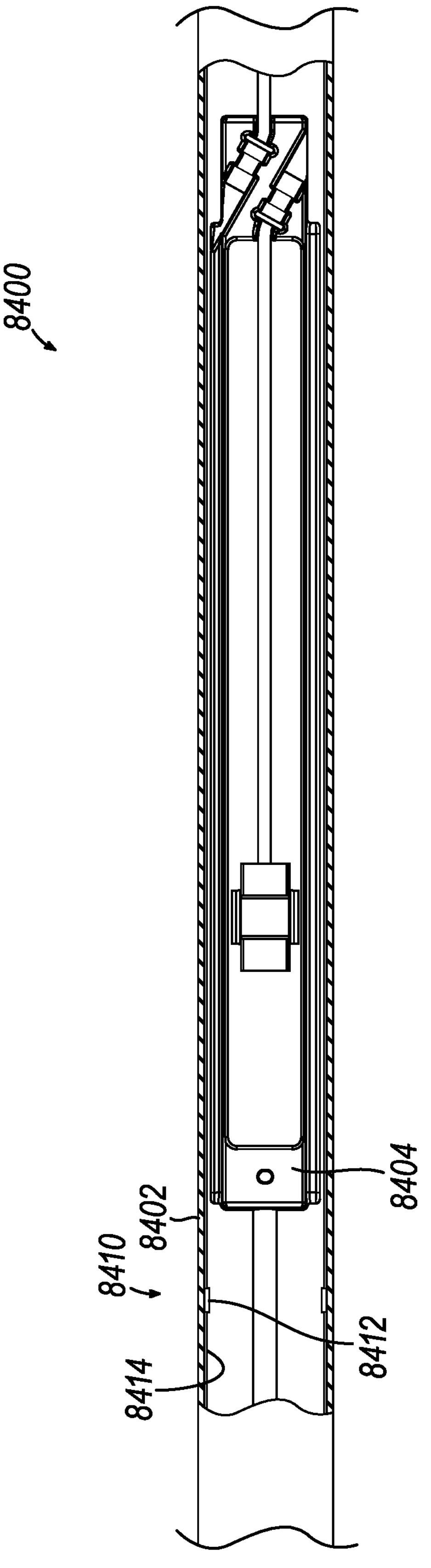
Figure 121A:
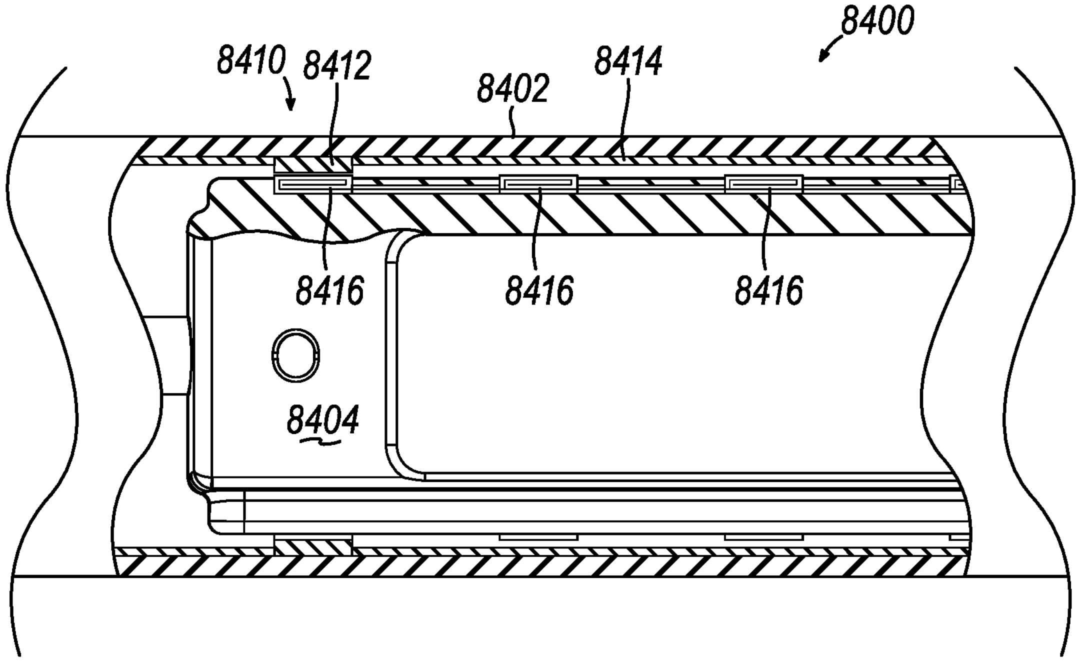
Figure 121B:
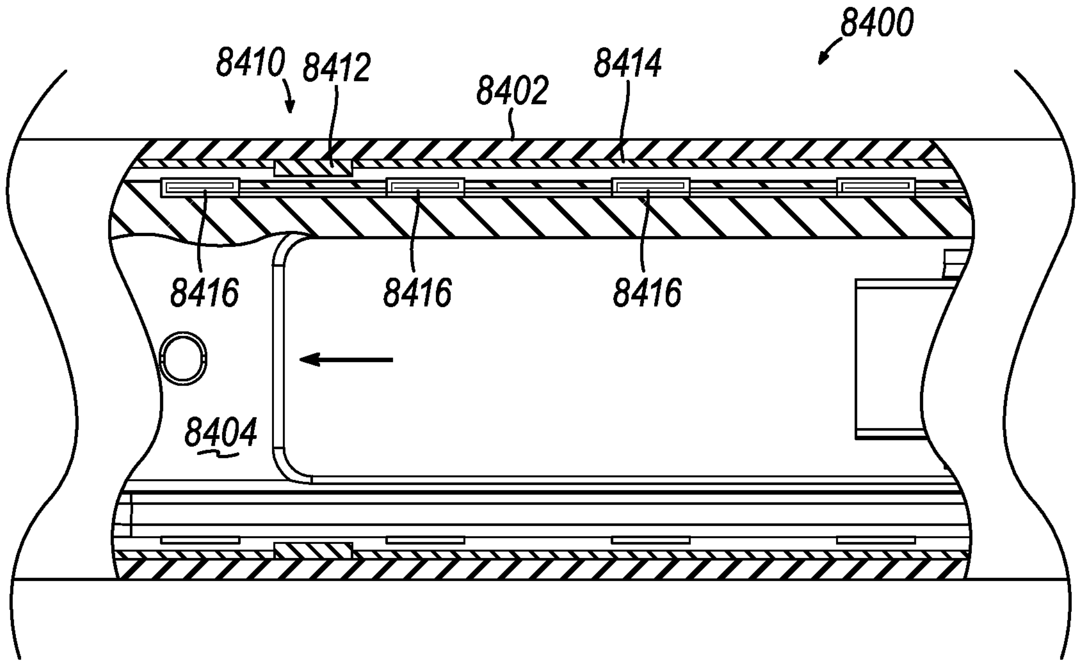
Figure 122:
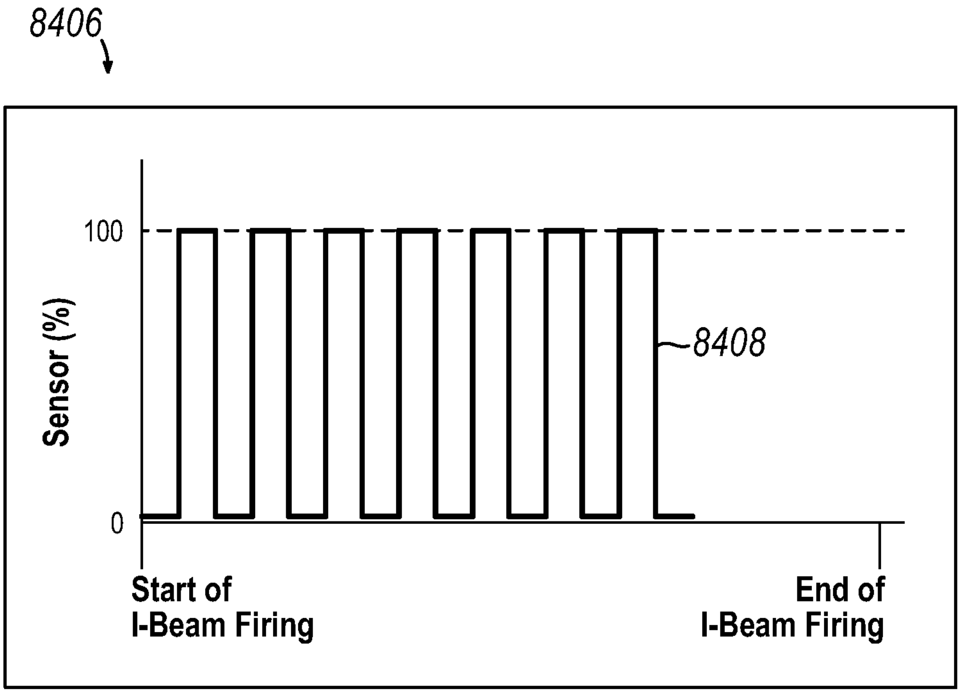
Figure 123:
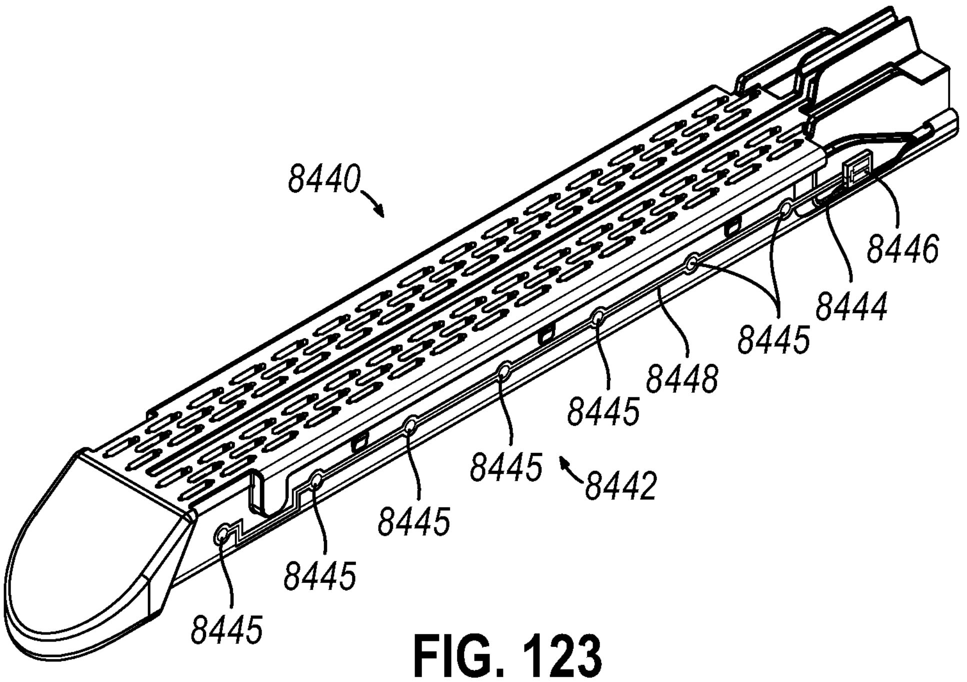
Figure 124:
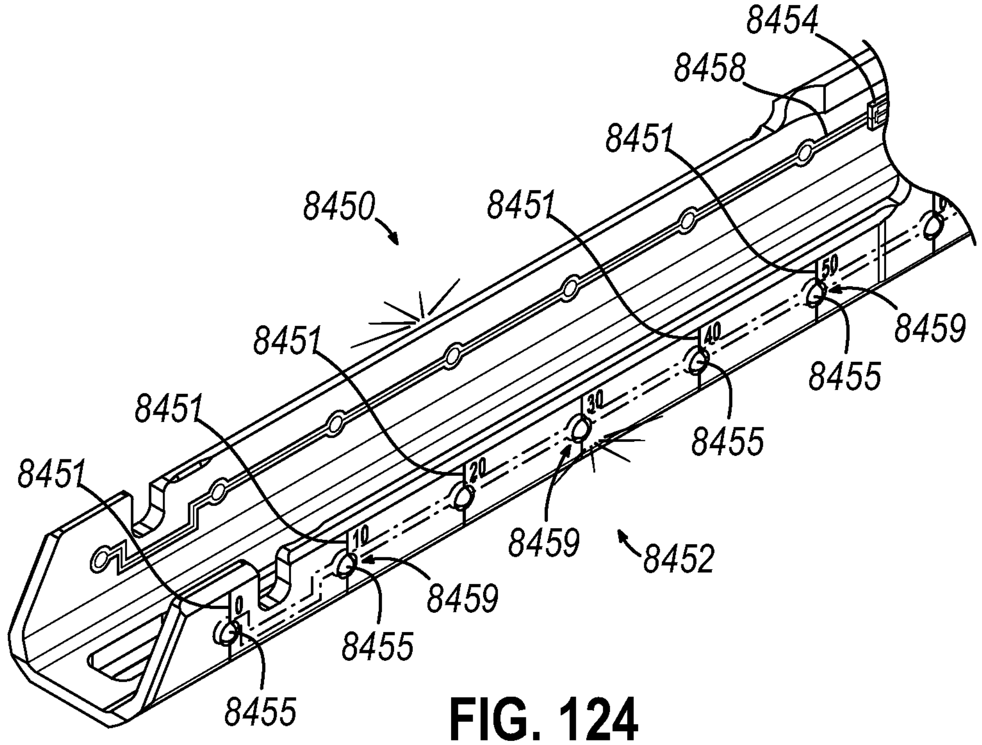
Figure 125A:
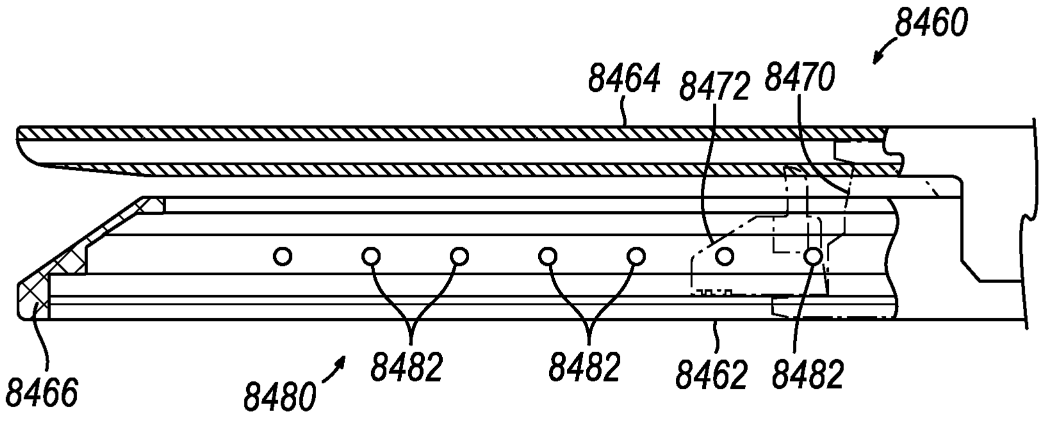
Figure 125B:
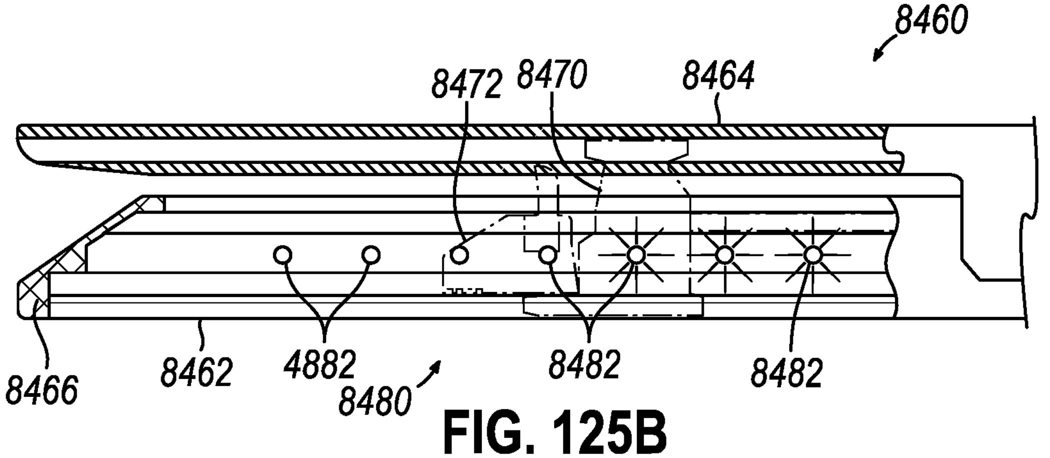
Figure 125C:
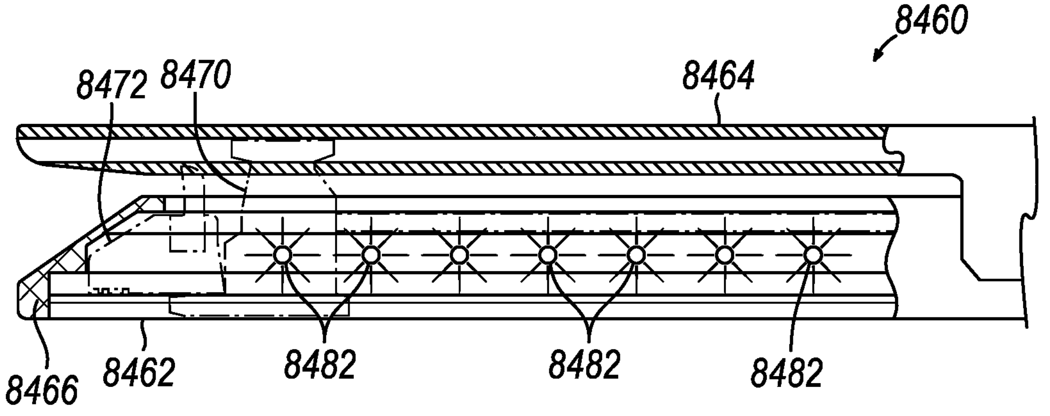
Figure 126:
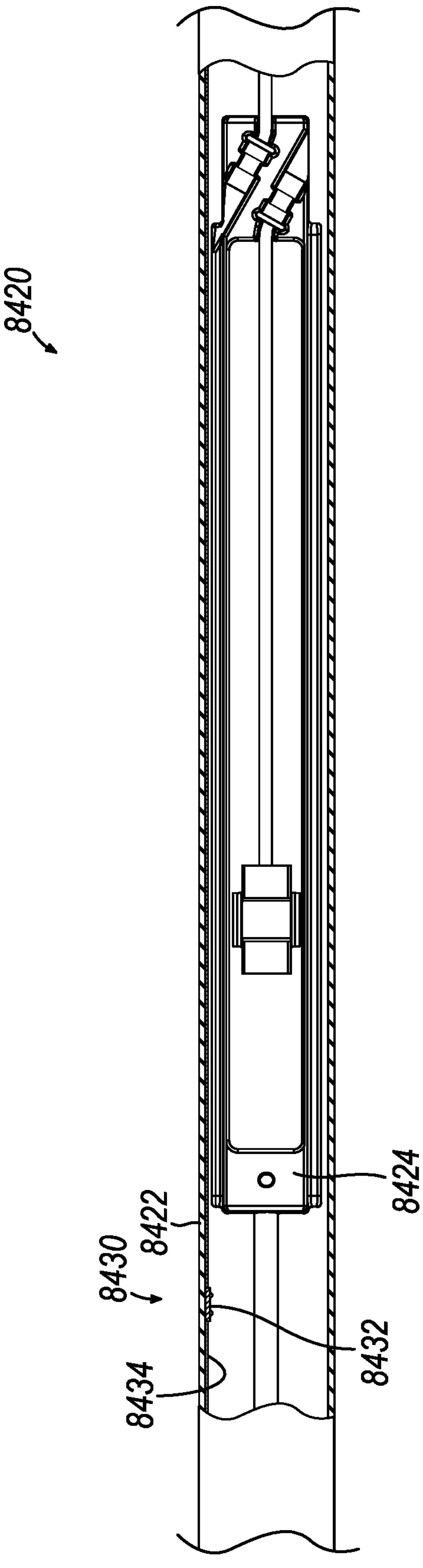
Figure 127A:
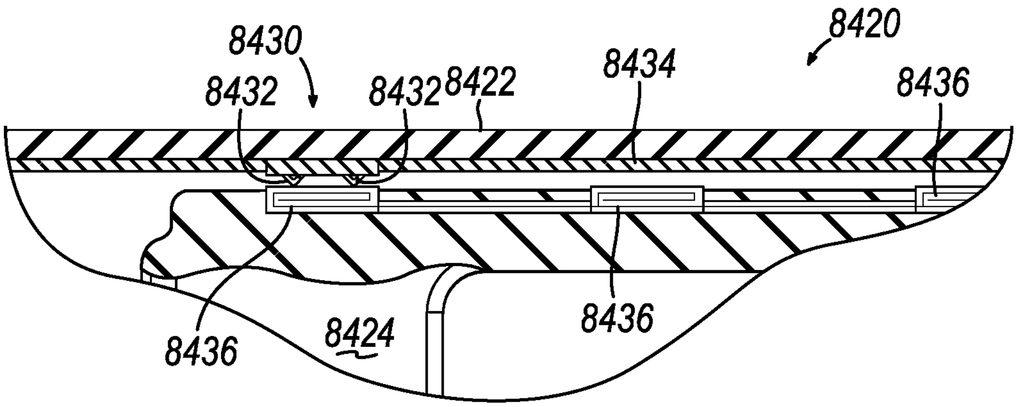
Figure 127B:
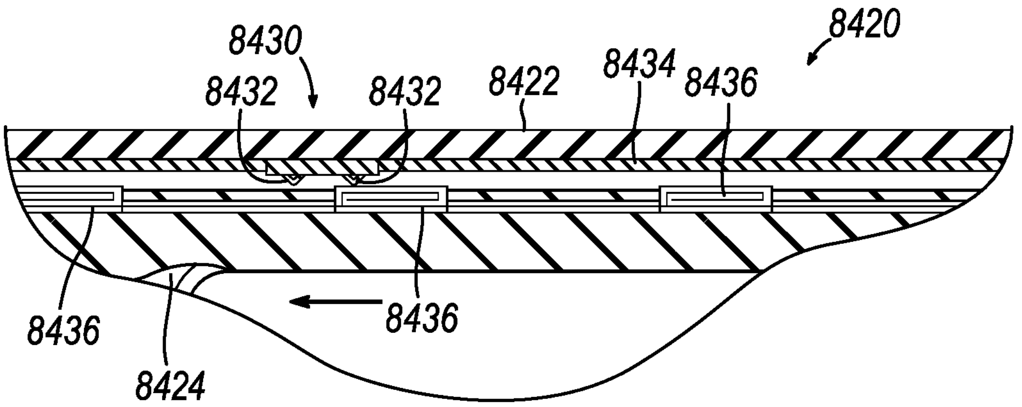
Figure 128:
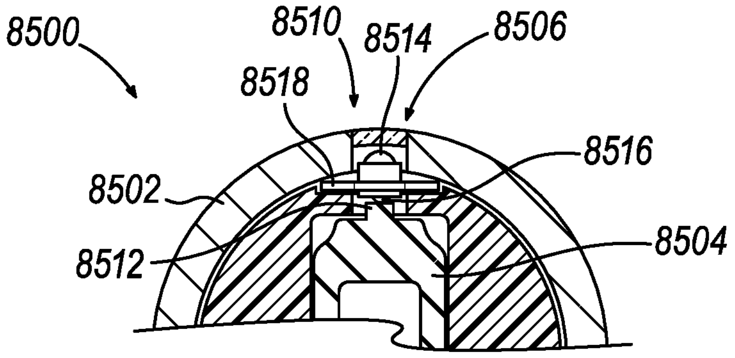
Figure 129:
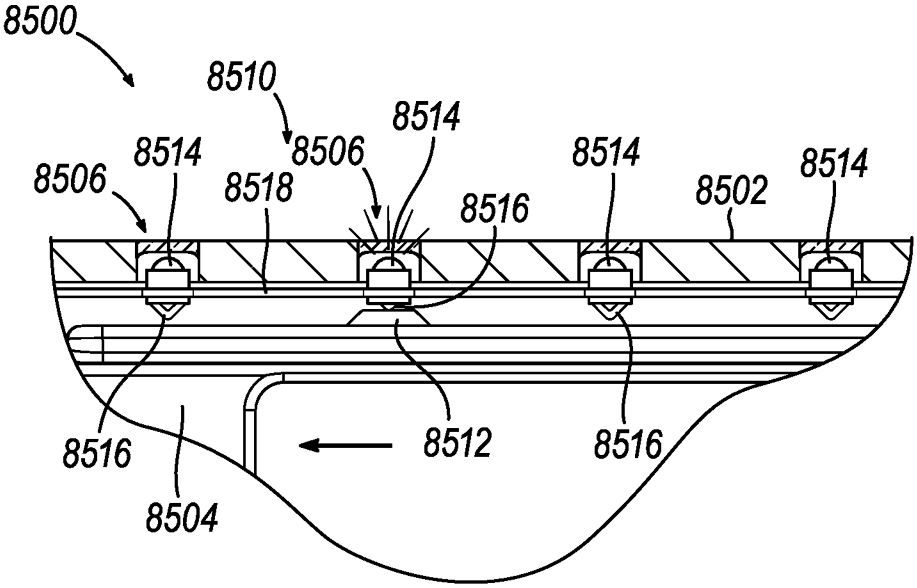
Figure 130:
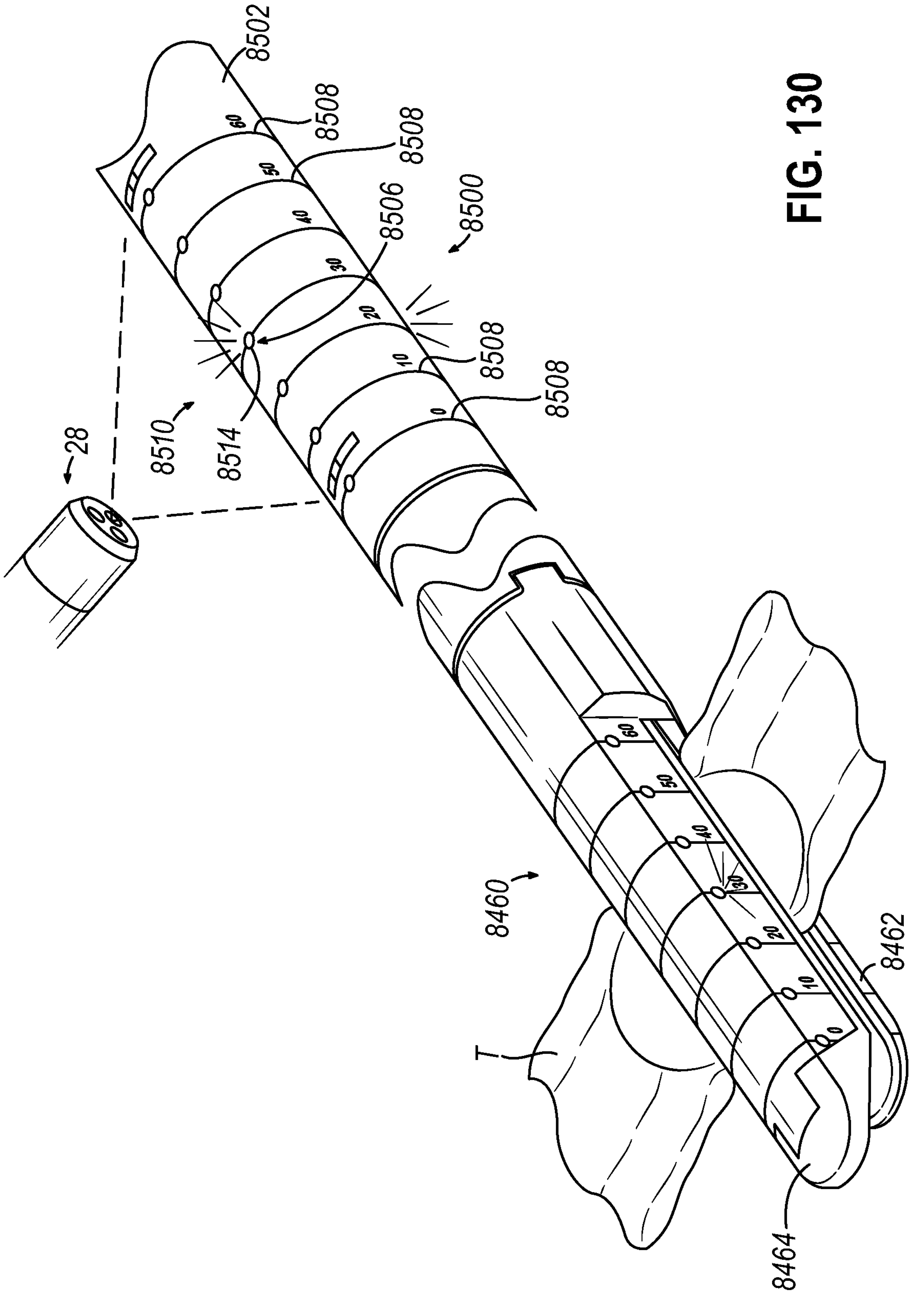
Figure 131:
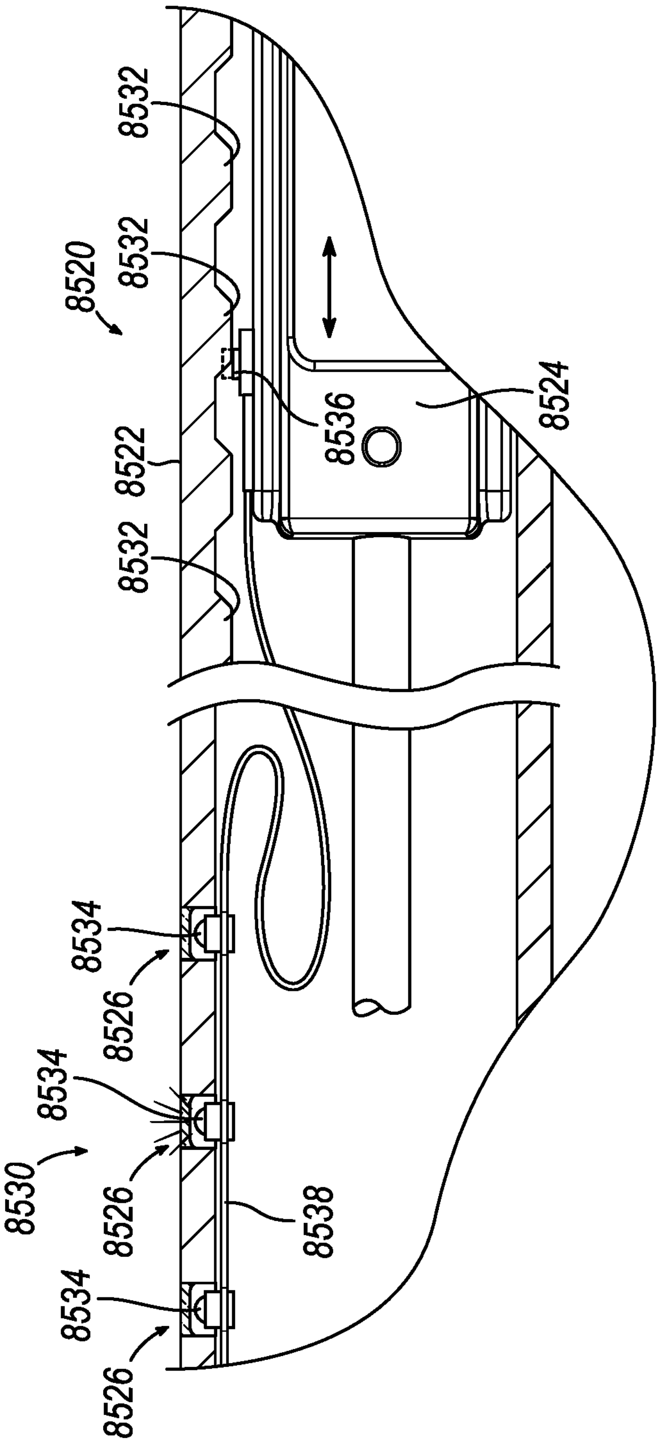
Figure 132:
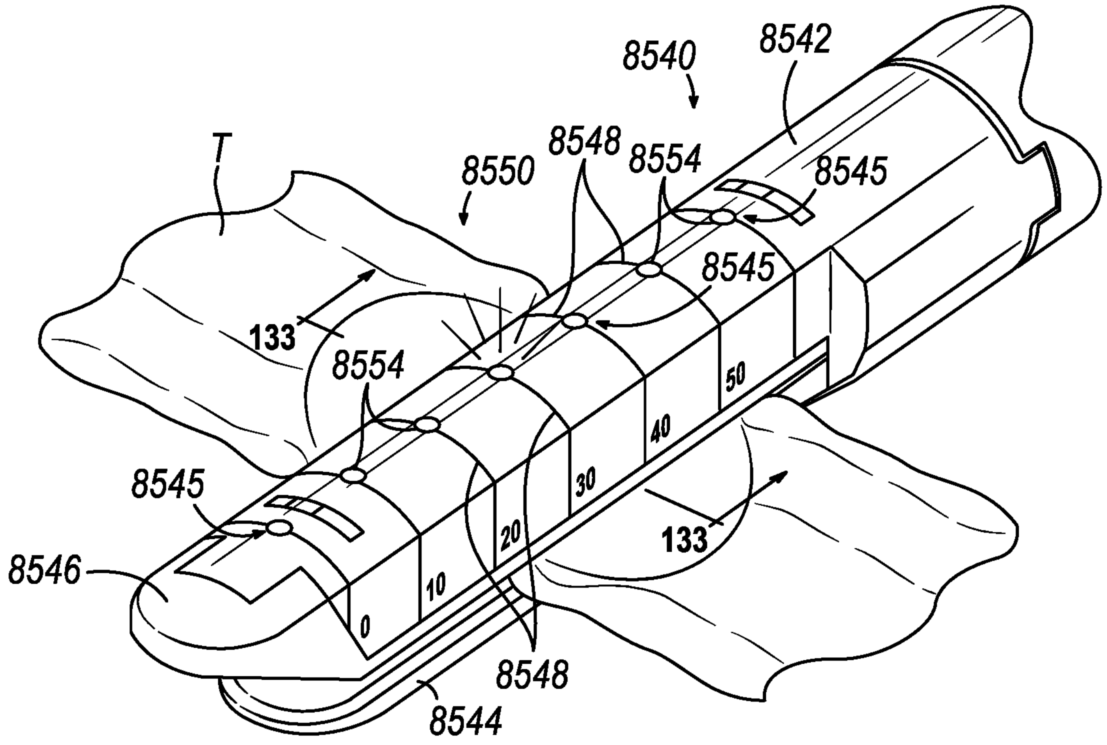
Figure 133:
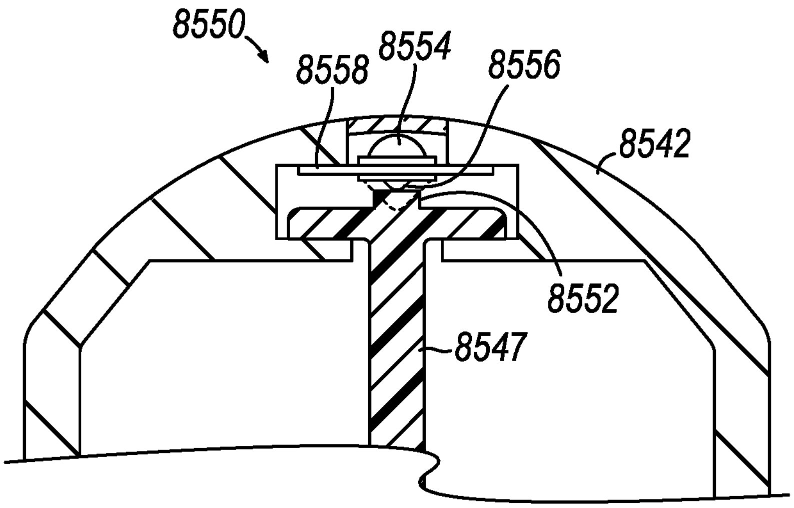
Figure 134:
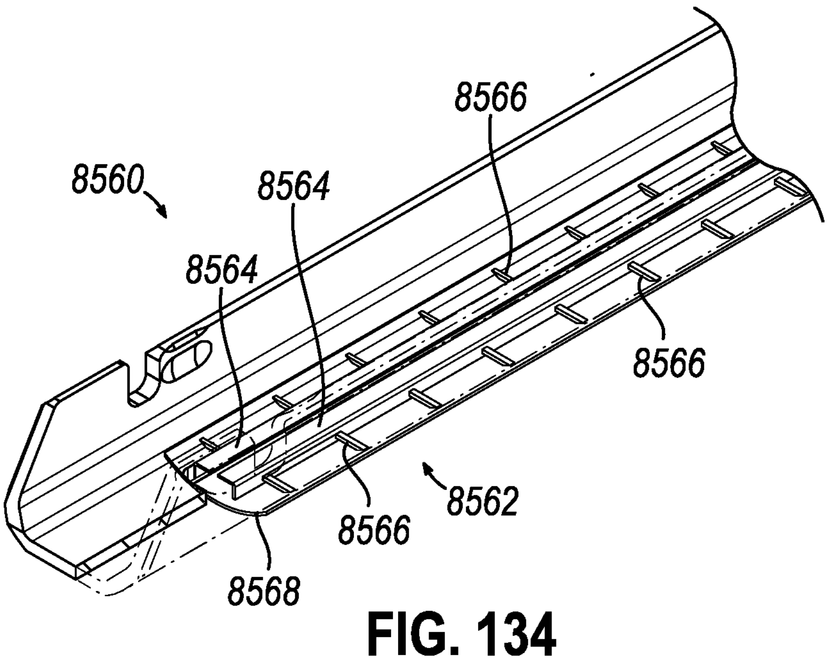
Figure 135:
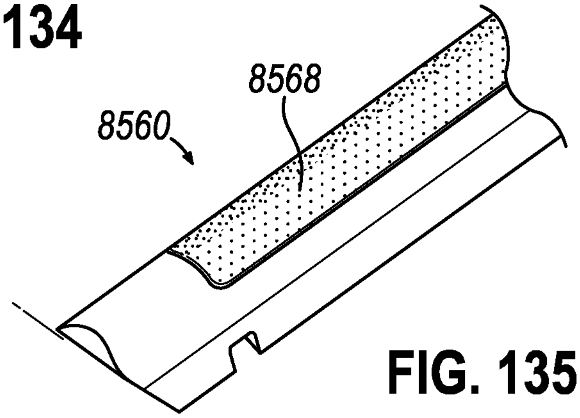
Figure 136:
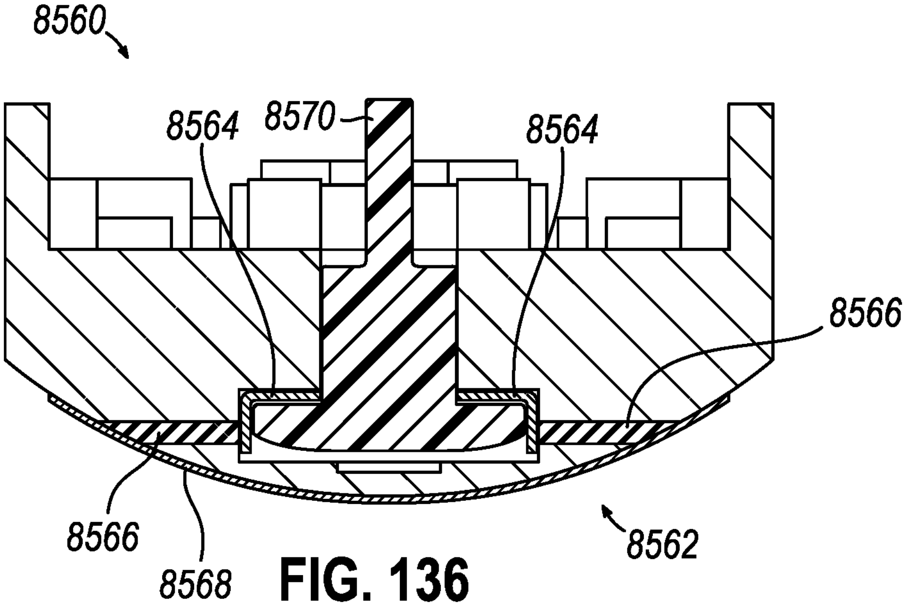
Figure 137:
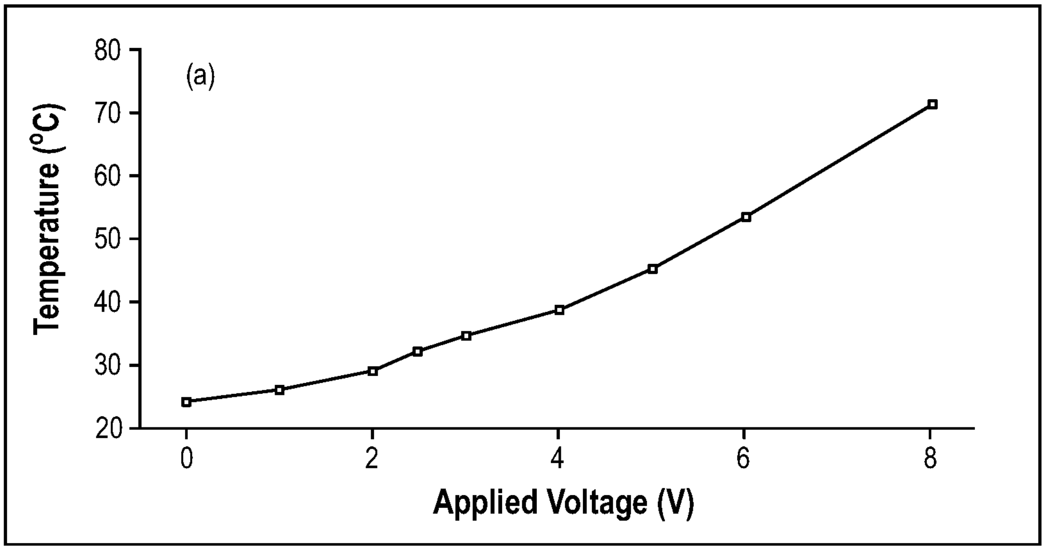
Figure 138:
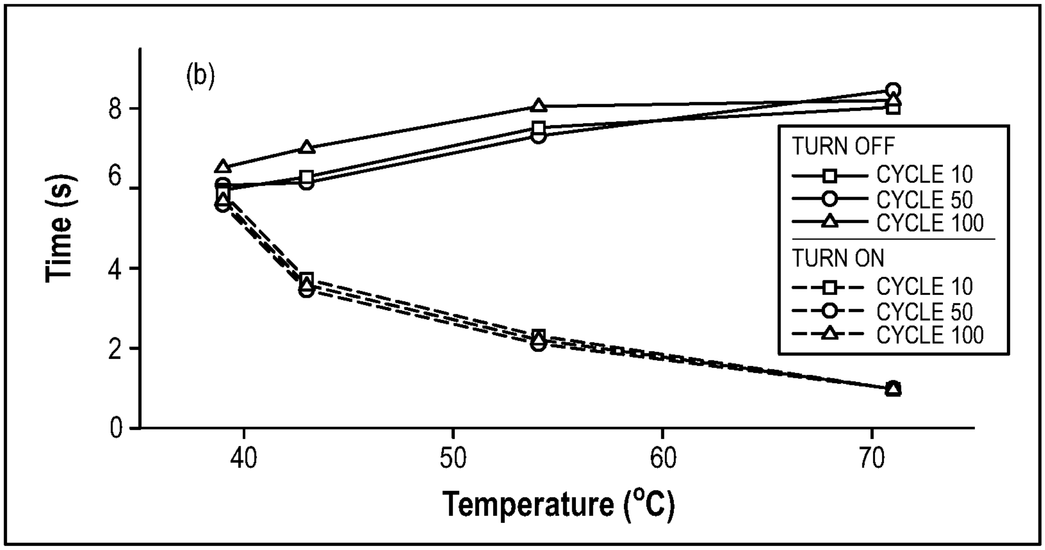
Figure 139:
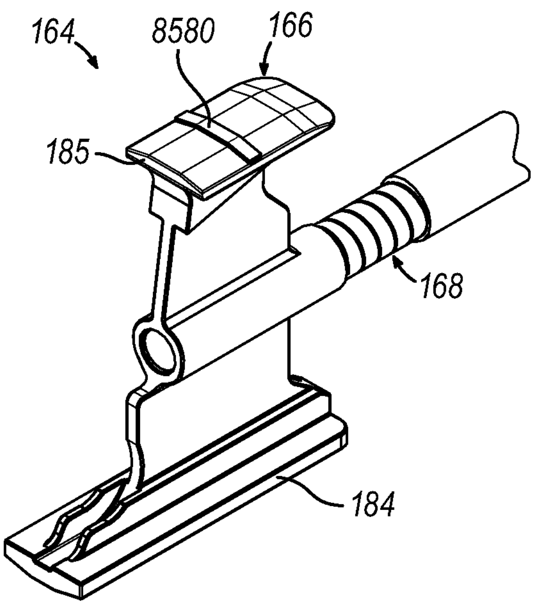
Figure 140:
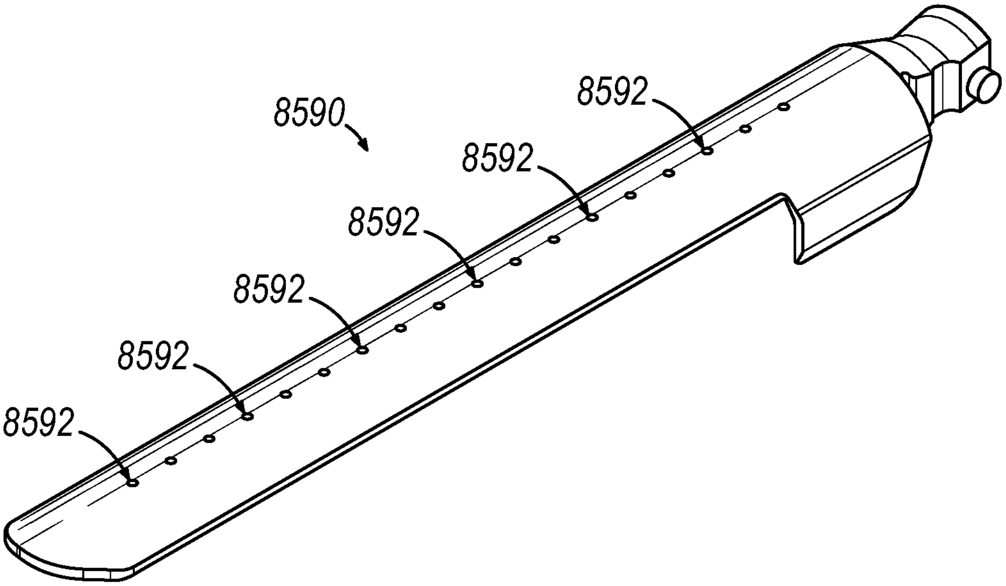
Figure 141:
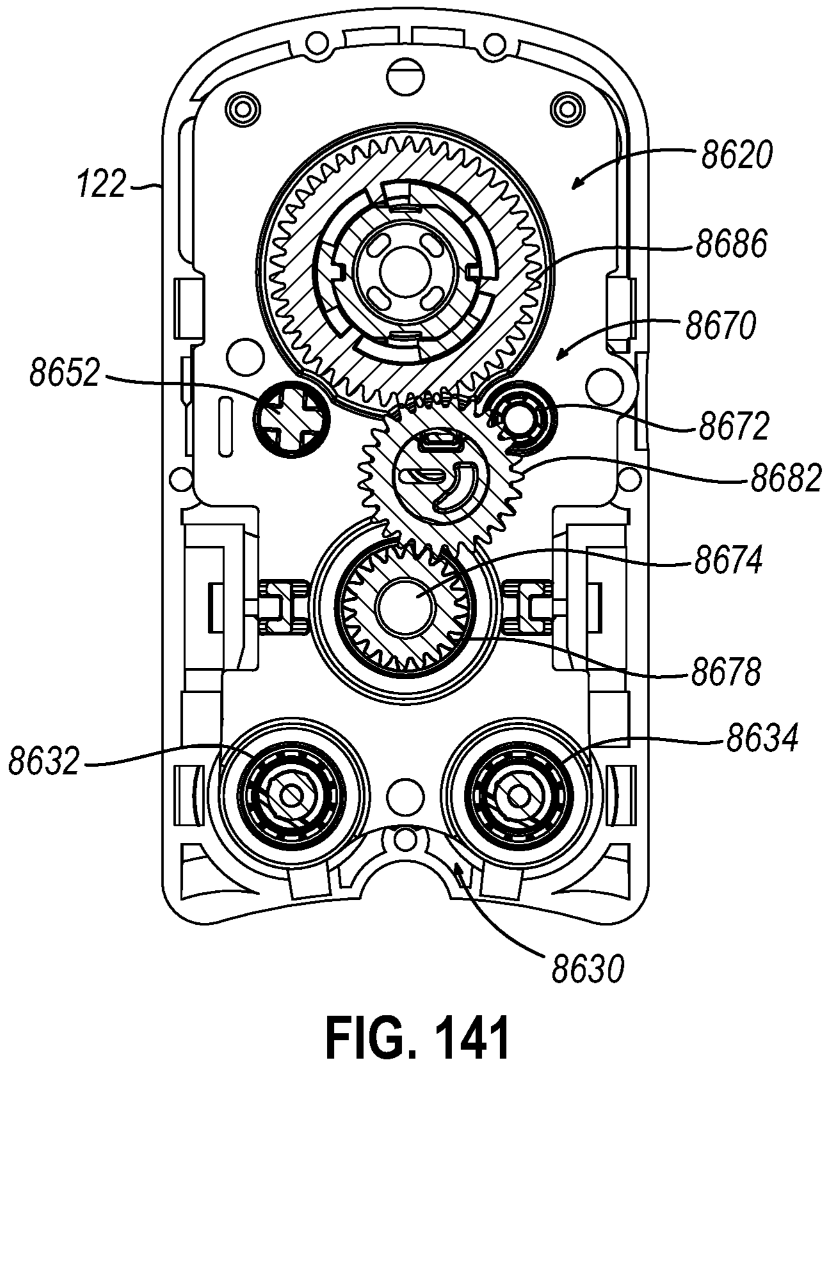
Figure 142:
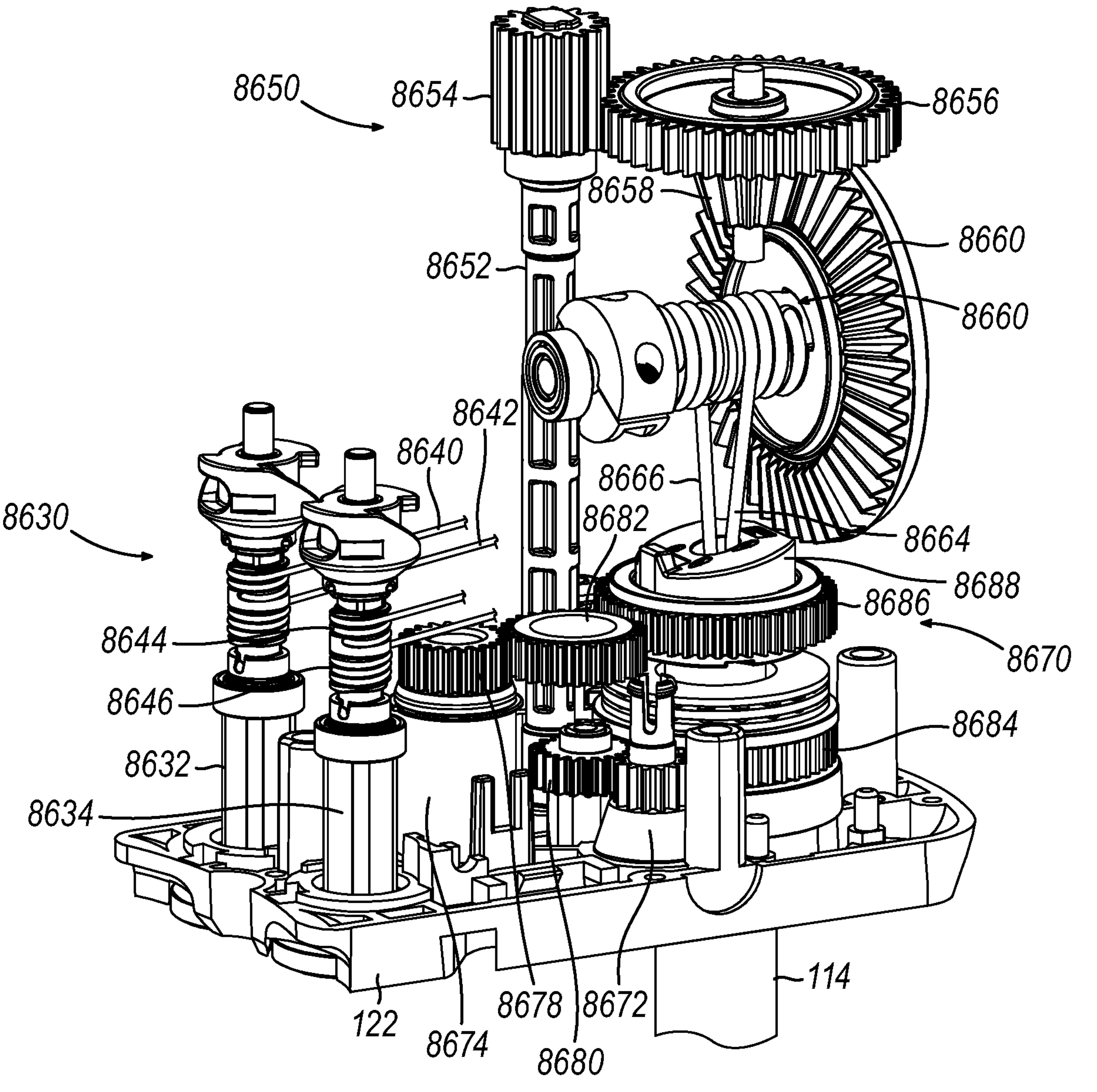
Figure 143B:
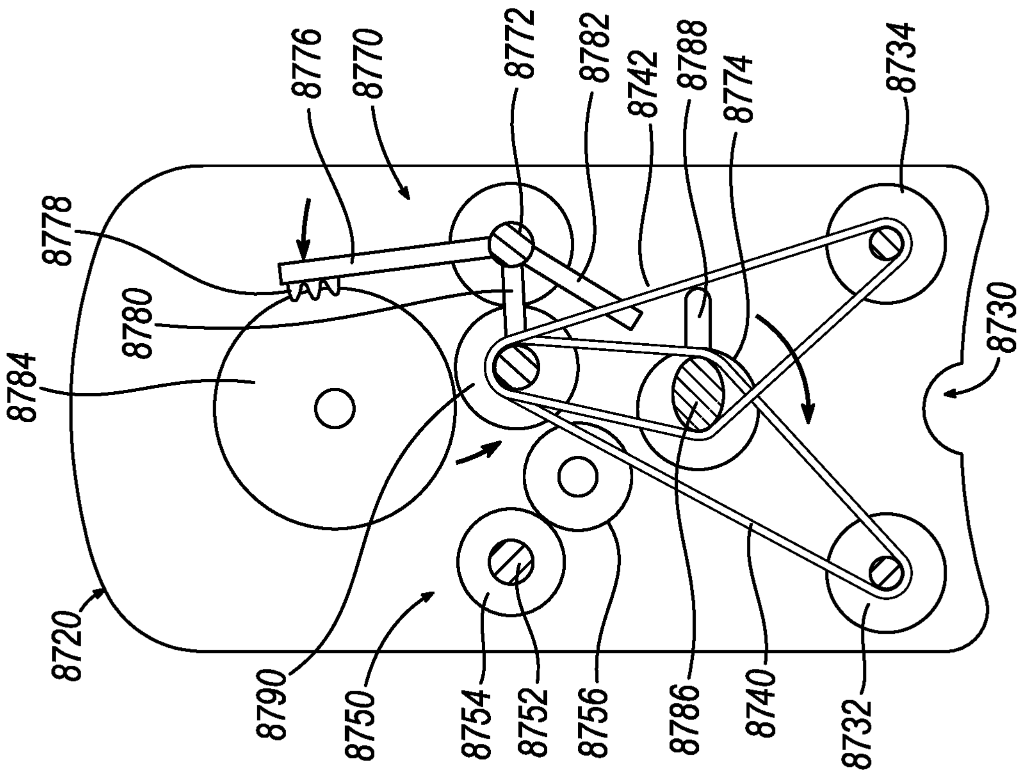
Figure 143A:
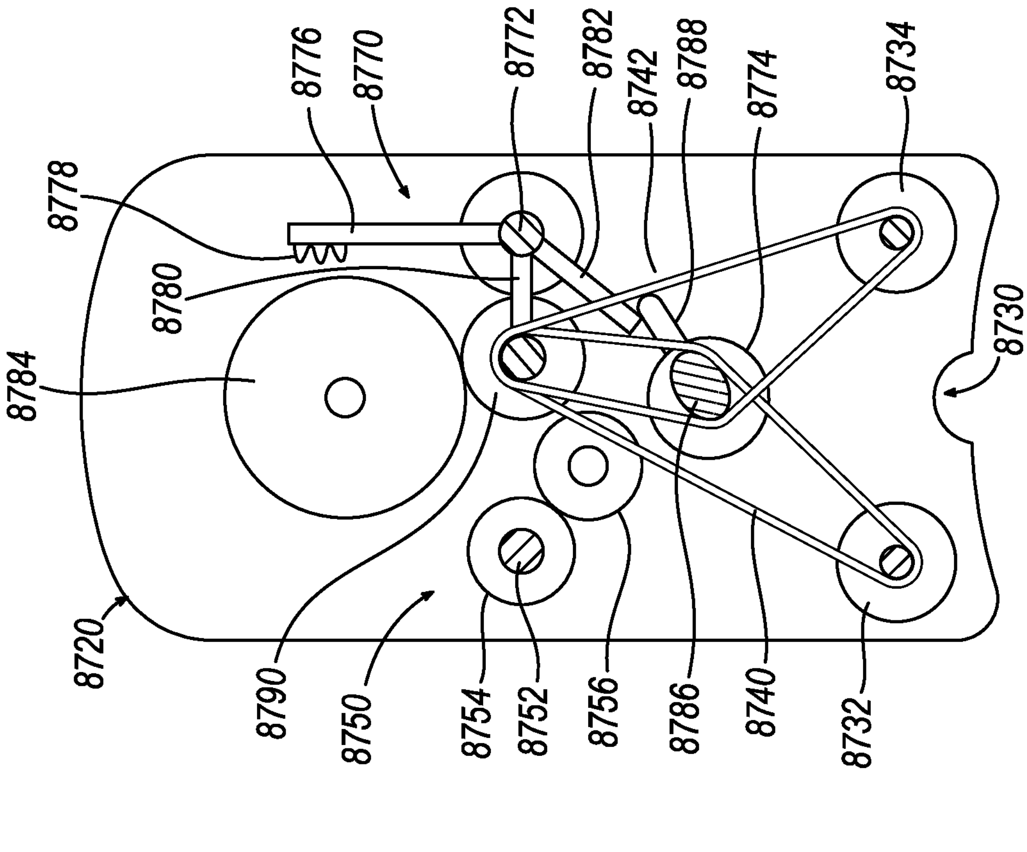
Figure 143D:
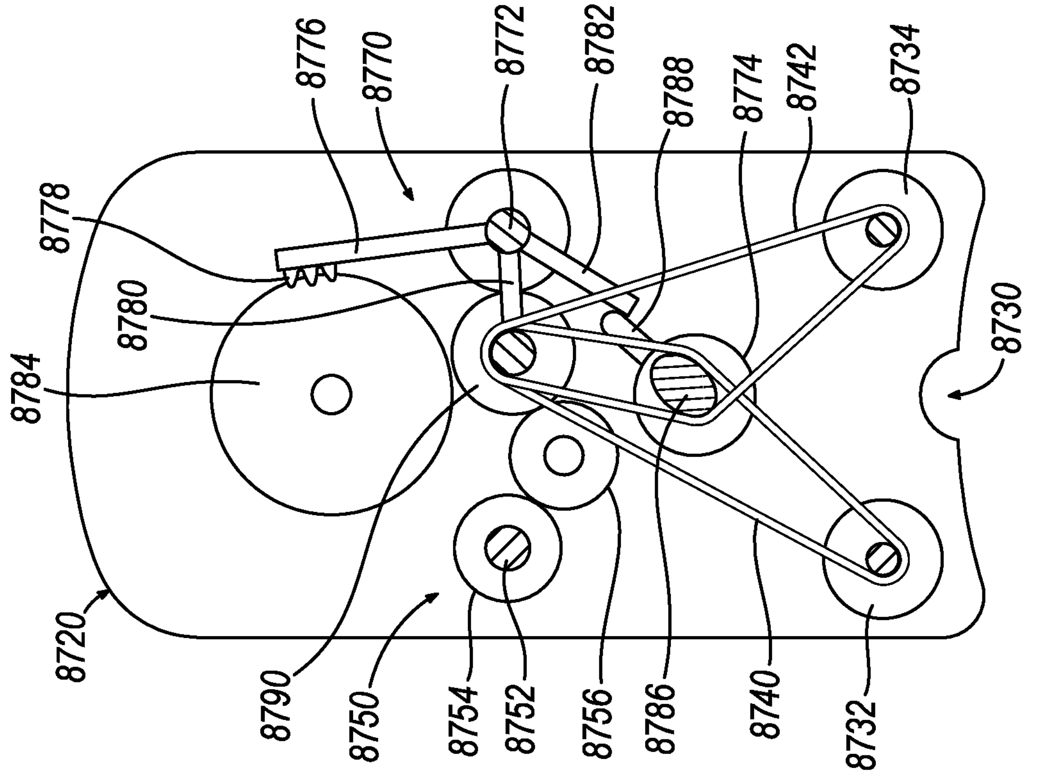
Figure 143C:
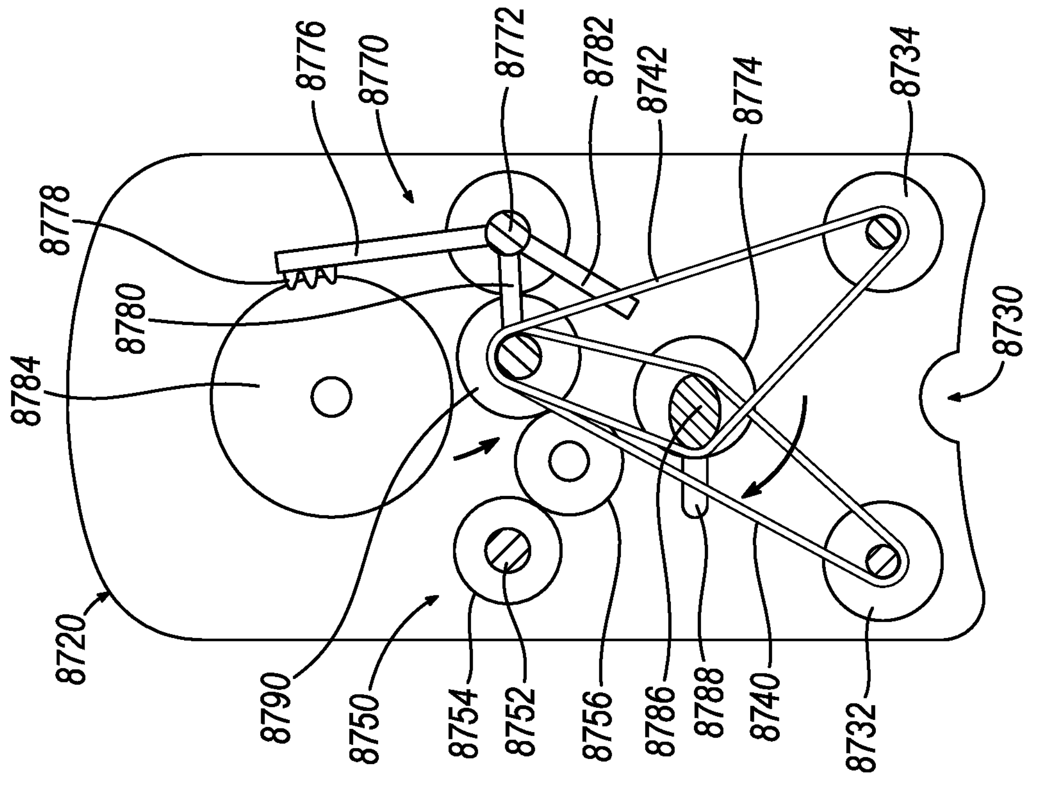
Figure 144B:
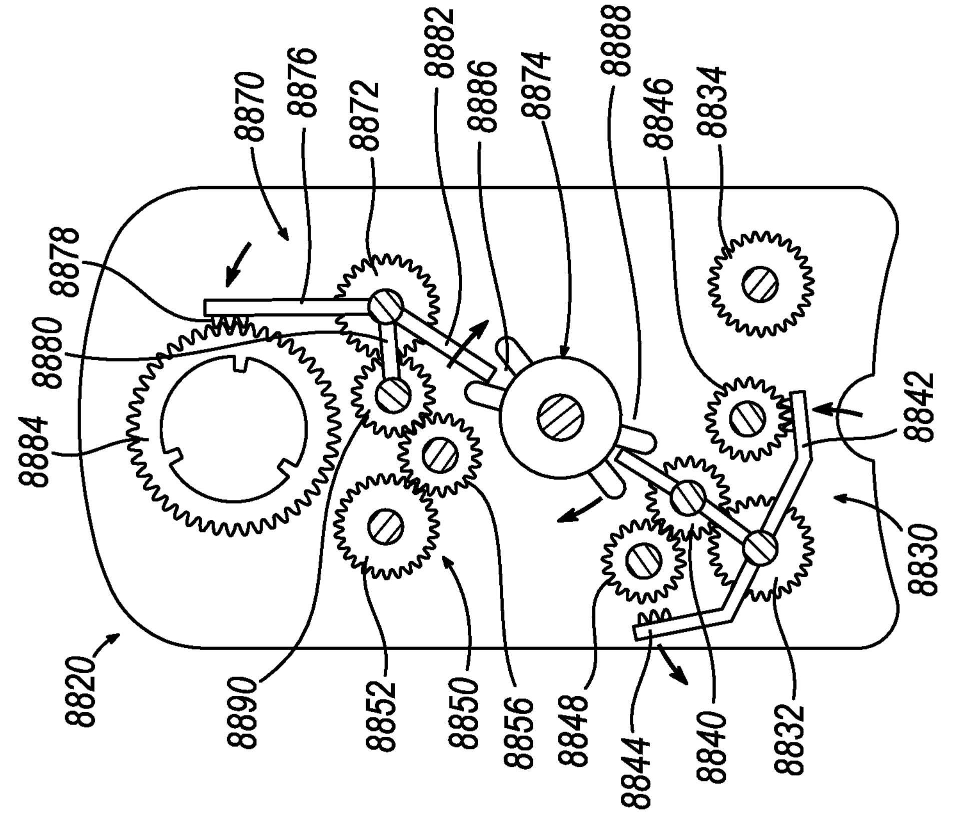
Figure 144A:
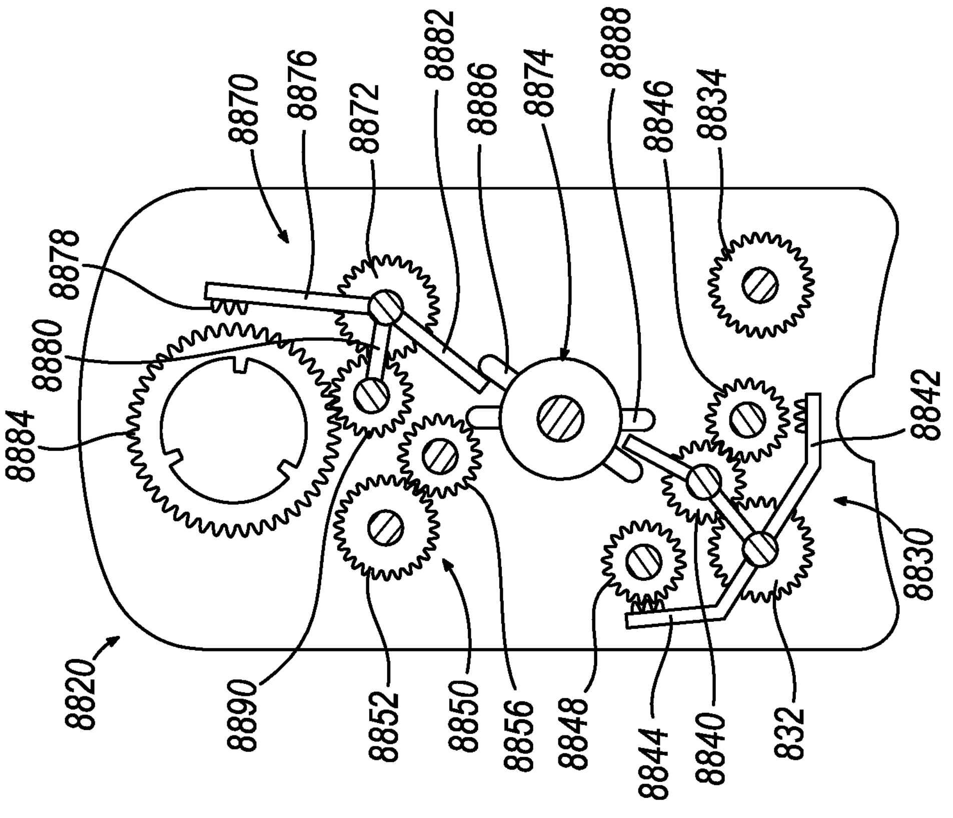
Figure 145A:
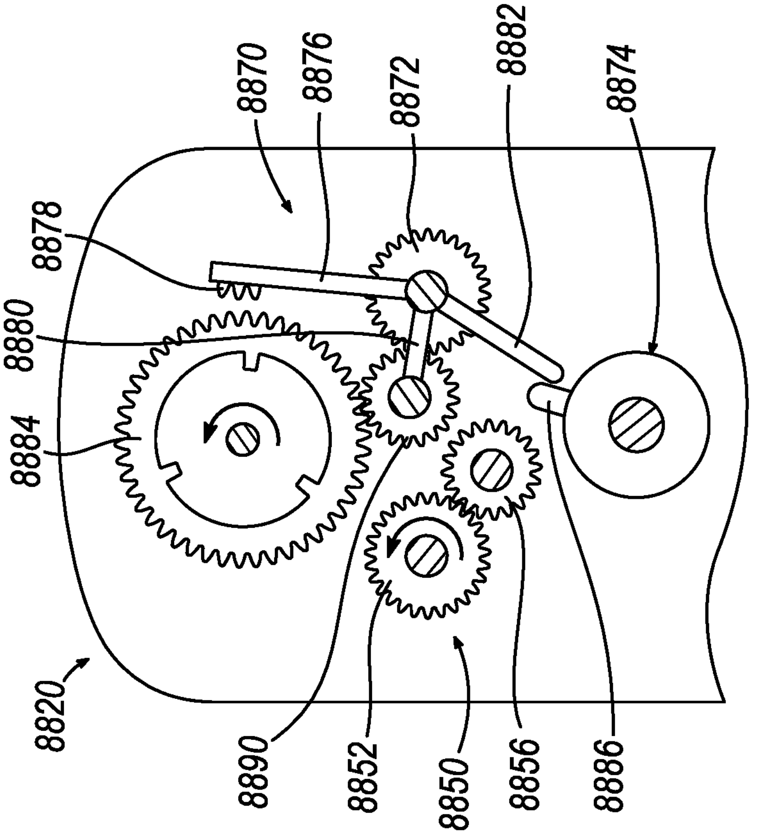
Figure 145B:
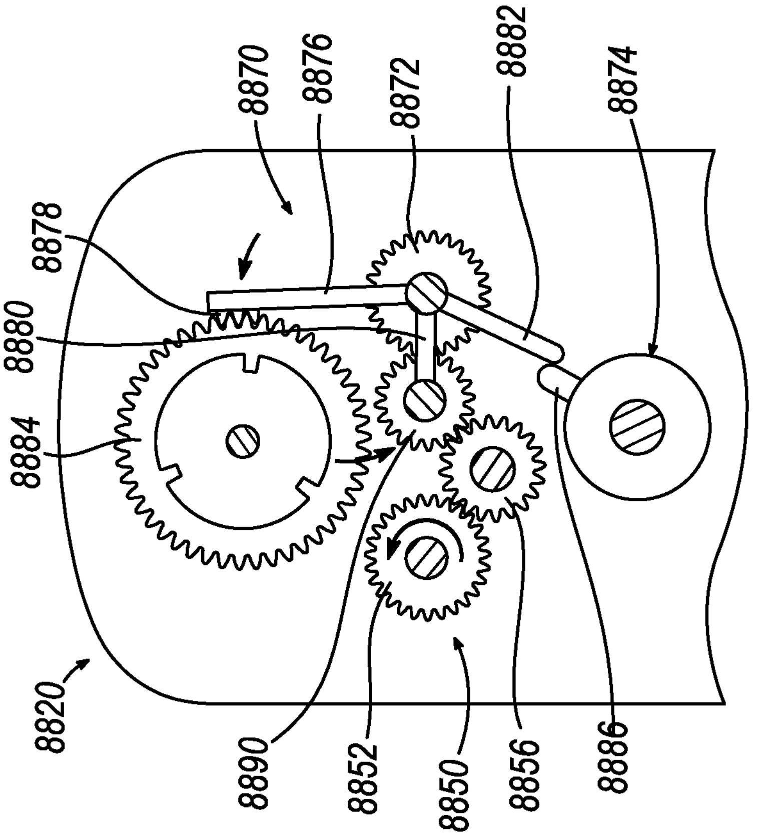
Figure 146A:
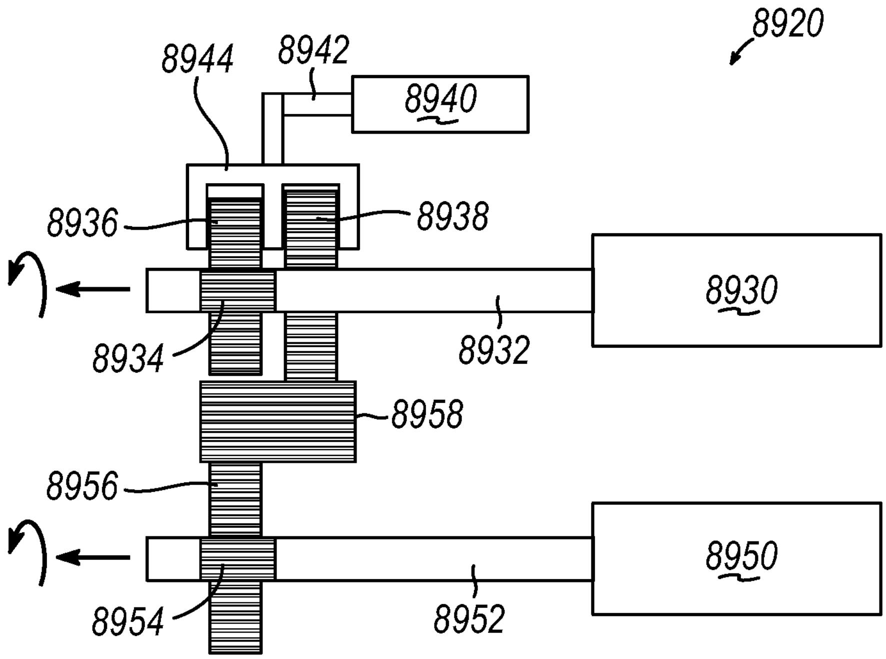
Figure 146B:
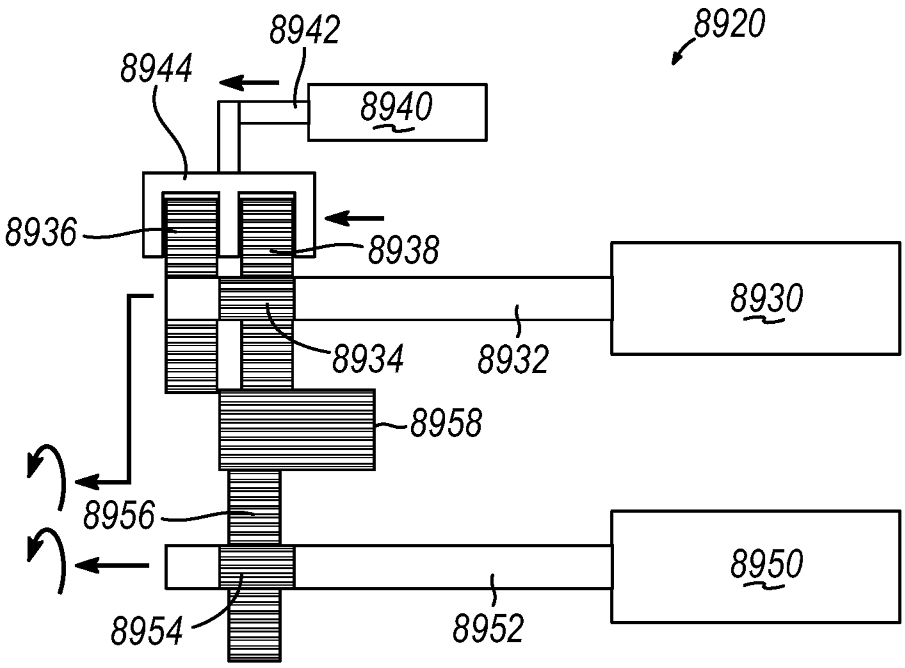
Figure 147A:
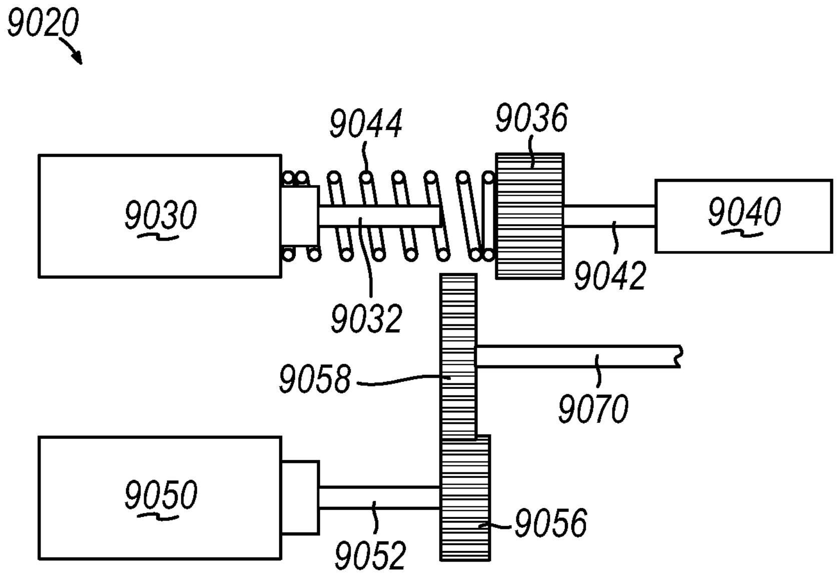
Figure 147B:
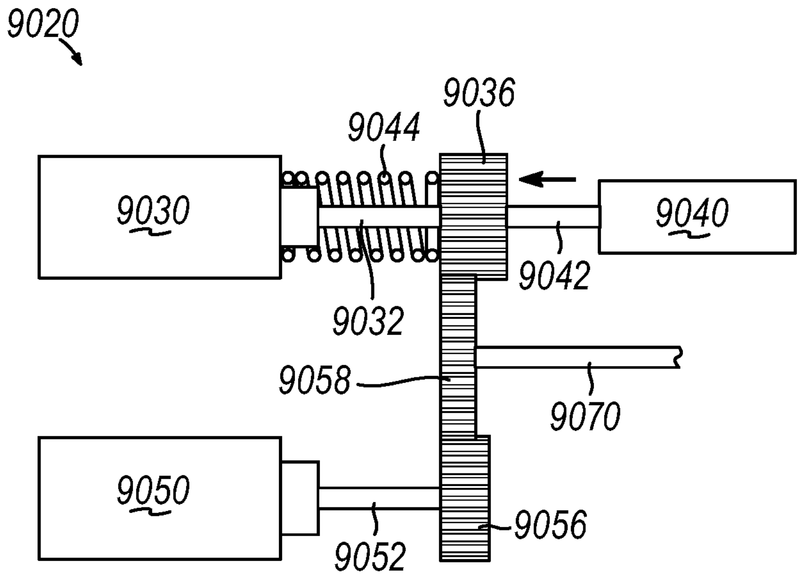
Figure 148:
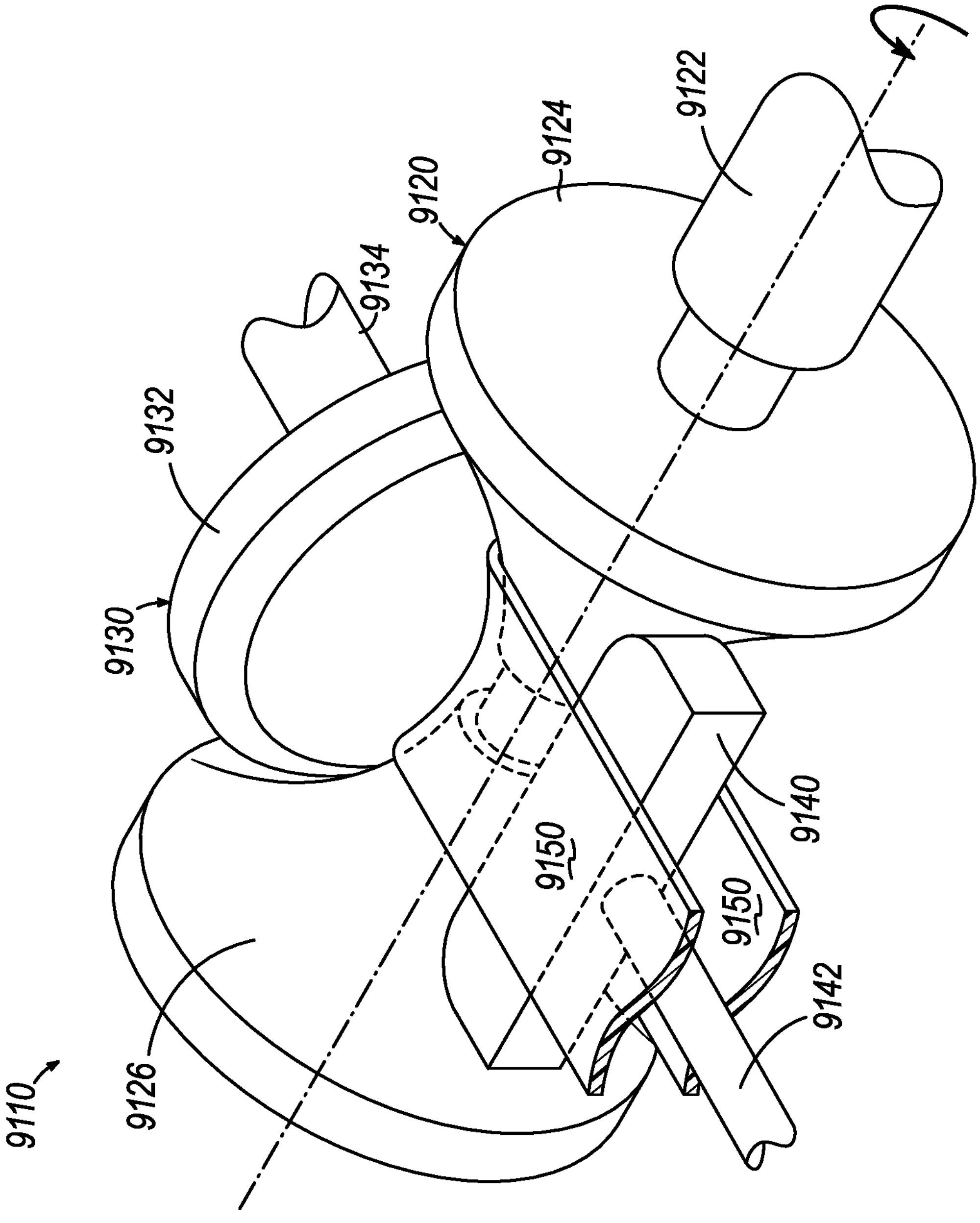
Figure 149:
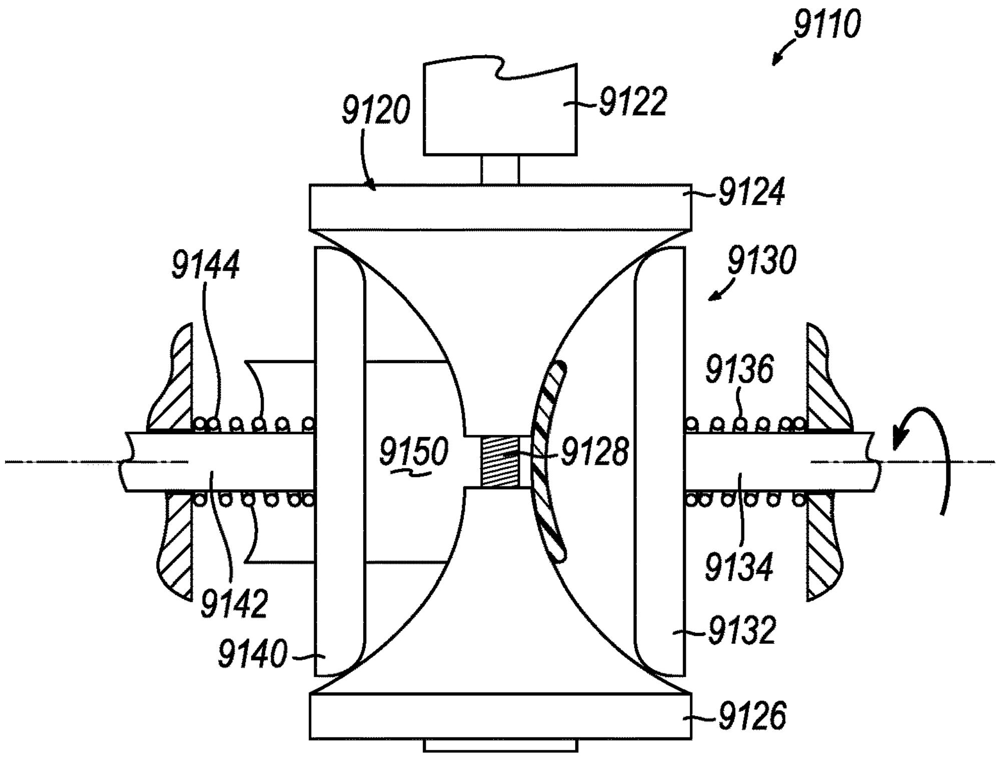
Figure 150:
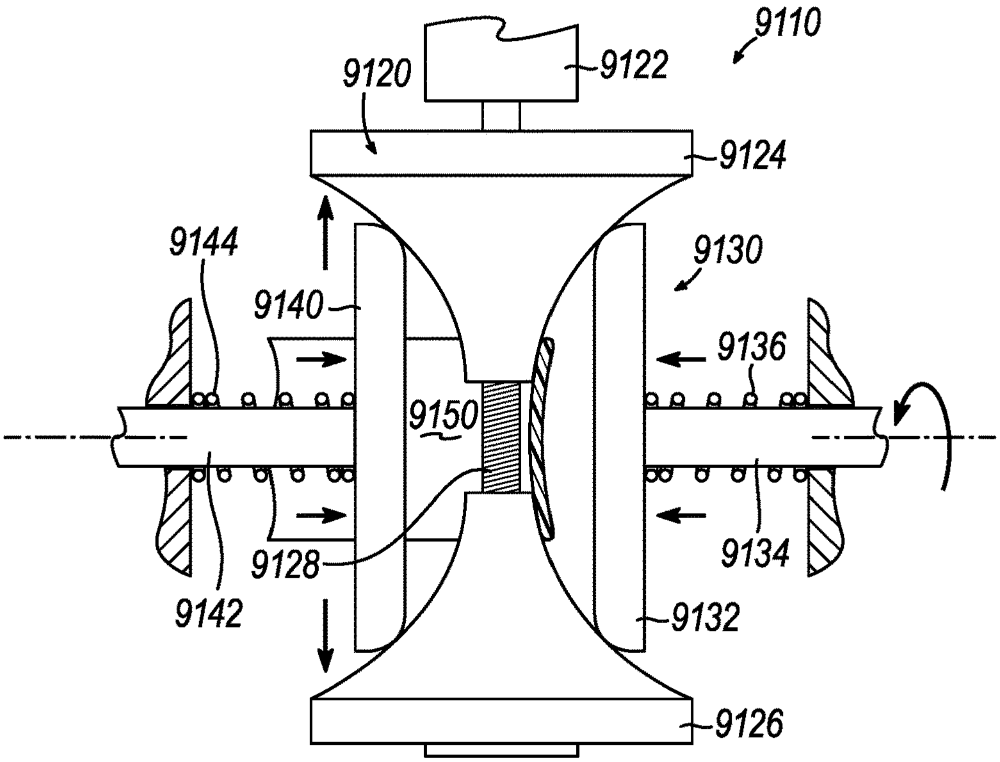
Figure 151:
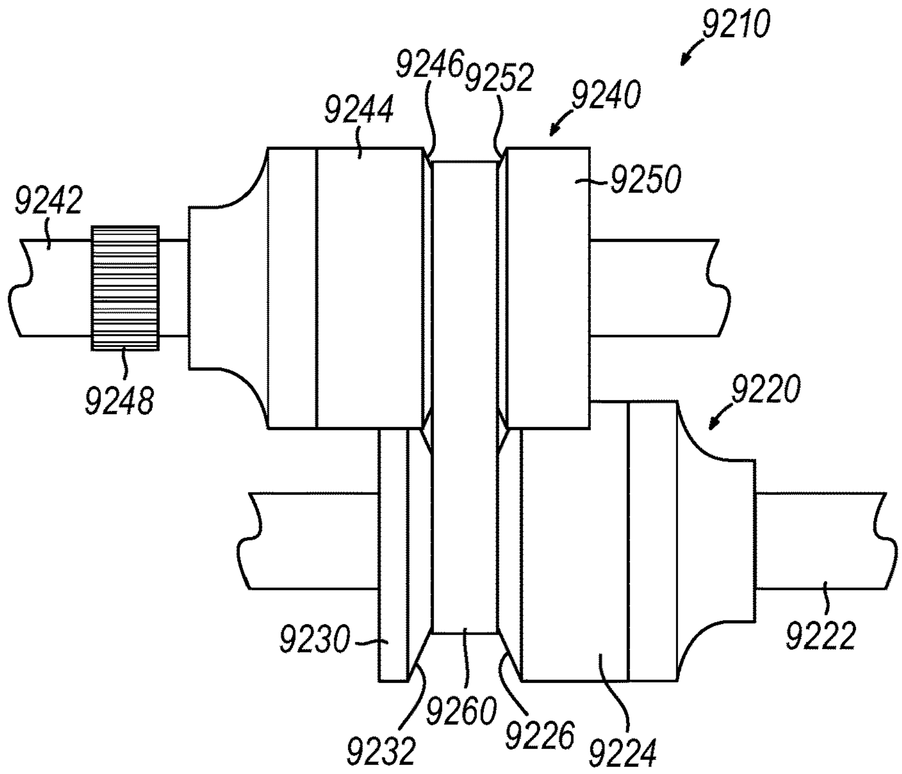
Figure 152:
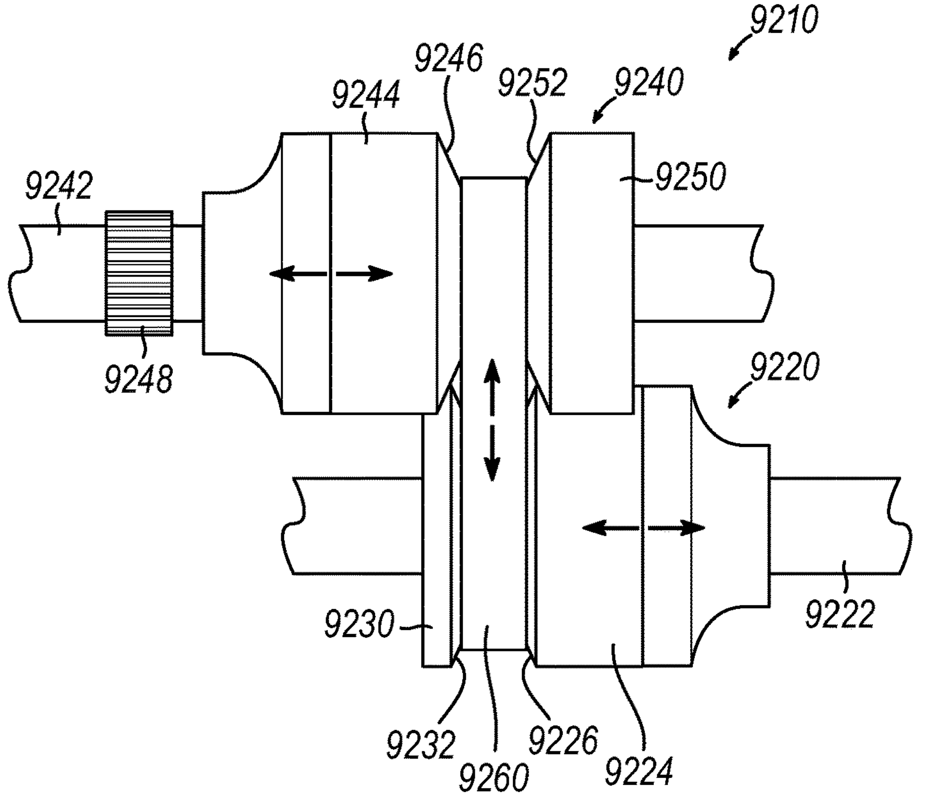
Figure 153:
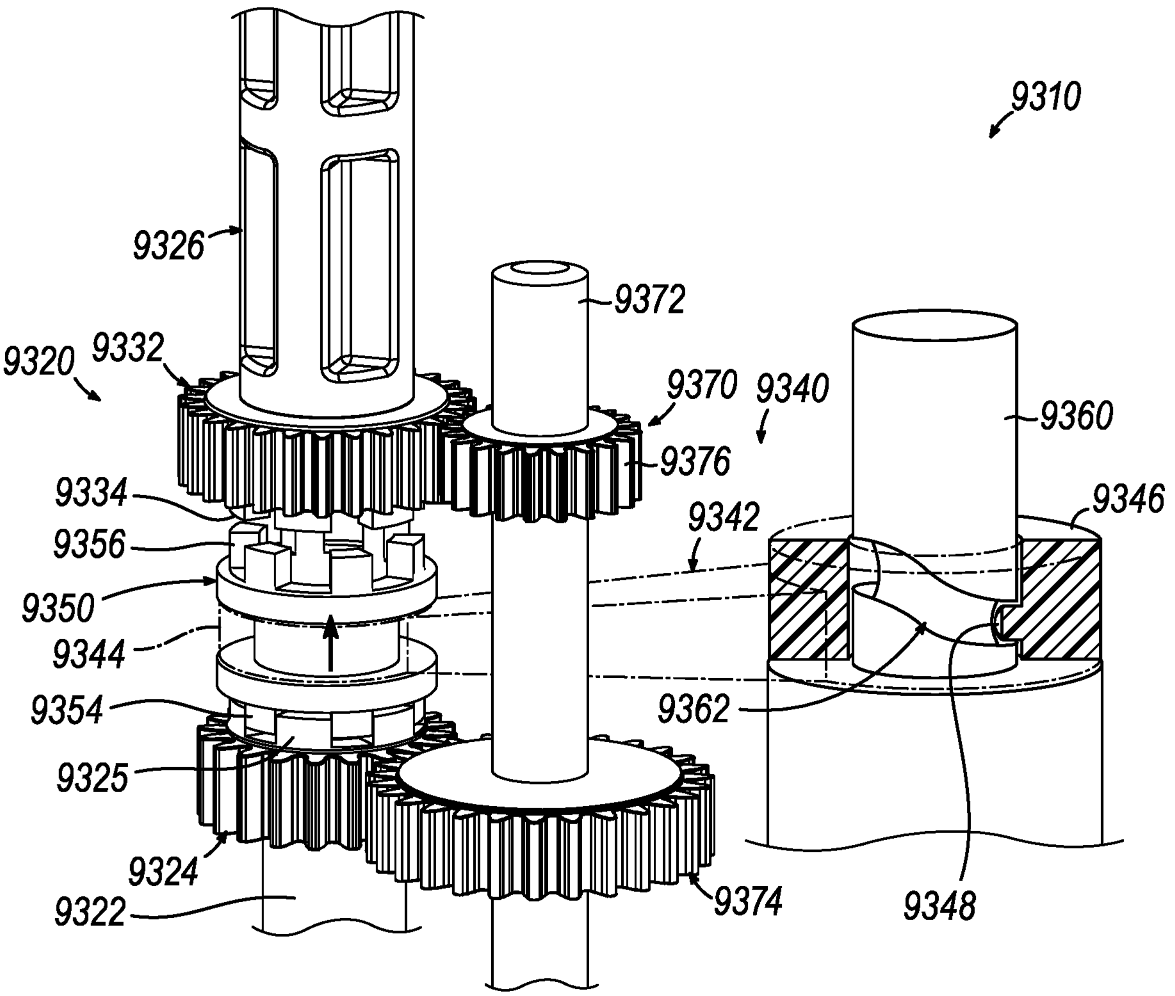
Figure 154:
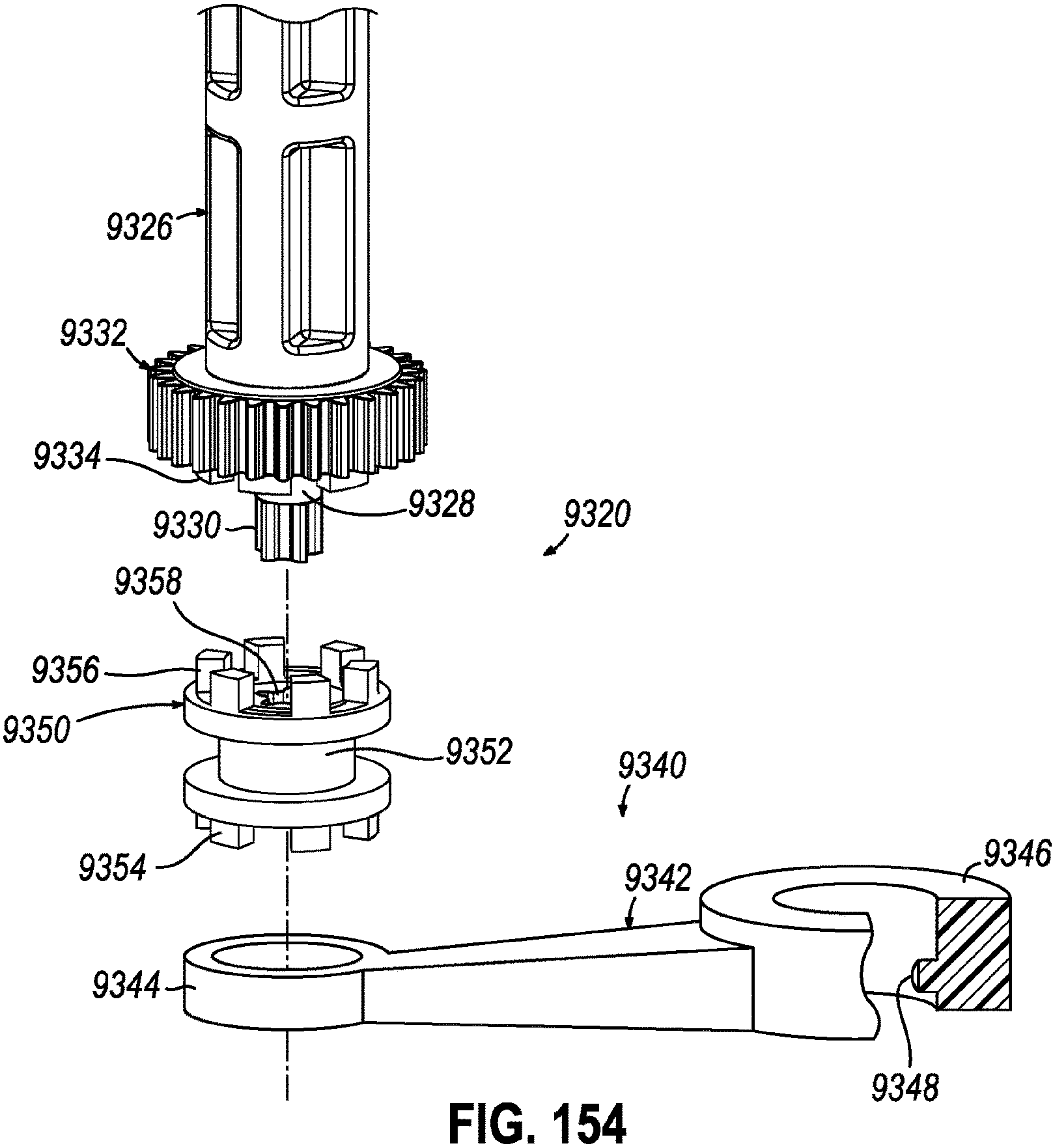
Figure 155:
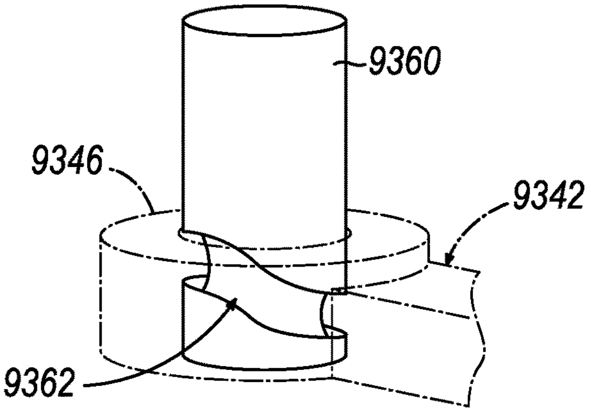
Figure 156A:
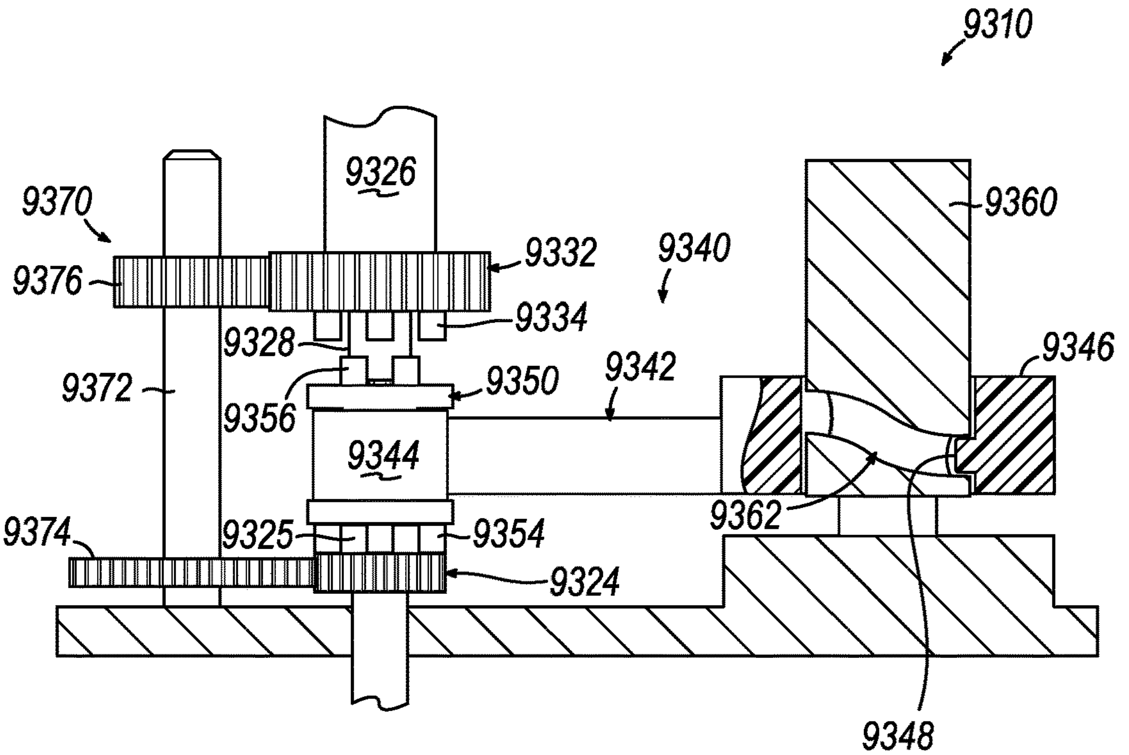
Figure 156B:
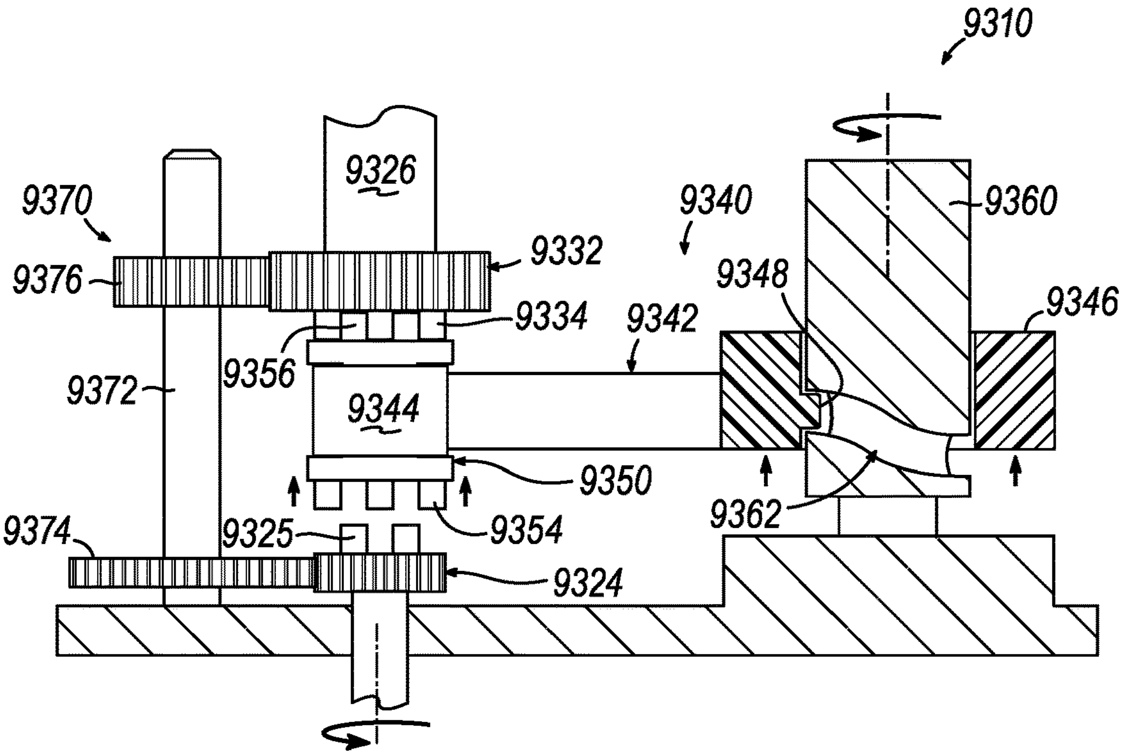
Figure 157:
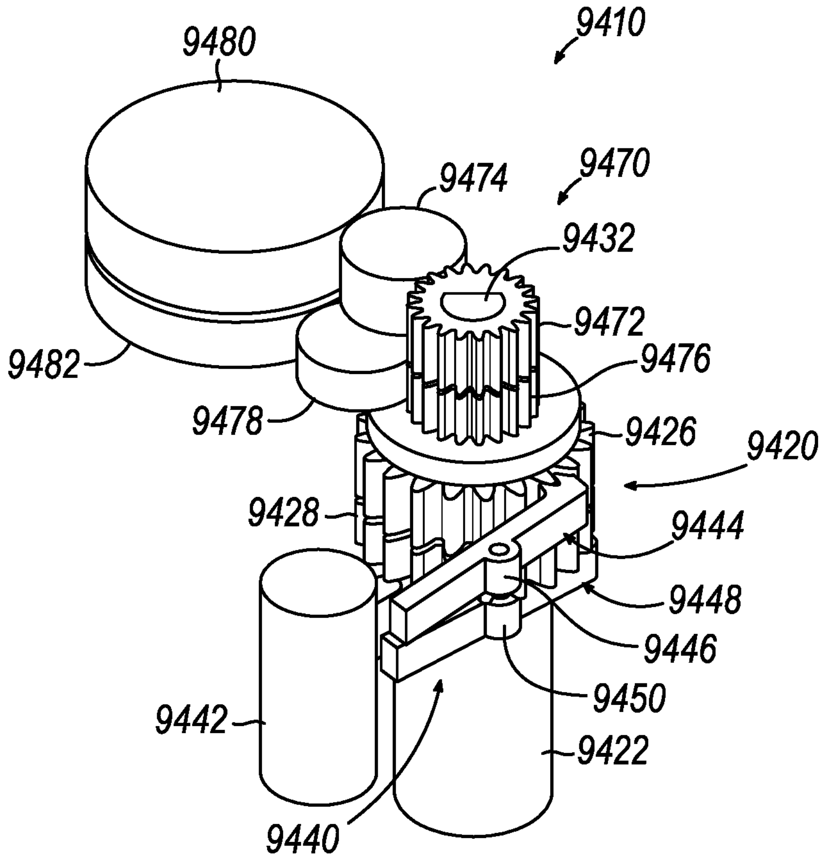
Figure 158:
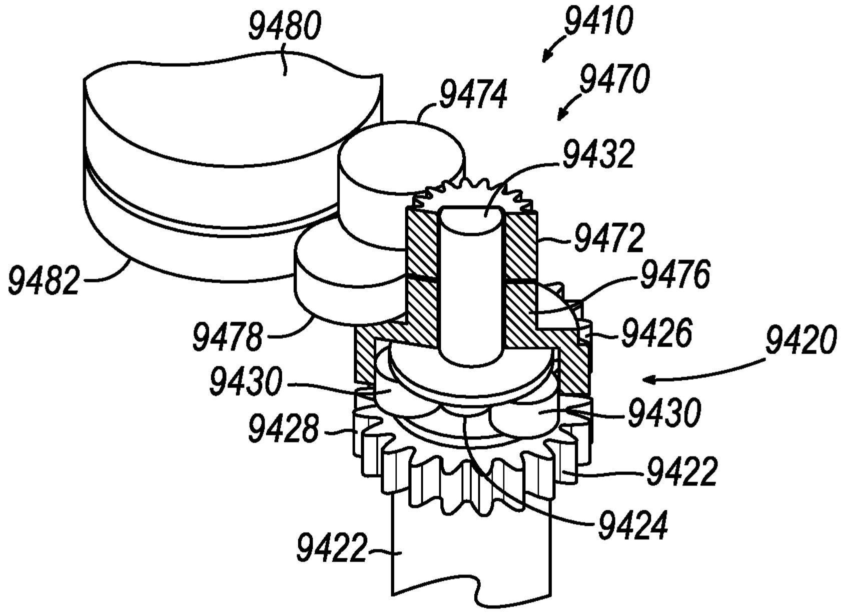
Figure 159:
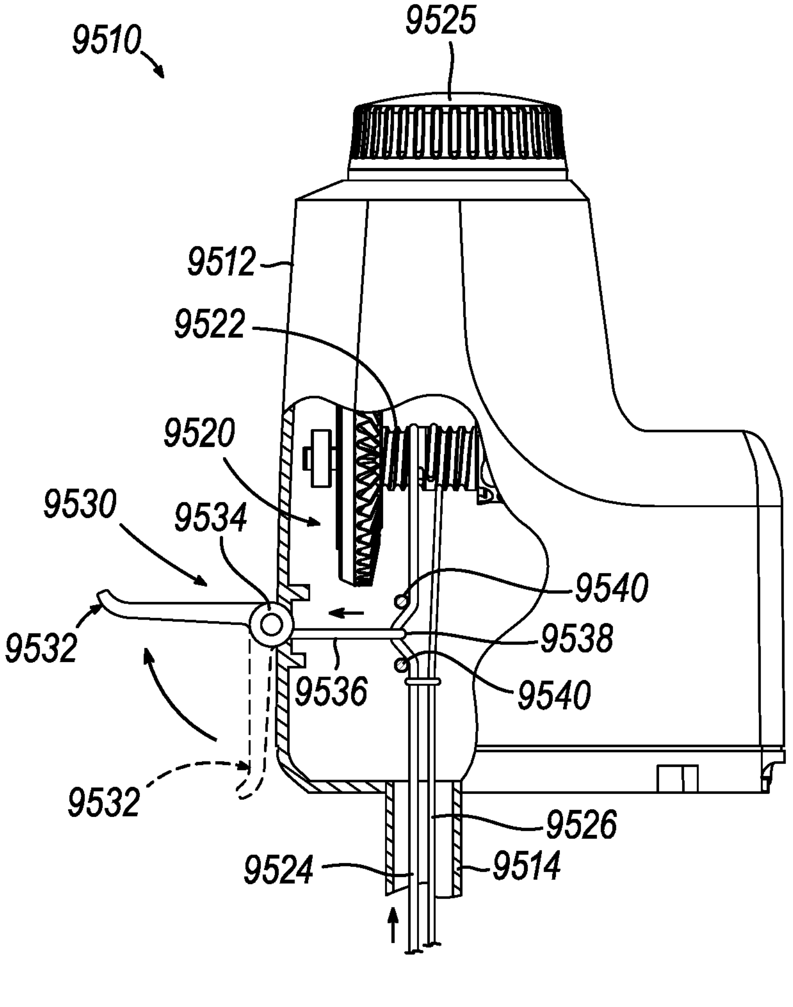
Figure 160A:
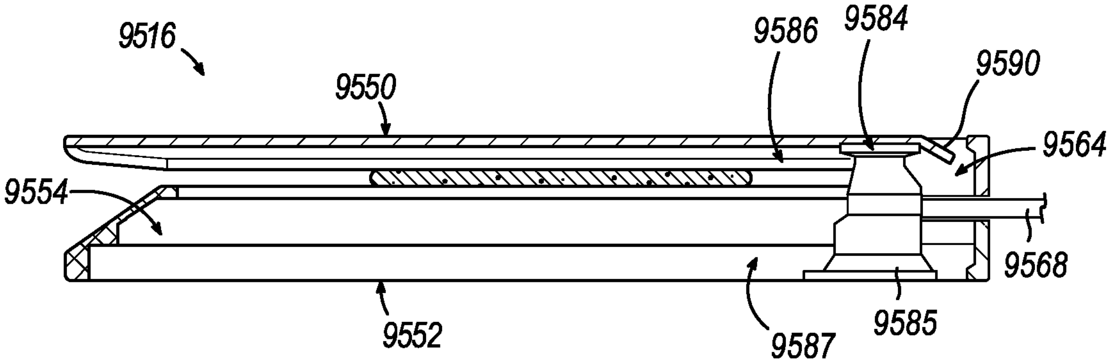
Figure 160B:
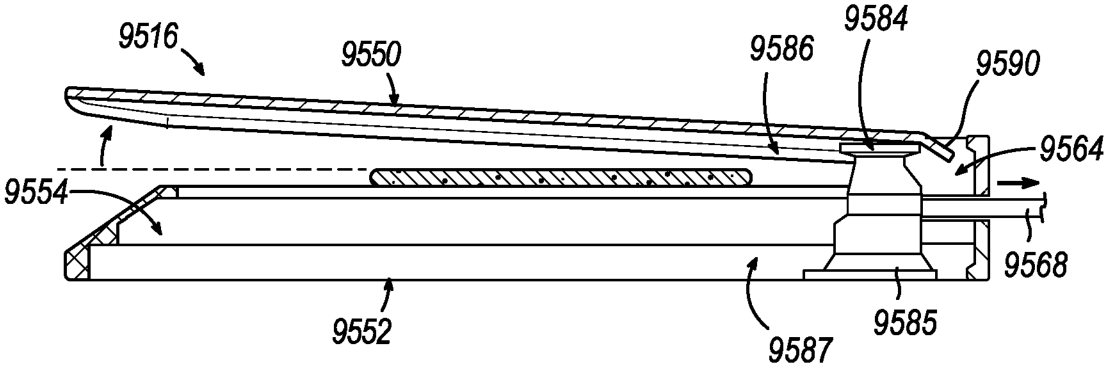
Figure 161A:
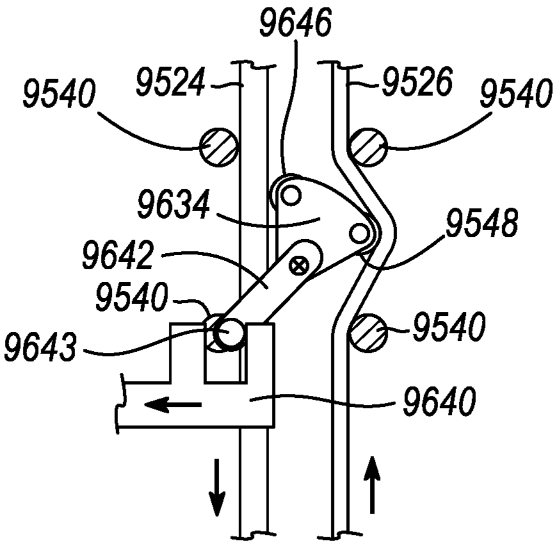
Figure 161B:
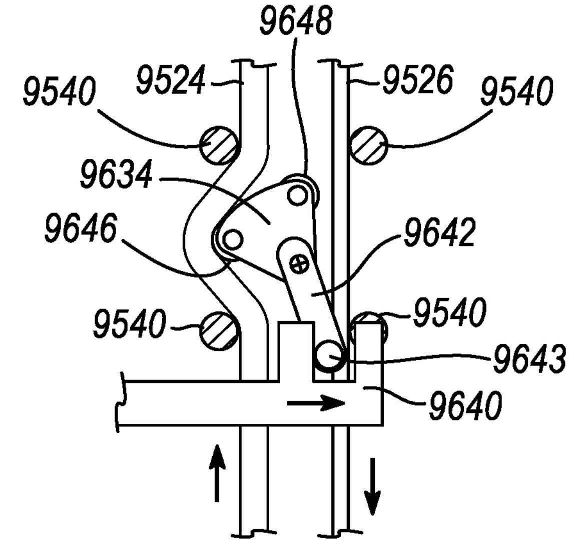
Figure 162:
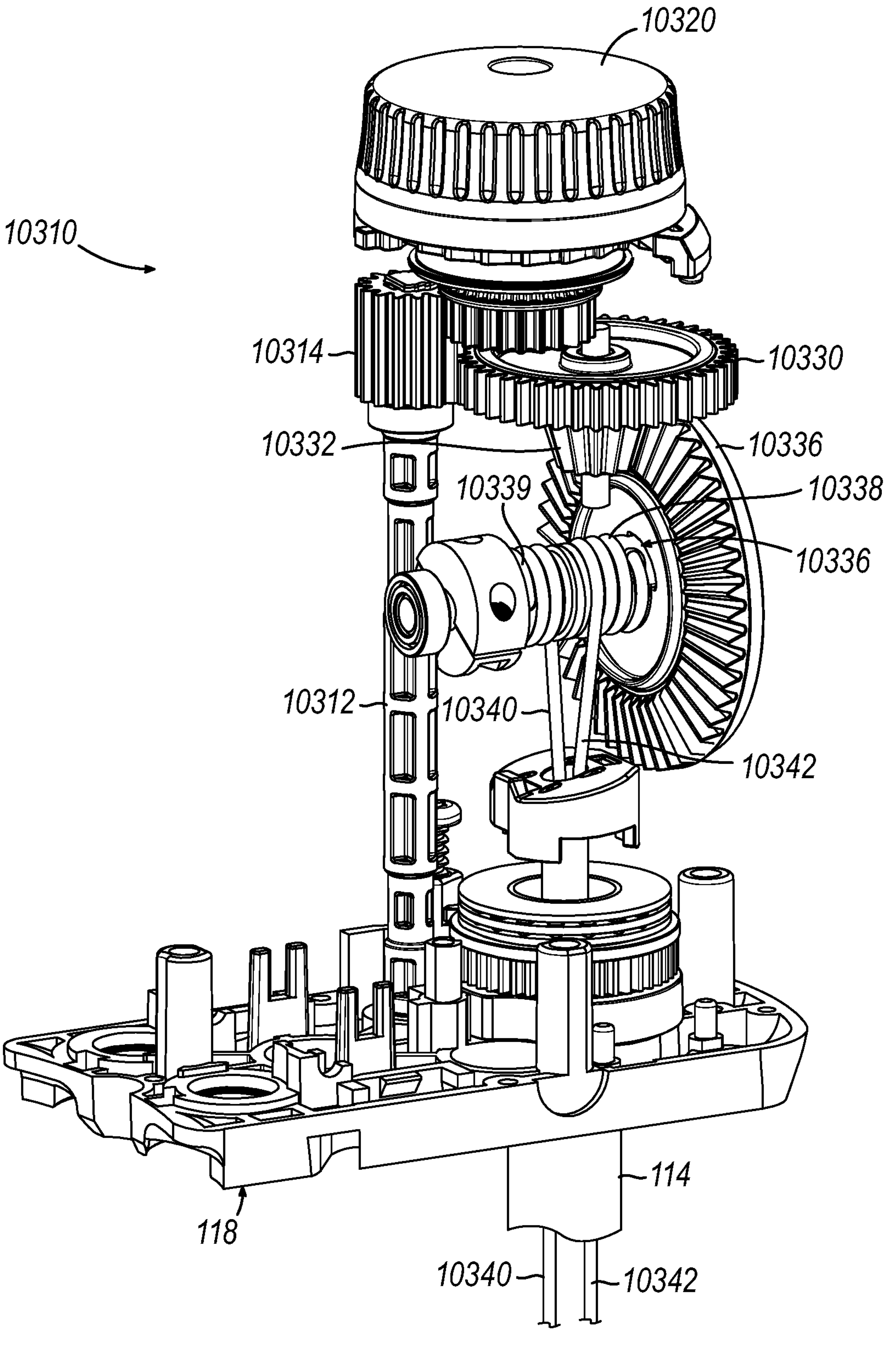
Figure 163:
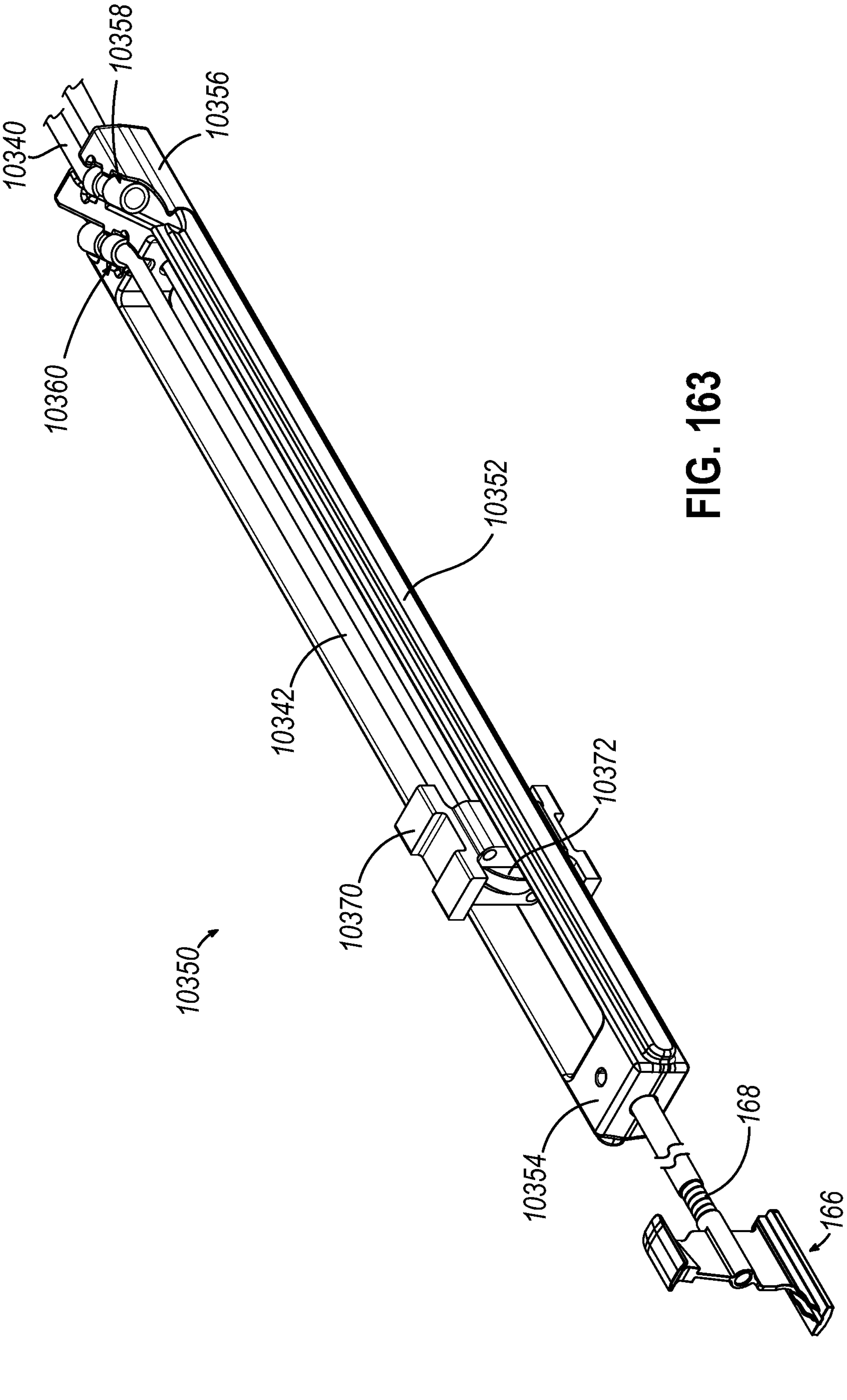
Figure 164:
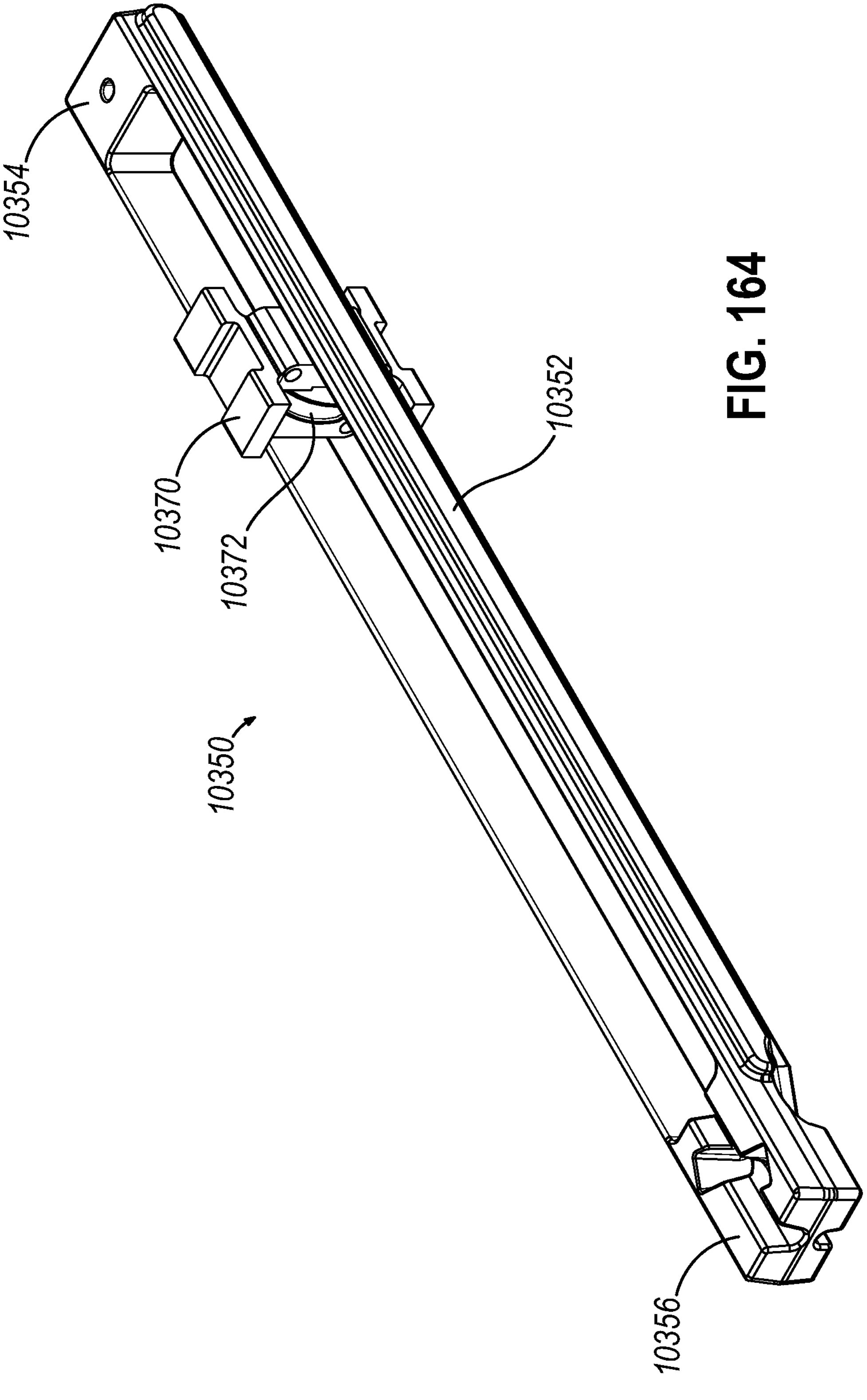
Figure 165:
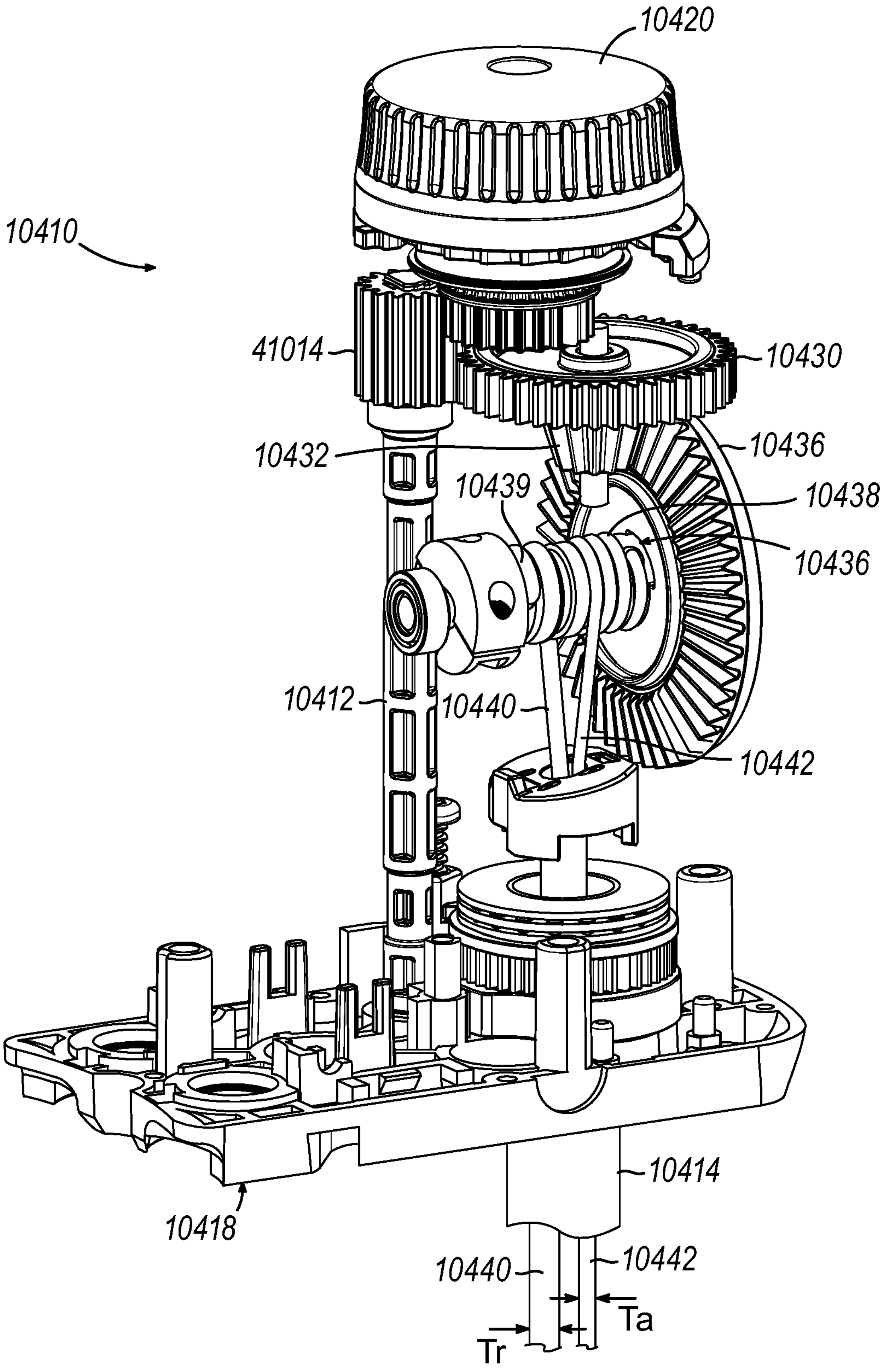
Figure 166:
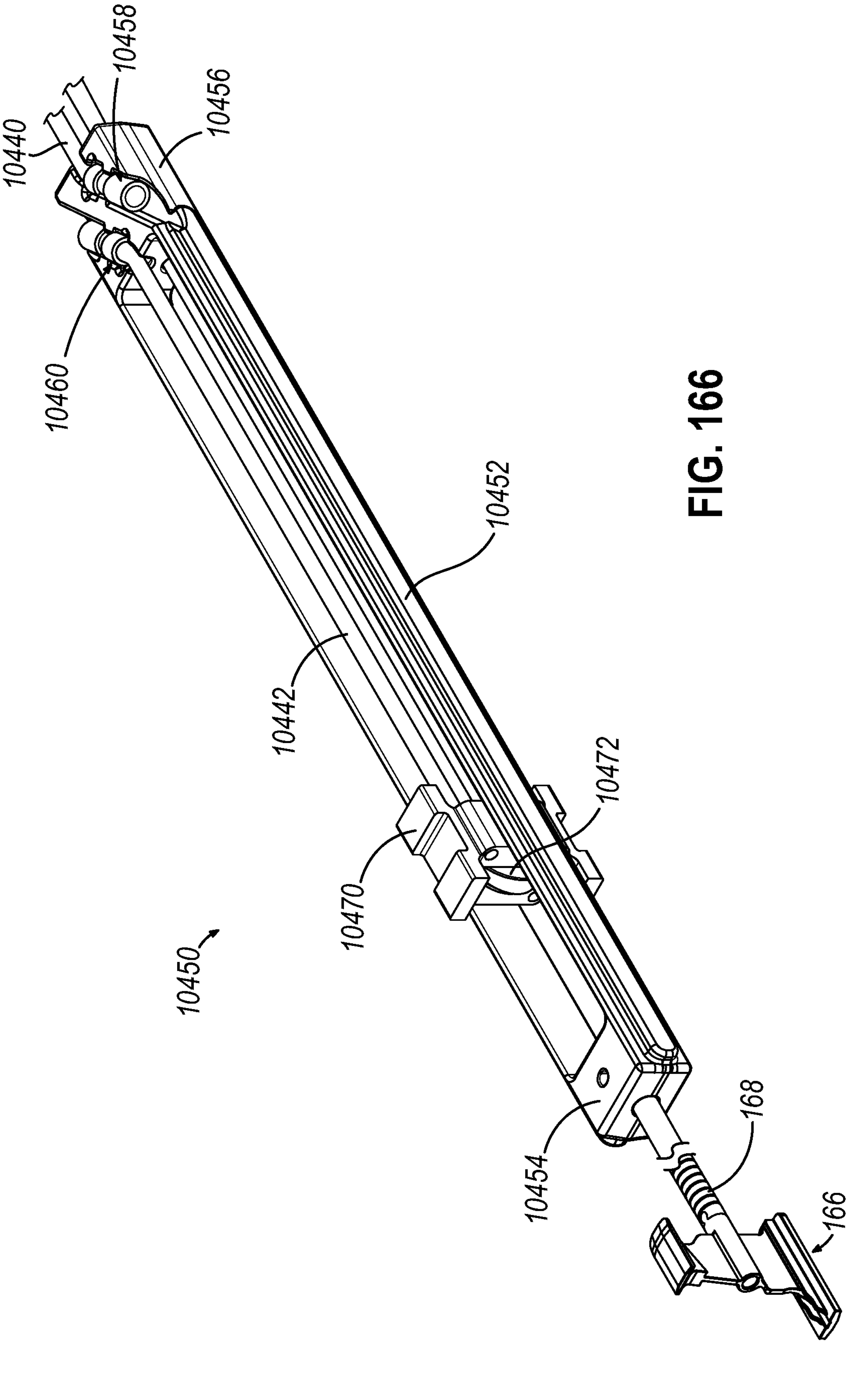
Figure 167:
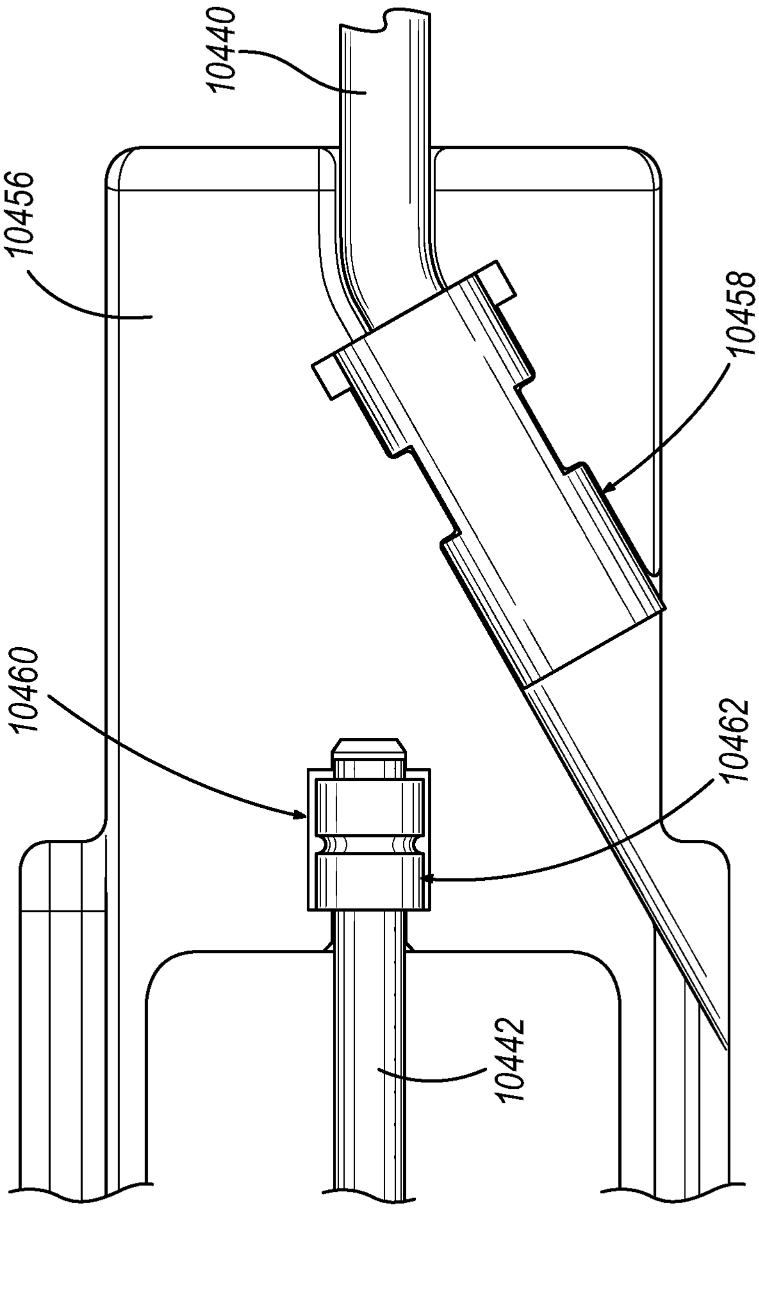
Figure 168:
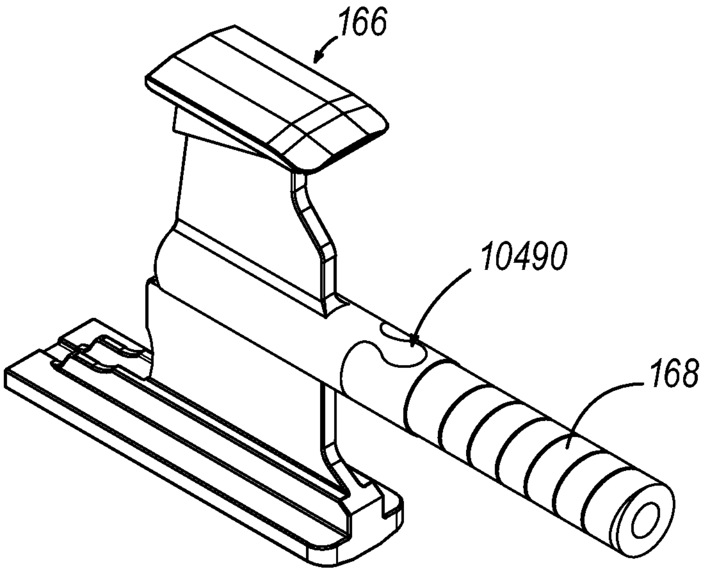
Figure 169A:
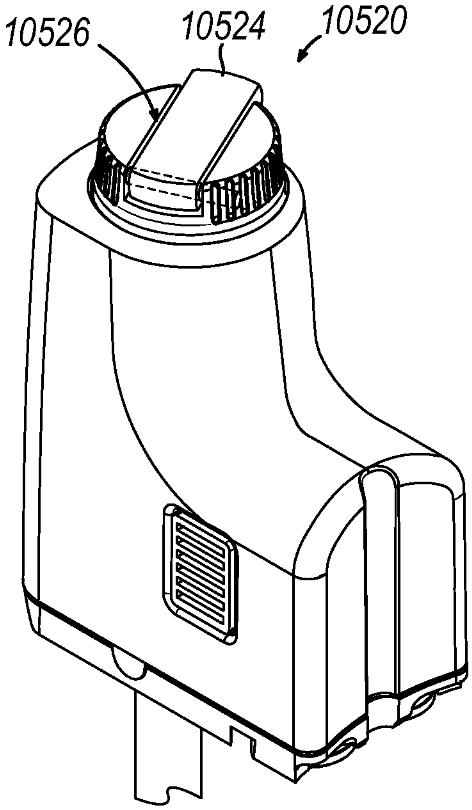
Figure 169A:
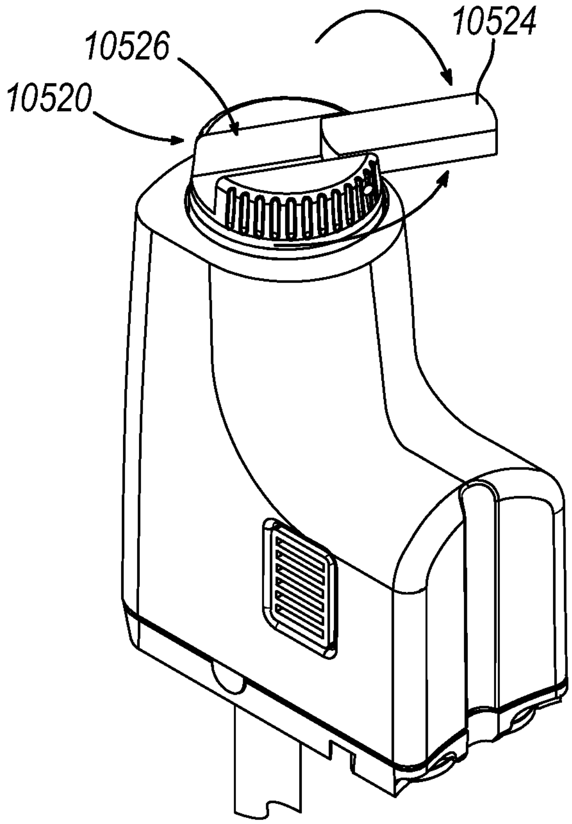
Figure 170:
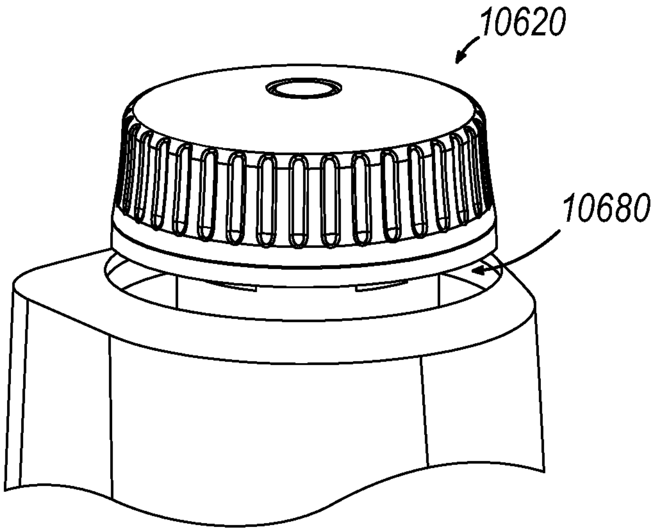
Figure 171:
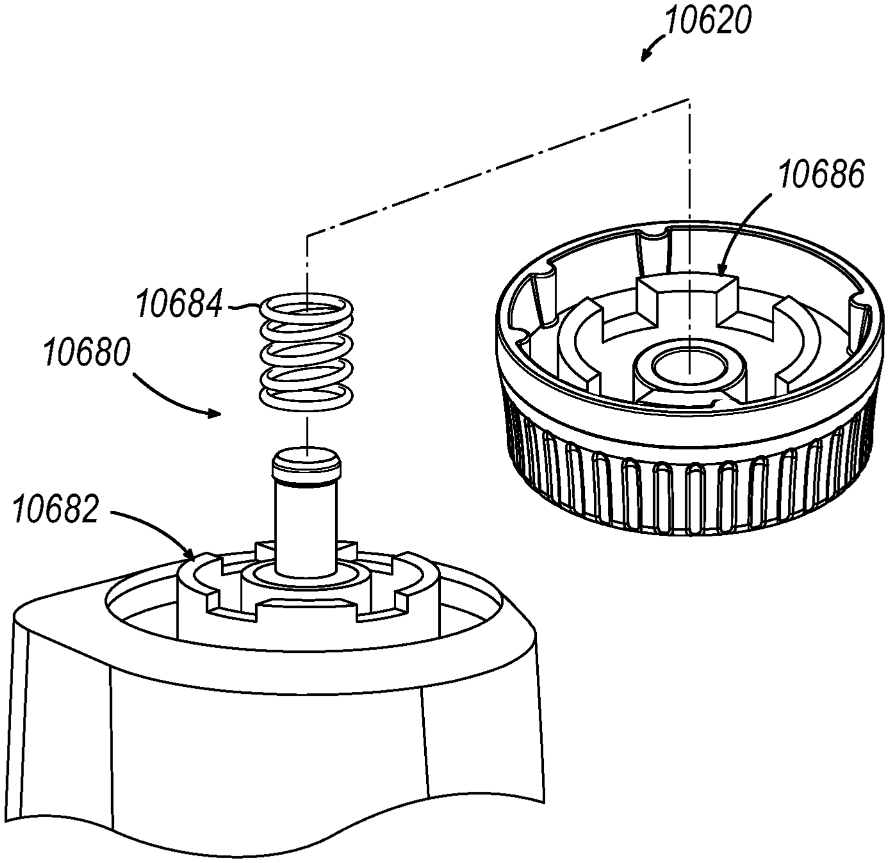
Figure 172:
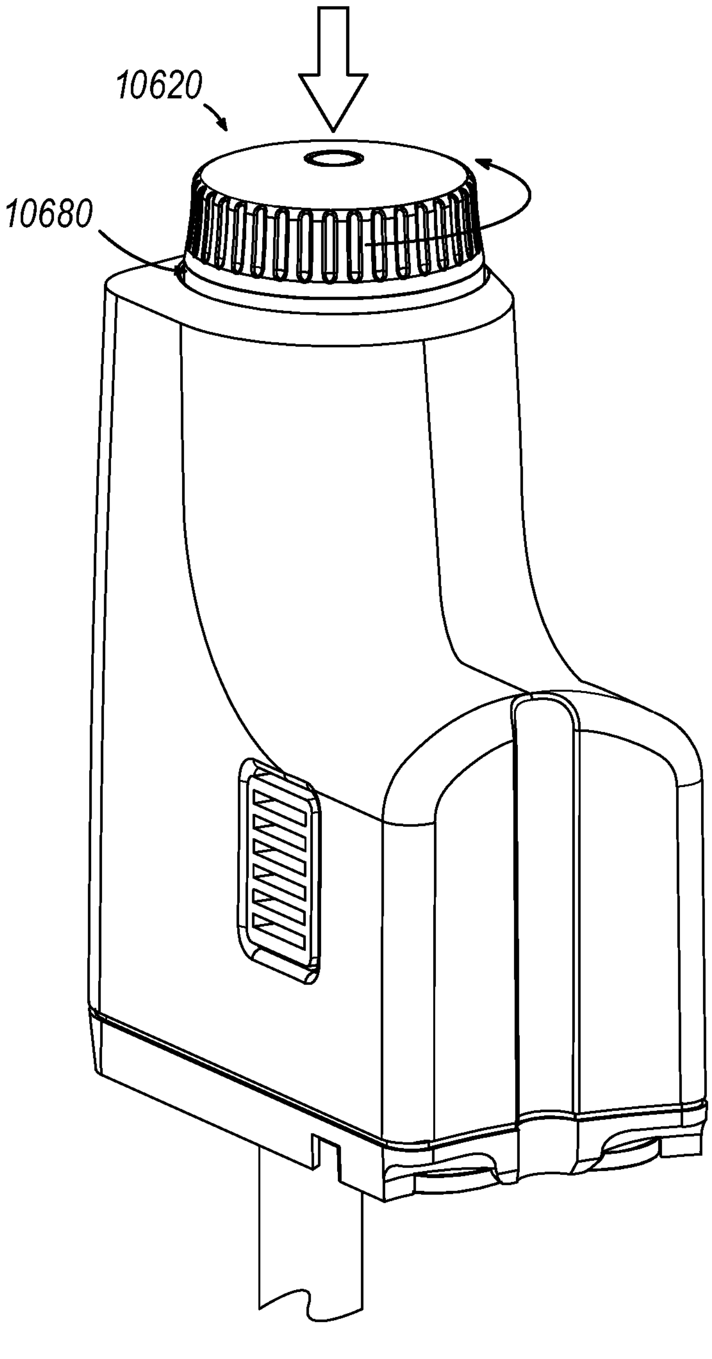
Figure 173:
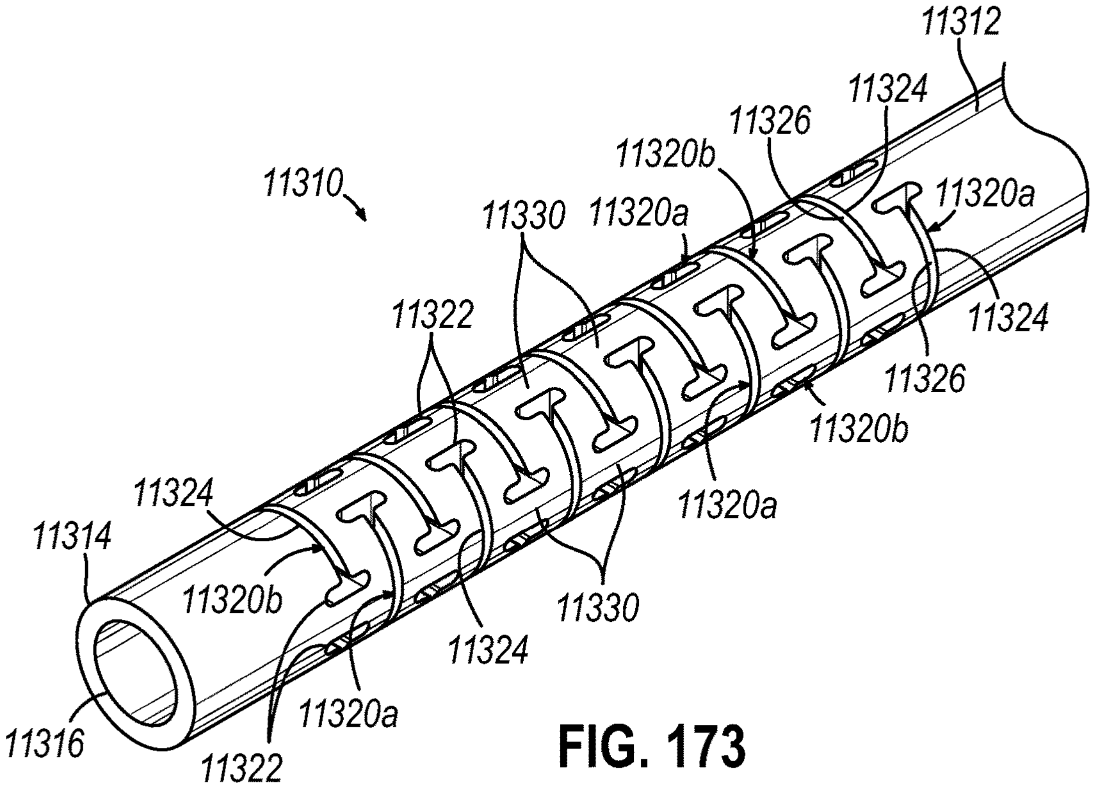
Figure 174:
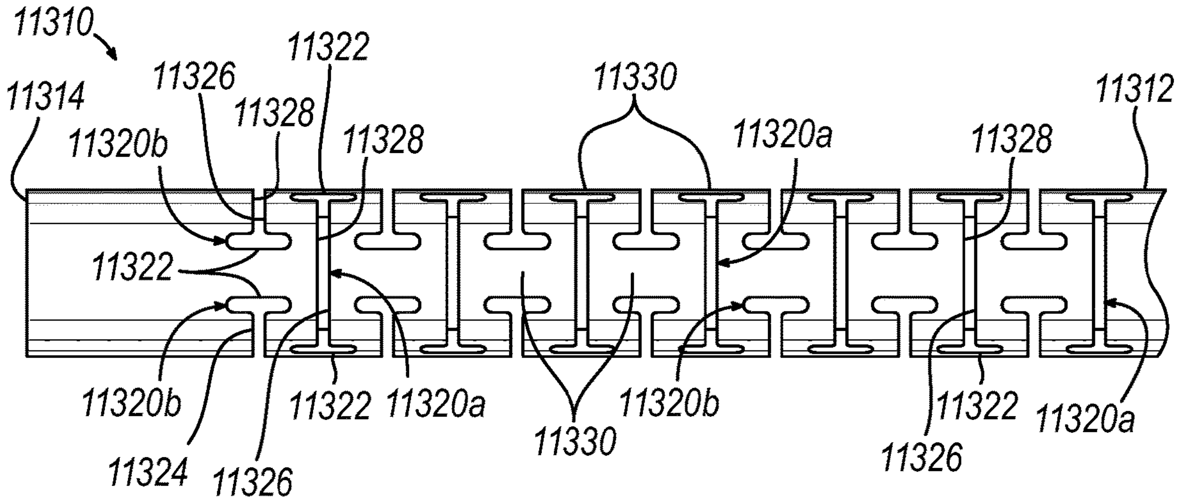
Figure 175A:
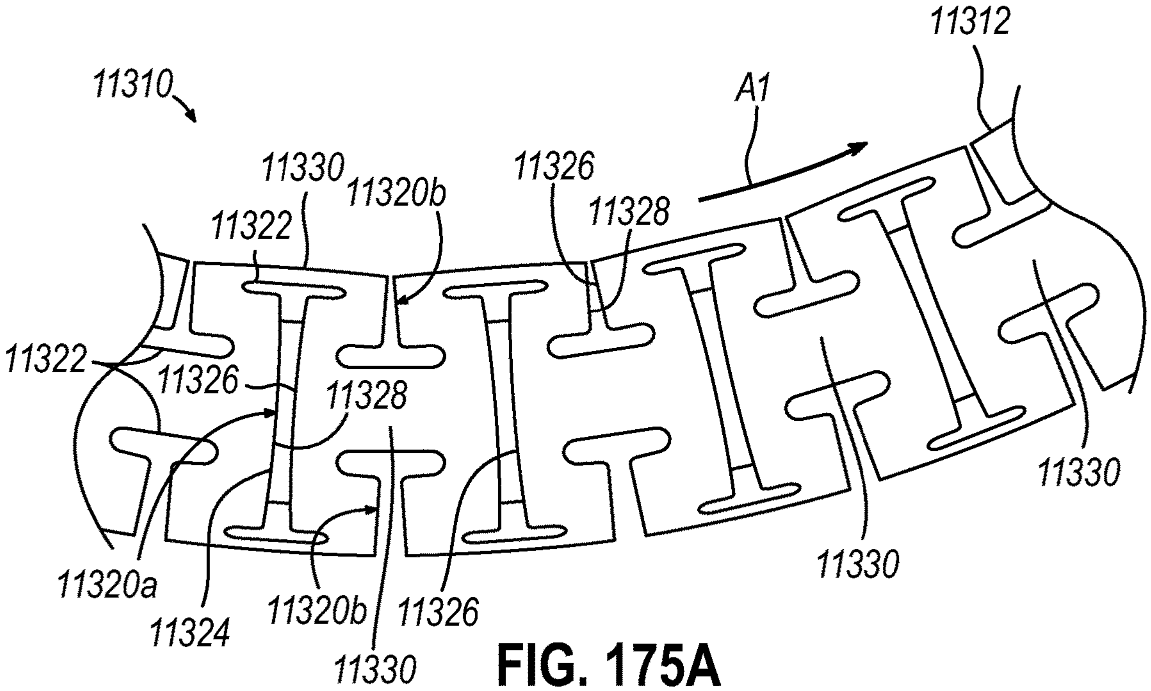
Figure 175B:
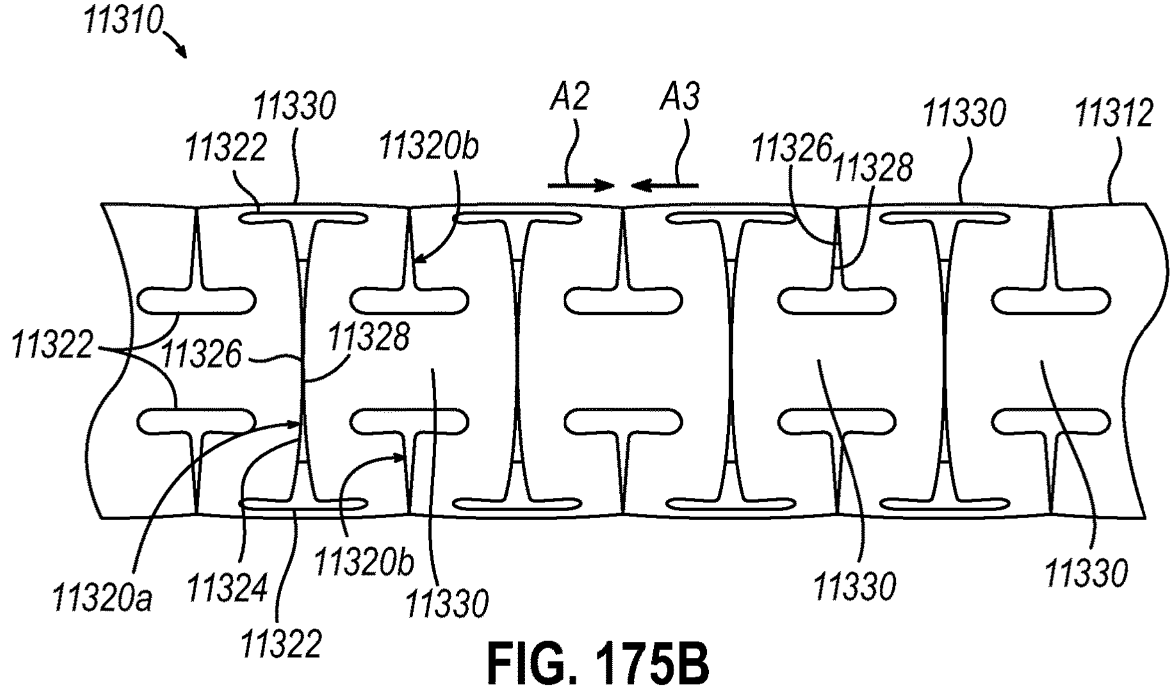
Figure 176:
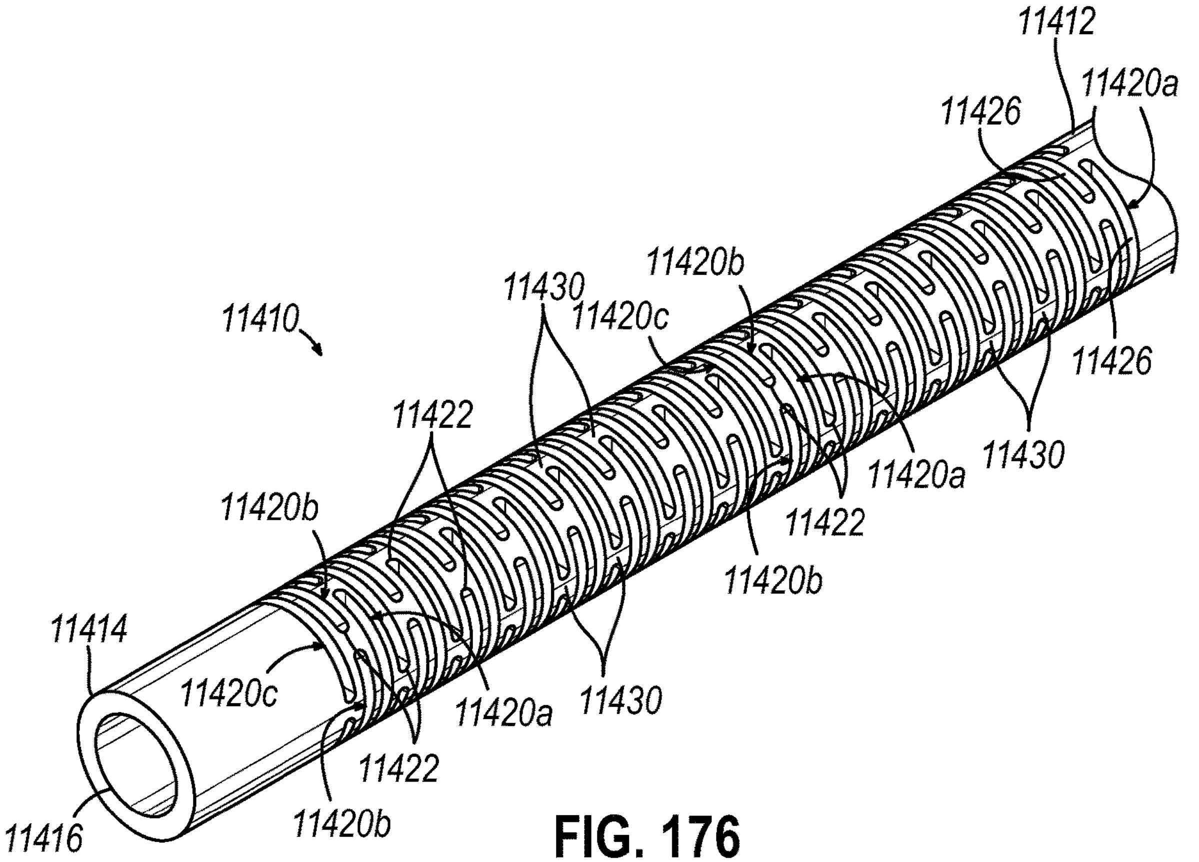
Figure 177:
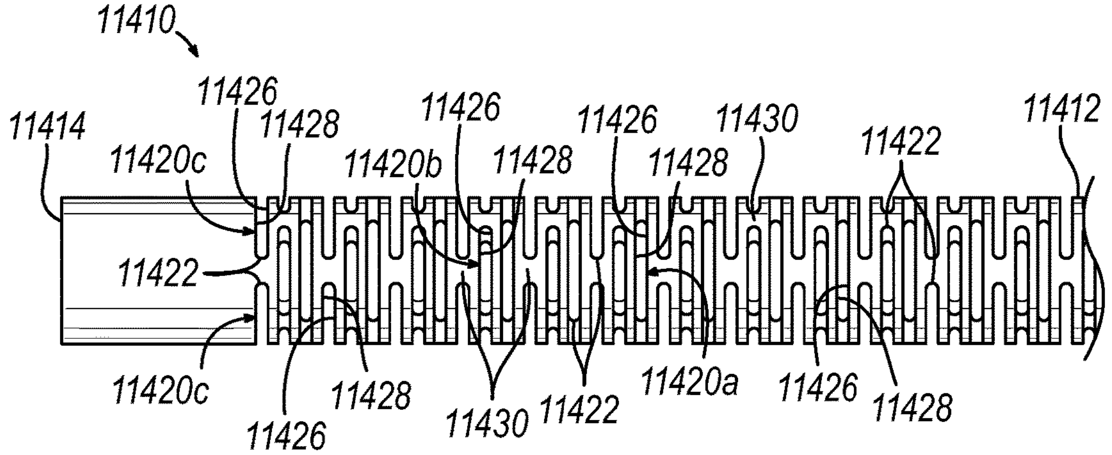
Figure 178A:
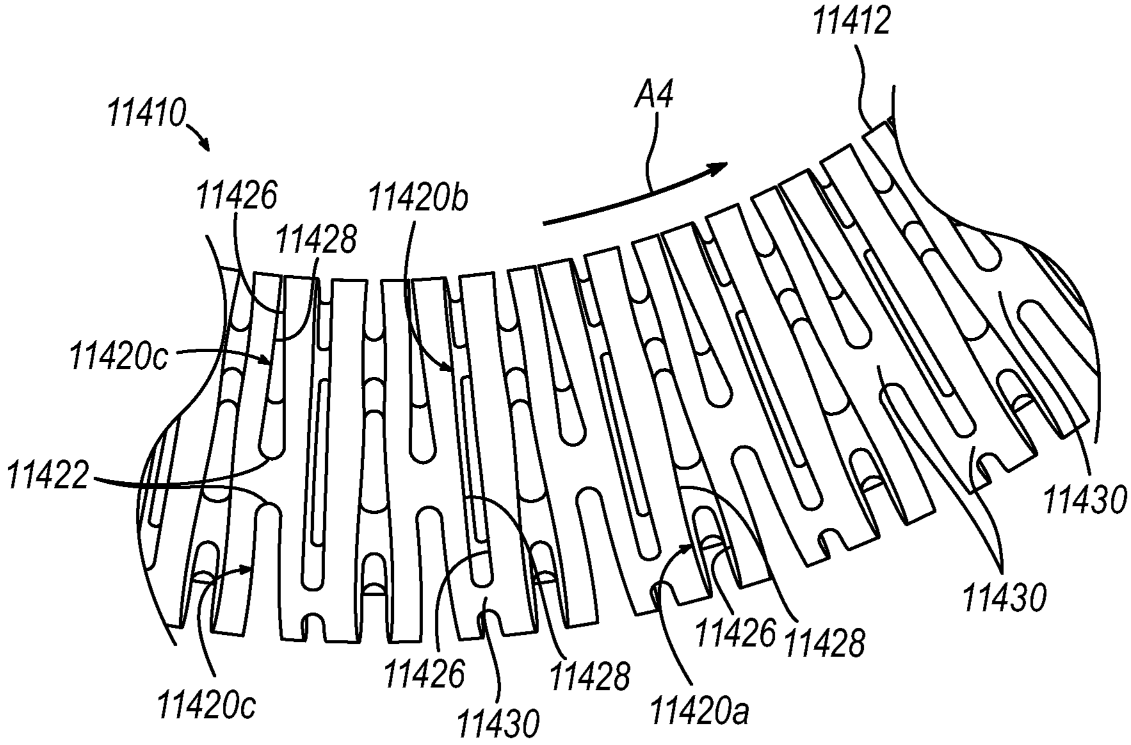
Figure 178B:
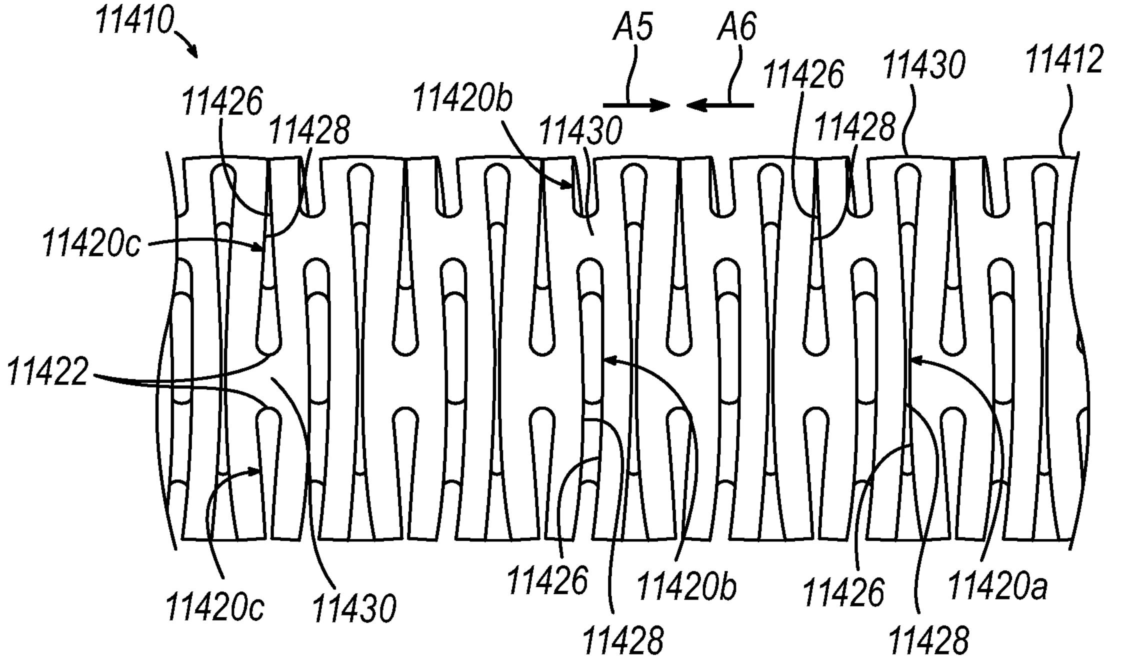
Figure 179:
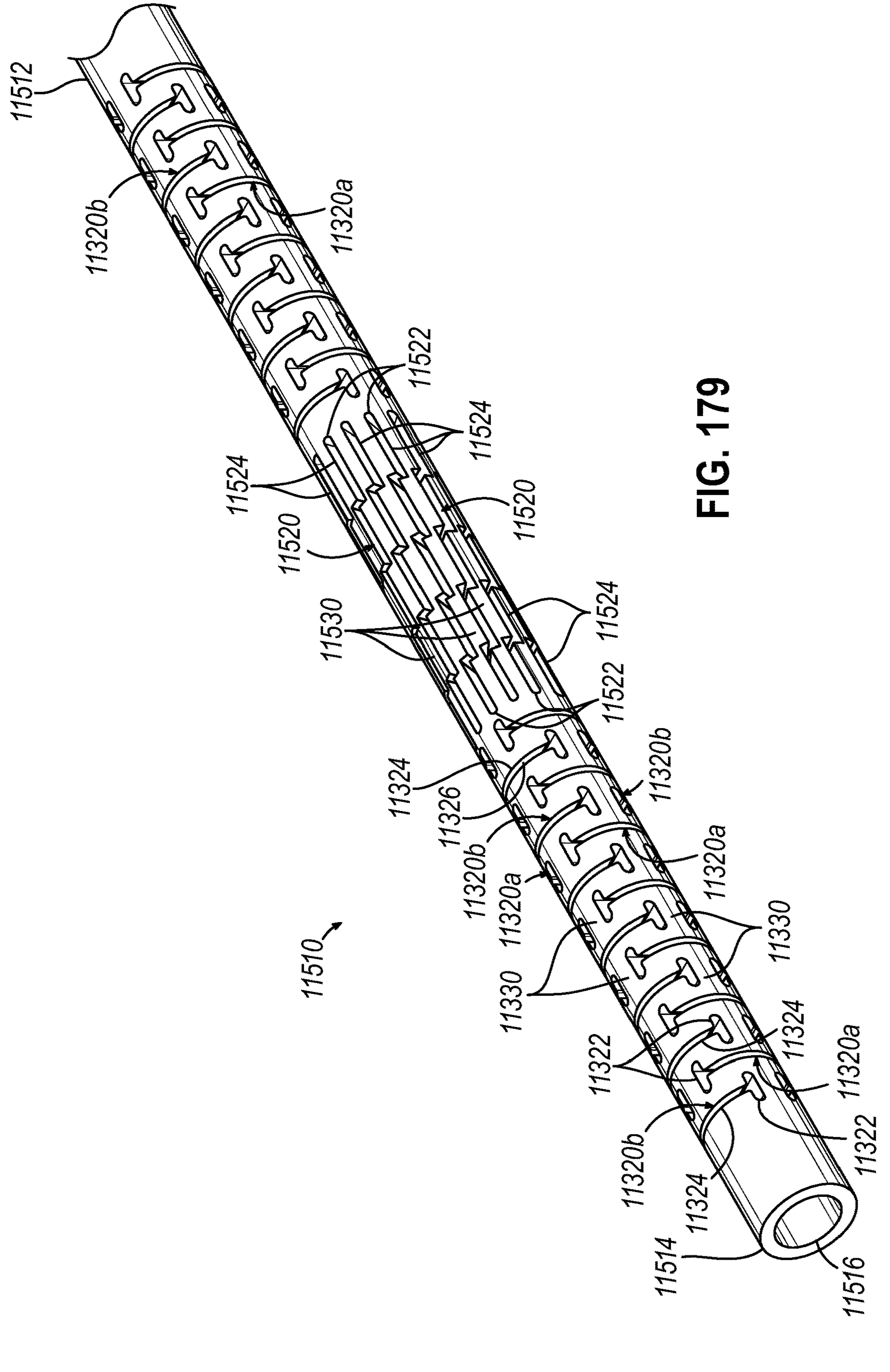
Figure 180:
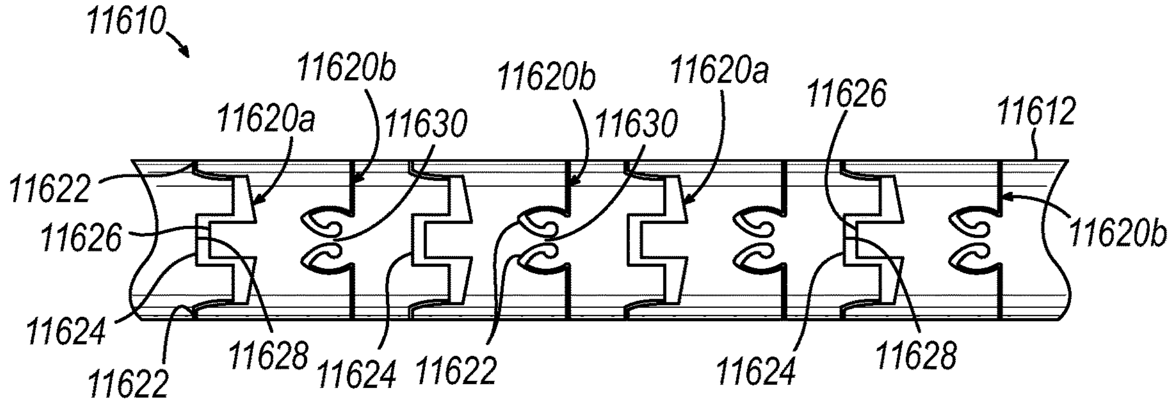
Figure 181:
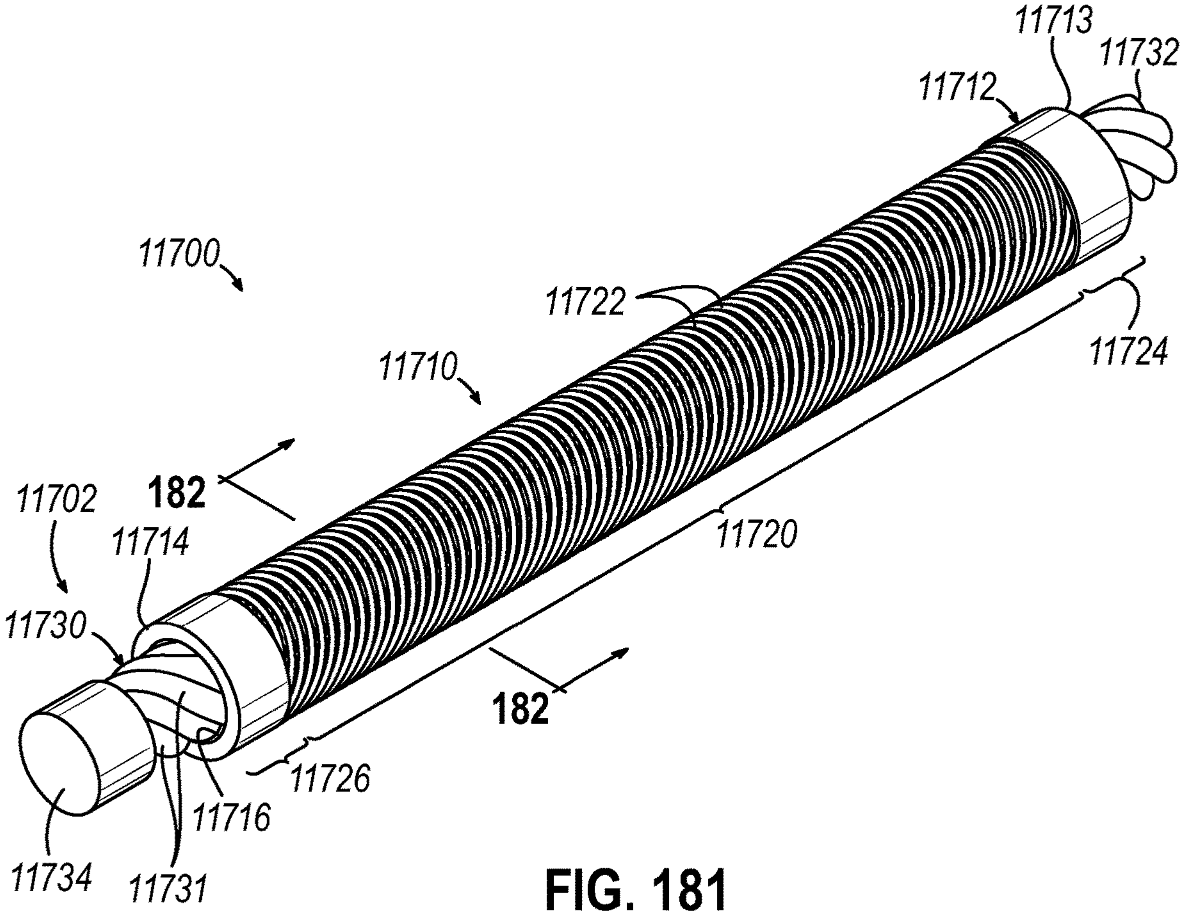
Figure 182:
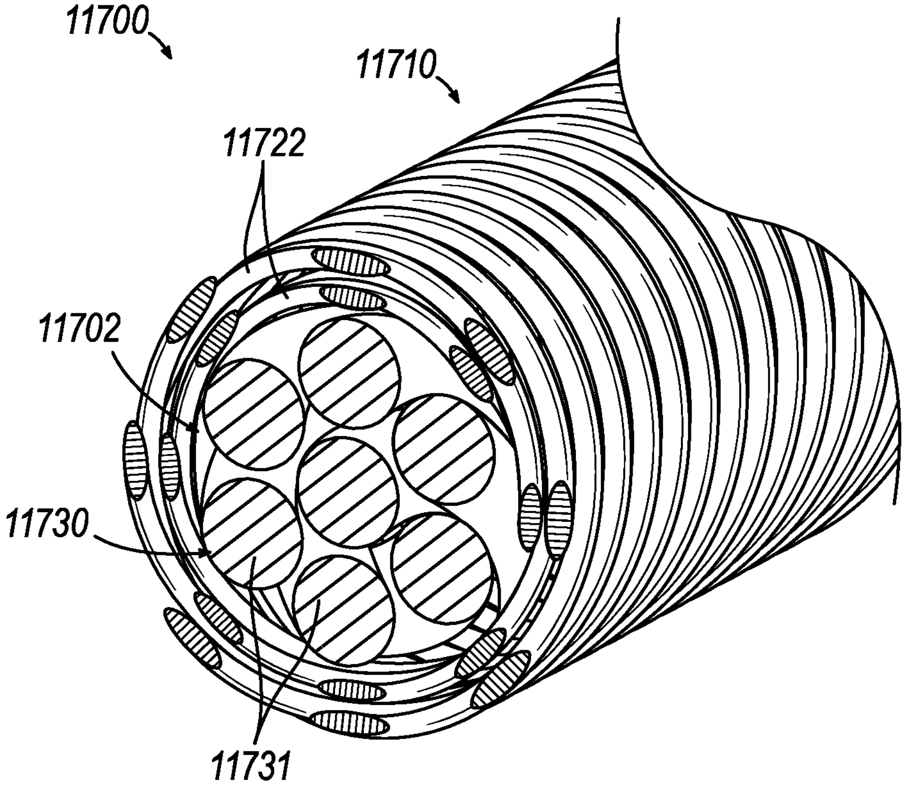
Figure 183:
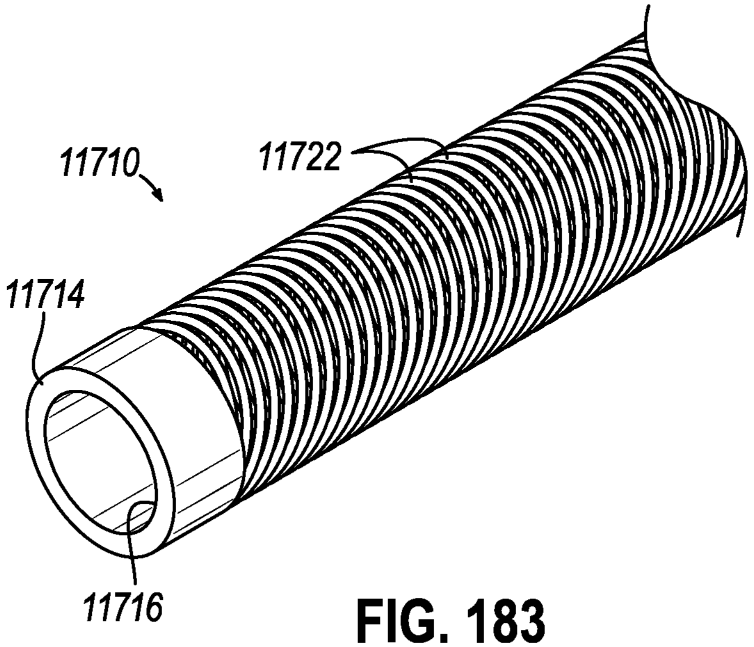
Figure 184A:
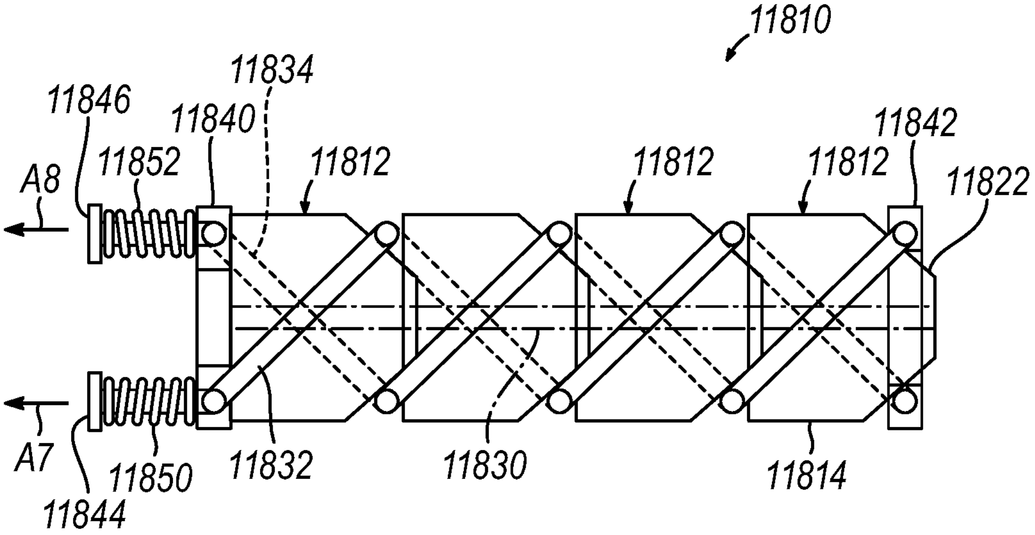
Figure 184B:
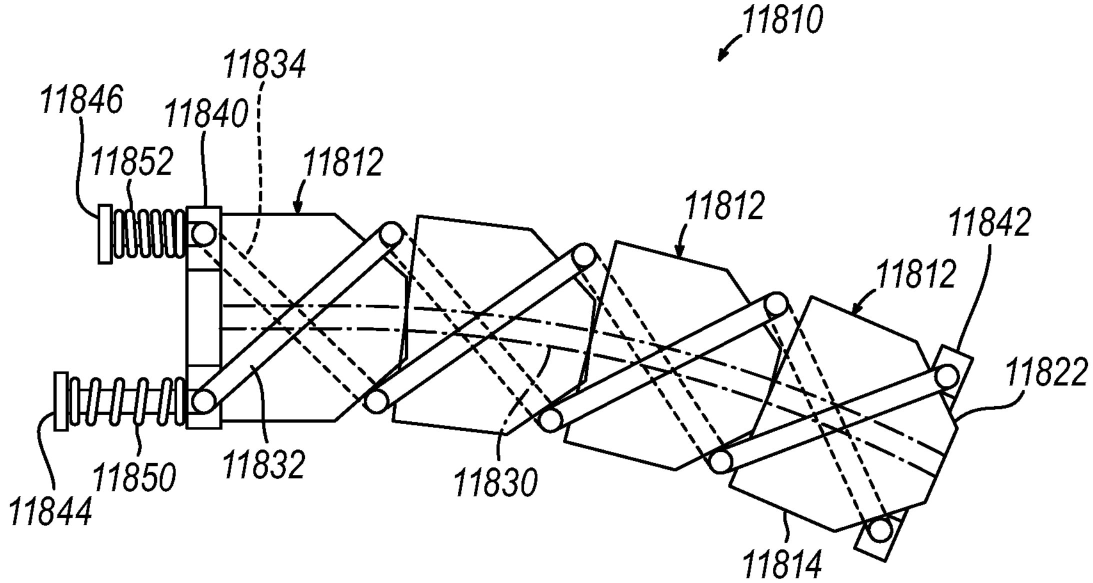
Figure 185:
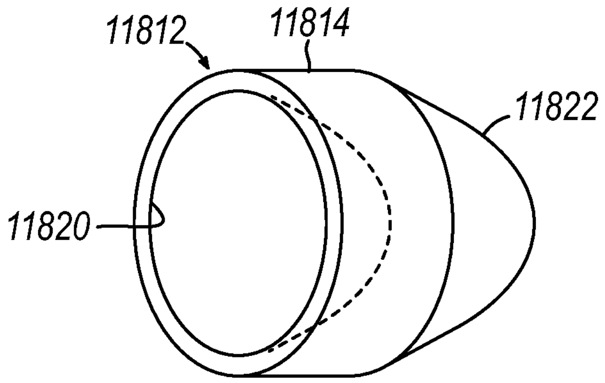
Figure 186:
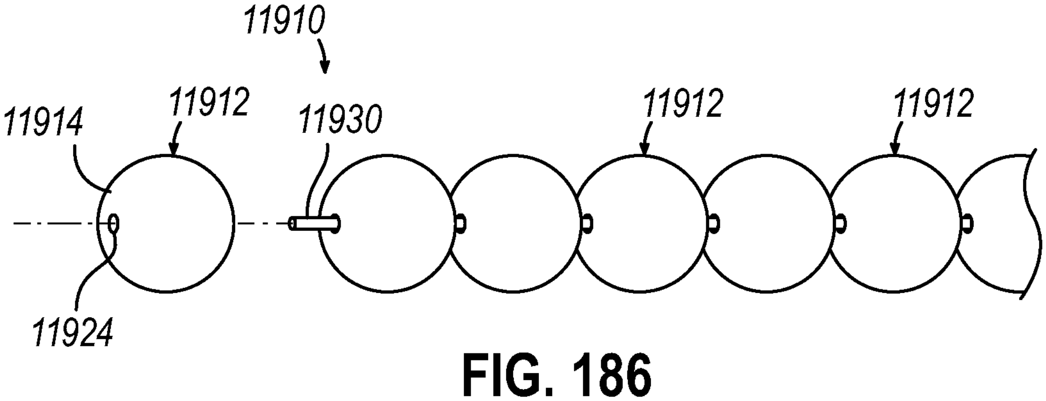
Figure 187:
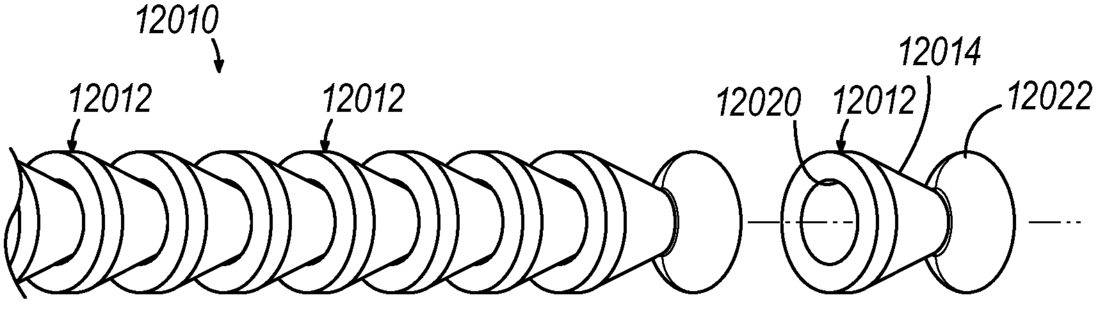
Figure 188:
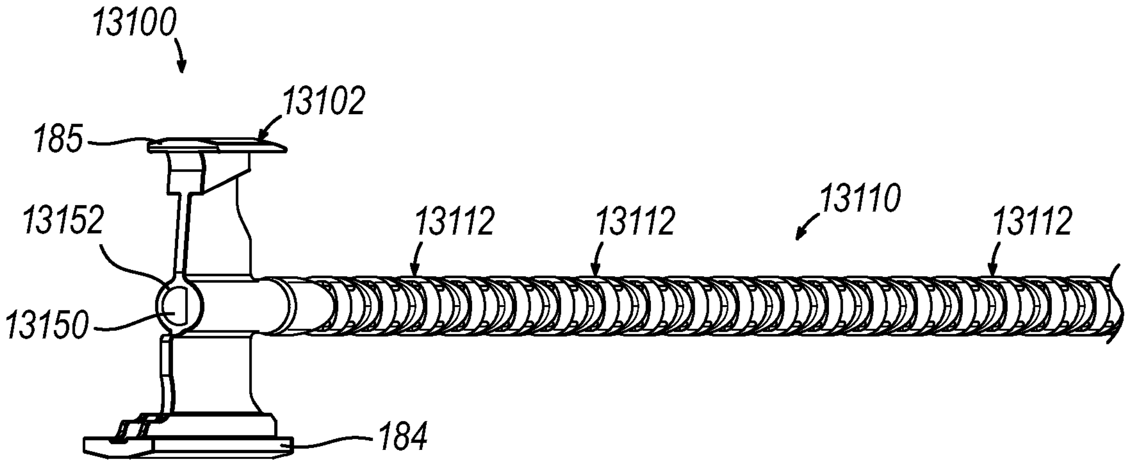
Figure 189:
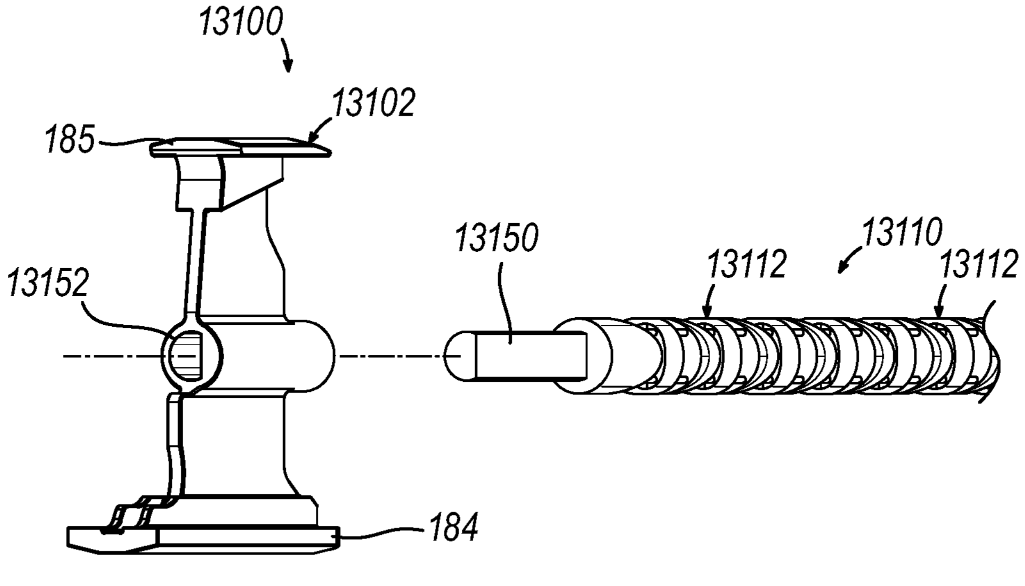

FIG. 94A depicts a side cross-sectional view of a proximal portion of another exemplary end effector for use with the robotic surgical system of FIG. 1, showing another exemplary lockout lever in an unlatched state for permitting proximal pulling of the pusher member shown in FIG. 8, and further showing the moveable member shown in FIG. 8 in a disengaged state for preventing firing of the end effector in the absence of a full staple cartridge;

FIG. 94B depicts a side cross-sectional view of the proximal portion of the end effector of FIG. 94A, showing the lockout lever in the unlatched state, and further showing the moveable member translated proximally together with the pusher member to remain in the disengaged state for preventing firing of the end effector in the absence of a full staple cartridge;

FIG. 94C depicts a side cross-sectional view of the proximal portion of the end effector of FIG. 94A, showing the lockout lever in a latched state for restricting proximal pulling of the pusher member, and further showing the moveable member translated proximally relative to the pusher member to an engaged state for allowing firing of the end effector with a full staple cartridge;

FIG. 95 depicts a perspective view of a proximal portion of another exemplary end effector for use with the robotic surgical system of FIG. 1, showing a lockout hook attached to the proximal end of the push rod shown in FIG. 8;

FIG. 96A depicts a side elevation view of the proximal portion of the end effector of FIG. 14, showing the lockout hook in an unavailable state, and further showing the moveable member shown in FIG. 8 in a proximal state;

FIG. 96B depicts a side elevation view of the proximal portion of the end effector of FIG. 95, showing the lockout hook in an available state, and further showing the moveable member in an intermediate state;

FIG. 97 depicts a bottom view of the proximal portion of the end effector of FIG. 95, showing the lockout hook in the available state, and further showing the moveable member in the intermediate state;

FIG. 98 depicts a bottom view of the proximal portion of the end effector of FIG. 95, showing the lockout hook in the unavailable state, and further showing the moveable member in the intermediate state;

FIG. 99 depicts a perspective view of an exemplary alternative staple cartridge for use with the surgical instrument of FIG. 4;

FIG. 100 depicts a partial perspective view of a cartridge tray of the staple cartridge of FIG. 99;

FIG. 101A depicts a side cross-sectional view of the staple cartridge of FIG. 99, with a restriction feature blocking distal movement of a wedge sled of the staple cartridge;

FIG. 101B depicts another side cross-sectional view of the staple cartridge of FIG. 99, with a portion of the restriction feature deformed to permit distal movement of the wedge sled of FIG. 101A;

FIG. 102 depicts a perspective view of another exemplary alternative staple cartridge for use with the surgical instrument of FIG. 4;

FIG. 103 depicts a perspective view of a restriction feature of the staple cartridge of FIG. 102;

FIG. 104 depicts a perspective view of the end effector of FIG. 4, the end effector in an open configuration;

FIG. 105A depicts a partial perspective view of the staple cartridge of FIG. 102 being inserted within the end effector of FIG. 4;

FIG. 105B depicts a partial perspective view of the staple cartridge of FIG. 102 disposed within the end effector of FIG. 4 and a portion of the end effector being used to actuate the restriction feature of FIG. 103;

FIG. 106A depicts a front cross-sectional view of the staple cartridge of FIG. 102 inserted within the end effector of FIG. 4, the restriction feature of FIG. 103 being in a locked position;

FIG. 106B depicts another front cross-sectional view of the staple cartridge of FIG. 102 inserted within the end effector of FIG. 4, the restriction feature of FIG. 103 being in an unlocked position;

FIG. 107 depicts a partial perspective view of another exemplary alternative staple cartridge for use with the surgical instrument of FIG. 4;

FIG. 108 depicts a detailed perspective view of a proximal end of the staple cartridge of FIG. 107;

FIG. 109 depicts a partial perspective cross-sectional view of the staple cartridge of FIG. 107;

FIG. 110 depicts another partial perspective cross-sectional view of the staple cartridge of FIG. 107;

FIG. 111A depicts a partial perspective view of the staple cartridge of FIG. 107, with portions of the staple cartridge removed to show engagement between a restriction member of the staple cartridge and a pusher member of the end effector of FIG. 4, the restriction member in a locked position;

FIG. 111B depicts another partial perspective view of the staple cartridge of FIG. 107, with portions of the staple cartridge removed to show engagement between the restriction member of FIG. 111A and the pusher member of the end effector of FIG. 4, the restriction member in an unlocked position;

FIG. 112 depicts a perspective view of a lower jaw and wedge sled of a third exemplary end effector, with select portions of the third exemplary end effector omitted to reveal internal features, the lower jaw and wedge sled having illumination features;

FIG. 113 depicts a perspective view of the third exemplary end effector of FIG. 112, shown clamping a tissue with the illumination features illuminated;

FIG. 114 depicts a perspective view of a fourth exemplary end effector, shown clamping a tissue with a second configuration of illumination features illuminated;

FIG. 115 depicts a cross-sectional side view of the end effector of FIG. 114;

FIG. 116 depicts a side view of the end effector of FIG. 114 in use and clamping a tissue, the tissue shown as transparent, with select internal portions of the end effector overlayed for functional clarity;

FIG. 117A depicts a cross-sectional side view of a fifth exemplary end effector with the upper jaw and lower jaw in a closed position, shown with select internal portions of the end effector in a first staple firing position and overlayed for functional clarity, shown with a third configuration of illumination features not illuminated;

FIG. 117B depicts a cross-sectional side view of the fifth exemplary end effector of FIG. 117A with the upper jaw and lower jaw in a closed position, shown with select internal portions of the end effector in a second staple firing position and overlayed for functional clarity, shown with the third configuration of illumination features illuminated;

FIG. 117C depicts a cross-sectional side view of the fifth exemplary end effector of FIG. 117A with the upper jaw and lower jaw in a closed position, shown with select internal portions of the end effector in a third staple firing position and overlayed for functional clarity, shown with the third embodiment of illumination features illuminated;

FIG. 118 depicts an end view of a wedge sled of the fifth exemplary end effector of FIG. 117A, with select portions of the third exemplary end effector omitted;

FIG. 119 depicts a perspective view of the lower jaw of the fifth exemplary end effector of FIG. 117A, with select portions of the fifth exemplary end effector omitted to reveal internal features;

FIG. 120 depicts a top cross-sectional view of a second exemplary configuration of an elongate shaft of an alternative exemplary surgical instrument that may be used with the robotic surgical system of FIG. 1, the elongate shaft having a movable feature disposed therein and a fourth configuration of illumination features;

FIG. 121A depicts a cross-sectional top view of the elongate shaft of FIG. 120, with the movable feature in a first position;

FIG. 121B depicts a cross-sectional top view of the elongate shaft of FIG. 120, with the movable feature in a second position;

FIG. 122 depicts a graphical representation of the output of the fourth configuration of illumination features during a staple firing stroke;

FIG. 123 depicts a perspective view of a staple cartridge of a sixth exemplary end effector, with select portions of the sixth exemplary end effector omitted, the staple cartridge having a fifth configuration of illumination features;

FIG. 124 depicts a perspective view of a lower jaw of a seventh exemplary end effector, with select portions of the seventh exemplary end effector omitted, the staple cartridge having a sixth configuration of illumination features;

FIG. 125A depicts a cross-sectional side view of an eighth exemplary end effector with the upper jaw and lower jaw in a closed position, shown with select internal portions of the end effector in a first staple firing position and overlayed for functional clarity, shown with a seventh configuration of illumination features not illuminated;

FIG. 125B depicts a cross-sectional side view of the eighth exemplary end effector of FIG. 125A with the upper jaw and lower jaw in a closed position, shown with select internal portions of the end effector in a second staple firing position and overlayed for functional clarity, shown with the seventh configuration of illumination features illuminated;

FIG. 125C depicts a cross-sectional side view of the eighth exemplary end effector of FIG. 125A with the upper jaw and lower jaw in a closed position, shown with select internal portions of the end effector in a third staple firing position and overlayed for functional clarity, shown with the seventh configuration of illumination features illuminated;

FIG. 126 depicts a top cross-sectional view of a third exemplary configuration of an elongate shaft of an alternative exemplary surgical instrument that may be used with the robotic surgical system of FIG. 1, the elongate shaft having a movable feature disposed therein and an eighth configuration of illumination features;

FIG. 127A depicts a cross-sectional top view of the elongate shaft of FIG. 126, with the movable feature in a first position;

FIG. 127B depicts a cross-sectional top view of the elongate shaft of FIG. 126, with the movable feature in a second position;

FIG. 128 depicts an end cross-sectional view of a portion of a fourth exemplary configuration of an elongate shaft of an alternative exemplary surgical instrument that may be used with the robotic surgical system of FIG. 1, the elongate shaft having a movable feature disposed therein and a ninth configuration of illumination features;

FIG. 129 depicts a side cross-sectional view of a portion of the elongate shaft of FIG. 128, shown with a portion of the ninth configuration of illumination features in an illuminated state;

FIG. 130 depicts a perspective view of the elongate shaft of FIG. 128 coupled with a ninth exemplary end effector, shown with the end effector clamping a tissue with a portion of the ninth configuration of illumination features illuminated;

FIG. 131 depicts a side cross-sectional view of a portion of the elongate shaft and end effector of FIG. 30, shown with a portion of the ninth configuration of illumination features illuminated;

FIG. 132 depicts a perspective view of a tenth exemplary end effector, shown clamping a tissue and having a portion of a tenth configuration of illumination features illuminated;

FIG. 133 depicts an end cross-sectional view of a portion of the end effector of FIG. 132;

FIG. 134 depicts a perspective view of a lower jaw of an eleventh exemplary end effector, with select portions of the eleventh exemplary end effector omitted or transparent to reveal internal features, the lower jaw having an eleventh configuration of illumination features;

FIG. 135 depicts a bottom perspective view of the end effector of FIG. 134;

FIG. 136 depicts an end cross-sectional view of the end effector of FIG. 134;

FIG. 137 depicts a first graphical representation of the thermochromic output of the illumination features of the end effector of FIG. 134 during a firing stroke, the first graphical representation illustrating the relationship between applied voltage and temperature;

FIG. 138 depicts a second graphical representation of the thermochromic output of the illumination features of the end effector of FIG. 134 during a firing stroke, the second graphical representation illustrating the relationship between temperature and time;

FIG. 139 depicts a second exemplary driving assembly, the driving assembly having a twelfth configuration of illumination features;

FIG. 140 depicts a pivotable anvil configured for use with the driving assembly of FIG. 139;

FIG. 141 depicts a top plan view of an exemplary drive system that may be used with the surgical instrument of FIG. 4;

FIG. 142 depicts a perspective view of the drive system of FIG. 141;

FIG. 143A depicts a top plan view of an exemplary alternative drive system that may be used with the surgical instrument of FIG. 4, the drive system in a single drive configuration;

FIG. 143B depicts another top plan view of the drive system of FIG. 143A, the drive system in a first multiple drive configuration;

FIG. 143C depicts yet another top plan view of the drive system of FIG. 143A, the drive system in a second multiple drive configuration;

FIG. 143D depicts still another top plan view of the drive system of FIG. 143A, the drive system in a third multiple drive configuration;

FIG. 144A depicts a top plan view of another exemplary alternative drive system that may be used with the surgical instrument of FIG. 4, the drive system in a first drive configuration;

FIG. 144B depicts another top plan view of the drive system of FIG. 144A, the drive system in a second drive configuration;

FIG. 145A depicts a detailed top plan view of the drive system of FIG. 144A, the drive system in the first drive configuration;

FIG. 145B depicts another detailed top plan view of the drive system of FIG. 144A, the drive system in the second drive configuration;

FIG. 146A depicts a side elevational view of an exemplary shifting mechanism that may be used with the surgical instrument of FIG. 4, the shifting mechanism in a single drive configuration;

FIG. 146B depicts another side elevational view of the shifting mechanism of FIG. 146A, the shifting mechanism in a multi-drive configuration;

FIG. 147A depicts a side elevational view of an exemplary alternative shifting mechanism that may be used with the surgical instrument of FIG. 4, the shifting mechanism in a single drive configuration;

FIG. 147B depicts another side elevational view of the shifting mechanism of FIG. 147A, the shifting mechanism in a multi-drive configuration;

FIG. 148 depicts a perspective view of another exemplary alternative shifting mechanism that may be used with the surgical instrument of FIG. 4;

FIG. 149 depicts a top plan view of the shifting mechanism of FIG. 148, the shifting mechanism in a first configuration;

FIG. 150 depicts another top plan view of the shifting mechanism of FIG. 148, the shifting mechanism in a second configuration;

FIG. 151 depicts a side elevational view of yet another exemplary alternative shifting mechanism that may be used with the surgical instrument of FIG. 4;

FIG. 152 depicts another side elevational view of the shifting mechanism of FIG. 151, the shifting mechanism being used as a continuously variable transmission;

FIG. 153 depicts a perspective view of still another exemplary alternative shifting mechanism that may be used with the surgical instrument of FIG. 4;

FIG. 154 depicts an exploded perspective view of a portion of the shifting mechanism of FIG. 153;

FIG. 155 depicts a detailed perspective view of a shift shaft of the shifting mechanism of FIG. 153;

FIG. 156A depicts a side elevational view of the shifting mechanism of FIG. 153, the shifting mechanism in a direct drive configuration;

FIG. 156B depicts a side elevational view of the shifting mechanism of FIG. 153, the shifting mechanism in a reduction drive configuration;

FIG. 157 depicts a perspective view of still another exemplary alternative shifting mechanism that may be used with the surgical instrument of FIG. 4;

FIG. 158 depicts a perspective cutaway view of the shifting mechanism of FIG. 157;

FIG. 159 depicts a cutaway side elevational view of a proximal base portion of an exemplary alternative surgical instrument that may be used with the robotic surgical system of FIG. 1;

FIG. 160A depicts a side elevational view of an end effector of the surgical instrument of FIG. 159, the end effector in a closed configuration;

FIG. 160B depicts another side elevational view of the end effector of FIG. 160A, the end effector in a partially open configuration;

FIG. 161A depicts a side elevational view of an exemplary alterative cable manipulator for use with the surgical instrument of FIG. 159, the cable manipulator in a first configuration;

FIG. 161B depicts another side elevational view of the cable manipulator of FIG. 161A, the cable manipulator in a second configuration;

FIG. 162 depicts a perspective view of an exemplary bailout mechanism that may be incorporated into the surgical instrument of FIG. 4;

FIG. 163 depicts a perspective view of a shuttle of the bailout mechanism of FIG. 162;

FIG. 164 depicts another perspective view of the shuttle of FIG. 163;

FIG. 165 depicts a perspective view of another exemplary bailout mechanism that may be incorporated into the surgical instrument of FIG. 4;

FIG. 166 depicts a perspective view of a shuttle of the bailout mechanism of FIG. 165;

FIG. 167 depicts a partial top plan view of the shuttle of FIG. 166;

FIG. 168 depicts a perspective view of an axial strengthening feature that may be incorporated into the surgical instrument of FIG. 4;

FIG. 169A depicts a perspective view of a manual drive wheel that may be incorporated into the bailout mechanisms of FIG. 162 or 163, with an arm of the manual drive wheel in a retracted position;

FIG. 169B depicts another perspective view of the manual drive wheel of FIG. 169A, with the arm of the manual drive wheel in an extended position;

FIG. 170 depicts a perspective view of another manual drive wheel that may be incorporated into the bailout mechanisms of FIG. 162 or 163;

FIG. 171 depicts an exploded perspective view of the manual drive wheel of FIG. 170;

FIG. 172 depicts another perspective view of the manual drive wheel of FIG. 170, with the manual drive wheel in an engaged position;

FIG. 173 depicts a perspective view of a distal portion of an exemplary push rod for use with the surgical instrument of FIG. 4;

FIG. 174 depicts a side elevational view of the distal portion of the push rod of FIG. 173;

FIG. 175A depicts a side elevational view of the distal portion of the push rod of FIG. 12, showing the distal portion of the push rod in a laterally deflected state;

FIG. 175B depicts a side elevational view of the distal portion of the push rod of FIG. 12, showing the distal portion of the push rod in a longitudinally compressed state;

FIG. 176 depicts a perspective view of a distal portion of another exemplary push rod for use with the surgical instrument of FIG. 4;

FIG. 177 depicts a side elevational view of the distal portion of the push rod of FIG. 176;

FIG. 178A depicts a side elevational view of the distal portion of the push rod of FIG. 176, showing the distal portion of the push rod in a laterally deflected state;

FIG. 178B depicts a side elevational view of the distal portion of the push rod of FIG. 176, showing the distal portion of the push rod in a longitudinally compressed state;

FIG. 179 depicts a perspective view of a distal portion of another exemplary push rod for use with the surgical instrument of FIG. 4;

FIG. 180 depicts a side elevational view of a distal portion of another exemplary push rod for use with the surgical instrument of FIG. 4;

FIG. 181 depicts a perspective view of a distal portion of an exemplary actuation assembly, including an exemplary pull rod and another exemplary push rod for use with the surgical instrument of FIG. 4;

FIG. 182 depicts a cross-sectional view of the distal portion of the actuation assembly of FIG. 181, taken along section line 182-182 in FIG. 181;

FIG. 183 depicts a perspective view of a distal portion of the push rod of FIG. 181;

FIG. 184A depicts a side elevational view of another exemplary push rod for use with the surgical instrument of FIG. 4, showing the push rod in an undeflected state;

FIG. 184B depicts a side elevational view of the push rod of FIG. 184A, showing the push rod in a laterally deflected state;

FIG. 185 depicts a perspective view of a link of the push rod of FIG. 184A;

FIG. 186 depicts a partially disassembled perspective view of a distal portion of another exemplary push rod for use with the surgical instrument of FIG. 4;

FIG. 187 depicts a partially disassembled perspective view of a distal portion of another exemplary push rod for use with the surgical instrument of FIG. 4;

FIG. 188 depicts a perspective view of another exemplary driving assembly for use with the surgical instrument of FIG. 4; and FIG. 189 depicts a partially disassembled perspective view of the driving assembly of FIG. 188.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "inner," "outer," "upper," "lower," "lateral," and the like also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

I. Exemplary Robotic Surgical System

A. Overview

FIG. 1 shows a top plan view of an exemplary robotic surgical system (10) that may be used for performing a diagnostic or surgical procedure on a patient (12) who is lying down on an operating table (14). Robotic surgical system (10) may be constructed and operable in accordance with at least some of the teachings of U.S. Pat. No. 9,839,487, entitled "Backup Latch Release for Surgical Instrument," issued Dec. 12, 2017; U.S. Pat. No. 10,485,621, entitled "Sterile Barrier Between Surgical Instrument and Teleoperated Actuator," issued Nov. 26, 2019; U.S. Pat. No. 10,806,530, entitled "System and Method for Patient-Side Instrument Control," issued Oct. 20, 2020; U.S. Pat. No. 10,537,400, entitled "Detection Pins to Determine Presence of Surgical Instrument and Adapter on Manipulator," issued Jan. 21, 2020; U.S. Pat. No. 10,863,988, entitled "Surgical Instrument with Lockout Mechanism," published Dec. 15, 2020; U.S. Pat. No. 10,610,313, entitled "Surgical Instrument with Shiftable Transmission," issued Apr. 7, 2020; U.S. Pub. No. 2018/0271608, entitled "Manual Release for Medical Device Drive System," published Sep. 27, 2018, issued as U.S. Pat. No. 11,076,926 on Aug. 3, 2021; U.S. Pub. No. 2018/0325606, entitled "Systems and Methods for Operating an End Effector," published Nov. 15, 2018, issued as U.S. Pat. No. 11,026,755 on Jun. 8, 2021; U.S. Pub. No. 2019/0200989, entitled "Stapler Reload Detection and Identification," published Jul. 4, 2019, issued as U.S. Pat. No. 11,364,029 on Jun. 21, 2022; U.S. Pub. No. 2019/0239967, entitled "Stapler Beam Architecture," published Aug. 8, 2019, issued as U.S. Pat. No. 11,166,773 on Nov. 9, 2021; U.S. Pub. No. 2019/0262088, entitled "Robotic Surgical Stapler Assembly Configured to Use Stapler Reload," published Aug. 29, 2019, issued as U.S. Pat. No. 11,259,884 on Mar. 1, 2022; U.S. Pub. No. 2019/0239877, entitled "Wrist Architecture," published Aug. 8, 2019, issued as U.S. Pat. No. 11,234,700 on Feb. 1, 2022; U.S. Pub. No. 2019/0201150, entitled "Push-Pull Surgical Instrument End Effector Actuation Using Flexible Tension Member," published Jul. 4, 2019, issued as U.S. Pat. No. 11,020,138 on Jun. 1, 2021; U.S. Pub. No. 2019/0282233, entitled "Stapler Cartridge With an Integral Knife," published Sep. 19, 2019, issued as U.S. Pat. No. 11,147,552 on Oct. 19, 2021; U.S. Pub. No. 2019/0262088, entitled "Robotic Surgical Stapler Assembly Configured to Use Stapler Reload," published Aug. 29, 2019, issued as U.S. Pat. No. 11,259,884 on Mar. 1, 2022; U.S. Pub. No. 2020/0138529, entitled "Locking System for Medical Device Drive System," published May 7, 2020, issued as U.S. Pat. No. 11,633,239 on Apr. 25, 2023; and/or U.S. Pub. No. 2020/0397430, entitled "Surgical Instrument With Lockout Mechanism," published Dec. 24, 2020, issued as U.S. Pat. No. 11,439,390 on Sep. 13, 2022. The disclosure of each of the above-cited U.S. Patents and U.S. Patent Publications is incorporated by reference herein in its entirety.

Robotic surgical system (10) may include a surgeon's console (16) for use by a surgeon (18) during a surgical procedure. One or more assistants (20) may also participate in the procedure. Robotic surgical system (10) may include a patient side cart (22) (i.e., a surgical robot) and an electronics cart (24). Patient side cart (22) may manipulate at least one surgical instrument (26) (also referred to as a "tool assembly" or "tool") through an incision in the body of patient (12) while surgeon (18) views the surgical site through surgeon's console (16). As will be described in greater detail below, surgical instrument(s) (26) and an imaging device (shown as an endoscope (28)) may be removably coupled with patient side cart (22). Electronics cart (24) may be used to process the images of the surgical site for subsequent display to the surgeon (18) through surgeon's console (16). Electronics cart (24) may be coupled with endoscope (28) and may include a processor (38) (shown schematically) to process captured images for subsequent display, such as to surgeon (18) on the surgeon's console (16), on a display (40) of electronics cart (24), or another suitable display located locally and/or remotely. The images may also be processed by a combination of electronics cart (24) and processor (38), which may be coupled together to process the captured images jointly, sequentially, and/or combinations thereof. Electronics cart (24) may overlay the captured images with a virtual control interface prior to displaying combined images to the surgeon (18) via surgeon's console (16).

Figure 2:
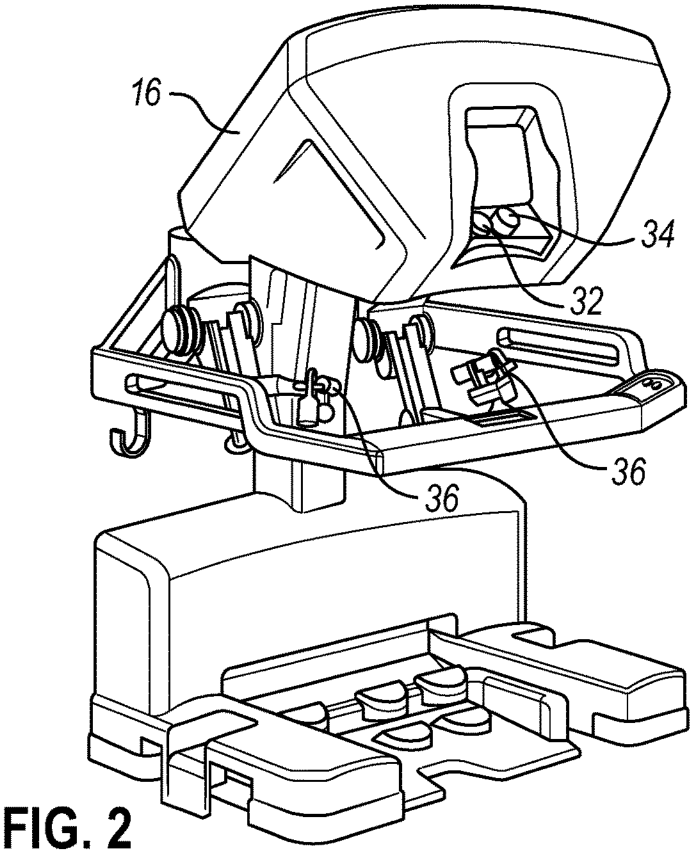
FIG. 2 depicts a perspective view of a surgeon's control console of the robotic surgical system of FIG. 1.

FIG. 2 shows a perspective view of surgeon's console (16). Surgeon's console (16) includes a left eye display (32) and a right eye display (34) for presenting surgeon (18) with a coordinated stereo view of the surgical site that enables depth perception. Surgeon's console (16) includes one or more input control devices (36) causing patient side cart (22) (shown in FIG. 1) to manipulate one or more surgical instruments (26). Input control devices (36) may provide the same degrees of freedom as their associated surgical instruments (26) (shown in FIG. 1) to provide surgeon (18) with telepresence, or the perception that the input control devices (36) are integral with surgical instruments (26). To this end, position, force, and tactile feedback sensors (not shown) may be employed to transmit position, force, and tactile sensations from surgical instruments (26) back to the surgeon's hands through input control devices (36). In some instances, surgeon's console (16) may be located in the same room as the patient so that surgeon (18) may directly monitor the procedure, be physically present if necessary, and speak to an assistant directly rather than over the telephone or other communication medium. Alternatively, surgeon (18) may be located in a different room, a completely different building, or other remote location from the patient allowing for remote surgical procedures.

Figure 3:
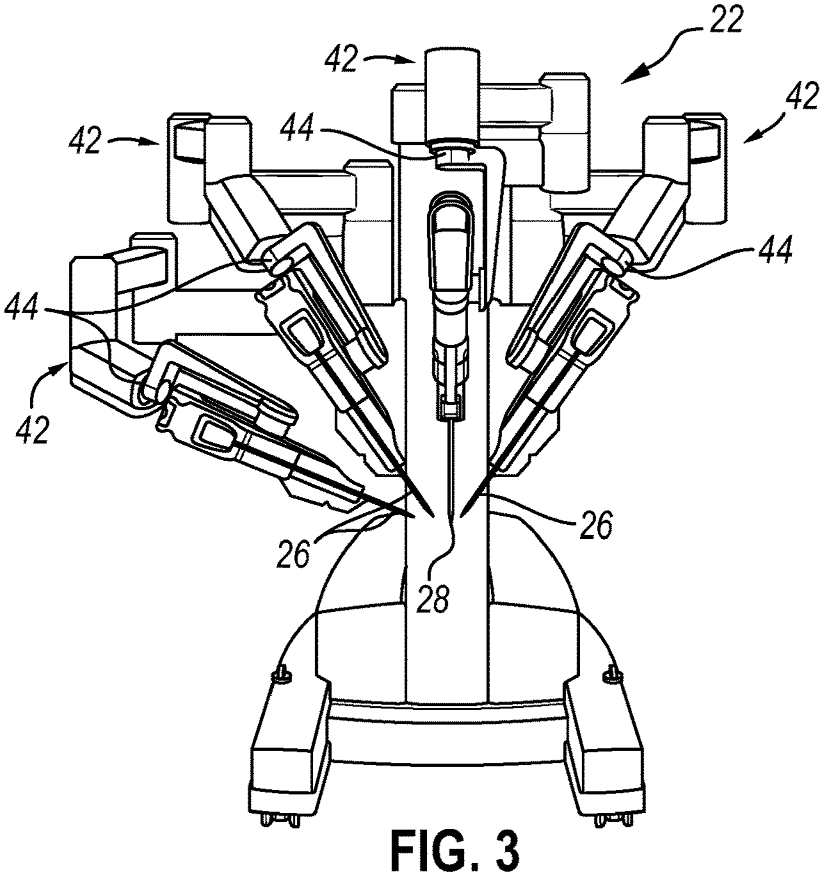
FIG. 3 depicts a front elevation view of a patient side cart of the robotic surgical system of FIG. 1.

FIG. 3 shows patient side cart (22) that manipulates surgical instruments (26). An image of the surgical site may be obtained by endoscope (28), which may include a stereoscopic endoscope. Manipulation is provided by robotic mechanisms, shown as robotic arms (42) that include at least one robotic joint (44) and an output coupler (not shown) that is configured to removable secure surgical instrument (26) with robotic arm (42). Endoscope (28) and surgical tools (26) may be positioned and manipulated through incisions in the patient so that a kinematic remote center is maintained at the incision to minimize the size of the incision. Images of the surgical site may include images of the distal ends of the surgical instruments (26) when they are positioned within the field-of-view of the endoscope (28). Patient side cart (22) may output the captured images for processing outside electronics cart (24). The number of surgical instruments (26) used at one time will generally depend on the diagnostic or surgical procedure and the space constraints within the operating room, among other factors. To change one or more of surgical instruments (26) being used during a procedure, assistant(s) (20) may remove surgical instrument (26) from patient side cart (22) and replace surgical instrument (26) with another surgical instrument (26) from a tray (30) (shown in FIG. 1) in the operating room.

B. Exemplary Surgical Instrument

Figure 5:
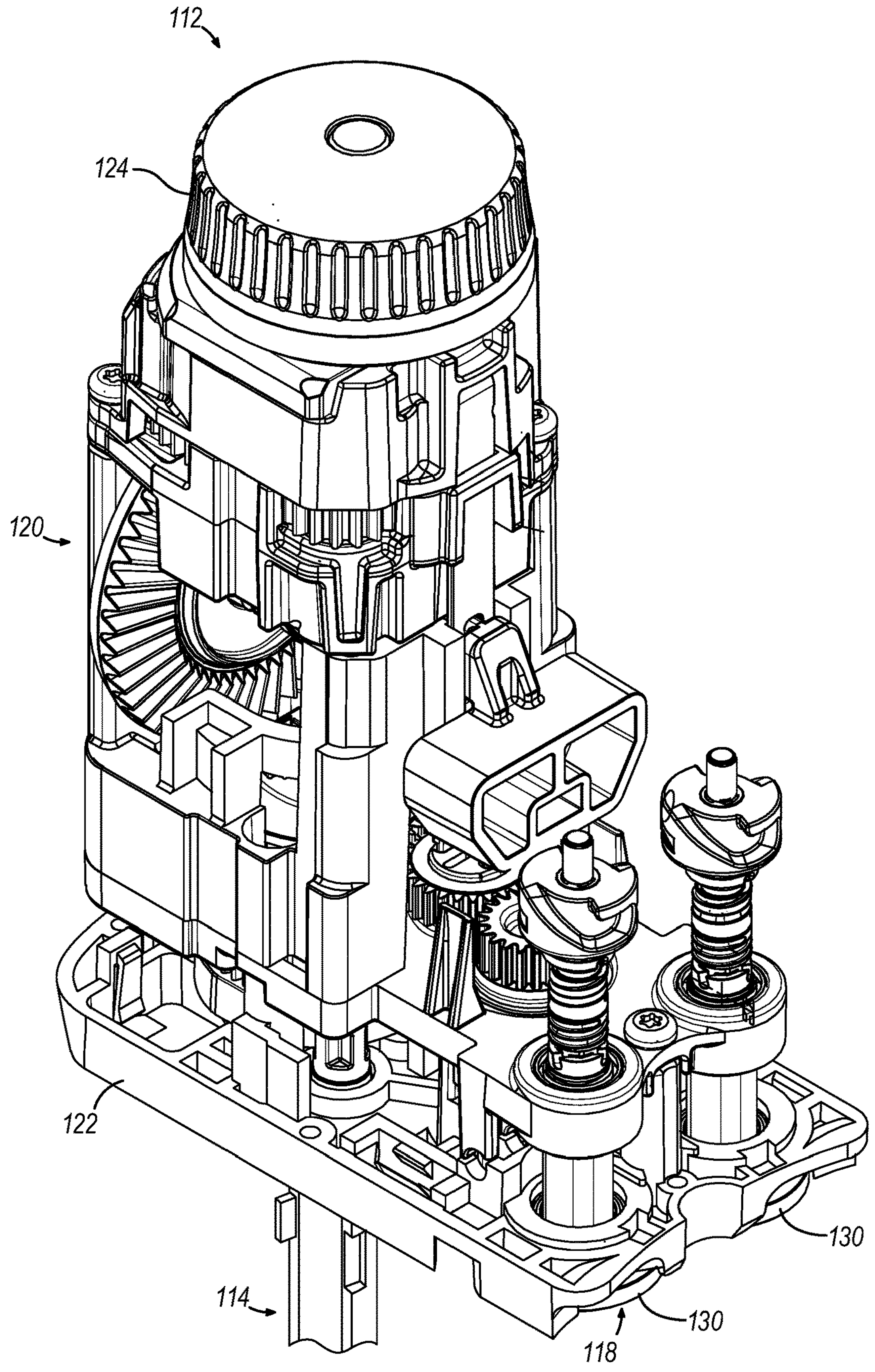
FIG. 5 depicts an enlarged perspective view of the instrument base of the surgical instrument of FIG. 4, with an outer housing omitted to reveal internal features.

FIGS. 4-5 show an exemplary surgical instrument (110) that may be mounted on and used with patient side cart (22) shown in FIG. 3. Surgical instrument (110) can have any of a variety of configurations capable of performing one or more surgical functions. As shown, surgical instrument (110) includes an instrument base (112), a shaft assembly (114) extending distally from instrument base (112), and an end effector (116) at a distal end of shaft assembly (114). An articulation joint (132) is disposed between shaft assembly (114) and end effector (116). As shown in phantom lines in FIG. 4, in the articulated state the entirety of end effector (116) (including upper and lower jaws (150, 152)) extends at an angle relative to shaft assembly (114). As shown in solid lines in FIG. 4, in the non-articulated state, end effector (116) extends parallel with shaft assembly (114). Instrument base (112) includes an attachment interface (118) that includes input couplers (130) that are configured to interface with and be driven by corresponding output couplers (not shown) of robotic arm (42) of patient side cart (22).

FIG. 5 shows an enlarged perspective view of instrument base (112) of surgical instrument (110). Instrument base (112) includes a drive system (120) mounted on a chassis (122) and having one or more actuators for actuating end effector (116) to clamp, staple, and cut tissue, and for articulating end effector (116) relative to a longitudinal axis defined by shaft assembly (114). Drive system (120) may include a manual actuator (124), which is shown in the form of a knob configured to be manually rotated. Manual actuator (124) may engage other components of surgical instrument (110) to serve as a "bailout" mechanism to obtain a desired movement in end effector (116) without powered actuation of drive system (120). Shaft assembly (114) may include additional drive components, such as portions of a drive train (126), that may couple instrument base (112) to a moveable feature (128) of shaft assembly (114) that may be coupled to end effector (116). Shaft assembly (114) may be configured for use with a variety of interchangeable end effectors (116), such as a cutter, grasper, a cautery tool, a camera, a light, or a surgical stapler, for example.

C. First Exemplary End Effector

Figure 6:
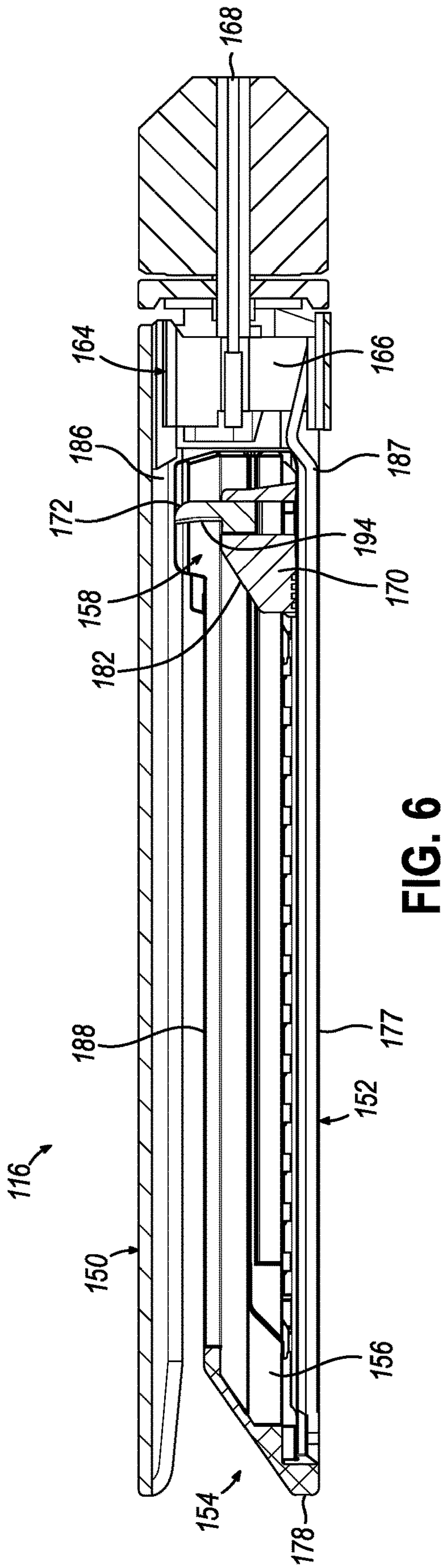
FIG. 6 depicts a side cross-sectional view of the end effector of FIG. 4, where the end effector includes a staple cartridge.

FIG. 6 shows a cross-sectional side view of end effector (116) of surgical instrument (110). End effector (116) extends distally from a distal end of shaft assembly (114). In the present example, end effector (116) comprises a surgical stapler, which may also be referred to herein as an "endocutter," configured to clamp, cut, and staple tissue. As illustrated, end effector (116) includes opposing upper and lower jaws (150, 152) configured to move relative to one another between open and closed positions for clamping and releasing tissue.

One or both of upper and lower jaws (150, 152) may be configured to pivot and thereby actuate end effector (116) between open and closed positions. Lower jaw (152) includes a staple cartridge tray (177) which accepts and supports a stapling assembly in the form of a removable staple cartridge (154) therein. In other examples, an entirety or a portion of the stapling assembly may be non-removably integrated into the structure of end effector (116). In the illustrated example, lower jaw (152) is pivotable relative to upper jaw (150) to move between an open, unclamped position and a closed, clamped position. In other examples, upper jaw (150) may move relative to lower jaw (152) (e.g., similar to end effector (210) of FIGS. 9-10). In still other examples, both and upper and lower jaws (150, 152) may move to actuate end effector (116) between open and closed positions. In the present example, lower jaw (152) is referred to as a "cartridge jaw" or "channel jaw," and upper jaw (150) is referred to as an "anvil jaw."

Figure 9:
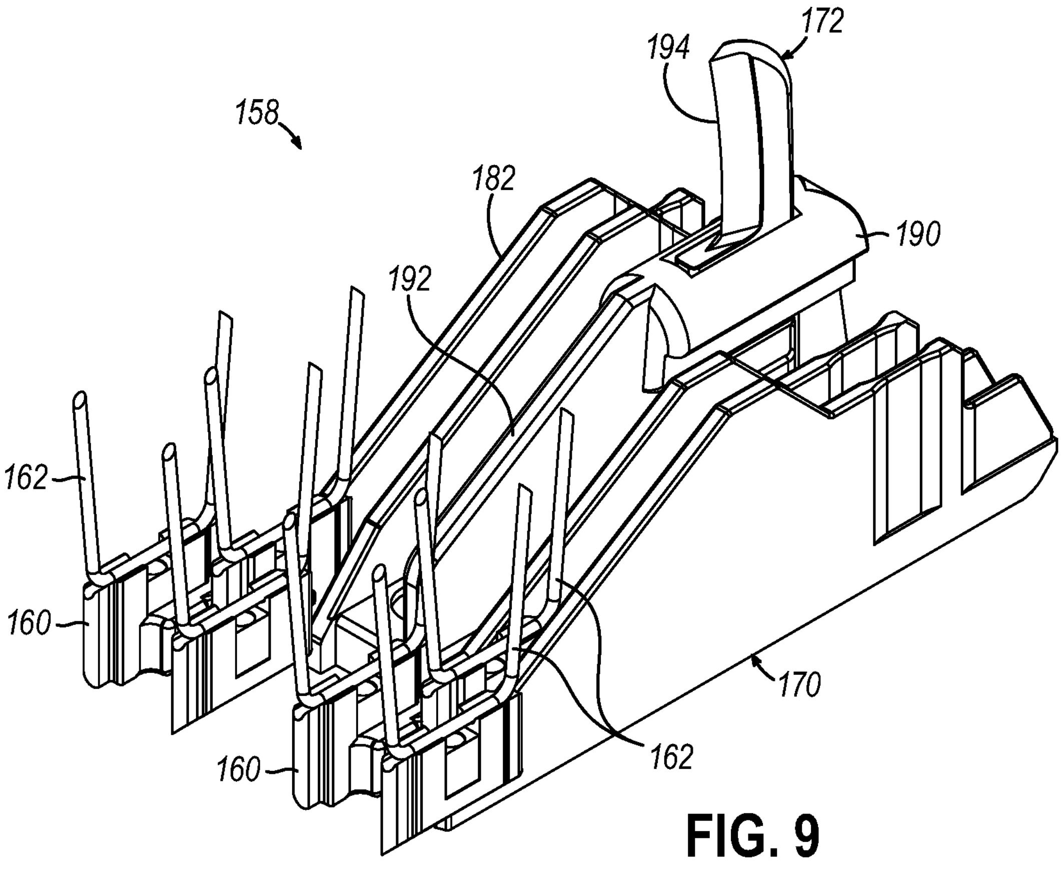
FIG. 9 depicts a firing assembly, staple drivers, and staples configured for use with the staple cartridge of FIG. 7.

Upper jaw (150) defines a surface that has a plurality of pockets (not shown) and operates as an anvil to deform staples ejected from staple cartridge (154) during operation. Staple cartridge (154) is replaceable, for example, by removing a used staple cartridge (154) from end effector (116) and inserting a new staple cartridge (154) into lower jaw (152). Staple cartridge (154) includes a staple cartridge body (156) that houses a firing assembly (158), a plurality of staple drivers (160) (also referred to as staple pushers), and a plurality of staples (162). As shown in FIGS. 6 and 8, end effector (116) includes a driving assembly (164) that includes a pusher member (166) that is operatively coupled with an actuation mechanism via a push rod (168). As shown in FIG. 6 and FIG. 9, firing assembly (158) includes a wedge sled (170) (also referred to as a staple pushing shuttle), and a knife member (172).

Figure 7:
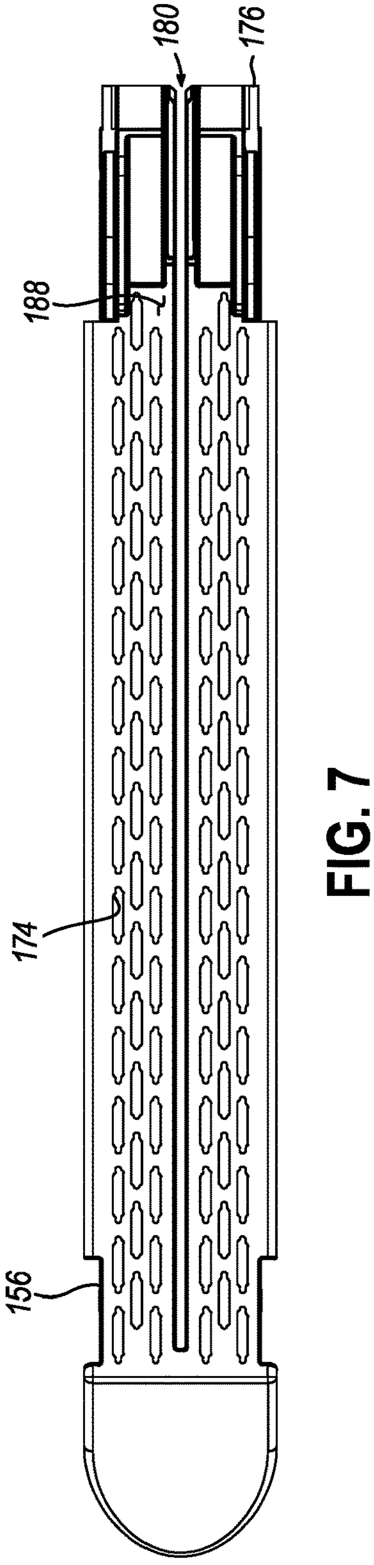
FIG. 7 depicts a top view of a deck of the staple cartridge of FIG. 6.

FIG. 7 shows a top view of staple cartridge body (156). Staple cartridge body (156) includes an array of staple accommodating apertures (174) (also known as openings) extending through an upper deck (188) of staple cartridge body (156). Each aperture (174) slidably houses a respective staple (162) in an unformed state and a free end of a corresponding staple driver (160) positioned beneath the unformed staple (162). Staple cartridge (154) includes proximal and distal ends (176, 178). In operation, staples (162) are sequentially deployed from apertures (174) by staple drivers (160) starting at proximal end (176) and advancing toward distal end (178). A vertical slot (180), configured to accommodate knife member (172), extends through part of staple cartridge (154).

FIG. 8 shows pusher member (166) as including first and second flanges (184, 185). First flange (184) is configured to be received in a longitudinal slot (186) (shown in FIG. 6) of upper jaw (150) and second flange (185) is configured to be received in a longitudinal slot (187) (shown in FIG. 6) of staple cartridge body (156) of lower jaw (152). First and second flanges (184, 185) move along longitudinal slots (186, 187) during actuation of pusher member (166). In some versions, pusher member (166) may include a single flange (e.g., omitting first flange (184)). As shown, longitudinal slot (186) is generally enclosed and longitudinal slot (187) opens to an exterior surface of lower jaw (152).

FIG. 9 shows a perspective view of firing assembly (158), which is configured to be slidably received within the proximal end (176) of staple cartridge body (156) in a longitudinal direction prior to engaging staple drivers (160) and staples (162). Wedge sled (170) of firing assembly (158) slidingly interfaces with staple cartridge body (156). More specifically, wedge sled (170) advances distally along staple cartridge body (156) such that ramp portions (182) of wedge sled (170) contact staple drivers (160). Staple drivers (160) push staples (162) out of apertures (174) of staple cartridge body (156) to penetrate through and staple tissue clamped between staple cartridge body (156) and upper jaw (150). An initial distal actuation of pusher member (166) may move pusher member (166) into contact with wedge sled (170), with further actuation pushing staples (162) transversely out of staple cartridge body (156).

At an initial proximal position of wedge sled (170), knife member (172) is housed within staple cartridge body (156). The position of knife member (172) is controlled during a first portion of the movement of wedge sled (170) from proximal end (176) of staple cartridge body (156) to distal end (178) of staple cartridge (154), so that a cutting edge (194) of knife member (172) extends through vertical slot (180). Vertical slot (180) accommodates cutting edge (194) of knife member (172) as firing assembly (158) is moved toward distal end (178) of staple cartridge (154). Wedge sled (170) includes a guide member (190) that provides a bearing surface that cooperates with a similarly shaped surface of staple cartridge body (156) to guide wedge sled (170). Guide member (190) extends from a vertical rib member (192) of wedge sled (170), which forms a central portion of wedge sled (170). In some versions, knife member (172), or at least cutting edge (194), may be retracted below upper deck (188) of staple cartridge body (156) prior to firing assembly (158) reaching its distal most position adjacent to distal end (178) of staple cartridge (154).

D. Second Exemplary End Effector

Figure 10:
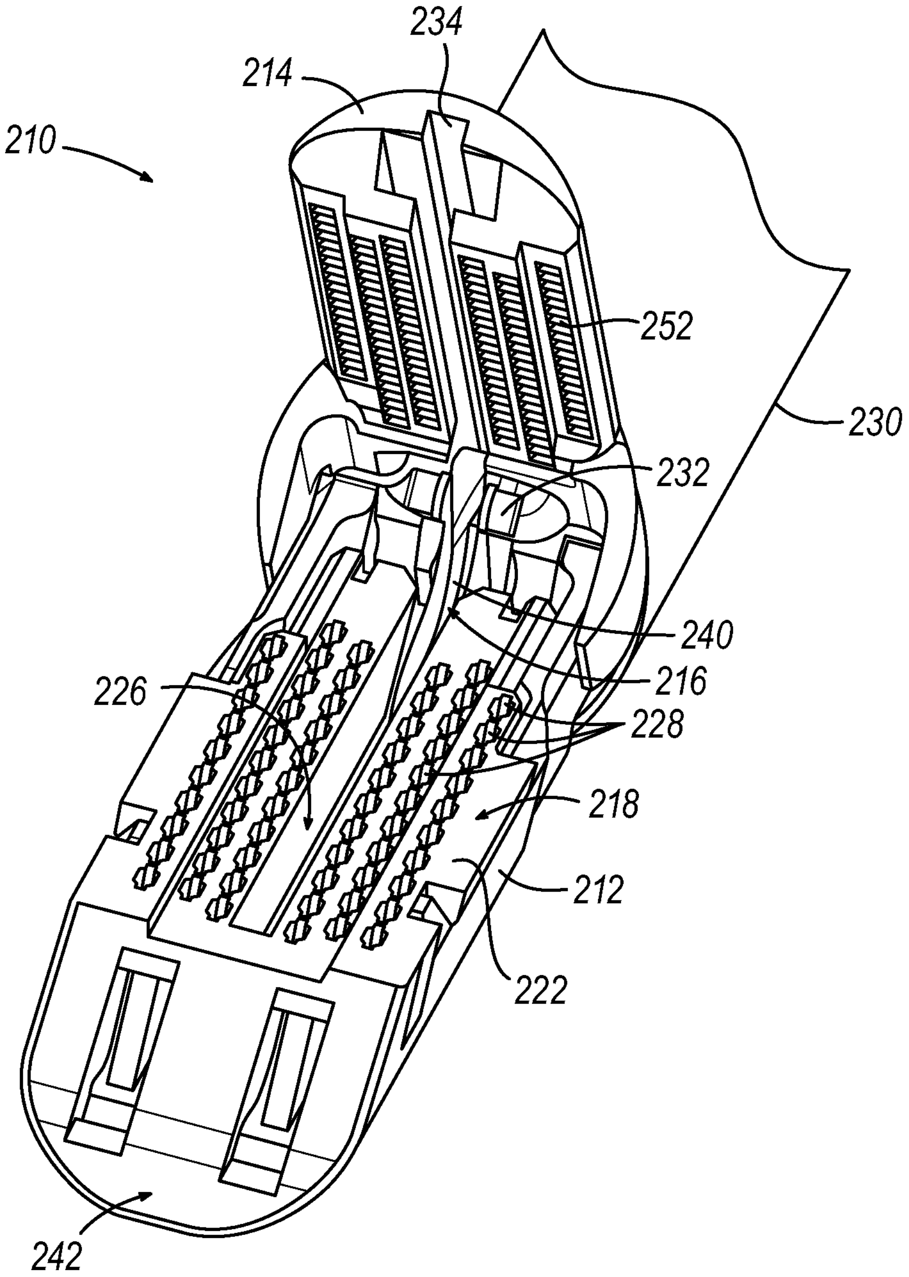
FIG. 10 depicts a second exemplary end effector that may be configured for use with the robotic surgical system of FIG. 1.
Figure 11:
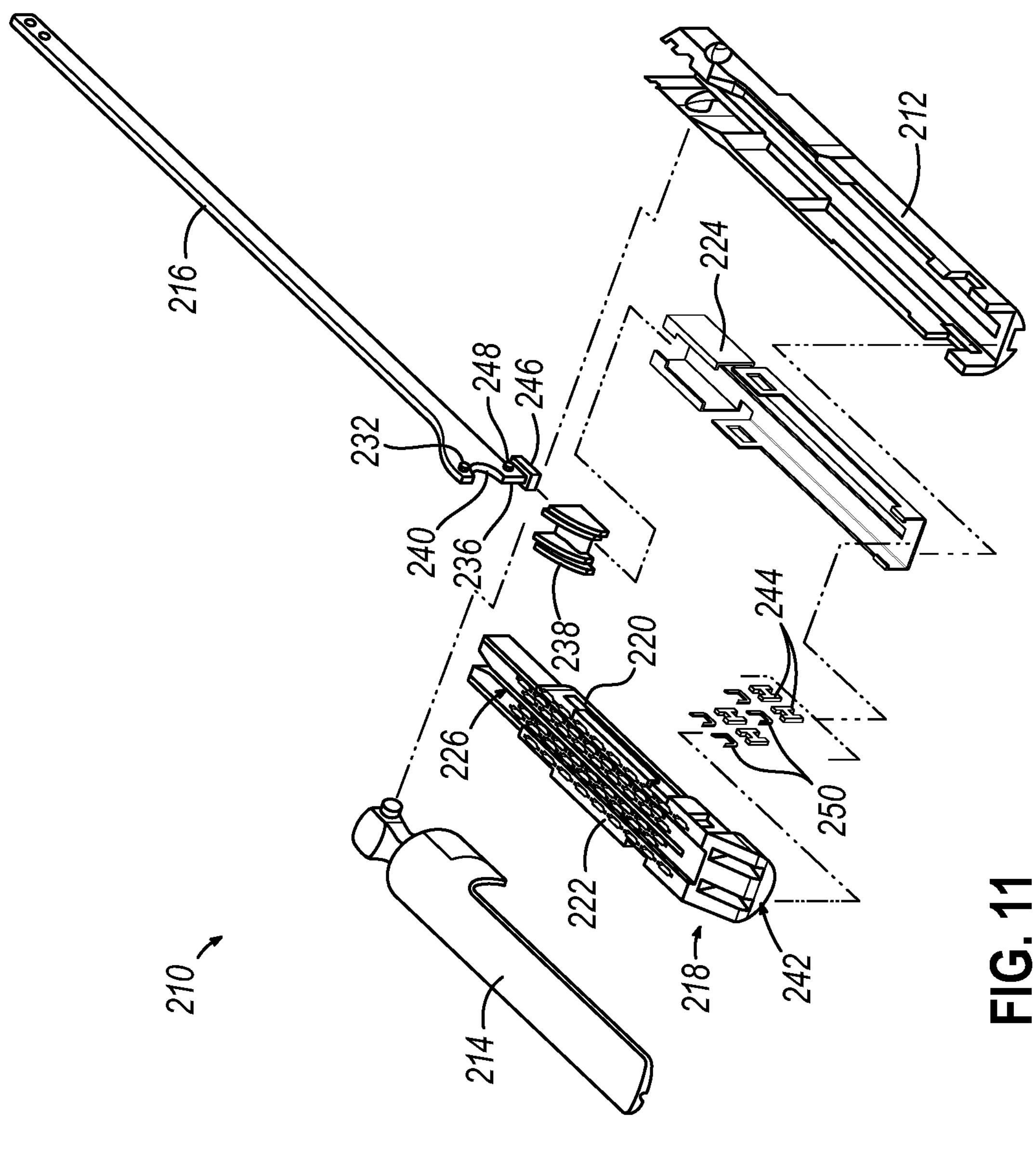
FIG. 11 depicts an exploded view of the end effector of FIG. 10.

FIGS. 10-11 show a second exemplary end effector (210), in an open position, that is configured to compress, cut, and staple tissue. End effector (210) may be configured for use with surgical instrument (110) of FIG. 4, or with surgical instruments of alternative constructions. End effector (210) may be constructed and operable in accordance with at least some of the teachings of U.S. patent application Ser. No. 16/916,295, entitled "Surgical Stapler Cartridge Retainer with Ejector Feature," filed Aug. 3, 2020, issued as U.S. Pat. No. 11,497,494 on Nov. 15, 2022, the disclosure of which is incorporated by reference herein in its entirety. End effector (210) of the present example includes a lower jaw (212) and an upper jaw in the form of a pivotable anvil (214). Lower jaw (212) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (214) may be constructed and operable in accordance with at least some of the teachings of U.S. Pat. No. 10,092,292, entitled "Staple Forming Features for Surgical Stapling Instrument," issued Oct. 9, 2018, the disclosure of which is incorporated by reference herein in its entirety.

FIG. 10 shows end effector (210), where anvil (214) is pivoted to an open position and a firing beam (216) is proximally positioned, allowing an unspent staple cartridge (218) to be removably installed into a channel of lower jaw (212). Staple cartridge (218) includes a cartridge body (220), which presents an upper deck (222) and is coupled with a lower cartridge tray (224). A vertical slot (226) is formed through part of staple cartridge (218) and opens upwardly through upper deck (222). One or more rows of staple apertures (228) are formed through upper deck (222) on one side of vertical slot (226), with one or more rows of staple apertures (228) being formed through upper deck (222) on the other side of vertical slot (226). End effector (210) is closed by distally advancing a closure tube (not shown) and a closure ring (230). Firing beam (216) is then advanced distally so that an upper pin of firing beam (216) enters longitudinal anvil slot (234). Simultaneously, a pusher block (236) located at the distal end of firing beam (216) engages a wedge sled (238) housed within cartridge body (220), such that wedge sled (238) is pushed distally by pusher block (236) as firing beam (216) is advanced distally through staple cartridge (218) and anvil (214).

During firing, cutting edge (240) of firing beam (216) enters vertical slot (226) toward distal end (242) of staple cartridge (218), severing tissue clamped between staple cartridge (218) and anvil (214). As best seen in FIG. 11, wedge sled (238) presents inclined cam surfaces that urge staple drivers (244) upwardly as wedge sled (238) is driven distally through staple cartridge (218). A firing beam cap (246) slidably engages a lower surface of lower jaw (212). Wedge sled (238) is movable longitudinally within staple cartridge (218), while staple drivers (244) are movable vertically within staple cartridge (218). A middle pin (248) and pusher block (236) of firing beam (216) together actuate staple cartridge (218) by entering into vertical slot (226) within staple cartridge (218), driving wedge sled (238) distally into upward camming contact with staple drivers (244) that in turn drive staples (250) out through staple apertures (228) and into forming contact with staple forming pockets (252) on the inner surface of anvil (214). Additional examples of alternative surgical instruments and/or associated features are described in U.S. patent application Ser. No. 16/946,363, entitled "Articulation Mechanisms for Robotic Surgical Tools," filed on Jun. 18, 2020, issued as U.S. Pat. No. 11,896,202 on Feb. 13, 2024, the disclosure of which is hereby incorporated by reference herein in its entirety.

It will be appreciated that any one or more of the teachings described below may be combined with any one or more of the teachings described above in connection with FIGS. 1-11.

II. Exemplary Multi-Threshold Motor Control Algorithm for Surgical Stapler

A. System Overview

It may be desirable to improve motor control of one or more motors associated with robotic arm (42) and/or surgical instrument (26) described above to better compensate for a particular state of the motor and thereby improve performance of surgical instrument (26) during a surgical procedure. For example, it may be beneficial to improve motor efficiency and transitions from a static state to n active state, as well as to account for variable manufacturing tolerances and/or differing powering capacities of the motor(s). The exemplary methods and configurations described below provide such enhanced capabilities.

FIG. 12 shows another exemplary robotic surgical system (310) that includes a robotic arm (312) and a surgical instrument, shown in the form of surgical instrument (110) which is configured to removably couple with robotic arm (312). Robotic surgical system (310) is similar to robotic surgical system (10) with differences described below. For example, robotic arm (312) may be similar to robotic arm (42) described above with reference to FIGS. 1-4. Robotic arm (312) may suitably interact with robotic surgical system (310) such that a medical professional operator may utilize robotic surgical system (310) to control instrument (110) via robotic arm (312), input control devices (36) of surgeon's console (16), and any other suitable intermediate components as would be apparent to one skilled in the art in view of the teachings described herein.

As previously described with reference to FIGS. 4-10, surgical instrument (110) includes shaft assembly (114), driving assembly (164), and end effector (116, 210). Driving assembly (164) may extend through at least a portion of shaft assembly (114) and end effector (116, 210). Driving assembly (164) is operable to staple and cut tissue based on instruction from motor controller (320). End effector (116, 210) includes first and second jaws (150, 152, 212, 214). At least one of first or second jaws (150, 152, 212, 214) is configured to pivot relative to the other of first or second jaws (150, 152, 212, 214). End effector (116, 210) is operatively coupled with shaft assembly (114). First jaw (150, 212) includes an anvil, and second jaw (152, 214) is configured to receive staple cartridge (154, 218) that includes staples (250). Lockout assembly (314) may be moved between a lockout configuration and a non-lockout configuration. The lockout configuration prevents actuation of firing assembly (158). In the lockout configuration, the complete firing of end effectors (116, 210) is prevented. Conversely, the non-lockout configuration allows for actuation of firing assembly (158).

Robotic arm (312) includes at least one motor (316), a sensor assembly (318), and a motor controller (320). One or more output couplers (322) of robotic arm (312) are configured to selectively couple with at least one or more input couplers (130) of surgical instrument (110). Input coupler (130) is configured to interface with and be driven by output coupler (322) of robotic arm (312). Output coupler (322) and input coupler (130) may include any suitable components as would be apparent to one skilled in the art in view of the teachings herein. Motor controller (320) may be in communication with input control devices (36) of surgeon's console (16).

Any suitable number of input couplers (130) and any suitable number of output couplers (322) may be utilized as would be apparent to one skilled in the art in view of the teachings herein. While not shown, a first output coupler (322) may couple with a first input coupler (130) and a second output coupler (not shown) may couple with a second input coupler (not shown). For example, the second input coupler may be controlled by a second motor to perform separate functions. In instances where end effector (210) is operatively attached to the distal end of shaft assembly (114), motor (316) and the respective output coupler (322) and input coupler (130) may be utilized to actuate firing beam (216); while second motor (not shown) and the respective output coupler (not shown) and second input coupler (not shown) may be utilized to actuate closure tube (not shown) and closure ring (230).

Motor (316) is configured to actuate driving assembly (164) to deploy staples from staple cartridge (154, 218). Motor (316) is configured to drive firing assembly (158) within end effector (116, 210) to advance knife through end effector (116, 210) or fire a plurality of staples (250) out of staple cartridge (154, 218). Motor controller (320) is in communication with motor (316). Sensor assembly (318) is configured to sense values of interrelated trigger related to operation of motor (316). As shown, sensor assembly (318) is disposed within robotic arm (312); however, it is envisioned that sensor assembly (318) may be positioned in a variety of locations that are suitable to instruct the operation of motor (316). For example, sensor assembly may be disposed within surgical instrument (110) (e.g., in or adjacent to end effector (116, 210)). Sensor assembly (318) may include one or more of a force sensor, a current sensor, a temperature sensor, or a position sensor. Data obtained from sensor assembly (318) may be stored on storage device (326) for later access by motor controller (320).

Motor controller (320) may also be in communication with storage device (326) such that motor controller (320) may communicate data to storage device (326), and such that motor controller (320) may access and utilize data stored on storage device (326). Motor controller (320) and storage device (326) may contain any suitable number of components as would be apparent to one skilled in the art in view of the teachings herein. Motor controller (320) may utilize data contained in storage device (326) in order to establish operational parameters for robotic arm (342) while controlling a specific instrument (110).

Motor controller (320) may recall and utilize data stored on storage device (326) related to specific instruments (110) when that specific instrument (110) is coupled to robotic arm (312) for exemplary use in accordance with the description herein. For example, storage device (326) may be configured to store predetermined thresholds (e.g., force thresholds, temperature thresholds, voltage thresholds) pertaining to the specific instrument (110) in accordance with the teachings herein. Storage device (326) may be configured to store information related to a specific instrument (110), such as any suitable data accumulated during exemplary use of a specific instrument (110) as would be apparent to one skilled in the art in view of the teachings herein. In some instances, a specific instrument (110) may have an identifiable chip or other electronic device that notifies motor controller (320) of the specific instrument (110) that is coupled with robotic arm (342), therefore allowing motor controller (320) to track the specific instrument (110) and data stored on storage device (326) related to the specific instrument (110). In some instances, the specific instrument (110) may include its own storage device (326) that establishes communication with motor controller (320) when instrument (110) is initially coupled with robotic arm (312). In such instances, information regarding prior use of a specific instrument (110) may be stored on that instrument's specific storage device and accessed by motor controller (320) when the specific instrument (110) is coupled to robotic arm (312).

While in the current example, storage device (326) is housed within robotic arm (312), storage device (326) may be associated with any suitable component as would be apparent to one skilled in the art in view of the teachings herein. For example, storage device (326) may be housed within instrument (110) such that storage device (326) may selectively establish communication with motor controller (320) while instrument (110) is coupled to robotic arm (312). As another example, storage device (326) may be associated with surgeon's console (16). In other instances, multiple storage devices (326) may be utilized, each associated with various components, such that each storage device (326) stores data related to the respective specific component.

B. Exemplary Method

Figure 13:
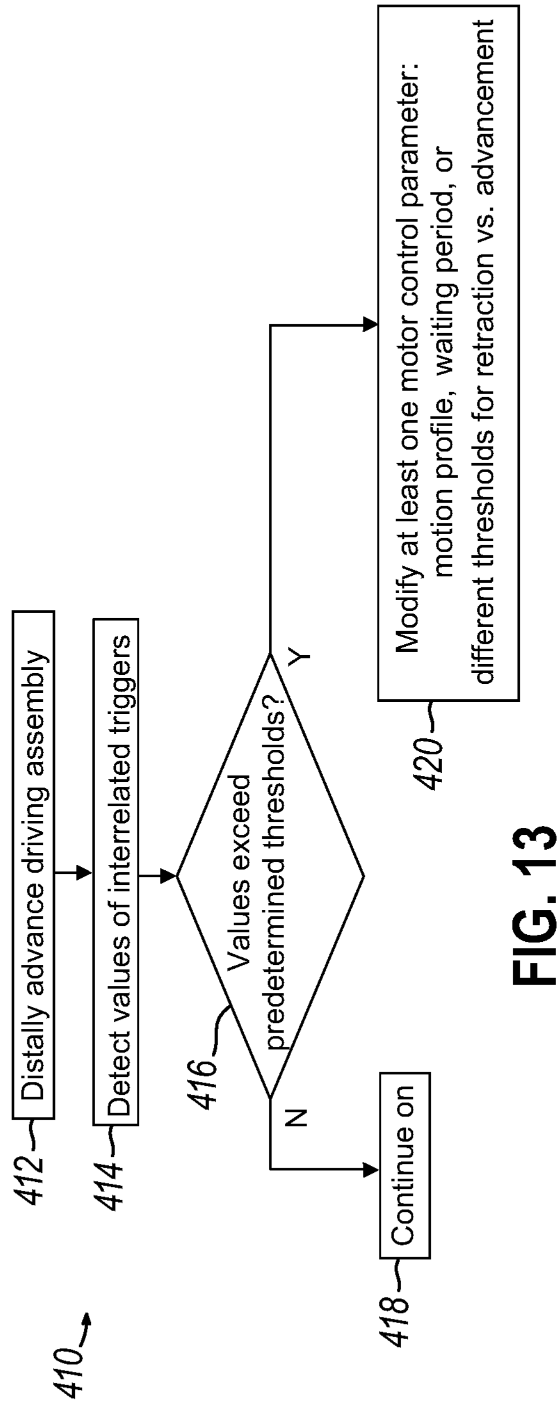
FIG. 13 depicts a block diagram of a first exemplary motor control algorithm that may be used by the robotic arm and surgical instrument shown in FIG. 12.

As described with reference to FIG. 13, method (410) includes exemplary steps (412, 414, 416, 418, 420). At step (412), motor controller (320) may activate motor (316) to distally advance driving assembly (164) into contact with firing assembly (158). At step (414), interrelated triggers may be measured or otherwise detected. In some versions, the values of the interrelated triggers may be detected using sensor assembly (318). The interrelated triggers affect at least one motor control parameter.

At step (416), motor controller (320) may determine whether the measured values of interrelated triggers exceed predetermined thresholds. For example, the predetermined thresholds may include a measured firing motor force that exceeds a maximum firing motor force threshold of motor (316), a measured temperature that exceeds a maximum temperature threshold of motor (316), a measured current that exceeds a maximum current threshold of motor (316) and/or a measured distance exceeds the lockout value (indicating lockout assembly (314) is in the non-lockout configuration). As will be described in greater detail below with reference to FIGS. 14-22, the interrelated triggers may include firing motor force, firing motor current, or firing motor temperature, and/or duty cycle. It is envisioned that any one of the triggers referenced in FIGS. 14-22 may be used in combination with another one or more triggers referenced in FIGS. 14-22. Using multiple triggers in combination may provide additional benefits, and may have a cumulative effect that is different than the triggers being assessed and modified separately. In other words, there are cooperative benefits associated with modifying the performance of motor (316) using multiple trigger variables in combination.

At step (418), if the measured values of the interrelated triggers do not exceed the predetermined thresholds, motor controller (320) continues operation according to a predetermined motion profile. However, at step (420), if one or more of the measured values of interrelated triggers do exceed the predetermined thresholds, motor controller (320) may modify at least one motor control parameter of motor (316). Exemplary motor control parameters may include, for example, a motion profile instituted by motor controller (320) using motor (316), a waiting period where power to motor (316) is reduced or stopped, or differing thresholds based on whether driving assembly (164) is distally advancing or proximally retracting. For example, the motor firing current threshold and/or the firing motor force threshold for retraction may be greater than the predetermined threshold for advancement. In some versions, in response to the values exceeding the predetermined thresholds, motor controller (320) is configured to modify two or more motor control parameters. As will be described in greater detail below with reference to FIGS. 14-22, the motor control parameters may cooperate to determine max control motions, waits, or change in operation. The control parameters may include wait time, alternating cycle rate, speed control, or changing the threshold limits. The motion profile may be sustained or intermittent pulse of motor power to change performance of driving assembly (164) (see FIG. 8) or firing beam (216) (see FIG. 11) on end effector (116, 210). In some versions, motor controller (320) is configured to withhold modification of at least one motor control parameter until each of the values of the first and second triggers exceed their respective predetermined thresholds. In some versions, the motor controller (320) is configured to modify one motor control parameter(s) differently in response to each of the values of the first and second interrelated trigger exceeding the predetermined thresholds as compared to a single one of the interrelated triggers exceeding the respective predetermined threshold.

During the firing process (either advancement prior or retraction), driving assembly (164) or firing beam (216) may become undesirably stuck due to frictional binding in a longitudinal position relative to staple cartridge (154, 218) such that driving assembly (164) or firing beam (216) relative to staple cartridge (154, 218) is inhibited beyond a tolerable degree. For example, during proximal retraction of pusher member (166) (see FIG. 8) in accordance with the description herein, flanges (184, 185) may overly engage or dig into portions of staple cartridge (154) and/or jaws (150, 152) defining associated longitudinal slots (186, 187), thereby inhibiting suitable movement due to an undesirable amount of frictional binding. As another example, during distal advancement of firing beam (216), upper pin (232) or firing beam cap (246) (see FIG. 11) may overly engage or dig into portions of staple cartridge (218) defining longitudinal anvil slot (234) or lower surface of lower jaw (212), respectively, thereby inhibiting suitable movement due to an undesirable amount of frictional binding. It is desirable for motor controller (320) to operate motor (316) in a manner that minimized or overcomes these issues.

C. Motor Control Using Algorithmic Bumping

Figure 15:
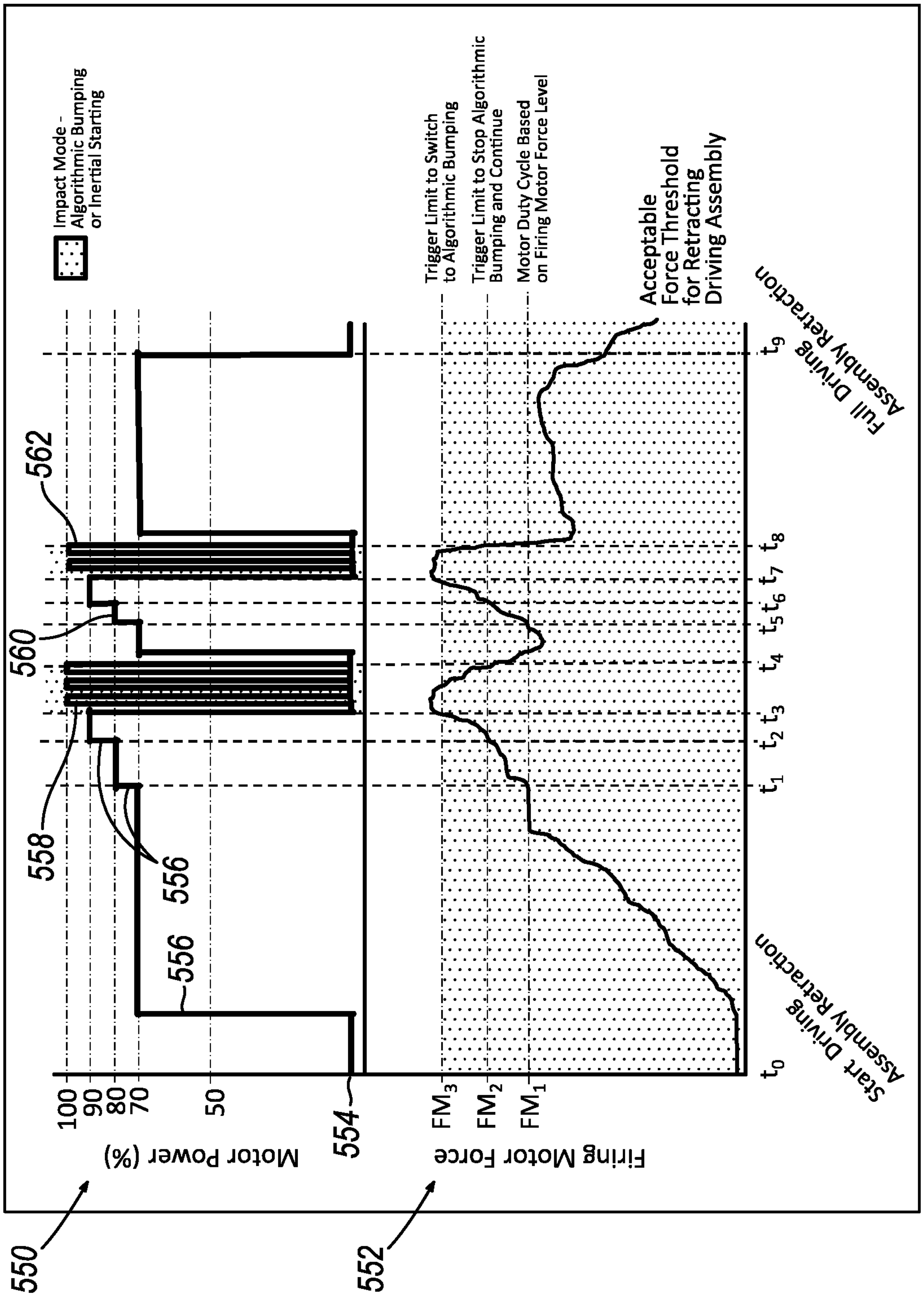
FIG. 15 depicts a multi-axis line graph with plots of motor power and firing motor force with respect to time.

As described with reference to FIG. 14-15, method (510) may include exemplary steps (512, 514, 516, 518, 520, 522, 524, 526, 528, 530, 532, 533, 534, 536, 538, 540, 542, 544, 546). While FIGS. 14-15 are described below with reference to the structures of FIGS. 1-9, method (510) may also be used with the structures of FIGS. 10-11. At step (512), motor controller (320) to activate motor (316) may distally advance driving assembly (164). At step (514), motor controller (320) may activate motor (316) so that driving assembly (164) contacts firing assembly (158). At step (516), motor controller (320) may activate motor (316) to distally advance driving assembly (164) and firing assembly (158). At step (518), firing motor force may be measured. This firing motor force may be measured by motor controller (320) interpreting data produced by motor (316) during operation and/or through the use of a sensor assembly (318) operatively coupled with motor (316) and motor controller (320). At step (520), motor controller (320) may determine whether the measured firing motor force exceeds the maximum advancement firing motor force threshold. Threshold values may be stored in storage device (326) for retrieval by motor controller (320). At step (522), if the measured firing motor force does not exceed the maximum advancement firing motor force threshold using motor controller (320), motor (316) may continue on using a predetermined firing sequence until completion of the firing sequence. At step (524), steps (518, 520, 522) may be repeated as described above (one or more times) to repeatedly determine whether the measured firing motor force exceeds the maximum advancement firing motor force.

At step (526), if the measured firing motor force exceeds the maximum advancement firing motor force threshold as determined by motor controller (320), motor controller (320) may instruct motor (316) to use algorithmic bumping or a soft start. As described below with reference to plot (550) of FIG. 15 showing retraction of driving assembly (164), algorithmic bumping (558, 562) repeatedly provides power to motor (316) then stop power to motor (316). For a soft start, motor controller (320) gradually increases power to motor (316) (e.g., by incrementally stepping up the power to motor (316)). At step (528), firing motor force may be measured, similar to step (518). At step (530), motor controller (320) may determine whether the measured firing motor force exceeds the maximum advancement firing motor force threshold, similar to step (520). At step (532), if the measured firing motor force does not exceed the maximum advancement firing motor force threshold as determined motor controller (320), motor (316) may continue on until completion of the firing sequence. At step (533), steps (528, 530, 532) may be repeated (one or more times) to determine whether the measured firing motor force exceeds the maximum advancement firing motor force.

At step (534), if the measured firing motor force exceeds the maximum advancement firing motor force threshold as determined by motor controller (320), motor controller (320) may instruct motor (316) to retract driving assembly (164) in a proximal direction, which is opposite to the distal direction of advancement. Plots (550, 552) of FIG. 15 show comparisons of motor power (as a percentage of maximum power) and firing motor force during retraction of driving assembly (164). Time (t0) refers to the time when driving assembly (164) starts being retracted, while time (t9) refers to the time when driving assembly (164) is fully retracted. At step (534), motor (316) optionally pauses or begins retracting driving assembly (164) based on instructions from motor controller (320). For example, at time (t0), shown by line (554) in plot (550), power to motor (316) may be approximately equal to zero to implement an optional waiting period. As shown, motor controller (320) instructs motor (316) to incrementally increase motor power using a soft start (556).

At step (536), firing motor force may be measured, similar to step (518). At step (538), if the measured firing motor force exceeds the maximum retraction firing motor force threshold using motor controller (320), motor controller (320) may instruct motor (316) to turn off or activate algorithmic bumping. It may be desirable to have different values for the maximum retraction firing motor force threshold as compared to the maximum advancement firing motor force threshold. In some versions, the maximum retraction firing motor force threshold exceeds the maximum advancement firing motor force threshold. Algorithmic bumping (also referred to as inertial starting) allows driving assembly (164) to improve the likelihood of moving relative to staple cartridge (154, 218) to overcome the static binding. At step (540), if the measured retraction firing motor force does not exceed the maximum retraction firing motor force threshold using motor controller (320), motor (316) may continue on (illustrated in FIG. 15 at times (t1, t2)) until completion of the retraction sequence. The stippling shaded region depicted of plot (552) of FIG. 15 represents the tolerable firing motor force threshold for retracting driving assembly (164). At step (544), steps (536, 538, 540) may be repeated as described above to repeatedly determine whether the measured firing motor force exceeds the maximum retraction firing motor force.

At step (542), if the measured retraction firing motor force exceeds the maximum retraction firing motor force threshold determined by motor controller (320), motor controller (320) instructs motor (316) to power off or switch to algorithmic bumping (558). As shown at time (t3) of FIG. 15, once firing motor force (FM3) is exceeded in plot (552), motor controller (320) instructs motor (316) to switch to algorithmic bumping (558) in plot (550). The stippling shaded regions depicted of plot (550) of FIG. 15 represents impact modes where algorithmic bumping (558, 562) is implemented to improve the effective firing motor force to provide an alternative to maximum retraction of driving assembly (164). In other words, motor controller (320) is configured to repeatedly start and stop motor (316) until the measured firing motor force is less than firing motor force threshold (FM2) to stop algorithmic bumping (558). To obtain this algorithmic bumping (558), motor controller (320) may modify the motion profile by instructing motor (316) to provide an intermittent pulse of power to alter performance of end effector (116, 210). As shown in FIG. 15, this algorithmic bumping (558) continues until time (t4) where the measured firing motor force no longer exceeds firing motor force (FM2), which acts as the trigger for stopping algorithmic bumping (558). Between time (t4) and time (t7), firing motor force is incrementally increased using a soft start (560) shown in plot (550) of FIG. 15. At time (t7), firing motor force again exceeds firing motor force (FM3), causing a switch to algorithmic bumping (562) similar to algorithmic bumping (558). This algorithmic bumping (662) continues until time (t8) where the measured firing motor force no longer exceeds firing motor force (FM2). At time, time(t9), driving assembly (164) or is fully retracted.

In some versions, motor current may serve as a substitute for firing motor force, such that firing motor current may be a trigger for alternating between the states. Additionally, the firing motor current (and optionally duty cycle) may cooperatively impact the wait period (dwell time) before engaging the second system or re-engaging the first. Duty cycle is the ratio of time a load or circuit is "on" compared to the time the load or circuit is "off". Duty cycle may be expressed as a percentage of time a load or circuit is "on". In other versions, motor (316) is configured to repeatedly start and stop motor (316) if the measured firing motor temperature is less than a maximum firing motor temperature threshold.

D. Motor Control Using Temperature

It may be desirable to prevent overheating of motor (316) by incorporating thermal control with trigger thresholds for adjustments to motor (316). As a result, motor controller (320) is able to mitigate overheat conditions and limit maximum firing motor performance due to heating.

Figure 16:
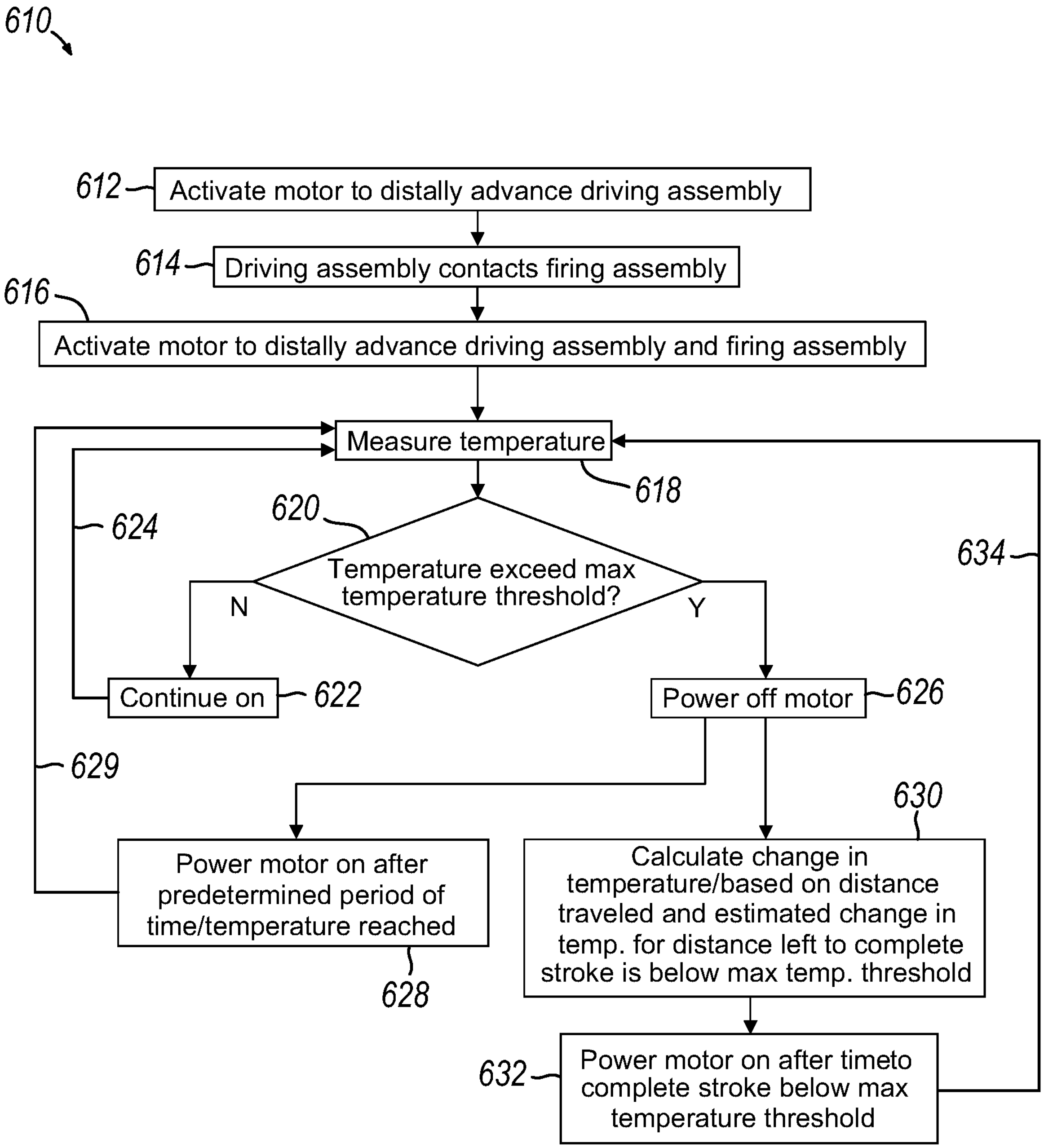
FIG. 16 depicts a block diagram of a third exemplary motor control algorithm that may be used by the robotic arm and surgical instrument shown in FIG. 12.
Figure 17:
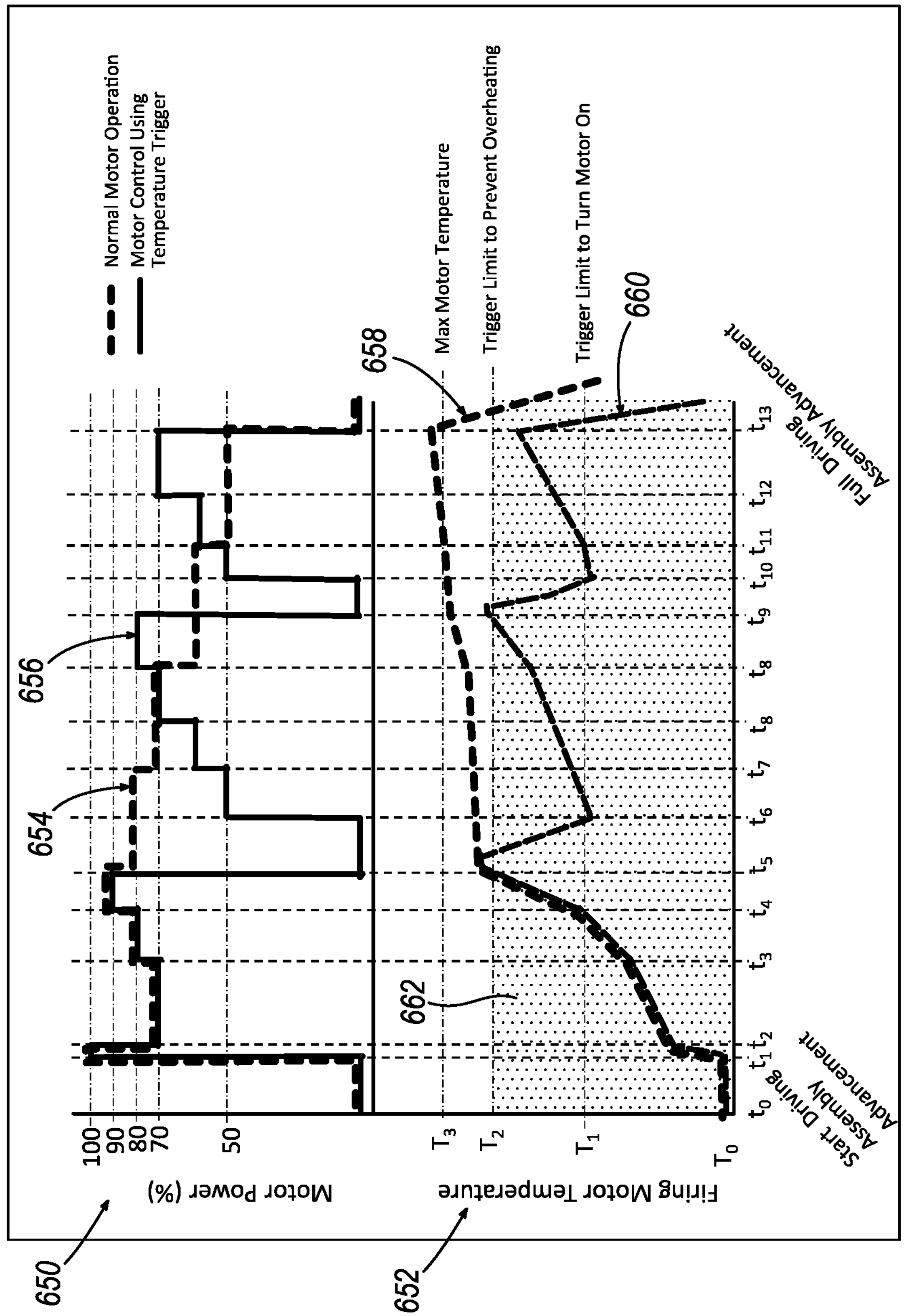
FIG. 17 depicts a multi-axis line graph with plots of motor power and firing motor temperature with respect to time.

As described with reference to FIGS. 16-17, method (610) includes exemplary steps (612, 614, 616, 618, 620, 622, 624, 626, 628, 629, 630, 632, 634) which is described together with plots (650, 652) of FIG. 17. While FIGS. 16-17 are described below with reference to the structures of FIGS. 1-9, method (610) may also be used with the structures of FIGS. 10-11. At step (612), motor controller (320) may activate motor (316) to distally advance driving assembly (164).

Plots (650, 652) of FIG. 17 show comparisons of firing motor power and firing motor temperature during advancement of driving assembly (164). Particularly, plot (650) shows overlying comparisons of firing motor power and respect to time of normal control operation (654) using a dashed line compared to motor control using firing motor temperature triggers (656) using a solid line. Similarly, plot (652) shows overlying comparisons of firing motor temperature and respect to time of normal control operation (658) using a dashed line compared to motor control using firing motor temperature triggers (660) using a solid line. Time (t0) refers to the time when driving assembly (164) starts being advanced distally, while time (t13) refers to the time when driving assembly (164) is fully advanced distally. The stippling shaded region depicted of plot (652) of FIG. 17 represents the tolerable firing motor temperature threshold for driving assembly (164).

At step (614), motor controller (320) may activate motor (316) so that driving assembly (164) contacts firing assembly (158). At step (616), motor controller (320) may activate motor (316) to distally advance driving assembly (164) and firing assembly (158). At step (618), firing motor temperature may be measured. This firing motor temperature may be measured by motor controller (320) interpreting data produced by motor (316) during operation and/or through the use of a sensor assembly (318) operatively coupled with motor (316) and motor controller (320).

At step (620), motor controller (320) may determine whether the measured firing motor temperature exceeds the maximum firing motor temperature threshold. The firing motor temperature threshold may be stored in storage device (326) for retrieval by motor controller (320). At step (622), if the measured firing motor force does not exceed the maximum temperature threshold using motor controller (320), motor (316) may continue on using a predetermined firing sequence until completion of the firing sequence. At step (624), steps (618, 620, 622) may be repeated as described above (one or more times) to determine whether the measured firing motor temperature exceeds the maximum firing motor temperature threshold. In FIG. 17, between time (t0) and time (t5), there is no change between normal control operation (654) compared to motor control using firing motor temperature triggers (656).

At step (626), if the measured firing motor temperature exceeds the maximum firing motor temperature threshold as determined by motor controller (320), motor controller (320) stop power to motor (316). As shown in FIG. 17, after time (t5), motor (316) turns off once firing motor temperature (T2) is exceeded. Power may be reactivated to motor (316), in various manners (e.g., using steps (628, 630)). For example, at step (628), motor controller (320) may provide power to motor (316) after a predetermined period of time has elapsed or after the measured firing motor temperature is below a predetermined firing motor temperature threshold. As shown in FIG. 17, after time (t5), motor (316) turns off until firing motor temperature decreases to firing motor temperature (T1), where motor controller (320) instructs motor (316) to soft start as described above. At step (629), steps (618, 620) may be repeated as described above to repeatedly determine whether the measured firing motor temperature exceeds the maximum temperature threshold. The soft start of motor (316) continues until firing motor temperature (T2) is reached corresponding to a trigger limit (threshold) to prevent overheating (which occurs at time (t9)). At time (t9), motor (316) turns off once firing motor temperature (T2) is exceeded.

At step (630), motor controller (320) may calculate the change in firing motor temperature for based on the distance already traveled and extrapolate the estimated change in temperature for distance left to complete firing stroke to ensure the estimated change in temperature is below maximum firing motor temperature threshold. The firing stroke may be completed when the staples are each deployed from staple cartridge (154) or when firing assembly (158) reaches the distal most position. Motor controller (320) may calculate the change in temperature/based on distance traveled and estimated change in temperature for distance left to complete stroke is below maximum firing motor temperature threshold. Motor (316) is configured to reduce or stop power to motor (316) based on a change in temperature of motor (316) due to the distance traveled by driving assembly (164) relative to an estimated change in temperature of motor (316) due to the distance still to travel for driving assembly (164) to complete the firing sequence. In other words, motor controller (320) calculates the change in temperature increase over the distance traveled thus far and estimates the expected temperature increase for the distance left to travel and remains off until it could complete the full firing stroke. For example, a greater expected temperature increase results in a longer waiting period where motor (316) remains off. As shown in FIG. 17, motor (316) turns off between time (t9) and time (t10), which allows for driving assembly (164) to complete the full firing stroke before motor (316) turns back on.

At step (632), motor controller (320) activates motor (316) to complete the firing stroke based on the calculation determined in step (630). At step (634), steps (618, 620) may be repeated as described above one or more times to determine whether the measured firing motor temperature exceeds the maximum firing motor temperature threshold.

E. Motor Control Based on Lockout Status

Figure 18:
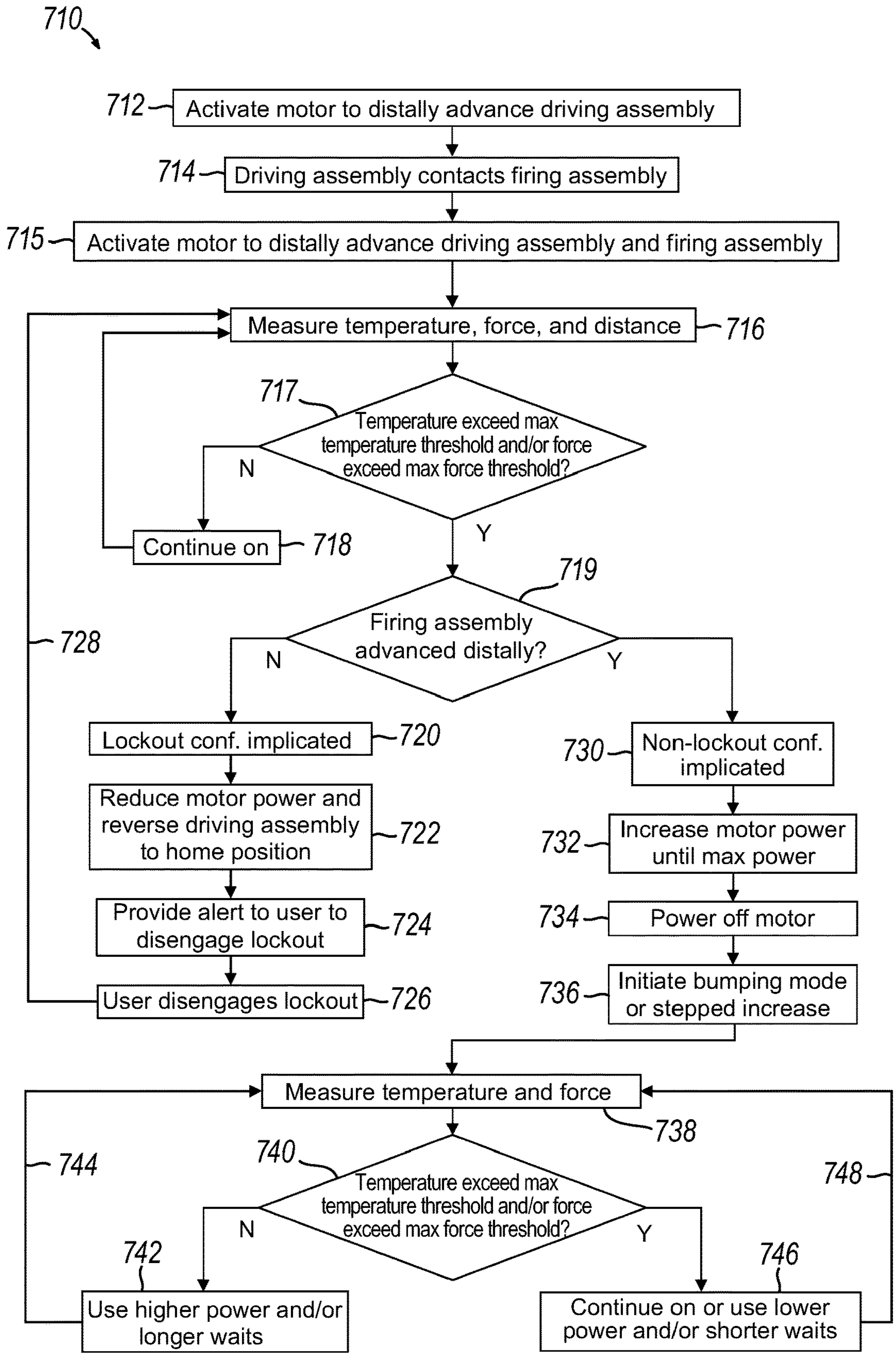
FIG. 18 depicts a block diagram of a fourth exemplary motor control algorithm that may be used by the robotic arm and surgical instrument shown in FIG. 12.
Figure 19A:
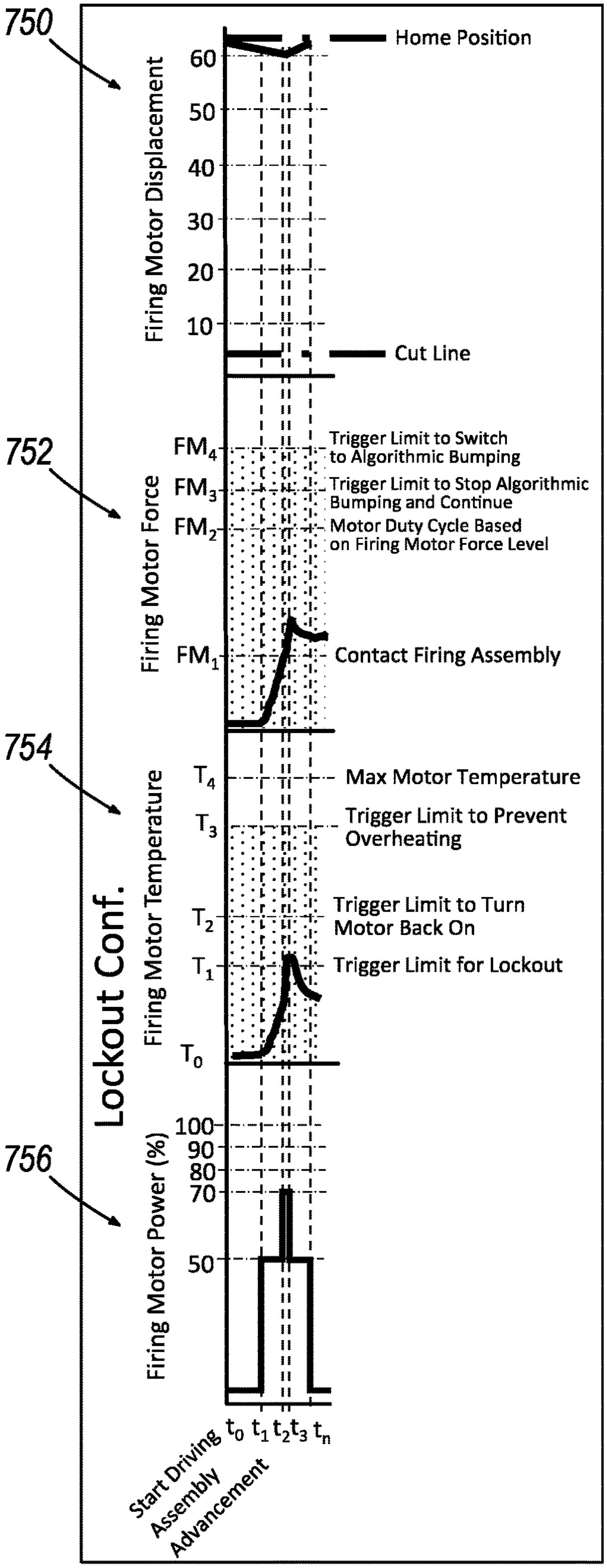
FIG. 19A depicts a multi-axis line graph with plots of firing motor displacement, firing motor force, firing motor temperature, and firing motor power with respect to time when a lockout assembly is in a lockout configuration for the exemplary method of FIG. 18.
Figure 19B:
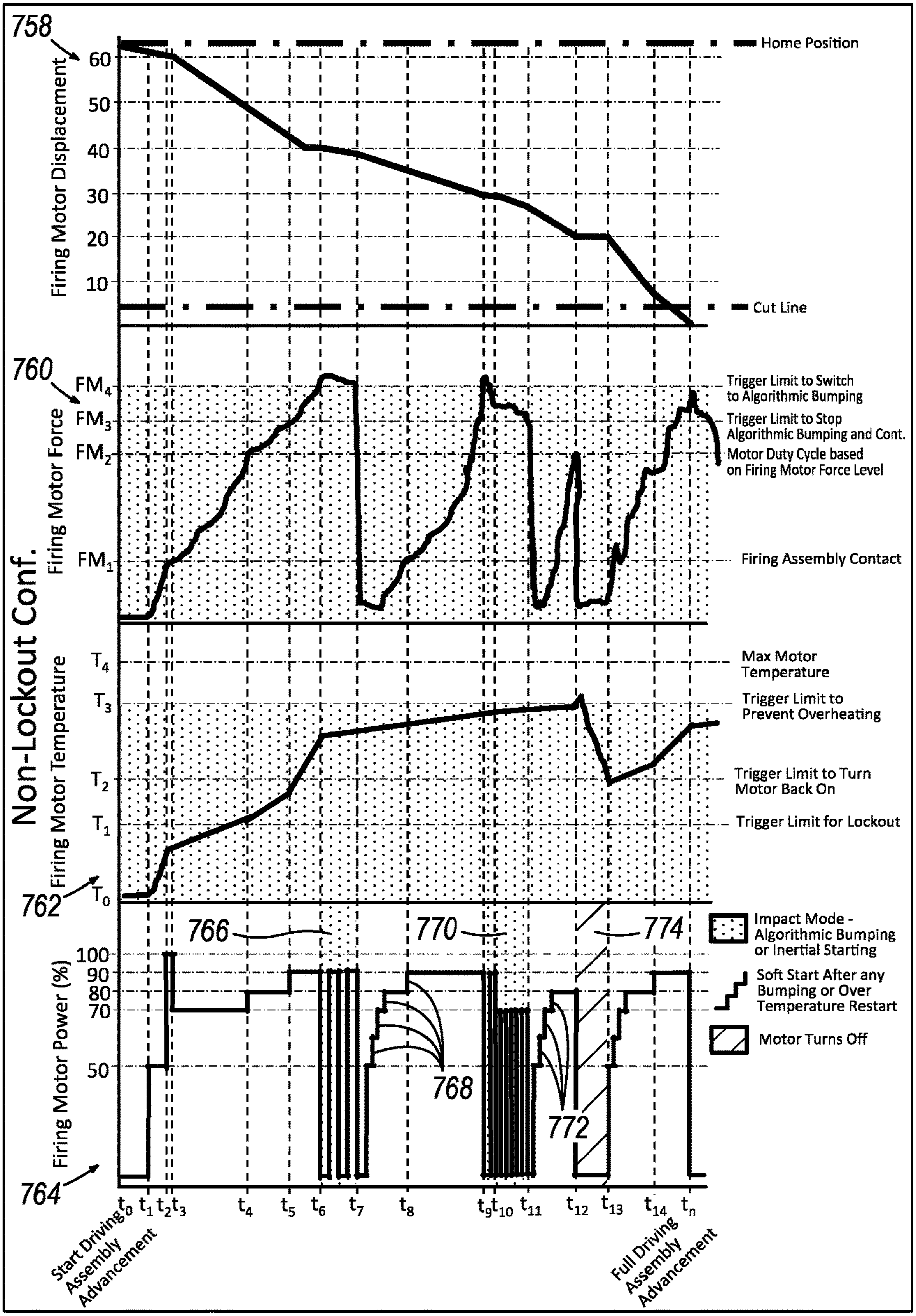
FIG. 19B depicts a multi-axis line graph with plots of firing motor displacement, firing motor force, firing motor temperature, and firing motor power with respect to time similar to FIG. 19A, but with the lockout assembly in a non-lockout configuration for the exemplary method of FIG. 18.

As described with reference to FIGS. 18-19B, method (710) includes exemplary steps (712, 714, 715, 716, 717, 718, 719, 720, 722, 724, 726, 728, 730, 732, 734, 736, 738, 740, 742, 744, 746, 748) which are described together with plots (750, 752, 754, 756, 758, 760, 762, 764) of FIGS. 19A-19B. While FIGS. 18-19B are described below with reference to the structures of FIGS. 1-9, method (710) may also be used with the structures of FIGS. 10-11. At step (712), motor controller (320) may activate motor (316) to distally advance driving assembly (164). At step (714), motor controller (320) may activate motor (316) so that driving assembly (164) contacts firing assembly (158), which is shown at time (t2) in plot (752) of FIG. 19A. FIG. 19 shows that at a predefined firing motor force limit that the firing motor temperature limit is hit indicating that the firing system made initial contact with wedge sled (170) of firing assembly (158).

At step (715), motor controller (320) may activate motor (316) to distally advance driving assembly (164) and firing assembly (158). At step (716), firing motor force, firing motor temperature, and/or distance may be measured. This firing motor force and firing motor temperature may be measured by motor controller (320) interpreting data produced by motor (316) during operation and/or through the use of a sensor assembly (318) operatively coupled with motor (316) and motor controller (320). In other words, sensor assembly (318) may measure at least one of a measured firing force of motor (316) or a measured firing motor temperature of motor (316) as motor (316) moves driving assembly (164). While not shown, sensor assembly (318) may include a position sensor may to determine if firing assembly (158) advances distally. In some versions, the position sensor is disposed in end effector (116, 210).

Step (717) may include determining whether the measured firing motor force exceeds the maximum firing motor force threshold and/or whether the measured firing motor temperature exceeds the maximum firing motor temperature threshold using motor controller (320). Threshold values may be stored in storage device (326) for retrieval by motor controller (320). At step (718), if the measured firing motor temperature exceeds the maximum firing motor temperature threshold and if the measured firing motor force does not exceed the maximum firing motor force threshold as determined by motor controller (320), motor (316) may continue on using a predetermined firing sequence until completion of the firing sequence. This measuring and determination may be repeated as described above (one or more times).

At step (719), if the measured firing motor temperature exceeds the maximum firing motor temperature and/or the measured firing motor force exceeds the maximum firing motor force threshold, motor controller (320) determines whether firing assembly is advanced distally. At step (720), if firing assembly (158) is not advanced distally, then the lockout mode implicated. As shown in plot (752) of FIG. 19A between time (t2) and time (t3), the firing motor temperature exceeds firing motor temperature (T1) which is the trigger limit for lockout assembly (314). As shown in plot (750) of FIG. 19A, firing motor displacement does not go below 60 millimeters (for a 60 mm staple cartridge), indicating firing assembly (158) is not advanced distally meaning that lockout assembly (314) is in the lockout configuration. At step (722), once motor controller (320) determines the lockout configuration is implicated, motor controller (320) may reduce/stop power of motor (316) and/or driving assembly (164) may be reversed to the home position. The lockout configuration does not allow the driving assembly (164) to advance once certain triggers are hit (e.g., firing motor temperature or firing motor force), and as driving assembly (164) continues to drive forward the firing motor force and firing motor temperature begin to increase since the lockout assembly (314) is not disengaged and motor (316) is trying to drive the system against itself. Motor (316) may proximally translate driving assembly (164) in response to motor controller (320) determining lockout assembly (314) is in the lockout configuration.

At step (724), an alert may be provided to the user to disengage lockout assembly (314). The alert may include one or more of a visual indication, a tactile indication, an audible indication. At step (726), the user may disengage lockout assembly (314) to switch lockout assembly (314) to the non-lockout configuration. After disengaging lockout assembly (314), step (716) may again be performed.

At step (730), if firing assembly (158) advances distally then the non-lockout configuration is implicated (since firing assembly (158) travels distally beyond the point where lockout assembly (314) prevents travel). As shown in plot (758) of FIG. 19B, firing motor displacement drops below 60 millimeters. At step (732), in response to determining the non-lockout configuration is implicated, motor controller (320) may increase power of motor (316). Motor (316) is configured to modify the motion profile by increasing power to motor (316) until a maximum firing motor force threshold of motor (316) is reached. Maximum firing motor power is reached at time (t2) in plot (764) of FIG. 19B. The non-lockout configuration proceeds forward if the firing motor distance, firing motor temperature, firing motor force limits are acceptable. As shown in FIG. 19B, the power of motor (316) increases as different firing motor force limits are hit allowing the motor (316) to step up until a maximum firing motor force threshold is hit.

At step (734), method (710) may include motor controller (320) ceasing power to motor (316). and response to the maximum firing motor force threshold of motor (316) being reached, powering off motor (316). Once the maximum firing motor force threshold is exceeded, motor controller (320) turns off motor (316). After powering off motor (316), restarting motor (316) after one of a predetermined time, a predetermined temperature, or an estimated temperature to deploy staples from staple cartridge (154, 218). At step (736), motor controller (320) may initiate algorithmic bumping mode (at time (t6) in plot (764) of FIG. 19B). At step (740), motor controller (320) determines whether the measured firing motor temperature exceeds max temperature threshold and/or whether the measured firing motor force exceed maximum firing motor force threshold. At step (738), if measured firing motor temperature does not exceed max temperature threshold and the measured firing motor force does not exceed the maximum firing motor force threshold motor controller (320) may instruct motor (316) to use higher power and/or longer waits (shown by soft start (768)). At step (740), if measured firing motor temperature exceeds max temperature threshold and/or the measured firing motor force exceeds the maximum firing motor force threshold, motor controller (320) may instruct motor (316) to continue on or use lower power and/or shorter waits.

In some versions, motor controller (320) may modify the motion profile by alternating cycle rate or changing the speed at which driving assembly (164) travels. The response of the impact/bumping mode depends on the response of the firing motor force of plot (760) and firing motor temperature of plot (762). As shown in plot (760), a first impact/bumping mode (766) (shown in plot (764) using stippling) continues with higher power and longer pauses/cycles since the measured firing motor force did not reduce. Once the firing motor force decreases below the tolerable trigger limit and temperature limit is tolerable, driving assembly (164) re-engages in a soft start mode for a defined set point then return to a variable motor power level based on predefined inputs. Motor (316) turns off for a predetermined time or temperature, a soft start may be used to turn motor (316) on at a lower state than originally reduce the likelihood of overheating motor (316) to overheat or slowly turn motor (316) on to be able to check parameters before returning to a normal state.

The second impact/bumping mode (770) (shown in plot (764) using stippling) initially starts with a high-power cycle and the firing motor force drops in which the response is the lower power quicker impacts/bumping until it hits the trigger limit to continue operation. As shown, once the firing motor temperature trigger (T3) is hit at time (t12), then power to motor (316) is cycled off until the firing motor temperature trigger (T2) is met in which driving assembly (164) re-engages firing assembly (158) and continues to drive forward until completion of the firing stroke. Cooperative or interrelated triggers may act upon each other to drive or change the response during a cycle. The cooperative or interrelated trigger optimize responses. Interrelated triggers (e.g., using both motor firing force and motor firing temperature) may change the response of the firing system. The cycle has alternative (or different response) after triggers were hit.

As shown in plot (764) of FIG. 19, motor controller (320) is configured to reduce or stop power to motor (316) for a predetermined period of time (e.g., between time (t12) and time (t13)) in response to either the firing motor force exceeding the predetermined firing motor force threshold or the temperature exceeding the predetermined firing motor temperature threshold. This waiting period (774) is shown in plot (764) using a hashed pattern. The waiting period (774) is where motor (316) turns off once firing motor temperature (T3) is exceeded, and the time off duration may be based on distance required to meet full travel and the delta temperature increase based on completed stroke.

F. Motor Control Using Voltage Modulation and/or Efficiency

Figure 20:
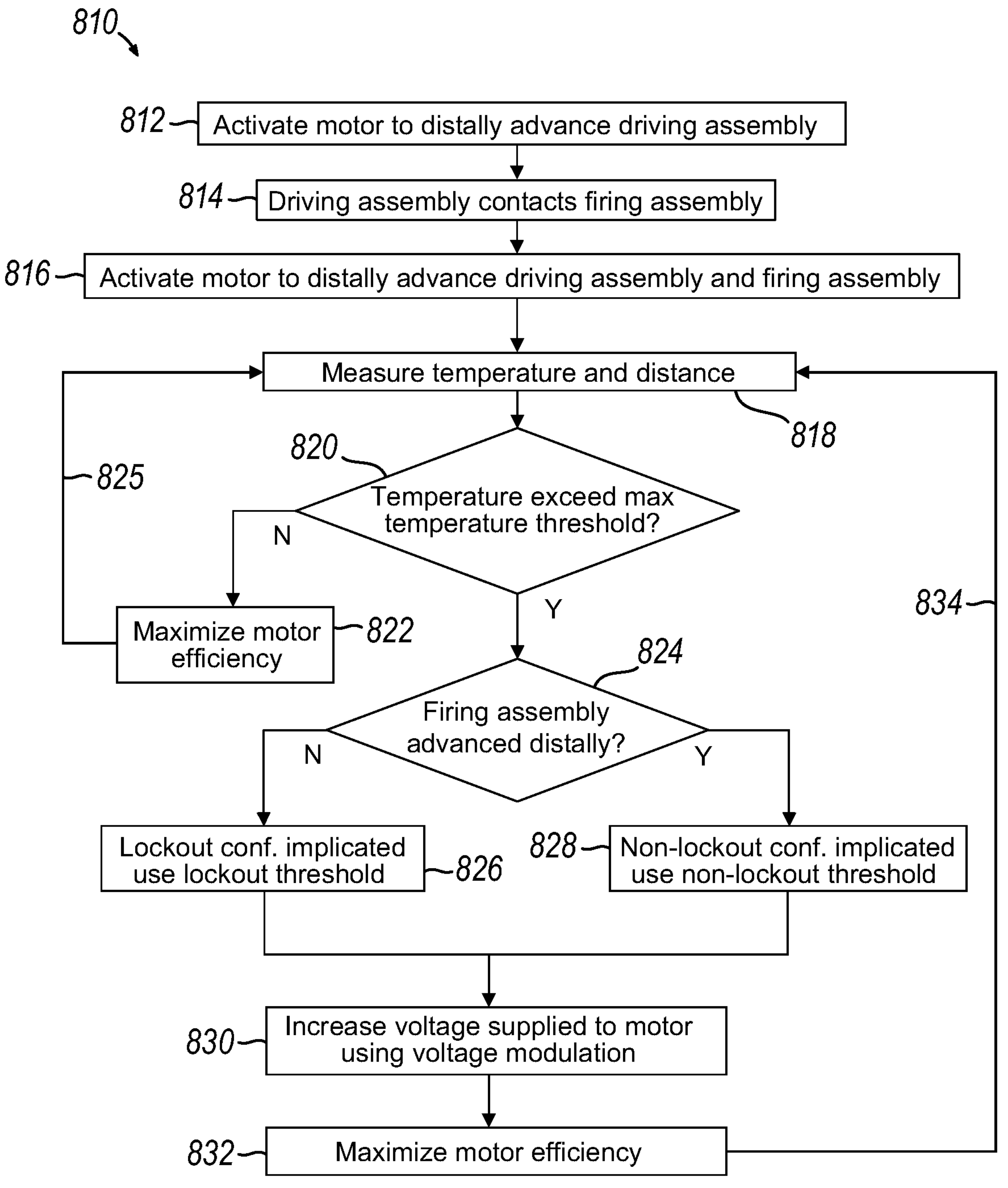
FIG. 20 depicts a block diagram of a fifth exemplary motor control algorithm that may be used by the robotic arm and surgical instrument shown in FIG. 12.
Figure 21A:
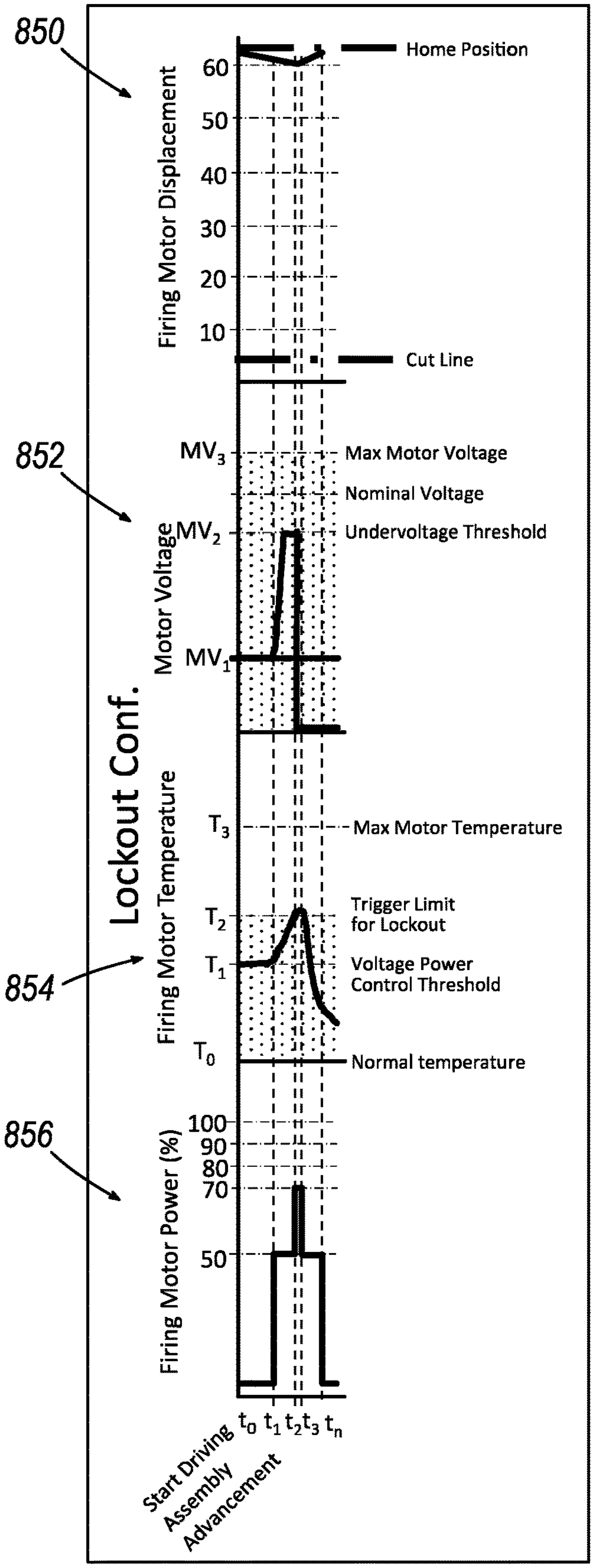
FIG. 21A depicts a multi-axis line graph with plots of firing motor displacement, motor voltage, firing motor temperature, and firing motor power with respect to time when a lockout assembly is in a lockout configuration for the exemplary method of FIG. 20.
Figure 21B:
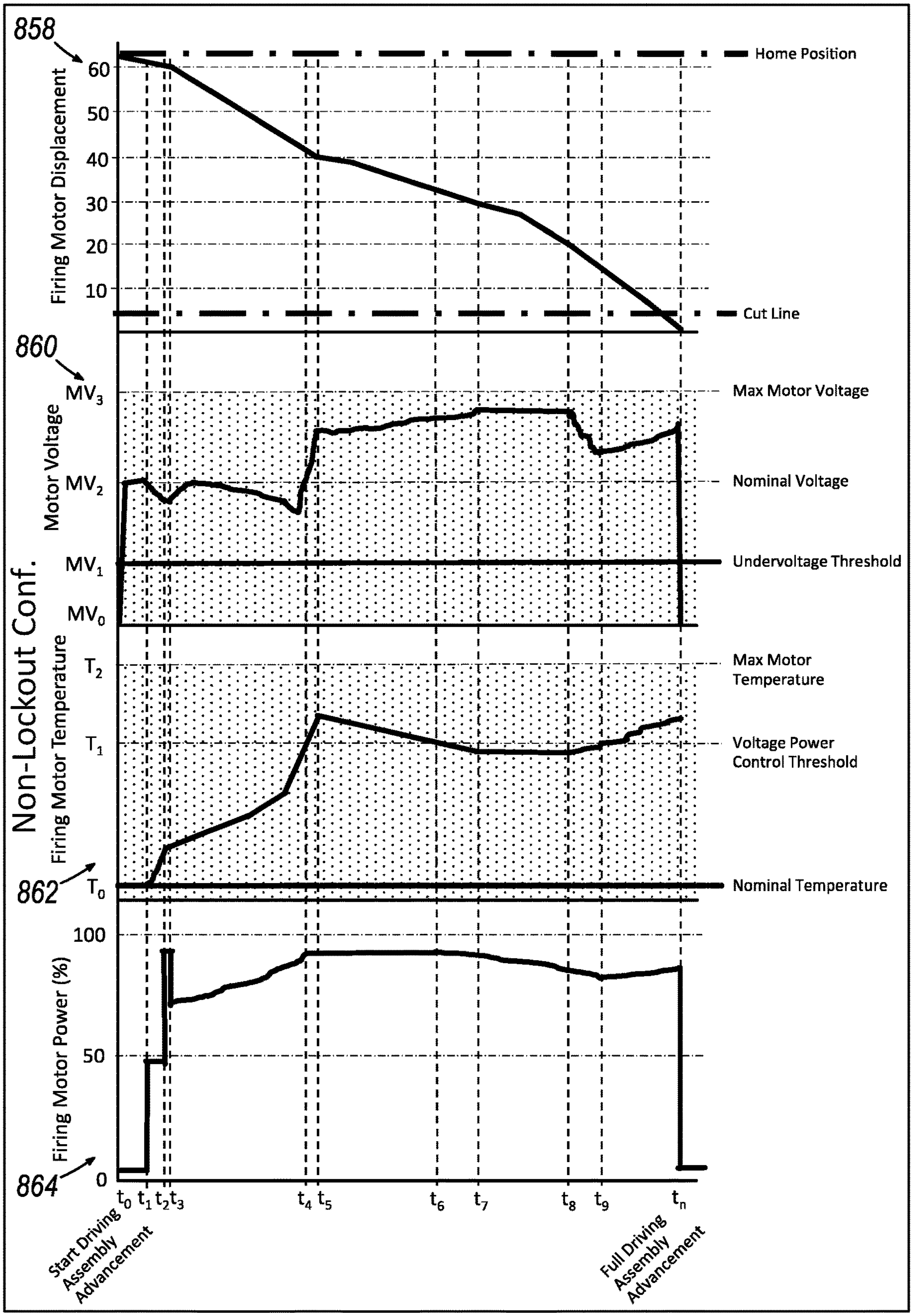
FIG. 21B depicts a multi-axis line graph with plots of firing motor displacement, motor voltage, firing motor temperature, and firing motor power with respect to time similar to FIG. 21A, but with the lockout assembly in a non-lockout configuration for the exemplary method of FIG. 20.
Figure 22:
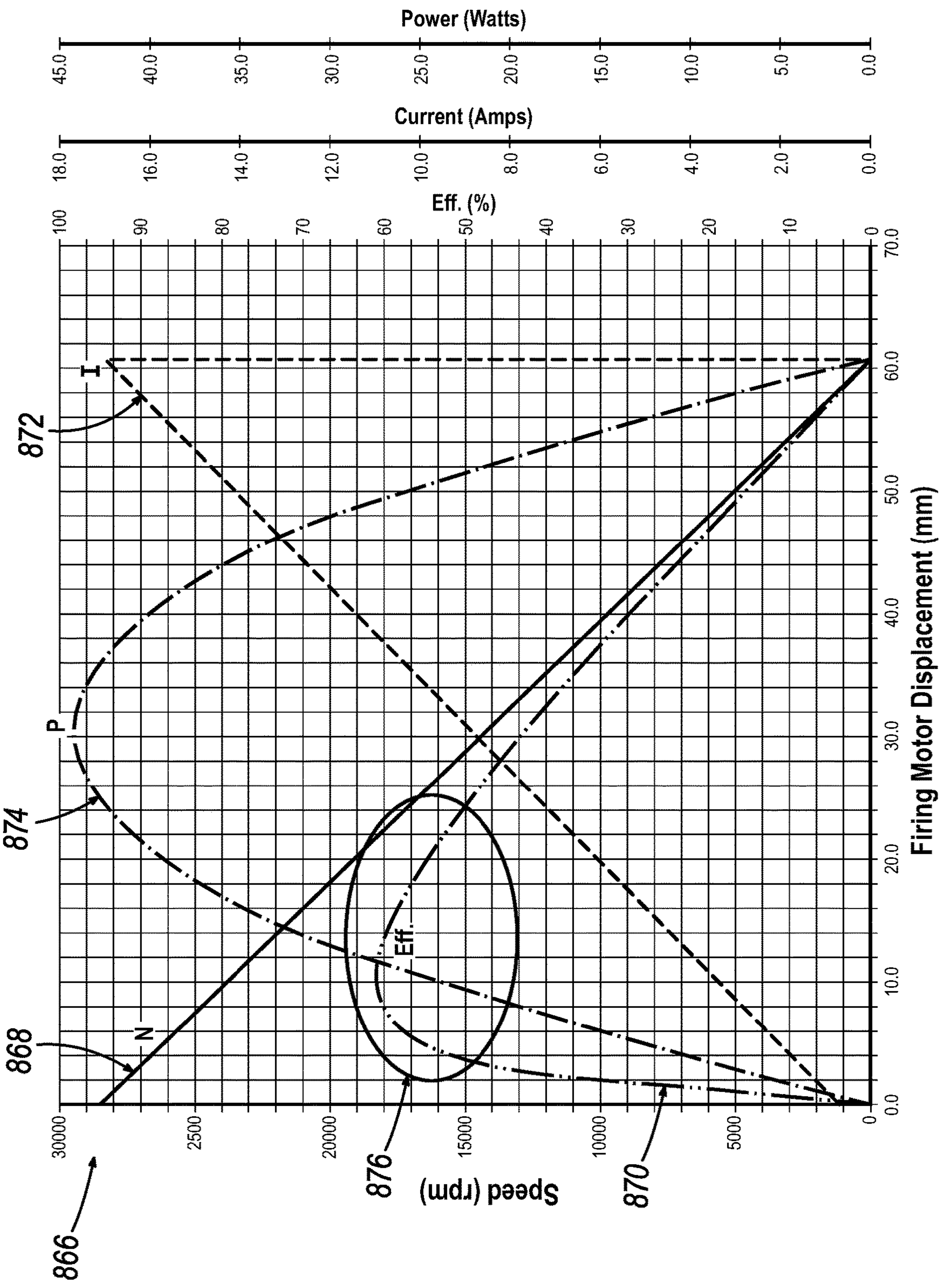
FIG. 22 depicts a multi-line graph with overlying plots of speed, efficiency, current, and power with respect to firing motor displacement for the exemplary method of FIG. 20.

As described with reference to FIGS. 20-22, method (810) includes exemplary steps (812, 814, 816, 818, 820, 822, 824, 825, 826, 828, 830, 832, 834), which is described together with plots (850, 852, 854, 856) of FIG. 21A, plots (858, 860, 862, 864) of FIG. 21B, and plots (868, 870, 872, 874) of FIG. 22. While FIGS. 20-22 are described below with reference to the structures of FIGS. 1-9, method (810) may also be used with the structures of FIGS. 10-11.

At step (812), motor controller (320) may activate motor (316) to distally advance driving assembly (164). At step (814), motor controller (320) may activate motor (316) so that driving assembly (164) contacts firing assembly (158). At step (816), motor controller (320) may activate motor (316) to distally advance driving assembly (164) and firing assembly (158). At step (818), temperature and distance may be measured. This temperature may be measured by motor controller (320) interpreting data produced by motor (316) during operation and/or through the use of a sensor assembly (318) operatively coupled with motor (316) and motor controller (320). Similar to step (716), step (818) may also include measuring distance.

At step (820), motor controller (320) may determine whether the measured firing motor temperature exceeds the maximum firing motor temperature threshold. The firing motor temperature thresholds may be stored in storage device (326) for retrieval by motor controller (320) to determine if firing assembly (158) moves distally similar to step (719). At step (822), if the measured firing motor temperature does not exceed the maximum firing motor temperature threshold as determined by motor controller (320), motor controller (320) may optimize efficiency of motor (316). Motor controller (320) adjusts performance of motor (316) to maximize the efficiency of motor (316) and regulate the thermal load. At least one control parameter of motor (316) may be modified based on the sensed values of interrelated triggers to maximize the efficiency curve of motor (316). At step (825), steps (818, 820, 822) may be repeated as described above (one or more times) to determine whether the measured firing motor temperature exceeds the maximum firing motor temperature threshold.

At step (824), and similar to step (719), if the measured firing motor temperature exceeds the maximum temperature threshold as determined by motor controller (320), motor controller (320) may determine if firing assembly (158) is in the lockout configuration or the non-lockout configuration based on distance traveled. In the lockout configuration, as shown at time (t2) in plot (854) of FIG. 21A, motor (316) turns off once firing motor temperature (T2) is exceeded. Additionally, in plot (852), motor voltage does not exceed motor voltage (MV2) which is the undervoltage threshold. As shown in plot (850) of FIG. 21A, firing motor displacement does not go below 60 millimeters, indicating firing assembly (158) is not advanced distally indicating lockout assembly (314) is in the lockout configuration.

At step (826) if the measured temperature exceeds the maximum firing motor temperature, motor controller (320) determines whether firing assembly (158) is advanced distally. At step (720), if firing assembly (158) is not advanced distally, then the lockout configuration is implicated. In FIGS. 21A-21B, time (t0) refers to the time when driving assembly (164) starts being advanced, while time (tn) refers to the time when driving assembly (164) is fully advanced. The stippling shaded region depicted of plots (852, 860) of FIGS. 21A-21B represent a tolerable range of firing motor force, and the stippling shaded region depicted of plots (854, 862) represent a tolerable range of firing motor temperature threshold for driving assembly (164).

At step (828), if firing assembly (158) advances distally then the non-lockout configuration is implicated (since firing assembly (158) travels distally beyond the point where lockout assembly (314) prevents travel). As shown in plot (858) of FIG. 21B, firing motor displacement drops below 60 millimeters. At step (830), increasing the firing motor voltage supplied to motor (316) using voltage modulation. Where one of the interrelated triggers includes the measured firing motor temperature exceeding the maximum firing motor temperature threshold of motor (316), the firing motor voltage supplied to motor (316) is increased in response to motor (316) reaching the predetermined firing motor temperature threshold. In response to the firing motor voltage supplied to motor (316) being increased, the speed of motor (316) is increased. Motor controller (320) is configured to modify the motion profile by instructing motor (316) to provide continuous power to alter performance of end effector (116, 210).

DC motors follow a defined performance curve for their performance. Motor heating is associated with current through the windings. From Ohm's law, the energy loss to heat is the current squared times the windings resistance $I^2R$. Power to the motor is defined by Power=Voltage x Current. When motor (316) begins to experience a thermal event, motor (316) responds by increasing the voltage supplied to motor (316). By increasing the voltage supplied to motor (316), the required current decreases, and the power remains the same, thus lowering the $I^2R$ in the motor windings. Due to the motor curve, the increase in voltage increases the speed of motor (316). This characteristic may be mitigated using pulse width modulation to affect the signal powering motor (316) to lower the overall power utilized by motor (316). At step (832), efficiency of motor (316) may be maximized as described above with reference to step (822).

FIG. 22 shows a graph (866) of plots (868, 870, 872, 874). Plot (868) refers to the distance travelled for firing assembly (158), shown as firing motor displacement in millimeters. Plot (868) shows motor speed linearly decreasing as the firing displacement decreases. Plot (870) shows firing motor efficiency at a maximum of over 60% at a firing motor displacement of approximately 10 millimeters. Plot (872) shows current linearly increasing. Plot (874) shows a parabolic curve of power reaching a maximum at approximately a firing motor displacement of approximately 30 millimeters. The encircled region (876) is where efficiency is maximized.

III. Exemplary Motor Control Algorithms for Powered Surgical Stapler

Figure 23:
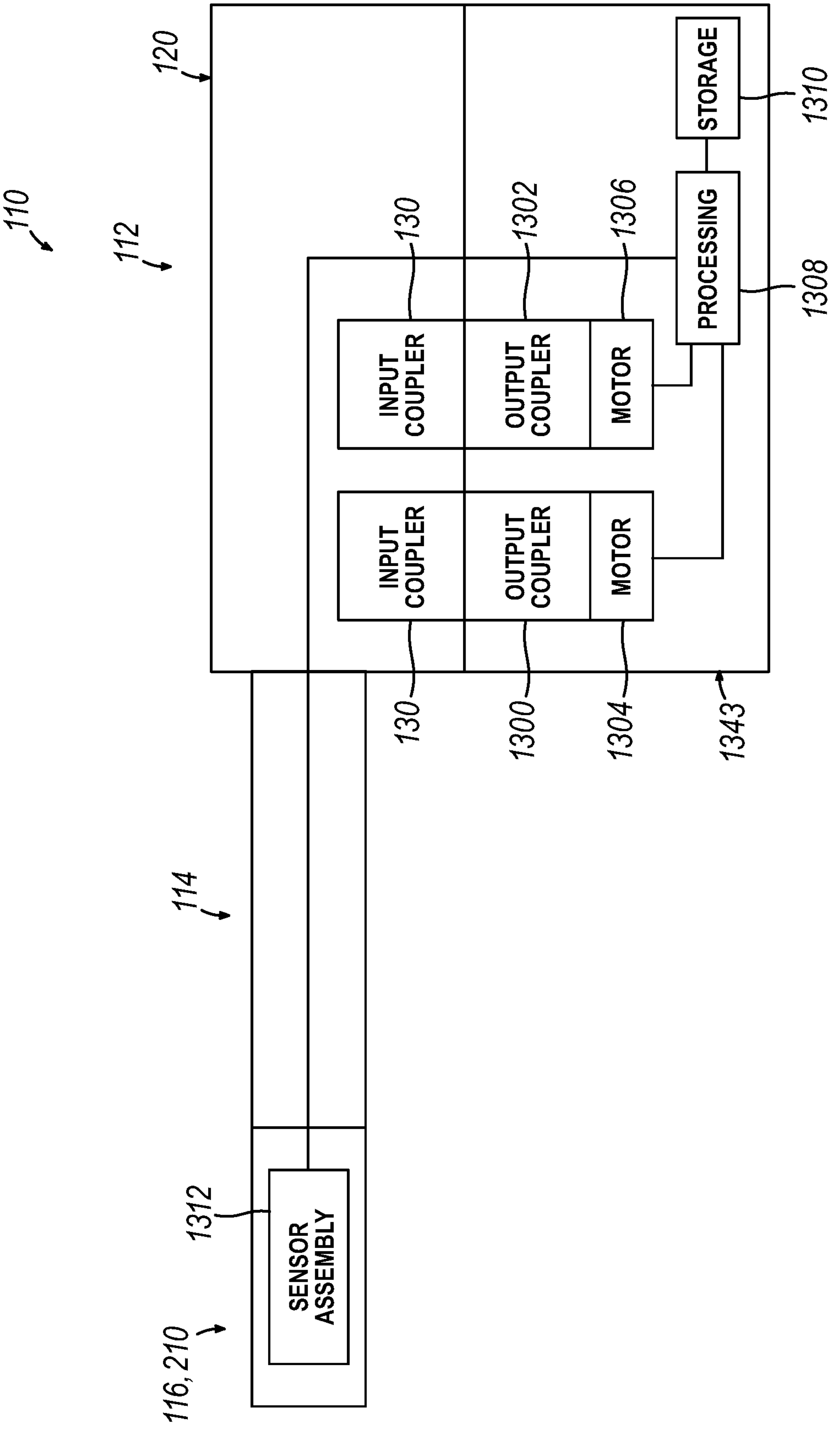
FIG. 23 depicts a schematic view of a robotic arm coupled with the surgical instrument of FIG. 4.

FIG. 23 shows a schematic view of instrument (110) suitably coupled with an exemplary robotic arm (1342). Robotic arm (1342) may be substantially similar to robotic arm (42) described above, with differences elaborated below. Therefore, it should be understood that robotic arm (1342) may suitably interact with robotic surgical system (10) described above such that a medical professional operator may utilize robotic surgical system (10) to control instrument (110) via robotic arm (1342), input control devices (36) of surgeon's console (16), and any other suitable intermediate components as would be apparent to one skilled in the art in view of the teachings herein. In some versions, motor controller (320) instructs motor (316) to operate in the encircled region (876) to maximize the cumulative benefits through assessing multiple trigger variables in combination. For example, encircled region (876) may use data from plots (868, 870, 872, 874).

As mentioned above, instrument base (112) includes input couplers (130). Input couplers (130) are configured to interface with and be driven by corresponding output couplers (1300, 1302) of robotic arm (1342). Output couplers (1300, 1302) may be actuated via one or more robotic motors (1304, 1306), respectively, which may be controlled by a processing unit (1308) in communication with input control devices (36) of surgeon's console (16). Processing unit (1308) may receive instructions from input control devices (36) in order to actuate robotic motors (1304, 1306) and corresponding output couplers (1300, 1302). While operatively interfacing with input couplers (130), output couplers (1300, 1302) of robotic arm (1342) may be used to actuate selective portions of either end effector (116, 210) in accordance with the description herein. Therefore, robotic motor(s) (1304, 1306) in communication with output couplers (1300, 1302) of robotic arm (1342) may be used to suitably control end effector (116, 210) in clamping, severing, and stapling tissue in accordance with the description herein.

Output couplers (1300, 1302) and input couplers (130) may include any suitable components as would be apparent to one skilled in the art in view of the teachings herein. While in the current example, two input couplers (130) and two respective output couplers (1300, 1302) are used, any suitable number of input couplers (130) and any suitable number of output couplers (1300, 1302) may be utilized as would be apparent to one skilled in the art in view of the teachings herein.

Robotic motors (1304, 1306) may include any suitable components as would be apparent to one skilled in the art in view of the teachings herein. Robotic motors (1304, 1306) and/or processing unit (1308) may include suitable components to measure suitable output characteristics, operating data, etc., of robotic motors (1304, 1306). For example, robotic motors (1304, 1306) may include components configured to measure motor temperature, motor displacement, the electrical current used by robotic motors (1304, 1306), motor power usage (either in a specified unit or represented as a percentage compared to a maximum motor power usage), etc., and may communicate such operating data to processing unit (1308) for use of such data in accordance with the description herein.

Processing unit (1308) may also be in communication with a storage device (1310) such that processing unit (1308) may communicate data to storage device (1310), and such that processing unit (1308) may access and utilize data stored on storage device (1310). Processing unit (1308) and storage device (1310) may contain any suitable number of components as would be apparent to one skilled in the art in view of the teachings herein.

Processing unit (1308) may utilize data contained in storage device (1310) in order to establish operational parameters for robotic arm (1342) while controlling a specific instrument (110). Storage device (1310) may be configured to store information related to a specific instrument (110), such as any suitable data accumulated during exemplary use of a specific instrument (110) as would be apparent to one skilled in the art in view of the teachings herein. In some instances, a specific instrument (110) may have an identifiable chip or other electronic device that notifies processing unit (1308) of the specific instrument (110) that is coupled with robotic arm (1342), therefore allowing processing unit (1308) to track the specific instrument (110) and data stored on storage device (1310) related to the specific instrument (110). In some instances, the specific instrument (110) may include its own storage device (1310) that establishes communication with processing unit (1308) when instrument (110) is initially coupled with robotic arm (1342). In such instances, information regarding prior use of a specific instrument (110) may be stored on that instrument's specific storage device and accessed by processing unit (1308) when the specific instrument (110) is coupled to robotic arm (1342).

Processing unit (1308) may recall and utilize data stored on storage device (1310) related to specific instruments (110) when that specific instrument (110) is coupled to robotic arm (1342) for exemplary use in accordance with the description herein. For example, storage device (1310) may be configured to store the number of times a specific instrument (110) is used and fired in accordance with the teachings herein. As another example, processing unit (1308) may be configured to determine when a noteworthy event occurred during operation of a specific instrument (110) and communicate such a noteworthy event to storage device (1310) such that processing unit (1308) may recall and utilize such noteworthy events when the specific instrument (110) is recoupled and reused with robotic arm (1342) in accordance with the teachings herein.

While in the current example, storage device (1310) is housed within robotic arm (1342), storage device (1310) may be associated with any suitable component as would be apparent to one skilled in the art in view of the teachings herein. For example, storage device (1310) may be housed within instrument (110) such that storage device (1310) may selectively establish communication with processing unit (1308) while instrument (110) is coupled to robotic arm (1342). As another example, storage device (1310) may be associated with surgeon's console (16). In other instances, multiple storage devices (1310) may be utilized, each associated with various components, such that each storage device (1310) stores data related to the respective specific component.

As mentioned above, instrument (110) may include either end effector (116, 210) operatively attached to the distal end of shaft assembly (114). End effector (116, 210) may include a sensor assembly (1312) configured to establish communication with processing unit (1308) when instrument (110) is operatively coupled with robotic arm (1342). Therefore, data obtained from sensor assembly (1312) may be stored on storage device (1310) for later access by processing unit (1308). Sensor assembly (1312) may include one or more sensors configured to measure any suitable data as would be apparent to one skilled in the art in view of the teachings herein. For instance, sensor assembly (1312) may be configured to measure a tissue load imparted on the jaws (150, 152, 212, 214) while grasping tissue in accordance with the description herein. Additionally, or alternatively, sensor assembly (1312) may be configured to measure the locations tissue is in contact with jaws (150, 152, 212, 214) while grasping tissue in accordance with the description herein.

In some instances, each input coupler (130) is controlled by a different motor (1304, 1306) may be used to perform separate functions. For example, in instances where end effector (210) is operatively attached to the distal end of shaft assembly (114), first motor (1304) and the respective output coupler (1300) and input coupler (130) may be utilized to actuate firing beam (216); while second motor (1306) and the respective output coupler (1302) and input coupler (130) may be utilized to acuate colure tube (not shown) and closure ring (230).

A. Exemplary Motor Control Algorithm Utilizing Impulse Actuation

During the firing process of either end effector (116, 210) in accordance with the description herein, driving assembly (164) (see FIG. 8) or firing beam (216) (see FIG. 11) may become undesirably stuck in a longitudinal position relative to staple cartridge (154, 218) such that driving assembly (164) or firing beam (216) relative to staple cartridge (154, 218) is inhibited beyond a tolerable degree. For example, during distal advancement of pusher member (166) (see FIG. 8) in accordance with the description herein, flanges (184, 185) may overly engage or dig into portions of staple cartridge (154) and/or jaws (150, 152) defining associated longitudinal slots (186, 187), thereby inhibiting suitable movement due to an undesirable amount of frictional braking force. As another example, during distal advancement of firing beam (216), upper pin (232) or firing beam cap (246) (see FIG. 11) may overly engage or dig into portions of staple cartridge (218) defining longitudinal anvil slot (234) or lower surface of lower jaw (212), respectively, thereby inhibiting suitable movement due to an undesirable amount of frictional braking force.

With movement of driving assembly (164) or firing beam (216) being undesirably inhibited, robotic surgical system (10) may need to (A) power robotic motor(s) (1304, 1306) past a predetermined maximum power output level for a specific instrument (110) in order to move driving assembly (164) or firing beam (216), or (B) use manual actuator (124) to manually "bailout" end effector (116, 210), in order to retract driving assembly (164) or firing beam (216) back toward a proximal position. Use of robotic motor(s) (1304, 1306) past a predetermined maximum power output level or use of manual actuator (124) to "bailout" instrument (110) may cause undesirable damage to instrument (110), thereby reducing the expected number of suitable uses of instrument (110), or even rendering instrument (110) unsuitable for further use.

Therefore, in some instances, it may be desirable to provide a robotic surgical system (10) that has robotic motor(s) (1304, 1306) that may utilize a motor control algorithm to increase the probability of proximally retracting firing beam (216) and/or other components of driving assembly (164) out of an undesirably stuck longitudinal position without having to power robotic motor(s) (1304, 1306) past a predetermined maximum power output level for a specific instrument (110); or without having to use manual actuator (124). Further, it may be desirable to utilize a motor control algorithm to increase the probability of overcoming an undesirably stuck longitudinal position and to further complete a firing process by distally actuating firing beam (216) and/or other components of driving assembly (164) in accordance with the description herein.

Figure 24:
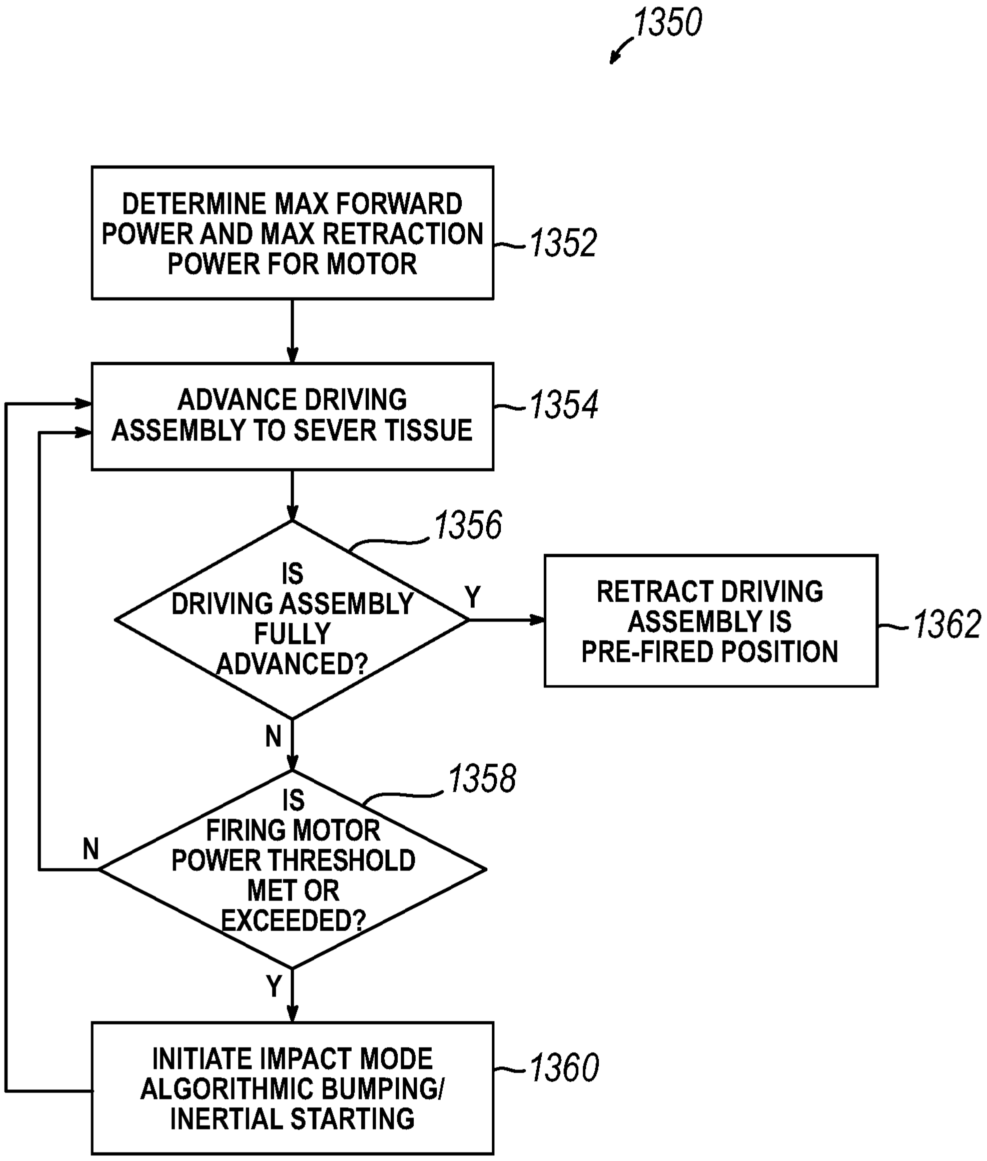
FIG. 24 depicts a block diagram of an exemplary impulse actuation motor control algorithm that may be used by the robotic arm and surgical instrument shown in FIG. 23.

FIG. 24 shows an exemplary impulse actuation motor control algorithm (1350), while FIGS. 25A-25E show an exemplary use of algorithm (1350). FIG. 26 shows a graph (1400) representing the firing motor displacement (1402) and the motor power consumption (1404) over the time (1406) elapsed during the exemplary use of algorithm (1350) as shown in FIGS. 25A-25E. Exemplary impulse actuation motor control algorithm (1350) may be utilized by robotic motors (1304, 1306), processing unit (1308), and/or storage device (1310) in order to increase the probability of retracting and/or fully firing end effector (116, 210) without having to (A) power robotic motor(s) (1304, 1306) past a predetermined maximum power output level for a specific instrument (110), or (B) use manual actuator (124).

In preparation of using robotic surgical system (10), a specific instrument (110) is coupled to robotic arm (1342) such that processing unit (1308) may establish various operational parameters for robotic arm (1342) in controlling the specific instrument (110). Therefore, in the first step of algorithm (1350), processing unit (1308) may determine and establish maximum power output limits (1352) for motors (1304, 1306) in actuating driving assembly (164)/firing beam (216) in accordance with the description herein.

Determining maximum power output limits (1352) may include determining (A) a separate maximum power output level for motors (1304, 1306) to distally advance driving assembly (164)/firing beam (216) (i.e., a maximum forward power output level) and (B) a maximum power output level for motors (1304, 1306) to proximally retract driving assembly (164)/firing beam (216) (i.e., a maximum retraction power output level). In other words, motors (1304, 1306) may be limited to a first power output level to fire staples and sever tissue, while motors (1304, 1306) may be limited to a second power output level to proximally retract driving assembly (164)/firing beam (216).

In some instances, determining maximum power output limits (1352) may be relatively simple, such as basing power output limits (1352) on the type of instrument (110) being coupled to robotic arm (1342). In other instances, processing unit (1308) may determine the motor power output limits (1352) for a specific instrument (110) based on various data accumulated throughout the life of the specific instrument (110) in use. Processing unit (1308) may determine the motor power output limits (1352) utilizing any suitable methods that would be apparent to one skilled in the art in view of the teachings herein, including the methods described herein. As mentioned above, processing unit (1308) and storage device (1310) may store specific data related to the prior use of a specific instrument (110). In such instances, processing unit (1308) and storage device (1310) (A) may store how many times a specific instrument (110) has been fully fired in accordance with the teachings herein, and/or (B) may store other suitable noteworthy events experienced by instrument (110) during exemplary use.

Figure 25A:
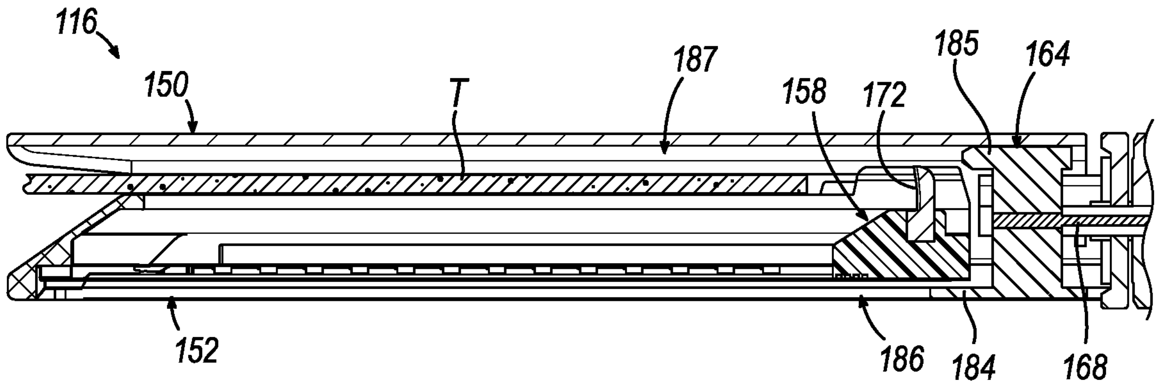
FIG. 25A depicts a cross-sectional side view of the end effector of FIG. 4, taken along a centerline thereof, in a pre-fired position.
Figure 25B:
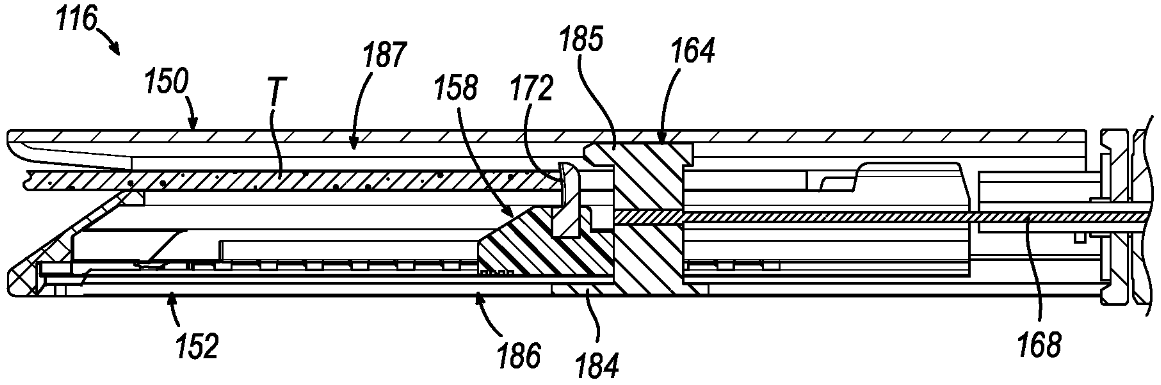
FIG. 25B depicts a cross-sectional side view of the end effector of FIG. 4, taken along a centerline thereof, in a partially fired position.
Figure 25C:
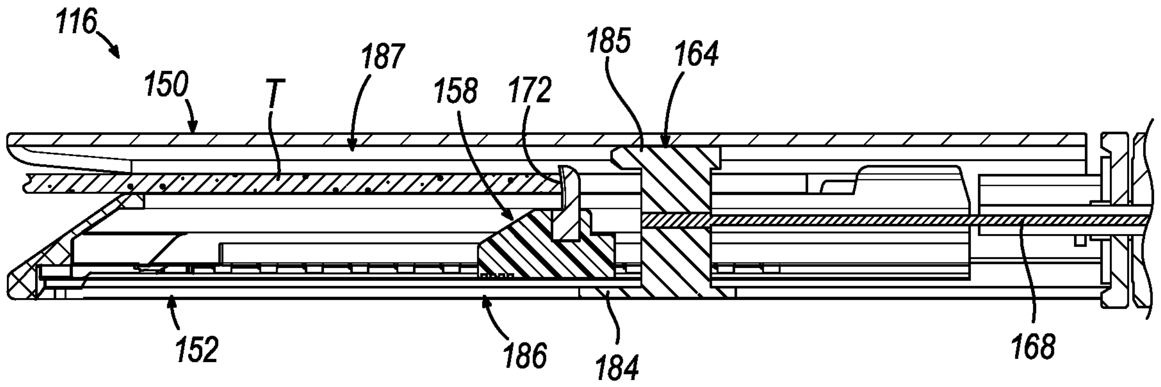
FIG. 25C depicts a cross-sectional side view of the end effector of FIG. 4, taken along a centerline thereof, with a driving assembly of the end effector partially retracted from the position shown in FIG. 25B.
Figure 26:
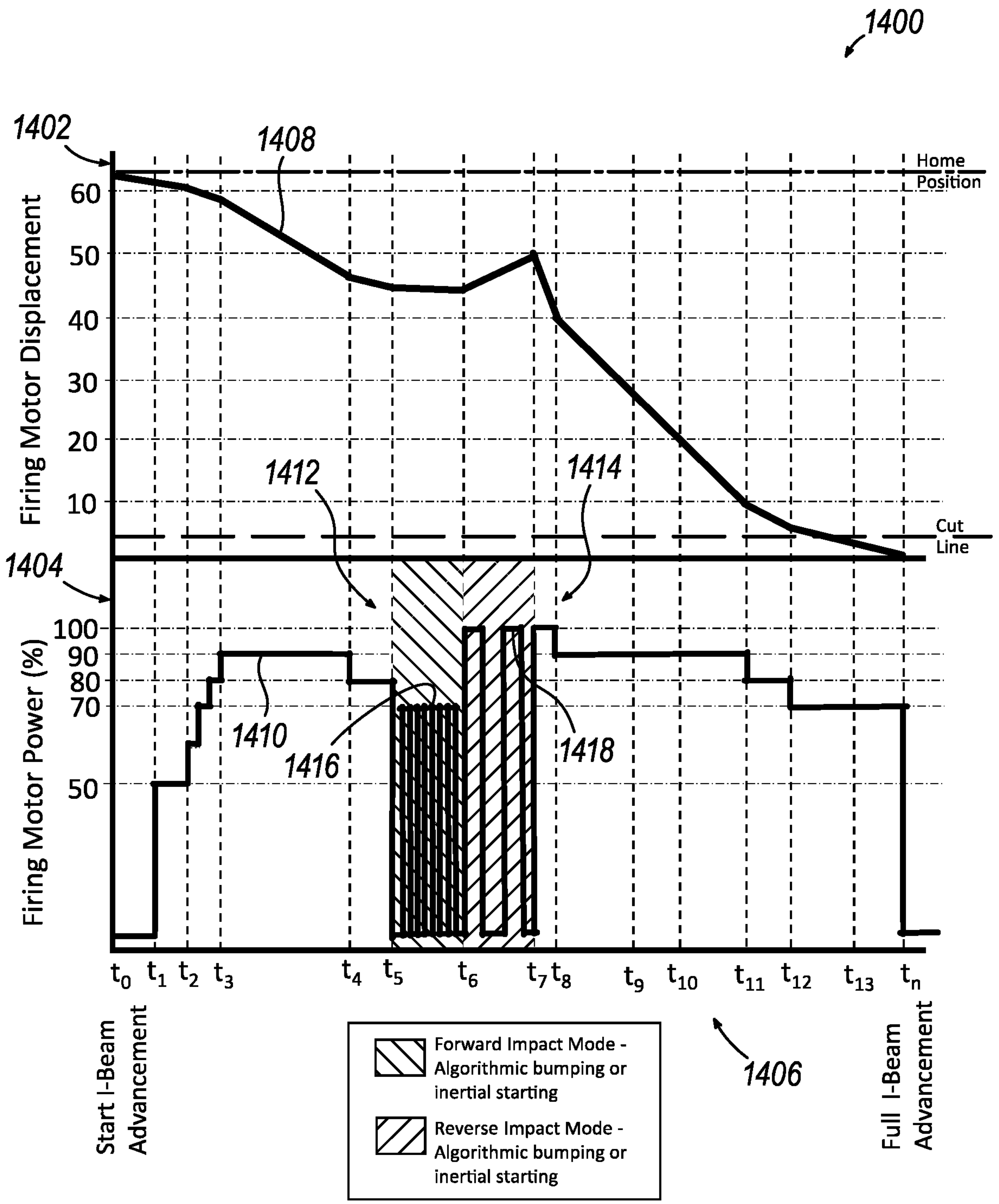
FIG. 26 depicts a graph representing the firing displacement and the firing motor power represented over time of the firing sequence shown in FIGS. 25A-25E.

With instrument (110) suitably coupled to robotic arm (1342), an operator may utilize input control devices (36) of surgeon's console (16) to manipulate end effector (116) in grasping tissue (T) of a patient, as shown in FIG. 25A. It should be understood that at the moment shown in FIG. 25A, an operator may not have initiated the firing sequence for end effector (116) to sever and staple tissue (T). This moment may be represented at time (t0) on graph (1400) shown in FIG. 26. Therefore, at the moment shown at time (t0), the firing motor displacement line (1408) (which represents the longitudinal position of driving assembly (164) during the firing process) is shown at a position corresponding to driving assembly (164) being in a proximal pre-fired position, while power output line (1410) (which represents the power output of motor (1304, 1306) actuating driving assembly (164)) is shown at a position corresponding to little or no power output for the motor (1304, 1306) configured to actuate driving assembly (164).

Once the operator is ready to sever and staple tissue (T) grasped between jaws (150, 152) of end effector (116), the operator may initiate the firing sequence via surgeon's console (16), which in turn causes processing unit (1308) to instruct motor (1304, 1306) to distally advance driving assembly (164), as shown in control algorithm (1350) of FIG. 24. Therefore, as shown between FIGS. 25A-25B, driving assembly (164) may advance distally, which in turn drives firing assembly (158) distally to sever and staple tissue (T) in accordance with the description herein. This movement may be respected between time (t0) and time (t4). Therefore, the firing motor displacement line (1408) is shown to move at a slope corresponding to driving assembly (164) being distally advanced, while the power output line (1410) is shown to increase up to 90% of motor's (1304, 1306) maximum power output.

Turning back to FIG. 24, while driving assembly (164) is being distally advanced (1352), processing unit (1308) may be running through selected portions of control algorithm (1350) in order to determine whether or not driving assembly (164) is undesirably stuck (i.e., inhibited from movement to a greater degree than preferred). In the current example, processing unit (1308) monitors if driving assembly (164) is fully advanced (1356) to the post-fired position. If the firing process is complete without driving assembly (164) becoming undesirably stuck, processing unit (1308) may instruct motor (1304, 1306) to retracted driving assembly (164) to the pre-fired position (1362) shown in FIG. 25A.

In the current example, processing unit (1308) may monitor the power output (1410) of motor (1304, 1306) to determine if the power output (1410) exceeds the predetermined power output limit (1358) established earlier.

As shown in FIG. 26 between time (t3) and time (t4), if the power output (1410) of motor (1304, 1306) reaches its maximum power output during normal operating use (in this case, 90% of maximum output) while motor displacement (1408) is indicative of driving assembly (164) being distally advanced at a suitable rate of travel, processing unit (1308) may continue to distally advance (1354) driving assembly (164). However, as shown between time (t4) and time (t5) in FIG. 26 (which correlates with the position of driving assembly (164) shown in FIG. 25B), if motor displacement line (1408) is indicative of driving assembly (164) resisting distal advancement (i.e., driving assembly (164) is not advancing distally as a suitable rate of travel), this may be indicative of driving assembly (164) being undesirably stuck in a longitudinal position. Therefore, processing unit (1308) may initiate impact mode algorithmic bumping (1360) in order to help driving assembly (164) become unstuck. Processing unit (1308) may also initiate impact mode algorithmic bumping (1360) in response to power output (1410) of motor (1304, 1306) exceeding a predetermined power output limit (1358). Any other suitable monitoring condition may be used in order to trigger initiation of impact mode algorithmic bumping (1360) as would be apparent to one skilled in the art in view of the teachings herein.

In the current example, as shown in FIG. 26, algorithmic bumping (1360) may involve a forward impact mode (1412) (shown between times (t5) and (t6)) followed by a reverse impact mode (1414) (shown between times (t6) and (t7)). In some instances, algorithmic bumping (1360) may include only forward impact mode (1412), only reverse impact mode (1414), reverse impact mode (1414) followed by forward impact mode (1412), or multiple alternations between forward and reverse impact modes (1412, 1414). In some instances, algorithmic bumping (1360) may automatically stop once processing device (1308) determines driving assembly (164) is no longer undesirably stuck. In some instances, algorithmic bumping (1360) may complete its predetermined cycle regardless of whether driving assembly (164) becomes unstuck during the bumping (1360) process.

Forward impact mode (1412) may include processing unit (1308) instructing motor (1304, 1306) to activate at a power output (1410) that fluctuates between little or no power output to a maximum forward impact power output (1416) at a first frequency. In the current example, this fluctuation occurs in the substantial shape of a step-function. It should be understood that in forward impact mode (1412), power output (1410) of motor (1304, 1306) actuates driving member (164) in a distal direction. While in forward impact mode (1412), sudden fluctuations of motor output (1410) between no power output and maximum forward impact power output (1416) may provide a jerk, jolt, shake, spasm, and/or bump-type reaction, leading to multiple impact-like starting and stopping of distal advancement of a driving member, also referred to as driving assembly (164). This impact-like motion may allow for driving member (164) to no longer be longitudinally stuck, thereby allowing the firing process to complete, along with retraction.

Reverse impact mode (1414) may include processing unit (1308) instructing motor (1304, 1306) to activate at a power output (1410) that fluctuates between little or no power output to a maximum reverse impact power output (1418) at a second frequency that is different than the first frequency of forward impact mode (1412). Additionally, in the current example, maximum reverse impact power output (1418) is greater than maximum forward impact power output (1416).

In the current example, this fluctuation occurs in the substantial shape of a step-function. It should be understood that in reverse impact mode (1414), power output (1410) of motor (1404, 1406) actuates driving member (164) in a proximal direction toward the pre-fired position. This impact-like motion may cause driving assembly (164) to actuate from the position shown in FIG. 25B toward the position shown in FIG. 14C. While in reverse impact mode (1414), sudden fluctuations of motor output (1410) between no power output and maximum reverse impact power output (1418) may provide a jerk, jolt, shake, spasm, and/or bump-type reaction, leading to multiple impact-like starting and stopping of proximal retraction of driving member (164). This impact-like motion may allow for driving member (164) to no longer be longitudinally stuck, thereby allowing the firing process to complete, along with retraction.

The difference in frequency and magnitude between forward and reverse impact mode (1412, 1414) may allow driving assembly (164) to have inertial starting and stopping (i.e., jerking, jolting, shaking, spasming, bumping) may increase the chances of driving assembly (164) becoming unstuck in the even one frequency and magnitude is not sufficient free driving assembly (164) from a stuck position.

Figure 25D:
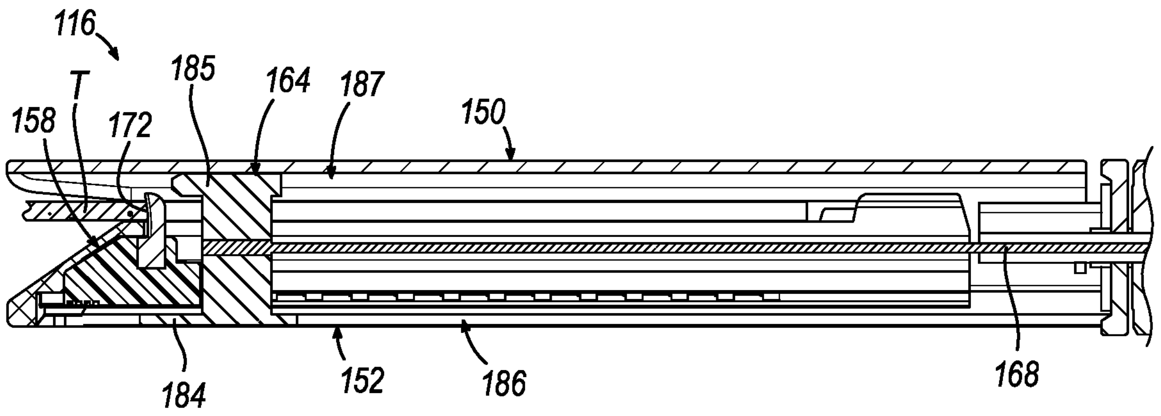
FIG. 25D depicts a cross-sectional side view of the end effector of FIG. 4, taken along a centerline thereof, with the end effector completely fired and the driving assembly of FIG. 25C in a distal position.
Figure 25E:
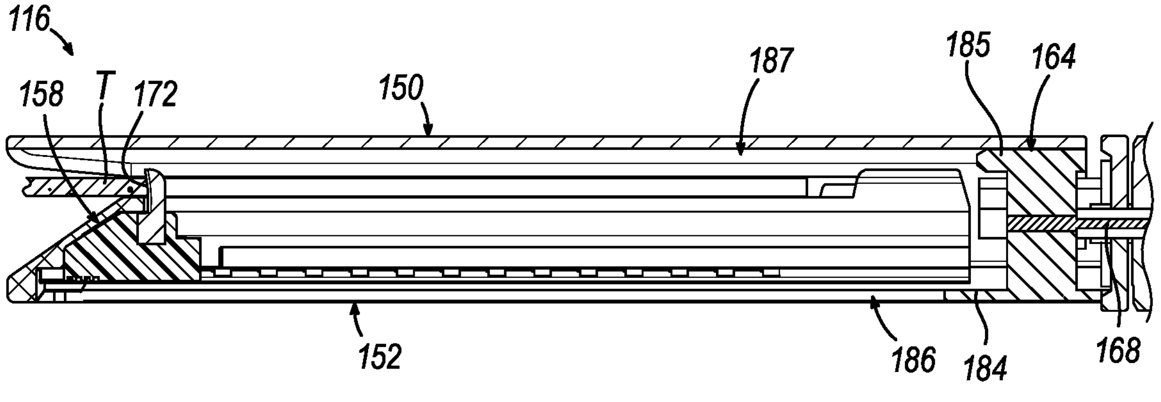
FIG. 25E depicts a cross-sectional side view of the end effector of FIG. 4, taken along a centerline thereof, with the end effector completely fired and the driving assembly of FIG. 25C retracted toward the pre-fired position.

Once the impact mode (1360) is complete, processing unit (1308) will then loop back to advancing (1354) driving assembly (164) until driving assembly (164) is fully advanced, as shown in FIG. 25D. Once fully advanced, processing unit (1308) may then instruct motor (1304, 1306) to retract driving assembly (164) back to the proximal, pre-fired position. It should be understood that impact mode (1360) may be initiated if driving assembly (164) becomes stuck while being proximally retracted to the pre-fired position after completing the firing process. It should be understood that processing unit (1308) may initiate impact mode (1360) more than one time if needed.

Once the firing process is complete, the operator may remove instrument (110) from the surgical site, remove instrument (110) from robotic arm (1342), and reprocess instrument (110) for another firing, if desired. It should be understood that while in the current example, end effector (116) was used, end effector (210) may be used in replacement of end effector (116).

While in the current example, processing unit (1308) monitors both the rate of travel which driving assembly (164) is advanced distally and the power output (1410) to determine whether or not to initiate algorithmic bumping (1360), this is merely optional. In some instances, processing unit (1308) may just monitor the rate of travel at which driving assembly (164) is being distally advanced to determine whether or not to initiate algorithmic bumping (1360). In other instance, processing unit (1308) may just monitor power output (1410) to determine whether or not to initiate algorithmic bumping (1360). In other instances, processing unit (1308) may measure to resistance force imparted on any suitable position of firing assembly (158) or driving assembly (164) in order to determine whether or not to initiate algorithmic bumping (1360).

It should be understood that processing unit (1308) may read all the data produced by motor (1304, 1306) and shown in graph (1400) in real time and utilize such data to execute algorithm (1350) described herein.

While in the current example, algorithmic bumping (1360) is initiated based off of driving assembly (164) resisting distal advancement and/or power output (1410) of motor (1304, 1306) exceeding a predetermined threshold, any other suitable responses may be utilized based on any other suitable motor control input as would be apparent to one having ordinary skill in the art in view of the teachings herein. For example, the clamping time/force at which end effector (116) grasps tissue could be modified based off rate of travel at which driving assembly (164) is distally advanced and/or the predetermined power output threshold of motor (1304, 1306). As another example, the rate of travel at which driving assembly (164) is distally advanced and/or the predetermined power output threshold of motor (1304, 1306) could be modified based on the number of clamping attempts required for end effector (116) to suitably grasp tissue. As another example, the rate of travel at which driving assembly (164) is distally advanced and/or the predetermined power output threshold of motor (1304, 1306) could be modified based on the thickness of tissue being grasped by end effector (116). As another example, the rate of travel at which driving assembly (164) is distally advanced and/or the predetermined power output threshold of motor (1304, 1306) could be modified based on the type of staple cartridge loaded on end effector (116). As another example, the rate of travel at which driving assembly (164) is distally advanced and/or the predetermined power output threshold of motor (1304, 1306) could be modified based on the number of pauses or the cumulative duration of pauses which driving assembly (164) experiences during distal advancement in order to staple and sever tissue in accordance with the description herein.

B. Exemplary Motor Control Algorithm for Determining Maximum Motor Power Output Levels for a Firing Assembly of Specific Instruments As mentioned above, when a specific instrument (110) initially couples with a robotic arm (1342), it may be desirable to determine a maximum forward power and a maximum retraction power for motors (1304, 1306) to actuate driving assembly (164)/firing beam (216) in order to staple and sever tissue in accordance with the description herein. Further, it may be desirable to utilize a motor control algorithm that adjusts the power output levels which motor(s) (1304, 1306) may operate at based on the number of uses and other noteworthy events experienced by a specific instrument (110). Modifying the power output levels which motor (1304, 1306) may operate a specific instrument (110) during the life of the specific instrument (110) may reduce the chances of mechanical failure of certain components of instrument (110)

Figure 27:
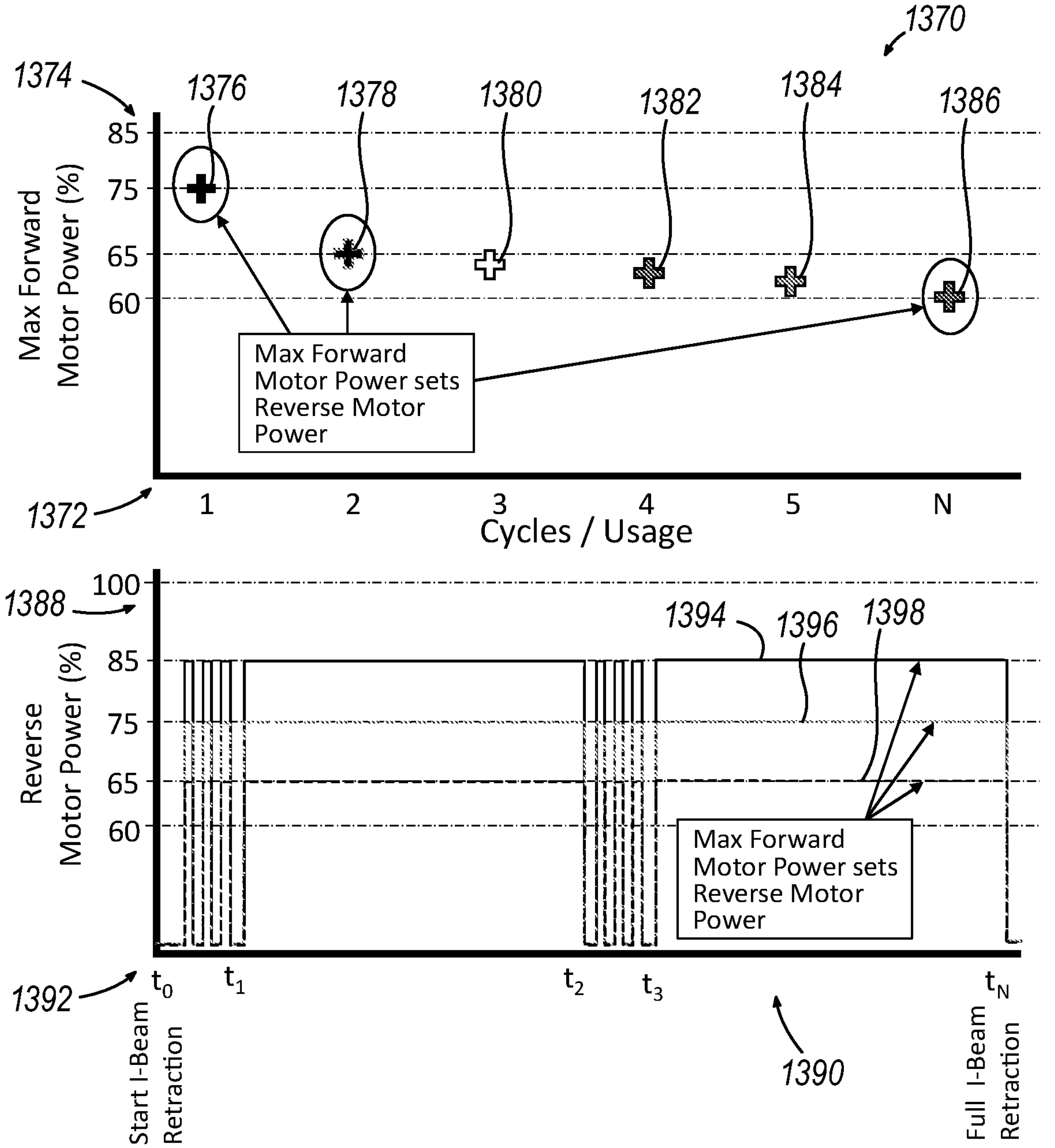
FIG. 27 depicts a graph representing the maximum forward and reverse motor power represented over the usage cycle and time, respectively.

FIG. 27 shows a first graph (1370) representing the cycles which instrument has been used compared to maximum forward power output level motors (1304, 1306) may be utilized to distally actuate driving assembly (164) or firing beam (216). Processing unit (1308) may recall a cycles/usage information (1372) once a specific instrument (110) is coupled to robotic arm (1342) to determine what the maximum forward power value (1374) motor (1304, 1306) may operate during exemplary use. Therefore, the number of cycles in which a specific instrument (110) is used may be utilized in determining the maximum forward power value (1374) at which motors (1304, 1306) may operate.

It should be understood that once a specific instrument (110) is used to fire staples and sever tissue in accord with the description herein, processing unit (1308) may add a cycle/usage to storage device (1310) for the specific instrument (110). Therefore, once the specific instrument (110) is reprocessed and recoupled with robotic arm (1342) for additional use, processing unit (1308) will then determine instrument (110) has been used one more time compared to the previous use and will therefore adjust the maximum motor power limits (1352) for operating the specific instrument (110) accordingly.

The maximum forward power value (1374) represents the maximum power output level motor (1304, 1306) may operate to distally advance driving assembly (164) or firing beam (216) to sever and staple tissue in accordance with the teachings herein. Processing unit (1308) may then utilize the determined maximum forward power value (1374) in order to determine a maximum reverse power value. The maximum reverse power value represents the maximum power output level motor (1304, 1306) may operate at while proximally retracting driving assembly (164) or firing beam (216) in accordance with the teachings herein. In some instances, the maximum reverse power value may be determined by the number of cycles a specific instrument (110) has been used, and the maximum forward power value may be determined based off the maximum reverse power value.

In the current example, as shown in FIG. 27, processing unit (1308) would determine the maximum forward motor power used for a specific instrument (110) during its first cycle/use (1376) to be 75% of the maximum power production of motor (1304, 1306). During the second cycle (1378), third cycle (1380), fourth cycle (1382), fifth cycle (1384), and $n^{th}$ cycle (1386), the maximum power capable of being achieved by motor (1304, 1306) may drop to 65%, 64%, 63%, 62%, and 61%, respectively, of the maximum power production of motor (1304, 1306). In the current example, the maximum forward power production of motors (1304, 1306) during the first cycle (1376) may be substantially greater than the sequential cycles. This greater drop after the first use may be due to break-in and/or initial wear of components of end effector (116, 210) after the first use.

Based on the information of the maximum forward motor power in the current example, as shown in the firing assembly retraction graph (1388), the maximum reverse motor power would be 85%, 75%, and 65% of the maximum power production of motor (1304, 1306) for the first cycle (1394), second cycle (1396), and third cycle (1398), respectively. In some instances, the maximum reverse motor power output level would not be allowed to surpass a defined amount over the maximum forward motor power output level. In the current example, that power difference margin would be 10%.

In the current example, the maximum forward and reverse motor power output levels are reduced as the number of cycles/usages increase for each specific instrument (110). This reduction in the forward motor power output level may be proportionate to the wear of the pusher member (166), pusher block (236), jaws (150, 152, 212, 214) and the channels defined by jaws due to the frictional engagement between respective components during exemplary firing of staples and severing of tissue. This wear due the exemplary use may lead to a reduction in lubrication as well as surface finish of metal components, thereby increasing the frictional resistance to distal advancement of driving assembly (164) or firing beam (216).The lowering of the maximum forward and reverse motor power output levels may help ensure motors (1304, 1306) do not accidentally break internal components of instrument (110) during exemplary use, as breaking such internal components may increase the difficulty of retracting driving assembly (164) or firing beam (216) in accordance with the description herein.

In the current example, the maximum reverse motor power is greater than the corresponding maximum forward motor power. This difference in maximum motor power may help ensure that driving assembly (164) or firing beam (216) may be retracted proximally if they become undesirably stuck in a longitudinal position during distal advancement with a maximum forward motor power output level in accordance with the description herein.

While in the current example, the maximum motor power output levels may be determined by the number of cycles a specific instrument (110) is used, any other suitable factor may be used to determine the maximum motor power output levels as would be apparent to one skilled in the art in view of the teachings herein. For instances, a calculation based on an accumulated number of noteworthy events, as described in greater detail below, may be used to determine the maximum motor power levers for a specific instrument (110) during a specific cycle of use.

C. Exemplary Motor Control Algorithm Utilizing Multiple Robotic Motors Cooperatively As mentioned above, during exemplary use of end effector (210), distal advancement of closure tube (not shown) and closure ring (230) (see FIGS. 10 and 33A-33E) are used to close end effector (210). In other words, distal advancement of closure tube (not shown) and closure ring (230) are used to move lower jaw (212) and anvil jaw (214) toward each other in order to grasp tissue in accordance with the description herein. As also mentioned above, with tissue grasped between staple cartridge (218) and anvil jaw (214), firing beam (216) may then be advanced distally in order to sever and staple tissue in accordance with the description herein.

Figure 28:
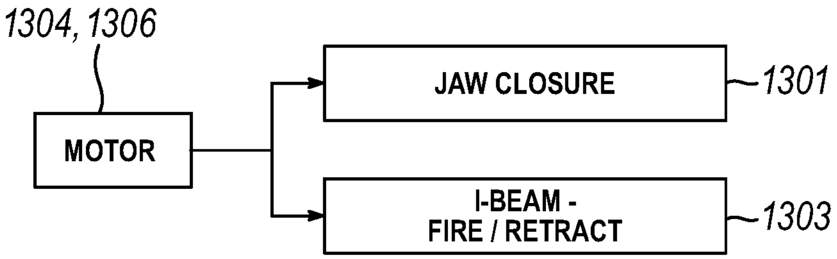
FIG. 28 depicts a schematic view of a motor assembly of the robotic arm of FIG. 23 coupled with the jaw closure assembly and the firing assembly of the surgical instrument of FIG. 4.

As schematically shown in FIG. 28, it should be understood that jaw closure assembly (1301), which includes closure tube (not shown), closure ring (230), and respective intermediary components, may be in communication with a first robotic motor (1304) via respective output coupler (1300) and input coupler (130); while a firing assembly (1303), which includes firing beam (216), and respective intermediary components, may be in communication with a second robotic motor (1306) via respective output coupler (1302) and input coupler (130). In other words, end effector (210) may be configured such that movement of jaws (212, 214) in order to grasp tissue may be performed independently with respect to actuation of firing beam (216) in order to sever and staple grasped tissue.

As mentioned above, while end effector (210) is used to staple and sever grasped tissue, distal advancement of firing beam (216) (see FIGS. 11 and 31A-31E) may be inhibited such that robotic surgical system (10) may have to power robotic motor (1304) past a predetermined maximum power output level in order to distally advance firing beam (216) further. In some instances, rather than using robot motor(s) past a predetermined power output level to further staple and sever grasped tissue is accordance with the description herein, robotic motor (1306) may be programed to temporarily stop, stall, halt, or otherwise delay advancement of firing beam (216) for a predetermined amount of time once the predetermined maximum motor power output level for advancing firing beam (216) is reached. In such instances, the temporary delay of advancing firing beam (216) may act as a passive means of reducing the required firing force for robotic motor (1306) to distally advance firing beam (216). This passive means of reducing the required firing force may allow for a "milking effect" to occur between jaws (212, 214) and grasped tissue, thereby reducing the amount of force required for firing beam (216) to staple and sever tissue in accordance with the teachings herein.

In some instances, instead of passively waiting for the "milking effect" to reduce the force required for robotic motor (1306) to distally advance firing beam (216) without exceeding a predetermined power output level of robotic motor (1306), it may be desirable to actively reduce the firing force required for robotic motor (1306) to advance firing beam (216) to thereby prevent robotic motor (1306) from operating past the predetermined power output level.

FIG. 18 shows a motor control algorithm (1420) may be utilized by robotic surgical system (10) in order to simultaneously or synchronously activate robotic motors (1304, 1306) that are in communication with jaw closure assembly (1301) and firing assembly (1303), respectively, thereby reducing the amount of firing force required to fully advance firing beam (216). FIGS. 31A-31E show an exemplary use of algorithm (1420), while FIG. 32 shows a graph (1440) representing the firing motor displacement (1444), the motor power output (1446) represented as a percentage, the closure motor force (1448), and the firing motor force (1450) over the time (1442) elapsed during exemplary use of algorithm (1420) as shown in FIGS. 31A-31E.

Figure 31A:
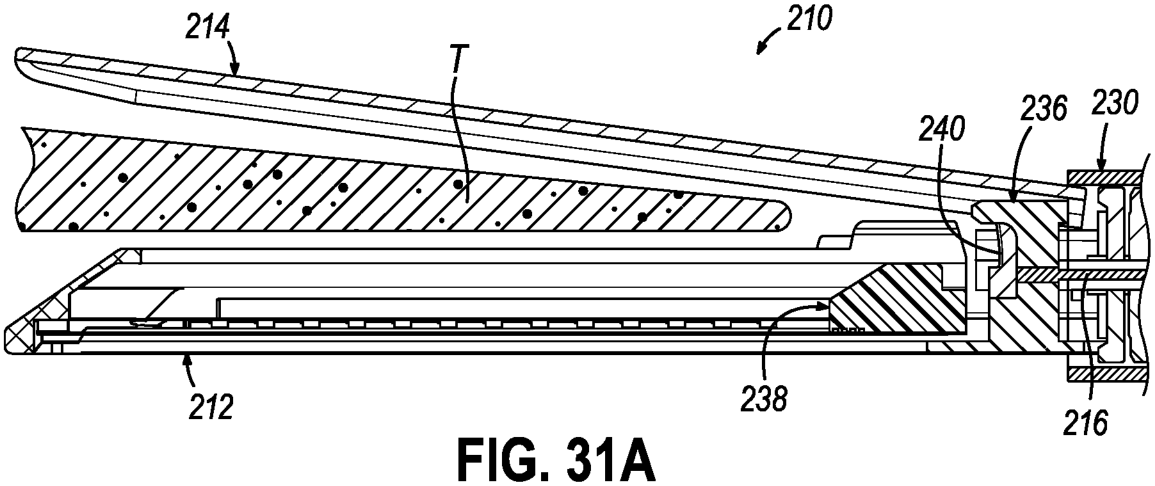
FIG. 31A depicts a cross-sectional side view of the end effector of FIG. 10, taken along a centerline thereof, with the jaws in an open position and the firing assembly in a pre-fired position.
Figure 31B:
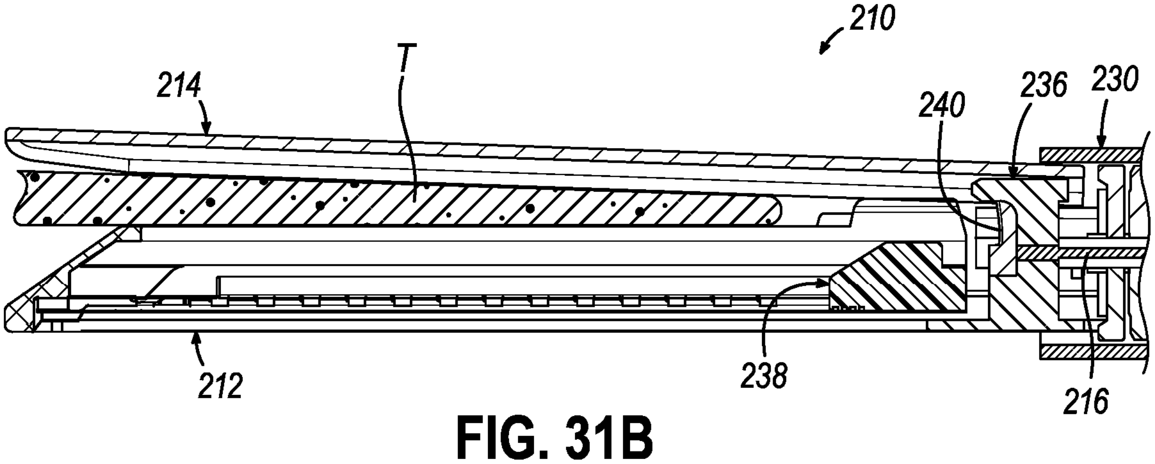
FIG. 31B depicts a cross-sectional side view of the end effector of FIG. 10, taken along a centerline thereof, with the jaws in a first closed position and the firing assembly in the pre-fired position.

First, as shown between FIGS. 31A-31B, an operator may utilize input control devices (36) of surgeon's console (16) to manipulate end effector (210) in grasping tissue (T) of a patient. This may be represented as the initial jaw closure (1422) in motor control algorithm (1420) shown in FIG. 29.

Figure 32:
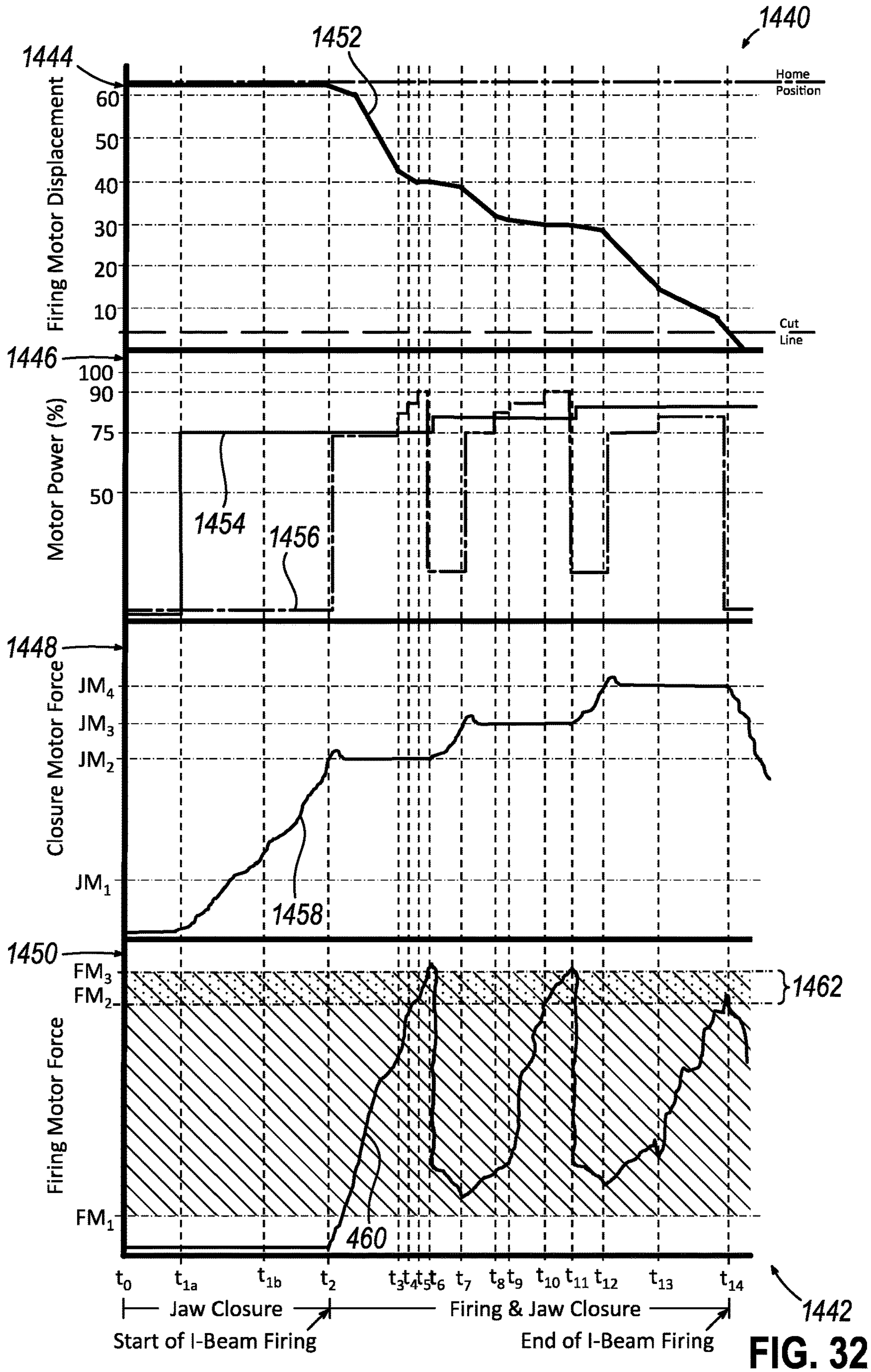
FIG. 32 depicts a graph showing the firing motor displacement, motor power, jaw closure force, and firing force over time of the firing sequence shown in FIGS. 31A-31E.

The initial closure of jaws (212, 214) to grasp tissue (T) is represented on graph (1440) of FIG. 32 between time (t0) and time (t2). Since jaw closure assembly (1301) and firing assembly (1303) are operated by separate motors (1304, 1306), respectively, and since actuation of firing beam (216) has not yet happened, firing motor displacement line (1452) (which represents the longitudinal position of pusher block (236)), firing motor output line (1456) (which represents output power of firing motor (1306)) and the firing motor force line (1460) (which represents the force imparted on firing motor (1306) in order to drive firing beam (216)) remain relatively unchanged between times (t0) and (t2).

However, the closure motor power output line (1454) (which may represent output power of closing motor (1304)) raises from little or no power output up to 75% in the current example in order to manipulate jaws (212, 214) to grasp tissue (T). Additionally, the closure motor force line (1458) (which represents the force imparted on closing motor (1304) in order to drive jaws (212, 214) closer together to grasp tissue (T)) increases to JM2 in response to motor (1304) driving jaws (212, 214) to grasp tissue (T). Therefore, closure motor (1304) is activated to drive jaws (212, 214) such that the reactive closure motor force line (1458) gradually increases due to contact between grasped tissue (T) and jaws (212, 214).

Figure 31C:
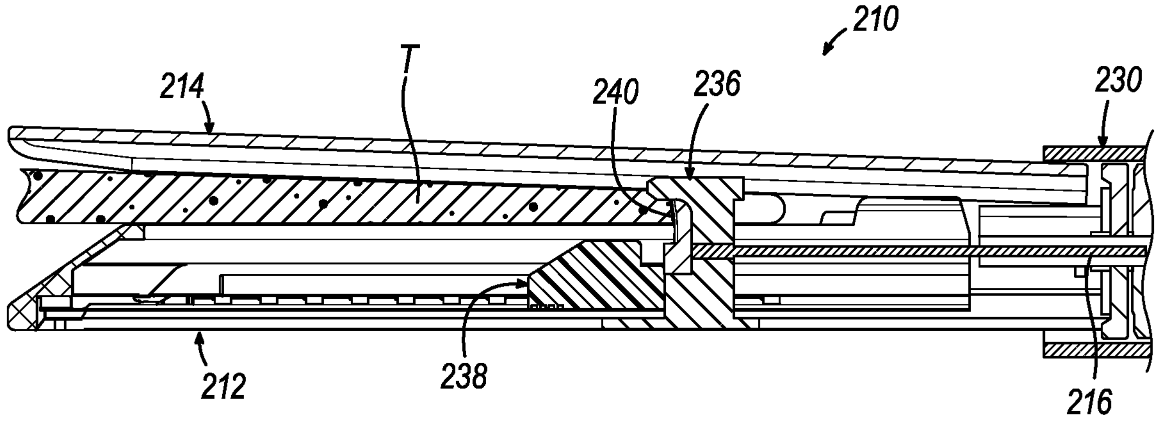
FIG. 31C depicts a cross-sectional side view of the end effector of FIG. 10, taken along a centerline thereof, with the jaws in the first closed position and the firing assembly in the partially fired position.

When the operator is ready to sever and staple tissue (T) grasped between jaws (212, 214) of end effector (210), the operator may initiate the firing sequence via surgeon's console (16), which in turn may initiate processing unit (1308) to instruct firing motor (1306) to advance (1424) (see FIG. 29) firing beam (216) as shown between FIGS. 31B-31C. The initial advancement of firing beam (216) to staple and sever tissue (T) is represented on graph (1440) of FIG. 32 between time (t2) and time (t6).

Since jaw closure assembly (1301) has not been substantially moved between times (t2) and (t6), the jaw motor force line (1458) and the closure motor power output line (1454) remain relatively unchanged between times (t2) and (t6). However, the firing motor power output line (1456) raises from little or no power output up to 75% initially, and then further to 90% in the current example, in order to advance firing beam (216). Additionally, in response to motor (1306) driving the firing beam (216) to staple and cut tissue (T), the firing motor force line (1460) increases from substantially zero all the way to within a limit zone (1462) defined by FM2 and FM3. Therefore, firing motor (1306) is activated such that the firing motor force line (1460) gradually increases due to firing beam (216) contacting both tissue (T) and wedge sled (238).

Figure 29:
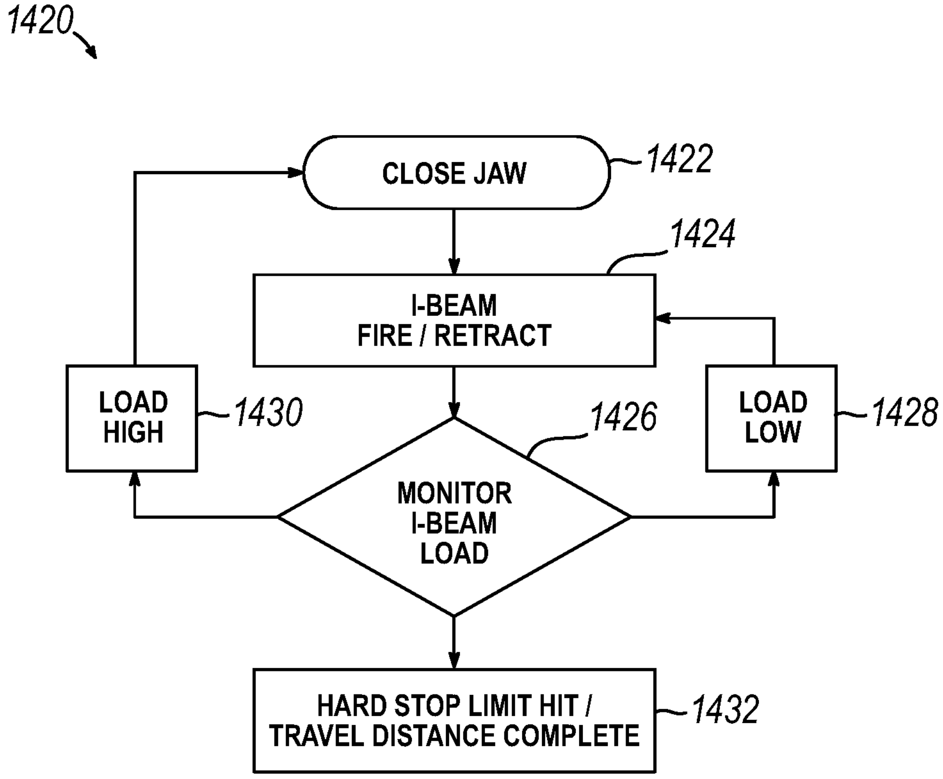
FIG. 29 depicts a block diagram of an exemplary motor control algorithm that may be used by the robotic arm and surgical instrument shown in FIG. 23.

As shown in FIG. 29, control algorithm (1420) includes monitoring (1426) the load on firing beam (216) such that if the load is below (1428) the trigger limit zone (1462), processing unit (1308) instructs firing motor (1306) to further advance firing beam (216). However, if the measured load on firing beam (216) is measured as a high load (1430) (i.e., within the limit zone (1462) defined by FM2 and FM3) this may be indicative of robotic motor (1304) operating past a predetermined maximum power output level, which may lead to undesirable consequences described above.

Figure 31D:
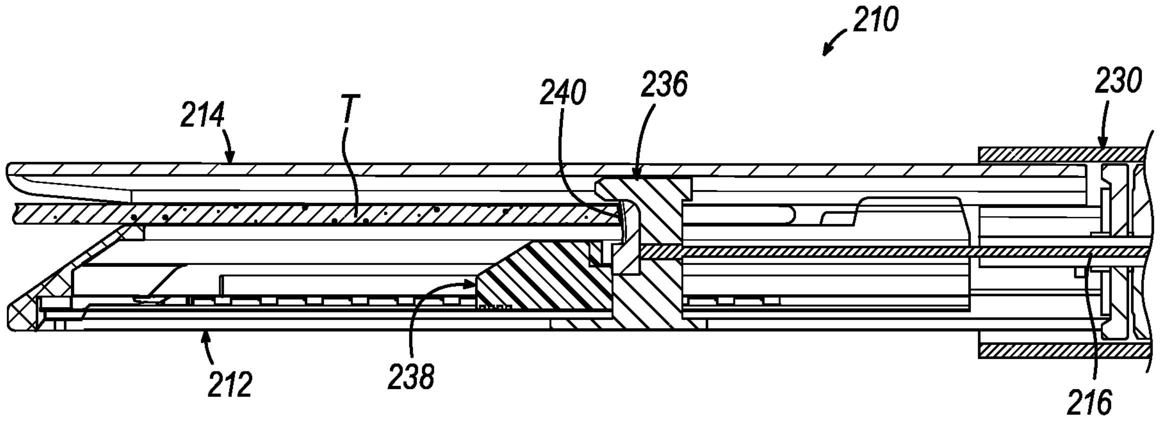
FIG. 31D depicts a cross-sectional side view of the end effector of FIG. 10, taken along a centerline thereof, with the jaws in a second closed position and the firing assembly in the partially fired position.
Figure 31E:
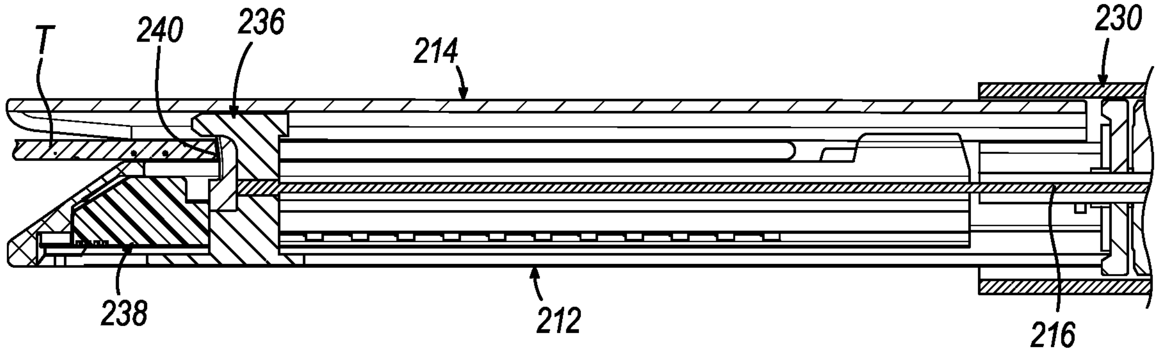
FIG. 31E depicts a cross-sectional side view of the end effector of FIG. 10, taken along a centerline thereof, with the jaws in the second closed position and the firing assembly in the fired position.

Instead of passively waiting for the milking effect to reduce the amount of force required to distally advance firing beam (216) such that firing motor (1306) is not forced to operate within limit zone (1462), processing unit (1308) instead instructs closing motor (1304) to further close jaws (212, 214), as shown in FIG. 31D. Further closing jaws (212, 214) during the firing process may reduce the gap distance between jaws (212, 214), which in turn may actively reduce the firing force required to advance firing beam (216) such that firing motor (1306) is not forced to operated past a predetermined maximum power output level.

Once the firing force required to advance firing beam (216) is sufficiently reduced, the processing unit (1308) may then instruct firing motor (1306) to distally advance (1424) firing beam (216) to sever and staple tissue (T). If firing motor (1306) experienced a firing force within limit zone (1462) again, processing unit (1308) may repeat the further closing of jaws (212, 214) to lower reduce the gap distance and firing forces required to actuate firing beam (216) until firing beam (216) reaches the fully fired position shown in FIG. 31E. One the fully fired position is achieved, processing unit (1308) may instruct firing motor (1306) to proximally retract firing beam (216).

As shown between times (t6) and (t7) in the graph (1440) on FIG. 32, the further activation of closing motor (1304) to reduce the gap distance occurs sequentially with the activation of firing motor (1306) to drive firing beam (216). However, it should be understood that this is merely optional, as the activation of closing motor (13040 and the activation of firing motor (1306) may occur simultaneously in order to actively reduce the gap distance while still stapling and severing tissue (T) in accordance with the description herein.

It should be understood this motor control algorithm (1420) may be initiated during at any suitable time during the firing process as would be apparent to one skilled in the art in view of the teachings herein. It should also be understood that processing unit (1308) may read all the data produced by motor (1304, 1306) and shown in graph (1400) in real time and utilize such data to execute algorithm (1350) described herein.

Figure 33A:
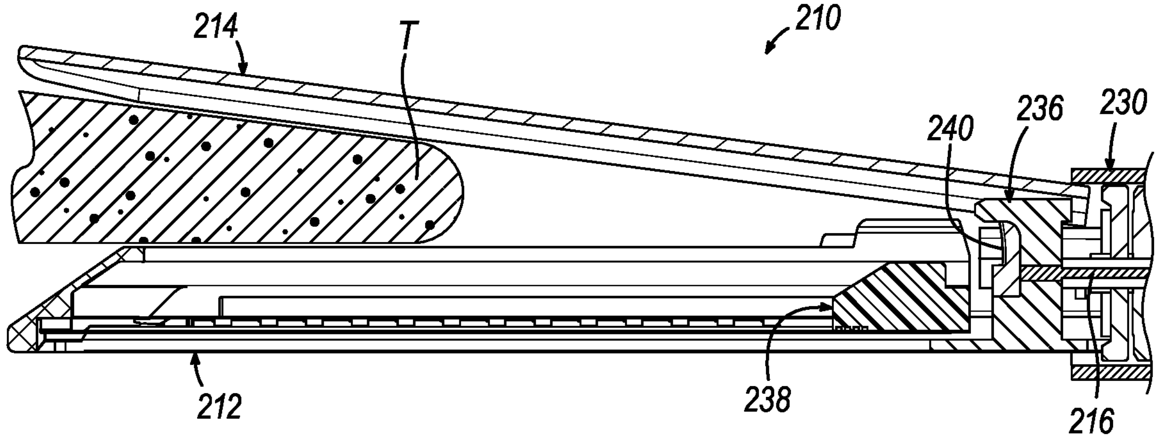
FIG. 33A depicts a cross-sectional side view of the end effector of FIG. 10, taken along a centerline thereof, prior to grasping tissue along a first depth of the end effector.
Figure 33B:
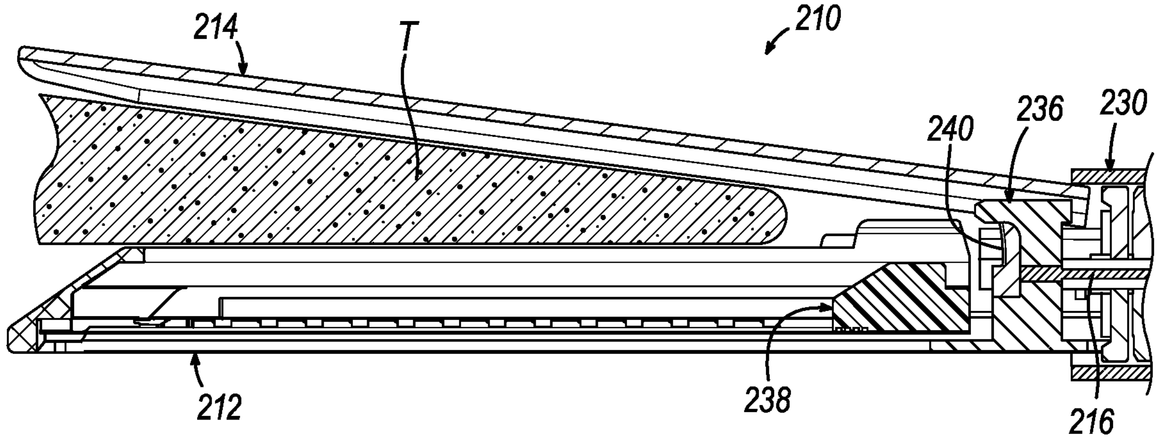
FIG. 33B depicts a cross-sectional side view of the end effector of FIG. 10, taken along a centerline thereof, prior to grasping tissue along a second depth of the end effector that is shallower than the first depth shown in FIG. 31A.
Figure 34:
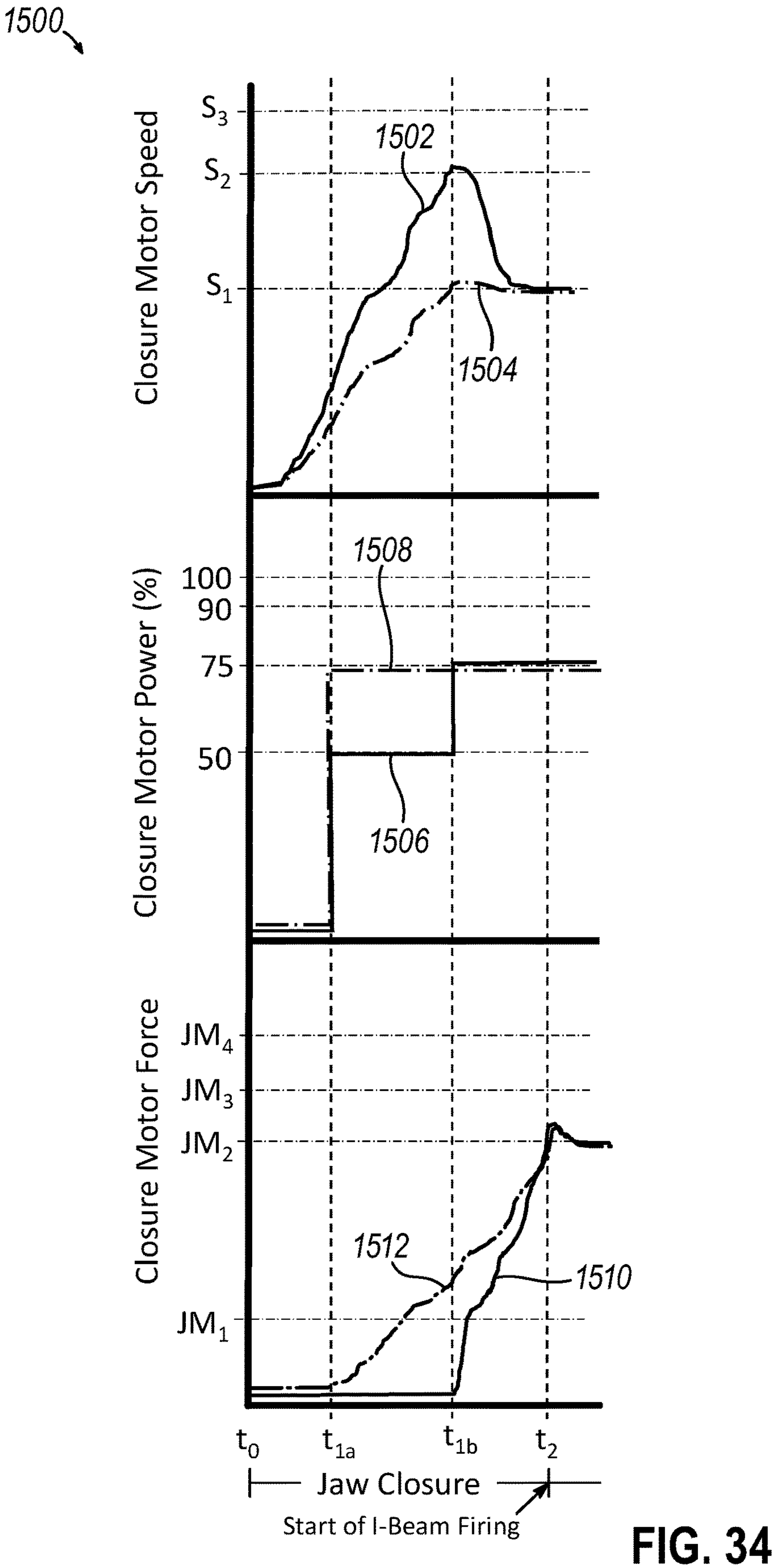
FIG. 34 depicts a graph showing closure motor speed, closure motor power, and closure motor force of the end effector of FIG. 10 grasping tissue at the positions shown in FIGS. 33A and 33B over time.

In some instances, as shown in FIGS. 33A-33B, tissue (T) may be grasped along different lengths of jaws (212, 214). For instances, FIG. 33A show tissue (T) being grasped at a proximal most end that is located halfway along jaws (212, 214), while FIG. 33B shows tissue (T) being grasped at a proximal most end that is located closer to the proximal end of jaws (212, 214). As can be seen in graph (1500) of FIG. 34, the closure motor speed, the closure motor power, and the closure motor force are different for when tissue is grasped halfway along jaws (212, 214) (as represented by lines (1502, 1506, 1510); as compared to when tissue (T) is fully grasped along the length of jaws (212, 214) (as represented by lines (1504, 1508, 1512).

As mentioned above, sensor assembly (1312) may be configured to determine the location along jaws (212, 214) which tissue is grasped, the tissue load imparted on jaws (212, 214) from grasping tissue (T), etc. FIG. 30 shows an algorithm (1470) that may be utilized after jaws (212, 214) grasp tissue (T) it order to establish the appropriate operating parameters. For instance, in block (1472), once tissue is grasped, the sensor assembly (1312) may communicate to processing unit (1308) the tissue load, the location of tissue in jaws (212, 214), and whether any milking effect is being experienced. In block (1474), processing unit (1308) may further determine the motor operating parameters for firing beam (216) based on data received from closing motor (1304) as well as the jaw closure data of block (1472). With these parameters, processing unit (1308) may instruct motors (1304, 1306) to close jaws (212, 214) and advance firing beam (216) at the determined power and speed based at least partially on recently obtained data, as shown in block (1476). If the load in jaws (212, 214) change, as indicated in block (1478), processing unit (1308) may then adjust the firing motor (1306) as shown in block (1480).

D. Exemplary Algorithm for Determining End-of-Life of Robotic Surgical Instrument As mentioned above, surgical instruments (110) being used during a procedure may be used in accordance with the description herein, removed from robotic arm (1342), and then replaced such that another instrument (110) is loaded back onto robotic arm (1342). For instance, assistant(s) (20) may remove surgical instrument (110) having end effector (116, 210) from patient side cart (22) and replace surgical instrument (110) with another surgical instrument (110) from a tray (30) (shown in FIG. 1) in the operating room. The recently removed surgical instrument (110) may have a spent end effector (116, 210). In other words, the recently removed surgical instrument (110) may have an end effector (116, 210) that has been fired in accordance with the description herein in order to sever and staple grasped tissue. In such instances, surgical instrument (110) may be reloaded with another staple cartridge (154, 218), reattached to robotic arm (1342), and then used for another cycle in order to sever and staple tissue in accordance with the teachings herein.

In some instances, a specific surgical instrument (110) may have components that wear-down after being used for multiple firing cycles. Additionally, a specific surgical instrument (110) may encounter unique operating conditions such that one specific surgical instrument (110) may wear-down faster compared to another specific surgical instrument (110). For instances, a specific surgical instrument (110) may require robotic motors (1304, 1306) to exceed their determined motor current limit during use of surgical instrument (110) for a specific use cycle. As another example, a specific surgical instrument (110) may experience an algorithmic bumping cycle (1360) during a specific use cycle.

Therefore, it may be desirable to track noteworthy events affecting the use-life of a specific surgical instrument (110) in order to (A) determine desirable operating parameters for the next use of a specific surgical instrument (110), and (B) to determine the end-of-life of a specific surgical instrument (110) such that it is recommended that surgical instrument (110) not be used for another cycle in accordance with the description herein.

Additionally, as mentioned above, processing unit (1308) may measure or receive operating data of robotic motors (1304, 1306) during exemplary use, transmit such data to a suitable storage device (1310) (which may be associated with a specific instrument (110), robotic arm (1342), or another suitable component of robotic surgical system (10)), and then recall such stored data for later use. Processing unit (1308) and storage device (1310) may store operating data of robotic motors (1304, 1306) accumulated during exemplary use of a specific instrument (110). As also mentioned above, processing unit (1308) may be configured to determine when a noteworthy event occurred during operation of a specific instrument (110) and communicate such a noteworthy event to storage device (1310) such that processing unit (1308) may recall and utilize such noteworthy events when the specific instrument (110) is recoupled and reused with robotic arm (1342) in accordance with the teachings herein.

Figure 35:
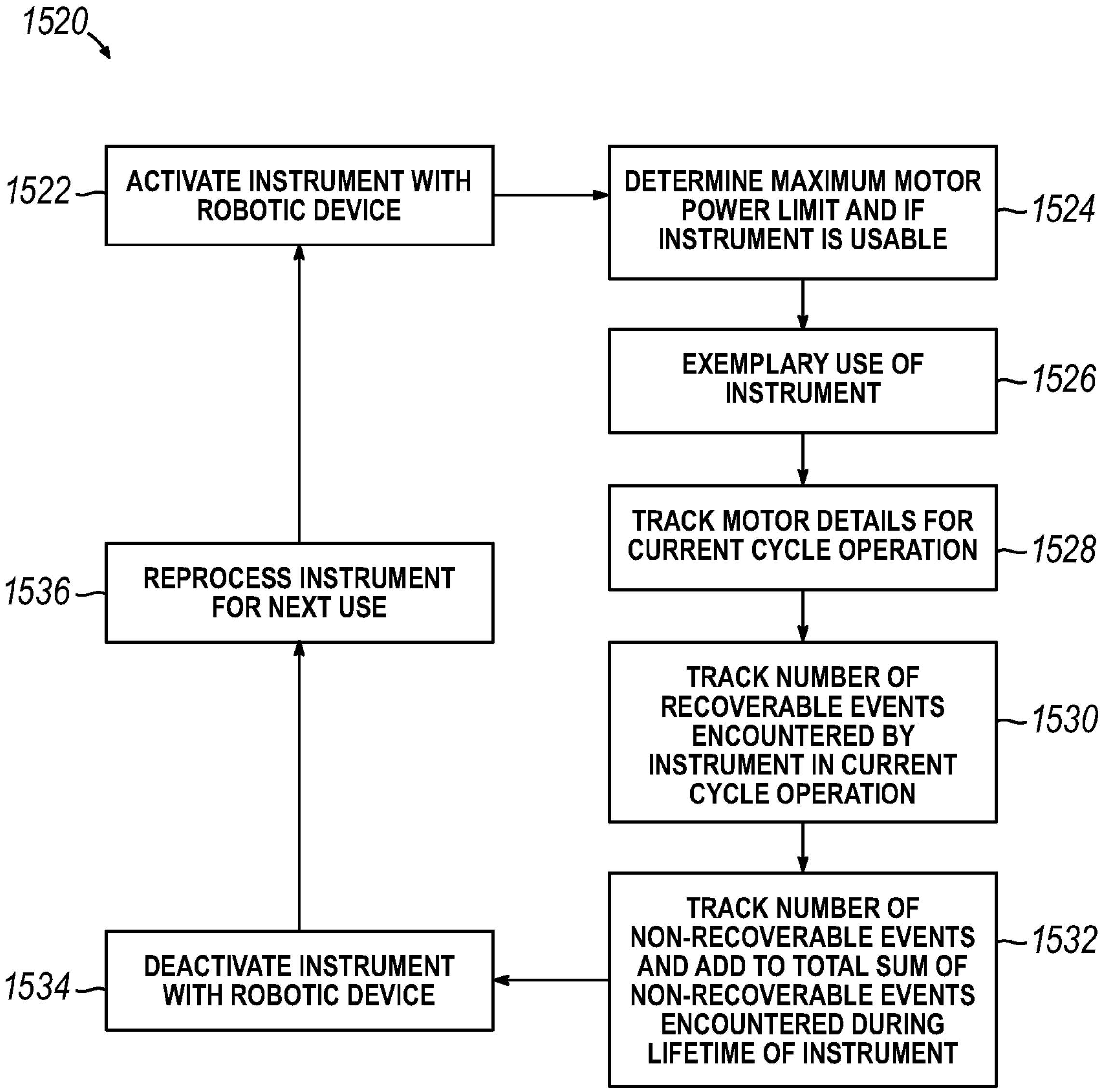
FIG. 35 depicts a block diagram of an exemplary end-of-life algorithm that may be used by the robotic arm and surgical instrument shown in FIG. 23.

Therefore, processing unit (1308) may be configured to utilize the exemplary end-of-life algorithm (1520) shown in FIG. 35. FIG. 36 shows an exemplary data table (1540) that may be utilized by processing unit (1308) in order to determine (A) operating parameters for motors (1304, 1306) during use a specific instrument (110) during a specific cycle, and (B) whether or not the specific instrument (110) should be used again in accordance with the description herein (i.e., the end-of-life of instrument (110)).

First, as shown in block (1522), an operator may couple a specific instrument (110) with robotic arm (1342) for exemplary use. After instrument (110) is coupled with robotic arm (1342), as shown in block (1524), processing unit (1308) use data obtained from previous uses of the specific instrument (110) to determine the operating parameters of motor (such as max motor power limit) and/or if specific instrument (110) should not be used again. If it is determined that the specific instrument (110) should not be used again, processing unit (1308) may notify a user that instrument (110) has reached its end-of-life and should not be used again and/or lock out further use of instrument (110).

Processing unit (1308) may determine if the specific instrument (110) should not be used again using any suitable criteria as would be apparent to one skilled in the art in view of the teachings herein. For example, if the max motor power limit determined by processing unit (1308) for a specific instrument (110) is below a predetermined threshold, then processing unit (1308) may determine instrument (110) has reached its end-of-life. As another example, if an accumulative number of events occurs for a specific noteworthy category (such a sum of non-recoverable events), then processing unit (1308) may determine instrument (110) has reached its end-of-life. It should be understood processing unit (1308) may determine the reduction in max motor power limit by accumulating any data or noteworthy events that would be apparent to one skilled in the art in view of the teachings herein. Additionally, each category of noteworthy events may have their own weight in determining the operating parameters of motors (1304, 1306) during the next use, or if instrument (110) should even be used at all.

As an example, processing unit (1308) may collect data in the form of a data table (1540). Processing unit (1308) may access data table (1540) after previous uses of a specific instrument (110) to determine the motor power limits that should be established for the upcoming use cycle.

Referencing data table (1540), when specific instrument (110) was coupled to robotic arm (1342) for the second use cycle, data collected during the first use cycle was used to drop the maximum motor power limit from 100% to 93%. This reduction was based on (A) the previous use of instrument, and (B) the fact processing unit (1308) detected four "non-recoverable" events during the first usage. When specific instrument (110) was coupled to robotic arm (1342) for the third use cycle and the sixth use cycle, a reduction in maximum motor power limit occurred due to (A) the previous use of instrument, and (B) the fact processing unit (1308) detected "recoverable" events during the first usage. In some instances, and shown between uses four and five, max motor power limits may drop due to accumulations within the "cycle operation counts" category, such as experiencing a moment where robotic motors (1304, 1306) excess an electrical current limit, a temperature limit, undergo an algorithmic bumping cycle (1360), or experience a passive "wait period" to allow for the milking effect to reduce the requiring firing force.

The difference between "non-recoverable" events and "recoverable" events may be determined by the degree of severity such an event has on the impact the specific instrument (110). For instance, a recoverable even may include the severing knife (172) coming into contact with a clip or other item that is not the intended tissue, while a non-recoverable even may be more sever.

If the specific instrument (110) is determined suitable for another use cycle the operator may use instrument (110) in accordance with the description herein, as shown in block (1526). During exemplary use, processing unit (1308) may track motor details for the current cycle operation, as shown in block (1528). Additionally, processing gun it (1308) may track the number of recoverable events for the current cycle operation, as shown in block (1530). Also, processing unit may track the number of non-recoverable events during a current cycle and add those to the sum of non-recoverable events encountered previously during the lifetime of the instrument (110), as indicted in block (1532).

After use of instrument (110), instrument (110) may be detached from robotic arm (1342) and reprocessed for next use as indicated in blocks (1534, 1536). Processing unit (1308) may then add the data information related to the current cycle used to data table (1540) in order to use such data in determining potential end-of-life of instrument (110) during next use, or in determining the new operating partakers of robotic arm (1342) for the next use of instrument (110).

IV. Exemplary Improvements to Jaw Closure Members

A. Exemplary Jaw Closure Member with Tapered Surfaces

As mentioned above, pusher member (166) includes flanges (184, 185) that may actuate within jaws (150, 152) in order to drive jaws (150, 152) toward and away from each other. In some instances, during actuation of pusher member (166) (see FIG. 8) in accordance with the description herein, a proximal or distal end of flanges (184, 185) may overly engage, bind against, or dig into portions of staple cartridge (154) and/or jaws (150, 152) defining associated longitudinal slots (186, 187). This over-engagement may cause surface irregularities on the portion of jaws defining channels, also referred to as slots (186, 187), which may increase the frictional resistance to advancing/retracing pusher member (166) within slots (186, 187) for future uses. The over-engagement and increase in frictional resistance to actuating pusher member (166) within slots (186, 187) may undesirably reduce the potential number of uses for instrument (110) with robotic surgical system (10). Therefore, it may be desirable to provide a pusher member (166) with features that may reduce the chances of over-engaging, or otherwise causing surface irregularities with, the portions of staple cartridge (154) and/or jaws (150, 152) defining longitudinal slots (186, 187).

Figure 37:
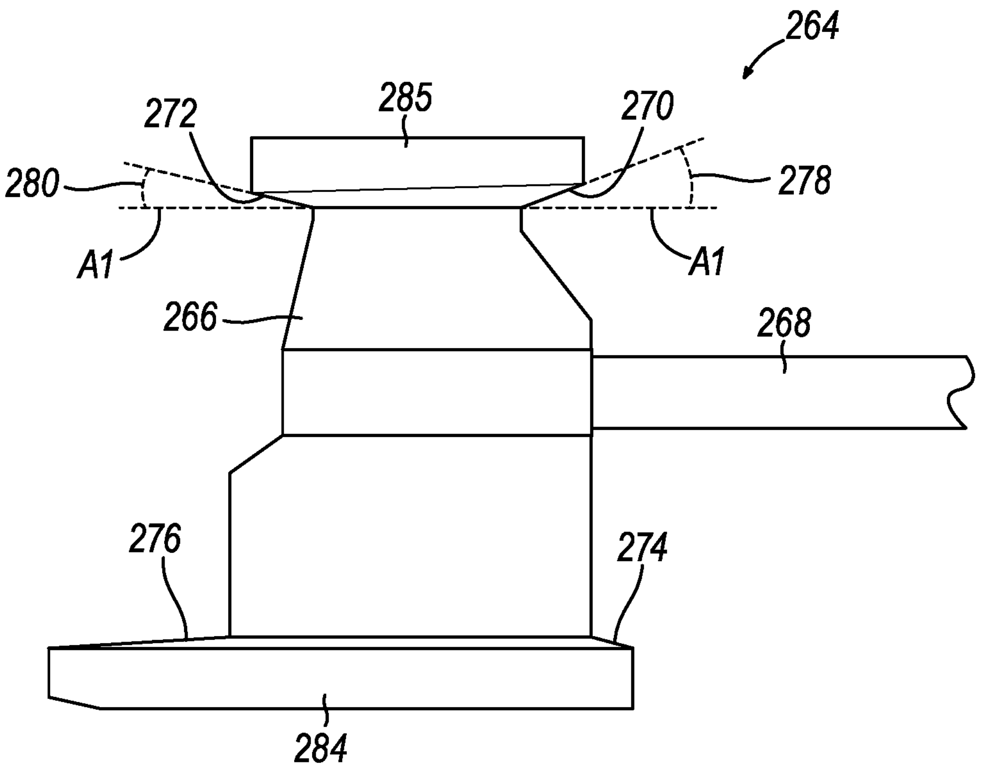
FIG. 37 depicts an elevational side view of an alternative driving assembly that may be readily incorporated into the end effector of FIG. 4.

FIG. 37 shows an exemplary alternative driving assembly (264) that may be readily incorporated into instrument (110) in replacement of driving assembly (164) described above. Therefore, driving assembly (264) may be substantially similar to driving assembly (164) described above, with differenced elaborated below.

Driving assembly (164) includes a pusher member (266) and a push rod (268). Push rod (268) is substantially similar to push rod (168) described above. Pusher member (266) is substantially similar to pusher member (166) described above, with difference elaborated below. Pusher member (266) includes first and second flanges (284, 285). First flange (284) is configured to be received in a longitudinal slot (187) (see FIGS. 38A-38E) of staple cartridge body (156) of lower jaw (152) and second flange (285) is configured to be received in a longitudinal slot (186) (see FIGS. 38A-38E) of upper jaw (150). First and second flanges (284, 285) may move within the confines of longitudinal slots (187, 186) during actuation of pusher member (266) in order to fire staples and sever tissue in accordance with the description herein.

Flanges (284, 285) include proximal facing tapered surfaces (274, 270) and distal facing tapered surfaces (276, 272), respectively. Proximal facing tapered surfaces (270, 274) extend proximally such that flanges (284, 285) decrease in width along the length of tapered surfaces (270, 274) in the proximal direction. Distal facing tapered surfaces (272, 276) extends distally such that flanges (284, 285) decrease in width in the distal direction along the length of tapered surfaces (272, 276) in the distal direction.

Tapered surfaces (270, 272, 274, 276) extend to define an angle with an axis extending parallel with the long axis of push rod (268). As exemplified with second flange (285), proximal facing tapered surface (270) defines a first angle (278) with a long axis (A1) that extends parallel with the long axis of push rod; while distal facing tapered surface (272) defines a second angle (280) with long axis (A1). First angle (278) may be greater than second angle (280).

Proximal facing tapered surfaces (270, 274) may have a steeper angle compared to distal facing tapered surfaces (282, 276), as the chance of pusher member (266) deforming the portions of upper jaw (150) and cartridge body (156) defining slots (186, 187) may be greater as pusher member (266) is retracted proximally after reaching a distal stopping point of the firing process.

Distal facing tapered surfaces (272, 276) are configured to cam against portions of upper jaw (150) and cartridge body (156) defining slots (186, 187) as pusher member (166) is driven distally; while proximal facing tapered surfaces (270, 274) are configured to cam against upper jaw (150) and cartridge body (156) defining slots (186, 187) as pusher member (166) is driven proximally. Due to the angles formed by tapered surfaces (270, 272, 274, 276), the portions of flanges (284, 285) in contact with upper jaw (150) and cartridge body (156) may be further away from the proximal and distal edges of flanges (284, 285), thereby reducing the chances of flanges (284, 285) digging into upper jaw (150) and staple cartridge (154). In other words, because tapered surfaces (270, 272, 274, 276) are angled, a portion of tapered surfaces (270, 272, 274, 276) may initiate contact with the portions of upper jaw (150) and cartridge body (156) defining slots (186, 187) in order to pivots jaws (150, 152), which be less likely to dig into, or otherwise deform the surfaces defining slots (186, 187) compared to a proximal or distal edge of flanges (284, 285).

Figure 38A:
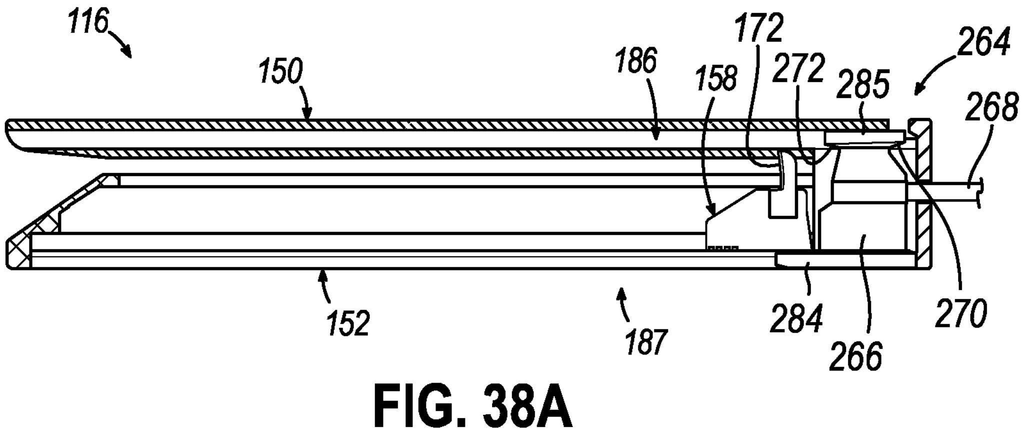
FIG. 38A depicts a cross-sectional side view of the driving assembly of FIG. 37 incorporated into the end effector of FIG. 4, taken along a centerline thereof, with the driving assembly in a pre-fired position.

FIGS. 38A-38E show an exemplary firing of driving assembly (264). First, as shown in FIG. 38A, driving assembly (264) may be in the pre-fired position. Push rod (268) may be driven distally to the position shown in FIG. 38B such that distal facing tapered surfaces (272, 276) cam against portions of upper jaw (150) and cartridge body (156) defining slots (186, 187). This interaction may be used to pivot jaws (150, 152) toward each other and grasp tissue. The angled nature of tapered surfaces (272, 276) may ensure a distal edge of flanges (284, 285) do not initiate contact between surfaces that cam against each other to pivot jaws (150, 152), which may reduce the chances of flanges (284, 285) digging into and damaging portions of upper jaw (150) and cartridge body (156) defining slots (186, 187).

Figure 38B:
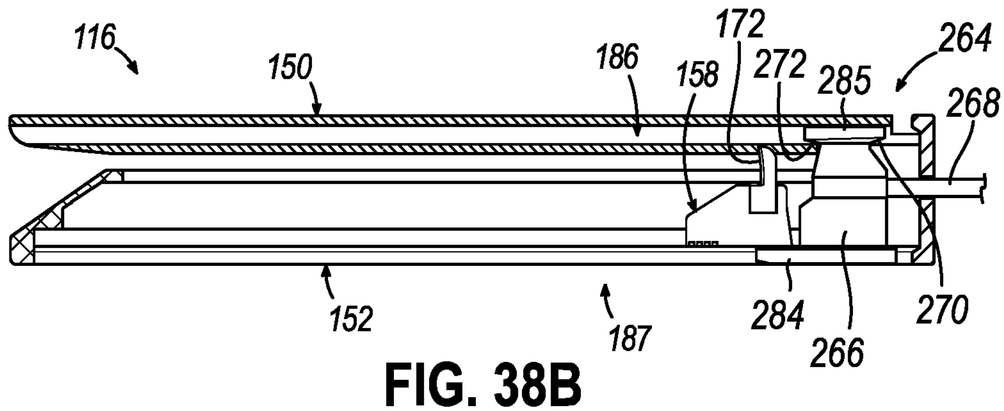
FIG. 38B depicts a cross-sectional side view of the driving assembly of FIG. 37 incorporated into the end effector of FIG. 4, taken along a centerline thereof, with the driving assembly in a partially advanced position.
Figure 38C:
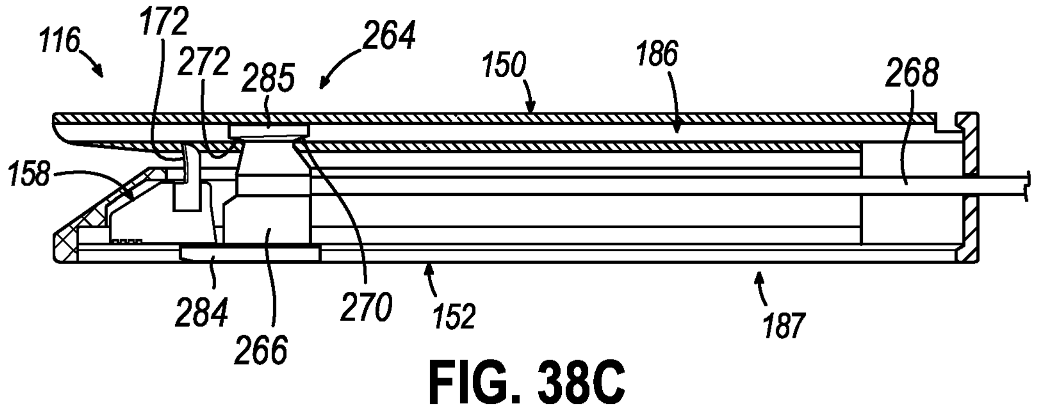
FIG. 38C depicts a cross-sectional side view of the driving assembly of FIG. 37 incorporated into the end effector of FIG. 4, taken along a centerline thereof, with the driving assembly in a fully advanced position.

Once the firing process starts, driving assembly (264) may be driven distally via movement of push rod (268) in order to staple and server tissue, as shown between FIGS. 38B-38C. It should be understood this distal movement may further pivot jaws (150, 152) toward each other via interaction between distal tapered surfaces (272, 276) and slots (186, 187), increasing the clamping force on tissue.

Figure 38D:
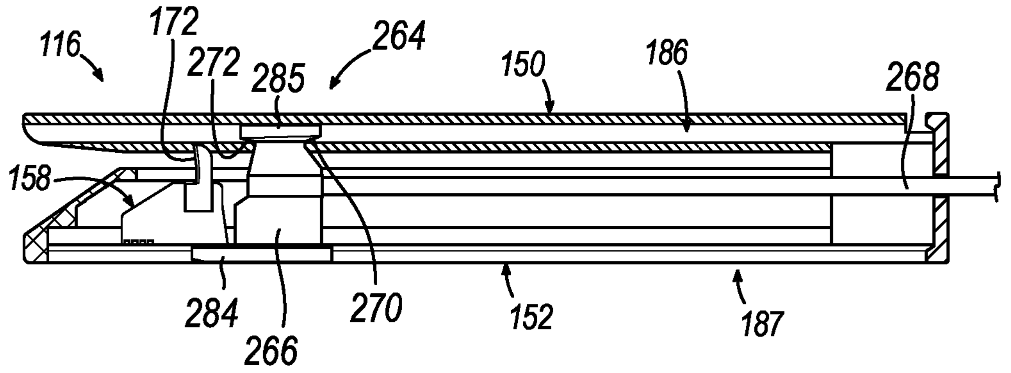
FIG. 38D depicts a cross-sectional side view of the driving assembly of FIG. 37 incorporated into the end effector of FIG. 4, taken along a centerline thereof, with the driving assembly initially retracted in the proximal direction from the fully advanced position.

With severing and stapling complete, push rod (268) may be driven proximally such that proximal facing tapered surfaces (270, 274) cam against portions of upper jaw (150) and cartridge body (156) defining slots (186, 187) to initially release tissue, as exemplified between FIGS. 38C-38D. The angled nature of tapered surfaces (270, 274) may ensure a proximal edge of flanges (284, 285) do not initiate contact between surfaces that cam against each other to pivot jaws (150, 152), which may reduce the chances of flanges (284, 285) digging into and damaging portions of upper jaw (150) and cartridge body (156) defining slots (186, 187).

Since distal movement of driving assembly (264) further clamps tissue between jaws (150, 152) the initial camming force between proximal facing tapered surfaces (270, 274) and slot (186, 187) may be greater to open jaws (150, 152) as compared to closing jaws (150, 152). Therefore, the steeper angle of proximal facings tapered surfaces (270, 274) as compared to distal facing tapered surfaces (272, 276) may be beneficial.

Figure 38E:
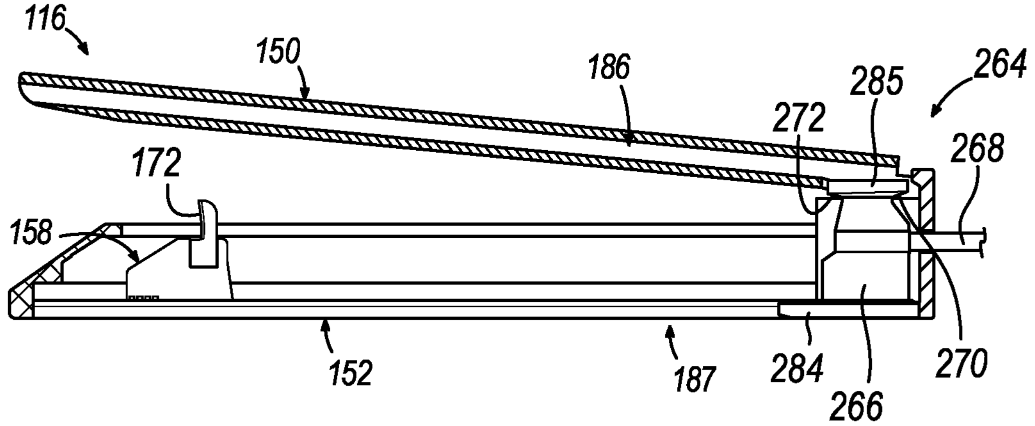
FIG. 38E depicts a cross-sectional side view of the driving assembly of FIG. 37 incorporated into the end effector of FIG. 4, taken along a centerline thereof, with the driving assembly fully retracted in the proximal direction from the fully advanced position.

With jaws (150, 152) initial pivoted open to release tissue, driving assembly (264) may then be driven to the pre-fired position as shown in FIG. 38E.

B. Exemplary Jaw Closure Member with Expandable Flange Members

As mentioned above, pusher member (166) is configured to actuate within jaws (150, 152) in order to drive jaws (150, 152) to close and open relative to each other and thereby grasp and release tissue. In particular, flanges (184, 185) of pusher member (166) abut against portions of staple cartridge (154) and/or jaws (150, 152) defining associated longitudinal slots (186, 187). When jaws (150, 152) grasp tissue, the tissue may impart a reactionary force onto jaws (150, 152). Such a reactionary force may attempt to drive jaws (150, 152) toward a more open position which may increase the frictional engagement between flanges (184, 185) and the portions of end effector (116) defining longitudinal slots (186, 187).

In some instances, if this frictional force between flanges (184, 185) and portions of end effector defining longitudinal slots (186, 187) becomes too great, flanges (184, 185) may overly engage or dig into portions of staple cartridge (154) and/or jaws (150, 152) defining associated longitudinal slots (186, 187), therefore inhibiting suitable movement of pusher number (166). With such suitable movement of driving assembly (164) being inhibited, an operator may have to (A) power robotic motor(s) (not shown) past a predetermined maximum power output level for a specific instrument (110) in order to move driving assembly (164), or (B) use manual actuator (124) to manually "bailout" end effector (116, 210), in order to retract driving assembly (164) back toward a proximal position. Use of robotic motor(s) (not shown) past a predetermined maximum power output level or use of manual actuator (124) to "bailout" instrument (110) may cause undesirable damage to instrument (110), thereby reducing the expected number of suitable uses of instrument (110), or even rendering instrument (110) unsuitable for further use.

Therefore, in instances where driving assembly (164) is inhibited from suitable movement to open and close jaws (150, 152) due to the frictional force between flanges (184, 185) and slots (186, 187) generated by the reactionary force of jaws (150, 152) grasping tissue, it may be desirable to allow flanges (184, 185) to selectively vertically expand relative to each other, thereby allowing jaws (150, 152) to slightly expand to thereby reduce the frictional force between flanges (184, 185) and slots (186, 187). Reducing the frictional force between flanges (184, 185) and slots (186, 187) may allow proximal retraction of pusher number (166) without use of robotic motor(s) (not shown) past a predetermined maximum power output level or use of manual actuator (124).

Figure 39:
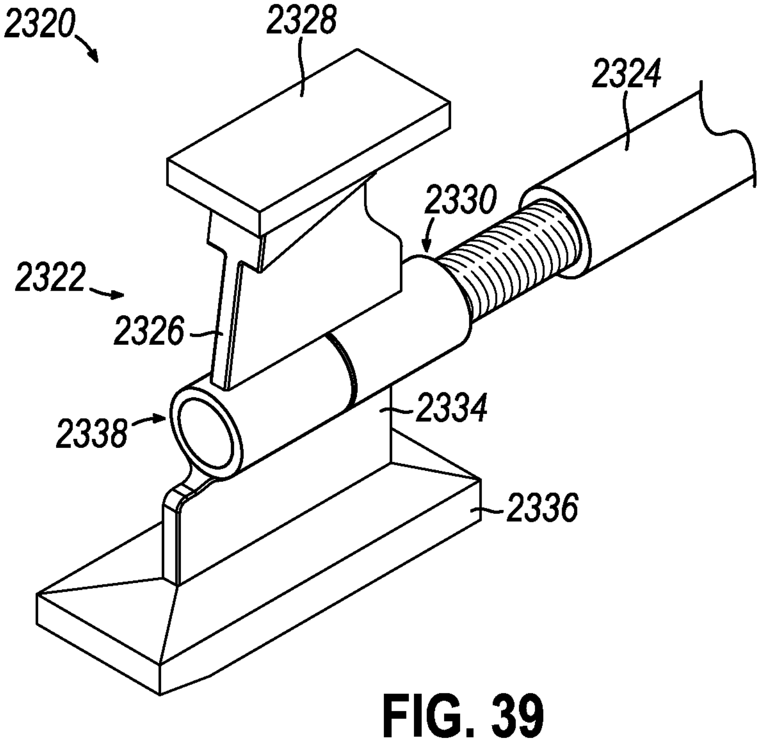
FIG. 39 depicts a perspective view of another alternative driving assembly that may be readily incorporated into the end effector of FIG. 4.
Figure 40A:
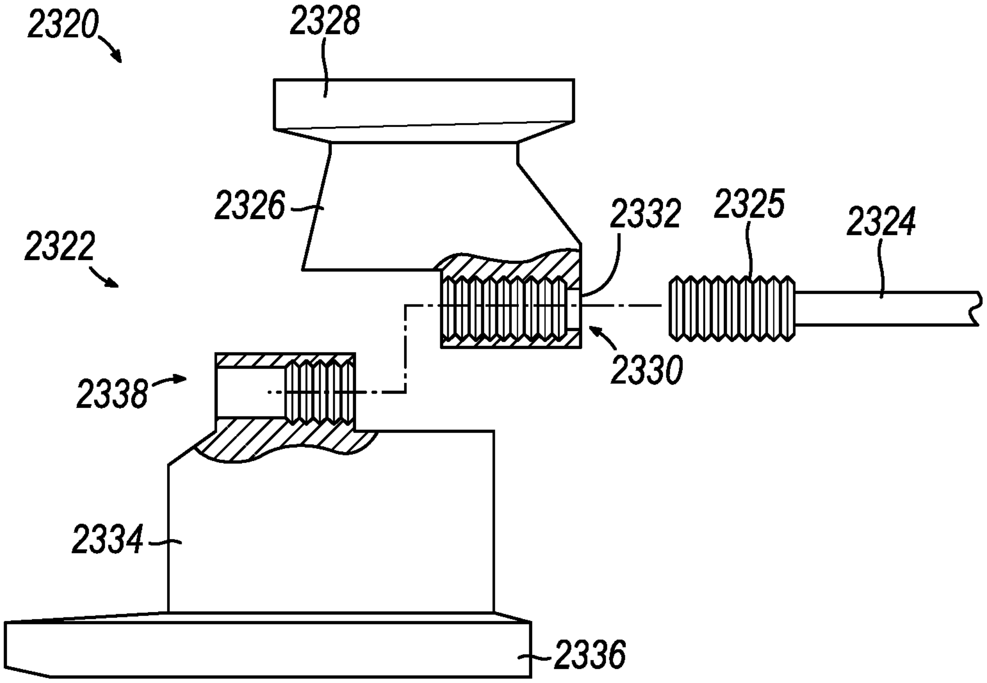
FIG. 40A depicts an exploded side view of the driving assembly of FIG. 39.
Figure 40B:
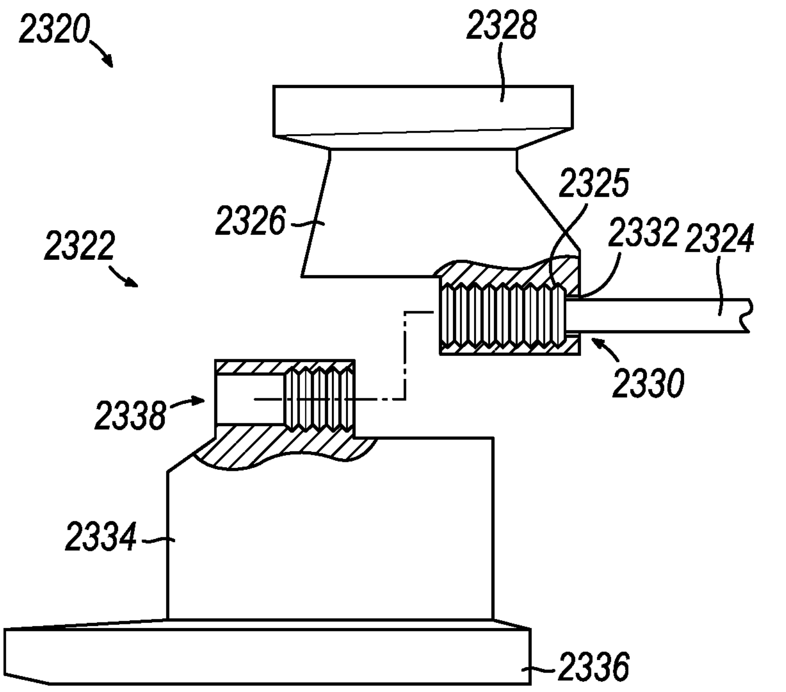
FIG. 40B depicts a side view of the driving assembly of FIG. 39, where a push rod is initially coupled to a first body of a pushing member.
Figure 40C:
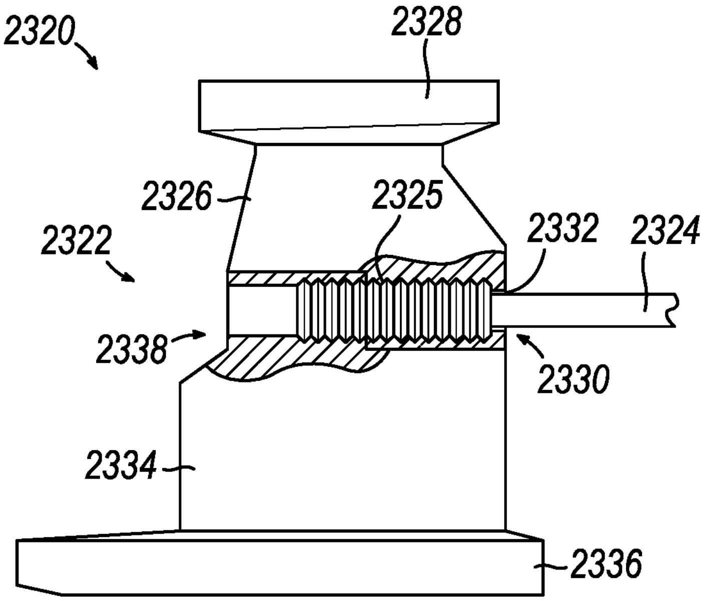
FIG. 40C depicts a side view of the driving assembly of FIG. 39, where the push rod of FIG. 40B is coupled to the first body of FIG. 40B, and where the first body is aligned with a second body of the pushing member.
Figure 40D:
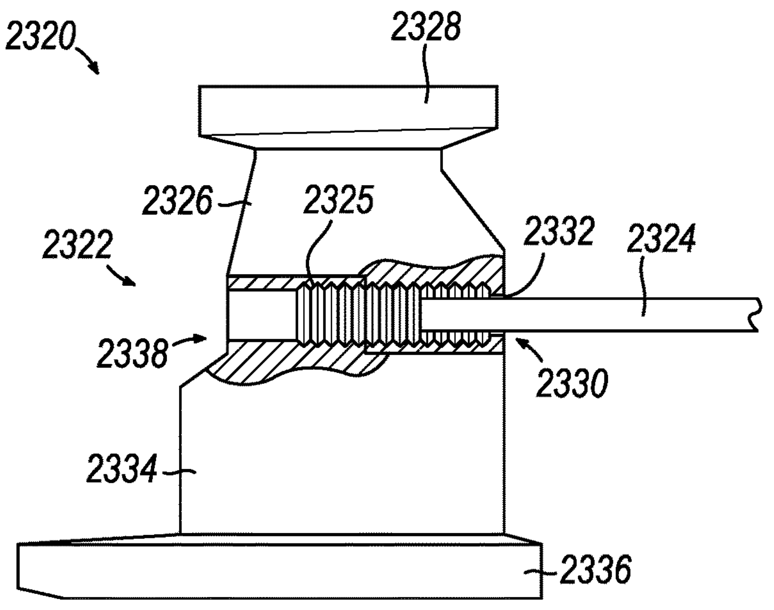
FIG. 40D depicts a side view if the driving assembly of FIG. 39 fully assembled.

FIGS. 39-40D show an exemplary driving assembly (2320) that may be readily incorporated into instrument (110) for use with end effector (116) in replacement of driving assembly (164) described above. Therefore, driving assembly (2320) may be substantially similar to driving assembly (164, 264) described above, with differences elaborated below.

As will be described in greater detail below, driving assembly (2320) includes a pusher member (2322) formed from two bodies (2326, 2334) each having a respective flange (2328, 2336) configured to (A) function substantially similar to flanges (184, 185) described above, and (B) selectively decouple from each other such that flanges (2328, 2336) may vertically actuate relative to each other. As will be described in greater detail below, since flange (2328, 2336) may selectively vertically actuate relative to each other, jaws (150, 152) may be allowed slightly expand to thereby reduce the frictional force between flanges (184, 185) and slots (186, 187) while grasping tissue. Therefore, in instances where suitable movement of driving assembly (2320) is inhibited due to tissue imparting a reactionary force onto jaws (150, 152), flanges (2328, 2336) may expand to allow movement of at least a portion of pusher member (2322) to release tissue without use of robotic motor(s) (not shown) past a predetermined maximum power output level or use of manual actuator (124).

Driving assembly (2320) includes pusher member (2322) and push rod (2324), which are substantially similar to pusher member (166) and push rod (168) described above, with differences elaborated below. Push rod (2324) includes a distal threaded portion (2325) fixed that the distal end of push rod (2324). Distal threaded portion (2325) suitably meshes within threaded openings (2330, 2338) of bodies (2326, 2334) such that rotation of distal threaded portion (2325) relative to bodies (2326, 2334) allows distal threaded portion (2325) to translate relative to threaded openings (2330, 2338) when suitably coupled.

Pusher member (2322) includes two bodies (2326, 2334) each having respective flanges (2328, 2336). Bodies (2326, 2334) also define a respective threaded opening (2330, 2338). Threaded openings (2330, 2338) are dimensioned to suitably align in order to both simultaneously mesh with distal threaded portion (2325) of push rod (2324). Therefore, distal threaded portion (2325) of push rod (2324) is configured to mesh with each threaded opening (2330, 2338) in order to couple first body (2326) and second body (2334) such that when coupled, push rod (2324) may actuate bodies (2326, 2334) unitarily in order to open and close jaws (150, 152) in accordance with the description herein.

Push rod (2324) may also rotate abouts its longitudinal axis in order to traverse a distance within threaded openings (2330, 2338). As will be described in greater detail below, if an operator desires to temporarily decouple first body (2326) with second body (2334), the operator may rotate push rod (2324) (either manually or via robotic motors) such that distal threaded portion (2325) only associated with first body (2326), thereby allowing flanges (2328, 2336) to expand relative to each other. Body (2332) also includes a proximal stop (2332). Proximal stop (2332) is configured to abut against distal threaded portion (2325) after distal threaded portion (2325) dissociates with threaded opening (2338) of second body (2334) in order to inhibit threaded portion (2325) from accidentally decoupling with first body (2326) as well. Therefore, proximal stop (2332) acts to prevent distal threaded portion (2325) from over rotating and proximally dissociating with first body (2326).

FIGS. 40A-40D show an exemplary initial coupling of first body (2326) with second body (2334) utilizing distal threaded portion (2325) of push rod (2324). First, as shown between FIGS. 40A-40B, proximal end of push rod (2324) may be fed through a distal opening of threaded opening (2330) until distal threaded portion (2325) is adjacent to threaded opening (2330). Distal threaded portion (2325) may be rotated in a first angular direction such that distal threaded portion (2325) meshes with threaded opening (2330). Distal threaded portion (2325) may be rotated until a proximal end of distal threaded portion (2325) engages stop (2332), as shown in FIG. 40B.

Next, as shown in FIG. 40C, bodies (2326, 2334) may be positioned such that threaded openings (2330, 2338) are suitably aligned. With threaded openings (2330, 2338) aligned, flanges (2328, 2336) may be suitably positioned relative to each other in order to close and open jaws (150, 152) in accordance with the description herein. As shown between FIGS. 40C-40D, with threaded openings (2330, 2338) suitably aligned, distal threaded portion (2325) may be rotated in a second angular direction, opposite the first angular direction, such that distal threaded portion longitudinally travels in the distal direction. Distal actuation of threaded portion (2325) allows distal threaded portion (2325) to suitably engage threaded opening (2338) of second body (2334), as shown in FIG. 40D. With distal threaded portion (2325) suitably engaged with both bodies (2326, 2334), pusher member (2322) and driving assembly (2320) are assembled.

FIGS. 31A-31G show an exemplary use of driving assembly (2320) to attempt to sever and staple tissue (T), but then release tissue (T) before the firing process is fully completed. FIG. 31A shows tissue (T) grasped between jaws (150, 152) and driving assembly (2320) in the pre-fired, proximal position. When the operator desires to sever and staple tissue in accordance with the description herein, the operator may initiate the firing process via surgeon's console (16) in accordance with the description herein.

Figure 41A:
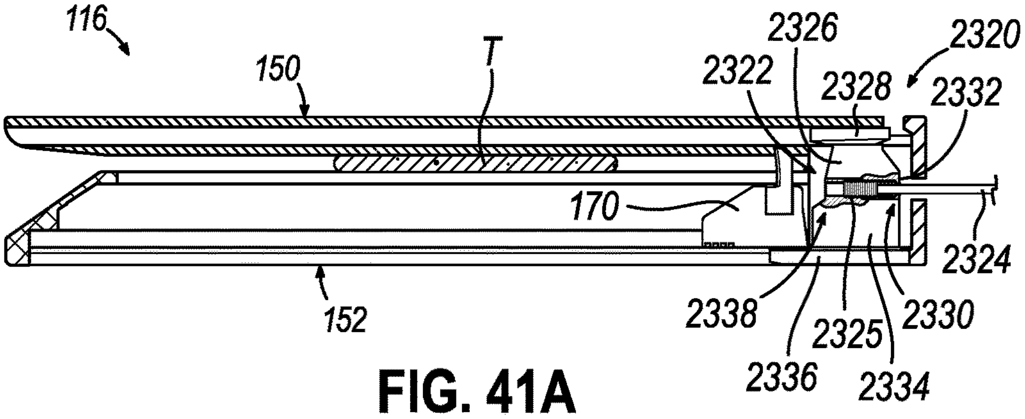
FIG. 41A depicts a cross-sectional side view of the driving assembly of FIG. 39 incorporated into the end effector of FIG. 4, where the driving assembly is in a pre-fired position.
Figure 41B:
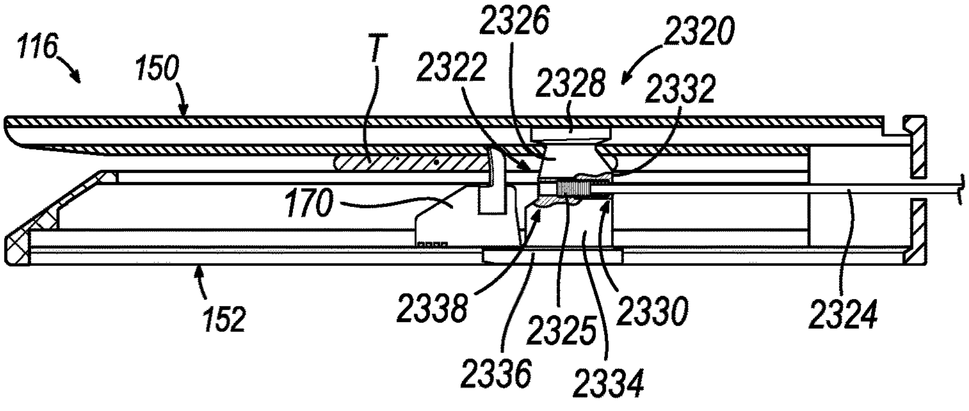
FIG. 41B depicts a cross-sectional side view of the driving assembly of FIG. 39 incorporated into the end effector of FIG. 4, where the driving assembly is advanced to a partially fired position.

As exemplified in FIG. 41B, for any suitable reasons, it may be desirable to release tissue (T) before the firing process is complete. In some instances, tissue (T) may provide a reactionary force on jaws (150, 152) to thereby inhibit further distal translation of driving assembly (2320) and/or proximal retraction of driving assembly (2320). Therefore, it may be desirable to allow flanges (2328, 2336) to selectively expand vertically relative to each other, thereby reducing the frictional force between flanges (2328, 2336) and slots (186, 187) and allowing proximal retraction of first body (2326) to release tissue (T) without use of robotic motor(s) (not shown) past a predetermined maximum power output level or use of manual actuator (124).

Figure 41C:
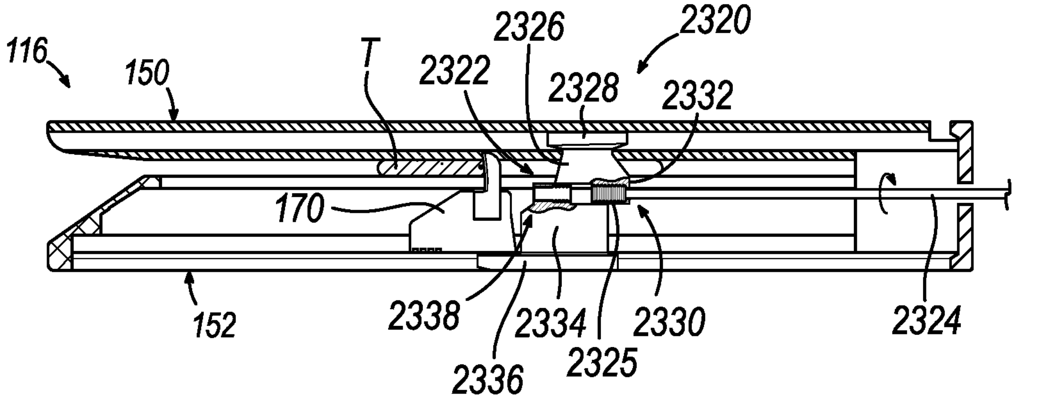
FIG. 41C depicts a cross-sectional side view of the driving assembly of FIG. 39 incorporated into the end effector of FIG. 4, where the driving assembly is advanced to a partially fired position and the first body of the pushing member is decoupled from the second body of the pushing member.

As shown between FIGS. 41B-41C, push rod (2324) may be rotated such that distal threaded portion (2325) disengages with threaded opening (2338) of second body (2334). Push rod (2324) may be rotated manually or with robotic motor. With distal threaded portion (2325) disengaged with second body (2334), second body (2334) and first body (2326) may expand relative to each other, thereby allowing the reactionary force tissue (T) imparts on jaws (150, 152) to at least slightly expand jaws (150, 152) to reduce the frictional force between flanges (2328, 2336) and slots (186, 187).

Figure 41D:
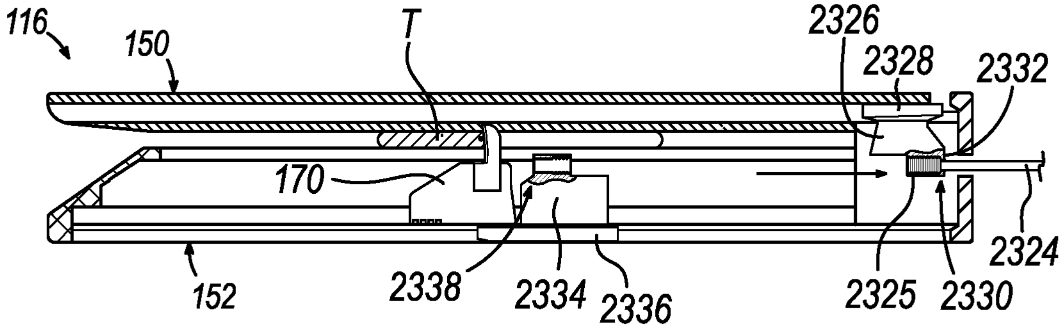
FIG. 41D depicts a cross-sectional side view of the driving assembly of FIG. 39 incorporated into the end effector of FIG. 4, where the first body of the pushing member is proximally retracted within the end effector.

Therefore, as shown between FIGS. 41C-41D, push rod (2324) may proximally actuate such that first body (2326) is returned to the pre-fired position, but such that second body (2334) remains in the position shown in FIG. 41C. With the reduced frictional force between flanges (2328, 2336) and slots (186, 187), push rod (2324) may be proximally retracted without use of robotic motor(s) (not shown) past a predetermined maximum power output level or use of manual actuator (124).

Figure 41E:
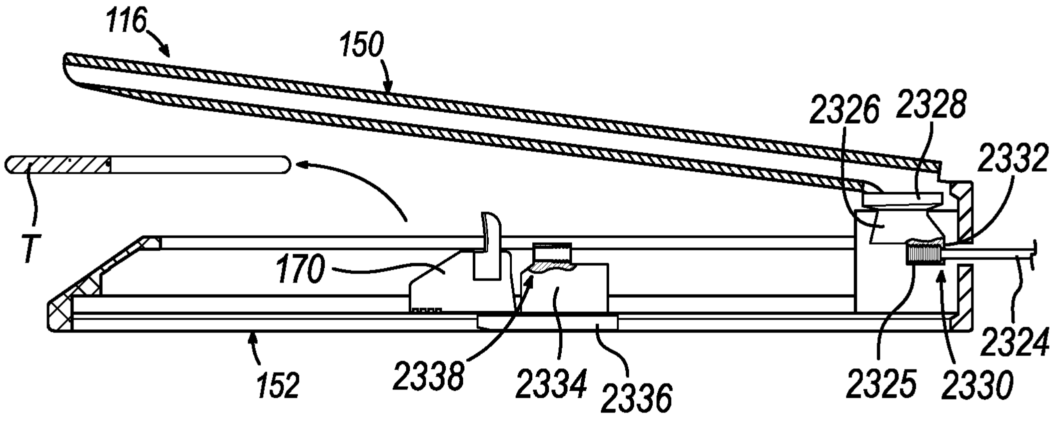
FIG. 41E depicts a cross-sectional side view of the driving assembly of FIG. 39 incorporated into the end effector of FIG. 4, where the first body of the pushing member is proximally retracted within the end effector and tissue is released from the jaws of the end effector.
Figure 41F:
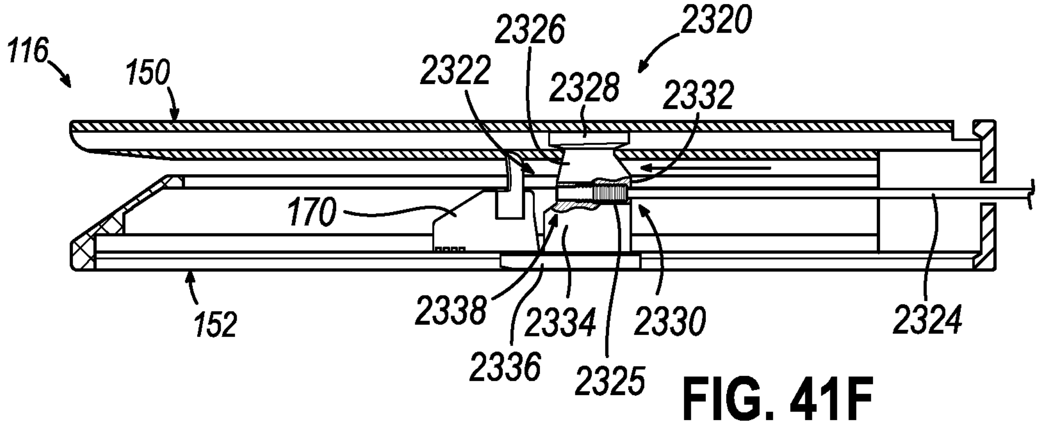
FIG. 41F depicts a cross-sectional side view of the driving assembly of FIG. 39 incorporated into the end effector of FIG. 4, where the first body of the pushing member is distally advanced to abut against the second body of the pushing member.
Figure 41G:
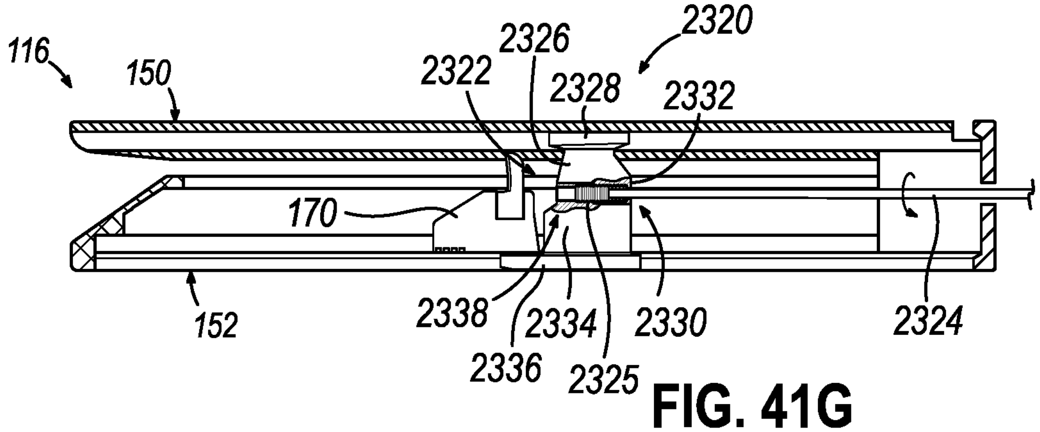
FIG. 41G depicts a cross-sectional side view of the driving assembly of FIG. 39 incorporated into the end effector of FIG. 4, where the first body of the pushing member is recoupled with the second body.

As shown in FIG. 41E, jaws (150, 152) may open relative to each other in order to release grasped tissue (T) that has been partially stapled and severed. With tissue (T) released, push rod (2324) may actuate first body (2326) back against second body (2334) such that threaded openings (2330, 2338) are aligned, as shown in FIG. 41F. Then, as shown in FIG. 41G, push rod (2324) may be rotated such that distal threaded portion (2325) engages with threaded opening (2338) of second body (2334), thereby suitably recoupling first body (2326) and second body (2334). With bodies (2326, 2334) recoupled, push rod (2324) may be proximally retracted back to pre-fired position for the purposes of loading a new staple cartridge (154).

The decoupling and recoupling process described herein may be automatically initiated in response to certain conditions sensed by instrument (110). Any suitable conditions may initiate the decoupling and recoupling process as would be apparent to one skilled in the art in view of the teachings herein.

As mentioned above, after first body (2326) and second body (2334) are decoupled, push rod (2324) may actuate first body (2326) back against second body (2334) such that threaded openings (2330, 2338) are aligned for purposes of recoupling distal threaded portion (2325) with threaded opening (2338) of second body (2334). Therefore, it may be desirable to ensure the threaded openings (2330, 2338) are suitably aligned such that distal threaded portion (2325) may suitably re-mesh with threaded opening (2338) during the recoupling process.

Figure 42:
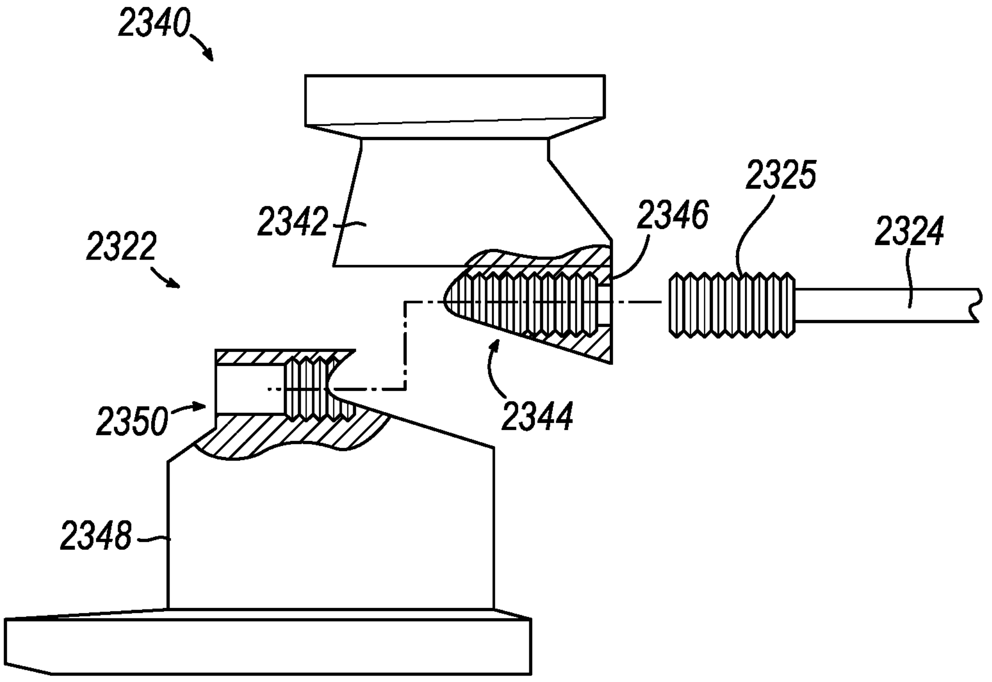
FIG. 42 depicts an exploded side view of another alternative driving assembly that may be readily incorporated into the end effector of FIG. 4.

FIG. 42 shows an exemplary pusher member (2340) that may be readily incorporated into driving assembly (2320) in replacement of pusher member (2322) described above. Pusher member (2340) may be substantially similar to pusher member (2322) described above, with differences elaborated below. Therefore, pusher member (2340) includes a first body (2342) and a second body (2348) defining a respective threaded opening (2344, 2450); which may be substantially similar to first body (2326), second body (2334), and threaded openings (2330, 2338) described above, with differences elaborated below.

In particular, threaded opening (2344) of first body (2342) includes an alignment protrusion (2346); while second body (2348) includes an alignment recess (2352). Alignment protrusion (2346) and alignment recess (2352) are complementary such that as first body (2342) is actuated to abut against second body (2348), protrusion (2346) and recess (2352) interact with each other to suitably align threaded openings (2344, 2350). This suitable alignment dues to interaction between protrusion (2346) and recess (2352) may allow distal threaded portion (2325) to more easily re-mesh with threaded opening (2350) of second body (2348). Additionally, the interaction between protrusion (2346) and recess (2352) may suitably space flanges of first body (2342) and second body (2348) such that jaws (150, 152) may close with an appropriate amount of closure force, even after first body (2342) and second body (2348) are recoupled in accordance with the description herein.

Figure 43:
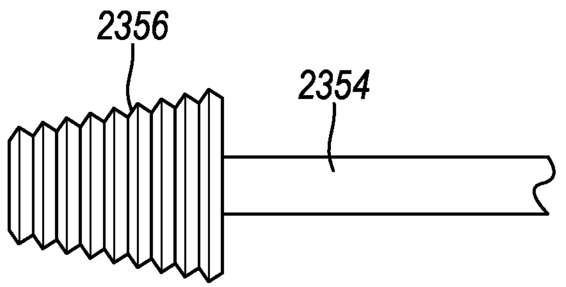
FIG. 43 depicts an elevation side view of an alternative push rod that may be readily incorporated into the driving assembly of FIG. 42.

FIG. 43 shows an alternate push rod (2354) that may be used to promote alignment of threaded openings (2330, 2338). Push rod (2354) may be substile similar to push rod (2324) described above, except that push rod (2354) includes a distal threaded portion (2356) having a conical profile. The conical profile of distal threaded portion (2356) may promote suitable alignment with first body (2326) and second body (2334) during the recoupling process in accordance with the description herein. It should be understood that in instances where distal threaded portion (2356) is used, threaded openings (2330, 2338) may have a complementary shape to that of conical threaded portion (2356) to promote suitable meshing between threads.

Figure 44:
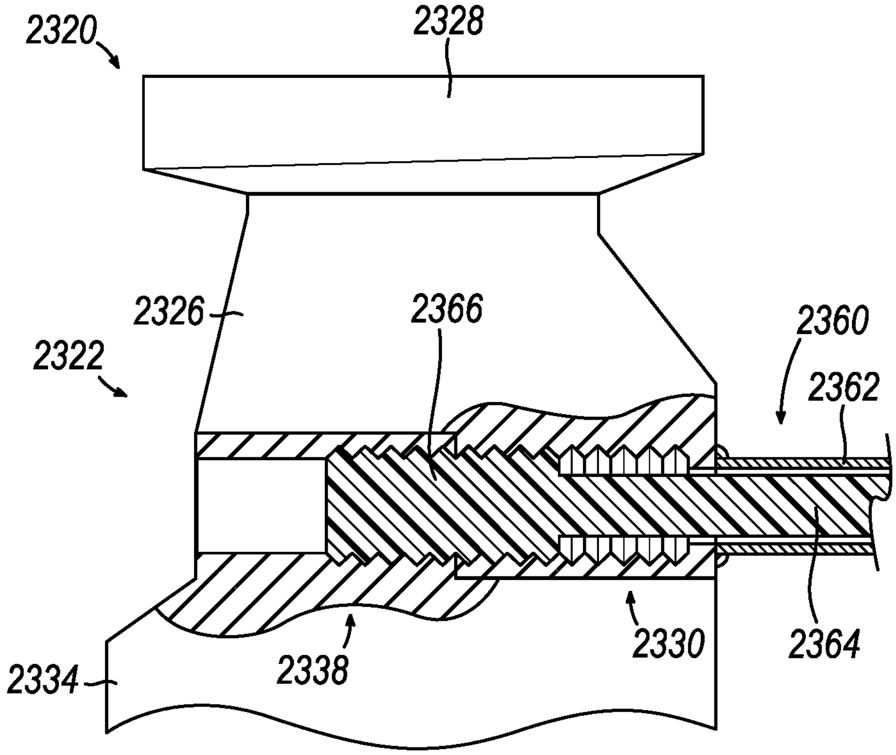
FIG. 44 depicts a cross-sectional side view of an alternative push rod assembly that is incorporated into the driving assembly of FIG. 39.

In some instances, it may be desirable to separate components of push rod (2324) that (A) translate in order to fire staples and sever tissue, and (B) rotate in order to selectively allow flanges (2328, 2336) to expand relative to each other. FIG. 44 shows a push rod (2360) having a translating member (2362) fixed to first body (2326), and a rotating member (2364) rotatably disposed within translating member (2362). Translating member (2362) may be coupled to a robotic motor and configured to translate to drive translation of pusher member (2322).

Rotating member (2364) may include a distal threaded portion (2366) which is substantially similar to distal threaded portion (2325) described above. Rotating member may be attached to a manual bailout feature or may be coupled to another robotic motor configured to rotate distal threaded portion (2325) in order to suitably decouple and recouple first body (2326) with second body (2334) in accordance with the description herein. Since rotating member (2364) and translating member (2363) are operable to function independent of each other, they may be coupled to separate driving components.

In some instances, it may be desirable to allow flanges (2328, 2336) to expand relative to each other, without having bodies (2326, 2334) completely disassociate with each other, as this may allow for simplification in recoupling bodies (2326, 2334) after releasing grasped tissue (T) that inhibits proximal translation of pusher member (2322) in accordance with the description herein.

Figure 45:
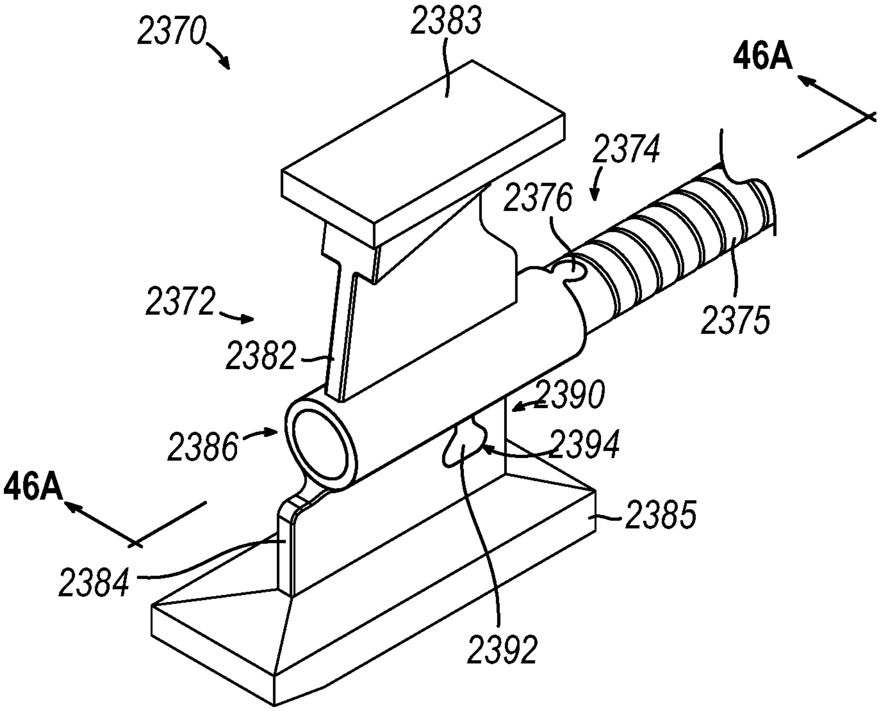
FIG. 45 depicts a perspective view of an alternative driving assembly that may be readily incorporated into the end effector of FIG. 4.
Figure 46A:
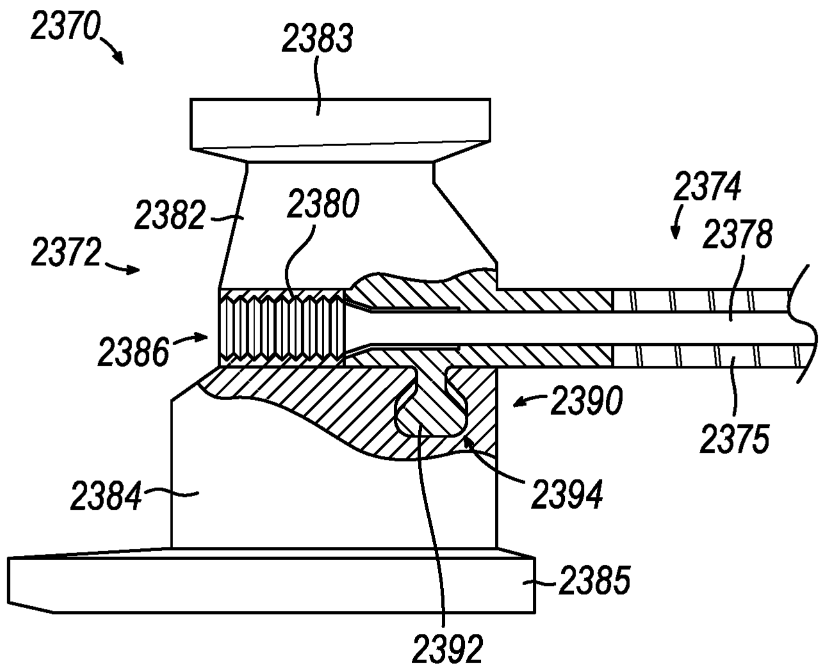
FIG. 46A depicts a partial cutaway side view of the driving assembly of FIG. 45 in a fully assembled position.
Figure 46B:
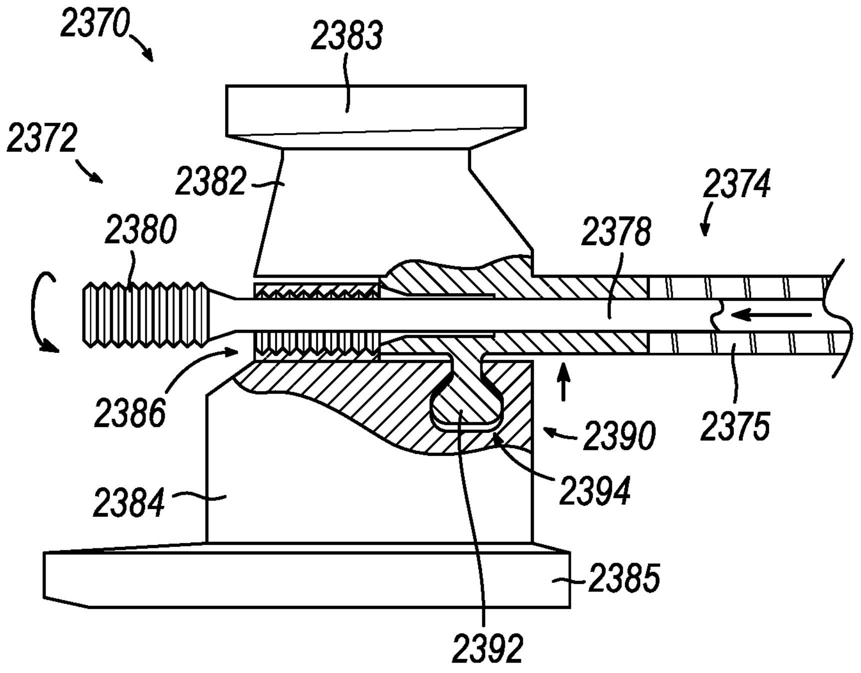
FIG. 46B depicts a partial cutaway side view of the driving assembly of FIG. 45 in a disassembled position.

FIGS. 45-46B show an exemplary driving assembly (2370) that may be readily incorporated into instrument (110) in replacement of driving assembly (2320) described above. Driving assembly (2370) includes a pusher member (2372) and a push rod assembly (2374). Pusher member (2372) may be substantially similar to pusher member (2322) described above with differences elaborated below; while push rod assembly (2374) may be substantially similar to push rod assembly (2360) described above, with differences elaborated below.

Push rod assembly (2374) includes a translating member (2375) and a rotating member (2378) having a distal threaded portion (2380); which may be substantially similar to translating member (2362), rotating member (2364), and distal threaded portion (2366) described above, with differences elaborated below. Translating member (2375) includes an undercut coupling (2376) that may help further promote the structural integrity of translating member's (2375) coupling with first body (2382) of pusher member (2372).

Pusher member (2372) includes a first body (2382) defining threaded opening and having a flange (2383), a second body (2384) defining threaded opening (2386) and having a flange (2383); which may be substantially similar to first body (2326), threaded openings (2330, 2338), flange (2328), second body (2334), and flange (2336), described above, with differences elaborated below. In particular, first body (2382) and second body (2384) together include an expansion feature (2390) that allows bodies (2382, 2384) to expand relative to each other without completely decoupling.

First body (2382) includes a projection (2392) while second body (2384) includes a complementary recess (2394). Recess (2394) is dimensioned to house projection (2392); while projection (2392) is dimensioned to vertically actuate within projection (2392). Therefore, as shown between FIGS. 46A-46B, if rotating member (2364) is rotated to double first body (2382) and second body (2384), such a decoupling will allow first body (2382) and second body (2384) to vertically accurate relative to each other, yet projection (2393) and recess (2394) will help ensure that translation of first body (2382) drives translation of second body (2384), even when rotating member (2364) is decoupled with threaded opening (2386). Therefore, when push rod assembly (2374) is proximally retracted in order to release tissue (T) in similar fashion to that shown in FIGS. 41D-41E, both first body (2382) and second body (2384) actuate to the proximal pre-fired position, instead of just first body (2326).

In some instances when first body (2326) and second body (2334) are configured to completely detach, as shown in FIGS. 41D-41E, it may be desirable to have some ability to open and close jaws (150, 152) while flanges (2328, 2336) actuate relative to each other. Allowing some ability to open and close jaws (150, 152) while first body (2326) and second body (2334) are decoupled may allow an operator to suitably release tissue (T) without the need of an external manipular to open jaws and close (150, 152).

Figure 47:
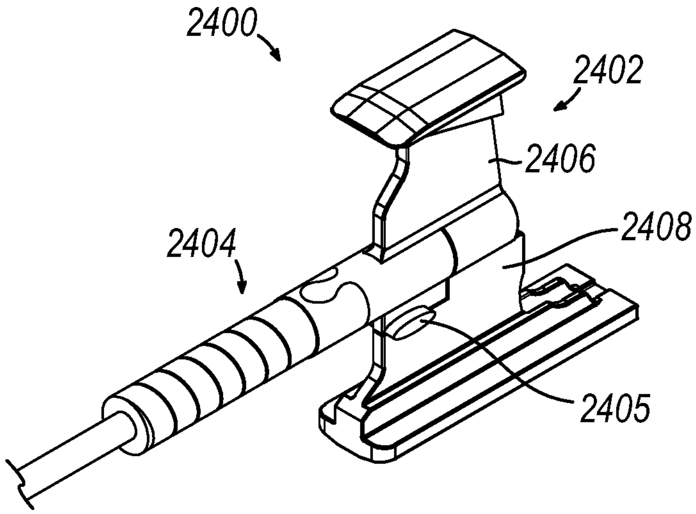
FIG. 47 depicts a perspective view of an alternative driving assembly that may be readily incorporated into the end effector of FIG. 4.
Figure 48:
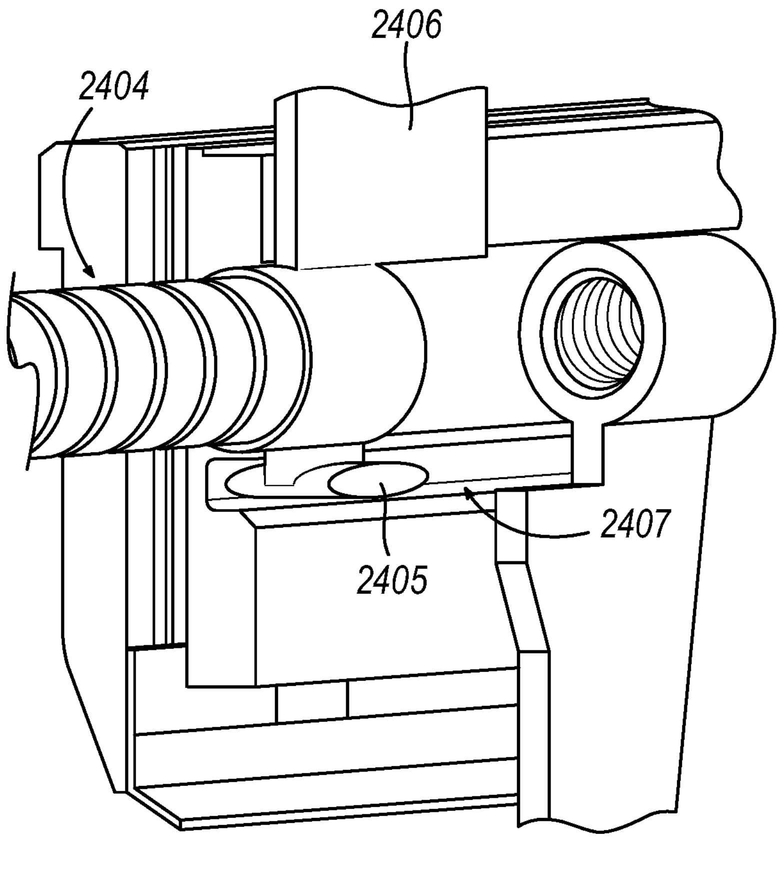
FIG. 48 depicts an enlarged perspective view of a selected portion of the driving assembly of FIG. 47 attached the end effector of FIG. 4.

FIGS. 47-48 show and exemplary driving assembly (2400) having a pusher member (2402) and a push rod assembly (2404). Pusher member (2402) may be substantially similar to pusher member (2322) described above, with differences elaborated below. Push rod assembly (2404) may be substantially similar to push rod assembly (2360) described above.

Pusher member (2402) includes a first body (2406) and a second body (2408) that are substantially similar to first body (2326) and second body (2334) described above, with difference elaborated below. In particular, first body (2406) includes a wing (2405) dimensioned to slidably fit within a lingual slot (2407) defined by removable staple cartridge (154). Wing (2405) is configured to suitable interact with slot (2407) such that when first body (2406) is decoupled from second body (2408) in accordance with the description herein, wing (2405) and flange of first body (2406) may interact with jaws (150, 152) in order to open and close jaws (150, 152) without the need for flange of second body (2408) to cam against slot (187) defined by removeable staple cartridge (154). Therefore, in instances where first body (2406) is proximally retracted in a similar fashion to that shown in FIGS. 41D-41E, jaw (150) will pivot open due to wing (2405) interacting with slot (2407) and flange of first body (2406) interacting with slot (186). Therefore, in instances where first body (2406) is decoupled from second body (2408), jaws (150, 152) may still be opened and closed without the need of an external manipulator/force.

V. Exemplary Instrument Having Sequential Firing and Jaw Closure Controlled by One Motor

A. Overview of Exemplary Robotic Arm and Instrument

As mentioned above, during exemplary use of end effector (210), distal advancement of closure tube (not shown) and closure ring (230) (see FIGS. 10 and 47A-47E) are used to close end effector (210). In other words, distal advancement of closure tube (not shown) and closure ring (230) are used to move lower jaw (212) and anvil jaw (214) toward each other in order to grasp tissue in accordance with the description herein. As also mentioned above, with tissue grasped between staple cartridge (218) and anvil jaw (214), firing beam (216) may then be advanced distally in order to sever and staple tissue in accordance with the description herein. In other words, end effector (210) may be configured such that movement of jaws (212, 214) in order to grasp tissue may be performed independently with respect to actuation of firing beam (216) in order to sever and staple grasped tissue.

Figure 49:
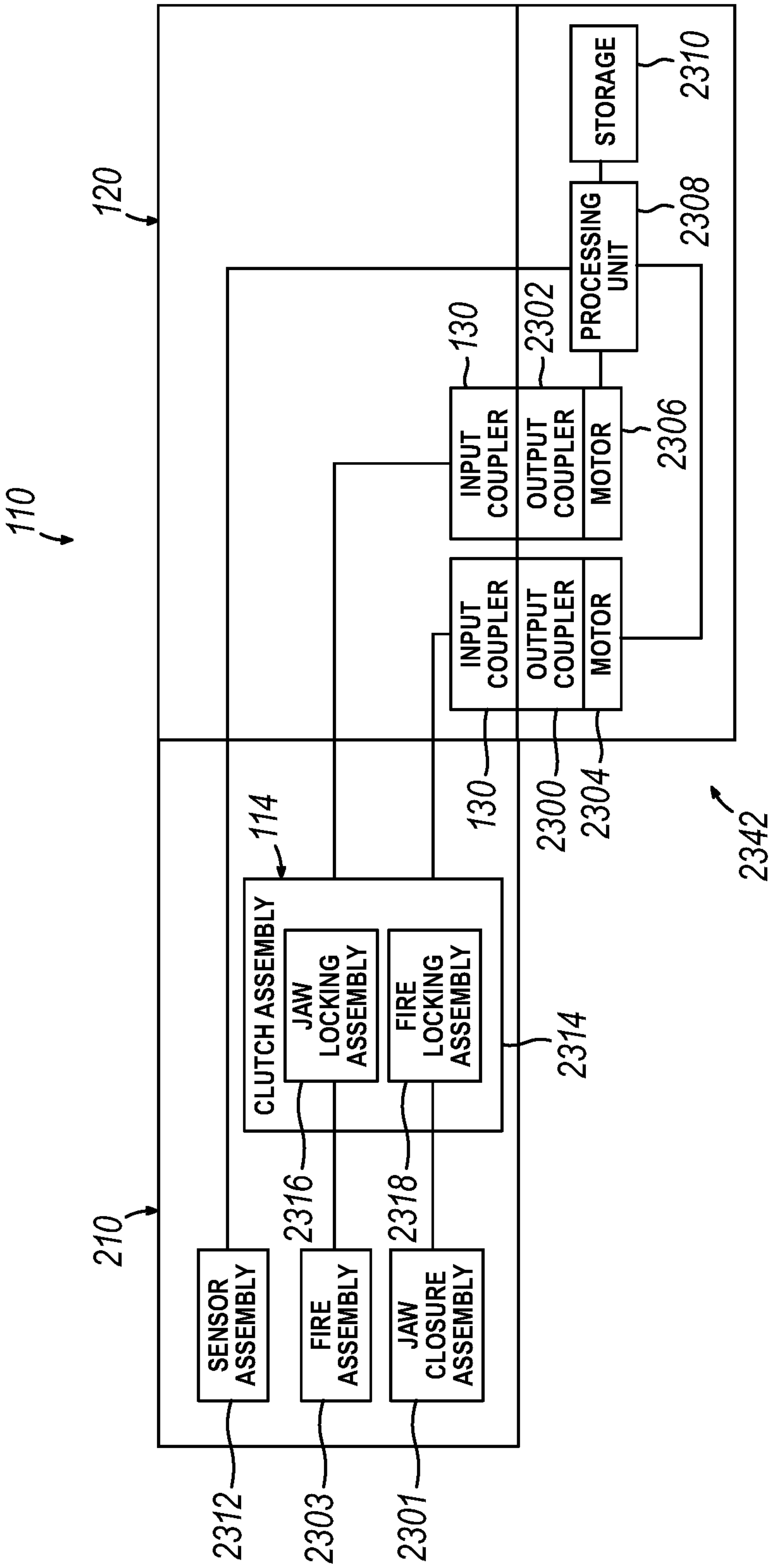
FIG. 49 depicts a schematic view of the instrument of FIG. 4 coupled with the end effector of FIG. 10 and an exemplary robotic arm.

FIG. 49 schematically shows an exemplary robotic arm (2342) that may be used to couple with instrument (110) in similar fashion to robotic arm (42) described above. Instrument (110) in the current example (110) incorporated end effector (210) described above, rather than end effector (116). Robotic arm (2343) may be substantially similar to robotic arm (42) described above, with differences elaborated below. Therefore, it should be understood that robotic arm (2343) may suitably interact with robotic surgical system (10) described above such that a medical professional operator may utilize robotic surgical system (10) to control instrument (110) via robotic arm (2343), input control devices (36) of surgeon's console (16), and any other suitable intermediate components as would be apparent to one skilled in the art in view of the teachings herein.

As mentioned above, instrument base (112) includes input couplers (130). Input couplers (130) are configured to interface with and be driven by corresponding output couplers (2300, 2302) of robotic arm (2343). Output couplers (2300, 2302) may be actuated via one or more robotic motors (2304, 2306), respectively, which may be controlled by a processing unit (2308) in communication with input control devices (36) of surgeon's console (16). Robotic motors (2304, 2306) may include any suitable components as would be apparent to one skilled in the art in view of the teachings herein. Robotic motors (2304, 2306) and/or processing unit (2308) may include suitable components to measure suitable output characteristics, operating data, etc., of robotic motors (2304, 2306). For example, robotic motors (2304, 2306) may include components configured to measure motor temperature, motor displacement, the electrical current used by robotic motors (2304, 2306), motor power usage (either in a specified unit or represented as a percentage compared to a maximum motor power usage), etc., and may communicate such operating data to processing unit (2308) for use of such data in accordance with the description herein.

Processing unit (2308) may receive instructions from input control devices (36) in order to actuate robotic motors (2304, 2306) and corresponding output couplers (2300, 2302). Processing unit (2308) may be in communication with a storage device (2310). Processing unit (2308) to write data to storage device (2310) or access data from storage device (2310) in order to operate in accordance with the description herein. While operatively interfacing with input couplers (130), output couplers (2300, 2302) of robotic arm (2343) may be used to actuate selective portions of either end effector (210) or shaft assembly (114) in accordance with the description herein.

End effector (210) includes a jaw closure assembly (2301) that includes closure tube (not shown) and closure ring (230), a fire assembly (2303) that includes firing beam (216), and a tissue sensor assembly (2312). Therefore, jaw closure assembly (2301) is configured to open and close jaws (212, 214), while fire assembly (2303) is configured to actuate in order to staple and sever tissue grasped by jaws (212, 214) in accordance with the description herein. Both jaw closure assembly (2301) and fire assembly (2303) are configured to be actuated and controlled independently of each other by a single motor (2304).

Sensor assembly (2312) is configured to establish communication with processing unit (2308) when instrument (110) is operatively coupled with robotic arm (2343). Therefore, data obtained from sensor assembly (2312) may be stored on storage device (2310) for later access by processing unit (2308). Sensor assembly (2312) may include one or more sensors configured to measure any suitable data as would be apparent to one skilled in the art in view of the teachings herein. For instance, sensor assembly (2312) may be configured to measure a tissue load imparted on the jaws (212, 214) while grasping tissue in accordance with the description herein. Additionally, or alternatively, sensor assembly (2312) may be configured to measure the locations tissue is in contact with jaws (212, 214) while grasping tissue in accordance with the description herein.

Shaft assembly (114) in the current example includes a clutch assembly (2314) configured to alternate between which assembly (2301, 2303) motor (2304) is configured to actuate. Clutch assembly (2314) alternate between which assembly (2301, 2303) motor (2304) may drive via a second motor (2306), or any other suitable structures as would be apparent to one skilled in the art in view of the teachings herein.

Additionally, clutch assembly (2314) includes locking assemblies (2316, 2318) configured to maintain the position of the assembly (2301, 2303) not operatively engaged with motor (2304) without utilizing any motor power from motor (2304). In other words, when fire assemble (2303) is not operatively engaged with motor (2304), fire locking assembly, also referred to as clutch assembly (2314) may ensure the position of firing beam (216) remains fixed relative to shaft assembly (114). Conversely, when jaw closure assembly (2301) is not operatively engaged with motor (2304), jaw locking assembly (2316) may ensure the position of closure ring (230) remains fixed relative to shaft assembly (114). Therefore, when motor (2304) is configured to actuate jaw closure assembly (2301), fire locking assembly (2318) may be activated to prevent unwanted movement of firing beam (216) without utilizing any power from motor (2304); and when motor (23040 is configured to actuate fire assembly (2303), jaw locking assembly (2316) may be activated to prevent unwanted movement of closure ring (230) without utilizing any power from motor (2304). It should be understood that clutch assembly (2314), jaw locking assembly (2316), and fire locking assembly (2318) may have any suitable components as would be apparent to one skilled in the art in view of the teachings herein.

B. Exemplary Algorithm for Sequentially Closing Jaws and Actuating Firing Assembly to Actively Reduce Required Firing Force While end effector (210) is used to staple and sever grasped tissue, distal advancement of firing beam (216) (see FIG. 11) may be inhibited such that robotic surgical system (10) may have to power robotic motor (2304) past a predetermined maximum power output level in order to distally advance firing beam (216) further. In some instances, rather than using robot motor(s) past a predetermined power output level to further staple and sever grasped tissue is accordance with the description herein, robotic motor (2304) may be programed to temporarily stop, stall, halt, or otherwise delay advancement of firing beam (216) for a predetermined amount of time once the predetermined maximum motor power output level for advancing firing beam (216) is reached. In such instances, the temporary delay of advancing firing beam (216) may act as a passive means of reducing the required firing force for robotic motor (2304) to distally advance firing beam (216). This passive means of reducing the required firing force may allow for a “milking effect” to occur between jaws (212, 214) and grasped tissue (e.g., where tissue is effectively squeezed out from the space between jaws (212, 214)), thereby reducing the amount of force required for firing beam (216) to staple and sever tissue in accordance with the teachings herein.

In some instances, instead of passively waiting for the “milking effect” to reduce the force required for robotic motor (2304) to distally advance firing beam (216) without exceeding a predetermined power output level of robotic motor (2304), it may be desirable to actively reduce the firing force required for robotic motor (2304) to advance firing beam (216) to thereby prevent robotic motor (2304) from operating past the predetermined power output level.

Figure 50:
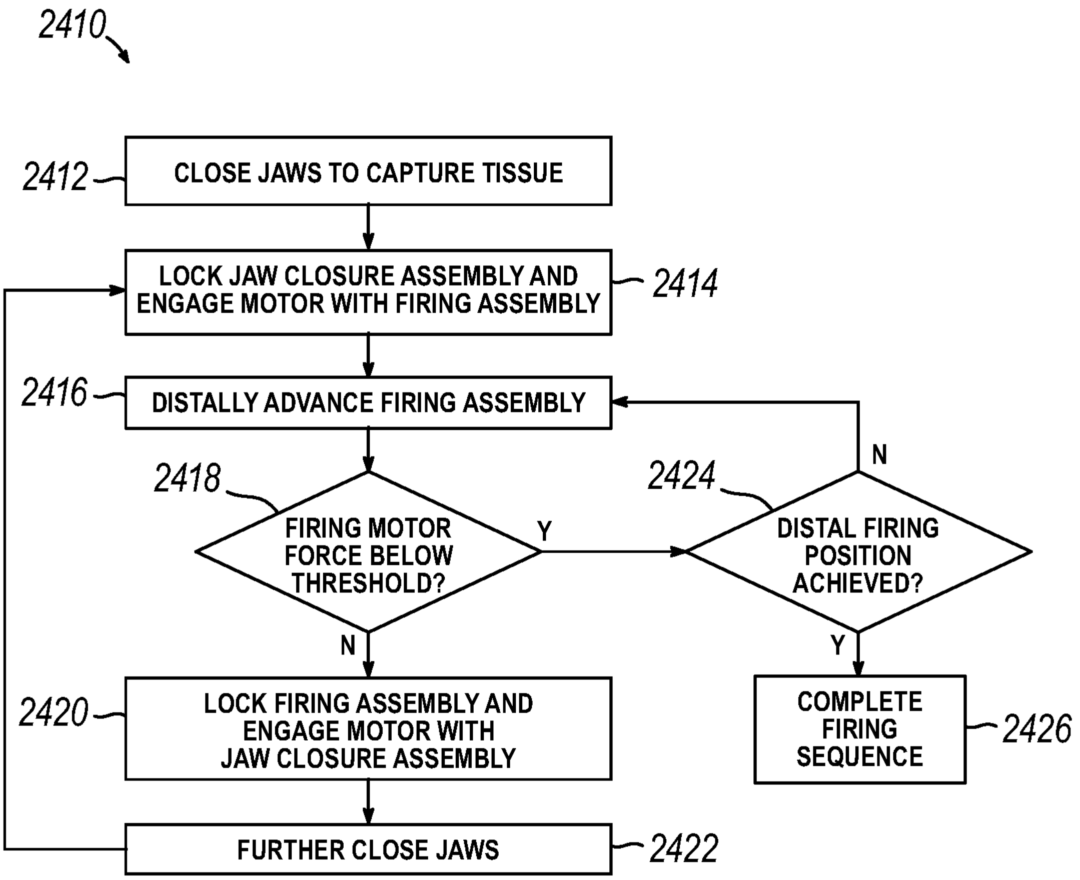
FIG. 50 depicts a block diagram of an exemplary motor control algorithm that may be used by the robotic arm of FIG. 49.
Figure 52:
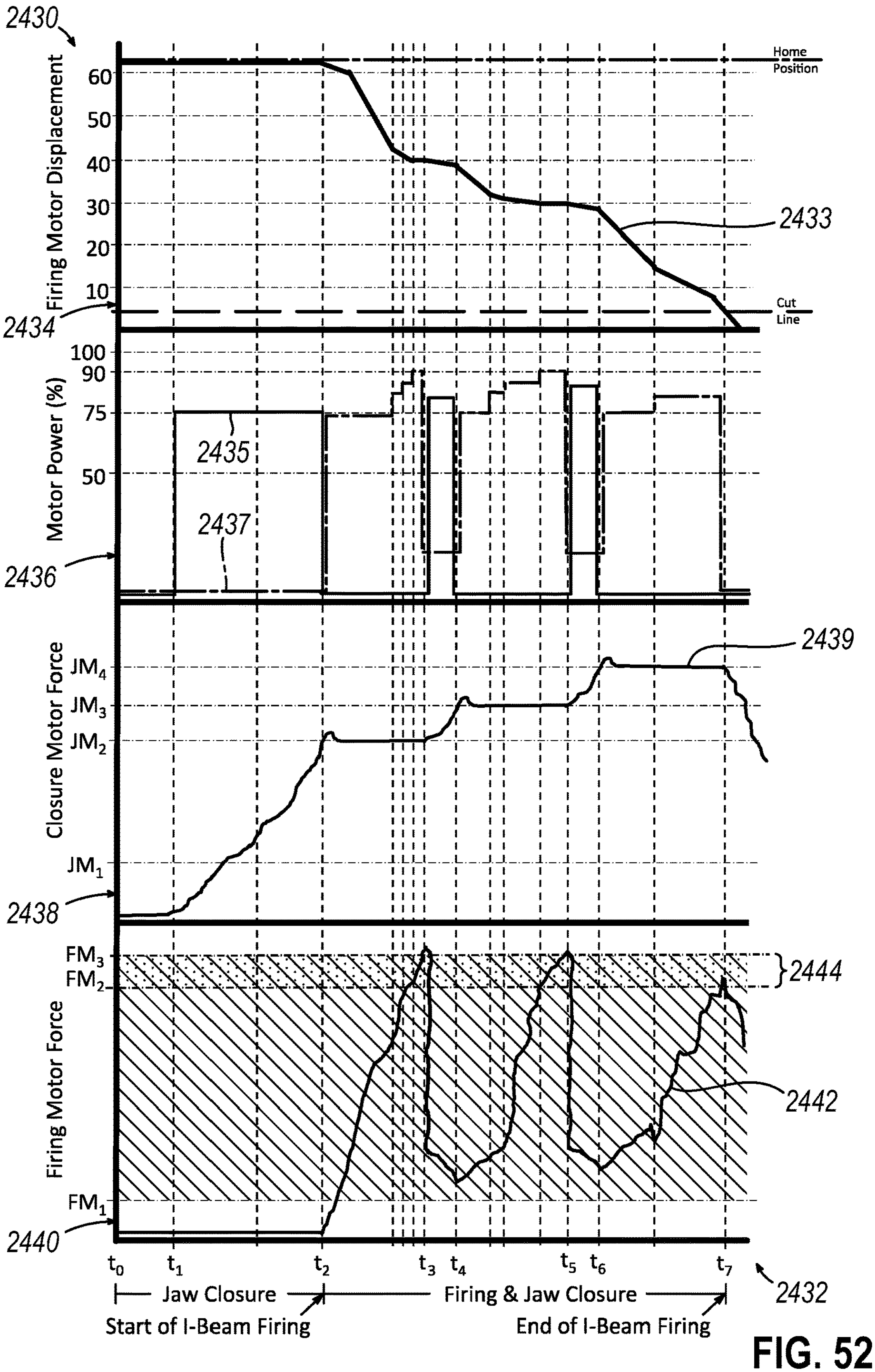
FIG. 52 depicts a graph representing the firing displacements, mort power, jaw closure force, and firing force over time of the firing sequence shown in the table of FIG. 51.

FIG. 50 shows a motor control algorithm (2410) that may be utilized by robotic surgical instrument (110), end effector (210), and robotic arm (2343) described above. FIG. 51 shows an exemplary use of motor control algorithm (2410) at various times (t0, t1, t2, t3, t4, t5, t6, t7) during the firing process; while FIG. 52 shows a graph (2430) representing the firing displacement (2434) caused when motor (2304) is operatively coupled to fire assembly (2303), the motor power output (2436) transmitted to both jaw closure assembly (2301) and fire assembly (2303) represented as a percentage, the closure force (2438) on jaw closure assembly (2301), and the firing force (2440) on fire assembly (2303), all measured over the time (2432) elapsed during exemplary use of the algorithm as shown in FIG. 51.

First, as shown between times (t0), (t1), and (t2), an operator may utilize input control devices (36) of surgeon’s console (16) to manipulate end effector (210) in grasping tissue (T) of a patient. This may be represented as block (2422) in motor control algorithm (2410) shown in FIG. 50. The initial closure of jaws (212, 214) to grasp tissue (T) is represented on graph (2430) of FIG. 52 between time (t0) and time (t2).

It should be understood that motor (2304) is operatively engaged with jaw closure assembly (2301) such that fire locking assembly (2318) of clutch assembly (2314) may be activated to substantially lock the position of firing beam (216) relative to shaft assembly (114). Therefore, since actuation of firing beam (216) has not yet happened, firing displacement line (2433) (which represents the longitudinal position of pusher block (236)), firing power line (2437) (which represents output power of motor (2304) with regards to fire assembly (2303)), and firing force line (2442) (which represents the force generated in order to drive firing beam (216)) remain relative unchanged between times (t0) and (t2).

However, with motor (2304) operative engaged with jaw closure assembly (2301) to drive closure ring (230) distally to close jaws (212, 214), the jaw closure power line (2435) (which may represent output power of motor (2304) with regards to jaw closure assembly (2301) raises from little or no power output up to 75% in the current example in order to manipulate jaws (212, 214) to grasp tissue (T). Additionally, the closure force line (2439) (which represents the force imparted on jaw closure assembly (2301) in order to grasp tissue (T)) increases to JM2 in response to motor (2304) driving jaws (212, 214) to grasp tissue (T). Therefore, between times (t0) and (t2), motor (2304) is activated to drive jaws (212, 214) such that the reactive closure force line (2439) gradually increases due to contact between grasped tissue (T) and jaws (212, 214).

When the operator is ready to sever and staple tissue (T) grasped between jaws (212, 214), the operator may initiate the firing sequence via surgeon’s console (16). In response, as shown in block (2414) of motor control algorithm (2410), motor (2304) may drive clutch assembly (2314) such that motor (2304) is operatively engaged with fire assembly (2303), rather than jaw closure assembly (2301). It should be understood that when motor (2304) is operatively engaged with fire assembly (2303), jaw locking assembly (2316) of clutch assembly (2314) may be activated to substantially lock the position of closure ring (230) relative to shaft assembly (114). Therefore, as shown between times (t2) and (t3), the jaw closure power line (2435) may drop to substantially zero while closure force line (2439) remains at around the same level between times (t2) and (t3), since motor (2304) is not needed to maintain the closed position of jaws (212, 214) between times (t2) and (t3).

With motor (2304) operatively engaged with fire assembly (2303), motor (2304) may advance firing beam (216) distally, as shown in block (2416) of motor control algorithm (2410) and as shown between times (t2) and (t3). Advancement of firing beam (216) changes the firing displacement line (2433), increases firing power line (2437), and increases firing force line (2442). Motor control algorithm may ask if the firing force line (2442) imparted on motor (2304) is below a predetermined threshold, as shown in block (2418). If firing force line (2442) never raises above the predetermined threshold, motor (2304) will continue to advance firing beam (216) until distal firing position is achieved, as shown in block (2424). Once the distal firing position is achieved, motor (2304) may retract firing beam (216) in order to complete the firing stroke (2426).

However, if it is determined that the firing force (2442) reaches a predetermined range (2444), as shown in FIG. 52, motor control algorithm (2410) may instruct motor (2304) to stop the distal advancement of firing beam (216), lock fire assembly (2303), and engage motor (2304) with jaw closure assembly (2301) in accordance with the description herein, and as shown in block (2420) of the motor control algorithm (2410). With motor (2304) engaged with jaw closure assembly (2301), motor (2304) may further close jaws (212, 214) as shown in block (2422) of the motor control algorithm (2410).

Further closure of jaws (212, 214) thereby increases both jaw closure power line (2435) and closure force line (2439) between times (t3) and (t4). Further closure of jaws (212, 214) may actively decrease the amount of firing force required for motor (2304) to distally advance firing beam (216). It should be understood that since fire locking assembly, also referred to as clutch assembly (2314) is activated, the position of firing beam (216) may not substantially change during times (t3) and (t4).

Once jaws (212, 214) are sufficiently closed further, motor (2304) may switch back to being operatively engaged with fire assembly (2303) in accordance with the description herein. Motor (2304) may then begin to advance fire beam (216) in accordance with the description herein. If the firing force line (2442) increase back into the undesirable predetermined range (2444), motor (2304) may actively engage jaw closure assembly (2301) once again in order to further close jaws (212, 214), as shown between times (t5) and (t6), in order to actively reduce the firing force required to advance firing beam (216).

Therefore, it should be understood the motor control algorithm (2410) may allow a single motor (2304) to control both a jaw closure assembly (2301) and a fire assembly (2303), and cycle between operative engagement with both assemblies (2301, 2303) in a cooperative fashion in order to actively reduce the firing force required, which may (A) reduce the time required to complete a the firing process of firing beam (216) in accordance with the description herein, and (B) reduce the chances of having to operate motor (2304) past a predetermined threshold or operate manual actuator (124).

VI. Exemplary Firing System Features for Surgical Stapler

In some instances, it may be desirable to provide one or more components of the firing system of an end effector (116, 210), such as one or more of staple cartridge (154, 218), wedge sled (170, 238), and/or staple drivers (160, 244) with features to improve the deployment of staples (162, 250) and/or the severing of tissue. More particularly, such features may be configured to assist in minimizing failure of staple cartridge (154, 218) and/or malformation of staples (162, 250), such as by minimizing undesirable rolling of staple drivers (160, 244) when cammingly contacted by wedge sled (170, 238). Each of the staple cartridges (3310, 3410, 3510, 3610, 3710, 3810, 3910) described below provides one or more of these functionalities.

A. First Alternative Staple Cartridge with Staple Driver Assemblies

FIGS. 53-57 show an exemplary staple cartridge (3310) for use with either end effector (116, 210) described above. Staple cartridge (3310) is similar to staple cartridge (154) described above except as otherwise described below. In this regard, staple cartridge (3310) includes a staple cartridge body (3312) that houses wedge sled (170) (FIGS. 60A-60C). Staple cartridge body (3312) includes a proximal end (3314) and a distal end (not shown), and further includes an array of staple accommodating apertures (also referred to as "staple apertures") (3316*a*, 3316*b*, 3316*c*) extending through an upper deck (3318) of staple cartridge body (3312). A vertical slot (3319), configured to accommodate a knife member (not shown), such as knife member (172), extends through part of staple cartridge (3310). Staple cartridge body (3312) is also configured to house a plurality of staple driver assemblies (3320, 3322, 3324*a*, 3324*b*, 3325*a*, 3325*b*, 3326, 3328*a*, 3328*b*) (FIGS. 54-62) in a variety of arrangements, and to house a plurality of staples (not shown), such as staples (162, 250).

In the example shown, staple apertures (3316*a*, 3316*b*, 3316*c*) are arranged in three longitudinal rows on each side of vertical slot (3319). More particularly, staple apertures (3316*a*, 3316*b*, 3316*c*) are arranged in a longitudinal row of laterally inner staple apertures (3316*a*), a longitudinal row of laterally intermediate staple apertures (3316*b*), and a longitudinal row of laterally outer staple apertures (3316*c*) on each side of vertical slot (3319). In the present version, staple apertures (3316*a*, 3316*b*, 3316*c*) are arranged symmetrically relative to vertical slot (3319) and are each oriented substantially parallel thereto, with laterally outer staple apertures (3316*c*) aligned in the lateral direction with respective laterally inner staple apertures (3316*a*), and with laterally intermediate staple apertures (3316*b*) offset from but overlapping in the lateral direction with laterally inner and outer staple apertures (3316*a*, 3316*c*). As shown, the proximal-most laterally inner staple apertures (3316*a*) on each side of vertical slot (3319) are aligned with each other in the lateral direction, and are positioned more proximally than the proximal-most laterally intermediate and outer staple apertures (3316*b*, 3316*c*). However, it will be appreciated that staple apertures (3316*a*, 3316*b*, 3316*c*), including the proximal-most laterally inner staple apertures (3316*a*), may be configured and/or arranged in any suitable manner, as described in greater detail below.

Figure 53:
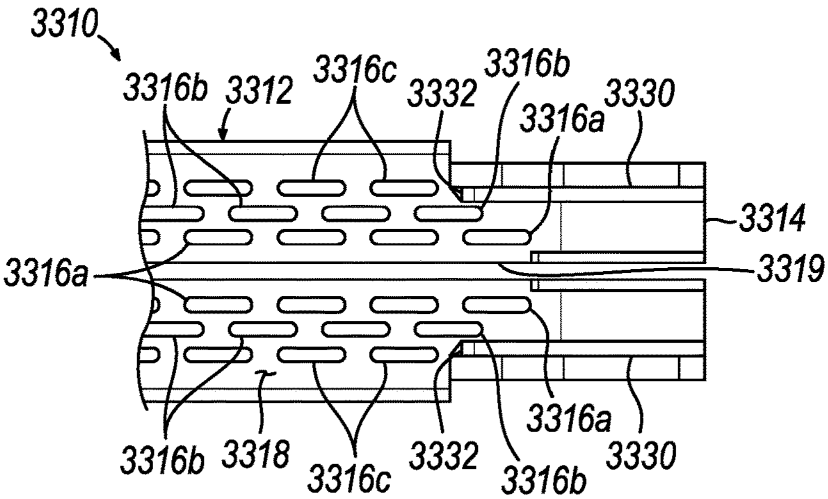
FIG. 53 depicts a partial top view of another exemplary staple cartridge having a plurality of staple apertures and a laterally-opposed pair of proximal tissue stops, with the proximal-most staple apertures positioned proximally of the distal ends of the tissue stops.

As shown in FIG. 53, staple cartridge body (3312) also includes a laterally-opposed pair of tissue stops (3330) protruding upwardly from a proximal portion of upper deck (3318) and terminating distally at respective distal ends (3332). Tissue stops (3330) may be configured to prevent or otherwise limit the ability of tissue to extend proximally past the respective distal ends (3332), such as for assisting in preventing such tissue from being severed too far proximally to receive staples (162, 250) for proper sealing. In this regard, the proximal-most laterally inner staple apertures (3316*a*) are each positioned substantially entirely proximally of the distal end (3332) of the respective tissue stop (3330), such that the corresponding staples (162, 250) deployed from proximal-most laterally inner staple apertures (3316*a*) are likewise positioned proximally of the distal end (3332) of the respective tissue stop (3330). Such positioning of proximal-most laterally inner staple apertures (3316*a*) relative to tissue stops (3330) may assist in providing proper sealing of the severed tissue, particularly in cases where a portion of the tissue inadvertently extends slightly proximally of the distal end (3332) of one or both tissue stops (3330).

i. Exemplary Staple Driver Assembly Arrangements

FIGS. 54-57 show various arrangements of staple driver assemblies (3320, 3322, 3324*a*, 3324*b*, 3325*a*, 3325*b*, 3326, 3328*a*, 3328*b*) that may be housed within staple cartridge body (3312) and aligned below (e.g., in the transverse direction) one or more corresponding staple apertures (3316*a*, 3316*b*, 3316*c*) for deploying staples (162, 250) therethrough.

Figure 54:
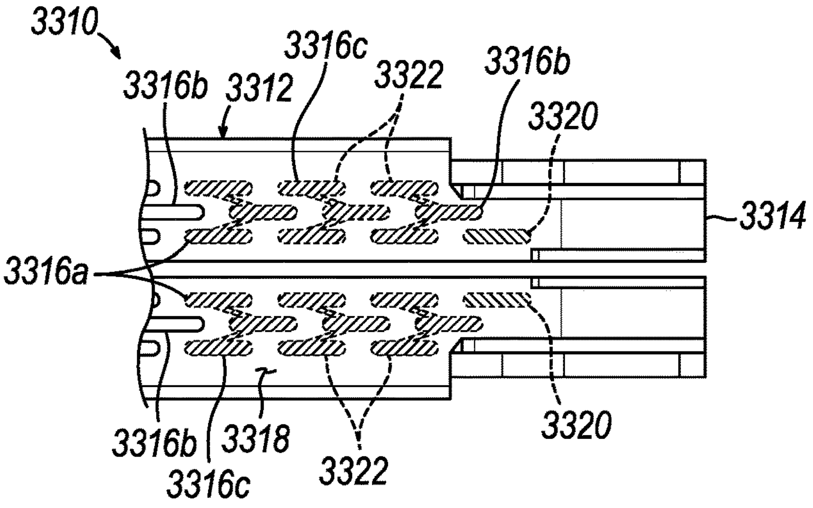
FIG. 54 depicts a partial top view of the staple cartridge of FIG. 53, schematically showing a first arrangement of staple driver assemblies positioned below corresponding staple apertures.

FIG. 54 shows a pair of single-staple driver assemblies (3320) aligned below corresponding proximal-most laterally inner staple apertures (3316*a*), and further shows a plurality of triple-staple driver assemblies (3322) aligned below corresponding sets of three neighboring staple apertures (3316*a*, 3316*b*, 3316*c*), each set including a distal, laterally inner staple aperture (3316*a*) aligned in the lateral direction with a distal, laterally outer staple aperture (3316*c*) and overlapping in the lateral direction with a proximal, laterally intermediate staple aperture (3316*b*). Triple-staple driver assembly (3322) is described in greater detail below in connection with FIGS. 61-62.

Figure 55:
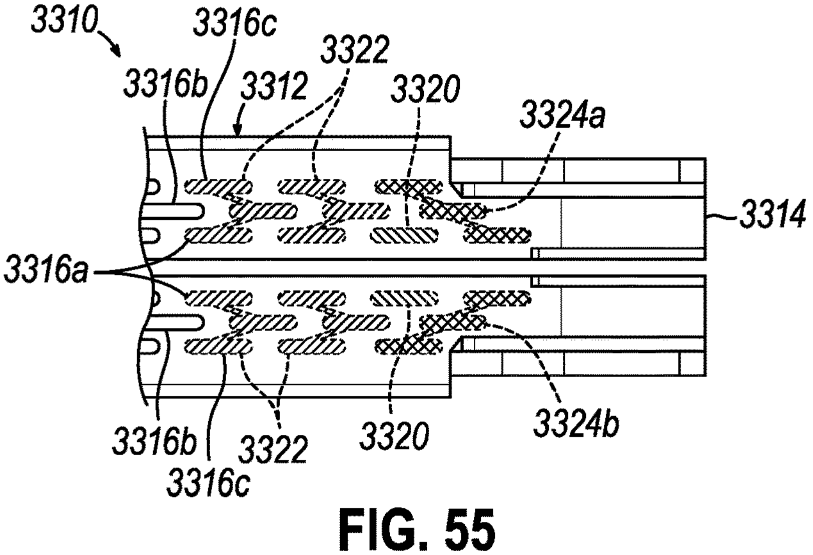
FIG. 55 depicts a partial top view of the staple cartridge of FIG. 53, schematically showing a second arrangement of staple driver assemblies positioned below corresponding staple apertures.

FIG. 55 shows a pair of triple-staple driver assemblies (3324*a*, 3324*b*) aligned below corresponding sets of three neighboring staple apertures (3316*a*, 3316*b*, 3316*c*), each set including the proximal-most laterally inner, intermediate, and outer staple apertures (3316*a*, 3316*b*, 3316*c*). FIG. 55 also shows a pair of single-staple driver assemblies (3320) aligned below corresponding laterally inner staple apertures (3316*a*) immediately distal of the respective proximal-most laterally inner staple aperture (3316*a*). FIG. 55 further shows a plurality of triple-staple driver assemblies (3322) aligned below corresponding sets of three neighboring staple apertures (3316*a*, 3316*b*, 3316*c*), each set including a distal, laterally inner staple aperture (3316*a*) aligned in the lateral direction with a distal, laterally outer staple aperture (3316*c*) and overlapping in the lateral direction with a proximal, laterally intermediate staple aperture (3316*b*).

Figure 56:
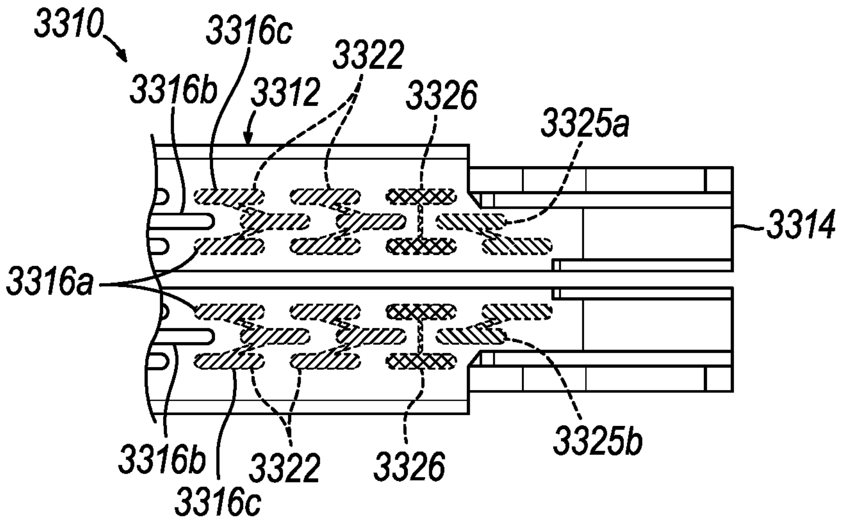
FIG. 56 depicts a partial top view of the staple cartridge of FIG. 53, schematically showing a third arrangement of staple driver assemblies positioned below corresponding staple apertures.

FIG. 56 shows a pair of double-staple driver assemblies (3325*a*, 3325*b*) aligned below corresponding sets of two neighboring staple apertures (3316*a*, 3316*b*), each set including the respective proximal-most laterally inner and intermediate staple aperture (3316*a*, 3316*b*). FIG. 56 also shows a pair of double-staple driver assemblies (3326) aligned below corresponding sets of two neighboring staple apertures (3316*a*, 3316*c*), each set including the respective proximal-most laterally outer staple aperture (3316*c*) aligned in the lateral direction with a laterally inner staple aperture (3316*a*). FIG. 56 further shows a plurality of triple-staple driver assemblies (3322) aligned below corresponding sets of three neighboring staple apertures (3316*a*, 3316*b*, 3316*c*), each set including a distal, laterally inner staple aperture (3316*a*) aligned in the lateral direction with a distal, laterally outer staple aperture (3316*c*) and overlapping in the lateral direction with a proximal, laterally intermediate staple aperture (3316*b*).

Figure 57:
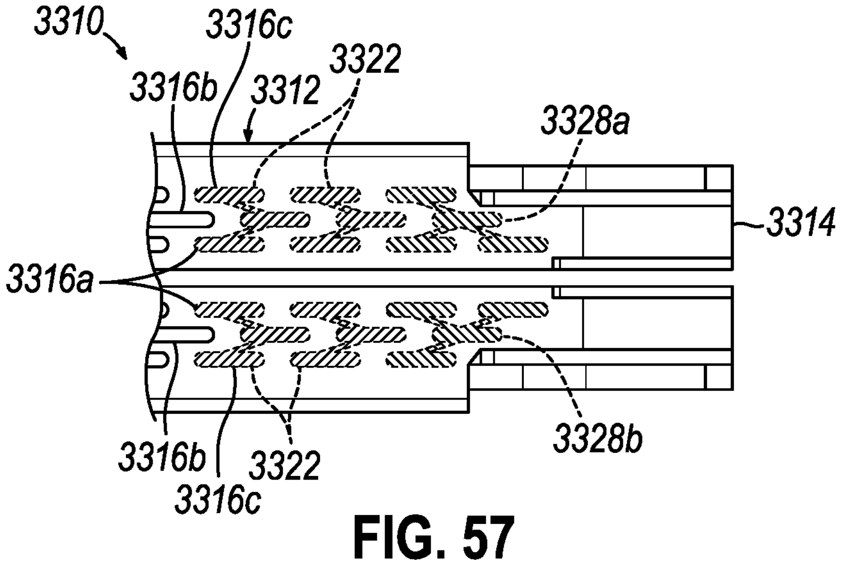
FIG. 57 depicts a partial top view of the staple cartridge of FIG. 53, schematically showing a fourth arrangement of staple driver assemblies positioned below corresponding staple apertures.

FIG. 57 shows a pair of quadruple-staple driver assemblies (3328*a*, 3328*b*) aligned below corresponding sets of four neighboring staple apertures (3316*a*, 3316*b*, 3316*c*), each set including the respective proximal-most laterally inner, intermediate, and outer staple apertures (3316*a*, 3316*b*, 3316*c*), as well as a laterally inner staple aperture (3316*a*) aligned in the lateral direction with the respective proximal-most laterally outer staple aperture (3316*c*). FIG. 57 further shows a plurality of triple-staple driver assemblies (3322) aligned below corresponding sets of three neighboring staple apertures (3316*a*, 3316*b*, 3316*c*), each set including a distal, laterally inner staple aperture (3316*a*) aligned in the lateral direction with a distal, laterally outer staple aperture (3316*c*) and overlapping in the lateral direction with a proximal, laterally intermediate staple aperture (3316*b*).

ii. Exemplary Quadruple Staple Driver Assembly

Figure 58:
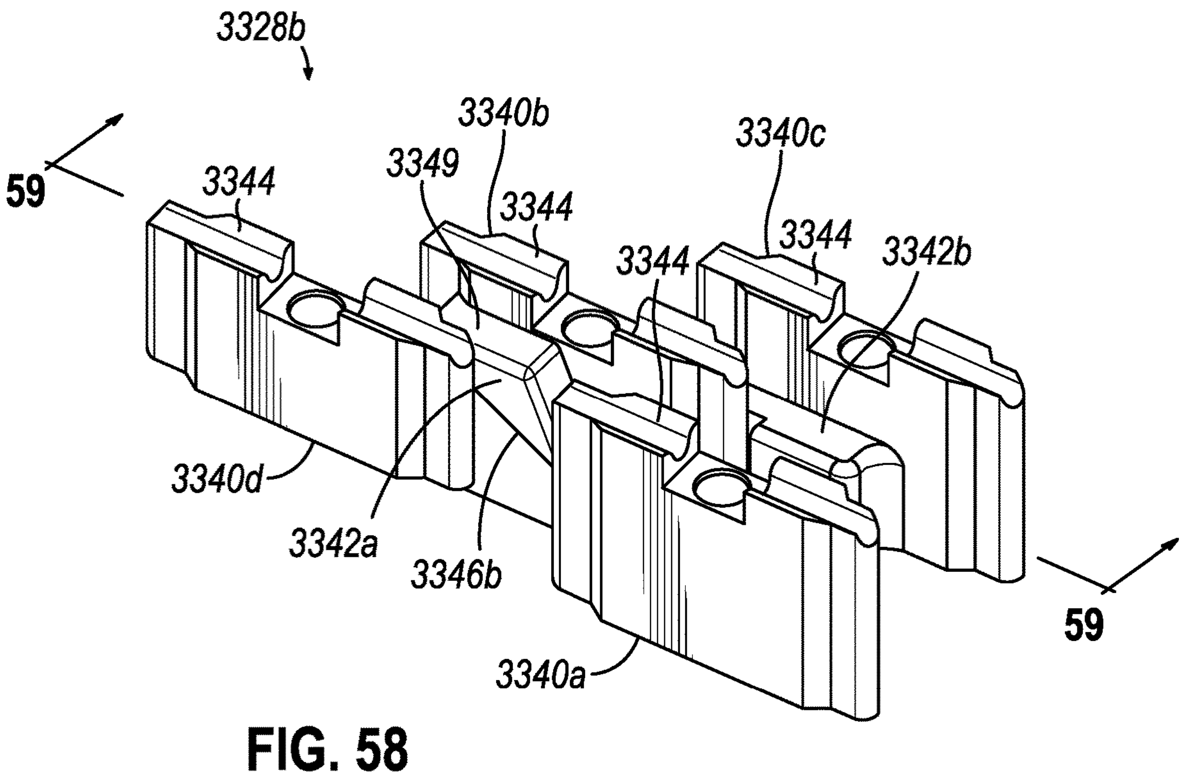
FIG. 58 depicts a perspective view of a quadruple staple driver assembly of the staple cartridge shown in FIG. 57.
Figure 59:
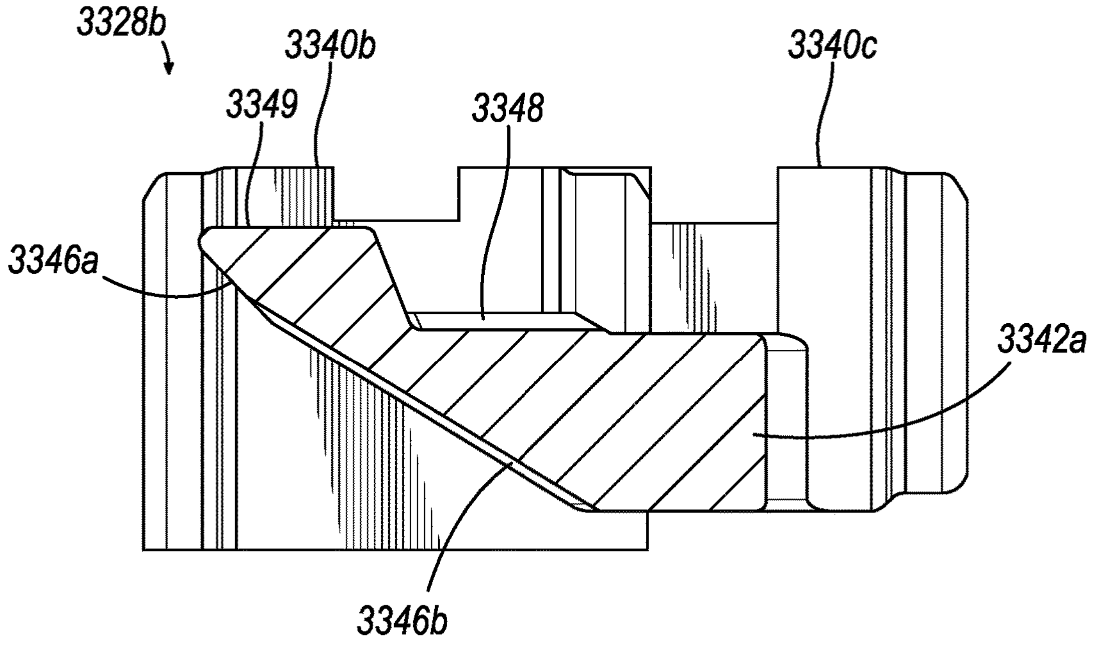
FIG. 59 depicts a cross-sectional view of the quadruple staple driver assembly of FIG. 58, taken along section line 59-59 in FIG. 58.
Figure 60A:
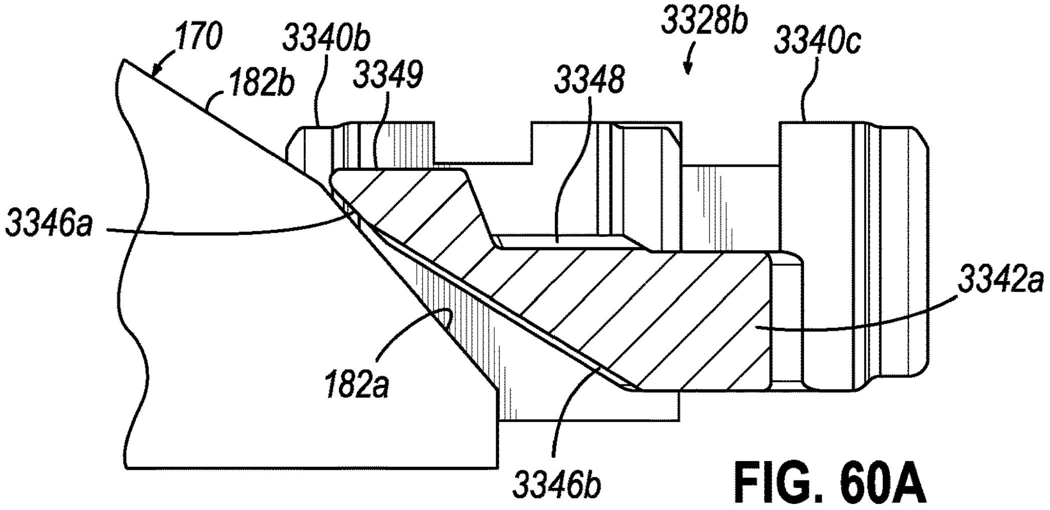
FIG. 60A depicts a cross-sectional view of the quadruple staple driver assembly of FIG. 58, showing a wedge sled of the firing assembly of FIG. 9 in a proximal position relative to the quadruple staple driver assembly.
Figure 60B:
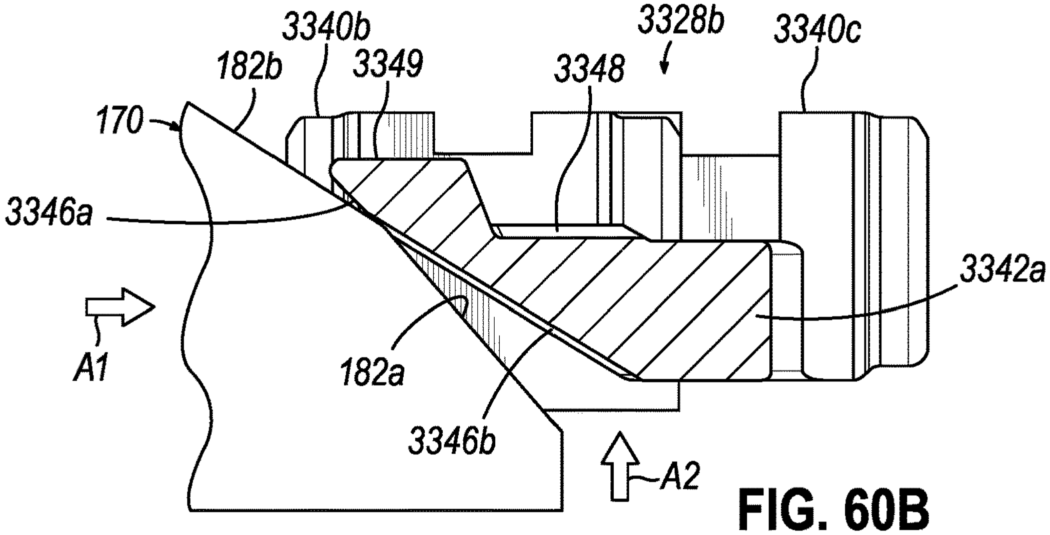
FIG. 60B depicts a cross-sectional view of the quadruple staple driver assembly of FIG. 58, showing the quadruple staple driver assembly lifted by a leading edge of the wedge sled of FIG. 9 during distal translation of the wedge sled.
Figure 60C:
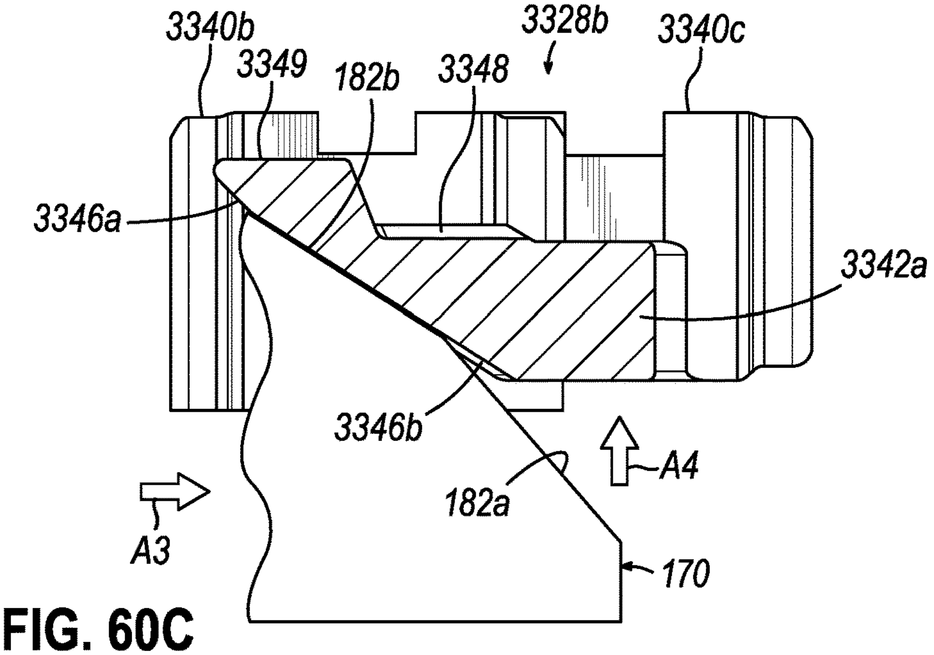
FIG. 60C depicts a cross-sectional view of the quadruple staple driver assembly of FIG. 58, showing the quadruple staple driver assembly lifted by a trailing edge of the wedge sled of FIG. 9 during distal translation of the wedge sled.

Referring now to FIGS. 58 and 59, quadruple staple driver assembly (3328*b*) includes a set of four staple drivers (3340*a*, 3340*b*, 3340*c*, 3340*d*) interconnected by one or more driver cams (3342*a*, 3342*b*) (also referred to as "riggers") extending therebetween. The set of four staple drivers (3340*a*, 3340*b*, 3340*c*, 3340*d*) generally includes a first distally positioned staple driver (3340*a*) and a proximally positioned staple driver (3340*d*) on a first lateral side of first driver cam (3342*a*), an intermediately positioned staple driver (3340*b*) on a second lateral side of first driver cam (3342*a*) and on a first lateral side of second driver cam (3342*b*), and a second distally positioned staple driver (3340*c*) on a second lateral side of second driver cam (3342*b*). Staple drivers (3340*a*, 3340*b*, 3340*c*, 3340*d*) for quadruple driver assembly (3328*b*) are generally positioned such that first and second distally positioned staple drivers (3340*a*, 3340*c*) are aligned in the lateral direction with each other, first and second distally positioned staple drivers (3340*a*, 3340*c*) each overlap in the lateral direction with intermediately positioned staple driver (3340*b*), and proximally positioned staple driver (3340*d*) overlaps in the lateral direction with intermediately positioned staple driver (3340*b*). Each staple driver (3340*a*, 3340*b*, 3340*c*, 3340*d*) further includes at least one longitudinal groove (3344) configured to cradle a crown (not shown) of a corresponding one of staples (162, 250).

As best shown in FIG. 59, first driver cam (3342*a*) of quadruple staple driver assembly (3328*b*) presents one or more inclined cam surfaces (3346*a*, 3346*b*) configured to be cammingly contacted by respective ramp portions (182*a*, 182*b*) (FIGS. 60A-60C) of wedge sled (170). In the example shown, first driver cam ((3342*a*) includes a proximal cam surface (3346*a*) oriented at a first angle ($\alpha$1) relative to a horizontal reference plane (e.g., defined by a flat bottom surface of first driver cam (3342*a*) and/or defined by a flat bottom surface of wedge sled (170) or any plane parallel thereto) and configured to be cammingly contacted by a leading ramp portion (182*a*) of wedge sled (170). First driver cam (3342*a*) also includes a distal cam surface (3346*b*) oriented at a second angle ($\alpha$2) relative to the horizontal reference plane and configured to be cammingly contacted by a trailing ramp portion (182*b*) of wedge sled (170). In the present version, first angle ($\alpha$1) is greater than second angle ($\alpha$2). It will be appreciated that leading and trailing ramp portions (182*a*, 182*b*) of wedge sled (170) may also be oriented at first and second angles ($\alpha$1, $\alpha$2), respectively, relative to the horizontal reference plane. In some versions, second angle ($\alpha$2) may be between approximately 15° and approximately 25°. For example, second angle ($\alpha$2) may be between approximately 15° and approximately 20°.

In the example shown, first driver cam (3342*a*) includes a distal main body portion (3348) and a proximal elevated portion (3349) extending upwardly therefrom. In this regard, proximal elevated portion (3349) may facilitate connecting proximal staple driver (3340*d*) to intermediate staple driver (3340*b*) at a location above distal main body portion (3348), for example. Proximal elevated portion (3349) may also provide first driver cam (3342*a*) with an increased cross-sectional area, at least by comparison to that which first driver cam (3342*a*) would have in the absence of proximal elevated portion (3349). In some versions, cartridge body (3312) may include a clearance feature such as a bore or a recess provided in upper deck (3318) for accommodating proximal elevated portion (3349) of first driver cam (3342*a*), such as during lifting of first driver cam (3342*a*) via wedge sled (170).

As shown, a distal end of distal cam surface (3346*b*) is positioned substantially distally relative to a centroid (C) of quadruple staple driver assembly (3328*b*) (which may coincide with a center of mass of quadruple staple driver assembly (3328*b*)), such that a majority of the operational loading range of distal cam surface (3346*b*) is distal of centroid (C), and such that the center of contact between distal cam surface (3346*b*) and trailing ramp portion (182*b*) is distal of centroid (C), at least when the corresponding staples (162, 250) are deployed into forming contact with staple forming pockets (252) on the inner surface of anvil (150, 214) (e.g., when driven upwardly between 0.05 inch and 0.065 inch). More particularly, the apex of the contact between distal cam surface (3346*b*) and trailing ramp portion (182*b*) when the corresponding staples (162, 250) contact the staple forming pockets (252) may be distal of centroid (C). Such positioning of the center of contact relative to centroid (C), particularly when the corresponding staples (162, 250) contact staple forming pockets (252), may assist in preventing undesirable rolling of quadruple staple driver assembly (3328*b*), such as by allowing the force applied by trailing ramp portion (182*b*) to distal cam surface (3346*b*) to counteract any moment arm about centroid (C) that might otherwise be applied to quadruple staple driver assembly (3328*b*) by staple forming pockets (252) via the corresponding staples (162, 250). For example, the force applied by trailing ramp portion (182*b*) to distal cam surface (3346*b*) when the corresponding staples (162, 250) contact the staple forming pockets (252) may be applied to distal cam surface (3346*b*) in a generally distal and upward direction at a load center (LC) distal of centroid (C) to thereby counteract a downwardly-directed moment arm about centroid (C) applied by staple forming pockets (252) via the corresponding staples (162, 250) to quadruple staple driver assembly (3328*b*) at the distal ends of grooves (3344) of distal drivers (3340*a*, 3340*c*) to prevent such a moment arm from causing quadruple staple driver assembly (3328*b*) to roll (e.g., clockwise in the frame of reference of FIGS. 1859-60C) about its centroid (C). In other words, the geometries of drivers (3340*a*, 3340*b*, 3340*c*, 3340*d*) are selected to balance the moment arms about centroid (C) and thereby resist rolling of quadruple staple driver assembly (3328*b*). Such a configuration may promote proper deployment of staples (162, 250) and avoid jamming of drivers (3340*a*, 3340*b*, 3340*c*, 3340*d*) or damage to staple cartridge (3310) which might otherwise result in insufficient tissue sealing. In some versions, a midpoint of distal cam surface (3346*b*) (e.g., halfway between its proximal and distal ends) may be distal of centroid (C).

It will be appreciated that each staple driver (3340*a*, 3340*b*, 3340*c*, 3340*d*) may be unitarily secured to the respective driver cam(s) (3342*a*, 3342*b*) relative to the other staple drivers (3340*a*, 3340*b*, 3340*c*, 3340*d*). It will be further appreciated that the term "assembly" as used herein is not intended to be limited to discrete assembled components. Rather the term "assembly" includes components that may be formed separately and assembled and components that may be formed integrally as a single part. Thus, the term "assembly" is not intended to limit the invention described herein.

Referring now to FIGS. 60A-60C, during firing, wedge sled (170) is driven distally from a proximal position shown in FIG. 60A into upward camming contact with quadruple staple driver assembly (3328*b*) that in turn drive staples (162, 250) out through staple apertures (3316*a*, 3316*b*, 3316*c*) and into forming contact with staple forming pockets (252) on the inner surface of anvil (150, 214). More particularly, leading ramp portion (182*a*) cammingly engages proximal cam surface (3346*a*) during distal translation of wedge sled (170), as indicated by arrow (A1) in FIG. 60B, to slightly lift quadruple staple driver assembly (3328*b*), as indicated by arrow (A2) in FIG. 60B. Trailing ramp portion (182*b*) then cammingly engages distal cam surface (3346*b*) during further distal translation of wedge sled (170), as indicated by arrow (A3) in FIG. 60C, to further lift quadruple staple driver assembly (3328*b*), as indicated by arrow (A4) in FIG. 60C. Due to first angle ($\alpha$1) at which proximal cam surface (3346*a*) is oriented being greater than second angle ($\alpha$2) at which distal cam surface (3346*b*) is oriented, the initial contact between wedge sled (170) and quadruple staple driver assembly (3328*b*) may occur when wedge sled (170) has been driven relatively more distal than wedge sled (170) would otherwise be driven if first angle ($\alpha$1) were equal to or less than second angle ($\alpha$2). Such a delay in the initial contact between wedge sled (170) and quadruple staple driver assembly (3328*b*) may assist in preventing undesirable rolling of quadruple staple driver assembly (3328*b*). It should be understood that cartridge body (3312) and anvil (150, 214) are intentionally omitted from the view in FIGS. 60A-60C.

While quadruple staple driver assembly (3328*b*) has been described in connection with FIGS. 59-60C, it will be appreciated that quadruple staple driver assembly (3328*a*) may have a mirrored configuration of that of staple driver assembly (3328*b*).

iii. Exemplary Triple Staple Driver Assembly

Figure 61:
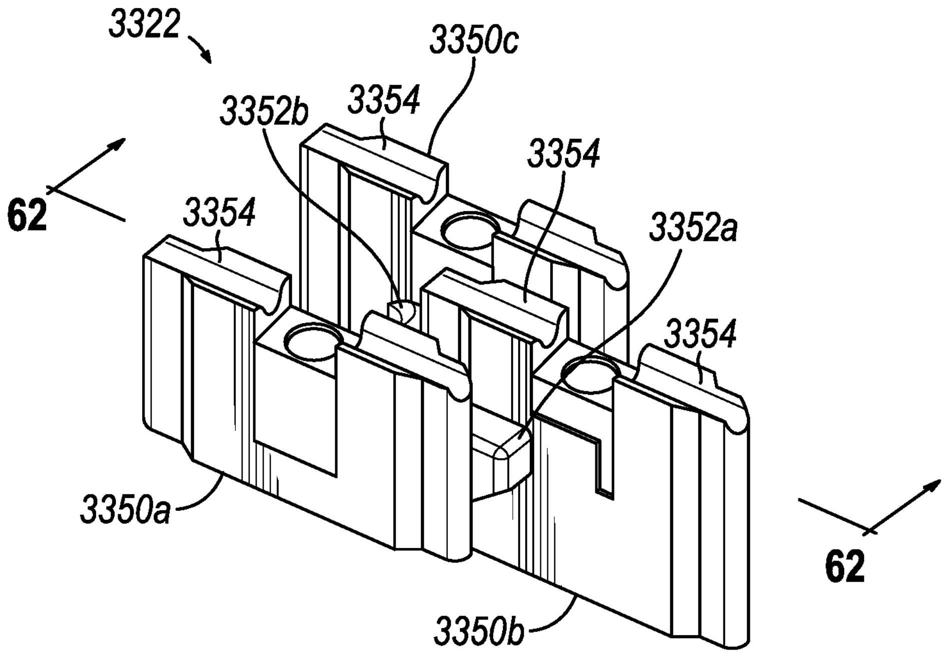
FIG. 61 depicts a perspective view of a triple staple driver assembly of the staple cartridge shown in FIGS. 54-57.
Figure 62:
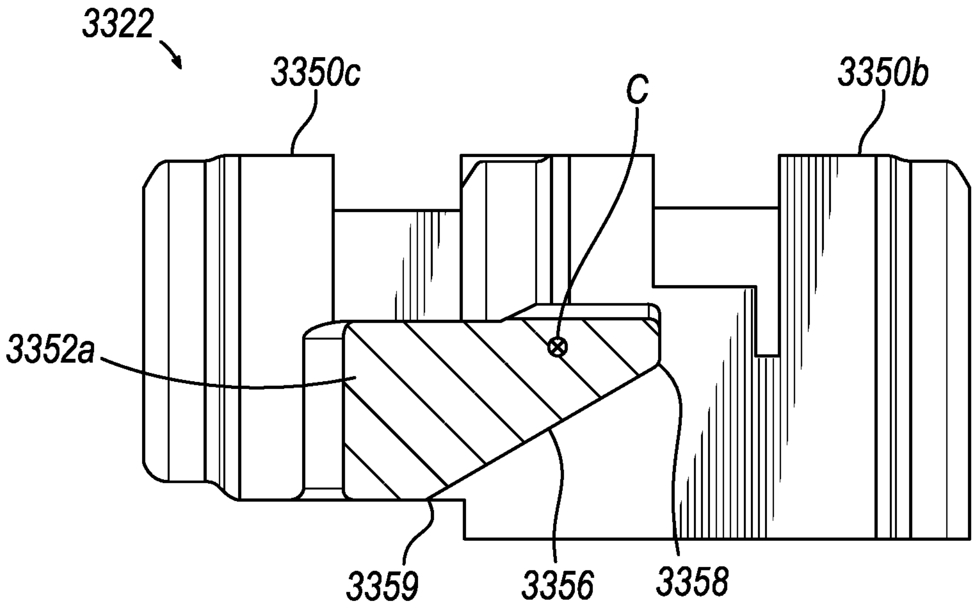
FIG. 62 depicts a cross-sectional view of the triple staple driver assembly of FIG. 61, taken along section line 62-62 in FIG. 61.

Referring now to FIGS. 61 and 62, triple staple driver assembly (3322) includes a set of three staple drivers (3350*a*, 3350*b*, 3350*c*) interconnected by one or more driver cams (3352*a*, 3352*b*) (also referred to as "riggers") extending therebetween. The set of three staple drivers (3350*a*, 3350*b*, 3350*c*) generally includes a first distally positioned staple driver (3350*a*) on a first lateral side of first driver cam (3352*a*), a proximally positioned staple driver (3350*b*) on a second lateral side of first driver cam (3352*a*) and on a first lateral side of second driver cam (3352*b*), and a second distally positioned staple driver (3350*c*) on a second lateral side of second driver cam (3352*b*). Staple drivers (3350*a*, 3350*b*, 3350*c*) for triple driver assembly (3322) are generally positioned such that first and second distally positioned staple drivers (3350*a*, 3350*c*) are aligned in the lateral direction with each other, and each overlap in the lateral direction with and are equidistantly spaced apart from proximally positioned staple driver (3350*b*). Each staple driver (3350*a*, 3350*b*, 3350*c*) further includes at least one longitudinal groove (3354) configured to cradle a crown (not shown) of a corresponding one of staples (162, 250).

As best shown in FIG. 62, first driver cam (3352*a*) of triple staple driver assembly (3322) presents an inclined cam surface (3356) configured to be cammingly contacted by a respective ramp portion (182, 182*a*, 182*b*) (FIGS. 9 and 60A-60C) of wedge sled (170). Cam surface (3356) has a proximal end (3358) and a distal end (3359), and is oriented at an angle ($\alpha$) relative to a horizontal reference plane (e.g., defined by a flat bottom surface of first driver cam (3352*a*) and/or defined by a flat bottom surface of wedge sled (170) or any plane parallel thereto). It will be appreciated that ramp portion (182) of wedge sled (170) may also be oriented at angle ($\alpha$) relative to the horizontal reference plane. In some versions, angle ($\alpha$) may be between approximately 15° and approximately 25°. For example, angle ($\alpha$) may be between approximately 15° and approximately 20°.

As shown, distal end (3359) of cam surface (3356) is positioned substantially distally relative to a centroid (C) of triple staple driver assembly (3322) (which may coincide with a center of mass of triple staple driver assembly (3322)), such that a majority of the operational loading range of cam surface (3356) is distal of centroid (C), and such that the center of contact between cam surface (3356) and ramp portion (182) is distal of centroid (C), at least when the corresponding staples (162, 250) are deployed into forming contact with staple forming pockets (252) on the inner surface of anvil (150, 214) (e.g., when driven upwardly between 0.05 inch and 0.065 inch). More particularly, the apex of the contact between cam surface (3356) and ramp portion (182) when the corresponding staples (162, 250) contact the staple forming pockets (252) may be distal of centroid (C). Such positioning of the center of contact relative to centroid (C), particularly when the corresponding staples (162, 250) contact staple forming pockets (252), may assist in preventing undesirable rolling of triple staple driver assembly (3322), such as by allowing the force applied by ramp portion (182) to cam surface (3356) to counteract any moment arm about centroid (C) that might otherwise be applied to triple staple driver assembly (3322) by staple forming pockets (252) via the corresponding staples (162, 250). For example, the force applied by ramp portion (182) to cam surface (3356) when the corresponding staples (162, 250) contact the staple forming pockets (252) may be applied to cam surface (3356) in a generally distal and upward direction at a load center (LC) distal of centroid (C) to thereby counteract a downwardly-directed moment arm about centroid (C) applied by staple forming pockets (252) via the corresponding staples (162, 250) to triple staple driver assembly (3322) at the distal ends of grooves (3354) of distal drivers (3350*a*, 3350*c*) to prevent such a moment arm from causing triple staple driver assembly (3322) to roll (e.g., counterclockwise in the frame of reference of FIG. 62) about its centroid (C). In other words, the geometries of drivers (3350*a*, 3350*b*, 3350*c*) are selected to balance the moment arms about centroid (C) and thereby resist rolling of triple staple driver assembly (3322). Such a configuration may promote proper deployment of staples (162, 250) and avoid jamming of drivers (3350*a*, 3350*b*, 3350*c*) or damage to staple cartridge (3310) which might otherwise result in insufficient tissue sealing. In some versions, a midpoint of cam surface (3356) (e.g., halfway between proximal and distal ends (3358, 3359)) may be distal of centroid (C).

It will be appreciated that load center (LC) may be distal relative to centroid (C) since there are two distal staples (162, 250) deployed by distal drivers (3350*a*, 3350*c*) and one proximal staple (162, 250) deployed by proximal driver (3350*b*). It will also be appreciated that a percentage of angle (α) may induce a clockwise rotation of triple staple driver assembly (3322) about centroid (C) during camming engagement between cam surface (3356) and ramp portion (182) that is substantially equal to and opposite the counterclockwise rotation of triple staple driver assembly (3322) about centroid (C) induced by the two distal staples (162, 250). Such balancing of the clockwise and counterclockwise rotations may prevent triple staple driver assembly (3322) from rotating. In this regard, each staple (162, 250) may require between approximately 1.0 lb. and approximately 3.0 lbs. (e.g., between approximately 1.5 and approximately 2.5 lbs.) to form, such that the total load on triple staple driver assembly (3322) may be between approximately 3 lbs, and approximately 9 lbs, in the vertical direction. In cases where wedge sled (170) presents leading and trailing ramp portions (182*a*, 182*b*), the non-forming initial raising of triple staple driver assembly (3322) by leading ramp portion (182*a*) may be effectively between approximately 0.5 lb, and approximately 1.0 lb., and second angle (α2) of trailing ramp portion (182*b*) may be may be between approximately 15° and approximately 25° (e.g., between approximately 15° and approximately 20°), such that the longitudinal load on wedge sled (170) to generate the vertical force may be between approximately 2 lbs. and approximately 4 lbs. Load center (LC) may be between approximately 0.025 inch and approximately 0.1 inch below centroid (C) causing a moment arm of approximately 0.1 in-lb. in the clockwise direction and the formation of the distal staples (162, 250) causing a moment arm of approximately 0.19 in-lb. in the counterclockwise direction. Any remaining moment arms acting upon triple staple driver assembly (3322) to resist rolling of triple staple drive assembly (3322) may be caused by the adjacent support walls of staple cartridge body (3312). Thus, decreasing the moment arms that the adjacent support walls of staple cartridge body (3312) resist may decrease the risk of triple staple driver assembly (3322) rolling.

In cases where wedge sled (170) presents leading and trailing ramp portions (182*a*, 182*b*), it will be appreciated that the apex of the contact between cam surface (3356) and ramp portions (182*a*, 182*b*) when the corresponding staples (162, 250) contact the staple forming pockets (252) may be along trailing ramp portion (182*b*). Moreover, the position of this apex may be at least partially defined by the orientation(s) of ramp portion(s) (182, 182*a*, 182*b*) of wedge sled (170). For example, a change in the orientation(s) of ramp portion(s) (182, 182*a*, 182*b*) from that shown may shift the apex. In such cases, centroid (C) may be shifted to be proximal of the apex.

It will be appreciated that each staple driver (3350*a*, 3350*b*, 3350*c*) may be unitarily secured to the respective driver cam(s) (3352*a*, 3352*b*) relative to the other staple drivers (3350*a*, 3350*b*, 3350*c*). It will be further appreciated that the term "assembly" as used herein is not intended to be limited to discrete assembled components. Rather the term "assembly" includes components that may be formed separately and assembled and components that may be formed integrally as a single part. Thus, the term "assembly" is not intended to limit the invention described herein.

B. Second Alternative Staple Cartridge with Offset Proximal Apertures

Figure 63:
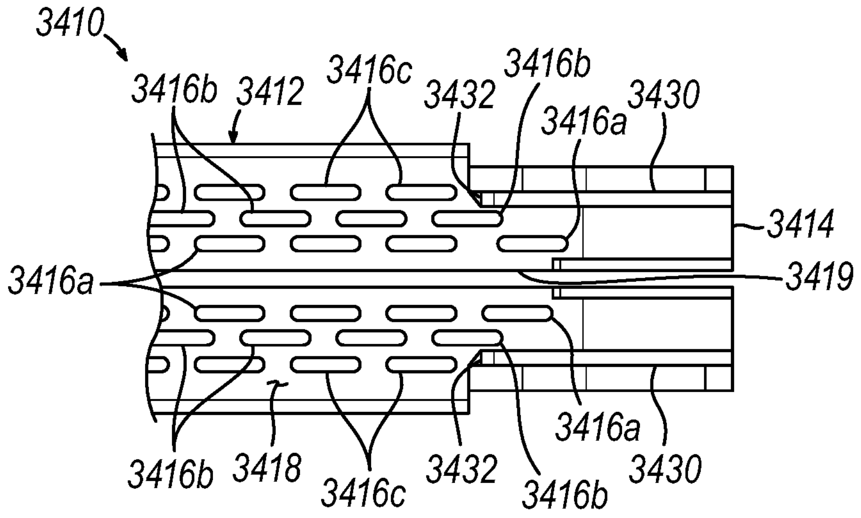
FIG. 63 depicts a partial top view of another exemplary staple cartridge having a plurality of staple apertures and a laterally-opposed pair of proximal tissue stops, with the proximal-most staple apertures positioned proximally of the distal ends of the tissue stops and offset from each other.
Figure 64:
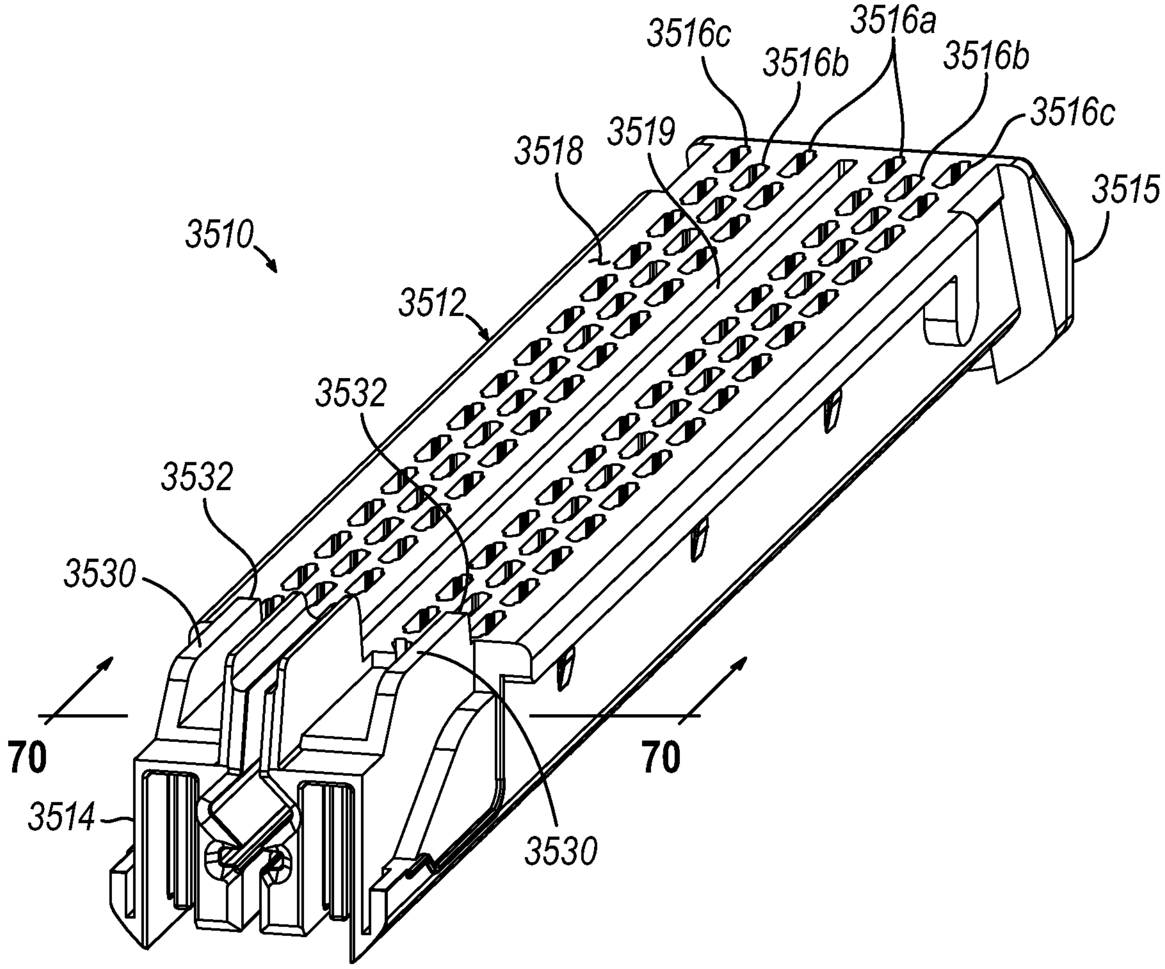
FIG. 64 depicts a perspective view of another exemplary staple cartridge having a diamond-shaped orifice for accommodating a push rod of the driving assembly shown in FIG. 8 and/or a guide member of the firing assembly shown in FIG. 9.
Figure 65:
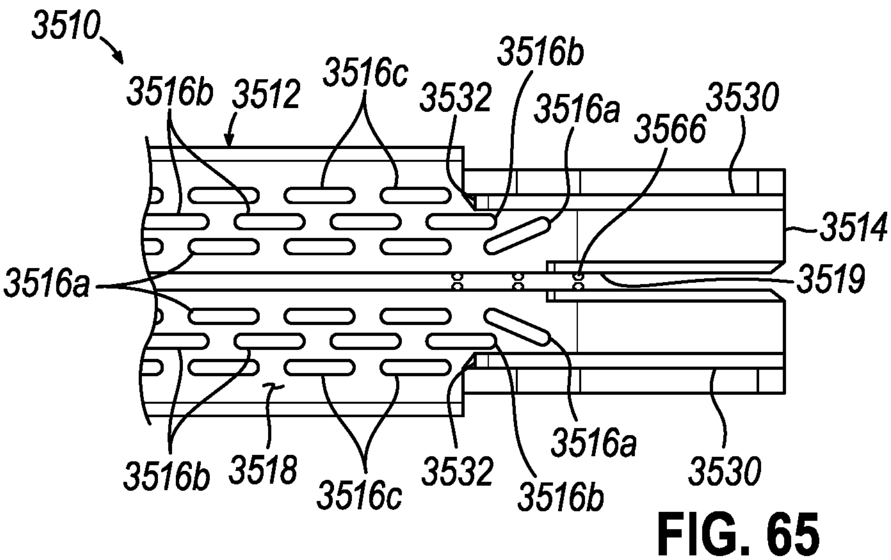
FIG. 65 depicts a partial top view of the staple cartridge of FIG. 64 having a plurality of staple apertures and a laterally-opposed pair of proximal tissue stops, with the proximal-most staple apertures positioned proximally of the distal ends of the tissue stops.

In some instances, it may be desirable to provide a staple cartridge with staple apertures arranged differently from those described above in connection with FIGS. 53-62. FIG. 63 shows an exemplary staple cartridge (3410) for use with either end effector (116, 210) described above that provides such functionalities. Staple cartridge (3410) is similar to staple cartridge (3310) described above except as otherwise described below. In this regard, staple cartridge (3410) includes a staple cartridge body (3412) having a proximal end (3414) and an array of staple apertures (3416*a*, 3416*b*, 3416*c*) extending through an upper deck (3418). A vertical slot (3419) extends through part of staple cartridge (3410), and a laterally-opposed pair of tissue stops (3430) protrude upwardly from a proximal portion of upper deck (3418) and terminate distally at respective distal ends (3432). The proximal-most laterally inner staple apertures (3416*a*) are each positioned substantially entirely proximally of the distal end (3432) of the respective tissue stop (3420).

In the present version, staple apertures (3416*a*, 3416*b*, 3416*c*) are arranged symmetrically relative to vertical slot (3419) with the exception of the proximal-most laterally inner staple apertures (3416*a*). As shown, the proximal-most laterally inner staple apertures (3416*a*) on each side of vertical slot (3419) are offset from each other in the lateral direction. More particularly, the proximal-most laterally inner staple aperture (3416*a*) on the righthand side of vertical slot (3419) (e.g., above vertical slot (3419) in the view of FIG. 63) is positioned more proximally than the proximal-most laterally inner staple aperture (3416*a*) on the left-hand side of vertical slot (3419) (e.g., below vertical slot (3419) in the view of FIG. 63). In some versions, the right-hand ramp portions (182) of wedge sled (170) may be positioned proximally relative to the left-hand ramp portions (182) of wedge sled (170) to accommodate the laterally-offset arrangement of the proximal-most laterally inner staple apertures (3416*a*) when wedge sled (170) is at its initial proximal position.

C. Third Alternative Staple Cartridge with Staple Driver Assemblies

In some instances, it may be desirable to provide a staple cartridge with staple apertures and staple drivers configured and/or arranged differently from those described above in connection with FIGS. 53-62. In addition, or alternatively, it may be desirable to provide a staple cartridge with cartridge support features and/or to provide a staple cartridge that is configured to permit the firing member and/or guide member to horizontally stabilize the cartridge body. FIGS. 64-71 show an exemplary staple cartridge (3510) for use with either end effector (116, 210) described above that provides such functionalities. Staple cartridge (3510) is similar to staple cartridge (3310) described above except as otherwise described below. In this regard, staple cartridge (3510) includes a staple cartridge body (3512) having a proximal end (3514) and a distal end (3515), and an array of staple apertures (3516*a*, 3516*b*, 3516*c*) extending through an upper deck (3518). A vertical slot (3519) extends through part of staple cartridge (3510), and a laterally-opposed pair of tissue stops (3530) protrude upwardly from a proximal portion of upper deck (3518) and terminate distally at respective distal ends (3532). The proximal-most laterally inner staple apertures (3516*a*) are each positioned substantially entirely proximally of the distal end (3532) of the respective tissue stop (3520). Staple cartridge body (3512) is also configured to house a plurality of staple driver assemblies (3320, 3322, 3326, 3523*a*, 3523*b*, 3527*a*, 3527*b*, 3529*a*, 3529*b*) (FIGS. 66-69) in a variety of arrangements, and to house a plurality of staples (not shown), such as staples (162, 250).

Figure 67:
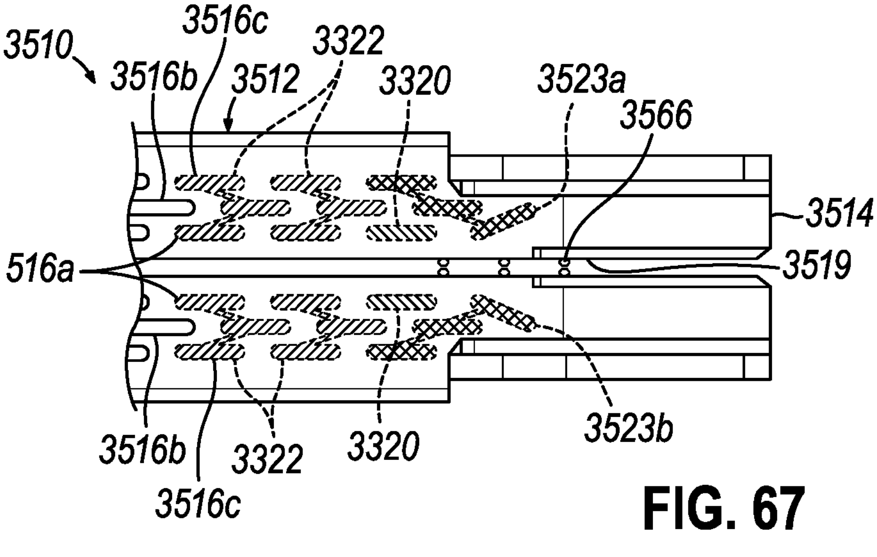
FIG. 67 depicts a partial top view of the staple cartridge of FIG. 64, schematically showing a second arrangement of staple driver assemblies positioned below corresponding staple apertures.

In the present version, staple apertures (3516*a*, 3516*b*, 3516*c*) are each oriented substantially parallel to vertical slot (3519) with the exception of the proximal-most laterally inner staple apertures (3516*a*). As best shown in FIG. 67, the proximal-most laterally inner staple apertures (3516*a*) on each side of vertical slot (3519) are each oriented at a same angle relative to vertical slot (3519). More particularly, the proximal-most laterally inner staple apertures (3516*a*) are each angled laterally outwardly in the proximal direction. Such angling of the proximal-most laterally inner staple apertures (3516*a*) may allow the proximal-most laterally inner staple apertures (3516*a*) to occupy a relatively footprint in the longitudinal direction, at least by comparison to the proximal-most laterally inner staple apertures (3316*a*, 3416*a*) described above, without requiring a reduction in the lengths of the proximal-most laterally inner staple apertures (3516*a*).

i. Exemplary Staple Driver Assembly Arrangements

FIGS. 66-69 show various arrangements of staple driver assemblies (3320, 3322, 3326, 3523*a*, 3523*b*, 3527*a*, 3527*b*, 3529*a*, 3529*b*) that may be housed within staple cartridge body (3512) and aligned below (e.g., in the transverse direction) one or more corresponding staple apertures (3516*a*, 3516*b*, 3516*c*) for deploying staples (162, 250) therethrough.

Figure 66:
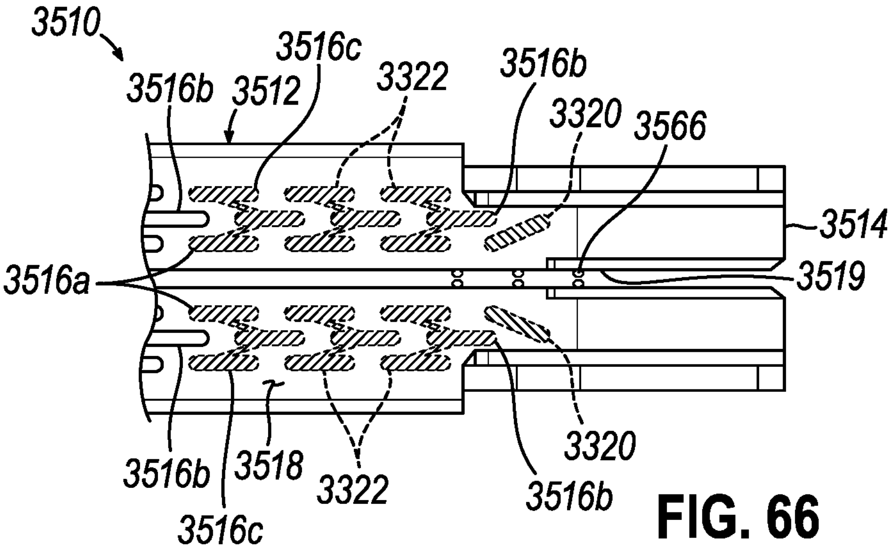
FIG. 66 depicts a partial top view of the staple cartridge of FIG. 64, schematically showing a first arrangement of staple driver assemblies positioned below corresponding staple apertures.

FIG. 66 shows a pair of single-staple driver assemblies (3320) aligned below corresponding proximal-most laterally inner staple apertures (3516*a*), and further shows a plurality of triple-staple driver assemblies (3322) aligned below corresponding sets of three neighboring staple apertures (3516*a*, 3516*b*, 3516*c*), each set including a distal, laterally inner staple aperture (3516*a*) aligned in the lateral direction with a distal, laterally outer staple aperture (3516*c*) and overlapping in the lateral direction with a proximal, laterally intermediate staple aperture (3516*b*).

FIG. 67 shows a pair of triple-staple driver assemblies (3523*a*, 3523*b*) aligned below corresponding sets of three neighboring staple apertures (3516*a*, 3516*b*, 3516*c*), each set including the proximal-most laterally inner, intermediate, and outer staple apertures (3516*a*, 3516*b*, 3516*c*). FIG. 67 also shows a pair of single-staple driver assemblies (3320) aligned below corresponding laterally inner staple apertures (3516*a*) immediately distal of the respective proximal-most laterally inner staple aperture (3516*a*). FIG. 67 further shows a plurality of triple-staple driver assemblies (3322) aligned below corresponding sets of three neighboring staple apertures (3516*a*, 3516*b*, 3516*c*), each set including a distal, laterally inner staple aperture (3516*a*) aligned in the lateral direction with a distal, laterally outer staple aperture (3516*c*) and overlapping in the lateral direction with a proximal, laterally intermediate staple aperture (3516*b*).

Figure 68:
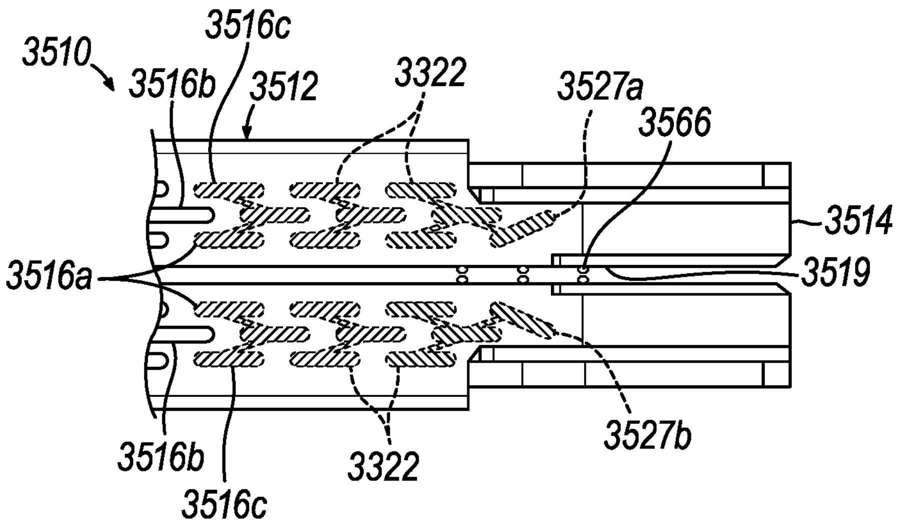
FIG. 68 depicts a partial top view of the staple cartridge of FIG. 64, schematically showing a third arrangement of staple driver assemblies positioned below corresponding staple apertures.

FIG. 68 shows a pair of quadruple-staple driver assemblies (3527*a*, 3527*b*) aligned below corresponding sets of four neighboring staple apertures (3516*a*, 3516*b*, 3516*c*), each set including the respective proximal-most laterally inner, intermediate, and outer staple apertures (3516*a*, 3516*b*, 3516*c*), as well as a laterally inner staple aperture (3516*a*) aligned in the lateral direction with the respective proximal-most laterally outer staple aperture (3516*c*). FIG. 68 further shows a plurality of triple-staple driver assemblies (3322) aligned below corresponding sets of three neighboring staple apertures (3516*a*, 3516*b*, 3516*c*), each set including a distal, laterally inner staple aperture (3516*a*) aligned in the lateral direction with a distal, laterally outer staple aperture (3516*c*) and overlapping in the lateral direction with a proximal, laterally intermediate staple aperture (3516*b*).

Figure 69:
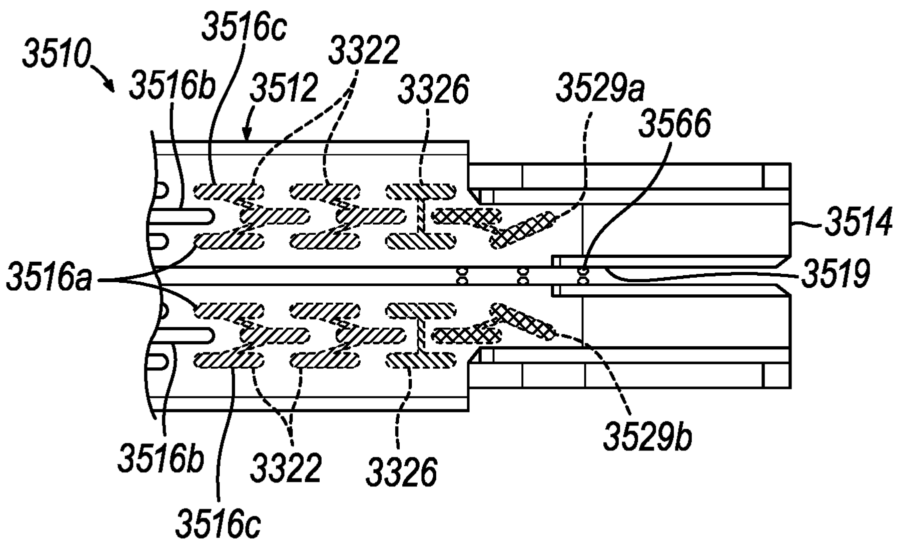
FIG. 69 depicts a partial top view of the staple cartridge of FIG. 64, schematically showing a fourth arrangement of staple driver assemblies positioned below corresponding staple apertures.

FIG. 69 shows a pair of double-staple driver assemblies (3529*a*, 3529*b*) aligned below corresponding sets of two neighboring staple apertures (3516*a*, 3516*b*), each set including the respective proximal-most laterally inner and intermediate staple aperture (3516*a*, 3516*b*). FIG. 69 also shows a pair of double-staple driver assemblies (3326) aligned below corresponding sets of two neighboring staple apertures (3516*a*, 3516*c*), each set including the respective proximal-most laterally outer staple aperture (3516*c*) aligned in the lateral direction with a laterally inner staple aperture (3516*a*). FIG. 69 further shows a plurality of triple-staple driver assemblies (3322) aligned below corresponding sets of three neighboring staple apertures (3516*a*, 3516*b*, 3516*c*), each set including a distal, laterally inner staple aperture (3516*a*) aligned in the lateral direction with a distal, laterally outer staple aperture (3516*c*) and overlapping in the lateral direction with a proximal, laterally intermediate staple aperture (3516*b*).

ii. Exemplary Diamond-Shaped Cartridge Orifice

Figure 70:
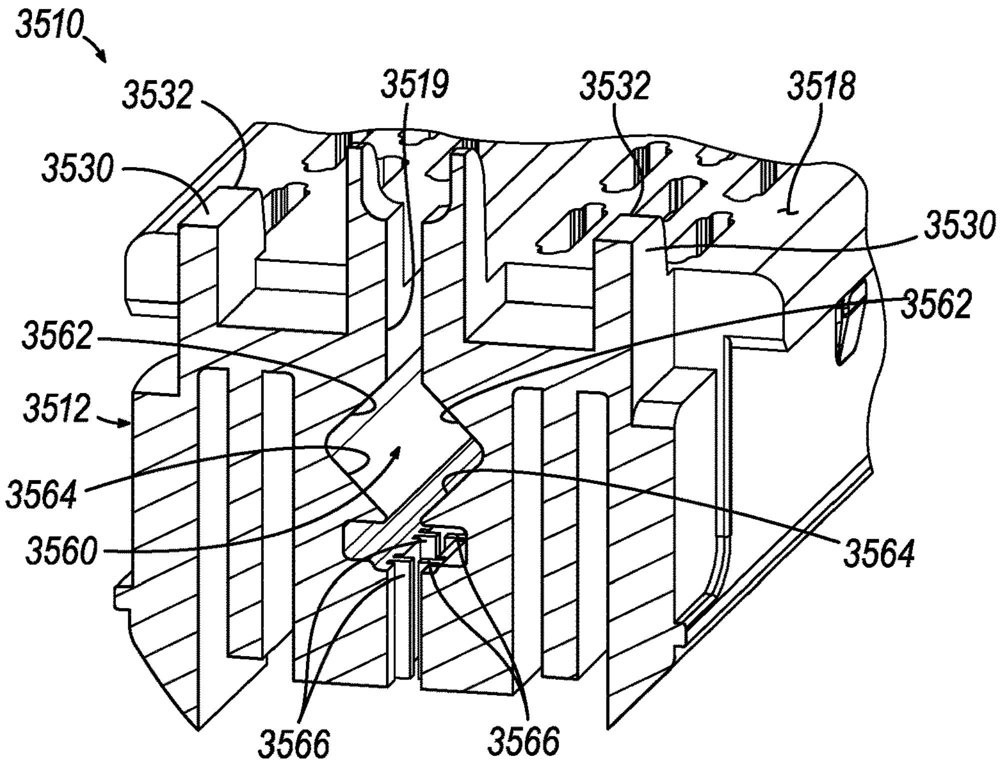
FIG. 70 depicts a cross-sectional perspective view of the staple cartridge of FIG. 64, taken along section line 70-70 in FIG. 64, showing cartridge support features of the staple cartridge extending laterally inwardly from respective sides of a vertical slot of the staple cartridge.
Figure 71:
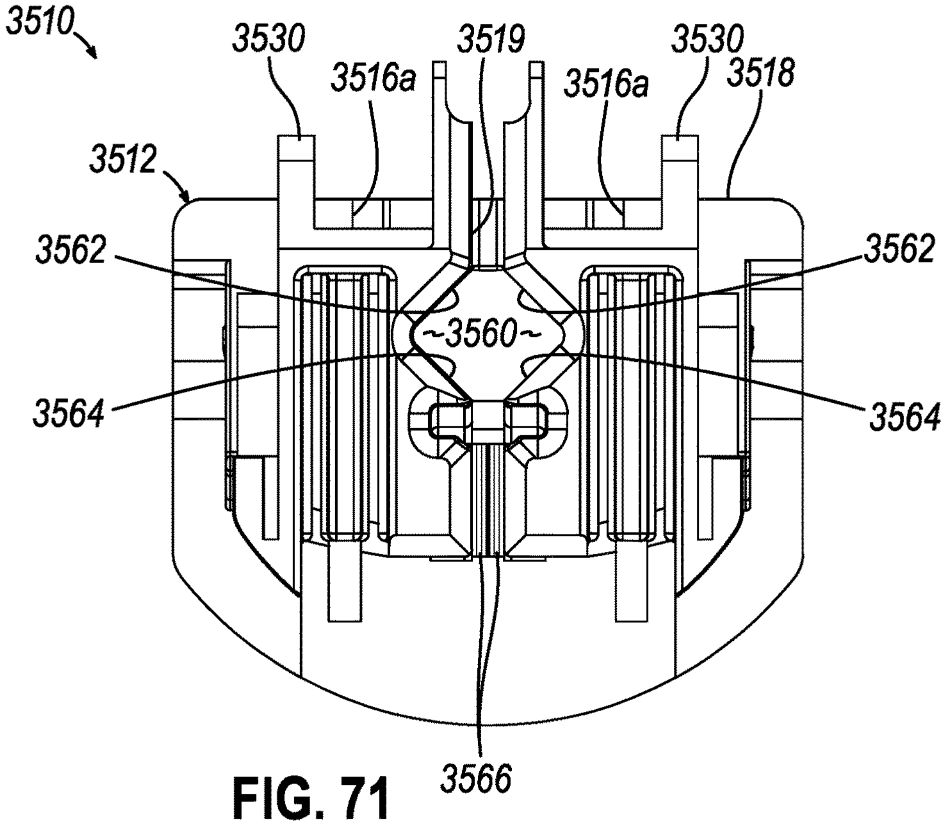
FIG. 71 depicts a rear elevation view of the staple cartridge of FIG. 64.

Referring now to FIGS. 70 and 71, a longitudinal orifice (3560), configured to accommodate a firing member (not shown), such as push rod (168), and/or to accommodate a guide member of a wedge sled (not shown), such as guide member (190), extends laterally outwardly from both sides of vertical slot (3519). In the example shown, orifice (3560) is defined by a laterally-opposed pair of upper flat surfaces (3562) extending laterally outwardly and downwardly from upper portions of respective sides of vertical slot (3519), and by a laterally-opposed pair of lower flat surfaces (3564) extending laterally outwardly and upwardly from lower portions of respective sides of vertical slot (3519) to corresponding upper flat surfaces (3562). In this manner, orifice (3560) may have a generally diamond-shaped cross section, bifurcated by and symmetrical relative to vertical slot (3519). In some versions, flat surfaces (3562, 3564) of orifice (3560) may have a uniform length, and each flat surface (3562, 3564) may be oriented generally perpendicularly relative to each of the adjacent flat surfaces (3562, 3564).

In some versions, the cross-sectional shape of orifice (3560) may be substantially different from that of the firing and/or guide member(s) accommodated by orifice (3560). For example, push rod (168) and guide member (190) described above each have generally round and/or circular cross-sectional shapes substantially different from the diamond cross-sectional shape of orifice (3560). Moreover, such differently-shaped firing and/or guide member(s) may be sized to contact flat surfaces (3562, 3564) of orifice (3560) at predetermined locations therealong. For example, the rounded and/or circular cross-sectional shapes of push rod (168) and/or guide member (190) may be defined by at least one radius substantially equal to or slightly greater than the shortest distances between a centerpoint of orifice (3560) and each of the flat surfaces (3562, 3564). It will be appreciated that such shortest distances may occur at or near a midpoint of each of the flat surfaces (3562, 3564). In this manner, the firing and/or guide member(s), such as push rod (168) and/or guide member (190), may contact each flat surface (3562, 3564) at or near the midpoint thereof while moving longitudinally through staple cartridge (3510) to thereby horizontally stabilize cartridge body (3512). For example, push rod (168) and/or guide member (190) may inhibit laterally inward deflection (e.g., buckling) of cartridge body (3512). In this regard, push rod (168) and/or guide member (190) may urge the corresponding portions of cartridge body (3512) on either side of vertical slot (3519) toward a substantially vertical orientation by counteracting any laterally-inwardly directed forces that might be applied to such portions of cartridge body (3512) during use (e.g., clamping and/or firing).

iii. Exemplary Cartridge Support Ribs

With continuing reference to FIGS. 70 and 71, a plurality of deflectable cartridge support features in the form of laterally-opposed pairs of vertical, flexible ribs (3566) extend laterally inwardly from both sides of vertical slot (3519). In some versions, each rib (3566) may be at least partially defined between generally parallel proximal and distal slots which extend laterally outwardly from the respective side of vertical slot (3519) into cartridge body (3512). Thus, each rib (3566) may be integrally formed with an adjoining portion of cartridge body (3512) and cantilevered relative thereto. In the example shown, ribs (3566) are arranged in a proximal, lower portion of cartridge body (3512), with each rib (3566) positioned below orifice (3560) and with the distal-most ribs (3566) positioned only slightly distally of tissue stops (3530).

In the present version, each rib (3566) is configured to flex (e.g., bend, swing, and/or fold) in the longitudinal direction (e.g., distally), and is resiliently biased in the longitudinal direction (e.g., proximally) to its unflexed state, as shown in FIGS. 70 and 71. The integrally formed, cantilevered configuration of each rib (3566) relative to the adjoining portion of cartridge body (3512) may assist in maintaining each rib (3566) in its unflexed state in the absence of longitudinally-directed external forces acting upon rib (3566).

In the example shown, each rib (3566) on each side of vertical slot (3519) is aligned with an opposing rib (3566) on the opposite side of vertical slot (3519) in the lateral direction, such that the laterally inner ends of each laterally-opposed pair of ribs (3566) confront and are configured to contact each other to thereby horizontally stabilize cartridge body (3512). For example, ribs (3566) may inhibit laterally inward deflection (e.g., buckling) of cartridge body (3512). In this regard, ribs (3566) on each side of vertical slot (3519) may each urge the portion of cartridge body (3512) on the opposite side of vertical slot (3519) toward a substantially vertical orientation by counteracting any laterally-inwardly directed forces that might be applied to such portions of cartridge body (3512) during use (e.g., clamping and/or firing). Due to the flexibility of ribs (3566) in the longitudinal direction, a portion of a driving assembly (not shown), such as pusher member (166) or vertical rib member (192) of wedge sled (170), may sequentially engage each pair of ribs (3566) and urge the respective ribs (3566) distally to their flexed states to thereby permit advancement of the driving assembly while moving longitudinally through staple cartridge (3510). Due to the biasing of ribs (3566) toward their unflexed states, once such a portion of the driving assembly has moved sufficiently distally to disengage a pair of ribs (3566), the respective ribs (3566) may return to their unflexed states to allow their laterally inner ends to resume confronting and/or contacting each other. In some versions, the laterally inner ends of ribs (3566) may be tapered laterally outwardly in the proximal direction to define one or more cam surfaces (not shown) for assisting in the urging of ribs (3566) distally by the driving assembly.

While six ribs (3566) are shown in three laterally-opposed pairs, it will be appreciated that any suitable number of ribs (3566) may be provided in any suitable arrangement. Moreover, deflectable cartridge support features may be provided in any other suitable configurations, as described in greater detail below.

D. Fourth Alternative Staple Cartridge with Truncated Circular Orifice

Figure 72:
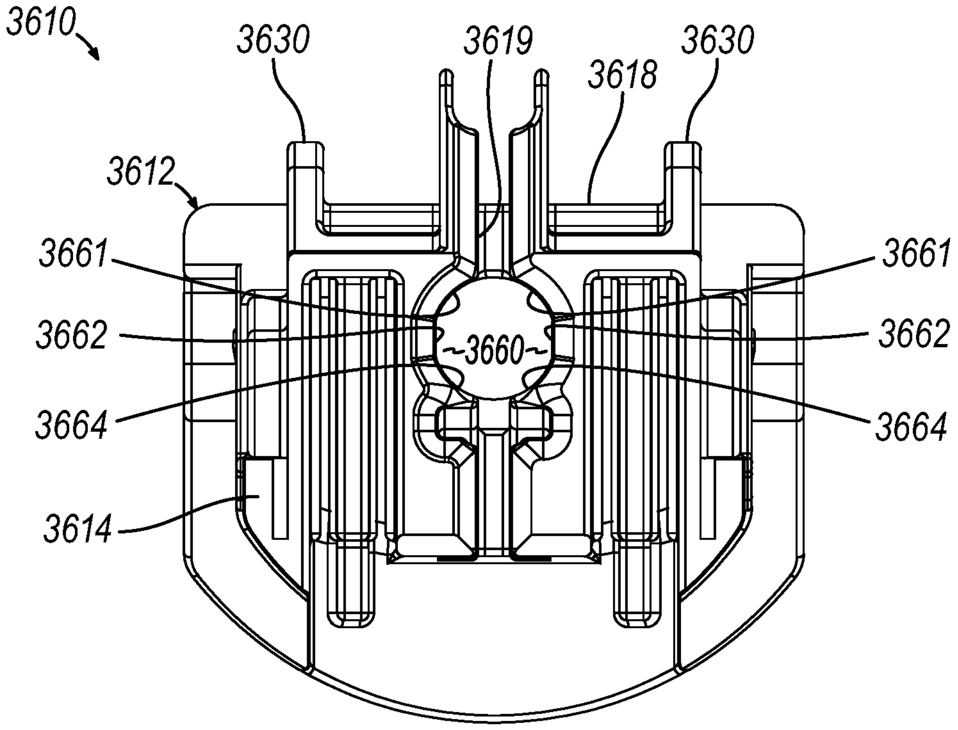
FIG. 72 depicts a rear elevation view of another exemplary staple cartridge having a truncated circle-shaped orifice for accommodating the push rod shown in FIG. 8 and/or the guide member shown in FIG. 9.

In some instances, it may be desirable to provide a staple cartridge configured for allowing the firing and/or guide member(s) to horizontally stabilize the cartridge body in a manner different from that described above in connection with FIGS. 70 and 71. FIG. 72 shows an exemplary staple cartridge (3610) for use with either end effector (116, 210) described above that provides such functionalities. Staple cartridge (3610) is similar to staple cartridge (3510) described above except as otherwise described below. In this regard, staple cartridge (3610) includes a staple cartridge body (3612) having a proximal end (3614) and an upper deck (3618). A vertical slot (3619) extends through part of staple cartridge (3610), and a laterally-opposed pair of tissue stops (3630) protrude upwardly from a proximal portion of upper deck (3518).

In the example shown, a longitudinal orifice (3660), configured to accommodate a firing member (not shown), such as push rod (168), and/or to accommodate a guide member of a wedge sled (not shown), such as guide member (190), extends laterally outwardly from both sides of vertical slot (3619). Orifice (3660) is defined by a laterally-opposed pair of upper arc-shaped surfaces (3661) extending laterally outwardly and downwardly from upper portions of respective sides of vertical slot (3619), a laterally-opposed pair of intermediate flat surfaces (3662) extending downwardly from corresponding upper arc-shaped surfaces (3661), and a laterally-opposed pair of lower arc-shaped surfaces (3664) extending laterally outwardly and upwardly from lower portions of respective sides of vertical slot (3619) to corresponding intermediate flat surfaces (3662). In this manner, orifice (3660) may have a generally truncated-circular cross section, bifurcated by and symmetrical relative to vertical slot (3619). In some versions, arc-shaped surfaces (3661, 3664) of orifice (3660) may be defined by a uniform radius, and each flat surface (3562, 3564) may be oriented generally parallel relative to vertical slot (3619).

In some versions, the cross-sectional shape of orifice (3660) may be substantially different from that of the firing and/or guide member(s) accommodated by orifice (3660). For example, push rod (168) and guide member (190) described above each have generally round and/or circular cross-sectional shapes substantially different from the truncated circular cross-sectional shape of orifice (3660). Moreover, such differently-shaped firing and/or guide member(s) may be sized to contact flat surfaces (3662) of orifice (3660) at predetermined locations therealong. For example, the rounded and/or circular cross-sectional shapes of push rod (168) and/or guide member (190) may be defined by at least one radius substantially equal to or slightly greater than the shortest distances between a centerpoint of orifice (3660) and each of the flat surfaces (3662). It will be appreciated that such shortest distances may occur at or near a midpoint of each of the flat surfaces (3662). In this manner, the firing and/or guide member(s), such as push rod (168) and/or guide member (190), may contact each flat surface (3662) at or near the midpoint thereof while moving longitudinally through staple cartridge (3610) to thereby horizontally stabilize cartridge body (3612). For example, push rod (168) and/or guide member (190) may inhibit laterally inward deflection (e.g., buckling) of cartridge body (3612). In this regard, push rod (168) and/or guide member (190) may urge the corresponding portions of cartridge body (3612) on either side of vertical slot (3619) toward a substantially vertical orientation by counteracting any laterally-inwardly directed forces that might be applied to such portions of cartridge body (3612) during use (e.g., clamping and/or firing).

E. Fifth Alternative Staple Cartridge with Cartridge Support Ribbon

Figure 73:
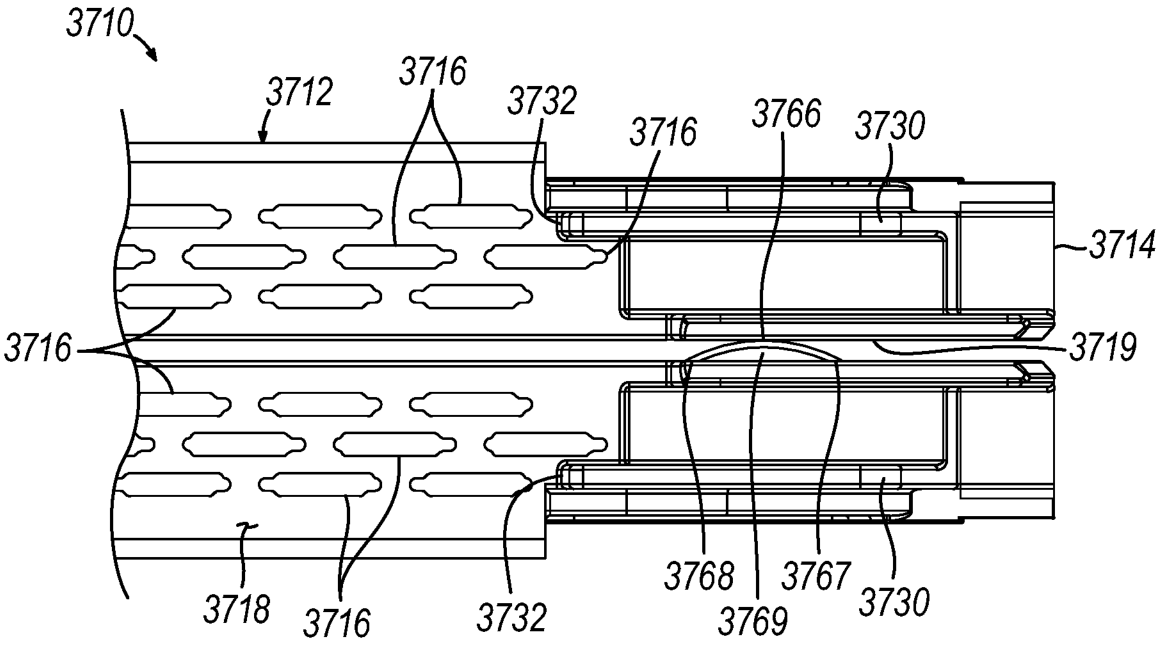
FIG. 73 depicts a partial top view of another exemplary staple cartridge having a cartridge support feature extending laterally inwardly from one side of a vertical slot of the staple cartridge toward an opposing side of the vertical slot.

In some instances, it may be desirable to provide a staple cartridge with a cartridge support feature different from those described above in connection with FIGS. 70 and 71. FIG. 73 shows an exemplary staple cartridge (3710) for use with either end effector (116, 210) described above that provides such functionalities. Staple cartridge (3710) is similar to staple cartridge (3510) described above except as otherwise described below. In this regard, staple cartridge (3710) includes a staple cartridge body (3712) having a proximal end (3714) and an array of staple apertures (3716) extending through an upper deck (3718). A vertical slot (3719) extends through part of staple cartridge (3710), and a laterally-opposed pair of tissue stops (3730) protrude upwardly from a proximal portion of upper deck (3718) and terminate distally at respective distal ends (3732).

In the example shown, a deflectable cartridge support feature in the form of a longitudinal, flexible ribbon (3766) extends laterally inwardly from one side of vertical slot (3719). Ribbon (3766) includes a proximal end (3767) and a distal end (3768), and is bowed laterally inwardly between proximal and distal ends (3767, 3768) to define a relief space (3769). In some versions, ribbon (3766) may be arranged in a proximal, upper portion of cartridge body (3712), such as with ribbon (3766) positioned above upper deck (3718) and/or proximally of distal ends (3732 of tissue stops (3730).

In the present version, ribbon (3766) is configured to flex (e.g., bend and/or fold) in the lateral direction (e.g., laterally outwardly) into relief space (3769), and is resiliently biased in the lateral direction (e.g., laterally inwardly) to its unflexed state away from relief space (3769), as shown in FIG. 73. For example, ribbon (3766) may be constructed as a leaf spring. The bowed configuration of ribbon (3766) relative to the adjoining portion of cartridge body (3712) may assist in maintaining ribbon (3766) in its unflexed state in the absence of longitudinally-directed external forces acting upon ribbon (3766).

In the example shown, ribbon (3766) bridges across vertical slot (3719), such that a midsection of ribbon (3766) confronts and is configured to contact the portion of cartridge body (3712) on the opposite side of vertical slot (3719) to thereby horizontally stabilize cartridge body (3712). For example, ribbon (3766) may inhibit laterally inward deflection (e.g., buckling) of cartridge body (3712). In this regard, ribbon (3766) may each urge the portions of cartridge body (3712) on both sides of vertical slot (3719) toward a substantially vertical orientation by counteracting any laterally-inwardly directed forces that might be applied to such portions of cartridge body (3712) during use (e.g., clamping and/or firing). Due to the flexibility of ribbon (3766) in the lateral direction, a portion of a driving assembly (not shown), such as pusher member (166) or vertical rib member (192) of wedge sled (170), may engage ribbon (3766) and urge ribbon (3766) laterally outwardly to its flexed state to thereby permit advancement of the driving assembly while moving longitudinally through staple cartridge (3710). Due to the biasing of ribbon (3766) toward its unflexed state, once such a portion of the driving assembly has moved sufficiently distally to disengage ribbon (3766), ribbon (3766) may return to its unflexed state to bridge across vertical slot (3719) and allow the midsection of ribbon (3766) to resume confronting and/or contacting the portion of cartridge body (3712) on the opposite side of vertical slot (3719). In some versions, the curvature of the outer, proximal surface of ribbon (3766) resulting from its bowed configuration may assist in the urging of ribbon (3766) laterally outwardly by the driving assembly.

F. Sixth Alternative Staple Cartridge with Driver Retention Detents

Figure 74:
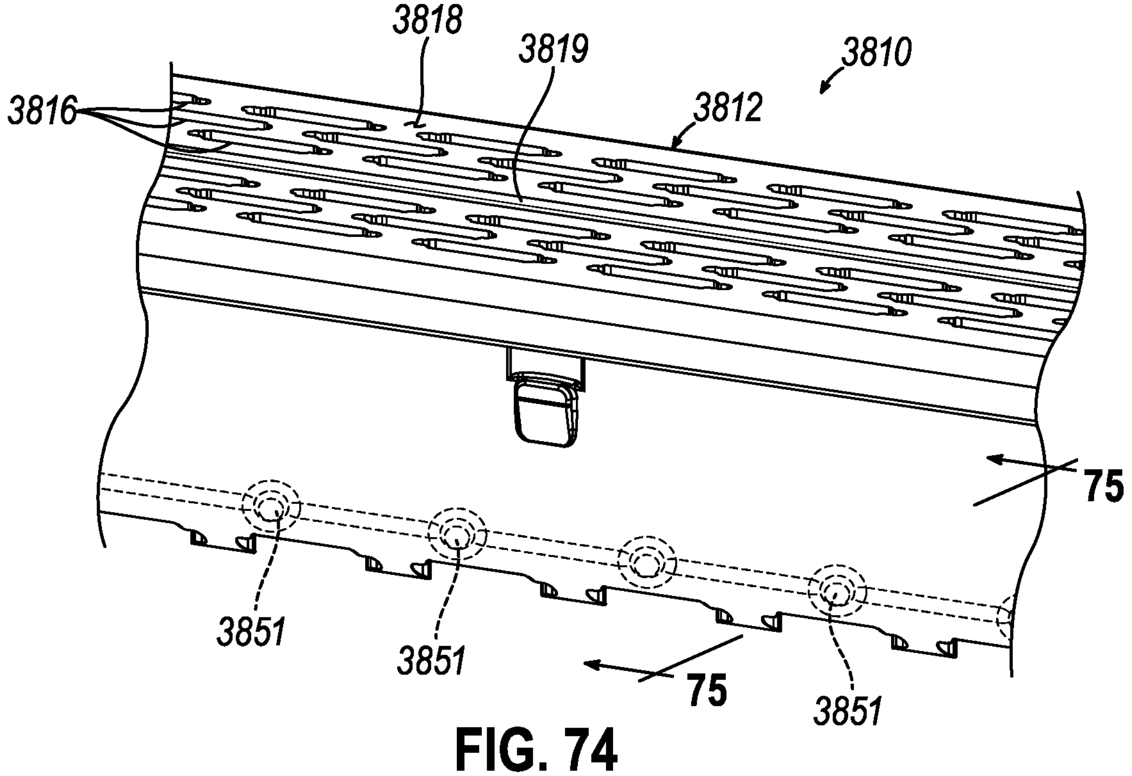
FIG. 74 depicts a partial perspective view of another exemplary staple cartridge having staple driver retention features.
Figure 75:
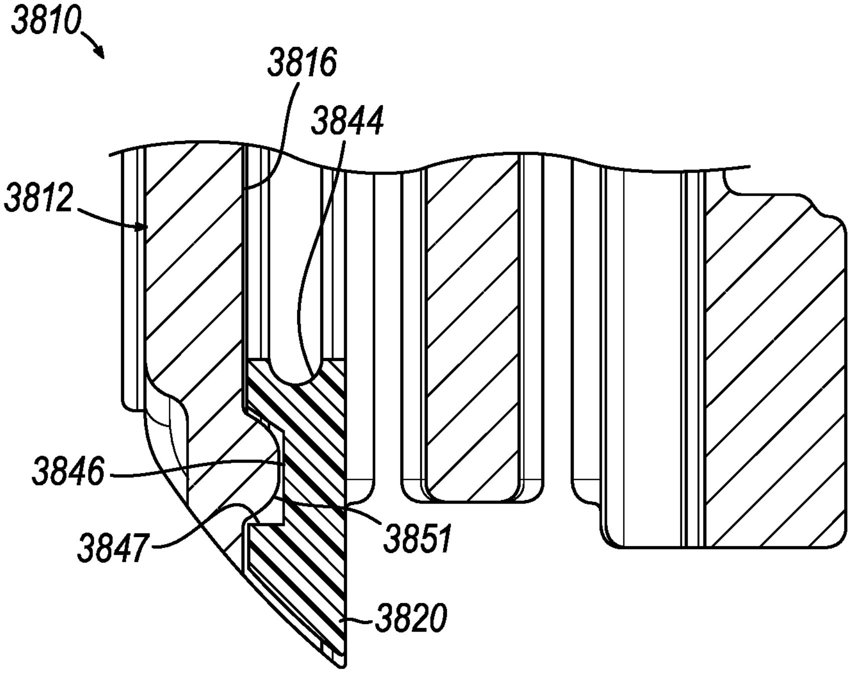
FIG. 75 depicts a cross-sectional view of the staple cartridge of FIG. 74, taken along section line 75-75 in FIG. 74, showing a staple driver retention feature engaging a staple driver of the staple cartridge.

In some instances, it may be desirable to provide a staple cartridge with staple driver retention features for assisting with maintaining staple drivers within the cartridge body prior to firing. FIGS. 74 and 75 show an exemplary staple cartridge (3810) for use with either end effector (116, 210) described above that provides such functionalities. Staple cartridge (3810) is similar to staple cartridge (3310) described above except as otherwise described below. In this regard, staple cartridge (3810) includes a staple cartridge body (3812) having an array of staple apertures (3816) extending through an upper deck (3818). A vertical slot (3819) extends through part of staple cartridge (3810). Staple cartridge body (3812) is also configured to house a plurality of staple drivers (3820) (FIG. 75), and to house a plurality of staples (not shown), such as staples (162, 250).

As shown in FIG. 75, each staple driver (3820) includes at least one longitudinal groove (3844) configured to cradle a crown (not shown) of a corresponding one of staples (162, 250), and presents an inclined cam surface (not shown)

configured to be cammingly contacted by a respective ramp portion (182) (FIG. 9) of wedge sled (170). In the present version, each staple driver (3820) further includes a driver retention recess (3846) extending laterally inwardly from a laterally outer surface of the staple driver (3820) to define a lower ledge (3847).

As best shown in FIG. 75, staple cartridge body (3812) also includes a plurality of driver retention detents (3851) (one shown) protruding laterally inwardly from a laterally inner side of staple cartridge body (3812) and aligned in the lateral direction with respective driver retention recesses (3846). In this manner, each driver retention detent (3851) may be at least partially received within the respective driver retention recess (3846) such that each driver retention detent (3851) may be configured to abut the lower ledge (3847) of the respective driver retention recess (3846) for inhibiting upward movement of each staple driver (3820) relative to staple cartridge body (3812). In some versions, driver retention detents (3851) may each be deflectable in the lateral direction (e.g., laterally outwardly) upon application of a threshold force thereto for disengaging the respective driver retention recess (3846). For example, driver retention detents (3851) may be deformable and biased toward their respective illustrated undeformed states, such that driver retention detents (3851) may each be capable of being deformed laterally outwardly from their respective undeformed states to their respective deformed states (not shown). In such cases, driver retention detents (3851) may be referred to as "crush bumps."

In any event, the threshold force for deflecting driver retention detents (3851) for disengaging the respective driver retention recess (3846) may be selected to be greater than any incidental forces that might be applied to a driver retention detent (3851) by the lower ledge (3847) of the respective driver retention recess (3846) during transit, loading, and/or general handling of staple cartridge (3810), and to be less than or equal to the force applied to each driver retention detent (3851) by the lower ledge (3847) of the respective driver retention recess (3846) when wedge sled (170) is driven distally into upward camming contact with staple drivers (3820) during firing. Thus, the interaction between lower ledges (3847) of driver retention recesses (3846) and driver retention detents (3851) may inhibit inadvertent dislodgement of staple drivers (3820) without interfering with deployment of staples (162, 250) during firing. In some versions, driver retention detents (3851) may be formed via heat staking. In addition or alternatively, lower ledges (3847) may be tapered laterally outwardly in the downward direction to define one or more cam surfaces (not shown) for assisting in the deflection of driver retention detents (3851) laterally outwardly during firing.

G. Seventh Alternative Staple Cartridge with Driver Retention Tabs

Figure 76A:
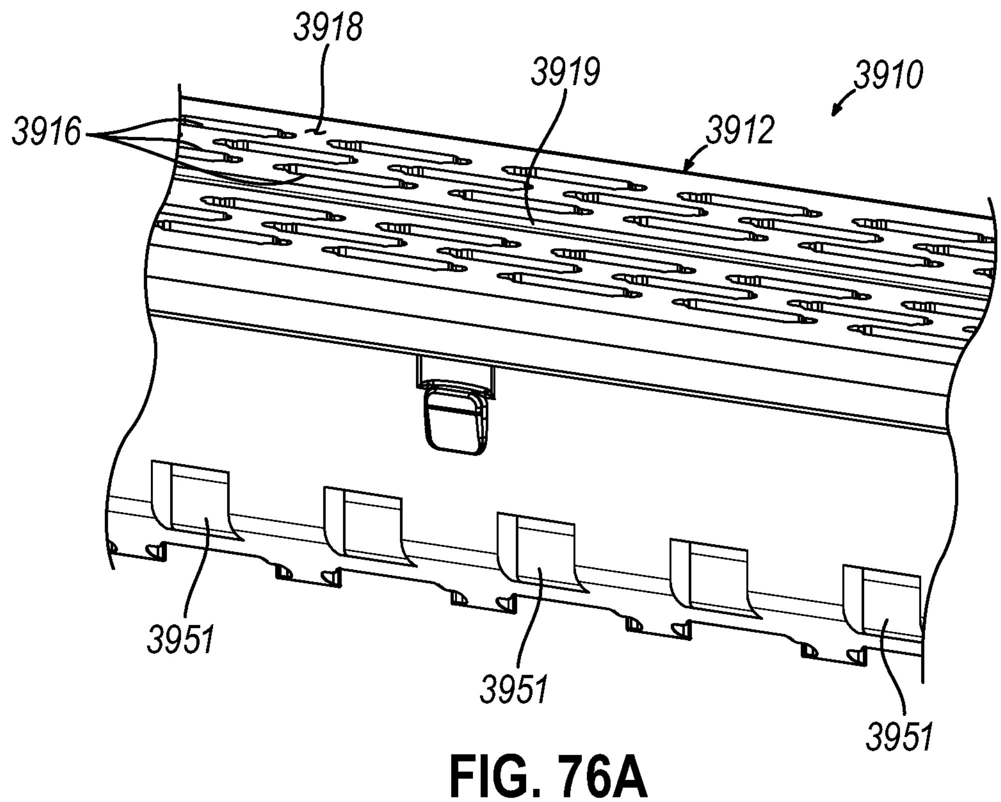
FIG. 76A depicts a partial perspective view of another exemplary staple cartridge having staple driver retention features, showing the staple driver retention features in respective undeformed states.
Figure 76B:
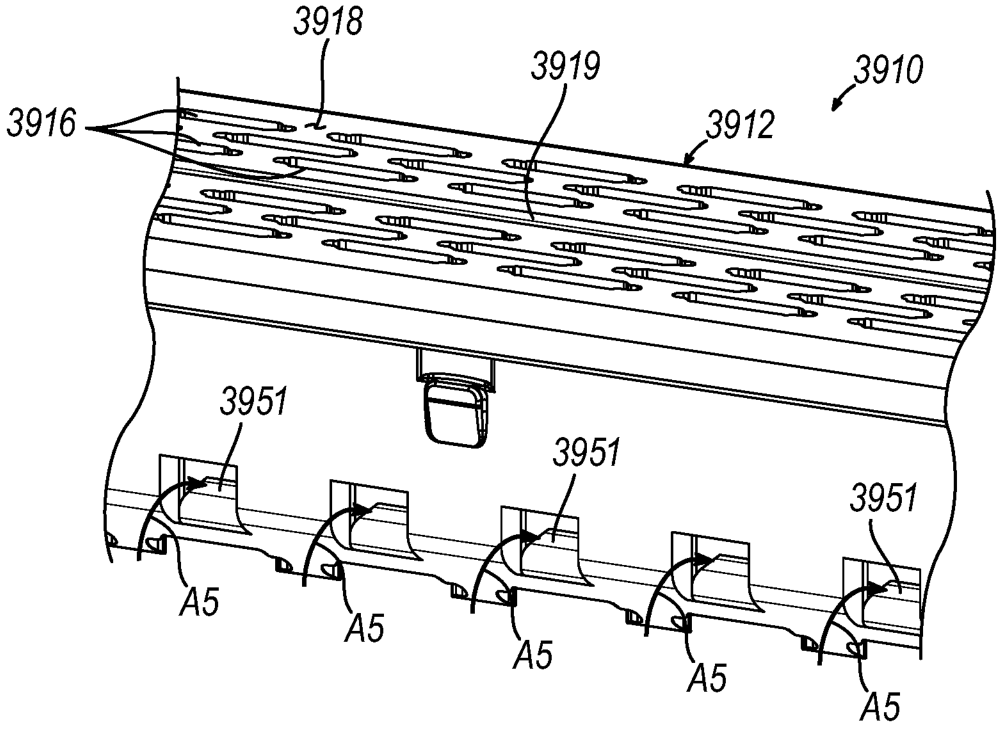
FIG. 76B depicts a partial perspective view of the staple cartridge of FIG. 76A, showing the staple driver retention features in respective deformed states for engaging respective staple drivers.

In some instances, it may be desirable to provide a staple cartridge with staple driver retention features different from those described above in connection with FIGS. 74 and 75. FIGS. 76A and 76B show an exemplary staple cartridge (3910) for use with either end effector (116, 210) described above that provides such functionalities. Staple cartridge (3910) is similar to staple cartridge (3810) described above except as otherwise described below. In this regard, staple cartridge (3910) includes a staple cartridge body (3912) having an array of staple apertures (3916) extending through an upper deck (3918). A vertical slot (3919) extends through part of staple cartridge (3910). Staple cartridge body (3912) is also configured to house a plurality of staple drivers (not shown), such as staple drivers (3820), and to house a plurality of staples (not shown), such as staples (162, 250).

As shown, staple cartridge body (3912) also includes a plurality of driver retention tabs (3951) bending laterally inwardly from a laterally outer side of staple cartridge body (3912) and which may be aligned in the lateral direction with respective driver retention recesses (3846). In this manner, each driver retention tab (3951) may be at least partially received within the respective driver retention recess (3846) such that each driver retention tab (3951) may be configured to abut the lower ledge (3847) of the respective driver retention recess (3846) for inhibiting upward movement of each staple driver (3820) relative to staple cartridge body (3912). In some versions, driver retention tabs (3951) may each be deflectable in the lateral direction (e.g., laterally outwardly) upon application of a threshold force thereto. For example, driver retention detents (3851) may be initially bent from respective undeformed states (FIG. 76A) to respective deformed states (FIG. 76B) for receipt within the respective driver retention recesses (3846), as indicated by arrows (A5) in FIG. 76B, such that driver retention tabs (3951) may each be capable of being subsequently deflected from their respective deformed states to their respective undeformed states upon application of a threshold force thereto for disengaging the respective driver retention recess (3846).

In any event, the threshold force for deflecting driver retention tabs (3951) for disengaging the respective driver retention recess (3846) may be selected to be greater than any incidental forces that might be applied to a driver retention tab (3951) by the lower ledge (3847) of the respective driver retention recess (3846) during transit, loading, and/or general handling of staple cartridge (3910), and to be less than or equal to the force applied to each driver retention tab (3951) by the lower ledge (3847) of the respective driver retention recess (3846) when wedge sled (170) is driven distally into upward camming contact with staple drivers (3820) during firing. Thus, the interaction between lower ledges (3847) of driver retention recesses (3846) and driver retention tabs (3951) may inhibit inadvertent dislodgement of staple drivers (3820) without interfering with deployment of staples (162, 250) during firing. In some versions, driver retention tabs (3951) may be formed via molding together with the remainder of staple cartridge body (3912).

H. Alternative Cartridge Tray with Support Tabs

Figure 77:
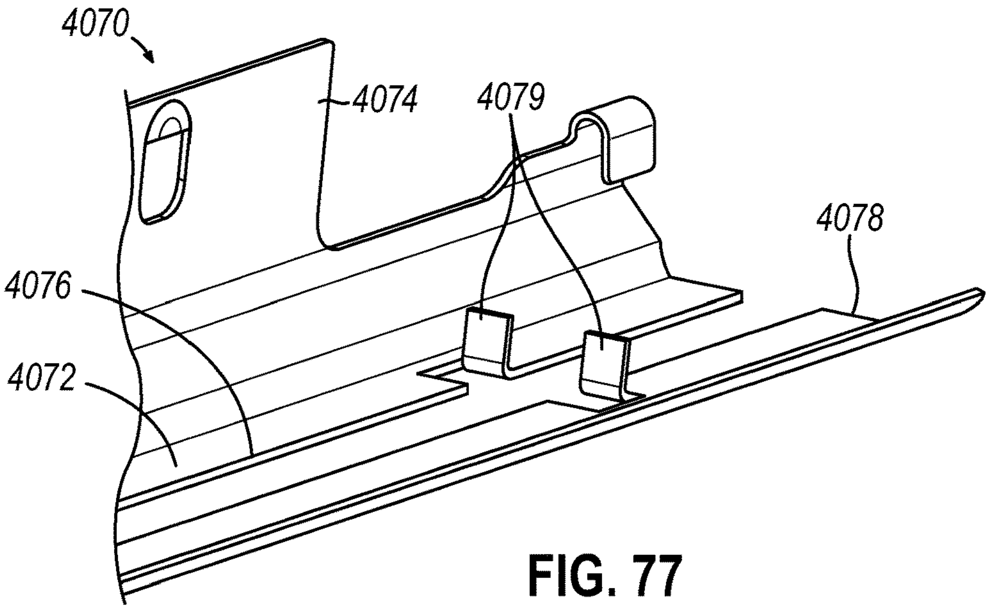
FIG. 77 depicts a partial perspective view of an exemplary cartridge tray having cartridge support features.

In some instances, it may be desirable to provide a cartridge tray that is configured to provide rigidity to any one or more of staple cartridges (154, 218, 3310, 3410, 3510, 3610, 3710, 3810, 3910) by supporting and/or stabilizing the sides of the respective staple cartridge body (156, 220, 3312, 3412, 3512, 3612, 3712, 3812, 3912) above the cartridge tray. FIGS. 77-78B show an exemplary cartridge tray (4070) for use with either end effector (116, 210) described above that provides such functionalities. Cartridge tray (4070) is similar to cartridge tray (224) described above except as otherwise described below, and is configured to snap-fit, clip, or otherwise couple to a lower portion of any one or more of cartridge bodies (156, 220, 3312, 3412, 3512, 3612, 3712, 3812, 3912). In some examples, cartridge tray (4070) comprises a metallic material to provide added structural rigidity to the respective staple cartridge (154, 218, 3310, 3410, 3510, 3610, 3710, 3810, 3910).

Cartridge tray (4070) of the present example includes a floor (4072) and a pair of sidewalls (4074) extending from a proximal end (4078) of cartridge tray (4070). A longitudinal slot (4076) is defined by floor (4072) extending from proximal end (4078) of cartridge tray (4070). Longitudinal slot (4076) is generally configured to permit a portion of an actuation assembly, also referred to as driving assembly (164) to pass through cartridge tray (4070) for engagement of second flange (185) with longitudinal slot (187) of lower jaw (152).

Cartridge tray (4070) further includes a pair of cartridge support tabs (4079) extending upwardly from floor (4072). The particular extension of each support tab (4079) in the present example is generally about perpendicular to a longitudinal axis defined by floor (4072), although other angles of extension relative to floor (4072) may be used in other examples. Each support tab (4079) is positioned proximate proximal end (4078) of cartridge tray (4070). It will be appreciated that support tabs (4079) may be positioned at any other suitable location(s) along the length of cartridge tray (4070).

The construction of each support tab (4079) of the present example is integral with floor (4072) and positioned on opposite sides of longitudinal slot (4076). Specifically, each support tab (4079) is defined by a cutout portion of floor (4072) that is bent upwardly or perpendicularly relative to the extension of floor (4072). Thus, each support tab (4079) in the present example is generally of the same material of floor (4072). The particular material used may be metal or other similarly rigid materials. Although an integral construction is used in the present example for support tab (4079), it should be understood that in other examples each support tab (4079) may be an independent component from floor (4072) and coupled thereto.

Each support tab (4079) in the present example is configured to have at least some rigidity. As will be described in greater detail below, such rigidity may permit each support tab (4079) to vertically support a cartridge body (156, 220, 3312, 3412, 3512, 3612, 3712, 3812, 3912) coupled to cartridge tray (4070). Additionally, such rigidity may also be configured in some examples to provide additional structural rigidity to cartridge tray (4070), particularly at the interface between floor (4072) and each support tab (4079). In some examples, such rigidity may permit each support tab (4079) to hold wedge sled (170) in a predetermined position. Examples of suitable cartridge trays (4070) having retention characteristics are described in Section XI of the pending application entitled "Exemplary Alternative Staple Cartridges with Sled Restriction Features"

Each support tab (4079) in the present example is also configured to have at least some flexibility. As will also be described in greater detail below, such flexibility may permit each support tab (4079) to move in response to movement of wedge sled (170) driven by pusher member (166). Each support tab (4079) may also have a resilient characteristic such that each support tab (4079) may be resiliently biased toward the upwardly extended position shown in FIGS. 77 and 78A.

Figure 78A:
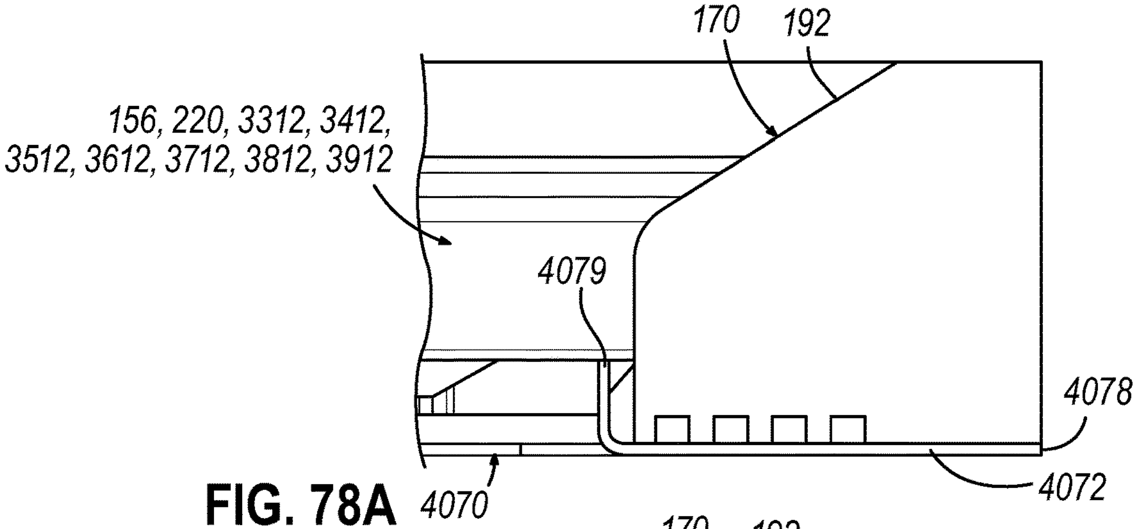
FIG. 78A depicts a side elevation view of the cartridge tray of FIG. 77, showing the wedge sled of FIG. 9 in a proximal position relative to the cartridge support features, and further showing the cartridge support features in vertical orientations.
Figure 78B:
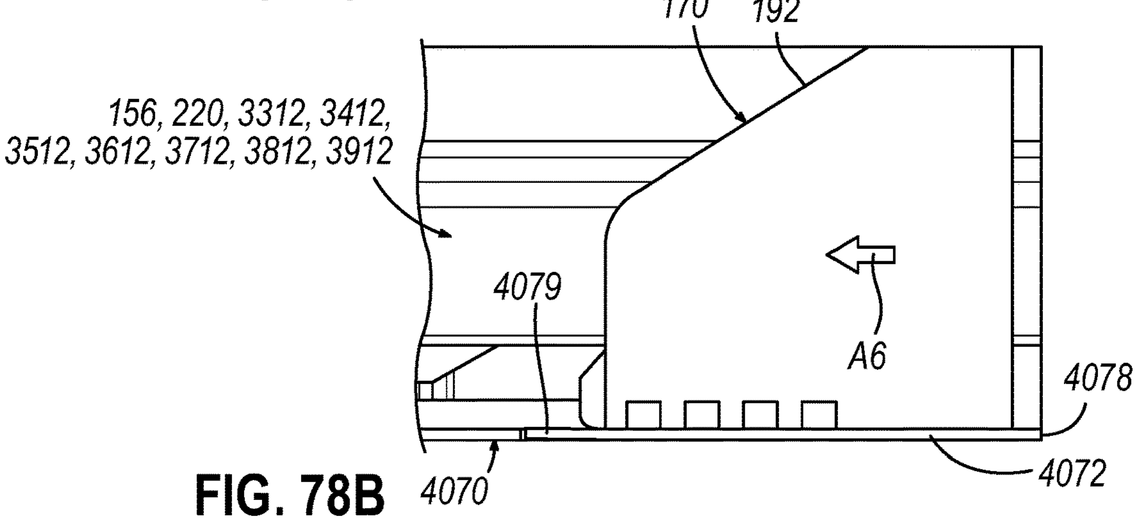
FIG. 78B depicts a side elevation view of the cartridge tray of FIG. 77, showing the cartridge support features flattened toward horizontal orientations by the wedge sled of FIG. 9 during distal translation of the wedge sled.

FIGS. 78A and 78B show an exemplary use of support tabs (4079) in connection with wedge sled (170). As can be seen, wedge sled (170) begins proximate proximal end (4078) of cartridge tray (4070). This position of wedge sled (170) may also correspond to wedge sled (170) being proximate the proximal end of the respective staple cartridge (154, 218, 3310, 3410, 3510, 3610, 3710, 3810, 3910). In this position, the upper ends of support tabs (4079) are configured to contact the portions of the respective cartridge body (156, 220, 3312, 3412, 3512, 3612, 3712, 3812, 3912) on the corresponding sides of longitudinal slot (4076) and thereby provide vertical support to cartridge body (156, 220, 3312, 3412, 3512, 3612, 3712, 3812, 3912).

As described above, wedge sled (170) may be driven distally within cartridge body (156, 220, 3312, 3412, 3512, 3612, 3712, 3812, 3912) to drive staples using wedge sled (170) and sever tissue using cutting edge (194) of knife member (172), as indicated by arrow (A6) in FIG. 78B. As seen in FIG. 78B, once wedge sled (170) is driven by pusher member (166), the force supplied by pusher member (166) may be sufficient to overcome the rigidity of each support tab (4079). This causes each support tab (4079) to move and/or pivot away from wedge sled (170) from the upward orientation described above to a horizontal position about parallel to the extension of floor (4072).

Once each support tab (4079) is pushed to the horizontal position, wedge sled (170) may be driven distally by pusher member (166) to drive staples and sever tissue. In the present example, each support tab (4079) is generally configured to resiliently bend in response to wedge sled (170) being driven by pusher member (166). Thus, each support tab (4079) may return to the upwardly extended position after wedge sled (170) has been driven distally past each support tab (4079) to resume vertically supporting cartridge body (156, 220, 3312, 3412, 3512, 3612, 3712, 3812, 3912).

I. Alternative Wedge Sled with Elongate Nose

Figure 79:
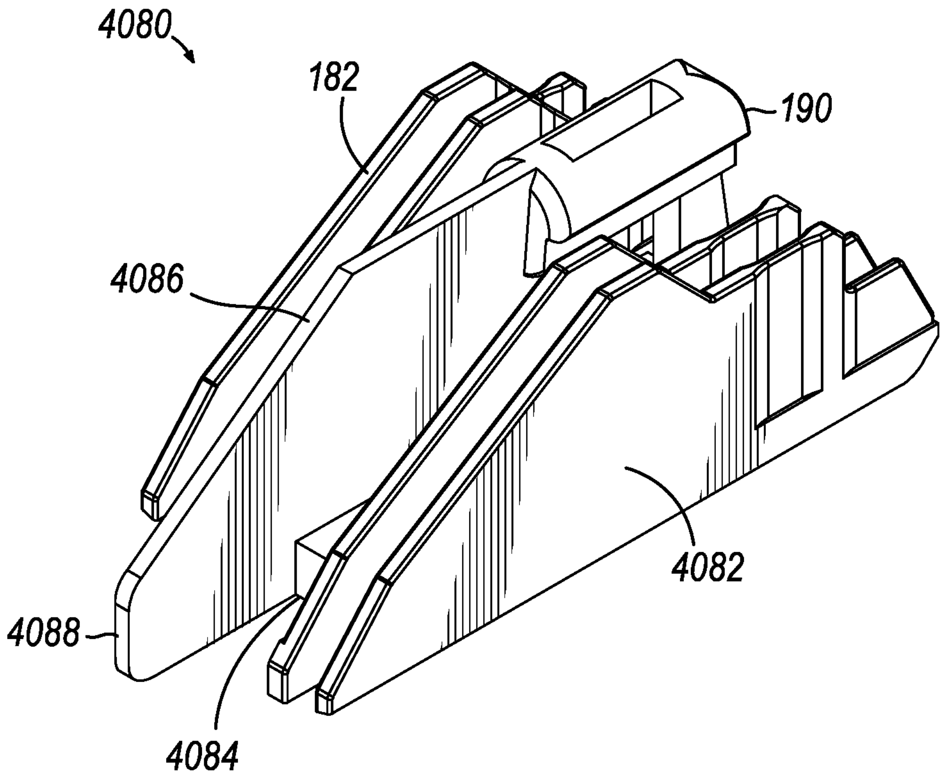
FIG. 79 depicts a perspective of another exemplary wedge sled having an elongate distal nose.

In some instances, it may be desirable to provide a wedge sled that is configured to provide rigidity to any one or more of staple cartridges (154, 218, 3310, 3410, 3510, 3610, 3710, 3810, 3910) by supporting and/or stabilizing the sides of the respective staple cartridge body (156, 220, 3312, 3412, 3512, 3612, 3712, 3812, 3912) adjacent to the wedge sled. FIG. 79 shows an exemplary wedge sled (4080) for use with either end effector (116, 210) described above that provides such functionalities. Wedge sled (4080) is similar to wedge sled (170) described above except as otherwise described below. In this regard, wedge sled (4080) includes ramp portions (182) and guide member (190), and is configured to advance distally along a staple cartridge body (not shown), such as any one or more of staple cartridge bodies (156, 220, 3312, 3412, 3512, 3612, 3712, 3812, 3912) such that ramp portions (182) cammingly contact staple drivers (not shown) housed therein.

In the example shown, ramp portions (182) are presented by respective rails (4082) extending upwardly from a base platform (4084). In the example shown, rails (4082) each terminate distally at respective distal rail ends that are distal relative to a distal end of base platform (4084). One or more rails (4082) may terminate proximally at respective proximal rail ends that are proximal relative to a proximal end of base platform (4084). In some versions, such proximal rail ends may be proximal relative to the proximal end of cartridge body (156, 220, 3312, 3412, 3512, 3612, 3712, 3812, 3912) when wedge sled (4080) is at its initial proximal position. Such proximal elongation of rails (4082) relative to base platform (4084) may assist with maintaining alignment of wedge sled (4080) with staple cartridge body (156, 220, 3312, 3412, 3512, 3612, 3712, 3812, 3912) during firing. In this regard, at least the proximal portions of rails (4082) may be configured to slidably contact or otherwise engage respective internal side surfaces of cartridge body (156, 220, 3312, 3412, 3512, 3612, 3712, 3812, 3912) while wedge sled (4080) moves longitudinally through the respective staple cartridge (154, 218, 3310, 3410, 3510, 3610, 3710, 3810, 3910) to maintain alignment of wedge sled (4080) with cartridge body (156, 220, 3312, 3412, 3512, 3612, 3712, 3812, 3912) in the lateral direction. Such engagement may also horizontally stabilize the cartridge body (156, 220, 3312, 3412, 3512, 3612, 3712, 3812, 3912). For example, at least the proximal portions of rails (4082) may inhibit laterally inward and/or laterally outward deflection (e.g., bending) of cartridge body (156, 220, 3312, 3412, 3512, 3612, 3712, 3812, 3912).

In the example shown, guide member (190) extends from a central nose (4086) of wedge sled (4080). Central nose (4086) extends upwardly from base platform (4084) between the laterally inner rails (4082) and also extends distally from base platform (4084) to a distal tip (4088). Such distal elongation of central nose (4086) relative to base platform (4084) may assist with maintaining alignment of wedge sled (4080) with a staple cartridge body (not shown), such as any one or more of staple cartridge bodies (156, 220, 3312, 3412, 3512, 3612, 3712, 3812, 3912), during firing. In this regard, at least the distal portion of central nose (4086) may be configured to slidably contact or otherwise engage both sides of the vertical slot of cartridge body (156, 220, 3312, 3412, 3512, 3612, 3712, 3812, 3912) while wedge sled (4080) moves longitudinally through the respective staple cartridge (154, 218, 3310, 3410, 3510, 3610, 3710, 3810, 3910) to maintain alignment of wedge sled (4080) with cartridge body (156, 220, 3312, 3412, 3512, 3612, 3712, 3812, 3912) in the lateral direction. Such engagement may also horizontally stabilize the cartridge body (156, 220, 3312, 3412, 3512, 3612, 3712, 3812, 3912). For example, at least the distal portion of central nose (4086) may inhibit laterally inward and/or laterally outward deflection (e.g., bending) of cartridge body (156, 220, 3312, 3412, 3512, 3612, 3712, 3812, 3912). In some versions, the distal elongation of central nose (4086) relative to base platform (4084) may also assist with inhibiting inadvertent rolling of wedge sled (4080) during firing.

VII. Exemplary Firing Lockout Features for Surgical Staplers

In some instances, it may be desirable to provide one or more components of the firing system of an end effector (116, 210), such as one or more of lower jaw (152), staple cartridge (154, 218), wedge sled (170, 238), and/or staple drivers (160, 244), with multiple features to separately and independently monitor a status of the staple cartridge (154, 218). The separate status signals from the independent monitoring features may therefore be corroborated before a firing is initiated.

Some systems may utilize spring biased or positioned biased mechanical lockouts as a positive means to ensure that a spent staple cartridge without staples, or a staple cartridge that is incompatible with the end effector, to inhibit firing (which would result in cut tissue without proper sealing of the tissue). For systems using a single-point-of-failure electronic lockout, the safety system may tend to erroneously disable the safety system. If a single safety monitor sensor is utilized, an incorrect signal from the sensor or a failure of the sensing electronics could result in the lack of signal or wrong signal that might still enable a staple firing under unsafe conditions. Likewise, an overly sensitive monitoring system that errs by initiating safety lockouts of unspent compatible staple cartridges may also provide operational concerns.

Accordingly, as described herein, multiple monitoring features may be configured to assist in minimizing unsatisfactory performance of staple cartridge (154, 218), such as by monitoring for any one or more of: errors in staple cartridge (154, 218) positioning; whether staple cartridge (154, 218) has been fired previously such that staple cartridge (154, 218) is "spent" (i.e., staples (162, 250) have already been deployed from staple cartridge (154, 218)); the compatibility of staple cartridge (154, 218) with instrument (26, 110) or end effector (116, 210); or other details of staple cartridge (154, 218). To that end, various features are described below for providing one or more of these functionalities.

It will be appreciated that in some versions, a first monitoring feature may be provided to detect a first condition of staple cartridge (154, 218) and/or lower jaw (152) that warrants a firing lockout state, and a second monitoring feature may be provided to independently detect a second condition of staple cartridge (154, 218) and/or lower jaw (152) that likewise warrants a firing lockout state. In other versions, a first monitoring feature may be provided to detect a condition of staple cartridge (154, 218) and/or lower jaw (152) that warrants a firing lockout state, and a second monitoring feature may be operatively coupled with and configured to detect whether the first monitoring feature is operating correctly.

A. Exemplary Lower Jaw Monitoring Features Using RFID

Lower cartridge tray (177, 224) can include various lower jaw (152) monitoring features adapted to monitor one or more conditions of the lower jaw (152) such, for example, the existence of staple cartridge (154, 218), the status of the staple cartridge (154, 218) (i.e., whether it has been spent), proper placement of the staple cartridge (154, 218) (i.e., ensuring the staple cartridge is properly seated within the channel), and/or the positioning of the wedge sled (170, 238) within the lower jaw (152).

Figure 80:
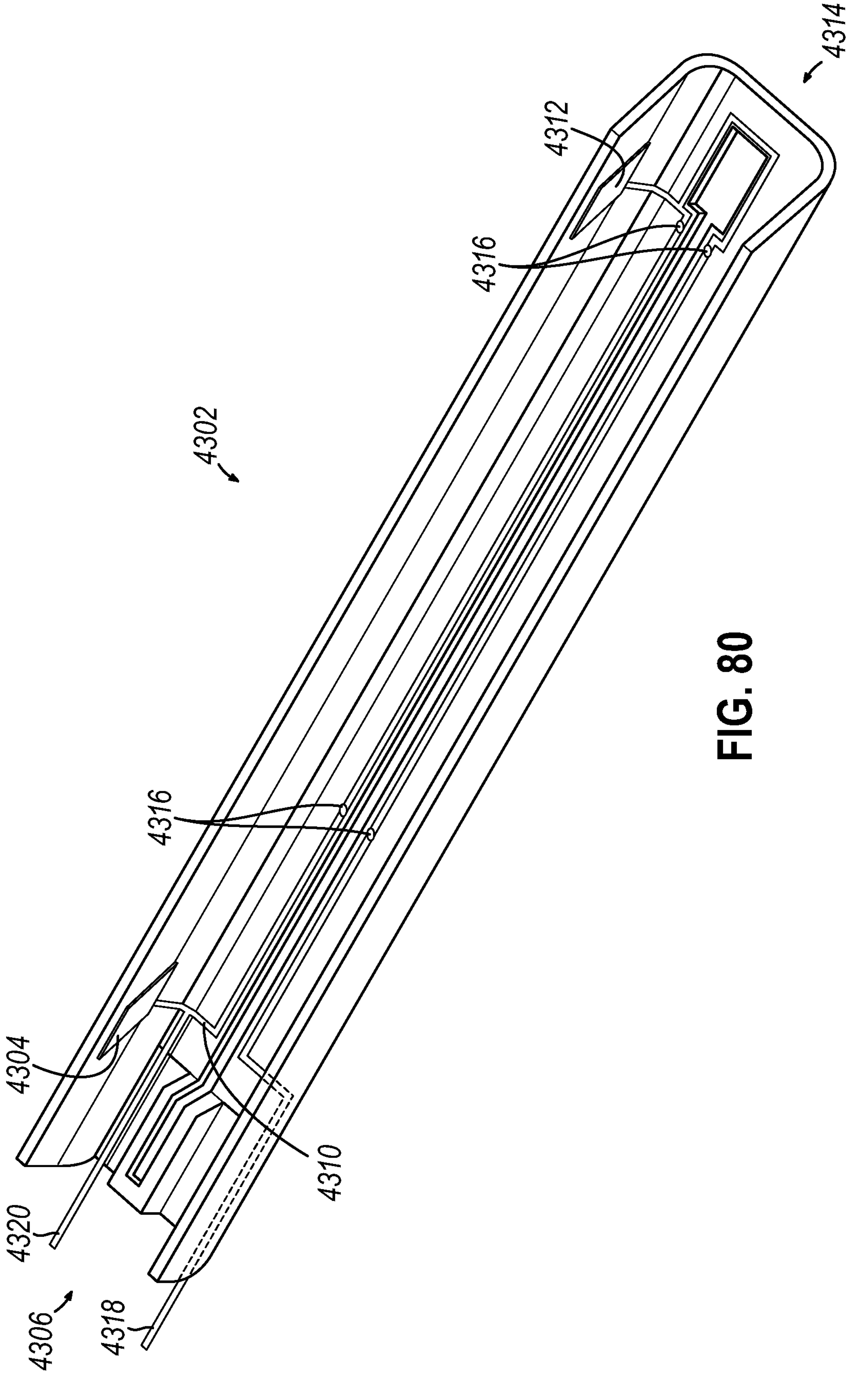
FIG. 80 depicts a perspective view of a first exemplary alternative lower cartridge tray shown removed from a surgical instrument end effector.

FIG. 80 shows an exemplary lower cartridge tray (4302) which forms a part of an end effector (4360) (see FIG. 81), end effector (4360) and lower cartridge tray (4302) each being configured to provide similar functions as end effectors (116, 210) and lower cartridge trays (177, 224) except as described below. Particularly, lower cartridge tray (4302) can include an RFID power coil (4304) at the proximal end (4306) of the lower cartridge tray (4302) that is configured to communicate with an RFID tag (4308) that is positioned on the wedge sled (4350) (see FIG. 82). Wedge sled (4350) of staple cartridge (154, 218) is configured to operate similar to wedge sleds (170, 238) described above. RFID power coil (4304) may be powered by a flex circuit, such as flex circuit (4310), by wiring, or by any other known methods of powering and RFID system. In some versions, lower cartridge tray (4302) can include a second RFID power coil (4312) at the distal end (4314) of lower cartridge tray (4302) that is also configured to communicate with the RFID tag (4308) on wedge sled (4350). To power RFID power coils (4304, 4312), flex circuit (4310) is electrically coupled with and driven by a portion of robotic surgical system (10), such as electronics cart (24) or processor (38).

In some versions, lower cartridge tray (4302) can include one or more electrical contacts (4316) arranged along the length of lower cartridge tray (4302) that are configured to monitor proper placement of staple cartridge (4352) (see FIG. 81) within lower cartridge tray (4302). For example, as staple cartridge (4352) is positioned into lower cartridge tray (4302), the one or more electrical contacts (4316) are configured to interact with portions (4354) of the staple cartridge (4352) disposed on the lower surface (4356) of staple cartridge (4352) to indicate to robotic surgical system (10) or surgical instrument (26, 110) that staple cartridge (4352) is seated properly. In one version, the one or more electrical contacts (4316) are formed as non-conductive gaps in the electrical path provided by flex circuit (4310) which are conductively bridged by corresponding portions (4354) of staple cartridge (4352), such a protrusions, as staple cartridge (4352) is seated into lower cartridge tray (4302).

Accordingly, corresponding portions (4354) of staple cartridge (4352) may be formed with conductive traces for bridging the non-conductive gaps of electrical contacts (4316). Therefore, as staple cartridge (4352) is seated into lower cartridge tray (4302), an electrical path is completed by flex circuit (4310) and electrical contacts (4316) thereby allowing current flow between electrical leads (4318, 4320). As seen by robotic surgical system (10) or surgical instrument (26, 110), electrical current flow through flex circuit (4310) is indicative of the presence of staple cartridge (4352) and also proper seating of staple cartridge (4352).

Figure 81:
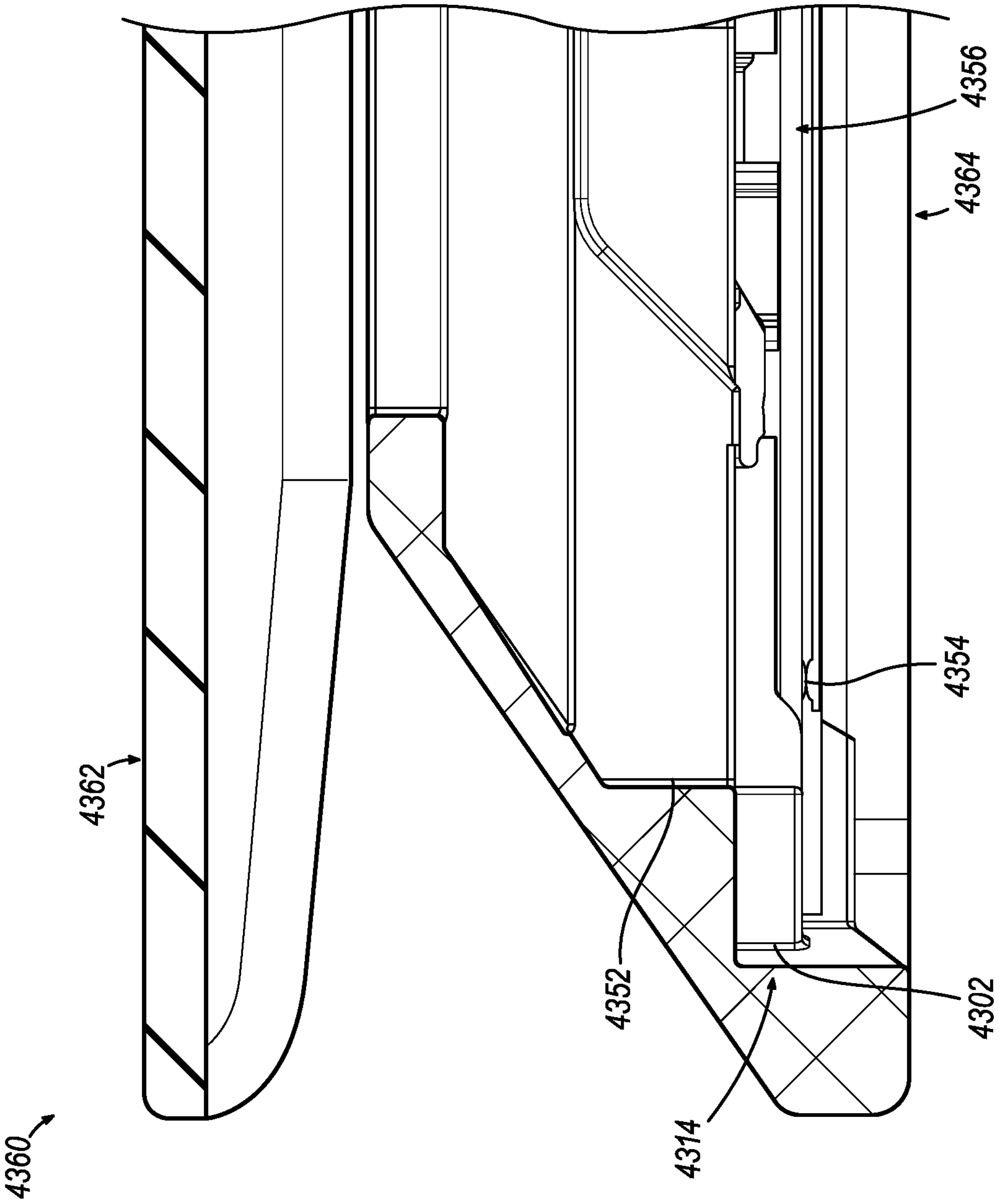
FIG. 81 depicts a cross-sectional view of a distal portion of an exemplary end effector having the lower cartridge tray of FIG. 80 disposed therein, the lower cartridge tray further having a staple cartridge installed therein.

An alternative example is depicted in FIG. 81. As shown in FIG. 81, staple cartridge (4352) is installed on an end effector (4360) having an upper jaw (4362) and a lower jaw (4364), the staple cartridge (4352) installed on the lower jaw (4364). In this version, the one or more electrical contacts (4316) arranged along the length of staple cartridge (4352) are configured with electrical switches operable as push buttons. Optionally, lower surface (4356) of staple cartridge (4352) can include corresponding portions (4354) shaped as protrusions for pressing the push-button electrical contacts (4316) as staple cartridge (4352) is aligned and properly seated on lower cartridge tray (4302). Alternatively, lower surface (4356) of staple cartridge (4352) may be shaped to press contacts as it seats into lower cartridge tray (4302) without the need for any protrusions.

Figure 82:
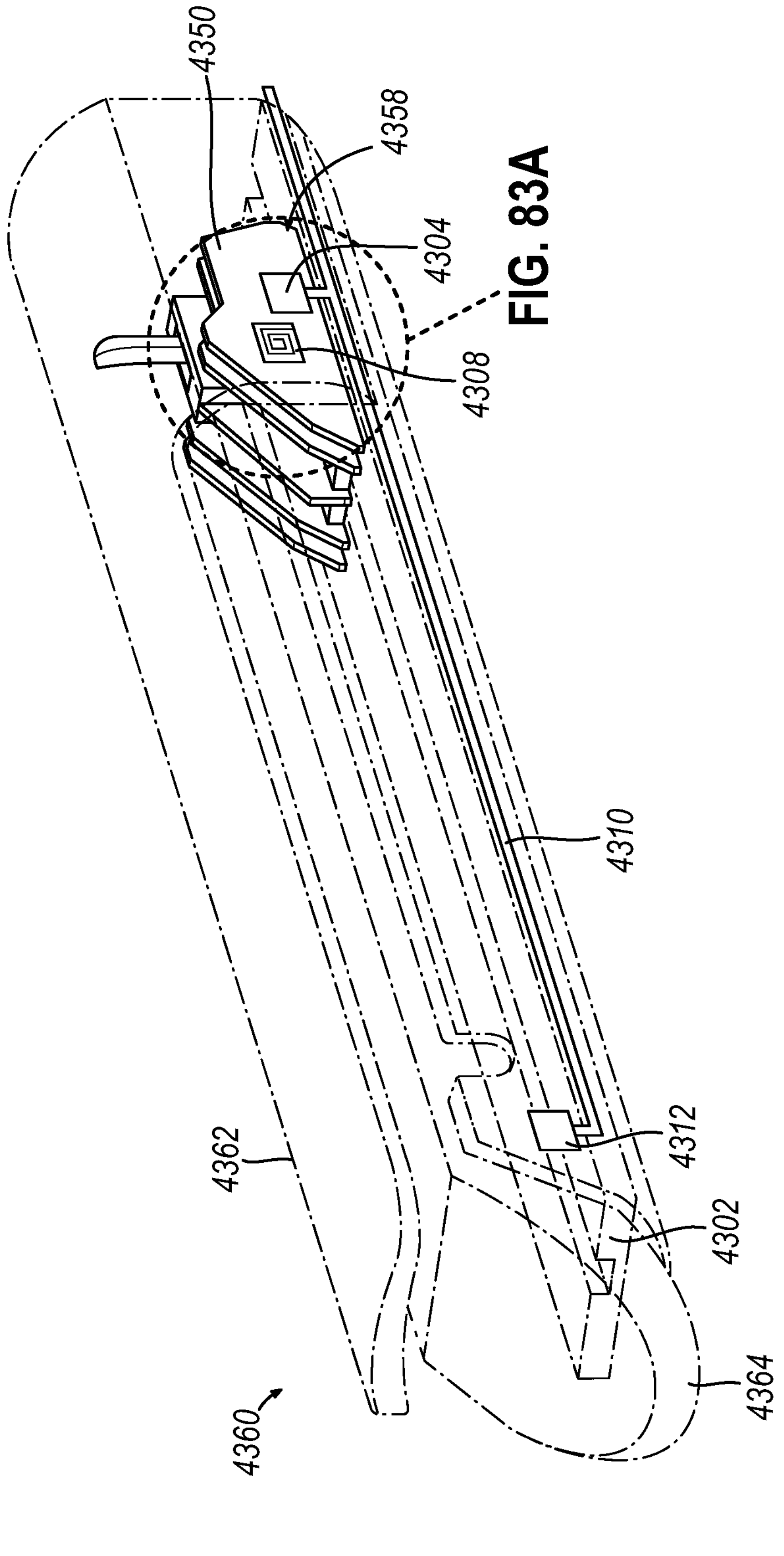
FIG. 82 depicts a perspective view of the end effector of FIG. 81 with portions thereof shown in broken lines to reveal internal features, showing a wedge sled in a proximal, un-fired position.
Figure 83A:
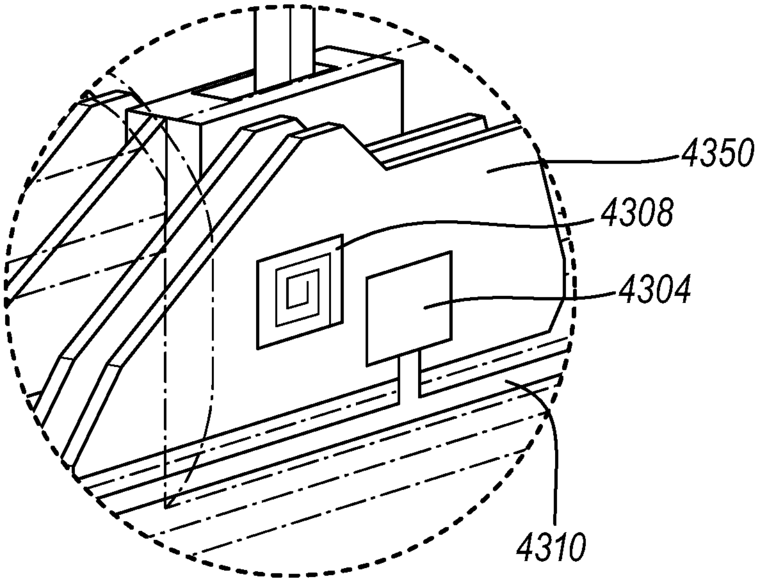
FIG. 83A depicts an enlarged perspective view of a portion of the end effector of FIG. 81 with portions thereof shown in broken lines to reveal internal features, showing the wedge sled in a proximal, un-fired position.
Figure 83B:
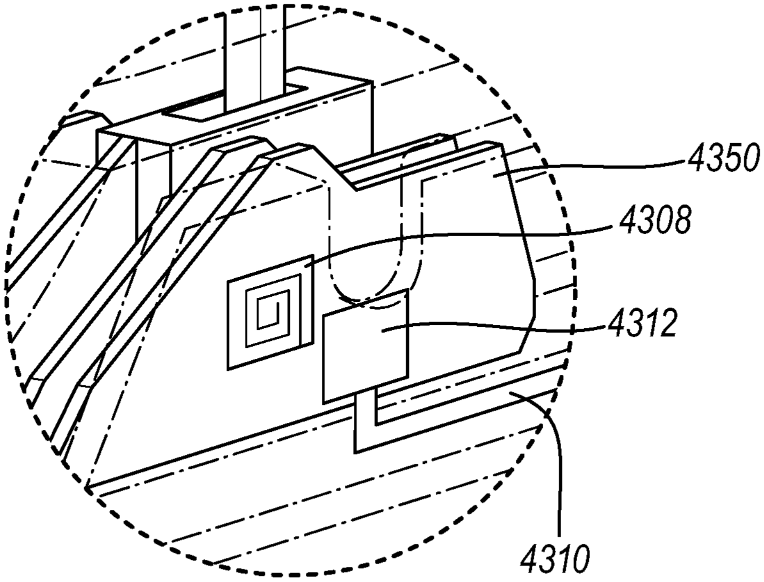
FIG. 83B depicts an enlarged perspective view of the end effector of FIG. 81 with portions thereof shown in broken lines to reveal internal features, showing the wedge sled in a distal, fired position.

Depicted in FIG. 82 is lower cartridge tray (4302) and staple cartridge (4352) showing portions of staple cartridge (4352) removed for clarity. Particularly, as described with reference to FIG. 80, lower cartridge tray (4302) includes a first RFID power coil (4304) and a second RFID power coil (4312) each configured to interact with RFID tag (4308) of staple cartridge (4352). RFID tag (4308) is placed, for example, on wedge sled (4350) of staple cartridge (4352), and specifically on an outer-facing surface (4358) of wedge sled (4350) to thereby align with and communicate with RFID power coils (4304, 4312) depending on the longitudinal positioning of wedge sled (4350) within staple cartridge (4352). In operation, as depicted in FIG. 83A, staple cartridge (4352) is first placed into lower cartridge tray (4302). In accordance with the description above, flex circuit (4310) may be included with one or more electrical contacts (4316) (see FIG. 80) to ensure proper placement and alignment of staple cartridge (4352). In some versions, the completed electrical circuit of the flex circuit (4310) may operate to provide power to each RFID power coil (4304, 4312), while in alternative versions the RFID power coils (4304, 4312) may be independently powered. Once surgical instrument (26, 110) has determined that staple cartridge (4352) is properly seated, proximal RFID power coil (4304) is powered on and configured to read RFID tag (4308) on wedge sled (4350). RFID tag (4308) on wedge sled (4350) may provide various staple cartridge (4352) information including, but not limited to, the color, size, serial number, and/or firing status. Firing status may be indicated by RFID tag (4308) having a memory storing a digital count value. For example, the initial default count value provided to RFID tag (4308) at the time of manufacturing may be 1. After firing and expending the staple cartridge (4352), as will be described below, distal RFID power coil (4312) is configured to write to RFID tag (4308) to incrementally increase the count value by 1 to become 2. Thereafter, if staple cartridge (4352) is inserted into lower jaw (4364) of end effector (4360) after having been spent and storing a count value of 2, proximal RFID power coil (4304) will recognize the count value being greater than 1 and initiate a lockout of surgical instrument (26, 110) to prevent an errant firing of the spent staple cartridge (4352). Depicted in FIG. 83B is wedge sled (4350) positioned at distal end (4314) of staple cartridge (4352) as result of a firing stroke to apply staples. Once distal RFID power coil (4312) detects RFID tag (4308) in proximity and provides initiation power to RFID tag (4308), distal RFID power coil (4312) writes to RFID tag (4308) to increase the count value as described above.

B. Exemplary Lower Jaw Monitoring Features Using Electrical Continuity

Figure 84:
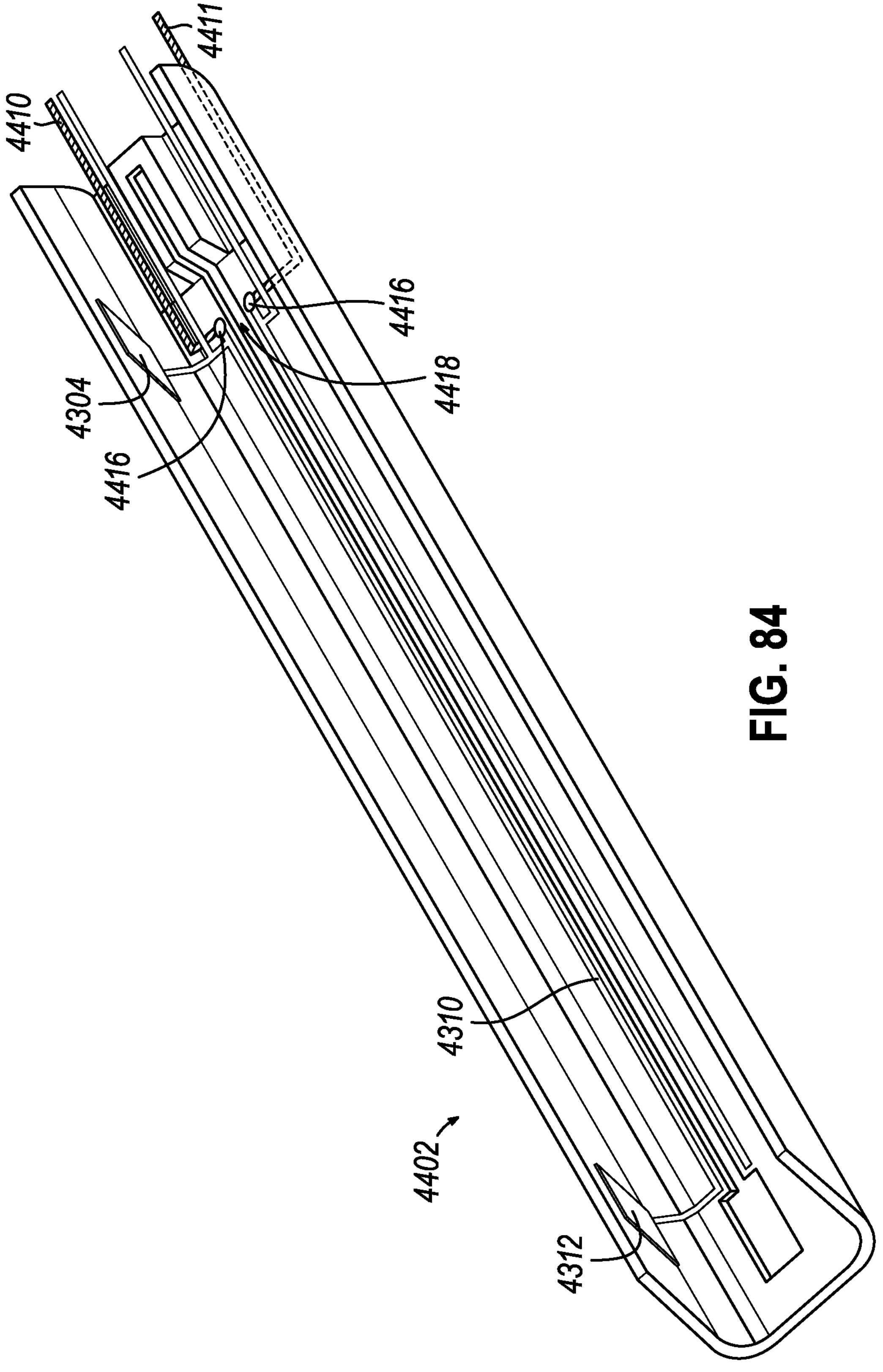
FIG. 84 depicts a perspective view of a second exemplary alternative lower cartridge tray shown removed from a surgical instrument end effector.
Figure 85:
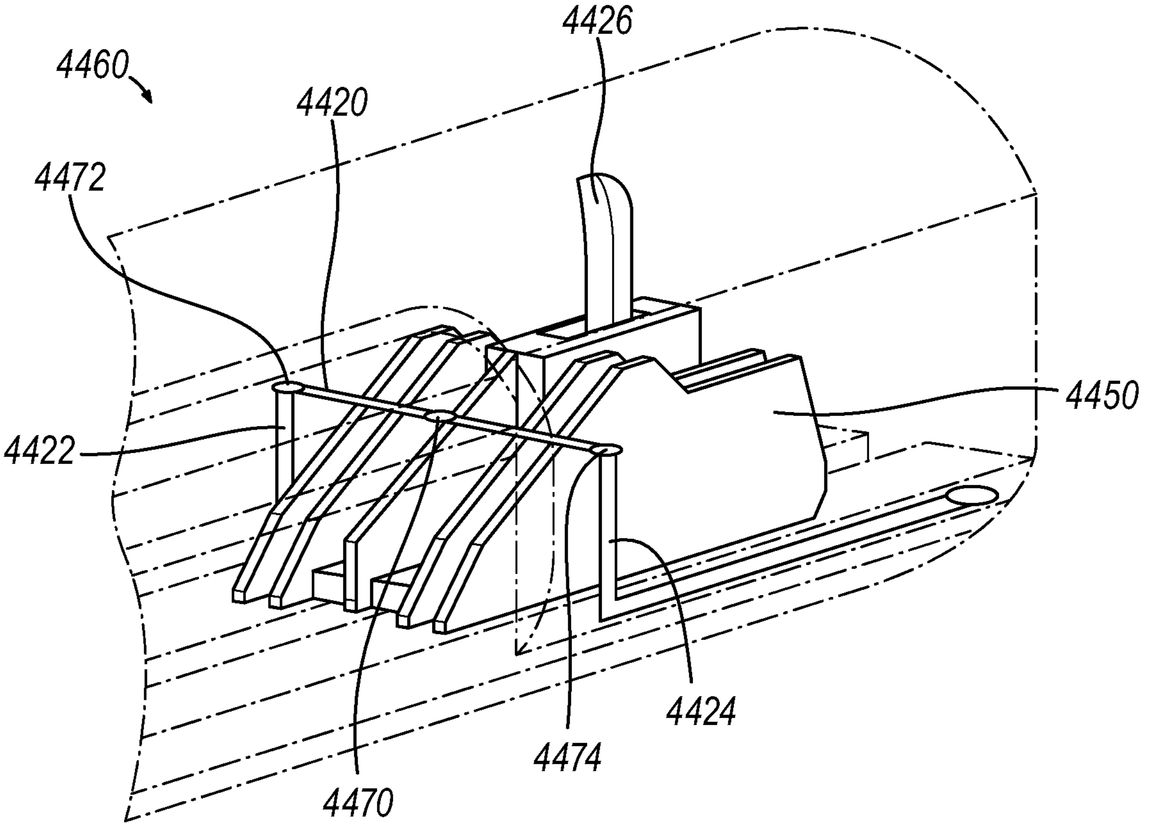
FIG. 85 depicts an enlarged perspective view of a portion of an end effector having the lower cartridge tray of FIG. 85 disposed therein, with portions of the end effector shown in broken lines to reveal internal features, showing a wedge sled in a proximal, un-fired position.

FIGS. 84-85 show another exemplary lower cartridge tray (4402) which forms a part of an end effector (4460) (see FIG. 85), end effector (4460) and lower cartridge tray (4402) each being configured to provide similar functions as end effectors (116, 210, 4360) lower cartridge trays (177, 224, 4302) except as described below. Particularly, in addition or alternative to RFID power coils (4304, 4312), RFID tag (4308), and flex circuit (4310), lower cartridge tray (4402) may include additional monitoring features for detecting the presence or status of a staple cartridge (4452) (see FIGS. 86A-86B) positioned therein. For example, as will be described in greater detail below, lower cartridge tray (4402) and staple cartridge (4452) may cooperate to form an electrical continuity fuse feature (4420) configured to indicate the spent or unspent status of staple cartridge (4452). Further, similar to staple cartridge (4352) described above, staple cartridge (4452) can include a flex circuit (4410, 4411) with one or more electrical contacts (4416) to ensure proper seating of staple cartridge (4452) within lower cartridge tray (4402).

More particularly, as shown in FIG. 84, lower cartridge tray (4402) may include an additional flex circuit (4410, 4411) having paths for coupling with a power source (not shown), such as electronics cart (24) or processor (38), and electrical contacts (4416) separated by a gap (4418) or alternatively by non-conductive material. As such, prior to seating staple cartridge (4452), electrical current is unable to flow from flex circuit (4410) to flex circuit (4411) across gap (4418).

As depicted in FIG. 85, wedge sled (4450) of staple cartridge (4452) includes a continuity fuse feature (4420) for detecting whether staple cartridge (4452) has been previously spent. Continuity fuse feature (4420) may be formed of any conductive material. Optionally, continuity fuse feature (4420) may include a protective, non-conductive coating (not shown) over the conductive material to prevent electrical current from making contact with other portions of staple cartridge (4452) or lower cartridge tray (4402). Continuity fuse feature (4420) includes electrical paths (4422, 4424) configured to contact and electrically couple each electrical contact (4416), thereby completing an electrical circuit between paths of flex circuits (4410, 4411) while in the un-fired position. Particularly, as described above, wedge sled (4450) advances distally during firing. Accordingly, continuity fuse feature (4420) may be disposed across an upper portion of wedge sled (4450) while wedge sled (4450) is posited in the proximal, un-fired position such that knife (4426) breaks continuity fuse feature (4420) during a firing stroke. Thereafter, electrical current is unable to flow through the electrical path formed by flex circuit (4410, 4411), electrical contacts (4416), and continuity fuse feature (4420), indicate to robotic surgical system (10) or surgical instrument (26, 110) that staple cartridge (4452) has been spent. Upon robotic surgical system or surgical instrument (26, 110) determining staple cartridge has been spent, robotic surgical system or surgical instrument (26, 110) may initiate a lockout procedure to prevent additional firings.

Figure 86A:
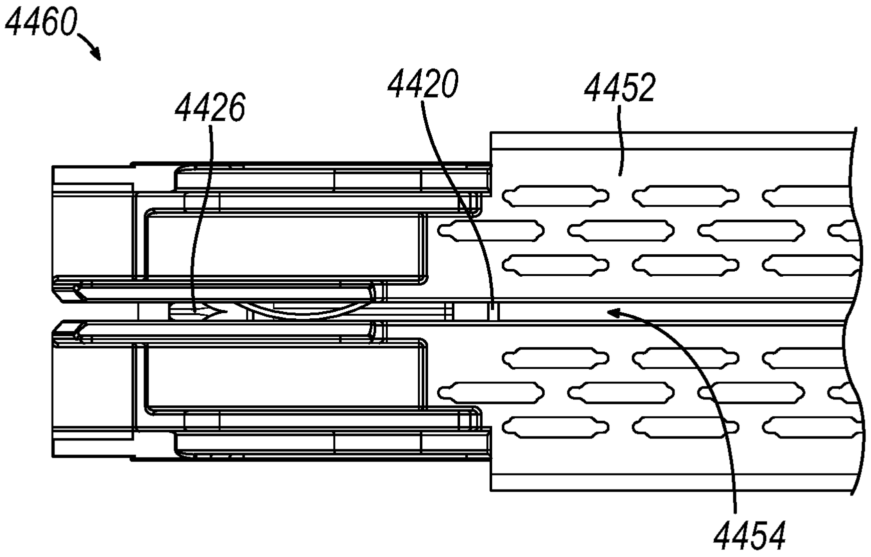
FIG. 86A depicts a top plan view of a proximal portion of a staple cartridge of the end effector of FIG. 85, showing the wedge sled in a proximal, un-fired position.
Figure 86B:
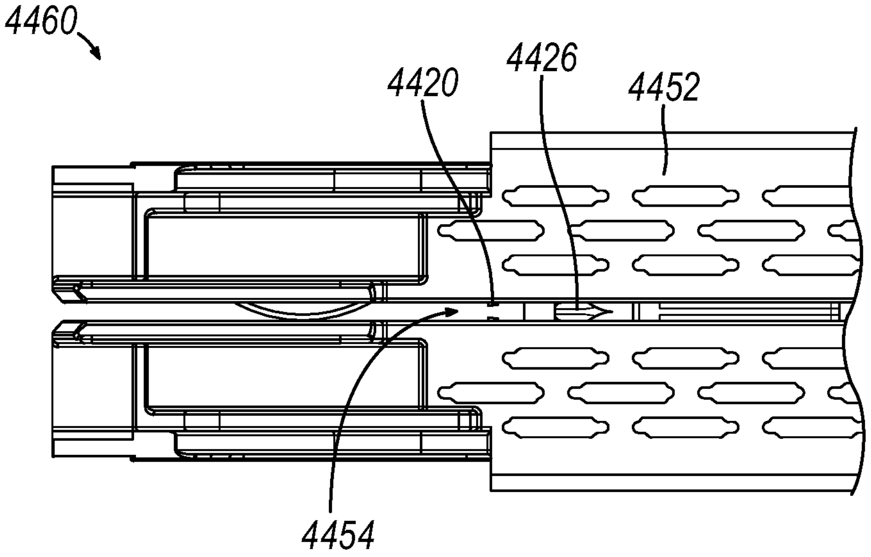
FIG. 86B depicts a top plan view of the proximal portion of the staple cartridge of FIG. 18A, showing the wedge sled in a mid-firing position.

FIG. 86A depicts an overview of staple cartridge (4452) in an unfired position whereby continuity fuse feature (4420) is bridged across knife slot (4454). During a staple firing, as depicted in FIG. 86B, knife (4426) advances distally and breaks through continuity fuse feature (4420). Once continuity fuse feature (4420) has been broken, electrical connectivity between paths of flex circuits (4410, 4411) has been broken thereby indicating to robotic surgical system (10) or surgical instrument (26, 110) that staple cartridge (4452) has been spent. In some versions, continuity fuse feature (4420) may be one-time use, while in other versions, continuity fuse feature (4420) may include a latch (4470) and hinge features (4472, 4474)) (see FIG. 85) that cooperatively allow continuity fuse feature (4420) to be reset. For instance, continuity fuse feature (4420) may be reset if staple cartridge (4452) is recycled and reloaded with staples for future use.

C. Exemplary Lower Jaw Monitoring Features Using Wedge Sled Sensors

Figure 87:
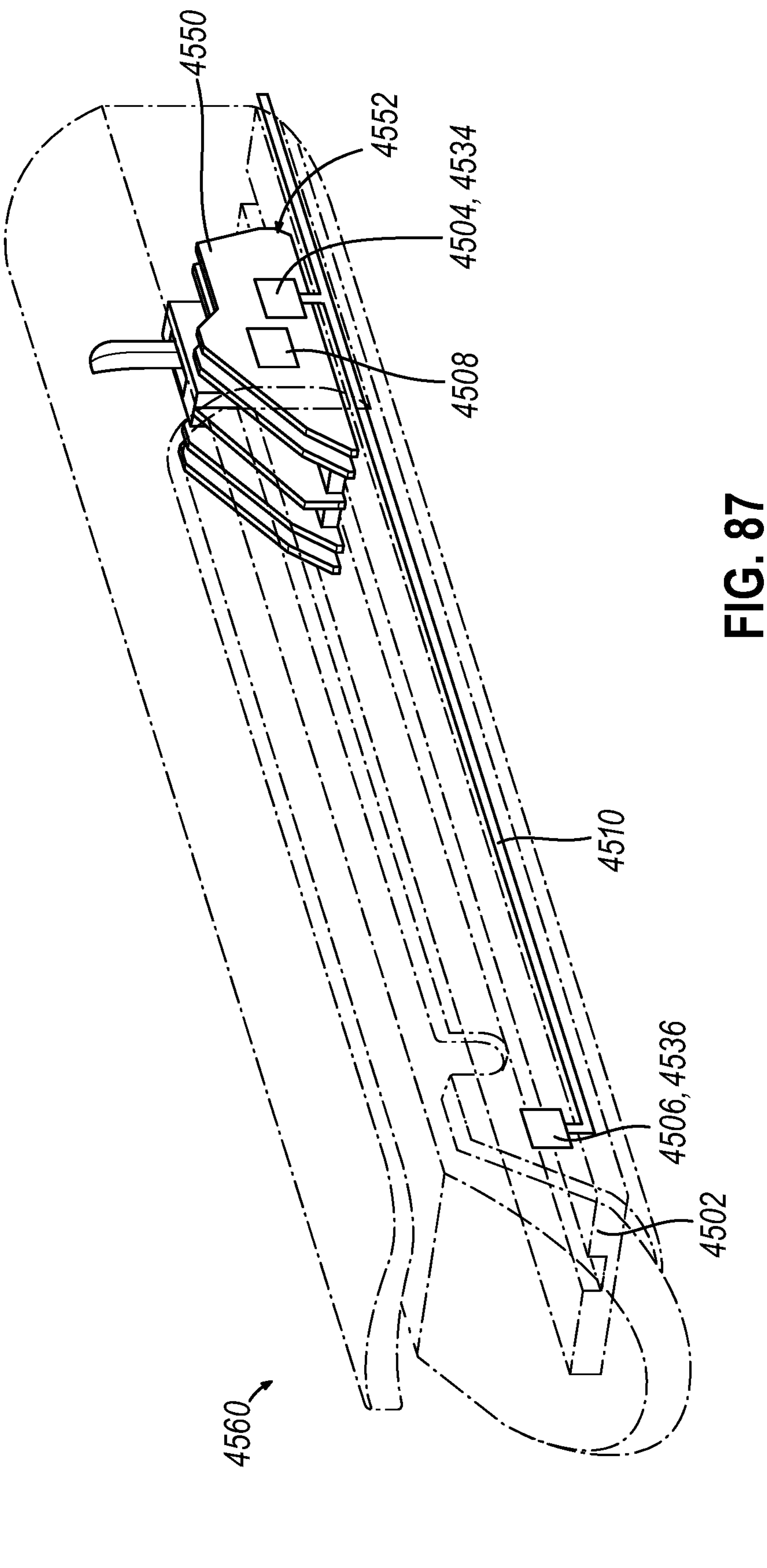
FIG. 87 depicts a perspective view of another exemplary end effector with portions thereof shown in broken lines to reveal internal features, showing a third exemplary alternative lower cartridge tray installed therein.

FIG. 87 shows another exemplary end effector (4560) having a lower cartridge tray (4502) configured to provide similar functions as end effectors (116, 210, 4360, 4460) and lower cartridge trays (177, 224, 4302, 4402) except as described below. Particularly, in addition or alternative to RFID power coils (4304, 4312), RFID tag (4308), flex circuits (4310, 4410, 4411), land continuity fuse feature (4420), lower cartridge tray (4502) may include additional monitoring features for detecting the presence or status of a staple cartridge.

In the exemplary version shown, lower cartridge tray (4502) includes a flex circuit (4510) disposed along the length of lower cartridge tray (4502) for coupling one or more hall effect sensors to robotic surgical system (10), such as electronics cart (24) or processor (38). Hall effect sensors (4504, 4506) are configured to detect the presence of a magnet (4508) disposed in close proximity and transmit a signal back to robotic surgical system (10) via flex circuit (4510) indicating the presence of magnet (4508) adjacent one of the hall effect sensors (4504, 4506). To that end, magnet (4508) may be positioned on wedge sled (4550), such as on an outer-facing surface (4552) of wedge sled (4550) adjacent hall effect sensors (4504, 4506), such that wedge sled (4550) translates magnet (4508) from a proximal first position adjacent proximal hall effect sensor (4504) prior to a firing stroke to a distal second position adjacent distal hall effect sensor (4506) after a firing stroke. By determining wedge sled (4550) is positioned adjacent proximal hall effect sensor (4504), robotic surgical system (10) may determine the staple cartridge containing wedge sled (4550) is in an unfired state. By determining wedge sled (4550) is positioned adjacent distal hall effect sensor (4506), robotic surgical system (10) may determine the staple cartridge containing wedge sled (4550) is in a fired state and may initiate a firing lockout. In an alternative version, magnet (4508) is integrated inside wedge sled (4550).

In another version, referencing FIG. 87, lower cartridge tray (4502) may include flex circuit (4510) disposed along the length of lower cartridge tray (4502) for coupling one or more inductive sensors (4534, 4536) to robotic surgical system (10), such as electronics cart (24) or processor (38). Inductive sensors (4534, 4536) are configured to detect the presence of metal, such as a metal wedge sled (4550) or metal staples within staple cartridge disposed in close proximity to inductive sensors (4534, 4536) and transmit a signal back to robotic surgical system (10) indicating the presence of the metal adjacent one of inductive sensors (4534, 4536). Wedge sled (4550) translates from a first position adjacent proximal inductive sensor (4534) prior to a firing stroke to a second position adjacent distal inductive sensor (4536) after a firing stroke. By determining wedge sled (4550) is positioned adjacent proximal inductive sensor (4534), robotic surgical system (10) may determine staple cartridge containing wedge sled (4550) is in an unfired state. By determining wedge sled (4550) is positioned adjacent distal inductive sensor (4536), robotic surgical system (10) may determine staple cartridge containing wedge sled (4550) is in a fired state and initiate a firing lockout. In some versions, wedge sled (4550) is formed of a definitive metal have a unique inductive signature. Inductive sensors (4534, 4536) in this version are used to verify staple cartridge has a full staple load.

VIII. Exemplary Firing Circuits for Surgical Staplers

While various alternative lockout monitoring features have been described above, it should be understood that two or more unique lockout monitoring features may be utilized concurrently and monitored independently. By monitoring two or more sensor features independently and corroborating the sensed status indicators as described above, additional care may be taken to ensure errors are avoided during a surgical procedure.

Figure 88:
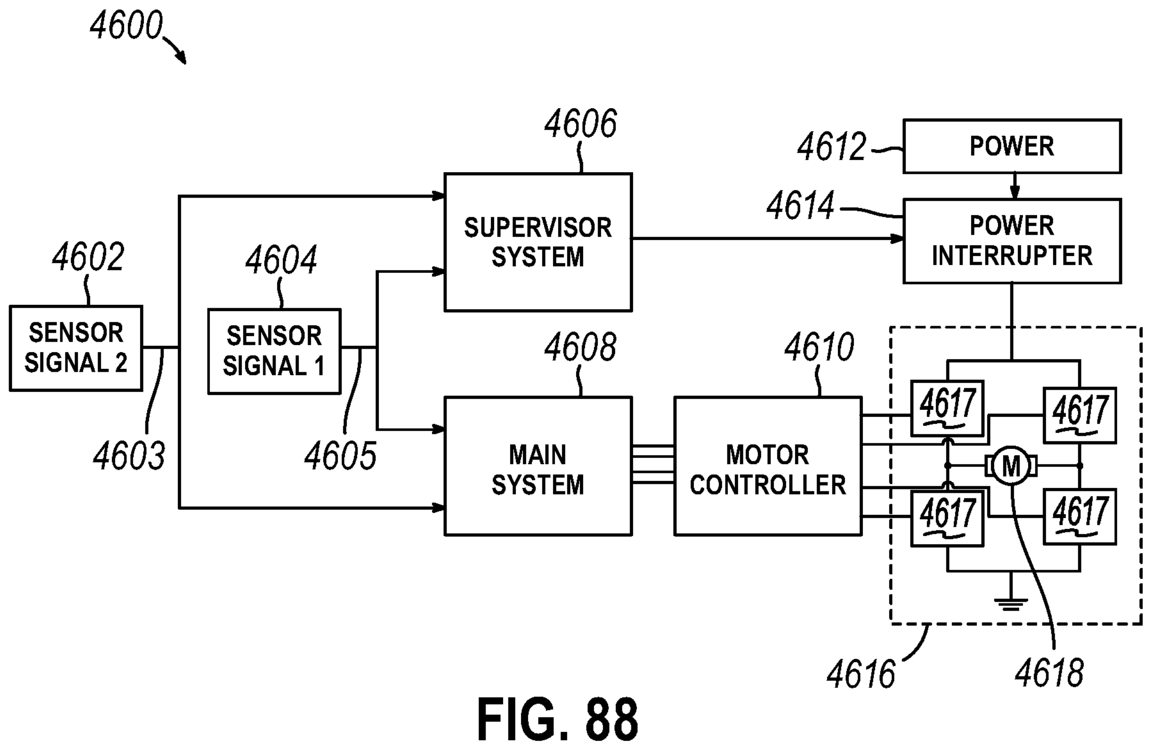

To that end, depicted in FIG. 88 is an exemplary staple firing circuit (4600). As described above, multiple lockout monitoring sensors (4602, 4604) may be included in an end effector, such as end effector (116), and particularly incorporated within the lower jaw (152) thereof, to separately and independently monitor the status of a staple cartridge (154) and provide two or more output signals (4603, 4605) indicative of such so they may be corroborated prior to firing. First lockout monitoring output signal (4603) and second lockout monitoring output signal (4605) are each split between a main processor (4608) and a supervising processor (4606). Main processor (4608) is configured to drive motor controller (4610), which is configured to drive a motor firing circuit (4616) coupling a power source (4612) to motor (4618). Motor firing circuit (4616) may include, for example, various electrical components (4617) such as transistors for selectively connecting and disconnecting motor (4618) to power source (4612) at the direction of motor controller (4610). Main processor (4608) is configured to receive first lockout monitoring output signal (4603) and second lockout monitoring signal (4605) and determine whether each signal (4603, 4605) indicates the end effector, particularly the staple cartridge installed within the end effector, is prepared for operation. If the signals (4603, 4605) do not indicate the end effector is prepared for operation, main processor (4608) controls motor controller (4610) to initiate a lockout condition on motor firing circuit (4616) to prevent a staple firing operation.

Supervising processor (4606) is configured to receive first lockout monitoring output signal (4603) and second lockout monitoring signal (4605) and redundantly determine whether each signal (4603, 4605) indicates the end effector, particularly the staple cartridge installed within the end effector, is prepared for operation. If the signals (4603, 4605) do not indicate the end effector is prepared for operation, supervising processor (4606) operates a power interrupter to disconnect power source (4612) from motor firing circuit (4616). Accordingly, circuit (4600) is configured to receive redundant safety condition signals from multiple independent lockout monitoring features prior to permitting a staple firing operation. If either safety condition signal indicates an unsafe condition, circuit (4600) is configured to initiate a motor firing lockout.

Figure 89:
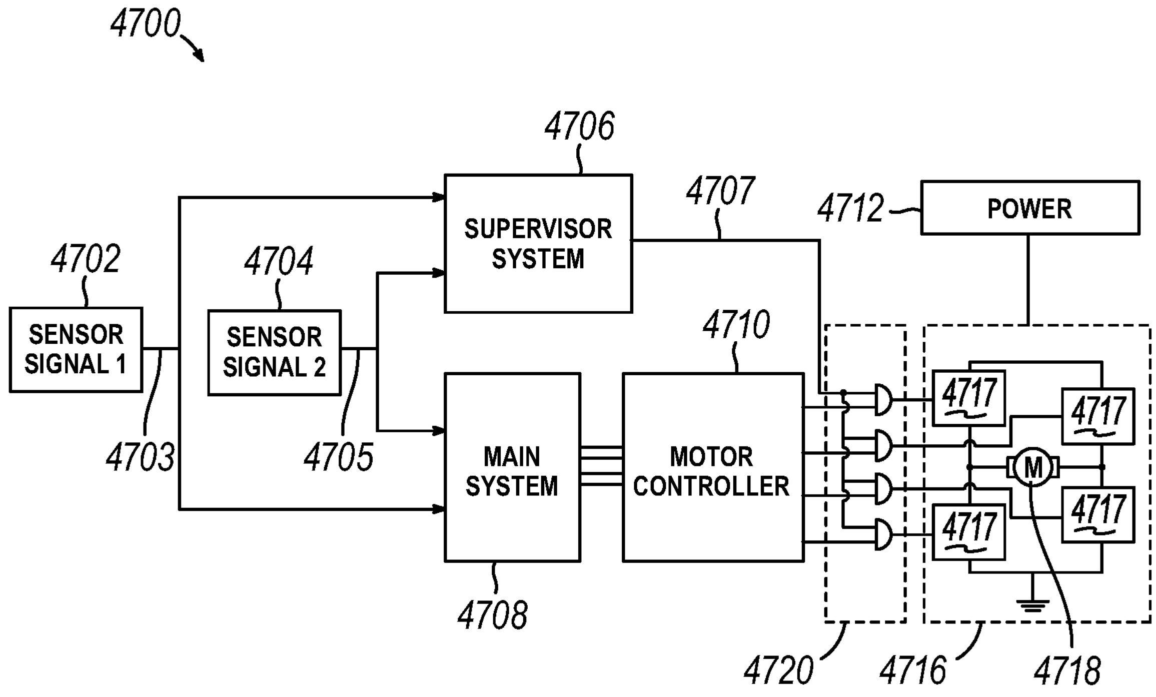
Figure 90:
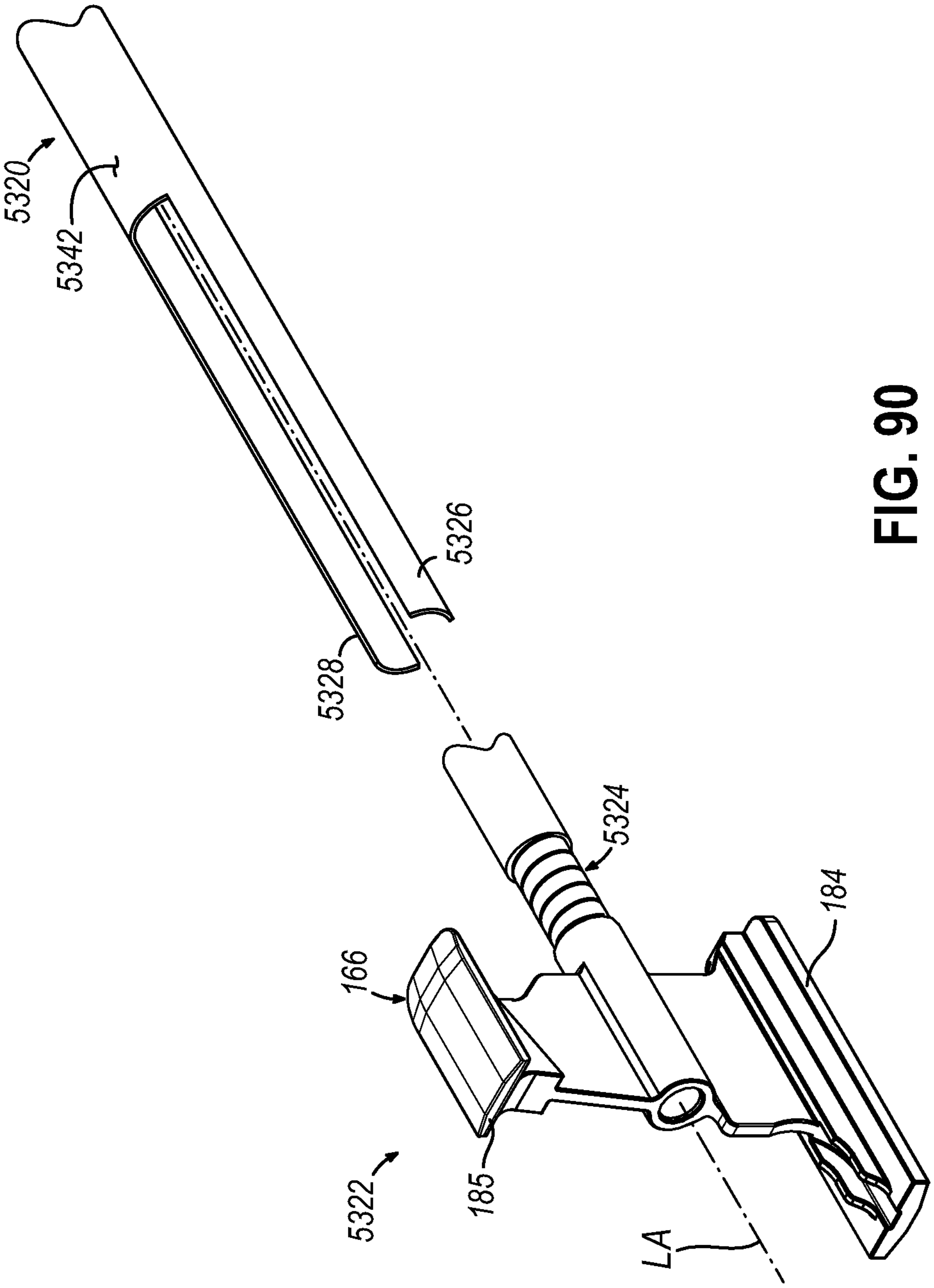

Depicted in FIG. 89 is an exemplary alternative staple firing circuit (4700). As described above, redundant lockout monitoring features may be included in the end effector, such as end effector (116), and particularly incorporated within the lower jaw (152), to monitor the status of a staple cartridge (154) and provide two or more output signals (4703, 4705) indicative of such. First lockout monitoring output signal (4703) and second lockout monitoring output signal (4705) are each split between a main processor (4708) and a supervising processor (4706). Main processor (4708) is configured to drive motor controller (4710), which is configured to drive a motor firing circuit (4716) via digital logic gates (4720) coupling a power source (4712) to motor (4718). Motor firing circuit (4716) may include, for example, various electrical components (4717) such as transistors for selectively connecting and disconnecting motor (4718) to power source (4712) at the direction of motor controller (4710). Main processor (4708) is configured to receive first lockout monitoring output signal (4703) and second lockout monitoring signal (4705) and determine whether each signal (4703, 4705) indicates the end effector, particularly staple cartridge installed within the end effector, is prepared for operation. If the signals (4703, 4705) do not indicate the end effector is prepared for operation, main processor (4708) controls motor controller (4710) to initiate a lockout condition on motor firing circuit (4716) to prevent a staple firing operation.

Supervising processor (4706) is configured to receive first lockout monitoring output signal (4703) and second lockout monitoring signal (4705) and redundantly determine whether each signal (4703, 4705) indicates the end effector, particularly staple cartridge installed within the end effector, is prepared for operation. If the signals (4703, 4705) do not indicate the end effector is prepared for operation, supervising processor (4706) outputs a signal (4707) to digital logic gates (4720) sufficient to initiate a lockout condition on motor firing circuit (4716) to prevent a staple firing operation. Accordingly, circuit (4700) is configured to receive redundant signals from multiple independent lockout monitoring features prior to permitting a staple firing operation. If either safety condition signal indicates an unsafe condition, circuit (4700) is configured to initiate a motor firing lockout.

It will be further appreciated that any of the exemplary features described above in connection with FIGS. 80-89 may be employed to ensure compatibility of a particular staple cartridge (154) with a given end effector (116) before a firing stroke is performed. For instance, end effector (116) may include a detection feature, which may employ RFID technology for example, configured to detect a type of staple cartridge (154) loaded into lower jaw (152) and compare the detected type to one or more predetermined types acceptable for use with end effector (116). If the detected type is not among the predetermined acceptable types, the surgical instrument and/or robotic surgical system (10) may determine that the staple cartridge (154) is incompatible for use with end effector (116) and subsequently engage a firing lockout mechanism to inhibit firing of end effector (116) on tissue with the incompatible staple cartridge (154). In this manner, robotic surgical system (10) may ensure that a surgical stapling procedure performed with end effector (116) is performed accurately without comprising the resulting arrays of staples formed into the patient tissue.

IX. Exemplary Firing Lockout Assembly for Surgical Instrument

In some instances, it may be desirable to provide surgical instrument (110) with a firing lockout assembly to prevent a firing member, such as push rod (168), from advancing when staple cartridge (154) is either absent, improperly installed, or already spent. For example, this may include when staple cartridge (154) is improperly installed within the channel of lower jaw (152) of end effector (116). Such prevention of distal actuation of pusher member (166) in the absence of a usable staple cartridge (154) may prevent inadvertent closing of end effector (116) which may otherwise occur via distal advancement of second flange (185) along longitudinal slot (187) of lower jaw (152); and/or may prevent inadvertent firing of end effector (116) which may otherwise occur via transmission of distal motion from pusher member (166) to wedge sled (170).

As will be described with reference to FIGS. 90-92C, surgical instrument (110) may include, amongst other components, end effector (116), an articulation joint (5310), a shaft assembly (5312), a firing system (5314), and a firing lockout assembly (5316). As previously described, surgical instrument (110) may be removably coupled with robotic arm (42) of robotic surgical system (10) using instrument base (112). As previously described with reference to FIGS. 4-5, instrument base (112) includes attachment interface (118) with input couplers (130) that are configured to interface with and be driven by corresponding output couplers (not shown) of robotic arm (42) of patient side cart (22). As previously described, end effector (116) includes upper and lower jaws (150, 152); however, use of end effector (210) is also envisioned. End effector (116, 210) is operatively coupled with shaft assembly (5312).

Shaft assembly (5312) extends distally from drive system (120) (see FIG. 4) and is similar to shaft assembly (114) described above except as otherwise described below. As shown, shaft assembly (5312) includes a deflecting member (5318) that may comprise a separate component of shaft assembly (5312) or may be coupled with an outer housing (not shown) of shaft assembly (5312). As will be described in greater detail with reference to FIGS. 92A-92C, deflecting member (5318) may move relative to a lockout member (5320) of firing lockout assembly (5316) between locked and unlocked configurations.

Articulation joint (5310) is similar to articulation joint (132) shown in FIG. 4, except as otherwise described below. Articulation joint (5310) is disposed between shaft assembly (5312) and end effector (116) similar to articulation joint (132). Articulation joint (5310) is configured to rotate end effector (116) between an articulated state and a non-articulated state similar to articulation joint (132) (see FIG. 4).

Firing system (5314) is operable to actuate end effector (116) from an open state (see FIG. 10) regarding end effector (210) to a closed state (see FIG. 4) regarding end effector (116). Firing system (5314) extends through at least a portion of shaft assembly (5312) and end effector (116). Firing system (5314) is operable to at least cut and staple tissue once upper and lower jaws (150, 152) are in the closed state. Firing system (5314) may be driven by an actuator either disposed within instrument base (112) or coupled with instrument base (112). Firing system (5314) includes a driving assembly (5322), similar to driving assembly (164), described above except as otherwise described below. FIG.

90 shows a partial exploded perspective view of driving assembly (5322) and a distal portion of firing lockout assembly (5316). Driving assembly (5322) includes pusher member (166) and an elongate rod (e.g., a push rod (5324) which may be similar to push rod (168)). Push rod (5324) may extend within portions of shaft assembly (5312) and end effector (116) along a longitudinal axis (LA) in the non-articulated state.

Firing lockout assembly (5316) is selectively coupled with firing system (5314). Firing lockout assembly (5316) is configured to move between a locked configuration (see FIGS. 91A and 92A) and an unlocked configuration (see FIGS. 91B and 92B). Firing lockout assembly (5316) may determine both a presence and a use status of staple cartridge (154) when staple cartridge (154) is inserted within a cartridge support channel of lower jaw (152). For example, firing lockout assembly (5316) may be operable to inhibit actuation of firing system (5314) to prevent repeated firing of end effector (116) when no staple cartridge (154) is present, when an already deployed staple cartridge (154) is inserted, or an incomplete coupling of staple cartridge (154) with lower jaw (152) occurs. In other words, firing lockout assembly (5316) is configured to inhibit actuation of firing system (5314) in the locked configuration in response to unspent usable staple cartridge (154) being absent from lower jaw (152). Firing lockout assembly (5316) may sense proximal end (176) of staple cartridge body (156).

Figure 91A:
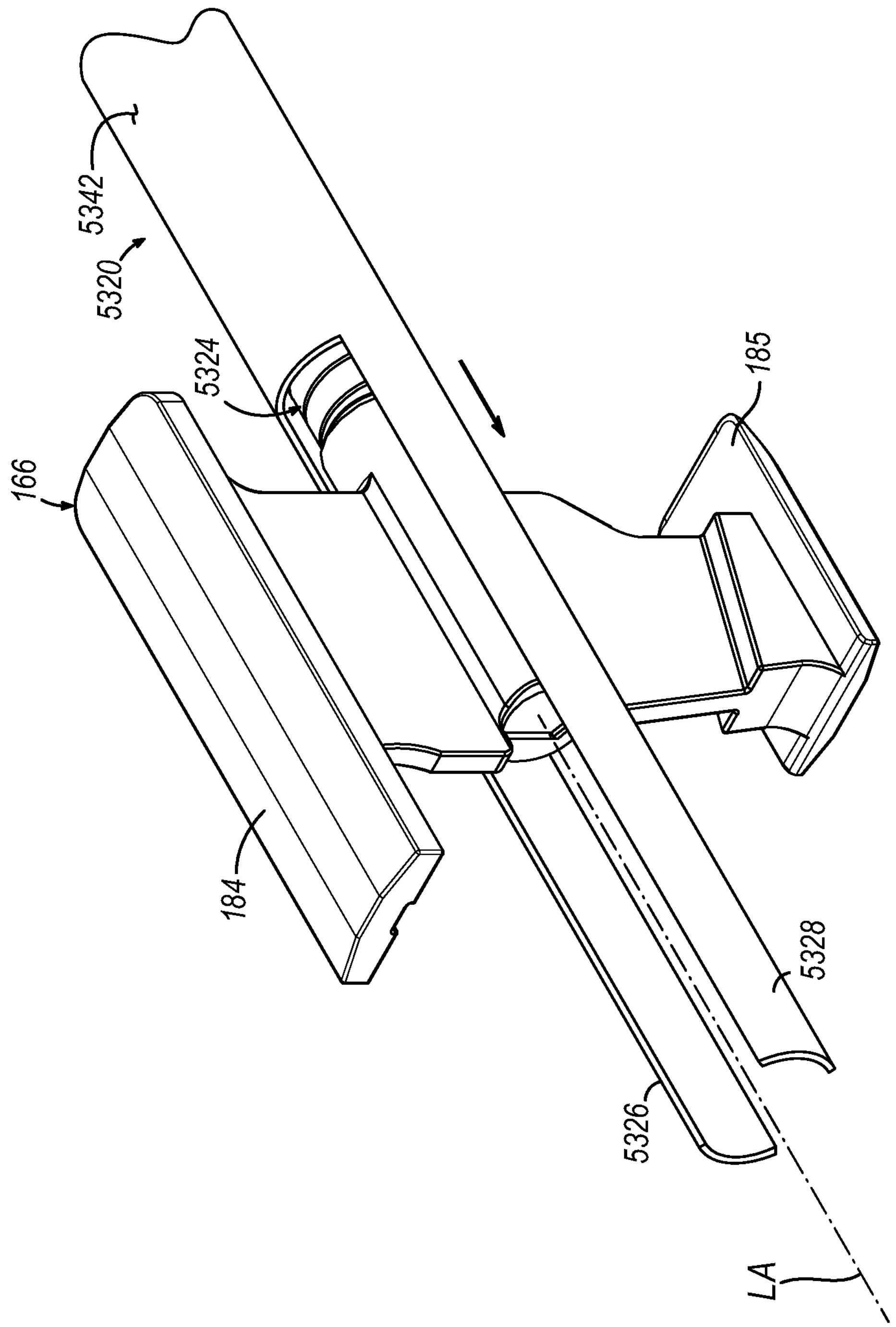
Figure 91B:
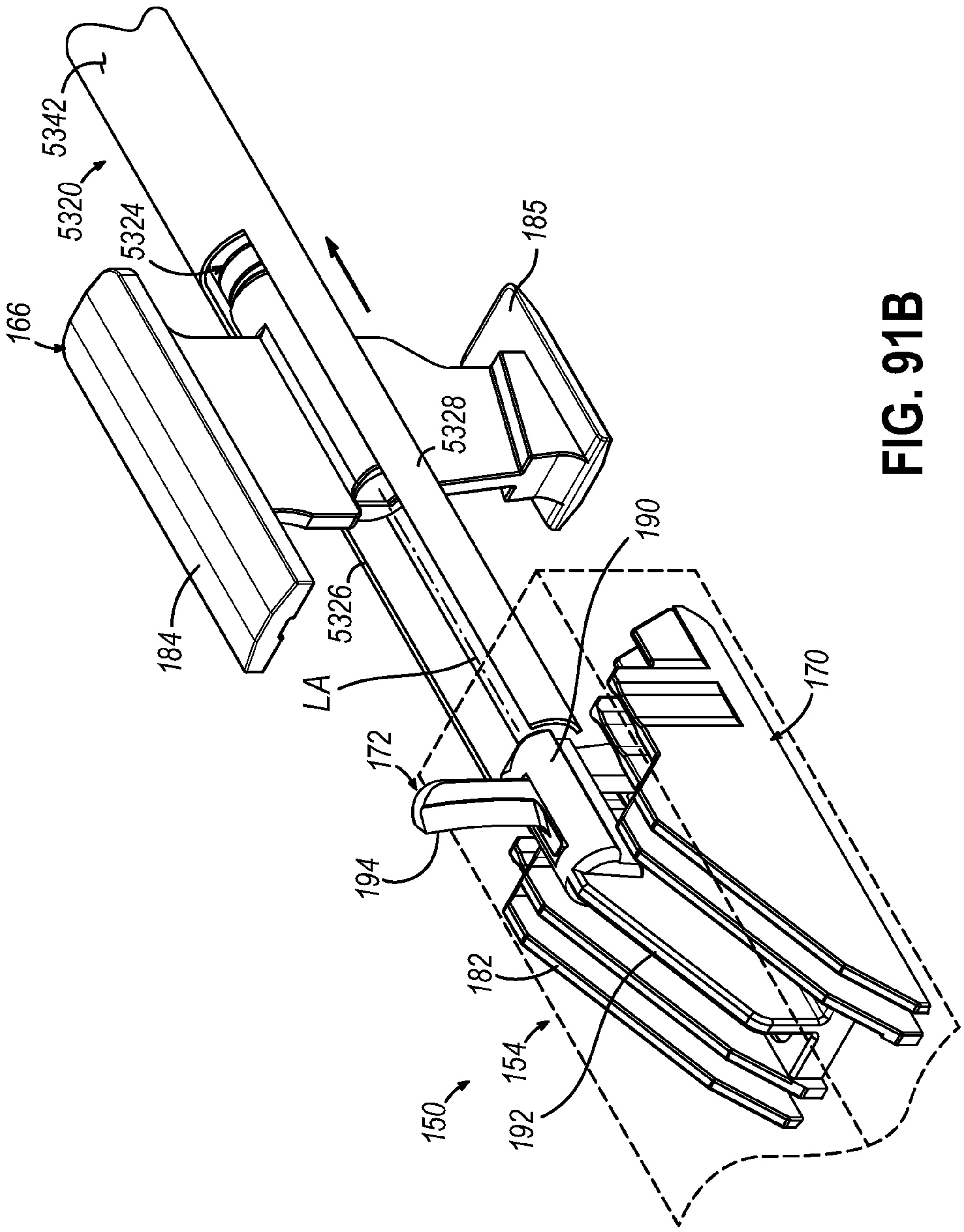
Figure 92A:
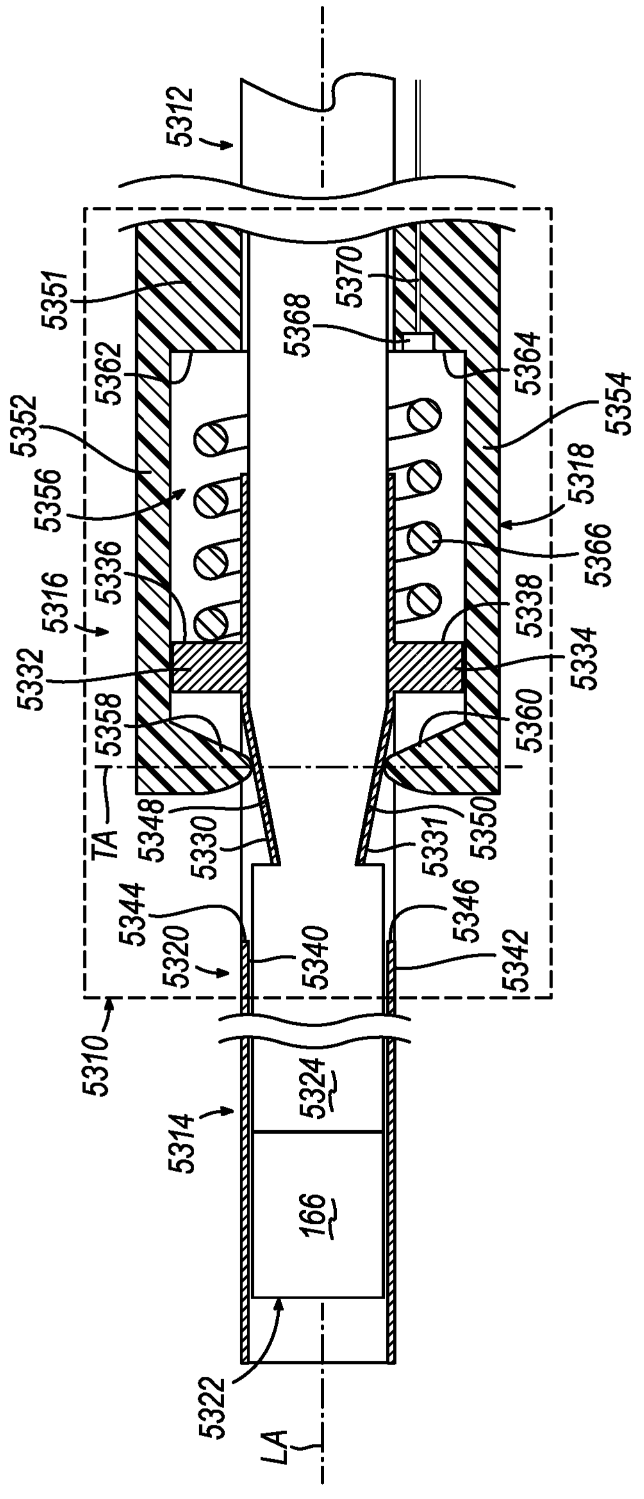

FIGS. 91A and 92A show firing lockout assembly (5316) in the locked configuration. Particularly, FIG. 91A shows a perspective view of driving assembly (5322) and a distal portion of firing lockout assembly (5316) in the locked configuration, and FIG. 92A shows a schematic sectional view of firing lockout assembly (5316) disposed proximal to end effector (116) of FIG. 6. Firing lockout assembly (5316) includes lockout member (5320) which is translatable at least through portions of articulation joint (5310) or shaft assembly (5312). Lockout member (5320) is configured to translate from a first position to a second position in response to unspent staple cartridge (154) being received by lower jaw (152). Lockout member (5320) extends into end effector (116) and has the ability to overcome the bias and unlock firing system (5314). Lockout member (5320) controls the distal translation of pusher member (166). Lockout member (5320), which may be spring biased, communicates the location of wedge sled (170) or the presence of staple cartridge (154) to deflecting member (5318) located proximal to the proximal end of vertical slot (180) of staple cartridge (154). As shown in FIGS. 91A-91B, lockout member (5320) includes opposing first and second arms (5326, 5328).

As will be described in greater detail with reference to FIGS. 92A-92C, firing lockout assembly (5316) is disposed proximal to end effector (116). As previously described, in some versions, firing lockout assembly (5316) may be located within articulation joint (5310). In this version, lockout member (5320) may be supported in the firing member support member and lock into the flexible firing member. Alternatively, firing lockout assembly (5316) may be located proximal to articulation joint (5310) for example, at a proximal end of articulation joint (5310). In this version, firing lockout assembly (5316) may include a biasing element (e.g., a compression spring) that is supported within the tube support member and locks into the flexible support member proximally or with push rod (5324).

As shown in FIG. 92A, lockout member (5320) includes first and second deflectable portions (5330, 5331) that are configured to deflect about a transverse axis (TA) that extends transversely to longitudinal axis to inhibit actuation of firing system (5314) while in the locked configuration. Lockout member (5320) includes opposing first and second projections (5332, 5334) defining first and second contact surfaces (5336, 5338). Lockout member (5320) includes inner and outer surfaces (5340, 5342). Lockout member (5320) includes first and second cutout portions (5344, 5346) extending through inner and outer surfaces (5340, 5342) of lockout member (5320). Inner surface (5340) of lockout member (5320) may surround at least a portion of push rod (5324). Push rod (5324) includes at least one recessed portion, with first and second recessed portions (5348, 5350) being shown. First and second recessed portions (5348, 5350) are configured to receive first and second deflectable portions (5330, 5331) of lockout member (5320) to inhibit actuation of firing system (5314) in the locked configuration of FIGS. 91A and 92A.

With continued reference to FIG. 92A, deflecting member (5318) includes a body (5351) with first and second arms (5352, 5354) disposed around outer surface (5342) of lockout member (5320) defining a cavity (5356). A first rigid engagement feature (5358) is disposed at the distal terminal end of first arm (5352), and a second rigid engagement feature (5360) is disposed at the distal terminal end of second arm (5354). Deflecting member (5318) includes first and second contact surfaces (5362, 5364). First and second rigid engagement features (5358, 5360) are configured to engage first and second deflectable portions (5330, 5331) of lockout member (5320) in the locked configuration. Firing lockout assembly (5316) includes a biasing element (shown as compression spring (5366)) configured to bias lockout member (5320) toward locked configuration. Compression spring (5366) is disposed within cavity (5356) between first and second contact surfaces (5362, 5364) of deflecting member (5318) at a proximal end and between first and second contact surfaces (5336, 5338) of lockout member (5320) at a distal end.

Figure 92B:
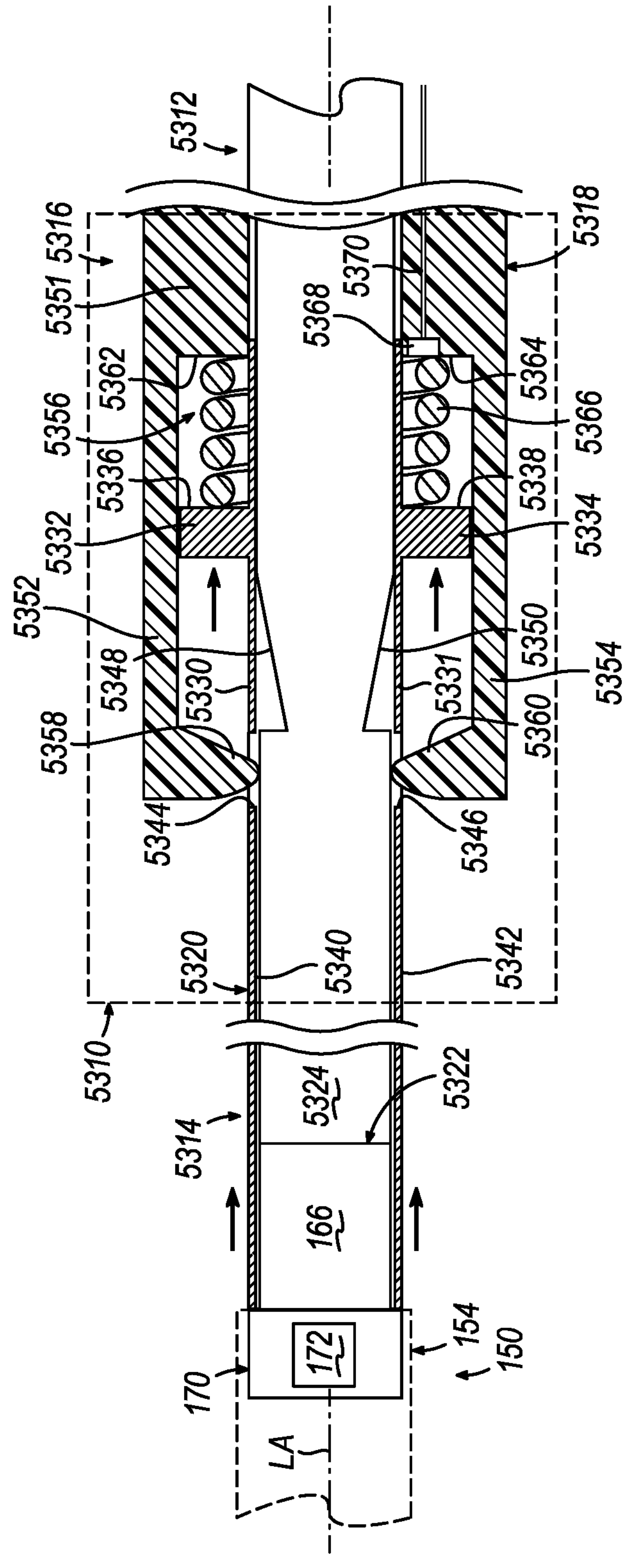
Figure 92C:
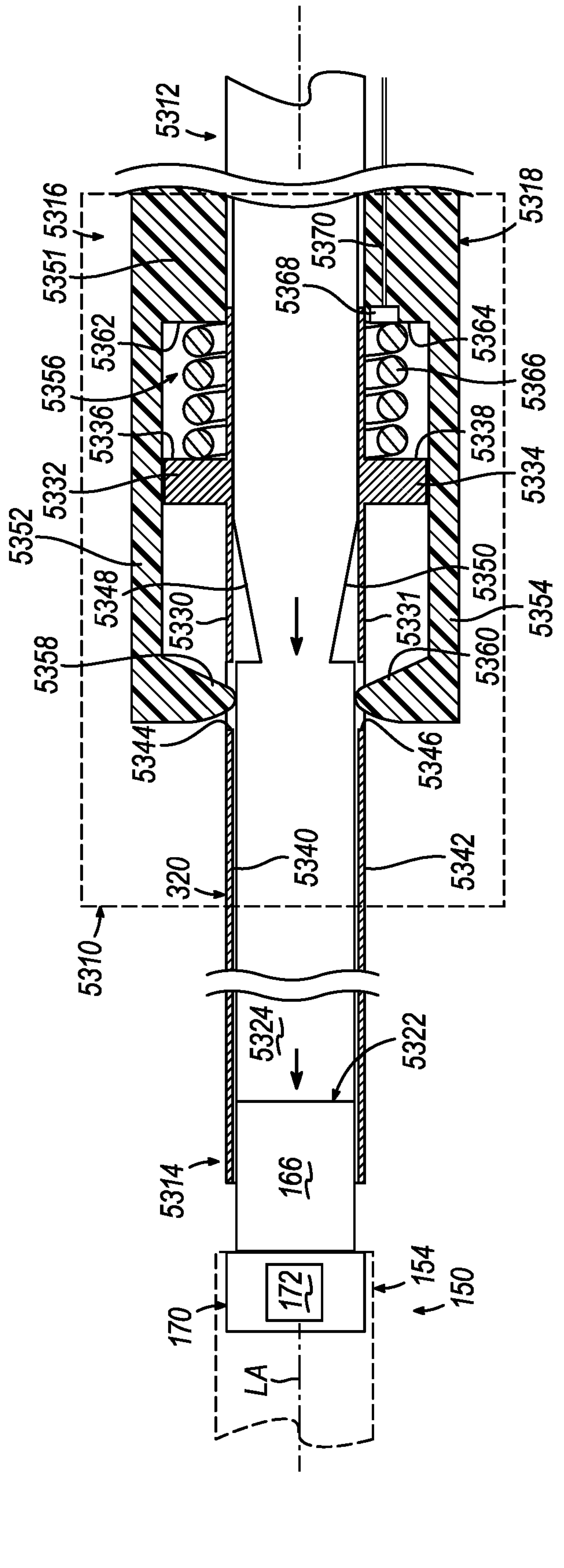

While FIGS. 92A-92C show first and second deflectable portions (5330, 5331), first and second projections (5332, 5334), first and second contact surfaces (5336, 5338), first and second cutout portions (5344, 5346), first and second recessed portions (5348, 5350), first and second arms (5352, 5354), first and second rigid engagement features (5358, 5360), and first and second contact surfaces (5362, 5364), it is envisioned that a single component/portion/surface may be incorporated for one or more of the component/portion/surface. For example, in some instances, an annular component/portion/surface may be incorporated.

FIGS. 91B and 92B show firing lockout assembly (5316) moved to the unlocked configuration. Particularly, FIG. 91B shows a perspective view of the driving assembly (5322) and lockout member (5320) of firing lockout assembly (5316) of FIG. 90 in the unlocked configuration in the presence of staple cartridge (154) of FIG. 6, and FIG. 92B shows a schematic sectional view of firing lockout assembly (5316) and end effector (116) of FIG. 92A, but with firing lockout assembly (5316) moved to the unlocked configuration of FIG. 91B. Firing lockout assembly (5316) is configured to allow actuation of firing system (5314) in the unlocked configuration in response to unspent staple cartridge (154) being coupled with second jaw. As shown in FIG. 92B, lockout member (5320) is moved relative to deflecting member (5318) as lockout member (5320) moves from the locked configuration to the unlocked configuration.

Driving assembly (5322) may contact lockout member (5320) to force lockout member (5320) to translate proximally. Particularly, guide member (190) of wedge sled (170)

may contact first and second arms (5352, 5354) to translate lockout member (5320) proximally which causes first and second deflectable portions (5330, 5331) to translate proximally and exit first and second recessed portions (5348, 5350) of push rod (5324). This proximal movement of first and second deflectable portions (5330, 5331) also causes first and second deflectable portions (5330, 5331) to disengage from or reduce the interference with first and second rigid engagement features (5358, 5360). As shown, first and second rigid engagement features (5358, 5360) are disposed adjacent first and second cutout portions (5344, 5346) thereby moving firing lockout assembly (5316) to the unlocked configuration. Proximal movement of lockout member (5320) causes proximal movement of first and second projections (5332, 5334) to compress compression spring (5366). Compression spring (5366) is resiliently biased to a compressed state between contact surfaces of deflecting member (5318) and lockout member (5320) in the unlocked configuration. In other words, the force exerted by the proximal end of staple cartridge (154) on lockout member (5320) exceeds the spring force of compression spring (5366) in the compressed state causing lockout member (5320) to move proximally. As a result of the movement of lockout member (5320), firing lockout assembly (5316) may sense the presence and absence of the proximal end of staple cartridge (154) within lower jaw (152) while being disposed proximal to end effector (116). Particularly, firing lockout assembly (5316) may sense proximal end (176) of staple cartridge body (156).

FIG. 92C shows a schematic sectional view of firing lockout assembly (5316) disposed proximal to end effector (116) of FIG. 92B. Since firing lockout assembly (5316) is in the unlocked configuration, push rod (5324) may be activated distally to cause driving assembly (5322) to actuate staple cartridge (154). Optionally, first and second rigid engagement features (5358, 5360) may contact push rod (5324) as push rod (5324) translates.

As shown in FIGS. 92A-92C, firing lockout assembly (5316) may include electrical lockout components in addition to mechanical lockout features. For example, in addition to or in place of the mechanical lockout provided by the interaction of deflecting member (5318) and lockout member (5320), an electrical signal continuity may be incorporated as a redundant safeguard to detect and provide feedback to the user and/or robotic surgical system (10) that that lockout member (5320) is either in the locked or unlocked configuration. Electrical monitoring of one or more motors of robotic surgical system (10) may supplement the monitoring of firing lockout assembly (5316). For example, firing lockout assembly (5316) may include at least one electrical contact (5368) disposed within firing lockout assembly (5316) and configured to sense at least one of a presence or an absence of unspent staple cartridge (154). As previously described, robotic surgical system includes at least one actuator (e.g., a motor). Electrical contact (5368) is configured to provide a signal wirelessly or using wire (5370) to surgical instrument (110) in indicate the state of firing lockout assembly (5316). As shown, electrical contact (5368) is disposed adjacent second contact surface (5364) of deflecting member (5318); however, electrical contact (5368) may be located in a variety of suitable positions.

Surgical instrument (110) is configured to prevent power to the motor in response to signal indicating that firing lockout assembly (316) is in the locked configuration. The signal received from electrical contact (368) may prevent power to the controlling motors. Lockout member (320) may be incapable of resisting the full force of pusher member (166) which is used cooperative with the monitoring of the torque or current of the motor which is related to the force experienced by knife member (172) and the location of knife member (172) to control advancement of the motor. If the limited force obstruction is detected in the stroke monitored zone, the motor may be deactivated preventing the firing of end effector (116).

X. Exemplary Cartridge-Based Firing Lockout Mechanisms for Surgical Stapler

In some instances, it may be desirable to provide surgical instrument (110) with a lockout feature for preventing a firing member of end effector (116), such as push rod (168), from actuating pusher member (166) distally when staple cartridge (154) is either spent, or otherwise improperly installed within or entirely absent from the channel of lower jaw (152) of end effector (116). Such prevention of distal actuation of pusher member (166) in the absence of a full staple cartridge (154) (also referred to as an "unspent" staple cartridge) that is properly seated may prevent inadvertent and improper closing of end effector (116) on tissue and resulting misalignment between staple cartridge (154) and anvil (214) that yields improper staple formation, which could otherwise occur via distal advancement of second flange (185) of pusher member (166) along longitudinal slot (187) of lower jaw (152). Such prevention of distal actuation of pusher member (166) in the absence of a full staple cartridge (154) that is properly seated may also prevent inadvertent and improper firing of end effector (116) on clamped tissue by cutting the tissue without also stapling the tissue, which could otherwise occur via transmission of distal motion from pusher member (166) to wedge sled (170). Each of the lockout mechanisms described below provides one or more of these functionalities.

A. First Exemplary Lockout Mechanism

Figure 93A:
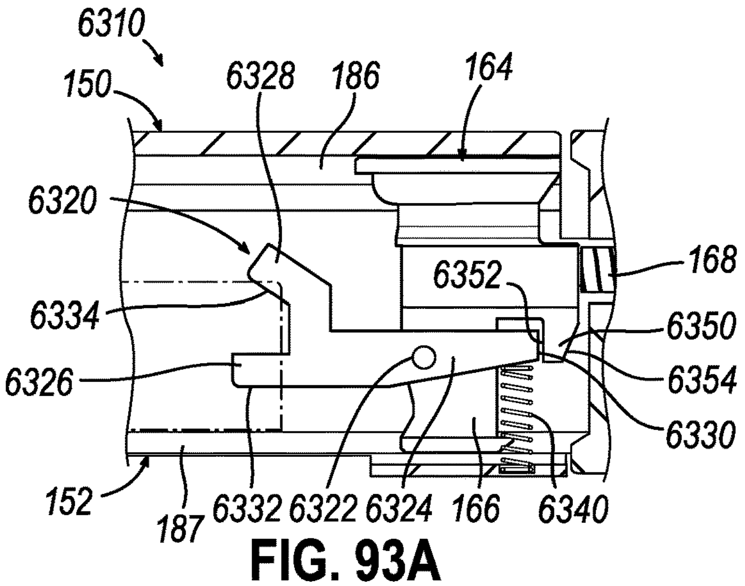
Figure 93B:
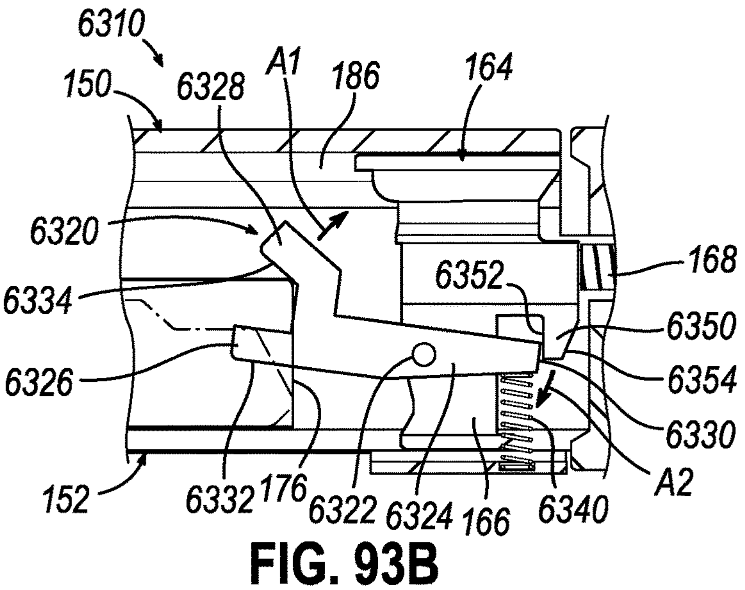
Figure 93C:
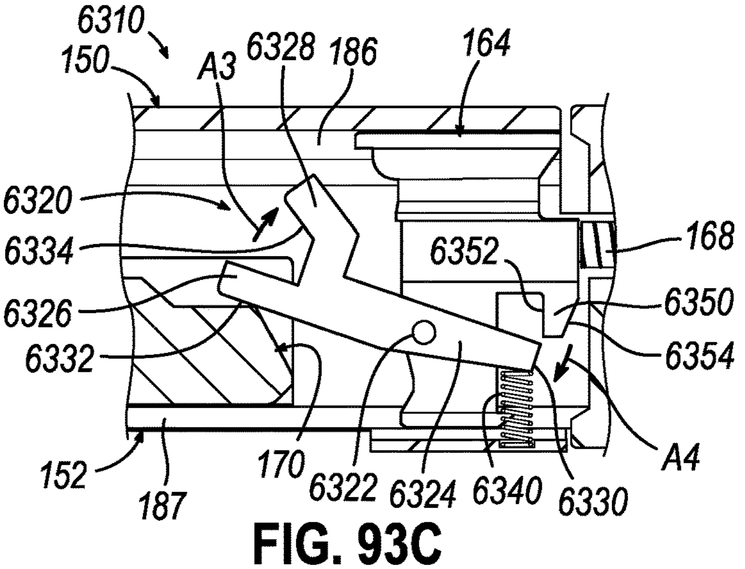

FIGS. 93A-93C show a proximal portion of an exemplary end effector (6310) for use with surgical instrument (110) described above. End effector (6310) is similar to end effector (116) described above except as otherwise described below. In this regard, end effector (6310) includes upper and lower jaws (150, 152) and driving assembly (164) having pusher member (166) operatively coupled with an actuation mechanism (not shown), such as moveable member (128), via push rod (168).

As shown in FIGS. 93A-93C, end effector (6310) includes at least a portion of a lockout mechanism that includes a lockout lever (6320) pivotably coupled to the channel of lower jaw (152) via a pivot pin (6322). For example, pivot pin (6322) may pivotably couple lockout lever (6320) to a sidewall (not shown) of the channel of lower jaw (152), such that lockout lever (6320) is positioned laterally inwardly relative to the sidewall and thus within the channel. In the example shown, lockout lever (6320) includes a proximal longitudinal portion (6324), a lower distal prong portion (6326) extending distally from a lower region of proximal longitudinal portion (6324), and an upper distal prong portion (6328) extending upwardly and distally from an upper region of proximal longitudinal portion (6324), such that lockout lever (6320) has a generally Y-shaped profile. In the example shown, pivot pin (6322) is received within a bore provided in an intermediate region of proximal longitudinal portion (6324).

As shown, a proximal end of proximal longitudinal portion (6324) defines an output surface (6330), a bottom of lower distal prong portion (6326) defines a lower input surface (6332), and a bottom of upper distal prong portion (6328) defines an upper input surface (6334), the purposes of which are described below. In some versions, output surface (6330) may be at least partially defined by a proximal end of a detent (not shown) extending laterally inwardly from a proximal region of proximal longitudinal portion (6324). At least a portion of lockout lever (6320), such as lower distal prong portion (6326), may be spaced apart from the laterally inner surface of the sidewall to which lockout lever (6320) is pivotably coupled by a clearance gap sufficiently sized to accommodate a laterally outer sidewall of staple cartridge (154). In this manner, lower distal prong portion (6326) may be configured to extend distally through proximal end (176) into an interior of staple cartridge (154) for accessing wedge sled (170) when staple cartridge (154) is installed within the channel of lower jaw (152), as described in greater detail below. In addition, or alternatively, at least lower and upper distal prong portions (6326, 6328), may be positioned laterally outwardly relative to pusher member (166) to avoid interfering with distal actuation of pusher member (166).

With continuing reference to FIGS. 93A-93C, lockout lever (6320) is pivotable relative to the channel of lower jaw (152) about a fulcrum defined by pivot pin (6322) between a fully locked state (FIG. 93A), a partially locked state (FIG. 93B), and an unlocked state (FIG. 93C). More particularly, lockout lever (6320) of the present version is configured to be pivoted in a clockwise direction from the fully locked state toward the partially locked state, and is further configured to be pivoted in the clockwise direction from the partially locked state toward the unlocked state. In the example shown, lockout lever (6320) is resiliently biased toward the fully locked state via a compression spring (6340) positioned proximally of pivot pin (6322) and extending between a bottom of proximal longitudinal portion (6324) and a floor of the channel of lower jaw (152). It will be appreciated that lockout lever (6320) may be resiliently biased toward the fully locked state in any other suitable manner, such as via a suitably-positioned tension spring, torsion spring, or any other suitable biasing member.

As best shown in FIG. 93B, upper input surface (6334) is configured to be cammingly engaged by a portion of staple cartridge (154), such as proximal end (176), when staple cartridge (154) is installed within the channel of lower jaw (152) for urging lockout lever (6320) from the fully locked state to the partially locked state. In this regard, upper input surface (6334) may be positioned at a predetermined location and/or oriented at a predetermined angle selected to provide a desired camming engagement with proximal end (176) of staple cartridge (154) for urging lockout lever (6320) from the fully locked state to the partially locked state. In some versions, upper input surface (6334) may be configured to only provide the desired camming engagement with compatible staple cartridges having a predetermined size and/or geometry. For example, compatible staple cartridges may have substantially the same size and/or geometry as that of staple cartridge (154) (e.g., at least the proximal portion thereof), such that upper input surface (6334) may not be capable of providing the desired camming engagement with incompatible staple cartridges having substantially different sizes and/or geometries from those of staple cartridge (154). In this manner, lockout lever (6320) may be configured to remain in the fully locked state when an incompatible staple cartridge is installed within the channel of lower jaw (152). Likewise, lockout lever (6320) may be configured to remain in the fully locked state when no staple cartridge is installed within the channel of lower jaw (152). It will be appreciated that a compatible staple cartridge is shown in phantom lines in FIG. 93A to illustrate the absence of such a compatible staple cartridge from lower jaw (152).

As best shown in FIG. 93C, lower input surface (6332) is configured to be cammingly engaged by a portion of wedge sled (170), such as a proximal portion thereof, when staple cartridge (154) is installed within the channel of lower jaw (152) with wedge sled (170) in its initial proximal position for urging lockout lever (6320) from the fully and/or partially locked state to the unlocked state. In this regard, lower input surface (6332) may be positioned at a predetermined location and/or oriented at a predetermined angle selected to provide a desired camming engagement with the proximal portion of wedge sled (170) when wedge sled (170) is in its initial proximal position for urging lockout lever (6320) from the fully and/or partially locked state to the unlocked state. In some versions, lower input surface (6332) may be configured to only provide the desired camming engagement with compatible wedge sleds having a predetermined size and/or geometry. For example, compatible wedge sleds may have substantially the same size and/or geometry as that of wedge sled (170) (e.g., at least the proximal portion thereof), such that lower input surface (6332) may not be capable of providing the desired camming engagement with incompatible wedge sleds having substantially different sizes and/or geometries from those of wedge sled (170). In this manner, lockout lever (6320) may be configured to remain in the fully and/or partially locked state when a staple cartridge having an incompatible wedge sled is installed within the channel of lower jaw (152). It will be appreciated that a compatible wedge sled is shown in phantom lines in FIG. 93B to illustrate the absence of such a compatible wedge sled from staple cartridge (154).

In addition or alternatively, lower input surface (6332) may be configured to only provide the desired camming engagement with the proximal portion of wedge sled (170) after upper input surface (6334) has been cammingly engaged by proximal end (176) of staple cartridge (154) for urging lockout lever (6320) from the fully locked state toward the partially locked state, such that lower input surface (6332) may not be capable of providing the desired camming engagement with the proximal portion of wedge sled (170) when lockout lever (6320) is in the fully locked state. In this manner, lockout lever (6320) may be configured to remain in the fully locked state when an incompatible staple cartridge having wedge sled (170) is installed within the channel of lower jaw (152). Likewise, lockout lever (6320) may be configured to remain in the partially locked state when staple cartridge (154) having an incompatible wedge sled is installed within the channel of lower jaw (152). Lockout lever (6320) may also be configured to remain in the partially locked state when staple cartridge (154) having wedge sled (170) is installed within the channel of lower jaw (152) with wedge sled (170) located distally of its initial proximal position.

In the present version, the lockout mechanism also includes a stop detent (6350) fixedly coupled to pusher member (166) and extending downwardly and/or laterally outwardly therefrom. As shown, a distal end of stop detent (6350) defines a vertical catch surface (6352) and a proximal end of stop detent (6350) defines a ramp surface (6354) tapered distally in a downward direction. Catch surface (6352) is configured to be proximal of and selectively aligned with output surface (6330) of lockout lever (6320) in the longitudinal direction for selectively confronting and/or contacting output surface (6330) when pusher member (166) is at an initial proximal position.

In this regard, output surface (6330) is configured to be substantially entirely aligned with catch surface (6352) in the longitudinal direction when pusher member (166) is at its initial proximal position with lockout lever (6320) in the fully locked state, such that output surface (6330) is substantially parallel to catch surface (6352) and such that a substantial entirety of output surface (6330) confronts and/or contacts catch surface (6352) as shown in FIG. 93A. For example, output surface (6330) may be positioned at a substantially same height as that of catch surface (6352) relative to the floor of lower jaw (152). Thus, output surface (6330) may fully abut or otherwise engage catch surface (6352) to restrict distal movement of catch surface (6352) together with pusher member (166). In this manner, output surface (6330) and catch surface (6352) may be configured to cooperate with each other to inhibit distal actuation of pusher member (166) when pusher member (166) is at its initial proximal position with lockout lever (6320) in the fully locked state.

Output surface (6330) is also configured to be partially aligned with catch surface (6352) in the longitudinal direction when pusher member (166) is at its initial proximal position with lockout lever (6320) in the partially locked state, such that output surface (6330) is obliquely oriented relative to catch surface (6352) and such that an upper portion of output surface (6330) confronts and/or contacts catch surface (6352) as shown in FIG. 93B. For example, the upper portion of output surface (6330) may be positioned at a substantially same height as that of catch surface (6352) relative to the floor of lower jaw (152). Thus, output surface (6330) may partially abut or otherwise engage catch surface (6352) to restrict distal movement of catch surface (6352) together with pusher member (166). In this manner, output surface (6330) and catch surface (6352) may be configured to cooperate with each other to inhibit distal actuation of pusher member (166) when pusher member (166) is at its initial proximal position with lockout lever (6320) in the partially locked state.

Output surface (6330) is further configured to be offset from catch surface (6352) in the longitudinal direction when pusher member (166) is at its initial proximal position with lockout lever (6320) in the unlocked state, such that output surface (6330) is obliquely oriented relative to catch surface (6352) and such that no portion of output surface (6330) confronts and/or contacts catch surface (6352) as shown in FIG. 93C. For example, output surface (6330) may be positioned at a substantially lower height than that of catch surface (6352) relative to the floor of lower jaw (152). Thus, output surface (6330) may be fully disengaged from catch surface (6352) to permit distal movement of catch surface (6352) together with pusher member (166). In this manner, output surface (6330) and catch surface (6352) may be configured to disengage from each other to permit distal actuation of pusher member (166) when pusher member (166) is at its initial proximal position with lockout lever (6320) in the unlocked state.

During operation, lockout lever (6320) may initially be in the fully locked state when staple cartridge (154) is absent from lower jaw (152), as shown in FIG. 93A, such that output surface (6330) fully engages catch surface (6352). A closing and/or firing of end effector (6310) in the absence of staple cartridge (154) may then be initiated, such as by transmitting distal motion to pusher member (166) from moveable member (128) via push rod (168). However, distal actuation of pusher member (166) may be inhibited by the engagement between output surface (6330) and catch surface (6352), thereby preventing the closing and/or firing from being completed.

A spent staple cartridge (154) (e.g., with wedge sled (170) either absent or located distally of its initial proximal position) may subsequently be installed within lower jaw (152), thereby allowing proximal end (176) of staple cartridge (154) to cammingly engage upper input surface (6334), as indicated by arrow (A1) in FIG. 93B, such that output surface (6330) partially disengages catch surface (6352), as indicated by arrow (A2) in FIG. 93B. A closing and/or firing of end effector (6310) with spent staple cartridge (154) may then be initiated, such as by transmitting distal motion to pusher member (166) from moveable member (128) via push rod (168). However, distal actuation of pusher member (166) may continue to be inhibited by the partial engagement between output surface (6330) and catch surface (6352), thereby preventing the firing from being completed. In some versions, slight distal actuation of pusher member (166) may be permitted by the partial disengagement of output surface (6330) from catch surface (6352), thereby allowing the closing to be completed.

A full staple cartridge (154) (e.g., with wedge sled (170) at its initial proximal position) may then be installed within lower jaw (152), thereby allowing the proximal portion of wedge sled (170) to cammingly engage lower input surface (6332), as indicated by arrow (A3) in FIG. 93C, such that output surface (6330) fully disengages catch surface (6352), as indicated by arrow (A4) in FIG. 93C. A closing and/or firing of end effector (6310) with full staple cartridge (154) may then be initiated, such as by transmitting distal motion to pusher member (166) from moveable member (128) via push rod (168). In this regard, distal actuation of pusher member (166) may be permitted by the disengagement of output surface (6330) from catch surface (6352), thereby allowing the closing and/or firing to be completed.

It will be appreciated that during firing of end effector (6310), wedge sled (170) is advanced distally via the distal actuation of pusher member (166) such that the proximal portion of wedge sled (170) disengages lower input surface (6332). Due to the resilient biasing of lockout lever (6320) toward its fully locked state via compression spring (6340), lockout lever (6320) may then automatically return to its partially locked state in which proximal end (176) of staple cartridge (154) engages upper input surface (6334). In instances where pusher member (166) is retracted to its initial proximal position after firing while spent staple cartridge (154) remains installed within lower jaw (152), output surface (6330) may resume partially engaging catch surface (6352), thereby preventing further firing of end effector (6310) with spent staple cartridge (154). In some versions, further closing of end effector (6310) with spent staple cartridge (154) may be permitted. In any event, spent staple cartridge (154) may be removed from lower jaw (152) after firing such that proximal end (176) of staple cartridge (154) disengages upper input surface (6334). Due to the resilient biasing of lockout lever (6320) toward its fully locked state via compression spring (6340), lockout lever (6320) may then automatically return to its fully locked state. In instances where pusher member (166) is retracted to its initial proximal position after firing, output surface (6330) may resume fully engaging catch surface (6352), thereby preventing further closing and/or firing of end effector (6310) in the absence of staple cartridge (154).

In some versions, when pusher member (166) is retracted toward its initial proximal position after firing, the ramp surface (6354) of detent (6350) may cammingly engage a portion of lockout lever (6320) (e.g., a distal end of a laterally-inwardly extending detent whose proximal end at least partially defines output surface (6330)) to thereby urge lockout lever (6320) from the fully and/or partially locked state toward the unlocked state to permit retraction of pusher member (166) to its initial proximal position. In this regard, ramp surface (6354) may be oriented at a predetermined angle selected to provide a desired camming engagement with such a portion of lockout lever (6320) for urging lockout lever (6320) from the fully and/or partially locked state toward the unlocked state.

B. Second Exemplary Lockout Mechanism

FIGS. 94A-94C show a proximal portion of another exemplary end effector (6410) for use with surgical instrument (110) described above, and further show a distal portion of shaft assembly (114) of surgical instrument (110) including moveable feature (128). End effector (6410) is similar to end effector (116) described above except as otherwise described below. In this regard, end effector (6410) includes upper and lower jaws (150, 152) and driving assembly (164) having pusher member (166) configured to be selectively operatively coupled with moveable feature (128) via push rod (168).

As shown in FIGS. 94A-94C, end effector (6410) includes at least a portion of a lockout mechanism that includes a lockout lever (6420) pivotably coupled to the channel of lower jaw (152) via a pivot pin (6422). For example, pivot pin (6422) may pivotably couple lockout lever (6420) to a pivot block (6423) extending upwardly from a floor of the channel of lower jaw (152), such that lockout lever (6420) is positioned within the channel. In the example shown, lockout lever (6420) includes a proximal longitudinal portion (6424), an intermediate angled portion (6426) extending upwardly and distally from a distal end of proximal longitudinal portion (6424), and a distal longitudinal portion (6428) extending distally from a distal end of intermediate angled portion (6426), such that lockout lever (6420) has a generally Z-shaped profile. In the example shown, pivot pin (6422) is received within a bore provided in intermediate angled portion (6426). Lockout lever (6420) of the present version further includes a detent (6429) extending upwardly and/or laterally inwardly from a proximal region of proximal longitudinal portion (6424).

As shown, a distal end of detent (6429) defines an output surface (6430) and a distal end of distal longitudinal portion (6428) defines an input surface (6432), the purposes of which are described below. At least a portion of lockout lever (6420), such as distal longitudinal portion (6428), may be spaced apart from the laterally inner surface of an adjacent sidewall of the channel of lower jaw (152) by a clearance gap sufficiently sized to accommodate a laterally outer sidewall of staple cartridge (154). In this manner, distal longitudinal portion (6428) may be configured to extend distally through proximal end (176) into an interior of staple cartridge (154) for accessing wedge sled (170) when staple cartridge (154) is installed within the channel of lower jaw (152), as described in greater detail below. In addition, or alternatively, any one or more of proximal longitudinal portion (6424), intermediate angled portion (6426), and/or distal longitudinal portion (6428) may be positioned laterally outwardly relative to pusher member (166) to avoid interfering with distal actuation of pusher member (166).

With continuing reference to FIGS. 94A-94C, lockout lever (6420) is pivotable relative to the channel of lower jaw (152) about a fulcrum defined by pivot pin (6422) between an unlatched state (FIGS. 94A and 94B) and a latched state (FIG. 94C). More particularly, lockout lever (6420) of the present version is configured to be pivoted in a counter-clockwise direction from the unlatched state toward the latched state. In the example shown, lockout lever (6420) is resiliently biased toward the unlatched state via a compression spring (6440) positioned distally of pivot pin (6422) and extending between a bottom of distal longitudinal portion (6428) and a recess (6441) provided in the floor of the channel of lower jaw (152). It will be appreciated that lockout lever (6420) may be resiliently biased toward the unlatched state in any other suitable manner, such as via a suitably-positioned tension spring, torsion spring, or any other suitable biasing member.

As best shown in FIG. 94C, input surface (6432) is configured to be cammingly engaged by a portion of wedge sled (170), such as a proximal portion thereof, when staple cartridge (154) is installed within the channel of lower jaw (152) with wedge sled (170) in its initial proximal position for urging lockout lever (6420) from the unlatched state to the latched state. In this regard, input surface (6432) may be positioned at a predetermined location and/or oriented at a predetermined angle selected to provide a desired camming engagement with the proximal portion of wedge sled (170) when wedge sled (170) is in its initial proximal position for urging lockout lever (6420) from the unlatched state to the latched state. In some versions, input surface (6432) may be configured to only provide the desired camming engagement with compatible wedge sleds having a predetermined size and/or geometry. For example, compatible wedge sleds may have substantially the same size and/or geometry as that of wedge sled (170) (e.g., at least the proximal portion thereof), such that input surface (6432) may not be capable of providing the desired camming engagement with incompatible wedge sleds having substantially different sizes and/or geometries from those of wedge sled (170). In this manner, lockout lever (6420) may be configured to remain in the unlatched state when a staple cartridge having an incompatible wedge sled is installed within the channel of lower jaw (152). Likewise, lockout lever (6420) may be configured to remain in the unlatched state when staple cartridge (154) having wedge sled (170) is installed within the channel of lower jaw (152) with wedge sled (170) located distally of its initial proximal position.

In the present version, the lockout mechanism also includes a stop pin (6450) fixedly coupled to pusher member (166) and extending laterally outwardly therefrom. As shown, a proximal end of stop pin (6450) defines a semi-circular catch surface (6452). Catch surface (6452) is configured to be distal of and selectively aligned with output surface (6430) of lockout lever (6420) in the longitudinal direction for selectively confronting and/or contacting output surface (6430) when pusher member (166) is at an initial proximal position.

In this regard, output surface (6430) is configured to be at least partially aligned with catch surface (6452) in the longitudinal direction when pusher member (166) is at its initial proximal position with lockout lever (6320) in the latched state, such that at least a portion of output surface (6430) confronts and/or contacts catch surface (6452) as shown in FIG. 94C. For example, output surface (6430) may be positioned at a substantially same height as that of catch surface (6452) relative to the floor of lower jaw (152). Thus, output surface (6430) may at least partially abut or otherwise engage catch surface (6452) to restrict proximal movement of catch surface (6452) together with pusher member (166). In this manner, output surface (6430) and catch surface (6452) may be configured to cooperate with each other to inhibit proximal pulling of pusher member (166) when pusher member (166) is at its initial proximal position with lockout lever (6420) in the latched state.

Output surface (6430) is further configured to be offset from catch surface (6452) in the longitudinal direction when pusher member (166) is at its initial proximal position with lockout lever (6420) in the unlatched state, such that no portion of output surface (6430) confronts and/or contacts catch surface (6452) as shown in FIGS. 94A and 94B. For example, output surface (6430) may be positioned at a substantially lower height than that of catch surface (6452) relative to the floor of lower jaw (152). Thus, output surface (6430) may be fully disengaged from catch surface (6452) to permit proximal movement of catch surface (6452) together with pusher member (166). In this manner, output surface (6430) and catch surface (6452) may be configured to disengage from each other to permit proximal pulling of pusher member (166) when pusher member (166) is at its initial proximal position with lockout lever (6420) in the unlatched state.

In the present version, the lockout mechanism further includes at least one transmission member in the form of a laterally-opposed pair of spring-loaded push pins (6460) (one shown) positioned at a distal region of moveable feature (128). Each push pin (6460) is configured to move in the lateral direction between a retracted state in which push pin (6460) is substantially housed within moveable feature (128) and an extended state in which push pin (6460) protrudes from moveable feature (128) in the lateral direction (e.g., laterally inwardly). Push pins (6460) may be resiliently biased toward the respective extended states by any suitable biasing member(s).

With continuing reference to FIGS. 94A-94C, moveable feature (128) is translatable relative to push rod (168) between a disengaged state (FIGS. 94A and 94B) and an engaged state (FIG. 94C). More particularly, moveable feature (128) of the present version is configured to be translated distally from the disengaged state toward the engaged state. In the example shown, moveable feature (128) is resiliently biased distally relative to push rod (168) toward the disengaged state via a compression spring (6462). In this regard, a distal ledge (6464) is fixedly coupled to moveable feature (128) via a longitudinal support (6466) extending between a lower, distal region of moveable feature (128) and a lower, proximal region of distal ledge (6464). Compression spring (6462) extends proximally from a proximal end of distal ledge (6464) toward distal ends of a laterally-opposed pair of proximal flag(s) (6468) (one shown) which extend downwardly and/or proximally from push rod (168). In some versions, proximal flag(s) (6468) may extend downwardly from one or more respective band(s) extending proximally from push rod (168). It will be appreciated that moveable feature (128) may be resiliently biased toward the disengaged state in any other suitable manner, such as via a suitably-positioned tension spring or any other suitable biasing member.

Push pins (6460) are configured to be offset from the corresponding flags (6468) in the lateral direction when moveable feature (128) is in the engaged state, such that push pins (6460) may resiliently return to their respective extended states as shown in FIG. 94C. For example, push pins (6460) may each be positioned proximally of the corresponding flag (6468). Thus, the distal ends of push pins (6460) may at least partially abut or otherwise engage the proximal ends of the corresponding flags (6468) to permit transmission of distal motion from push pins (6460) to flags (6468) and thereby operatively couple pusher member (166) with moveable feature (128). In this manner, push pins (6460) and flags (6468) may be configured to cooperate with each other to permit distal actuation of pusher member (166) when moveable feature (128) is in the engaged state.

Push pins (6460) are further configured to be at least partially aligned with the corresponding flags (6468) in the lateral direction when moveable feature (128) is in the disengaged state, such that push pins (6460) may be urged toward their respective retracted states by the laterally outer surfaces of the corresponding flags (6468) as shown in FIGS. 94A and 94B. For example, push pins (6460) may each be positioned at a substantially same longitudinal position as that of at least a portion of the corresponding flag (6468). Thus, the distal ends of push pins (6460) may be distal of, and thus disengaged from, the proximal ends of the corresponding flags (6468) to restrict transmission of distal motion from push pins (6460) to flags (6468) and thereby operatively decouple pusher member (166) from moveable feature (128). In this manner, push pins (6460) and flags (6468) may be configured to cooperate with each other to inhibit distal actuation of pusher member (166) when moveable feature (128) is in the disengaged state.

During operation, lockout lever (6420) may initially be in the unlatched state and moveable feature (128) may initially be in the disengaged state when staple cartridge (154) is absent from lower jaw (152), as shown in FIG. 94A, such that output surface (6430) is disengaged from catch surface (6452) and such that push pins (6460) engage the laterally outer surfaces of flags (6468) and are thereby urged to their retracted states. A closing and/or firing of end effector (6410) in the absence of staple cartridge (154) may then be initiated, such as by translating moveable feature (128) slightly proximally relative to end effector (6410), as indicated by arrow (A5) in FIG. 94B, prior to translating moveable feature (128) distally for attempting distal actuation of pusher member (166). Such initial, slight proximal translation may detect whether a full staple cartridge (154) is installed within lower jaw (152). In this regard, proximal pulling of pusher member (166) from its initial proximal position by moveable feature (128) via compression spring (6462) may be permitted by the disengagement of output surface (6430) from catch surface (6452), as indicated by arrow (A6) in FIG. 94B, to maintain moveable feature (128) in the disengaged state (e.g., with push pins (6460) being translated slightly proximally together with the corresponding flags (6468)), thereby maintaining push pins (6460) in their retracted states such that the distal ends of push pins (6460) remain disengaged from the proximal ends of flags (6468). Thus, distal actuation of pusher member (166) may be inhibited by the disengagement of the distal ends of push pins (6460) from the proximal ends of flags (6468) resulting from the disengagement of output surface (6430) from catch surface (6452), thereby preventing the closing and/or firing from being completed. More particularly, distal translation of moveable feature (128) following the slight proximal translation of moveable feature (128) may be performed without transmitting sufficient distal motion from push pins (6460) to flags (6468) for achieving distal actuation of pusher member (166).

A full staple cartridge (154) (e.g., with wedge sled (170) at its initial proximal position) may then be installed within lower jaw (152), thereby allowing the proximal portion of wedge sled (170) to cammingly engage input surface (6432), as indicated by arrow (A7) in FIG. 94C, such that output surface (6430) engages catch surface (6452), as indicated by arrow (A8) in FIG. 94C. A closing and/or firing of end effector (6410) with full staple cartridge (154) may then be initiated, such as by translating moveable feature (128)

slightly proximally relative to end effector (6410) as described above and as indicated by arrow (A9) in FIG. 94C. In this regard, proximal pulling of pusher member (166) from its initial proximal position by moveable feature (128) via compression spring (6462) may be restricted by the engagement of output surface (6430) with catch surface (6452) to allow moveable feature (128) to translate distally relative to push rod (168) toward the engaged state (e.g., with push pins (6460) being translated slightly proximally relative to the corresponding flags (6468)) while compressing compression spring (6462), thereby allowing push pins (6460) to resiliently return to their extended states such that the distal ends of push pins (6460) engage the proximal ends of flags (6468). Thus, distal actuation of pusher member (166) may be permitted by the engagement between push pins (6460) and the proximal ends of flags (6468) resulting from the engagement of output surface (6430) with catch surface (6452), thereby allowing the closing and/or firing to be completed. More particularly, distal translation of moveable feature (128) following the slight proximal translation of moveable feature (128) may be performed while transmitting sufficient distal motion from push pins (6460) to flags (6468) for achieving distal actuation of pusher member (166).

It will be appreciated that during firing of end effector (6410), wedge sled (170) is advanced distally via the distal actuation of pusher member (166) such that the proximal portion of wedge sled (170) disengages input surface (6432). Due to the resilient biasing of lockout lever (6420) toward its unlatched state via compression spring (6440), lockout lever (6420) may then automatically return to its unlatched state. In instances where pusher member (166) is retracted to its initial proximal position after firing while spent staple cartridge (154) remains installed within lower jaw (152), output surface (6430) may remain disengaged from catch surface (6452), thereby preventing further closing and/or firing of end effector (6410) with spent staple cartridge (154). In any event, spent staple cartridge (154) may be removed from lower jaw (152) after firing, such that output surface (6430) may remain disengaged from catch surface (6452), thereby preventing further closing and/or firing of end effector (6410) in the absence of staple cartridge (154).

C. Third Exemplary Lockout Mechanism

FIGS. 95-98 show a proximal portion of another exemplary end effector (6510) for use with surgical instrument (110) described above, and further show a distal portion of shaft assembly (114) of surgical instrument (110) including moveable feature (128), which is moveably housed within an outer tube (6512). End effector (6510) is similar to end effector (116) described above except as otherwise described below. In this regard, end effector (6510) includes upper and lower jaws (not shown), such as upper and lower jaws (150, 152), and driving assembly (164) having a pusher member (not shown), such as pusher member (166), configured to be selectively operatively coupled with moveable feature (128) via push rod (168).

As shown in FIGS. 95, 96B, and 97-98, end effector (6510) includes at least a portion of a lockout mechanism that includes a lockout hook (6520) extending proximally from push rod (168). In some versions, lockout hook (6520) may extend proximally from one or more bands extending proximally from push rod (168). In the example shown, lockout hook (6520) includes a proximal lateral portion (6524), an intermediate longitudinal portion (6526) extending distally from a first lateral end of proximal lateral portion (6524) to a lateral end of a distal lateral portion (6528) coupled to push rod (168), such that lockout hook (6520) has a generally C-shaped profile. As shown, proximal lateral portion (6524), intermediate longitudinal portion (6526), and distal lateral portion (6528) collectively define a recess (6530), the purpose of which is described below. In the present version, a proximal end of proximal lateral portion (6524) defines a ramp surface (6532) curved distally in a laterally-outward direction and positioned at or near a second lateral end of proximal lateral portion (6524) opposite the first lateral end of proximal lateral portion (6524).

With reference to FIGS. 96A-98, lockout hook (6520) is translatable relative to outer tube (6512) of shaft assembly (114) between an unavailable state in which recess (6530) is distal of a predetermined pickup location (FIGS. 96A and 98) and an available state in which recess (6530) is at the predetermined pickup location (FIGS. 96B and 97), as described in greater detail below. More particularly, lockout hook (6520) of the present version is configured to be translated proximally from the unavailable state toward the available state. Lockout hook (6520) may be resiliently biased toward the unavailable state via a suitably-positioned compression spring, tension spring, or any other suitable biasing member (not shown).

A portion of driving assembly (164), such as pusher member (166), may define an input surface (not shown) configured to be engaged by a portion of wedge sled (170), such as a proximal portion thereof, when staple cartridge (154) is installed within the channel of lower jaw (152) with wedge sled (170) in its initial proximal position for urging pusher member (166) slightly proximally from its initial proximal position, thereby urging lockout hook (6520) from the unavailable state to the available state. In this regard, the input surface may be positioned at a predetermined location and/or oriented at a predetermined angle selected to provide a desired pushing engagement with the proximal portion of wedge sled (170) when wedge sled (170) is in its initial proximal position for urging lockout hook (6520) from the unavailable state to the available state. In some versions, the input surface may be configured to only provide the desired pushing engagement with compatible wedge sleds having substantially the same size and/or geometry of wedge sled (170) (e.g., at least the proximal portion thereof), such that the input surface may not be capable of providing the desired pushing engagement with incompatible wedge sleds having substantially different sizes and/or geometries from those of wedge sled (170). In this manner, lockout hook (6520) may be configured to remain in the unavailable state when a staple cartridge having an incompatible wedge sled is installed within the channel of lower jaw (152). Likewise, lockout hook (6520) may be configured to remain in the unavailable state when staple cartridge (154) having wedge sled (170) is installed within the channel of lower jaw (152) with wedge sled (170) located distally of its initial proximal position.

In the present version, the lockout mechanism also includes at least one transmission member in the form of a detent (6560) extending in a first radial direction (e.g., laterally or transversely) from a longitudinal support (6566) which extends distally from moveable feature (128). A tooth (6570) extends from moveable feature (128) in a second radial direction perpendicular to the first radial direction. For example, detent (6560) may extend one of laterally or transversely from longitudinal support (6566) and tooth (6570) may extend the other of laterally or transversely from moveable feature (128), as described in greater detail below.

With continuing reference to FIGS. 96A-96B, moveable feature (128) is twistable relative to outer tube (6512) between a proximal state (FIG. 96A) and an intermediate state (FIG. 96B), and is translatable relative to outer tube (6512) between the intermediate state and a distal state (not shown). More particularly, moveable feature (128) of the present version is configured to be twisted counterclockwise and distally from the proximal state toward the intermediate state, and to be translated distally from the intermediate state to the distal state. In this regard, outer tube (6512) includes a groove (also referred to as a thread) (6580) extending radially outwardly from a radially inner surface of outer tube (6512) and configured to slidably receive tooth (6570) for guiding movement of moveable feature (128) relative to outer tube (6512). In the example shown, groove (6580) includes a proximal quarter-helical groove portion (6582) for guiding twisting of moveable feature (128) relative to outer tube (6512) and a distal longitudinal groove portion (6584) for guiding translation of moveable feature (128) relative to outer tube (6512). Proximal quarter-helical groove portion (6582) is configured to guide tooth (6570) from a first orientation about the longitudinal axis in which tooth (6570) extends transversely from moveable feature (128) such that detent (6560) extends laterally from longitudinal support (6566) proximal of the predetermined pickup location when moveable feature (128) is in the proximal state (FIG. 96A) to a second orientation about the longitudinal axis in which tooth (6570) extends laterally from moveable feature (128) such that detent (6560) extends transversely from longitudinal support (6566) at the predetermined pickup location when moveable feature (128) is in the intermediate state (FIG. 96B). Distal longitudinal groove portion (6584) is configured to maintain tooth (6570) in the second orientation such that tooth (6570) continues extending laterally from moveable feature (128) and detent (6560) continues extending transversely from longitudinal support (6566) when moveable feature is between the intermediate and distal states. In this manner, tooth (6570) and groove (6580) may be configured to cooperate with each other to reorient detent (6560) about the longitudinal axis during twisting of moveable feature (128) from the proximal state to the intermediate state, and to maintain the orientation of detent (6560) about the longitudinal axis during translation of moveable feature (128) from the intermediate state to the distal state. Moveable feature (128) may be resiliently biased toward the proximal state via a suitably-positioned compression spring, tension spring, torsion spring, or any other suitable biasing member (not shown).

Detent (6560) is configured to be at least partially aligned with recess (6530) in the transverse direction when moveable feature (128) is in the intermediate state with lockout hook (6520) in the available state, such that detent (6560) may be received within recess (6530) as shown in FIGS. 96B and 97. For example, detent (6560) and recess (6530) may each be positioned at the predetermined pickup location. Thus, the distal end of detent (6560) may at least partially abut or otherwise engage the distal end of recess (6530) to permit transmission of distal motion from detent (6560) to recess (6530) and thereby operatively couple pusher member (166) with moveable feature (128). In this manner, detent (6560) and recess (6530) may be configured to cooperate with each other to permit distal actuation of pusher member (166) when moveable feature (128) is in the intermediate state with lockout hook (6520) in the available state.

Detent (6560) is further configured to be offset from recess (6530) in the transverse direction when moveable feature (128) is in the intermediate state with lockout hook (6520) in the unavailable state, such that detent (6560) may be positioned outside of recess (6530) as shown in FIG. 98. For example, detent (6560) may be positioned at the predetermined pickup location while recess (6530) may be positioned distal of the predetermined pickup location such that the distal end of detent (6560) is disengaged from the distal end of recess (6530). In some versions, detent (6560) may be configured to cammingly engage ramp surface (6532) of lockout hook (6520) to thereby urge lockout hook (6520) laterally away from detent (6560) and thereby permit detent (6560) to bypass recess (6530) distally without being received therein, such that the distal end of detent (6560) remains disengaged from the distal end of recess (6540) to restrict transmission of distal motion from detent (6560) to recess (6530) and thereby operatively decouple pusher member (166) from moveable feature (128). In this manner, detent (6560) and recess (6530) may be configured to cooperate with each other to inhibit distal actuation of pusher member (166) when moveable feature (128) is in the intermediate state with lockout hook (6520) in the unavailable state.

During operation, lockout hook (6520) may initially be in the unavailable state in which recess (6530) is distal of the predetermined pickup location and moveable feature (128) may initially be in the proximal state when staple cartridge (154) is absent from lower jaw (152), as shown in FIG. 96A, such that detent (6560) is positioned outside of recess (6530) with the distal end of detent (6560) disengaged from the distal end of recess (6530). A closing and/or firing of end effector (6510) in the absence of staple cartridge (154) may then be initiated, such as by transmitting distal motion to moveable member (128) via portions of drive train (126), thereby twisting moveable feature from the proximal state to the intermediate state as proximal quarter-helical groove portion (6582) guides tooth (6570) from the first orientation to the second orientation for reorienting detent (6560) to extend transversely from longitudinal support (6566) at the predetermined pickup location, as shown in FIG. 98. However, detent (6560) may remain outside of recess (6530) such that the distal end of detent (6560) remains disengaged from the distal end of recess (6530). Thus, distal actuation of pusher member (166) may be inhibited by the disengagement of the distal end of detent (6560) from the distal end of recess (6530), thereby preventing the closing and/or firing from being completed. More particularly, distal translation of moveable feature (128) from the intermediate state to the distal state may be performed without transmitting sufficient distal motion from detent (6560) to recess (6530) for achieving distal actuation of pusher member (166). In this regard, detent (6560) may cammingly engage ramp surface (6532) of lockout hook (6520) during distal translation of moveable feature (128) toward the distal state as described above to permit detent (6560) to bypass recess (6530) distally without being received therein.

A full staple cartridge (154) (e.g., with wedge sled (170) at its initial proximal position) may then be installed within lower jaw (152), thereby allowing the proximal portion of wedge sled (170) to push the input surface of pusher member (166) for urging lockout hook (6520) from the unavailable state to the available state in which recess (6530) is at the predetermined pickup location, as indicated by arrow (A10) in FIG. 96B. A closing and/or firing of end effector (6510) with full staple cartridge (154) may then be initiated, such as by transmitting distal motion to moveable member (128) via one or more portions of drive train (126), as indicated by arrow (A11) in FIG. 96B, thereby twisting moveable feature from the proximal state to the intermediate state as proximal quarter-helical groove portion (6582) guides tooth (6570) from the first orientation to the second orientation for reorienting detent (6560) to extend transversely from longitudinal support (6566) at the predetermined pickup location, as indicated by arrow (A12) in FIG. 96B. In this regard, detent (6560) may be received within recess (6530) at the predetermined pickup location such that the distal end of detent (6560) engages the distal end of recess (6530), as shown in FIG. 97. Thus, distal actuation of pusher member (166) may be permitted by the engagement of the distal end of detent (6560) with the distal end of recess (6530), thereby allowing the closing and/or firing to be completed. More particularly, distal translation of moveable feature (128) from the intermediate state to the distal state may be performed while transmitting sufficient distal motion from detent (6560) to recess (6530) for achieving distal actuation of pusher member (166).

It will be appreciated that during firing of end effector (6510), wedge sled (170) is advanced distally via the distal actuation of pusher member (166), such that the proximal portion of wedge sled (170) may disengage the input surface of pusher member (166) upon retraction of pusher member (166) to its initial proximal position. In some versions, retraction of pusher member (166) may be achieved by translating moveable feature (128) from the distal state to the intermediate state via engagement of the proximal end of detent (6560) with the proximal end of recess (6530), such that lockout hook (6520) may be returned to the available state. Twisting moveable feature (128) from the intermediate state to the proximal state may then remove detent (6560) from recess (6530) such that the proximal end of detent (6560) may disengage the proximal end of recess (6530). Due to the resilient biasing of lockout hook (6520) toward its unavailable state, lockout hook (6520) may then automatically return to its unavailable state in which recess (6530) is distal of the predetermined pickup location. In instances where pusher member (166) is retracted to its initial proximal position after firing while spent staple cartridge (154) remains installed within lower jaw (152), the proximal portion of wedge sled (170) may remain disengaged from the input surface of pusher member (166), thereby preventing further closing and/or firing of end effector (6510) with spent staple cartridge (154). In any event, spent staple cartridge (154) may be removed from lower jaw (152) after firing such that the proximal portion of wedge sled (170) may remain disengaged from the input surface of pusher member (166), thereby preventing further closing and/or firing of end effector (6410) in the absence of staple cartridge (154).

XI. Exemplary Alternative Staple Cartridges with Sled Restriction Features

In some examples, structures similar to wedge sled (170) may include sharp tissue cutting features similar to knife member (172) and/or cutting edge (194). Incorporation of such sharp features into structures similar to wedge sled (170) may be desirable in some circumstances to, for example, promote tissue cutting in a relatively tight sequence with stapling. However, in other examples, it may be desirable to incorporate such sharp features into other components like firing beam (216) discussed above. Such a configuration may be desirable to avoid premature engagement between sharp features and other surfaces such as tissue, tubes, sutures, or ancillary clinical equipment. Thus, in some contexts it may be desirable to incorporate features into structures similar to staple cartridge (154) to provide additional control over structures similar to wedge sled (170) to obtain the benefits of incorporating certain sharp features into structures similar to wedge sled (170) while also retaining the benefits associated with such sharp features being incorporated into other alternative structures.

Although various embodiments are described herein as including additional control structures, it should be understood that in other examples other alternative features may be added to the embodiments described herein without departing from the concepts described herein. Additionally, some specific features of the embodiments described herein may be combined with other specific features of other embodiments also without departing from the concepts described herein. Various suitable combinations of features will be apparent to those skilled in the art in view of the teachings herein.

A. Exemplary Alternative Staple Cartridge with Pan Having Restriction Feature FIG. 99 shows an exemplary alternative staple cartridge (7454) that may be readily used with end effector (116, 210) described above in lieu of staple cartridges (154, 254). Staple cartridge (7454) is substantially similar to staple cartridge (154) described above, unless where otherwise noted herein. For instance, like with staple cartridge (154), staple cartridge (7454) of the present example includes a staple cartridge body (7456) that is configured to house a firing assembly (7458), a plurality of staple drivers (not shown), and a plurality of staples (not shown). As with firing assembly (158) described above, firing assembly (7458) of the present example includes a wedge sled (7470) and a knife member (7472) (see FIG. 101A).

Staple cartridge body (7456) of the present example is similar to staple cartridge body (156) in that staple cartridge body (7456) includes an array of staple accommodating apertures (7474) extending through an upper deck (7488) of staple cartridge body (7456). Staple cartridge (7454) includes proximal and distal ends (7476, 7478). In operation, staples (not shown) are sequentially deployed starting at proximal end (7476) by advancing wedge sled (7470) toward distal end (7478). A vertical slot (7480) configured to accommodate knife member (7472) through part of staple cartridge (7454) to permit a cutting edge (7494) to cut tissue as the staples are driven via wedge sled (7470).

Staple cartridge (7454) further includes a blade guard (7455) (also referred to as a cover, sheath, and/or compartment). Blade guard (7455) extends upwardly from upper deck (7488) and is disposed at a proximal end of cartridge body (7456). In the present example, blade guard (7455) is defined by two upwardly extending slats disposed on each side of vertical slot (7480). As will be understood, blade guard (7455) is configured to contain knife member (7472) to avoid inadvertent contact with cutting edge (7494) when staple cartridge (7454) is not in use. As such, the particular position of blade guard (7455) relative to cartridge body (7456) corresponds to a proximal or home position of wedge sled (7470).

As best seen in FIGS. 99 and 100, staple cartridge (7454) of the present example includes a cartridge tray (7410) (also referred to as a pan). Although not described above, it should be understood that staple cartridge (154) may also include structures similar to cartridge tray (7410) in some examples. Cartridge tray (7410) of the present example is configured to snap-fit, clip, or otherwise couple to a lower portion of cartridge body (7456). In some examples, cartridge tray (7410) comprises a metallic material to provide added structural rigidity to staple cartridge (7454).

Cartridge tray (7410) of the present example includes a floor (7412) and a pair of sidewalls (7414) extending from a proximal end (7418) of cartridge tray (7410). A longitudinal slot (7416) is defined by floor (7412) extending from proximal end (7418) of cartridge tray (7410). Longitudinal slot (7416) is generally configured to permit a portion of actuation assembly (164) to pass through cartridge tray (7410) for engagement of second flange (185) with longitudinal slot (187) of lower jaw (152).

Cartridge tray (7410) further includes a restriction feature (7420). As will be described in greater detail below, restriction feature (7420) is generally configured to manipulate wedge sled (7470) to avoid premature and/or unintended actuation of wedge sled (7470). In other words, restriction feature (7420) is generally configured to prevent unintended movement of wedge sled (7470), yet permit intended movement of wedge sled (7470).

Restriction feature (7420) of the present example includes a pair of retainers (7422, 7424) extending upwardly from floor (7412). The particular extension of each retainer (7422, 7424) in the present example is generally about perpendicular to a longitudinal axis defined by floor (7412), although other angles of extension relative to floor may be used in other examples. Each retainer (7422, 7424) is positioned proximate proximal end (7418) of cartridge tray (7410). As will be described in greater detail below, this positioning is generally configured to correspond to an initial positioning of wedge sled (7470).

The construction of each retainer (7422, 7424) of the present example is integral with floor (7412) and positioned on opposite sides of longitudinal slot (7416). Specifically, each retainer (7422, 7424) is defined by a cutout portion of floor (7412) that is bent upwardly or perpendicularly relative to the extension of floor (7412). Thus, each retainer (7422, 7424) in the present example is generally of the same material of floor (7412). As described above, the particular material used may be metal or other similarly rigid materials. Although an integral construction is used in the present example for each retainer (7422, 7424), it should be understood that in other examples each retainer (7422, 7424) may be an independent component from floor (7412) and coupled thereto.

Each retainer (7422, 7424) in the present example is configured to have at least some rigidity. As will be described in greater detail below, such rigidity may permit each retainer (7422, 7424) to hold wedge sled (7470) in a predetermined position. Additionally, such rigidity may also be configured in some examples to provide additional structural rigidity to cartridge tray (7410), particularly at the interface between floor (7412) and each retainer (7422, 7424).

Each retainer (7422, 7424) in the present example is also configured to have at least some flexibility. As will also be described in greater detail below, such flexibility may permit each retainer (7422, 7424) to move in response to movement of wedge sled (7470) driven by pusher member (166). In other words, each retainer (7422, 7424) may be configured to permit intentional movement of wedge sled (7470) via flexibility of each retainer (7422, 7424), yet prevent incidental movement of wedge sled (7470) via rigidity of each retainer (7422, 7424).

FIGS. 101A and 101B show an exemplary use of restriction feature (7420) in connection with wedge sled (7470). As can be seen, wedge sled (7470) begins proximate proximal end (7418) of cartridge tray (7410) with knife member (7472) disposed within blade guard (7455). This position of wedge sled (7470) may also correspond to wedge sled (7470) being proximate proximal end (7476) of staple cartridge (7454). In this position, restriction feature (7420) is configured to prevent incidental movement of wedge sled (7470) and thereby hold knife member (7472) within blade guard (7455). Specifically, each retainer (7422, 7424) is oriented approximately perpendicularly relative to floor (7412). As can be seen in FIG. 101A, this orientation blocks distal movement of wedge sled (7470), thereby holding wedge sled (7470) proximate proximal end (7418) and within blade guard (7455).

As described above, wedge sled (7470) may be driven distally within cartridge body (7456) to drive staples using wedge sled (7470) and server tissue using cutting edge (7494) of knife member (7472). As similarly described above with respect to wedge sled (170), wedge sled (7470) of the present example may be similarly driven by pusher member (166). As seen in FIG. 101B, once wedge sled (7470) is driven by pusher member (166), the force supplied by pusher member (166) may be sufficient to overcome the rigidity of each retainer (7422, 7424). This causes each retainer (7422, 7424) to move and/or pivot away from wedge sled (7470) from the upward orientation described above to a horizontal position about parallel to the extension of floor (7412).

Once each retainer (7422, 7424) is pushed to the horizontal position, wedge sled (7470) may be driven distally by pusher member (166) to drive staples and sever tissue. In the present example, each retainer (7422, 7424) is generally configured to bend in response to wedge sled (7470) being driven by pusher member (166). In other words, each retainer (7422, 7424) is deformed by wedge sled (7470) such that each retainer (7422, 7424) may remain in the horizontal position after wedge sled (7470) has been driven distally past each retainer (7422, 7424). This configuration may be desirable in some examples to, for example, prevent reuse of staple cartridge (7454).

In other examples, each retainer (7422, 7424) may alternatively have a resilient characteristic such that each retainer (7422, 7424) may return to the upwardly extended position after wedge sled (7470) has been driven distally past each retainer (7422, 7424). In other words, each retainer (7422, 7424) may be resiliently biased toward the upwardly extended position described above. In such examples, this resilient characteristic may be desirable to promote structural stability of cartridge tray (7410) during actuation of wedge sled (7470) distally. Examples of suitable cartridge trays (7410) having resilient characteristics are described in Section VI of the pending application entitled "Exemplary Firing System Features for Surgical Stapler.".

B. Exemplary Alternative Staple Cartridge with Movable Restriction Feature

FIG. 102 shows an exemplary alternative staple cartridge (7554) that may be readily used with end effector (116, 210) described above in lieu of staple cartridges (154, 254). Staple cartridge (7554) is substantially similar to staple cartridge (154) described above, unless where otherwise noted herein. For instance, like with staple cartridge (154), staple cartridge (7554) of the present example includes a staple cartridge body (7556) that is configured to house a firing assembly (7558), a plurality of staple drivers (not shown), and a plurality of staples (not shown). As with firing assembly (158) described above, firing assembly (7558) of the present example includes a wedge sled (7570) and a knife member (7572) (see FIG. 106A).

Staple cartridge body (7556) of the present example is similar to staple cartridge body (156) in that staple cartridge body (7556) includes an array of staple accommodating apertures (7574) extending through an upper deck (7588) of staple cartridge body (7556). Staple cartridge (7554) includes proximal and distal ends (7576, 7578). In operation, staples (not shown) are sequentially deployed starting at proximal end (7576) by advancing wedge sled (7570) toward distal end (7578) from proximal end (7576). A vertical slot (7580) configured to accommodate knife member (7572) through part of staple cartridge (7554) to permit a cutting edge (7594) to cut tissue as the staples are driven via wedge sled (7570).

Staple cartridge (7554) further includes a blade guard (7555) (also referred to as a cover, sheath, and/or compartment). Blade guard (7555) extends upwardly from upper deck (7588) and is disposed at a proximal end of cartridge body (7556). In the present example, blade guard (7555) is defined by two upwardly extending slats disposed on each side of vertical slot (7580). As will be understood, blade guard (7555) is configured to contain knife member (7572) to avoid inadvertent contact with cutting edge (7594) when staple cartridge (7554) is not in use. As such, the particular position of blade guard (7555) relative to cartridge body (7556) corresponds to a proximal or home position of wedge sled (7570).

Unlike staple cartridge (154) described above, staple cartridge (7554) of the present example includes a restriction feature (7520). Restriction feature (7520) is generally configured to move within cartridge body (7556) to selectively lock and unlock movement of wedge sled (7570). As will be described in greater detail below, a portion of restriction feature (7520) is generally configured to protrude from a portion of cartridge body (7556) proximate blade guard (7555). This portion of restriction feature (7520) is generally configured to engage a portion of end effector (116, 210) to move at least a portion of restriction feature (7520) and thereby unlock movement of wedge sled (7570).

As best seen in FIG. 103, restriction feature (7520) includes a body having an actuation portion (7524) and a lock portion (7530). Actuation portion (7524) includes a proximal ramp (7526) and a catch (7528). Proximal ramp (7526) is generally configured to engage a portion of end effector (116, 210) to drive movement of restriction feature (7520). The orientation of proximal ramp (7526) is such that a face is positioned toward proximal end (7576) of staple cartridge (7554). As will be understood, this orientation is generally configured to promote engagement between proximal ramp (7526) and a portion of end effector (116, 210). Proximal ramp (7526) is also oriented at an angle relative to the longitudinal extension of upper deck (7588). Proximal ramp (7526) may be oriented at a variety of suitable angles. For instance, in some examples, proximal ramp (7526) may be oriented at 35°, 45°, 65° or other suitable angles relative to the longitudinal extension of upper deck (7588).

Catch (7528) extends downwardly from proximal ramp (7526). In the present example, catch (7528) is configured to engage at least a portion of upper deck (7588) to provide at least some resistance to movement of restriction feature (7520). In some circumstances, this feature may be desirable to avoid inadvertent movement of restriction feature (7520). Catch (7528) of the present example is configured as a L-shaped ledge, shelf, or protrusion extending from proximal ramp (7526). In other examples, catch (7528) may take on a variety of forms such as one or more rounded or square-shaped detent, one or more ribs, and/or etc. In other examples, catch (7528) may be more or less prominent than the version shown. For instance, in some examples catch (7528) may protrude minimally or not at all from proximal ramp (7526). Instead, catch (7528) may simply be a roughened or knurled surface configured to engage upper deck (7588). In still other examples, catch (7528) may be omitted entirely.

As described above, lock portion (7530) includes a lock member (7532). As will be described in greater detail below, lock member (7532) is generally configured to selectively engage a portion of wedge sled (7570) to restrict movement of wedge sled (7570) within cartridge body (7556). Lock member (7532) is disposed on an opposite end of body (7522) relative to actuation portion (7524), proximal ramp (7526), and/or catch (7528). Specifically, body (7522) extends downward or laterally away from upper deck (7588) from actuation portion (7524) towards lock portion (7530). Additionally, lock member (7532) extends outwardly or perpendicularly relative to an extension axis of body (7522). In the present example, lock member (7532) defines a generally rectangular shape, although it should be understood various alternative shapes may be used in other examples.

Referring to FIG. 102, restriction feature (7520) extends through a portion of upper deck (7588) for actuation of restriction feature (7520) from an exterior of cartridge body (7556) and for engagement between restriction feature (7520) and wedge sled (7570) within cartridge body (7556). In particular, at least a portion of actuation portion (7524) rests on an upper surface of upper deck (7588) exposing proximal ramp (7526) to the exterior of cartridge body (7556). Body (7522) of restriction feature (7520) then extends downwardly though upper deck (7588) into the interior of cartridge body (7556). As will be described in greater detail below, inside cartridge body (7556), lock portion (7530) or restriction feature (7520) may selectively engage wedge sled (7570) to selectively prevent movement of wedge sled (7570). To facilitate such an extension through upper deck (7588), in some examples upper deck (7588) may include an opening, channel, bore, void, chamber, or other spaces configured to receive one or more portions of restriction feature (7520).

The particular orientation of restriction feature (7520) relative to upper deck (7588) generally corresponds to the position of wedge sled (7570) prior to actuation. In other words, restriction feature (7520) is positioned to engage wedge sled (7570) when wedge sled (7570) is proximate proximal end (7576) of staple cartridge (7554). Additionally, restriction feature (7520) is generally positioned off-center and/or laterally offset relative to a central longitudinal axis extending through staple cartridge (7554). In other words, restriction feature (7520) is offset towards a particular side of staple cartridge (7554). The particular position of restriction feature (7520) in the present example is generally configured to promote selective engagement between restriction feature (7520) and wedge sled (7570). Thus, it should be understood that in other examples, a variety of alternative orientations may be used for restriction feature (7520) sufficient to promote selective engagement between restriction feature (7520) and wedge sled (7570).

FIG. 104 shows an alternative view of end effector (116) described above. As can be seen, end effector (116) includes an inner support member (153) (also referred to as a strut, frame member, or protrusion). Inner support member (153) is associated with lower jaw (152) and/or upper jaw (150) and extends along an inner surface of lower jaw (152) between and lower jaw (152) and upper jaw (150). Inner support member (153) may be used for a variety of purposes. For instance, in some examples, inner support member (153) may be configured to promote movement of lower jaw (152) relative to upper jaw (150). In addition, or in the alternative, support member (153) may be configured to provide support to staple cartridge (7554) during closure of end effector (116). Still other purposes for inner support member (153) will be apparent to those of ordinary skill in the art in view of the teachings herein.

Regardless of the particular purpose of inner support member (153) in the context of end effector (116), inner support member (153) in the present example may be configured to engage a portion of restriction feature (7520). As will be described in greater detail below, restriction feature (7520) is generally movable laterally into cartridge body (7556) and away from lower jaw (152). As such, in some examples, inner support member (153) may be configured to manipulate restriction feature (7520).

FIGS. 105A through 106B show an exemplary use of staple cartridge (7554) of the present example in connection with end effector (116) described above. Although the use shown and described herein is in connection with end effector (116), it should be understood that in other uses the same steps and/or principles described herein may be readily applied to use with end effector (210) described above.

As best seen in FIG. 105A, staple cartridge (7554) is initially inserted into lower jaw (152). At this stage, restriction feature (7520) is positioned in an initially locked position. In this position, restriction feature (7520) is positioned such that lock member (7532) is disposed in engagement with wedge sled (7570) to prevent distal movement of wedge sled (7570) from proximal end (7576) to distal end (7578) of staple cartridge (7554). This position of restriction feature (7520) is generally desirable to hold knife member (7572) within blade guard (7555). Specifically, as best seen in FIG. 106A, lock member (7532) is positioned to engage a portion of knife member (7572) to prevent distal movement of wedge sled (7570) and hold knife member (7572) within blade guard (7555). This locked position may be desirable to prevent inadvertent contact with cutting edge (7594) due to unexpected movement of wedge sled (7570) during installation of staple cartridge (7554) or other preliminary procedures.

While restriction feature (7520) is positioned in the locked position, staple cartridge (7554) can be installed within lower jaw (152) as shown in FIG. 105B. Once staple cartridge (7554) is installed within lower jaw (152), restriction feature (7520) may transition from the locked position to the unlocked position. As best seen in FIG. 105B, during insertion of staple cartridge (7554), inner support member (153) engages proximal ramp (7526) of restriction feature (7520). Engagement between inner support member (153) and proximal ramp (7526) causes movement of restriction feature (7520) downwardly and/or away from lower jaw (152) and into cartridge body (7556) into the position shown in FIG. 106B. Although inner support member (153) is described herein as being used to engage proximal ramp (7526), it should be understood that in other examples, other portions of end effector (116) may be used to engage proximal ramp (7526). For instance, in some examples, lower jaw (152) may include one or more features extending therefrom specifically configured to engage proximal ramp (7526). In still other examples, various other components of end effector (116) may be used to engage proximal ramp (7526) including, for example, dedicated components or assemblies configured to actuate restriction feature (7520).

Although transition of restriction feature (7520) from the locked position to the unlocked position is shown in the present example as corresponding to insertion of staple cartridge (7554) into lower jaw (152), in some uses this transition may occur at other stages of use. For instance, in some examples, restriction feature (7520) may remain in the locked position after insertion of staple cartridge (7554). This may be desirable in the present use to prevent unintentional contact with cutting edge (7594) prior to cutting and stapling of tissue. In such a use, restriction feature (7520) may be moved to the unlocked position using closure of end effector (116). For instance, as end effector (116) closes, upper jaw (150) moves in closer proximity to lower jaw (152). This movement may be used to actuate restriction feature (7520) using a feature similar to inner support member (153), but associated with upper jaw (150) instead of lower jaw (152).

Regardless of how proximal ramp (7526) is engaged, such engagement may cause restriction feature (7520) to transition from the locked position to the unlocked position. As can be seen in FIG. 106B, once restriction feature (7520) is transitioned to the unlocked position, lock member (7532) is moved out of engagement with wedge sled (7570). This movement permits distal movement of wedge sled (7570) within cartridge body (7556). Thus, once restriction feature (7520) is moved to the unlocked position, wedge sled (7570) may be freely actuated by pusher member (166) to drive one or more staples and/or sever tissue.

Although not shown, it should be understood that in some examples, restriction feature (7520) may include a resilient feature such as a spring to bias restriction feature (7520) towards the locked position. In such examples, movement of wedge sled (7570) may thus be unlocked upon closure of end effector (116). Upon reopening of end effector (116), movement of wedge sled (7570) may then be locked due to the spring bias of restriction feature (7520). Such a spring bias may be desirable to promote reuse of staple cartridge (7554) either in a single procedure or in one or more follow-up procedures. Of course, in circumstances where prevention of reuse of staple cartridge (7554) is desired, such a spring bias may be omitted entirely.

C. Exemplary Alternative Staple Cartridge with Slidable Restriction Feature

FIG. 107 shows an exemplary alternative staple cartridge (7654) that may be readily used with end effector (116, 210) described above in lieu of staple cartridges (154, 254). Staple cartridge (7654) is substantially similar to staple cartridge (154) described above, unless where otherwise noted herein. For instance, like with staple cartridge (154), staple cartridge (7654) of the present example includes a staple cartridge body (7656) that is configured to house a firing assembly (7658), a plurality of staple drivers (not shown), and a plurality of staples (not shown). As with firing assembly (158) described above, firing assembly (7658) of the present example includes a wedge sled (7670) and a knife member (7672) (see FIG. 111A).

Staple cartridge body (7656) of the present example is similar to staple cartridge body (156) in that staple cartridge body (7656) includes an array of staple accommodating apertures (7674) extending through an upper deck (7688) of staple cartridge body (7656). Staple cartridge (7654) includes proximal end (7676) and a distal end (not shown). In operation, staples (not shown) are sequentially deployed starting at proximal end (7676) by advancing wedge sled (7670) toward the distal end from proximal end (7676). A vertical slot (7680) configured to accommodate knife member (7672) through part of staple cartridge (7654) to permit a cutting edge (7694) to cut tissue as the staples are driven via wedge sled (7670).

Staple cartridge (7654) further includes a blade guard (7655) (also referred to as a cover, sheath, and/or compartment). Blade guard (7655) extends upwardly from upper deck (7688) and is disposed at a proximal end of cartridge body (7656). In the present example, blade guard (7655) is defined by two upwardly extending slats disposed on each side of vertical slot (7680). As will be understood, blade guard (7655) is configured to contain knife member (7672) to avoid inadvertent contact with cutting edge (7694) when staple cartridge (7654) is not in use. As such, the particular position of blade guard (7655) relative to cartridge body (7656) corresponds to a proximal or home position of wedge sled (7670).

Unlike staple cartridge (154) described above, staple cartridge (7654) of the present example includes a restriction feature (7620). Restriction feature (7620) is generally configured to resist movement of wedge sled (7670) to prevent inadvertent advancement of wedge sled (7670). In the present example, restriction feature (7620) is received within a proximal channel (7660) defined by cartridge body (7656). As best seen in FIG. 108, proximal channel (7660) defines a U-shaped cross-section and extends distally though at least a portion of cartridge body (7656). Although proximal channel (7660) in the present example is defined by cartridge body (7656), it should be understood that in other examples proximal channel (7660) may be defined by other suitable components of staple cartridge (7654).

Cartridge body (7656) includes one or more detent features (7662) extending into a portion of proximal channel (7660). Detent features (7662) are generally configured to releasably hold restriction feature (7620) in a predetermined position. Specifically, the present example includes a detent feature (7662) extending downwardly into a portion of proximal channel (7660) and a detent feature (7662) extending upwardly into a portion of proximal channel (7660). In this configuration, detent features (7662) engage a top and bottom portion of restriction feature (7620) to releasably hold restriction feature (7620) in a predetermined position.

Each detent feature (7662) of the present example includes a protrusion defining a simi-circular cross-section. Each detent feature (7662) also extends longitudinally along the axis of extension of proximal channel (7660). In some examples, each detent feature (7662) may extend along the entire length of proximal channel (7660). In other examples, each detent feature (7662) may extend along only a portion of proximal channel (7660). In still other examples, each detent feature (7662) may instead be configured as a plurality of individual bumps or hemispheres arranged in a line oriented parallel to the extension of proximal channel (7660). Of course, other configurations of detent features (7662) suitable to releasably hold restriction feature (7620) in position will be apparent to those of ordinary skill in the art in view of the teachings herein.

As best seen in FIG. 109, restriction feature (7620) includes a body (7622) having an actuation portion (7624) and a lock portion (7630) with a notch (7628) disposed between actuation portion (7624) and lock portion (7630). Actuation portion (7624) includes a proximal ramp (7626) (also referred to as a cam surface) disposed on a proximal end of restriction feature (7620). Proximal ramp (7626) defines a ramped surface oriented proximally and at an angle such that proximal ramp (7626) extends in cross-section from the proximal end of proximal ramp (7626) to the distal end of proximal ramp (7626). As will be described in greater detail below, proximal ramp (7626) is generally configured to engage portions of actuation assembly (164), such as pusher member (166), to drive movement of restriction feature (7620) away from wedge sled (7670).

Lock portion (7630) is disposed opposite of actuation portion (7624) proximate a distal end of restriction feature (7620). As will be described in greater detail below, lock portion (7630) is generally configured to restrict movement of wedge sled (7670). In the present example, lock portion (7630) includes a lock member (7632) generally configured to engage at least a portion of wedge sled (7670) to restrict movement of wedge sled (7670). The particular shape of lock member (7632) of the present example is generally a square or rectangular shape, although other shapes suitable to restrict movement of wedge sled (7670) may be used.

As described above, body (7622) defines a notch (7628) between actuation portion (7624) and lock portion (7630). Notch (7628) is generally configured to receive at least a portion of wedge sled (7670). The particular depth of notch (7628) as defined by body (7622) is configured to permit engagement between at least a portion of wedge sled (7670) and lock member (7632) when wedge sled (7670) is disposed within notch (7628). Although notch (7628) is shown in the present example as having a U-shape or rectangular shape, it should be understood that in other examples various alternative shapes suitable to receive a portion of wedge sled (7670) may be used.

Restriction feature (7620) further includes a retaining feature (7636) extending from the distal end of body (7622) to the proximal end of body (7622). Retaining feature (7636) is generally complementary in shape to detent feature (7662) described above. In other words, retaining feature (7636) and detent feature (7662) are configured to operate cooperatively to releasably hold restriction feature (7620) in a predetermined position. Consequently, retaining feature (7636) defines an indentation within body (7622) of a shape corresponding to detent feature (7662). As described above, detent feature (7662) defines a semi-circular cross-section. Thus, retaining feature (7636) of the present example likewise defines a simi-circular cross-section configured to receive detent feature (7662). Of course, in other examples where the shape of detent feature (7662) is varied, the shape of retaining feature (7636) may likewise be varied.

Although FIG. 109 shows retaining feature (7636) being disposed on one side of body (7622), it should be understood that a similar retaining feature (7636) may be disposed on an opposite side of body (7622). Although the present example includes retaining feature (7636) as an indentation and detent feature (7662) as a protrusion, it should be understood that in other examples the configuration may be reversed with retaining feature (7636) being a protrusion and detent feature (7662) being an indentation. In other examples, retaining feature (7636) and detent feature (7662) may be omitted entirely and instead the same functionality may be achieved via an interference fit between restriction feature (7620) and cartridge body (7656).

FIGS. 111A and 111B show an exemplary use of restriction feature (7620). As can be seen, restriction feature (7620) may begin in an initially locked position as shown in FIG. 111A. In this position, at least a portion of wedge sled (7670) is received within notch (7628) of restriction feature (7620). With at least a portion of wedge sled (7670) received within notch (7628), movement of wedge sled (7670) distally relative to cartridge body (7656) is generally prevented via engagement between lock member (7632) and wedge sled (7670). This prevention of movement of wedge sled (7670) holds knife member (7672) of wedge sled (7670) within blade guard (7655) to prevent inadvertent contact with cutting edge (7694). Additionally, restriction feature (7620) is held in the locked position via engagement between retaining feature (7636) and detent feature (7662).

Restriction feature (7620) may be shifted from the locked position to an unlocked position upon firing of wedge sled (7670) via actuation assembly (164). Specifically, as best seen in FIG. 111B, pusher member (166) of actuation assembly (164) may be moved distally to move wedge sled (7670) distally. Distal movement of actuation assembly (164) may result in engagement between pusher member (166) and restriction feature (7620). Specifically, a portion of pusher member (166) may contact proximal ramp (7626) of restriction feature (7620), thereby overcoming engagement between retaining feature (7636) and detent feature (7662) and pushing restriction feature (7620) laterally away from both pusher member (166) and wedge sled (7670).

Once restriction feature (7620) is pushed laterally as shown in FIG. 111B, wedge sled (7670) may no longer be disposed within notch (7628). With wedge sled (7670) no longer disposed within notch (7628), wedge sled (7670) may be disengaged from lock member (7623). Once lock member (7623) is disengaged from wedge sled (7670), restriction feature (7620) is in the unlocked position and wedge sled (7670) may move distally relative to cartridge body (7656) without restriction via restriction feature (7620).

In the present example, restriction feature (7620) may remain in the unlocked position after being transitioned from the locked position. This configuration may be desirable for single use applications where staple cartridge (7654) is configured to be used only once and then replaced with another staple cartridge (7654). However, it other examples, staple cartridge (7654) may be configured for multi-use applications. In such applications, restriction feature (7620) may be associated with a spring or other resilient member to bias restriction feature (7620) toward the locked position. In such examples, the resilient feature may return restriction feature (7620) to the locked position after pusher member (166) has passed restriction feature (7620). Of course, in such examples, restriction feature (7620) may include other features such as distal ramps, cam surfaces, or the like to facilitate relocking upon retraction of wedge sled (7670) and/or pusher member.

XII. Exemplary Tracking Features for Firing a Surgical Stapler

As mentioned above, pusher member (166) and wedge sled (170) of end effector (116) may be actuated distally while jaws (150, 152) grasp tissue in order to simultaneously staple and sever the grasped tissue. Similarly, pusher block (236) and wedge sled (238) of end effector (210) may be actuated distally while jaws (212, 214) grasp tissue in order to simultaneously staple and sever the grasped tissue.

In some instances, it may be desirable to visually locate, approximate, or otherwise represent the longitudinal position of pusher member (166), pusher block (236), and/or wedge sled (170, 238) within jaws (150, 152, 212, 214). For instance, a visual representation of the longitudinal position of pusher block (236) or wedge sled (170) during the firing process may inform an operator of the progress made by end effector (116, 210) in stapling and severing tissue. Further, when an image of the surgical site is obtained by endoscope (28), it may be desirable to easily view such a visual representation via endoscope (28) and display (40) without having to further manipulate the position of endoscope (28). The following show various examples that may be readily incorporated into shaft assembly (114) and/or end effector (116, 210) in order to allow an operator to visually locate, approximate and/or otherwise represent the longitudinal location of pusher member (166), pusher block (236), and/or wedge sled (170, 238) within jaws (150, 152, 212, 214).

A. End Effector with Illumination Feature Associated with Wedge Sled

FIG. 113 shows an exemplary end effector (8300) that may be readily incorporated into instrument (110) described above in replacement of either end effector (116, 210). End effector (8300) is substantially similar to end effector (116, 210) described above, with differences elaborated below. In particular, as shown in FIG. 112, end effector (8300) includes an illumination assembly (8320) configured to illuminate to thereby visually represent the progression of wedge sled (8314) actuating through jaws (8302, 8304) of end effector (8300).

End effector (8300) includes a lower jaw (8302), an upper jaw (8304), and a removable staple cartridge (8306); which may be substantially similar to lower jaw (152, 212), upper jaw (150, 214), and staple cartridge (154, 218), respectively, with difference elaborated herein. As best seen in FIG. 112, lower jaw (8302) includes a pair of side walls (8310) coupled to each other by a base (8312). Side walls (8310) and base (8312) together define a cartridge receiving channel (8308) dimensioned to selectively couple with staple cartridge (8306). As also best seen in FIG. 112, staple cartridge (8306) includes wedge sled (8314), which may be substantially similar to wedge sled (170, 238) described above, with difference elaborated below. Therefore, during the firing process, wedge sled (8314) may actuate along a longitudinal path within staple cartridge (8306) relative to lower jaw (8302) such that end effector (8300) may staple and sever tissue (T) in accordance with the description herein.

Lower jaw (8302) includes an array of indicator markers (8305). Indicator markers (8305) are located along discrete longitudinal locations of lower jaw (8302) and include a specific value associated with each marker (i.e., the 50 mm marker, the 40 mm marker, the 30 mm marker, etc.). The specific number associated with each marker (8305) represents the distance that wedge sled (8314) and/or the associated knife member (not shown) needs to travel further in order to complete the firing processes. For example, when wedge sled (8314) and/or the associated knife member (not shown) is adjacent to the 20 mm indicator marker (8305), wedge sled (8314) still needs to travel 20 mm distally in order to complete the firing processes. As another example, when wedge sled (8314) and/or the associated knife member (not shown) is adjacent to the 0 mm indicator marker (8305), wedge sled (8314) has reached the distal end of the firing process.

In the current example, wedge sled (8314) and lower jaw (8302) together form an illumination assembly (8320). A portion of lower jaw (8302) defining channel (8308) includes a linear array of electromagnetic coils (8324), each coupled to flex circuit wiring (8322). Additionally, wedge sled (8314) includes its own electromagnetic coil (8326) and a light (8325) coupled to each other via circuit wiring (8328).

Flex circuit wiring (8322) is configured to communicate electrical power to electromagnetic coils (8324) such that coils (8324) may suitably emit wireless energy for wireless power transfer to electromagnetic coil (8326) of wedge sled (8314). Linear array of electromagnetic coils (8324) are configured to wirelessly transfer energy to electromatic coil (8326) of wedge sled (8314) such that light (8325) may emit an illumination (8318) (see FIG. 113) that may be viewed from the outside of jaws (8302, 8304). Since wedge sled (8314) is housed within a body of removable staple cartridge (8306), the wireless transfer of energy may allow the linear array of electromagnetic coils (8326) to power light (8325) even though coils (8324, 8326) are not in direct contact.

Linear array of electromagnetic coils (8324) extends along a suitable length of lower jaw (8304) such that electromagnetic coils (8324) may suitably transfer wireless power to electromagnetic coil (8326) of wedge sled (8314) as wedge sled (8314) travels within channel (8308) to complete the firing process of severing and stapling tissue (T). Since light (8325) is fixed to wedge sled (8314), the illumination (8318) provided by light (8325) may provide a visual representation of where wedge sled (8314) is located along the length of lower jaw (8302), thereby indicating the progress wedge sled (8314) has made in the firing process. This visual representation of illumination (8318) may be captured by endoscope (28) and viewed on display (40) during exemplary use of the firing process.

Flex circuit wiring (8322) extends proximally from lower jaws (8302) and through other suitable components in order to couple with a power source in order to communicate electrical power to electromagnetic coils (8324). In some instances, the power source may be housed within surgical instrument (110), while in other instances, flex circuit wiring (8322) may be configured to couple with a power source when surgical instrument (110) is suitably coupled to robotic arm (42). Flex circuit wiring (8322) may couple with a power source utilizing any suitable means as would be apparent to one skilled in the art in view of the teachings herein.

While wedge sled (8314) and lower jaw (8302) form illumination assembly (8320) in the current example, it should be understood that any other suitable components may form illumination assembly (8320) as would be apparent to one skilled in the art in view of the teachings herein. For instance, any component that actuates with wedge sled (8314) may include the illumination features associated with wedge sled (8314) in the current example, while any component that remains substantially stationary relative to lower jaw (8302) (such as upper jaw (8304) or shaft assembly (114)) during the firing process may be include the illumination features associated with lower jaw (8302).

B. End Effector with Firing Assembly Position Tracker for Augmented Reality

In some instances, it may be desirable to visually represent the longitudinal location of pusher member (166), pusher block (236), and/or wedge sled (170, 238) within jaws (150, 152, 212, 214) by overlaying a digital representation of such components onto the image of jaws (150, 152, 212, 214) captured by endoscope (28) and shown in display (40). In other words, it may be desirable to augment the images shown on display (40) of jaws (150, 152, 212, 214) stapling and severing (T) with a visual representation of pusher member (166), pusher block (236), and/or wedge sled (170, 238) relative to the capture image of jaws (150, 152, 212, 214) during the exemplary firing process.

FIGS. 114-115 show an exemplary end effector (8330) while FIG. 116 shows an image captured by endoscope (28) and shown on display (40) with an augmented projection (8356) of pusher member (8340) and wedge sled (8342) during the firing process. As will be described in greater detail below, end effector (8330) may be used in conjunction with endoscope (28), display (40), and processor (38) to track the longitudinal position of a pusher member (8340) and wedge sled (8342) during the firing process and digitally project that longitudinal position onto images of jaws (8332, 8334) shown on display (40).

End effector (8330) includes a lower jaw (8332), an upper jaw (8334), and a removable staple cartridge (8336); which may be substantially similar to lower jaw (152, 212), upper jaw (150, 214), and staple cartridge (154, 218), respectively, with difference elaborated herein. As best seen in FIG. 116, end effector (8330) further includes a pusher member (8340) while staple cartridge (8336) includes wedge sled (8342), which may be substantially similar to pusher member (166, 236) and wedge sled (170, 238) described above, respectively with difference elaborated below. Therefore, during the firing process, pusher member (8340) and wedge sled (8342) may actuate along a longitudinal path relative to jaws (8332, 8334) such that end effector (8330) may staple and sever tissue (T) in accordance with the description herein.

Jaws (8332, 8334) include an array of indicator markers (8335). Indicator markers (8335) are located along discrete longitudinal locations of jaws (8302, 8304) and include a specific value associated with each marker (i.e., the 50 mm marker, the 40 mm marker, the 30 mm marker, etc.). The specific number associated with each marker (8335) represents the distance that pusher member (8340) and wedge sled (8342) need to travel further in order to complete the firing processes. Endoscope (28) may capture images of indicator markers (8335) such that processor (38) may utilize markers (8335) in a visualization system as reference points. As will be described in greater detail below, processor (38) may utilize these reference points provided by markers (8335), as well as data provided by linear displacement sensor assembly (8350), in order to accurately project an augmented reality projection of pusher member (8340) and wedge sled (8342) relative to jaws (8332, 8334). Markers (8335) may include any suitable components as would be apparent to one skilled in the art in view of the teachings herein.

As best shown in FIG. 115, end effector (8330) includes a linear displacement sensor assembly (8350). Linear displacement sensor assembly (8350) is configured to measure the linear displacement to pusher member (8340) relative to jaws (8332, 8334) during the firing process. Further, linear displacement sensor assembly (8350) is in communication with processor (38) such that linear displacement sensor assembly (8350) may communicate the measured linear displacement of pusher member (8340) relative to jaws (8332, 8334) to processor (38). Processor (38) may utilize this information to digitally project an augmented reality projection (8356) of pusher member (8340) and wedge sled (8342) onto images captured by endoscope (28) and shown on display (40) such that a user may track the progression of pusher member (8340) and wedge sled (8342) during the firing process.

In the current example, linear displacement sensor assembly (8350) includes a spring (8352) and a linear variable displacement transducer "LVDT" (8354). Spring (8352) is housed within a longitudinal slot (8338) of upper jaw (8334). Longitudinal slot (8338) may be substantially similar to longitudinal slot (186, 234) described above, with difference elaborated below. Therefore, longitudinal slot (8338) is dimensioned to receive a flange of pusher member (8340) during the firing process.

A proximal end of spring (8352) is fixed to the flange of pusher member (8340) configured to actuate within slot (8338) of upper jaw (8332), while a distal end of spring (8352) is suitably coupled to LVDT (8354). LVDT (8354) is coupled to a distal end of upper jaw (8334) within longitudinal slot (8338). As pusher member (8340) actuates distally relative to jaws (8332, 8334), spring (8352) may compress between pusher member (8340) and LVDT (8354). Conversely, as pusher member (8340) actuates proximally relative to jaws (8332, 8334), spring (8352) may expand between pusher member (8340) and LVDT (8354).

LVDT (8354) may measure the longitudinal position of pusher member (8340) due to the change in length of spring (8352) during the firing process of pusher member (8340). LVDT (8354) is in communication with processor (38) such that LVDT (8354) may communicate the measured linear displacement of pusher member (8340) relative to jaws (8332, 8334) to processor (38). Processor (38) may utilize this information provided by LVDT (8354), along with the reference points provided by markers (8335) captured by endoscope (28), in order to accurately project an augmented reality projection (8356) of pusher member (8340) and wedge sled (8342) relative to jaws (8332, 8334) during the firing process. Therefore, the operator may track the progress of pusher member (8340) and wedge sled (8342) during the firing process via an approximated augmented reality projection (8356).

While in the current example, spring (8352) and LVDT (8354) are used to track the linear displacement of pusher member (8340) and communicate that linear displacement to processor (38), any other suitable means may be utilized to track and communicate the linear dispatchment of pusher member (8340) relative to jaws (8332, 8334) as would be apparent to one skilled in the art in view of the teachings herein. For instance, the portion of robotic arm (42) configured to drive movement of pusher member (8340) may have an encoder configured to monitor the rotational displacement of the portion of robotic arm (42) configured to drive pusher member (8340), therefore allowing the encoder to monitor the position of pusher member (8340) relative to jaws (8332, 8334). Such an encoder may be in communication with processor (38) such that processor (38) may utilize information provided by encoder in order to project an augmented reality projection (8356) onto images captured by endoscope (28) and shown on display 40).

C. End Effectors and Shaft Assemblies with Various Position Tracking Features for Firing Assemblies FIGS. 117A-117C show an exemplary end effector (8360) that may be readily incorporated into instrument (110) described above in replacement of either end effector (116, 210). End effector (8360) is substantially similar to end effector (116, 210) described above, with differences elaborated below. In particular, end effector (8360) includes an illumination assembly (8370) comprising a linear array of lights (8372) configured sequentially illuminate to thereby visually represent the progression of wedge sled (8368) actuating through jaws (8362, 8364) of end effector (8360).

End effector (8360) includes a lower jaw (8362), an upper jaw (8364), and a removable staple cartridge (8366); which may be substantially similar to lower jaw (152, 212), upper jaw (150, 214), and staple cartridge (154, 218), respectively, with difference elaborated herein. As best seen in FIG. 118, staple cartridge (8366) includes wedge sled (8368), which may be substantially similar to wedge sled (170, 238) described above, with difference elaborated below. Therefore, during the firing process, wedge sled (8368) may actuate along a longitudinal path within staple cartridge (8366) relative to lower jaw (8362) such that end effector (8360) may staple and sever tissue (T) in accordance with the description herein.

In the current example, wedge sled (8368) and lower jaw (8362) together form an illumination assembly (8370). As best shown in FIGS. 117A-117C, lower jaw (8362) includes a linear array of lights (8372) located on an outer surface of lower jaw (8362). Therefore, as an individual light in the linear array of lights (8372) illuminate in accordance with the description herein, such an illumination may be easily visible via endoscope (28). As shown in FIG. 119, the flanges of lower jaw (8362) define a corresponding linear array of openings (8384) dimensioned to house a respect light (8372) of the linear array. Similar to lower jaw (8302) described above, lower jaw (8362) may include a plurality of indicator markers. Lights (8372) may be located at a corresponding indicator marker such that illumination of an individual light (8372) may signify the progress of wedge sled (8368) being advanced through lower jaw (8362) during the firing process.

As best shown in FIG. 119, illumination assembly (8370) includes a first flex circuit (8378) having a plurality of contacts (8379) and a second flex circuit (8380) also having a plurality of contacts (8381). Each flex circuit (8378, 8380) extends along a length of jaw (8362). One flex circuit (8378, 8380) may extend proximally to couple with a suitable power source, while contacts (8379, 8381) of the other flex circuit (8378, 8380) may be in communication with a respective light (8372).

As best shown in FIG. 118, wedge sled (8368) includes a pair a laterally presented contacts (8374) that are electrically coupled to each other and a cartridge identifying resistor (8376) interposed between contacts (8374). Contacts (8374) are located on wedge sled (8368) such that when staple cartridge (8366) is initially coupled with lower jaw (8362), contacts (8374) may be in communication with a proximal most contact (8379, 8381) of each flex circuit (8378, 8380). Therefore, wedge sled (8368) may complete an electrically circuit with proximal most contacts (8379, 8381) of flex circuits (8378, 8380) when staple cartridge (8366) is initially coupled to lower jaw (8362). Resistor (8376) may contain a specific resistance associated with the specific type of staple cartridge (8366) being coupled with lower jaw (8362). Therefore, robotic surgical system (10) may identify the type of staple cartridge (8366) coupled with lower jaw (8362) by reading the resistance value of resistor (8376).

Additionally, as wedge sled (8368) is actuated distally to staple and sever tissue, contacts (8374) may complete an electrical circuit with adjacent contacts (8379, 8381) of flex circuits (8378, 8380). When specific contacts (8379, 8381) are electrically coupled by contacts (8374) of sled (8368), the individual light (8372) associated with the specific contacts (279, 281) of flex circuits (8378, 8380) may illuminate, thereby indicting to a user where wedge sled (8368) is relative to lower jaw (8362). Once wedge sled (8368) is advanced past individual contacts (8379, 8381), the circuit illuminating light (8372) may no longer be formed such that light (8372) is no longer illuminated. Therefore, illumination assembly (8370) may be used to visually approximate the location of wedge sled (8368), and therefore allow a user to monitor the progression of wedge sled (8368) actuating relative to lower jaw (8362).

In some instances, a portion of an illumination assembly may associate with the shaft assembly (114) rather than end effector (116). FIGS. 120-121B show a shaft (8400) having an exemplary illumination activation assembly (8410) configured to generate a signal in order to activate illumination features associated with the firing of any suitable end effector described herein. Shaft assembly (8400) may be substantially similar to shaft assembly (114) described above, with differences elaborated below. Shaft assembly (8400) includes a stationary portion (8402) and a translating shuttle (8404). Translating shuttle (8404) is configured to actuate within stationary portion (8402) to thereby actuate any suitable firing mechanism(s), (e.g., wedge sled (170, 238)). Therefore, the longitudinal position of translating shuttle (8404) relative to stationary portion (8402) may correspond to the progression as which any suitable end effector is firing to staple and sever tissue in accordance with the description herein.

Illumination activation assembly (8410) includes a magnetic sensor (8412) and flex circuit wiring (8414), both associated with stationary portion (8402). Flex circuit wiring (8414) is electrically coupled with magnetic sensor (8412). Flex circuit wiring (8414) extends proximally and couples with a suitable power source and/or processing unit. Flex circuit wiring (8414) extends distally and is coupled to an illumination assembly, such as any suitable illumination assembly described herein. Additionally, illumination activation assembly (8410) includes an array of magnets (8416) longitudinally disposed on translating shuttle (8404).

Magnets (8416) are suitably adjacent to magnetic sensor (8412) such that when shuttle (8404) actuates during the firing process, an individual magnet (8416) may be directly under magnetic sensor (8412) without physically contacting sensor (8412). When an individual magnetic (8416) is directly under magnetic sensor (8412), as shown in FIG. 121A, magnetic sensor (8412) may generate a signal and transfer that signal to suitable illumination features of instrument (110). When an individual magnet (8416) is not directly under magnetic sensor (8412), as shown in FIG. 121B, magnetic sensor (8412) fails to generate a signal. Therefore, as shown in the graph (8406) of FIG. 122, a signal generation line (8408) alternates between generating a signal and not generating a signal as shuttle (8404) actuates within stationary portion (8402).

Magnets (8416) are disposed on shuttle (8404) in order to generate a signal in magnetic sensor (8412) as shuttle (8404) fires end effector (116, 210) in accordance with the description herein. Magnets (8416) are strategically placed on shuttle (8404) such that the signal generated by sensor (8412) may be indicative of the progression at which end effector (116, 210) is being fired to staple and sever tissue. Signals generated by magnetic sensor (8412) may be used in conjunction with any suitable illumination assembly described herein to light such an illumination assembly, thereby tracking the progression as which shuttle (8404) fires end effector (116, 210).

FIG. 123 shows an exemplary replaceable staple cartridge (8440) having an illumination assembly (8442) that may be used in conjunction with shaft assembly (8400) described above. Illumination assembly (8442) includes an electrical chip (8444) having a counter functionality, a flex circuit (8448) extending along a length of the body of staple cartridge (8440), and a longitudinal array of lights (8445) disposed on an outer surface of replaceable staple cartridge (8440). The longitudinal array of lights (8445) are electrically coupled to electrical chip (8444) via flex circuit (8448).

Electrical chip (8444) includes electrical contacts (8446) which may selectively couple with corresponding electrical contacts on a lower jaw of end effector. Corresponding electrical contacts on the lower jaw may be in electrical communication with a proximal end of flex circuit (8414) extending within stationary portion (8402) of shaft assembly (8400). Therefore, when replaceable staple cartridge (8440) is coupled with a suitable lower jaw, flex circuit (8414) may communicate signals generated by illumination activation assembly (8410) to electrical chip (8444).

Longitudinal array of lights (8445) may be exposed to an outer surface of lower jaw via a complementary array of openings defined by lower jaw when cartridge (8440) is suitably coupled to lower jaw. Therefore, as lights (8445) become illuminated, they may be easily viewed via endoscope (28).

As mentioned above, electrical chip (8444) has a counter functionality. Therefore, electrical chip (8444) may count the number of times illumination activation assembly (8410) transmits a signal in accordance with the description herein. As mentioned above, signals generated by sensor (8412) may be indicative of the progression at which end effector (116, 210) is being fired to staple and sever tissue. Lights (8445) may be selectively placed along the length of staple cartridge (8440) in order to represent or approximate the location of a wedge sled of staple cartridge (8440) as shuttle (8404) drives wedge sled distally. Electrical chip (8444) may activate and/or deactivate lights (8445) based on the number of signals counted by electrical chip (8444).

For example, if electrical chip (8444) counts one signal being received during the firing process, electrical chip (8444) may activate the most proximal light (8445). The most proximal light (8445) may be placed along a location that approximates the location of wedge sled of cartridge (8440) when electrical chip (8444) counts the first signal. As another example, if electrical chip (8444) counts a second signal being received during the firing process, electrical chip (8444) may activate the second most proximal light (8445). The second most proximal light (8445) may be placed along a location that approximates the location of the wedge sled of cartridge (8440) when electrical chip (8444) counts the second signal. In some instances, once a light (8445) is activated, chip (8444) may keep that specific light (8445) activated until wedge sled of staple cartridge (8440) is fully advanced, until the firing process is completed, or until any other suitable event that would be apparent to one skilled in the art in view of the teachings herein. Therefore, in some instances, the linear array of lights (8445) may remain activated to visually approximate the length at which wedge sled has traveled during the firing process. In some instances, only one light (8445) may be activated at a time, such that once the second light (8445) is activated by chip (8444), chip (8444) deactivates the first light (8445), and so on. Therefore, in some instances, the linear array of lights (8445) may be sequentially activated to visually approximate the general position at which wedge sled is located during the firing process.

FIG. 124 shows an exemplary lower jaw (8450) having an illumination assembly (8452) that may be used in conjunction with shaft assembly (8400) described above. Illumination assembly (8452) may be substantially similar to illumination assembly (8442) described above, except components of illumination assembly (8452) are associated with lower jaw (8450) rather than a replaceable cartridge (8440). Lower jaw (8450) includes a plurality of indicator markers (8451) that are substantially similar to indicator markers (8305, 8335) described above. Therefore, the specific number associated with each marker (8451) represents the distance that a wedge sled and/or the associated knife member needs to travel further in order to complete the firing processes.

Illumination assembly (8452) includes an electrical chip (8454) having a counter functionality, a flex circuit (8458) extending along a length of the body of lower jaw (8450), and a longitudinal array of lights (8455) disposed within openings (8459) defined by flanges of lower jaw (8450). The longitudinal array of lights (8455) are coupled to electrical chip (8454) via flex circuit (8448).

Electrical chip (8454) may be in electrical communication with a proximal end of flex circuit (8414) extending within stationary portion (8402) of shaft assembly (8400). Therefore, flex circuit (8414) may communicate signals generated by illumination activation assembly (8410) to electrical chip (8454).

As mentioned above, electrical chip (8454) has a counter functionality. Therefore, electrical chip (8454) may count the number of times illumination activation assembly (8410) transmits a signal in accordance with the description herein. As mentioned above, signals generated by sensor (8412) may be indicative of the progression at which end effector (116, 210) is being fired to staple and sever tissue. Lights (8455) may be selectively placed along the length of lower jaw (8450) with a corresponding indicator marker (8451) in order to represent or approximate the location of a wedge sled as shuttle (8404) drives wedge sled distally. Electrical chip (8454) may activate and/or deactivate lights (8455) based on the number of signals counted by electrical chip (8454).

For example, if electrical chip (8454) counts one signal being received during the firing process, electrical chip (8454) may activate the most proximal light (8455). The most proximal light (8455) may be placed along a location that approximates the location of wedge sled of cartridge (8440) when electrical chip (8454) counts the first signal. As another example, if electrical chip (8454) counts a second signal being received during the firing process, electrical chip (8454) may activate the second most proximal light (8455). The second most proximal light (8455) may be placed along a location that approximates the location of the wedge sled when electrical chip (8454) counts the second signal. In some instances, once a light (8455) is activated, chip (8454) may keep that specific light (8455) activated until wedge sled is fully advanced, until the firing process is completed, or until any other suitable event that would be apparent to one skilled in the art in view of the teachings herein. Therefore, in some instances, the linear array of lights (8455) may remain activated to visually approximate the length at which wedge sled has traveled during the firing process. In some instances, only one light (8455) may be activated at a time, such that once the second light (8455) is activated by chip (8454), chip (8454) deactivates the first light (8455), and so on. Therefore, in some instances, the linear array of lights (8455) may be sequentially activated to visually approximate the general position at which wedge sled is located during the firing process.

FIGS. 125A-125C show an exemplary firing of an exemplary end effector (8460) in accordance with the teachings herein. End effector (8460) includes a lower jaw (8462), an upper jaw (8464), a removable staple cartridge (8466) having a wedge sled (8472), a pusher member (8470), and an illumination assembly (8480) having a linear array of lights (8482). Lower jaw (8462), upper jaw (8462), removable staple cartridge (8466), wedge sled (8472), and pusher member (8470) may be substantially similar to lower jaw (152, 212), upper jaw (150, 214), removable staple cartridge (154, 218), wedge sled (170, 238), and pusher member/block (166, 236), described above, respectively, with differences elaborated below. Illumination assembly (8480) may include any suitable other features of any illumination assembly (8442, 8452, 8480, 8510, 8530) or illumination activation assembly (8410, 8430) described herein.

As shown in FIG. 125A-125C, as pusher member (8470) and wedge sled (8472) are advanced distally in order to complete the firing process of stapling and severing tissue, linear array of lights (8482) begin to illuminate from the proximal most light (8482) to the distal most light (8482) in order to visually approximate the progress of wedge sled (8472) stapling and severing tissue during the firing process. In particular, once a single light (8482) is illuminated, that light (8482) remains active during the distal actuation of pusher member (8470). Therefore, the linear array of lights (8482) may remain activated to visually approximate the length at which wedge sled (8472) has traveled during the firing process.

Once pusher member (8470) actuated wedge sled (8472) to the distal most position, as shown in FIG. 125C, every light (8482) is activated, thereby visually indicating to the operator that wedge sled (8472) has reached the distal most position. In some instances, when pusher member is reacted, lights (8482) may deactivate, sequentially from distal most light (8482) to the proximal most light (8482) in order to approximate the proximal retraction of pusher member (8470) back to a pre-fired position.

FIGS. 126-127B show a shaft (8420) having an exemplary illumination activation assembly (8430) configured to generate a signal in order to activate illumination features associated with the firing of end effector (116). Therefore, shaft (8420) may be used in replacement of shaft (8400) described above in order to activate illumination assemblies (8442, 8452) described above. Shaft assembly (8420) may be substantially similar to shaft assembly (114) described above, with differences elaborated below. Shaft assembly (8420) includes a stationary portion (8422) and a translating shuttle (8424). Translating shuttle (8424) is configured to actuate within stationary portion (8422) to thereby actuate any suitable firing mechanism(s) (e.g., wedge sled (170, 238)). Therefore, the longitudinal position of translating shuttle (8424) relative to stationary portion (8422) may correspond to the progression at which any suitable end effector is firing to staple and sever tissue in accordance with the description herein.

Illumination activation assembly (8430) includes a pair of stationary contacts (8432) and flex circuit wiring (8434), both associated with stationary portion (8402). Flex circuit wiring (8434) is electrically coupled with stationary contacts (8432). Flex circuit wiring (8434) extends proximally from stationary contacts (8432) and couples with a suitable power source and/or processing unit. Flex circuit wiring (8434) extends distally from stationary contacts (8432) and is coupled to an illumination assembly, such as any suitable illumination assembly (8442, 8452) described herein. One stationary contact (8432) is in electrical communication with the illumination assembly (8442, 8452) while the second electrical contact (8432) is in electrically communication with the power source and/or processing unit. Stationary contacts (8432) are normally electrically isolated from each other such that stationary contacts (8432) provide a normally open circuit between illumination features and the power source and/or processing unit.

Additionally, illumination activation assembly (8430) includes an array of actuating contacts (8436) longitudinally disposed on translating shuttle (8424). Actuating contacts (8436) are suitably adjacent to stationary contacts (8432) such that when shuttle (8424) actuates during the firing process, individual contacts (8436) come into direct contact with both stationary contacts (8432). Once an individual contact (8436) is in direct contact with both stationary contacts (8432), both stationary contacts (8432) are in electrically communication with each other such that the normally open electrical circuit is temporarily closed.

With stationary contacts (8432) in electrical communication with each other, proximal portion of flex circuit (8414) and a distal portion of flex circuit (8414) are in electrical communication with each other. Therefore, stationary contacts (8432) and individual actuating contacts (8436) are configured to selectively close the circuit between illumination features and power source/processing unit in order to activate illumination features in accordance with the description herein. When an individual actuating contact (8436) is in contact with both stationary contacts (8432), as shown in FIG. 127A, the closed circuit may generate a signal and transfer that signal to suitable illumination features, such as illumination assemblies (8442, 8452) described above. When an actuating contact (8436) is not directly in contact with both stationary contacts (8432) as shown in FIG. 127B, stationary contacts (8432) form an open circuit, thereby failing to generate a signal.

Actuating contacts (8436) are disposed on shuttle (8424) in order to generate a signal as shuttle (8424) fires end effector (116, 210) in accordance with the description herein. Actuating contacts (8436) are strategically placed on shuttle (8424) such that the signal generated by closing the circuit via the connection between contacts (8432, 8436) may be indicative of the progression at which end effector (116, 210) is being fired to staple and sever tissue. Signals generated by the connection between contacts (8432, 8436) may be used in conjunction with any suitable illumination assembly (8442, 8452) thereby tracking the progression as which shuttle (8424) fires end effector (116, 210).

In some instances, it may be desirable to visually track the approximate progress of the firing process to staple and sever tissue at a location other than the location of end effector. For example, it may be desirable to visually track the approximate progress of the firing process via indication markers and lights located on a portion of shaft assembly.

FIGS. 128-130 show an exemplary shaft assembly (8500) having an illumination assembly (8510). As shown in FIG. 130, shaft assembly (8500) is coupled to end effector (8460) described above. However, shaft assembly (8500) may be coupled to any suitable end effector (116, 210, 8300, 8330, 8360) as would be apparent to one skilled in the art in view of the teachings herein. As illustrated with the broken lines shown in FIG. 130, illumination assembly (8510) may be located on any suitable portion of shaft assembly (8500) as would be apparent to one skilled in the art in view of the teachings herein.

Shaft assembly (8500) includes a stationary portion (8502) and a translating shuttle (8504) housed within stationary portion (8502). Stationary portion (8502) and translating shuttle (8504) may be substantially similar to stationary portion (8402, 8422) and translating shuttle (8404, 8424) described above, with differences elaborated below. Therefore, translating shuttle (8504) is configured to actuate within stationary portion (8502) to thereby actuate any suitable firing mechanism(s), (e.g., wedge sled (8472)). Therefore, the longitudinal position of translating shuttle (8504) relative to stationary portion (8502) may correspond to the progression at which any suitable end effector is firing to staple and sever tissue in accordance with the description herein.

Stationary portion (8502) defines a linear array of openings (8506). Each opening (8506) is dimensioned to house a respective light (8514) of the illumination assembly (8510). Therefore, when the respective light (8514) is illuminated in accordance with the description herein, such an illumination will be viewable through openings (8506). As best seen in FIG. 130, stationary portion (8502) also includes a plurality of indicator markers (8508) associated with a respective light (8514) of illumination assembly (8510). Indicator markers (8508) may be substantially similar to indicator markers (8305, 8335, 8451) described above, with difference elaborated below. Rather than being located on an end effector, indicator makers (8508) in the current example are located on shaft assembly (8500).

Illumination assembly (8510) includes a projection (8512) attached to translation shuttle (8504) and a linearly array of lights (8514) fixed to stationary portion (8502) and disposed within a respective opening (8506). Each light (8514) includes a switch (8516). Lights (8514) are electrically coupled to each other with a flex circuit (8518). Flex circuit (8518) extends proximally and couples with a power source configured to power illumination assembly (8510) in accordance with the description herein. During the firing process of end effector (8460) in order to staple and sever tissue (T) in accordance with the description herein, projection (8512) is configured to acuate past switches (8516) in a sequential fashion during the firing process of end effector (8460). Projection (8512) is dimensioned in order to suitably engage switches (8516) such that switches (8516) in turn activate the illumination of their respective light (8514).

Indicator markers (8508) are located along discrete longitudinal locations of stationary portion (8502) and include a specific value associated with each marker (i.e., the 50 mm marker, the 40 mm marker, the 30 mm marker, etc.). The specific number associated with each marker (8508) represents the distance that wedge sled (8472) and/or the associated knife member needs to travel further in order to complete the firing processes.

Lights (8514) may be located at a corresponding indicator marker (8508), while projection (8512) is located at a suitable longitudinal location on shuttle (8504), such that illumination of an individual light (8514) via contact between projection (8512) and the corresponding switch (8516) may signify the progress at which wedge sled (8472) is advanced through lower jaw (8462) during the firing process. For example, when projection (8512) engages the switch (8516) of light (8514) that is adjacent to the 20 mm indicator marker (8508), that light (8514) may illuminate to signify wedge sled (8472) still needs to travel 20 mm distally in order to complete the firing processes. As another example, when projection (8512) engages the switch (8516) of light (8514) that is adjacent to the 0 mm indicator marker (8508), that light (8514) may illuminate to signify wedge sled (8472) has reached the distal end of the firing process.

In some instances, once a specific light (8514) is illuminated via initial contact with projection (8512) actuating distally, that light (8514) may stay illuminated until projection (8512) engages that specific switch (8516) again during proximal retraction of shuttle (8504). Therefore, in some instances, the linear array of lights (8514) may remain activated to visually approximate the length at which wedge sled has traveled during distal actuation of shuttle (8504); while the linear array of lights (8514) may be used to visually approximate the length at which shuttle (8504) needs to proximally acuate to reach the pre-fired position after the firing process. In some instances, only one light (8514) may be activated at a time, such that once the second light (8514) activates during distal advancement of shuttle (8504), the first light (8514) deactivates, and so on. Therefore, in some instances, the linear array of lights (8514) may be sequentially activated to visually approximate the general position at which wedge sled is located during the firing process.

FIG. 131 shows another exemplary shaft assembly (8520) having an illumination assembly (8530). Shaft assembly (8520) may be substantially similar to shaft assembly (8500) described above, with difference elaborated below. In particular, illumination assembly (8530) includes a single switch (8536) fixed to a translating shuttle (8524), while a stationary portion (8522) includes a longitudinal array of projections (8532) configured to selectively engage switch (8536) as shuttle (8524) actuates during the firing process to thereby activate lights (8534) in accordance with the description herein.

Shaft assembly (8520) includes a stationary portion (8522) and a translating shuttle (8524) housed within stationary portion (8522). Stationary portion (8522) and translating shuttle (8524) may be substantially similar to stationary portion (8502) and translating shuttle (8504) described above, with differences elaborated below. Therefore, translating shuttle (8524) is configured to actuate within stationary portion (8522) to thereby actuate any suitable firing mechanism(s), (e.g., wedge sled (8472)). Therefore, the longitudinal position of translating shuttle (8504) relative to stationary portion (8502) may correspond to the progression at which any suitable end effector is firing to staple and sever tissue in accordance with the description herein.

Stationary portion (8522) defines a linear array of openings (8526). Each opening (8526) is dimensioned to house a respective light (8534) of the illumination assembly (8530). Therefore, when the respective light (8534) is illuminated in accordance with the description herein, such an illumination will be viewable through openings (8526). Stationary portion (8522) may include a plurality of indication markers (not shown) similar to indication markers (8508) described above.

As mentioned above, illumination assembly (8530) includes a linear array of projections (8532) fixed to stationary portion (8502), a switch (8536) attached to shuttle (8524), a linear array of lights (8534) fixed to stationary portion (8522) and disposed within a respective opening (8526), and a flex circuit (8538). Flex circuit (8538) electrical couples linear array of lights (8534) with switch (8536). Flex circuit (8538) extends proximally and couples with a power source configured to power illumination assembly (8530) in accordance with the description herein. Switch (8536) is configured to activate linear array of lights (8534) sequentially, from the proximal most light (8534) to the distal most light (8534), in response to activating switch (8536) repeated number of times. For instance, if switch (8536) is activated one time, the proximal most light (8534) may illuminate. If switch (8536) is then activated a second time, the next proximal most light (8534) may illuminate, and so on until the distal most light (8534) is illuminated.

During the firing process of end effector (8460) in order to staple and sever tissue (T) in accordance with the description herein, switch (8536) is configured to acuate past projections (8532) in a sequential fashion during the firing process of end effector (8460). Projections (8532) are dimensioned in order to suitably engage switch (8536) such that switch (8536) in turn activates to illuminate the linear array of lights (8514) in accordance with the description herein. Flex circuit (8538) has a suitable length between the proximal most light (8535) and switch (8536) in order to accommodate translation of shuttle (8524) relative to stationary portion (8522) during the exemplary firing process. Therefore, switch (8536) may actuate relative to lights (8534) during the firing process, while flex circuit (8538) may suitably maintain the electrical coupling between lights (8534) and switch (8536).

Similar to lights (8514) described above, lights (8534) may be located at a corresponding indicator marker (not shown), while the placement of projections (8532) and switch (8536) are located at a suitable longitudinal location on stationary portion (8522) and shuttle (8504), respectively, such that illumination of an individual light (8534) via contact between the corresponding projection (8532) and switch (8536) may signify the progress at which wedge sled (8472) is advanced through lower jaw (8462) during the firing process.

In some instances, once a specific light (8534) is illuminated via initial contact between the corresponding projection (8532) and switch (8536), that light (8534) may stay illuminated until the corresponding projection (8532) engages switch (8536) again during proximal retraction of shuttle (8524). Therefore, in some instances, the linear array of lights (8534) may remain activated to visually approximate the length at which wedge sled has traveled during distal actuation of shuttle (8524); while the linear array of lights (8534) may be used to visually approximate the length at which shuttle (8524) needs to proximally acuate to reach the pre-fired position after the firing process. In some instances, only one light (8534) may be activated at a time, such that once the second light (8534) activates during distal advancement of shuttle (8524), the first light (8534) deactivates, and so on. Therefore, in some instances, the linear array of lights (8534) may be sequentially activated to visually approximate the general position at which wedge sled is located during the firing process.

FIGS. 132-133 show another exemplary end effector (8540) that may be readily incorporated into instrument (110) described above. End effector (8540) includes a lower jaw (8542), an upper jaw (8544), a removable staple cartridge (8546), and a pusher member (8547); which may be substantially similar to lower jaw (152, 212), upper jaw (150, 214), staple cartridge (154, 218), and pusher member/block (166, 236), respectively, with difference elaborated herein. In particular, end effector (8540) includes an illumination assembly (8550) configured to illuminate to thereby visually represent the progression of a wedge sled actuating through jaws (8542, 8544) of end effector (8540).

Lower jaw (8544) includes a plurality of indicator markers (8548) that are substantially similar to indicator markers (8305, 8335, 8451) described above. Additionally, lower jaw (8544) defines a longitudinal array of openings (8545) associated with a corresponding indicator marker (8548). Each opening (8545) is dimensioned to house a respective light (8554) of the illumination assembly (8550). Therefore, when the respective light (8554) is illuminated in accordance with the description herein, such an illumination will be viewable through openings (8545).

Illumination assembly (8550) includes a projection (8552) attached pusher member (8547) and a linearly array of lights (8554) fixed to lower jaw (8542) and disposed within a respective opening (8545). Each light (8554) includes a switch (8556). Lights (8554) are electrically coupled to each other with a flex circuit (8558). Flex circuit (8558) extends proximally and couples with a power source configured to power illumination assembly (8550) in accordance with the description herein. During the firing process of end effector (8540) in order to staple and sever tissue (T) in accordance with the description herein, projection (8552) is configured to acuate past switches (8556) in a sequential fashion during the firing process of end effector (8540). Projection (8552) is dimensioned in order to suitably engage switches (8556) such that switches (8556) in turn activate the illumination of their respective light (8554).

Indicator markers (8548) are located along discrete longitudinal locations of lower jaw (8542) and include a specific value associated with each marker (i.e., the 50 mm marker, the 40 mm marker, the 30 mm marker, etc.). The specific number associated with each marker (8548) represents the distance that wedge sled and/or the associated knife member needs to travel further in order to complete the firing processes.

Lights (8554) may be located at a corresponding indicator marker (8548), while projection (8552) is located at a suitable longitudinal location on pusher member (8547), such that illumination of an individual light (8554) via contact between projection (8552) and the corresponding switch (8556) may signify the progress at which wedge sled is advanced through lower jaw (8542) during the firing process. For example, when projection (8552) engages the switch (8556) of light (8554) that is adjacent to the 20 mm indicator marker (8548), that light (8554) may illuminate to signify wedge sled still needs to travel 20 mm distally in order to complete the firing processes. As another example, when projection (8552) engages the switch (8556) of light (8554) that is adjacent to the 0 mm indicator marker (8548), that light (8554) may illuminate to signify wedge sled has reached the distal end of the firing process.

Lights (8554) may be configured to activate and deactivate illumination using any suitable process as would be apparent to one skilled in the art in view of the teachings herein. For example, lights (8554) may activate only when projection (8552) is in contact with switch (8556). As another example, lights (8554) may remain activated after contact with switch (8556) until the distal firing process in complete.

FIGS. 134-136 show an exemplary fire progress monitoring assembly (8562) that may visually approximate the firing process via thermochromic film (8568), rather than through illumination. In the current example, fire progress monitoring assembly (8562) is applied to a lower jaw (8560). However, it should be understood that fire progress monitoring assembly (8562) may be applied to an upper jaw or any other suitable component as would be apparent to one skilled in the art in view of the teachings herein.

Fire progress monitoring assembly (8562) includes a pair of longitudinally extending flex circuits (8564) that are electrically separated from each other, a piece of thermochromic film (8568) extending along the length of an exterior surface of lower jaw (8560), and a plurality of conducting elements (8566) extending in two longitudinal arrays, one from each piece of flex circuit (8564) to thermochromic film (8568). Each flex circuit (8564) extends proximally to a power source. However, since flex circuits (8564) are electrically separated from each other, the potential circuit formed by power source and both flex circuits (8564) may remain normally open. As best seen in FIG. 136, a pusher member (8570) is configured to actuate along the length of lower jaw (8560) such that a portion of pusher member (8570) directly adjacent to each flex circuit (8564) is in contact with each flex circuit (8564). Pusher member (8570) may be formed of a material that is configured to complete an electrical circuit between each flex circuit (8564).

Thermochromic film (8568), flex circuits (8564) and the array of conducting elements (8566) extend along a length of lower jaw (8560) corresponding with the travel length required for pusher member (8570) to suitably fire an end effector in accordance with the description herein. Thermochromic film (8568) is configured to change color in response to a temperature change. As shown in FIGS. 137 and 138, such a temperature change may be function of an applied voltage to thermochromic film (8568) over a period a time.

As pusher member (8570) actuates along the length of lower jaw (8560) in order to fire an end effector in accordance with the description herein, the portion of flex circuits (8564) in contact with pusher member (8570) may transmit a voltage to thermochromic film (8568) via plurality of conducting elements (8566). The electrical conducting element (8566) closest the pusher member (8570) may apply the highest voltage to thermochromic film (8568), thereby causing the greater change in color. Therefore, a user may be able to approximate the location of pusher member (8570), and therefore approximate the progress of firing an end effector to staple and sever tissue, by viewing where the change in color is located along the length of thermochromic film (8568).

While in the current example thermochromic film (8568) is used, any other suitable material may be used to provide visual indication of where pusher member (8570) is located based on completing an electrical circuit with flex circuits and pusher member (8570). For instance, a pressure sensitive material may be incorporated that may show the current flowing the conducting elements (8566), thereby providing a visual approximation of the location of pusher member (8570).

In some instances, as shown in FIG. 139, pusher member (166) may incorporate a magnetic strip (8580), while a portion of lower jaw (152) or upper jaw (150) that is viewable from an exterior of end effector (116) may include a piece magnetic viewing film extending along a length that pusher member (166) travels in order to fire end effector (116) in accordance with the description herein. Therefore, as pusher member (166) travels along jaws (152, 150), the magnetic viewing film will distort where magnetic strip (8580) is located. Such a distortion may provide an approximation of where pusher member (166) is located to track the progression of firing end effector (116).

FIG. 140 show an exemplary upper jaw (8590) that may be used to track the progression of pusher member (166) traveling along the length of end effector (116) in order to staple and sever tissue in accordance with the description herein. Therefore, upper jaw (8590) may be readily incorporated into end effector (116) in replacement of upper jaw (150) described above.

Upper jaw (8590) includes a plurality of micro-holes (8592) extending along a length of upper jaw (8590). Micro-holes (8592) extend from an interior channel of upper jaw (8590) dimensioned to receive slidably pusher number (166) all the way to an exterior surface of upper jaw (8590). The interior channel of upper jaw (8590) maybe "flooded" with light via an LED light or any other suitable light source as would be apparent to one skilled in the art in view of the teachings herein. Therefore, light emitted from the light source within the interior channel of upper jaw (8590) may illuminate out of all micro-holes (8592). As pusher member (166) acerates within the interior channel of upper jaw (8590), the portion of pusher member (166) directly adjacent to specific micro-holes (8592) may block light from illuminating out of directly adjacent micro-holes (8592). Therefore, a user may be able to approximate the location of pusher member (166) during the exemplary firing of end effector (116) by noting which micro-holes (8592) are not illuminating light.

XIII. Exemplary Drive Systems for Surgical Instrument

A. Exemplary Drive System

FIGS. 141 and 142 show an exemplary drive system (8620) that may be readily incorporated into surgical instrument (110) described above in lieu of drive system (120). As with drive system (120) described above, drive system (8620) of the present example is mounted to chassis (122) of instrument base (112). Similarly, drive system (8620) includes one or more actuators for actuating end effector (116) to clamp, staple, and cut tissue, for rotating end effector (116) and/or shaft assembly (114), and for articulating end effector (116) relative to a longitudinal axis defined by shaft assembly (114). Drive system (8620) may also include a manual actuator (not shown) similar to manual actuator (124) described above, which may be in the form of a knob configured to be manually rotated.

As best seen in FIG. 141, drive system (8620) of the present example includes a plurality of drive inputs (8632, 8634, 8652, 8672, 8674), which may extend through chassis (122) and into the interior of surgical instrument (110). Although not shown, it should be understood that each drive input (8632, 8634, 8652, 8672, 8674) is configured to communicate with a corresponding drive output (not shown) of robotic arm (42) to transmit rotary input from robotic arm (42) to other portions of surgical instrument (110). Each drive input (8632, 8634, 8652, 8672, 8674) of the present example is associated with one or more drive modules (8630, 8650, 8670) to control various functions of surgical instrument (110) as will be described in greater detail below.

Drive system (8620) of the present example includes an articulation drive module (8630), an actuation drive module (8650), and a rotation drive module (8670). Drive modules (8630, 8650, 8670) are together configured to drive movement of one or more of end effector (116) and or shaft assembly (114), as will be described in greater detail below. For instance, articulation drive module (8630) is generally configured to drive articulation of end effector (116) relative to a longitudinal axis defined by shaft assembly (114). Actuation drive module (8650) is generally configured to drive actuation of end effector (116) to clamp, staple, and cut tissue. Rotation drive module (8670) is generally configured to rotate one or more components of shaft assembly (114) and/or components associated therewith.

Articulation module (8650) includes a first articulation drive input (8632) and a second articulation drive input (8634). Each of first articulation drive input (8632) and second articulation drive input (8634) define a shaft extending proximally from chassis (122) and into the interior of surgical instrument (110). Although not shown, it should be understood each of first articulation drive input (8632) and second articulation drive input (8634) may be configured to engage a drive output (not shown) of robotic arm (42) to rotate via one or more motors associated with robotic arm (42). As will be understood, such rotation may be desirable to manipulate one or more articulation cables (8640, 8642, 8644, 8646) to control articulation of end effector (116) relative to shaft assembly (114) using articulation drive inputs (8632, 8634).

A first articulation capstan (8636) and a second articulation capstan (8638) are disposed proximate a proximal end of first articulation drive input (8632) and second articulation drive input (8634), respectively. Articulation capstans (8636, 8638) are generally configured to simultaneously tension and release a respective set of articulation cables (8640, 8642, 8644, 8646) to control articulation of end effector (116) relative to shaft assembly (114). As such each of articulation capstans (8636, 8638) are configured as dual-capstans to permit each respective articulation cable (8640, 8642, 8644, 8646) to be opposingly threaded relative to another articulation cable (8640, 8642, 8644, 8646). Although not shown, it should be understood that articulation cables (8640, 8642, 8644, 8646) may extend from each articulation capstan (8636, 8638) and through shaft assembly (114) to communicate with various features configured to drive articulation of end effector (116) relative to shaft assembly (114).

Actuation drive module (8650) includes an actuation drive input (8652). Actuation drive input (8652) defines an elongate shaft extending proximally from chassis (122) and into the interior of surgical instrument (110). Although not shown, it should be understood that actuation drive input (8652) may be configured to engage a drive output (not shown) of robotic arm (42) to rotate via one or more motors associated with robotic arm (42). As will be understood, such rotation may be desirable to manipulate one or more actuation cables (8664, 8666) to control actuation of end effector (116) and other components associated with end effector (116) to clamp, staple, and cut tissue using actuation drive input (8652).

A proximal end of actuation drive input (8652) includes an actuation drive gear (8654). Actuation drive gear (8654) is configured to rotate with actuation drive input (8652) to move other components of actuation drive module (8650). In particular, actuation drive gear (8654) is configured to mesh with an idler gear (8656), which is configured to mesh with a capstan gear (8660) to drive movement of an actuation capstan (8662). Idler gear (8656) further includes a bevel gear (8658) that is configured to directly mesh with capstan gear (8660), thereby permitting a different orientation of capstan gear (8660) relative to idler gear (8656).

Actuation capstan (8662) is generally configured to simultaneously tension and release a set of actuation cables (8664, 8666) to control movement of end effector (116) and other components associated with end effector (116) to clamp, staple, and cut tissue. In particular, actuation drive module (8650) further includes a first actuation cable (8664) and a second actuation cable (8666). First actuation cable (8664) and second actuation cable (8666) are wrapped in opposing directions around actuation capstan (8662) such that rotation of actuation capstan (8662) may cause one actuation cable (8664, 8666) to tension and the other actuation cable (8666, 8664) to release, depending on the direction of rotation of actuation capstan (8662). Actuation cables (8664, 8666) extend distally from actuation capstan (8662) into shaft assembly (114). Although not shown, it should be understood that actuation cables (8664, 8666) may couple to other components within shaft assembly (114) to control movement of end effector (116) and other components associated with end effector (116) to clamp, staple, and cut tissue via rotation of actuation drive input (8652).

Rotation drive module (8670) includes a primary rotation drive input (8672) and a secondary rotation drive input (8674). Primary rotation drive input (8672) and secondary rotation drive input (8674) each define a shaft extending proximally from chassis (122) and into the interior of surgical instrument (110). The particular length of extension for primary rotation drive input (8672) is different from secondary rotation drive input (8674) to promote driving of different elements of rotation drive module (8670) via primary rotation drive input (8672) or secondary rotation drive input (8674). In the present example, the length of extension for secondary rotation drive input (8674) is longer than the length of extension of primary rotation drive input (8672). Although not shown, it should be understood that each of primary rotation drive input (8672) and secondary rotation drive input (8674) may be configured to engage a respective drive output (not shown) of robotic arm (42) to rotate via one or more motors associated with robotic arm (42). As will be understood, such rotation may be desirable to manipulate one or more components associated with shaft assembly (114) to rotate shaft assembly (114) and/or components associated therewith using primary rotation drive input (8672) and secondary rotation drive input (8674).

A proximal end of each rotation drive input (8672, 8674) includes a respective rotation drive gear (8676, 8678) configured to communicate rotary motion of a respective rotation drive input (8672, 8674) to other components of rotation drive module (8670). For instance, primary rotation drive input (8672) includes a primary rotation drive gear (8676). Primary rotation drive gear (8676) is in communication with a primary idler gear (8680), which is in communication with a primary rotation input (8684). Primary rotation input (8684) is coupled to shaft assembly (114) such that rotation of primary rotation input (8684) is configured to drive rotation of shaft assembly (114). Thus, it should be understood that primary rotation drive input (8672) is configured to rotate shaft assembly (114) by rotating primary rotation drive gear (8676), which rotates primary idler gear (8680), which rotates primary rotation input (8684) to ultimately rotate shaft assembly (114).

Secondary rotation drive input (8674) includes a secondary rotation drive gear (8678). Secondary rotation drive gear (8678) is in communication with a secondary idler gear (8682), which is in communication with a secondary rotation input (8686). Secondary rotation input (8686) is secured or otherwise in communication with a cable manipulator (8688). Cable manipulator (8688) includes one or more openings configured to direct and/or manipulate any one or more of cables (8640, 8642, 8644, 8646, 8664, 8666) described above. Thus, cable manipulator (8688) is generally configured to rotate with shaft assembly (114) to maintain separation and alignment of cables (8640, 8642, 8644, 8646, 8664, 8666) or otherwise avoid entanglement of cables (8640, 8642, 8644, 8646, 8664, 8666). Accordingly, secondary rotation drive input (8674) is generally configured to control the position of cables (8640, 8642, 8644, 8646, 8664, 8666) during rotation of shaft assembly (114) by rotating cable manipulator (8688) using secondary rotation drive gear (8674), secondary idler gear (8682), and secondary rotation input (8686).

In use, drive inputs (8632, 8634, 8652, 8672, 8674) may be rotated in various sequences by one or more motors within robotic arm (42) to control various functions of surgical instrument (110). For instance, in one merely exemplary use, first articulation drive input (8632) and second articulation drive input (8634) may be rotated together or independently to articulate end effector (116) relative to a longitudinal axis defined by shaft assembly (114). Such movement may be used to manipulate end effector (116) into a predetermined position relative to a patient. In some examples, articulation may include both pitch and yaw articulation with one articulation drive input (8632, 8634) controlling pitch, and another articulation drive input (8634, 8632) controlling yaw.

While positioning end effector (116), it may also be desirable to rotate shaft assembly (114) to provide further control of the position of end effector (116) relative to a patient. Such rotation of shaft assembly (114) may be controlled by rotation drive module (8670) by rotating primary rotation drive input (8672) and/or secondary rotation drive input (8674) either together or independently. For instance, rotation of primary rotation drive input (8672) may be used to rotate shaft assembly (114) itself. Meanwhile, rotation of secondary rotation drive input (8674) may be used to control rotation of cable manipulator (8688) to maintain cables (8640, 8642, 8644, 8646, 8664, 8666) in a desired arrangement or position relative to each other during rotation of shaft assembly (114).

Once end effector (116) is in a desired position relative to a patient, it may be desirable to use end effector (116) for the purpose of clamping, stapling, and/or cutting tissue. At this stage, end effector (116) may be further manipulated using articulation drive inputs (8632, 8634) and/or rotation drive inputs (8672, 8674) as described above to position end effector (116) relative to tissue of interest. Simultaneously or independently of such manipulation of the position of end effector (116), jaws (150, 152), wedge sled (170), and/or other components of end effector (116) may be actuated using actuation drive module (8650) to clamp, staple, and/or cut the tissue of interest. Specifically, actuation drive input (8652) may be rotated to manipulate actuation assembly, also referred to as driving assembly (164) of end effector (116) via actuation cables (8664, 8666). Such manipulation of actuation assembly (164) may then cause, for example, opening and/or closing of jaws (150, 152) for tissue clamping, translation of wedge sled (170) for tissue stapling, and/or translation of knife member (172) for tissue cutting.

B. Exemplary Alternative Drive System with Adjustable Tension Bands

In some examples, it may be desirable to incorporate a drive system similar to drive system (8610) described above into surgical instrument (110) with various features to improve operation of surgical instrument (110), improve the efficiency of surgical instrument (110), and/or improve the simplicity or adaptability of surgical instrument (110). For instance, in some examples, it may be desirable to control multiple functions of surgical instrument (110) using a single drive input. In addition, or in the alternative, it may be desirable to control multiple aspects of the same function of surgical instrument (110) using a single drive input. Configurations of such drive systems controlling multiple functions and/or multiple aspects of the same function of surgical instrument (110) may be desirable to reduce the number of motors used to drive surgical instrument (110) such as those in robotic arm (42). Thus, such configurations may improve the efficiency of surgical instrument (110), may make surgical instrument (110) more adaptable, and/or may generally simplify surgical instrument (110).

Further in addition, or in the alternative, it may be desirable to incorporate features into such drive mechanisms to provide control over the mechanical advantage communicated to one or more functions of surgical instrument (110) from such drive systems. For instance, during use of some functions, it may be desirable to actuate surgical instrument (110) with a preference for either speed or power. Thus, features to provide selectability between either speed or power for actuation may be desirable to improve overall operation of surgical instrument (110) or to improve the efficiency of surgical instrument (110). While a variety of suitable drive mechanisms are described below as including such features in specific configurations, it should be understood that in other examples such features may be combined in different configurations without departing from the various concepts described herein.

FIG. 143A shows an exemplary alternative drive system (8720) that may be readily incorporated into surgical instrument described above. Drive system (8720) of the present example is similar to drive system (8620) described above in that drive system (8720) of the present example is generally configured to receive external rotary inputs to drive one or more actuators for actuating end effector (116) to clamp, staple, and cut tissue, for rotating end effector (116) and/or shaft assembly (114), and for articulating end effector (116)

relative to a longitudinal axis defined by shaft assembly (114). Drive system (8720) may also include a manual actuator (not shown) similar to manual actuator (124) described above, which may be in the form of a knob configured to be manually rotated.

Like drive system (8620) described above, drive system (8720) of the present example includes one or more drive modules (8730, 8750, 8770) configured to drive various functions of surgical instrument (110). Unlike drive modules (8630, 8650, 8670) described above, which were described as being operable independently of each other, drive modules (8730, 8750, 8770) of the present example are interconnected with each other. As will be described in greater detail below, this configuration may be generally desirable to selectively permit multiple motors to drive a single function of surgical instrument (110) and thereby increase the mechanical advantage provided to a given function of surgical instrument (110).

Drive system (8720) includes an articulation drive module (8730), an actuation drive module (8750), and a rotation drive module (8770). Articulation drive module (8730) is similar to articulation drive module (8630) described above in that articulation drive module (8730) includes a first articulation drive input (8732) and a second articulation drive input (8734). Although not shown, it should be understood that drive inputs (8732, 8734) may likewise each include a respective articulation capstan (not shown) similar to articulation capstans (8636, 8638) described above. Like articulation capstans (8636, 8638), such articulation capstans in the present example may be configured to selectively tension one or more respective articulation cables similar to articulation cables (8640, 8642, 8644, 8646) described above to ultimately control movement of end effector (116) relative to a longitudinal axis defined by shaft assembly (114).

Unlike articulation drive module (8630) described above, articulation drive module (8730) of the present example includes one or more drive bands (8740, 8742) extending from articulation drive module (8730) to one or more other drive modules (8750, 8770). Drive bands (8740, 8742) are generally configured to communicate power from one or more of drive inputs (8732, 8734) to one or more other drive modules (8750, 8770) or receive power from one or more other drive modules (8750, 8770). Thus, drive bands (8740, 8742) may be generally configured to shift power between drive modules (8730, 8750, 8770) to selectively increase the mechanical advantage of a given function of surgical instrument (110). In addition, or in the alternative, drive bands (8740, 8742) may be generally configured to shift power between drive modules (8730, 8750, 8770) to power multiple functions of surgical instrument (110) to eliminate one or more drive inputs and instead use only drive inputs (8732, 8734) or drive inputs (8732, 8734) in combination with other drive inputs described below.

Actuation drive module (8750) of the present example is similar to actuation drive module (8650) described above in that actuation drive module (8750) includes an actuation drive input (8752) configured to engage a drive output of robotic arm (42) to control actuation of end effector (116) and other components associated with end effector (116) to clamp, staple and cut tissue. To promote such functionality, actuation drive input (8752) includes an actuation drive gear (8754), which is configured to mesh with an idler gear (8756). Although not shown, it should be understood that idler gear (8756) may mesh or otherwise communicate with one or more structures similar to bevel gear (8658), capstan gear (8660), actuation capstan (8662). As similarly described above, such structures may permit actuation drive input (8752) to rotate an actuation capstan (not shown) to selectively tension/release one or more actuation drive cables (not shown) similar to actuation drive cables (8664, 8666) described above. The actuation drive cables may then communicate with structures associated with end effector (116) to clamp, staple and cut tissue.

Unlike actuation drive module (8650) described above, actuation drive module (8750) of the present example is generally configured to selectively communicate with articulation drive module (8730) and/or rotation drive module (8770). As will be described in greater detail below, this feature may be desirable to permit actuation drive module (8750) of the present example to selectively actuate end effector (116) with increased mechanical advantage. In some examples, this may be facilitated by, for example, communicating power from first articulation drive input (8732) and/or second articulation drive input (8734) to actuation drive gear (8752) via meshing between idler gear (8756) and one or more structures associated with rotation drive module (8770).

Rotation drive module (8770) of the present example is similar to rotation drive module (8670) described above in that rotation drive module (8770) is configured to drive rotation of shaft assembly (114) of surgical instrument (110) and other components associated therewith. However, unlike rotation drive module (8670) described above, rotation drive module (8770) of the present example is configured to selectively divert rotary power from articulation drive inputs (8732, 8734) of articulation drive module (8730) to other portions of either articulation drive module (8730) and/or actuation drive module (8750).

Rotation drive module (8770) of the present example omits structures similar to primary rotation drive input (8672) and secondary rotation drive input (8674). Instead, rotation drive module (8770) includes a drive pivot (8772) and a shifting drive input (8774). Drive pivot (8772) is positioned similarly to primary rotation drive input (8672) described above. However, instead of being configured to receive rotary input, drive pivot (8772) is configured to be manipulated by other structures of rotation drive module (8770) to drive either rotation of shaft assembly (114) or other functions of surgical instrument (110).

Drive pivot (8772) is coupled to a lock arm (8776), a pivot arm (8780) and a selector arm (8782). Drive pivot (8772) is generally configured to permit pivoting of lock arm (8776), pivot arm (8780) and selector arm (8782) about an axis defined by drive pivot (8772). Although drive pivot (8772) itself is not configured to directly provide movement of lock arm (8776), pivot arm (8780) and selector arm (8782), it should be understood that in some examples, drive pivot (8772) may be configured to manipulate such movement by providing a ratcheting action and/or biasing lock arm (8776), pivot arm (8780) and selector arm (8782) toward one or more predetermined positions. It still other examples, drive pivot (8772) may be configured to drive movement of lock arm (8776), pivot arm (8780), and selector arm (8782) directly via rotation from one or more motors.

Drive pivot (8772) is further configured as a drive input to communicate rotary motion from one or more motors in robotic arm (42) to other components of rotation drive module (8770). Although drive pivot (8772) is shown schematically in the present example, it should be understood that in practice at least a portion of drive pivot (8772) may be configured as a gear or other feature configured to mesh or communicate rotary motion from drive pivot (8772) to other portions of rotation drive module (8770). As will be described in greater detail below, such communication may be used to drive rotation of shaft assembly (114) via drive pivot (8772).

Lock arm (8776), pivot arm (8780), selector arm (8782) extend outwardly from drive pivot (8772). Additionally, lock arm (8776), pivot arm (8780) and selector arm (8782) each extend at a fixed angle relative to each other. In other words, lock arm (8776), pivot arm (8780), and selector arm (8782) are configured to pivot about drive pivot (8772) while maintaining a fixed position relative to each other. Lock arm (8776) includes a plurality of lock teeth (8778) disposed on an outer end of lock arm (8776) opposite of drive pivot (8772). As will be described in greater detail below, lock teeth (8778) are configured to engage primary rotation input (8784) to selectively lock rotation of shaft assembly (114).

Pivot arm (8780) is disposed between lock arm (8776) and selector arm (8782). Pivot arm includes an output gear (8790) disposed on an outer end of pivot arm (8780) opposite of drive pivot (8772). Output gear (8790) is rotatably coupled to pivot arm (8780) and is in communication with first drive band (8740) and second drive band (8742) to rotate via drive bands (8740, 8742). Output gear (8790) is further configured to mesh with a gear portion of drive pivot (8772) to also be rotated directly by drive pivot (8772). As will be described in greater detail below, pivot arm (8780) is configured to pivot about drive pivot (8772) to move output gear (8790) into communication with primary rotation input (8784) or idler gear (8756) of actuation drive module (8750).

Selector arm (8782) extends outwardly from pivot arm (8780) and terminates at an outer end opposite of drive pivot (8772). Selector arm (8782) is generally configured to engage with one or more portions of shifting drive input (8774) as will be described in greater detail below to pivot lock arm (8776) and pivot arm (8780) about drive pivot (8772). Thus, selector arm (8782) is configured to shift rotation drive module (8770) into various drive configurations to control rotation of shaft assembly (114) and/or a portion of the actuation associated with actuation drive module (8750).

Shifting drive input (8774) is generally configured to be driven by one or more motors to shift rotation drive module (8770) into various drive configurations. Shifting drive input (8774) includes a band tensioner (8786) and a shifting arm (8788). Band tensioner (8786) is generally configured to rotate via shifting drive input (8774) to selectively adjust a tension on drive bands (8740, 8742). Specifically, band tensioner (8786) defines an oval shaped or oblong cross-section. Band tensioner (8786) is further disposed in an off-center position relative to the rotation axis of shifting drive input (8774). Together, these features permit band tensioner (8786) to manipulate drive bands (8740, 8742), which are threaded around band tensioner (8786) upon rotation of band tensioner (8786). As will be described in greater detail below, such manipulation may include applying greater tension to one drive band (8740, 8742) over another drive band (8742, 8740) by band tensioner (8786) moving into a position that engages one drive band (8740, 8742) over the other drive band (8742, 8740).

Shifting arm (8788) extends outwardly from the rotation axis of shifting drive input (8774), protruding from an outer perimeter of shifting drive input (8774) and/or band tensioner (8786). Shifting arm (8788) is generally configured to manipulate selector arm (8782) to selectively pivot lock arm (8776) and pivot arm (8780) using rotation of shifting drive input (8774). Shifting arm (8788) may be further used to hold lock arm (8776) and pivot arm (8780) in a predetermined position, as will be described in greater detail below.

An exemplary use of drive system (8720) is shown in FIGS. 143A through 143D. As can be seen, drive bands (8740, 8742) extend from articulation drive module (8730) to rotation drive module (8770). In use, drive bands (8740, 8742) may be used to transfer power from first articulation drive input (8732), second articulation drive input (8734) or both to power rotation of shaft assembly (114) or actuation of end effector (116) with power from first articulation drive input (8732), second articulation drive input (8734) or both. Such power may be controlled using tension on drive bands (8740, 8742). For instance, as best seen in FIG. 143A, drive system (8720) may be initially operated in a single drive configuration. In this configuration, each drive module (8730, 8750, 8770) may be driven by the particular drive input (8732, 8734, 8752) or drive pivot (8772) associated with a given drive module (8730, 8750, 8770). In other words, the particular function (e.g., rotation of shaft assembly (114), actuation of end effector (116), pitch articulation of end effector (116), and yaw articulation of end effector (116)) associated with each drive module (8730, 8750, 8770) may be driven by only a single motor input.

In the single drive configuration, shifting drive input (8774) of rotation drive module (8770) may be rotated to position band tensioner (8786) in an approximately 2 o'clock position as shown in FIG. 143A. It should be understood that clock positions referred to herein are relative to the position of shifting drive input (8774) as shown in FIGS. 143A through 143D. Thus, in other contexts, different clock positions may be used. In the 2 o'clock position, the longitudinal axis of band tensioner (8786) is generally oriented in a proximal direction with a slight lateral skew. In this position, band tensioner (8786) engages drive bands (8740, 8742) with a relatively low tension. With such a low tension on drive bands (8740, 8742), friction between drive bands (8740, 8742) and output gear (8790) is sufficiently low such that drive bands (8740, 8742) may not communicate rotary motion to output gear (8790).

Also in the single drive configuration, shifting drive input (8774) may be rotated to position shifting arm (8788) also in the 2 o'clock position. In this position, a counterclockwise rotational force may be applied to shifting drive input (8774) to push selector arm (8782) in a clockwise direction. This may cause pivoting of pivot arm (8780) also in the clockwise direction to promote engagement between output gear (8790) and primary rotation input (8784).

With shifting drive input (8774) positioned as described above, drive inputs (8732, 8734, 8752) and drive pivot (8772) may be used to independently drive their respective functions. Specifically, primary rotation input (8784) may be used to rotate shaft assembly (114) via output gear (8790) and drive pivot (8772). Similarly, actuation drive input (8752) may be used to actuate end effector (116) clamp, staple and cut tissue via idler gear (8756). First articulation drive input (8732) may likewise drive one aspect of articulation (e.g., pitch, yaw, etc.) of end effector (116) by driving one or more articulation capstans (not shown) associated with first articulation drive input (8732). Second articulation drive input (8734) may drive another aspect of articulation (e.g., pitch, yaw, etc.) of end effector (116) by driving one or more articulation capstans (not shown) associated with second articulation drive input (8734).

During use, it may be desirable to drive a given function of surgical instrument (110) with an additional motor for increased mechanical advantage for the given function. For instance, as shown in FIG. 143B, drive system (8720) may be transitioned to a first multiple drive configuration. In the first multiple drive configuration, drive system (8720) is generally configured to provide additional power to first articulation drive input (8732) to effectively double the power used for one aspect of articulation (e.g., pitch, yaw, etc.) of end effector (116).

To transition drive system (8720) to the first multiple drive configuration, shifting drive input (8774) is rotated to move band tensioner (8786) and shifting arm (8788) to about a 3 o'clock position. In this position, band tensioner (8786) is laterally offset relative to the rotation axis of shifting drive input (8774) toward second drive band (8742). This laterally offset position permits band tensioner (8786) to apply additional tension to first drive band (8740), thereby increasing the friction on first drive band (8740) and output gear (8790). With this added friction, first drive band (8740) may be used to communicate power from drive pivot (8772) to first articulation drive input (8732) via first drive band (8740) and output gear (8790).

As noted above, shifting arm (8788) is also moved to about the 3 o'clock position. As can be seen in FIG. 143B, this move disengages shifting arm (8788) from selector arm (8782), which permits pivot arm (8780) to pivot in a counterclockwise direction moving output gear (8790) out of engagement with primary rotation input (8784), thereby diverting power from primary rotation input (8784) to first articulation drive input (8732). Lock arm (8776) is similarly pivoted in a counterclockwise direction, which moves lock teeth (8778) into engagement with primary rotation input (8784). Thus, rotation of shaft assembly (114) may be locked in the first multiple drive configuration via lock teeth (8778).

With shifting drive input (8774) positioned as described above, some drive inputs (8732, 8734, 8752) may still be used independently to drive their respective functions, while drive pivot (8772) may be used to provide supplementary power to articulation drive module (8730). Specifically, drive pivot (8772) may be used in combination with first articulation drive input (8732) to drive one aspect of articulation (e.g., pitch, yaw, etc.) of end effector (116) by driving one or more articulation capstans (not shown) associated with first articulation drive input (8732). Meanwhile, actuation drive input (8752) may be used to actuate end effector (116) clamp, staple and cut tissue via idler gear (8756). Second articulation drive input (8734) may likewise drive another aspect of articulation (e.g., pitch, yaw, etc.) of end effector (116) by driving one or more articulation capstans (not shown) associated with second articulation drive input (8734).

During use, it may be desirable to alternatively drive another given function of surgical instrument (110) with an additional motor for increased mechanical advantage for the given function. For instance, as shown in FIG. 143C, drive system (8720) may be transitioned to a second multiple drive configuration. In the second multiple drive configuration, drive system (8720) is generally configured to provide additional power to second articulation drive input (8734) to effectively double the power used for one aspect of articulation (e.g., pitch, yaw, etc.) of end effector (116).

To transition drive system (8720) to the second multiple drive configuration, shifting drive input (8774) is rotated to move band tensioner (8786) and shifting arm (8788) to about a 9 o'clock position. In this position, band tensioner (8786) is laterally offset relative to the rotation axis of shifting drive input (8774) toward first drive band (8740). This laterally offset position permits band tensioner (8786) to apply additional tension to second drive band (8742), thereby increasing the friction of second drive band (8742) and output gear (8790). With this added friction, second drive band (8742) may be used to communicate power from drive pivot (8772) to second articulation drive input (8734) via second drive band (8742) and output gear (8790).

As noted above, shifting arm (8788) is also moved to about the 9 o'clock position. As can be seen in FIG. 143C, this move continues the disengagement of shifting arm (8788) from selector arm (8782), which maintains pivot arm (8780) in a position with output gear (8790) out of engagement with primary rotation input (8784), thereby diverting power from primary rotation input (8784) to second articulation drive input (8734). Lock arm (8776) also maintains a position with lock teeth (8778) engaged with primary rotation input (8784). Thus, rotation of shaft assembly (114) may be locked in the second multiple drive configuration via lock teeth (8778).

With shifting drive input (8774) positioned as described above, some drive inputs (8732, 8734, 8752) may still be used independently to drive their respective functions, while drive pivot (8772) may be used to provide supplementary power to articulation drive module (8730). Specifically, drive pivot (8772) may be used in combination with second articulation drive input (8734) to drive one aspect of articulation (e.g., pitch, yaw, etc.) of end effector (116) by driving one or more articulation capstans (not shown) associated with second articulation drive input (8734). Meanwhile, actuation drive input (8752) may be used to actuate end effector (116) to clamp, staple and cut tissue via idler gear (8756). First articulation drive input (8732) may likewise drive another aspect of articulation (e.g., pitch, yaw, etc.) of end effector (116) by driving one or more articulation capstans (not shown) associated with second articulation drive input (8734).

During use, it may be desirable to alternatively drive still another given function of surgical instrument (110) with an additional motor for increased mechanical advantage for the given function. For instance, as shown in FIG. 143D, drive system (8720) may be transitioned to a third multiple drive configuration. In the third multiple drive configuration, drive system (8720) is generally configured to provide additional power to actuation drive module (8750) to effectively double the power used for actuation of end effector (116).

To transition drive system (8720) to the third multiple drive configuration, shifting drive input (8774) is rotated to move band tensioner (8786) and shifting arm (8788) to about a 1 o'clock position. In this position, band tensioner (8786) is approximately oriented vertically or proximally. This proximal position permits band tensioner (8786) to release tension from both first drive band (8740) and second drive band (8742). With the tension released, first drive band (8740) and second drive band (8742) may be configured to not transmit power between output gear (8790), first articulation drive input (8732), and second articulation drive input (8734).

As noted above, shifting arm (8788) is also moved to about the 1 o'clock position. As can be seen in FIG. 143D, this move reengages shifting arm (8788) with selector arm (8782), but from an opposite side of selector arm (8782) in comparison to the single drive configuration described above. This engagement may cause shifting arm (8788) to pivot selector arm (8782) in a counterclockwise direction. As a result, pivot arm (8780) may likewise pivot in a counterclockwise direction, which may move output gear (8790) into communication with idler gear (8756) of actuation drive module (8750). Once output gear (8790) and idler gear (8756) are engaged, drive pivot (8772) may rotate idler gear (8756) via output gear (8790).

With shifting drive input (8774) positioned as described above, some drive inputs (8732, 8734, 8752) may still be used independently to drive their respective functions, while drive pivot (8772) may be used to provide supplementary power to actuation drive module (8750). Specifically, drive pivot (8772) may be used in combination with actuation drive input (8752) to actuate end effector (116) to clamp, staple and cut tissue via idler gear (8756). First articulation drive input (8732) may be used to drive one aspect of articulation (e.g., pitch, yaw, etc.) of end effector (116) by driving one or more articulation capstans (not shown) associated with first articulation drive input (8732). Meanwhile, second articulation drive input (8734) may be used to drive another aspect of articulation (e.g., pitch, yaw, etc.) of end effector (116) by driving one or more articulation capstans (not shown) associated with second articulation drive input (8734).

C. Exemplary Alternative Drive System with Movable Gears

FIG. 144A shows an exemplary alternative drive system (8820) that may be readily incorporated into surgical instrument described above. Drive system (8820) of the present example is similar to drive system (8620) described above in that drive system (8820) of the present example is generally configured to receive external rotary inputs to drive one or more actuators for actuating end effector (116) to clamp, staple, and cut tissue, for rotating end effector (116) and/or shaft assembly (114), and for articulating end effector (116) relative to a longitudinal axis defined by shaft assembly (114). Drive system (8820) may also include a manual actuator (not shown) similar to manual actuator (124) described above, which may be in the form of a knob configured to be manually rotated.

Like drive system (8620) described above, drive system (8820) of the present example includes one or more drive modules (8830, 8850, 8870) configured to drive various functions of surgical instrument (110). Unlike drive modules (8630, 8650, 8670) described above, which were described as being operable independently of each other, one or more of drive modules (8830, 8850, 8870) of the present example may be configured to communicate with another drive module (8830, 8850, 8870). As will be described in greater detail below, this configuration may be generally desirable to selectively permit multiple motors to drive a single function of surgical instrument (110) and thereby increase the mechanical advantage provided to a given function of surgical instrument (110). In addition, or in the alternative, this configuration may be generally desirable to selectively permit a single motor to drive multiple functions of surgical instrument (110).

Drive system (8820) includes an articulation drive module (8830), an actuation drive module (8850), and a rotation drive module (8870). Articulation drive module (8830) is similar to articulation drive module (8630) described above in that articulation drive module (8830) includes a first articulation drive input (8832) and a second articulation drive input (8834). Although not shown, it should be understood that drive inputs (8832, 8834) may likewise each include a respective articulation capstan (not shown) similar to articulation capstans (8636, 8638) described above. Like articulation capstans (8636, 8638), such articulation capstans in the present example may be configured to selectively tension one or more respective articulation cables similar to articulation cables (8640, 8642, 8644, 8646) described above to ultimately control movement of end effector (116) relative to a longitudinal axis defined by shaft assembly (114).

Unlike articulation drive module (8630) described above, articulation drive module (8830) of the present example includes an articulation shift arm (8836) configured to control the function of first articulation drive input (8832). Specifically, articulation shift arm (8836) extends outwardly from a central axis of first articulation drive input (8832) and terminates at an engagement portion (8838). An articulation idler gear (8840) is disposed on articulation shift arm (8836) between first articulation drive input (8832) and engagement portion (8838). Articulation shift arm (8836) is generally configured to move articulation idler gear (8840) relative to first articulation drive input (8832). As will be described in greater detail below, actuation shift arm (8836) is configured to pivot about first articulation drive input (8832) to selectively control communication rotary motion from first articulation drive input (8832) to other components of articulation drive module (8830) via articulation idler gear (8840).

Articulation shift arm (8836) is associated with an articulation lock arm (8842) and a tensioning lock arm (8844). Articulation shift arm (8836), articulation lock arm (8842) and tensioning lock arm (8844) are coupled to each other at the central axis of first articulation drive input (8832). Thus, articulation shift arm (8836), articulation lock arm (8842) and tensioning lock arm (8844) are generally configured to pivot together.

Articulation lock arm (8842) and tensioning lock arm (8844) each include a plurality of teeth. As will be described in greater detail below, articulation lock arm (8842) and tensioning lock arm (8844) are each configured to mesh or otherwise engage with other components of articulation drive module (8830) via the plurality of teeth to lock certain functions of surgical instrument (110).

Articulation drive module (8830) further includes an articulation gear (8846) and a tensioning gear (8848) associated with first articulation drive input (8832). Articulation gear (8846) is generally configured to mesh with articulation idler gear (8840) to selectively receive rotary motion from first articulation drive input (8832). Although not shown, it should be understood that such rotary motion of articulatio gear (8846) may be used to drive one or more structures of articulation drive module (8830) to control an aspect of articulation of end effector (116) relative to shaft assembly (114). For instance, in some examples a capstan (not shown) similar to capstans (8636, 8638) described above may be in communication with articulation gear (8846) rather than being directly in communication with first articulatio drive input (8832). Such a capstan may be configured to selectively tension and/or release one or more articulation cables (not shown) similar to articulation cables (8640, 8642, 8644, 8646) described above, which may be used to control an aspect of articulation of end effector (116) (e.g., pitch, yaw, etc.).

Tensioning gear (8848) is generally configured to mesh with articulation idler gear (8840) to selectively receive rotary motion from first articulation drive input (8832). Although not shown, it should be understood that such rotary motion of tensioning gear (8848) may be used to drive one or more structures of articulation drive module (8830). For instance, in some examples, tensioning gear (8848) may be configured to communicate with gears, sheaves, belts, cams, and/or etc. to apply tension to one or more articulation cables (not shown) similar to articulation cables (8640, 8642, 8644, 8646). Such a tensioning feature may be desirable during use of surgical instrument (110) to add rigidity to shaft assembly (114) at the point of articulatio for end effector (116).

Actuation drive module (8850) of the present example is similar to actuation drive module (8650) described above in that actuation drive module (8850) includes an actuation drive input (8852) configured to engage a drive output of robotic arm (42) to control actuation of end effector (116) and other components associated with end effector (116) to clamp, staple and cut tissue. To promote such functionality, actuation drive input (8852) includes gear teeth such that actuation drive input (8852) is configured to mesh with an idler gear (8856). Although not shown, it should be understood that idler gear (8856) may mesh or otherwise communicate with one or more structures similar to bevel gear (8658), capstan gear (8660), actuation capstan (8662). As similarly described above, such structures may permit actuation drive input (8752) to rotate an actuation capstan (not shown) to selectively tension/release one or more actuation drive cables (not shown) similar to actuation drive cables (8664, 8666) described above. The actuation drive cables may then communicate with structures associated with end effector (116) to clamp, staple and cut tissue.

Unlike actuation drive module (8650) described above, actuation drive module (8850) of the present example is generally configured to selectively communicate with rotation drive module (8870). As will be described in greater detail below, this feature may be desirable to permit actuation drive module (8850) of the present example to selectively actuate end effector (116) with increased mechanical advantage. In some examples, this may be facilitated by, for example, communicating power from rotation drive module (8870) to actuation drive module (8850) via idler gear (8856).

Rotation drive module (8870) of the present example is similar to rotation drive module (8670) described above in that rotation drive module (8870) is configured to drive rotation of shaft assembly (114) of surgical instrument (110) and other components associated therewith. However, unlike rotation drive module (8670) described above, rotation drive module (8870) of the present example is configured to selectively communicate rotary power from rotation drive module (8870) to actuation drive module (8850).

Rotation drive module (8870) of the present example omits structures similar to primary rotation drive input (8672) and secondary rotation drive input (8674). Instead, rotation drive module (8870) includes a rotation drive input (8872) and a shifting drive input (8874). Rotation drive input (8872) is positioned similarly to primary rotation drive input (8672) described above. However, instead of being configured to receive rotary input for rotation of shaft assembly (114), rotation drive input (8862) is configured to be manipulated by other structures of rotation drive module (8870) to drive either rotation of shaft assembly (114) or other functions of surgical instrument (110).

Rotation drive input (8872) is coupled to a lock arm (8876), a pivot arm (8880) and a selector arm (8882). Rotation drive input (8872) is generally configured to permit pivoting of lock arm (8876), pivot arm (8880) and selector arm (8882) about an axis defined by drive pivot (8872). Although rotation drive input (8872) itself is not configured to directly provide movement of lock arm (8876), pivot arm (8880) and selector arm (8882), it should be understood that in some examples, rotation drive input (8872) may be configured to manipulate such movement by providing a ratcheting action and/or biasing lock arm (8876), pivot arm (8880) and selector arm (8882) toward one or more predetermined positions.

Rotation drive input (8872) is further configured as a drive input to communicate rotary motion from one or more motors in robotic arm (42) to other components of rotation drive module (8870). This, the structure of rotation drive input (8872) may be configured as a gear or other feature configured to mesh or communicate rotary motion from rotation drive input (8872) to other portions of rotation drive module (8870) or actuation drive module (8850). As will be described in greater detail below, such communication may be used to drive rotation of shaft assembly (114) via rotation drive input (8872) or to provide additional power to actuation drive module (8850).

Lock arm (8876), pivot arm (8880), selector arm (8882) extend outwardly from rotation drive input (8872). Additionally, lock arm (8876), pivot arm (8880) and selector arm (8882) each extend at a fixed angle relative to each other. In other words, lock arm (8876), pivot arm (8880), and selector arm (8882) are configured to pivot about rotation drive input (8872) while maintaining a fixed position relative to each other. Lock arm (8876) includes a plurality of lock teeth (8878) disposed on an outer end of lock arm (8876) opposite of rotation drive input (8872). As will be described in greater detail below, lock teeth (8878) are configured to engage primary rotation input (8884) to selectively lock rotation of shaft assembly (114).

Pivot arm (8880) is disposed between lock arm (8876) and selector arm (8882). Pivot arm includes an output gear (8890) disposed on an outer end of pivot arm (8880) opposite of rotation drive input (8872). Output gear (8890) is rotatably coupled to pivot arm (8880) and is configured to mesh with either primary rotation input (8884) or idler gear (8856) of actuation drive module (8850) to communicate rotary motion from rotation drive input (8872) to either primary rotation input (8884) or idler gear (8856). As will be described in greater detail below, pivot arm (8880) is configured to pivot about rotation drive input (8872) to move output gear (8890) into communication with primary rotation input (8884) or idler gear (8856) of actuation drive module (8850).

Selector arm (8882) extends outwardly from pivot arm (8880) and terminates at an outer end opposite of rotation drive input (8872). Selector arm (8882) is generally configured to engage with one or more portions of shifting drive input (8874) to pivot lock arm (8876) and pivot arm (8880) about rotation drive input (8872). Thus, selector arm (8882) is configured to shift rotation drive module (8870) into various drive configurations to control rotation of shaft assembly (114) and/or a portion of the actuation associated with actuation drive module (8850).

Shifting drive input (8874) is generally configured to be driven by one or more motors to shift rotation drive module (8870) into various drive configurations. Shifting drive input (8874) includes a pair of rotation shifting members (8886) and a pair of articulation shifting members (8888). Rotation shifting members (8886) are generally configured to rotate via shifting drive input (8874) to selectively adjust the position of lock arm (8876) and pivot arm (8880) via selector arm (8882). Similarly, articulation shifting members (8888) are generally configured to rotate via shifting drive input (8874) to selectively adjust the position of articulation shift arm (8836), articulation lock arm (8842) and tensioning lock arm (8844) of articulation drive module (8830).

An exemplary use of drive system (8820) is shown in FIGS. 144A through 145B. During use, drive system (8820) is generally configured to shift functionality of surgical instrument (110) by adjusting the configuration of articulation drive module (8830), actuation drive module (8850), and/or rotation drive module (8870) using rotation of shifting drive input (8874). For instance, drive system (8820) may initially be operated in a first drive configuration shown in FIG. 144A.

In the first drive configuration, drive system (8820) may operate similarly to drive system (8620) described above with each drive module (8830, 8850, 8870) being configured to drive a respective function of surgical instrument (110). Specifically, articulation drive module (8830) may be configured to drive aspects of articulation of end effector (116) relative to a longitudinal axis defined by shaft assembly (114), actuation drive module (8850) may be configured to drive actuation of end effector (116) to clamp, staple and cut tissue, and rotation drive module (8870) may be configured to drive rotation of shaft assembly (114).

As best seen in FIG. 144A, articulation drive module (8830) is configured in the first drive configuration to use drive inputs (8832, 8834) for articulation of end effector (116). In this configuration, first articulation drive input (8832) is configured to drive one aspect of articulation (e.g., pitch, yaw, etc.). Specifically, articulation shift arm (8836) is positioned relative to first actuation drive input (8832) such that articulation idler gear (8840) meshes with first actuation drive input (8832) and articulation gear (8846). First actuation drive input (8832) may thus drive one aspect of articulation by communicating rotary motion to articulation gear (8846), which may be coupled to a capstan (not shown). As described above, the capstan configured to tension and/or release articulation cables similar to articulation cables (8640, 8642) described above to drive articulation of end effector (116). Meanwhile, second articulation drive input (8834) may drive another aspect of articulation by directly or indirectly rotating another capstan (not shown) similarly configured to tension and/or release articulation cables.

Actuation drive module (8850) is configured in the first drive configuration to use actuation drive input (8852) to drive actuation of end effector (116) to clamp, staple, and cut tissue. In this configuration, actuation drive module (8850) may operate similarly to actuation drive module (8650) described above. For instance, actuation drive input (8852) may communicate rotary motion to idler gear (8856). Idler gear (8856) may then in turn drive rotation of one or more bevel gears (not shown), one or more capstan gears (not shown), and/or other structures associated with actuation drive module (8850) to ultimately rotate an actuation capstan (not shown). As similarly described above, such a capstan may be used to tension and/or release actuation cables, similar to actuation cables (8664, 8666), which may be used to actuate end effector (116).

Rotation drive module (8870) is configured in the first drive configuration to use rotation drive input (8852) to drive rotation of shaft assembly (114). In this configuration, rotation drive module (8870) may operate similarly to rotation drive module (8670) described above. For instance, rotation drive input (8872) may communicate rotary motion to primary rotation input (8884) via output gear (8890). Primary rotation input (8884) may then rotate shaft assembly (114) using rotary motion from rotation drive input (8872).

During use it may be desirable to change the operation of drive system (8820) to change one or more functions of surgical instrument (110). For instance, in some examples it may be desirable to increase the mechanical advantage of one or more functions of surgical instrument. In addition, or in the alternative, it may be desirable to divert power from one function for use with another function. To this end, FIGS. 144B through 145B show drive system (8820) in a second drive configuration. In the second drive configuration, drive system (8820) is generally configured to divert power from rotation drive module (8870) to actuation drive module (8850). Additionally, drive system (8820) is also generally configured to divert power within articulation drive module (8830) from one function to another.

As best seen in FIG. 144B, transitioning of drive system (8820) in the present example from the first drive configuration to the second drive configuration is accomplished by rotating shifting drive input (8874) of rotation drive module (8870). During rotation of shifting drive input (8874), rotation shifting members (8886) and articulation shifting members (8888) move with shifting drive input (8874) to move and/or pivot selector arm (8882) of rotation drive module (8870) and articulation shift arm (8836) of articulation drive module (8830), respectively.

Movement of selector arm (8882) drives corresponding movement of pivot arm (8880) and lock arm (8876). Movement of pivot arm (8880) moves output gear (8890) away from primary rotation input (8884) to mesh with or otherwise engage idler gear (8856) of actuation drive module (8850). Meanwhile, movement of lock arm (8876) moves lock teeth (8878) of lock arm (8876) into engagement with primary rotation input (8884) to lock rotation of shaft assembly (114). In this configuration, rotation drive input (8872) may communicate rotary motion to actuation drive module (8850) via idler gear (8856) to approximately double the power used for actuation of end effector (116).

Articulation shift arm (8836) moves in an opposite direction relative to selector arm (8882) to shift articulation drive module (8830). Specifically, movement of articulation shift arm (8836) drives corresponding movement articulation idler gear (8840), which is coupled to articulation shift arm (8836). This movement disengages articulation idler gear (8840) from articulation gear (8846) and engages articulation idler gear (8840) with tensioning gear (8848). In this configuration, first articulation drive input (8832) may communicate rotary motion to tensioning gear (8848) via articulation idler gear (8840). Such motion of tensioning gear (8848) may then be used to tension one or more articulation cables associated with articulation drive module (8830). By way of example only, such tensioning may be used in some examples to increase the rigidity of end effector (116) where articulation occurs, limiting pitch and/or yaw articulation of end effector (116). Such a feature may be desirable in some examples to eliminate backlash from articulation of end effector (116) and/or to use end effector (116) for manipulation of tissue or other anatomical structures.

Movement of articulation shift arm (8836) simultaneously drives corresponding movement of articulation lock arm (8842) and tensioning lock arm (8844). Specifically, in the first drive configuration, tensioning lock arm (8844) engages tensioning gear (8848) to prevent rotation of or otherwise lock tensioning gear (8848). Similarly, in the second drive configuration, articulation lock arm (8842) engages articulation gear (8846) to prevent rotation of, or otherwise lock articulation gear (8846).

D. Exemplary Shifting Mechanism

FIG. 146A shows an exemplary shifting mechanism (8920) that may be readily incorporated into any of drive systems (8620, 8720, 8820) described above. Shifting mechanism (8920) is generally configured to selectively transfer power from one input to input to increase the mechanical advantage provided to a selected power output. Thus, shifting mechanism (8920) may be incorporated into drive systems (8620, 8720, 8820) described above for use with one or more drive inputs (8632, 8634, 8652, 8672, 8674, 8732, 8734, 8752, 8772, 8832, 8834, 8852, 8872) to selectively increase the mechanical advantage for a given function of surgical instrument (110).

Shifting mechanism (8920) includes a first power source (8930) and a second power source (8950). Power sources (8930, 8950) in the present example may correspond to one or more of drive inputs (8632, 8634, 8652, 8672, 8674, 8732, 8734, 8752, 8772, 8832, 8834, 8852, 8872) described above when shifting mechanism (8920) is incorporated into a given drive system (8620, 8720, 8820). Alternatively, in other applications, power sources (8930, 8950) may correspond to separate independent motors configured to provide a rotary output.

First power source (8930) and second power source (8950) include a first output shaft (8932) and a second output shaft (8952), respectively. As will be described in greater detail below, output shafts (8932, 8952) are generally configured to communicate power to one or more operational functions. For instance, in examples where shifting mechanism (8920) is incorporated into drive systems (8620, 8720, 8820), each output shaft (8932, 8952) may be configured to communicate power to a given function of surgical instrument (110). Regardless, output shafts (8932, 8952) are generally configured to communicate power independently of each other in some configurations to power separate operational functions. Meanwhile, in other configurations, output shafts (8932, 8952) are generally configured to combine power for a single operational function.

First output shaft (8932) includes a splined portion (8934) disposed proximate an end of output shaft (8932) opposite first power source (8930). Splined portion (8934) includes a plurality of teeth or other features configured to transmit rotary motion to other portions of shifting mechanism (8920). Specifically, shifting mechanism (8920) includes a first drive gear (8936) and a transfer gear (8938) associated with first output shaft (8932). Splined portion (8934) is generally configured to engage a corresponding interior of either first drive gear (8936) or transfer gear (8938) depending on the relative position of first drive gear (8936) and transfer gear (8938). As will be described in greater detail below, first output shaft (8932) is generally configured to rotate first drive gear (8936) or transfer gear (8938) via splined portion (8934) depending on the position of first drive gear (8936) and transfer gear (8938) relative to splined portion (8934).

Shifting mechanism (8920) further includes an actuator (8940) associated with first drive gear (8936) and transfer gear (8938). Actuator (8940) is generally configured to selectively move first drive gear (8936) and transfer gear (8938) relative to splined portion (8934) to control communication of rotary motion from first output shaft (8932) to either first drive gear (8936) or transfer gear (8938). Although actuator (8940) is shown schematically in the present example, it should be understood that actuator (8940) may take on a variety of forms. By way of example only, suitable forms for actuator (8940) may include solenoids, pneumatic or hydraulic rams, lead screw mechanisms, and/or etc.

Actuator (8940) includes a drive rod (8942) extend from a side of actuator (8940). Drive rod (8942) is coupled to a gear housing (8944), which is configured to hold first drive gear (8936) and transfer gear (8938) while permitting rotation of first drive gear (8936) and transfer gear (8938) within gear housing (8944). As will be described in greater detail below, actuator (8940) is configured to translate gear housing (8944) via drive rod (8942) to move gears (8936, 8938) relative to splined portion (8934) of first output shaft (8932) to control rotation of gears (8936, 8938) via first output shaft (8932).

Second output shaft (8952) also includes a splined portion (8954) disposed proximate an end of second output shaft (8952) opposite second power source (8950). Splined portion (8954) includes a plurality of teeth or other features configured to transmit rotary motion to other portions of shifting mechanism (8920). Specifically, shifting mechanism (8920) includes a second drive gear (8956) and an intermediate gear (8958) associated with second output shaft (8952). Splined portion (8954) is generally configured to engage a corresponding interior of second drive gear (8956). Thus, second output shaft (8952) is generally configured to rotate second drive gear (8956) via splined portion (8934).

Intermediate gear (8958) is configured as an elongate spur gear. In this configuration, intermediate gear (8958) is configured to mesh with second drive gear (8956) and transfer gear (8938). As will be described in greater detail below, transfer gear (8938) may idle in some configurations without having any impact on rotation of intermediate gear (8958), second drive gear (8956) and/or second output shaft (8952). Yet in other configurations, transfer gear (8938) may mesh with splined portion (8934) of first output shaft (8932) to transfer power from first output shaft (8932) to second drive gear (8956) via intermediate gear (8958).

FIGS. 146A and 146B show an exemplary use of shifting mechanism (8920). In use, shifting mechanism (8920) is configured to shift from a single drive configuration for driving a different operational function with first power source (8930) and second power source (8950) to a multi-drive configuration for driving a single operational function using both first power source (8930) and second power source (8950). In use with drive systems (8620, 8720, 8820) described above, this may include, for example, driving rotation of shaft assembly (114) and actuation of end effector (116) with shifting mechanism (8920) in the single drive configuration and then driving only rotation of shaft assembly (114) or actuation of end effector (116) with increased mechanical advantage in the multi-drive configuration. It should be understood that this is merely one example and that shifting mechanism (8920) may be used with other combinations of functions of surgical instrument (110) including rotation of shaft assembly (114), actuation of end effector (116), and/or various aspects of articulation of end effector (116).

As best seen in FIG. 146A, shifting mechanism (8920) may initially be in the single drive configuration. As noted above, this configuration corresponds to shifting mechanism (8920) providing two rotary outputs with one powered by first power source (8930) and the other provided by second power source (8950). In this configuration, actuator (8940) retracts drive rod (8942) to align first drive gear (8936) with splined portion (8934) of first output shaft (8932). As a result, first output shaft (8932) may rotate first drive gear (8936) via splined portion (8934). Although not shown, it should be understood that first drive gear (8936) may mesh with other gears associated with a given operational function. For instance, when shifting mechanism (8920) is used with drive systems (8620, 8720, 8820), first drive gear (8936) may mesh with any suitable gear associated with drive systems (8620, 8720, 8820) to ultimately drive a given function of surgical instrument (110).

Also in the single drive configuration, second drive gear (8956) is engaged with splined portion 9654) of second output shaft (8952). As a result, second output shaft (8952) may rotate second drive gear (8956) via splined portion (8954). Although not shown, it should be understood that second drive gear (8956) may likewise mesh with other gears associated with a given operational function. For instance, when shifting mechanism (8920) is used with drive systems (8620, 8720, 8820), second drive gear (8956) may mesh with any suitable gear associated with drive systems (8620, 8720, 8820) to ultimately drive a given function of surgical instrument (110).

During rotation of second drive gear (8956), intermediate gear (8958) may rotate and idle transfer gear (8938). For instance, while first drive gear (8936) is engaged with splined portion (8934), transfer gear (8938) is disengaged from splined portion (8934). Thus, transfer gear (8938) may be configured to freely rotate about first output shaft (8932) when shifting mechanism (8920) is in the single drive configuration. First drive gear (8936) is not configured to mesh with intermediate gear (8958), so rotation of first output shaft (8932) is generally independent of second output shaft (8952) when shifting mechanism (8920) is in the single drive configuration.

As best seen in FIG. 146B, shifting mechanism (8920) may be transitioned to the multi-drive configuration from the single drive configuration via actuator (8940). Specifically, actuator (8940) may advance drive rod (8942) to translate first drive gear (8936) and transfer gear (8938) relative to first output shaft (8932). Translation of first drive gear (8936) disengages first drive gear (8936) from splined portion (8934). Meanwhile, translation of transfer gear (8938) engages transfer gear (8938) with splined portion (8934). First output shaft (8932) may then rotate transfer gear (8938) rather than first drive gear (8936).

With rotation of transfer gear (8938), power from first power source (8930) is transferred from first output shaft (8932) to second drive gear (8956) via transfer gear (8938) and intermediate gear (8958). This configuration may increase the power provided by second drive gear (8956). In some examples, this may effectively double the power provided by second drive gear (8956). Meanwhile, first drive gear (8936) is disengaged from splined portion (8934), so any operational functions associated with first drive gear (8936) may be unpowered when shifting mechanism (8920) is in the multi-drive configuration.

E. Exemplary Selectable Multi-Drive Mechanism

FIG. 147A shows an exemplary multi-drive mechanism (9020) that may be readily incorporated into any of drive systems (8620, 8720, 8820) described above. Multi-drive mechanism (9020) is generally configured to selectively increase the output power of multi-drive mechanism (9020) by using one or two power sources (9030, 9050) simultaneously to drive a single output. Thus, multi-drive mechanism (9020) may be incorporated into drive systems (8620, 8720, 8820) described above for use with one or more drive inputs (8632, 8634, 8652, 8672, 8674, 8732, 8734, 8752, 8772, 8832, 8834, 8852, 8872) to selectively increase the mechanical advantage for a given function of surgical instrument (110).

Multi-drive mechanism (9020) includes a first power source (9030) and a second power source (9050). Power sources (9030, 9050) in the present example may correspond to one or more of drive inputs (8632, 8634, 8652, 8672, 8674, 8732, 8734, 8752, 8772, 8832, 8834, 8852, 8872) described above when multi-drive mechanism (9020) is incorporated into a given drive system (8620, 8720, 8820). Alternatively, in other applications, power sources (9030, 9050) may correspond to separate independent motors configured to provide a rotary output.

First power source (9030) and second power source (9050) include a first output shaft (9032) and a second output shaft (9052), respectively. As will be described in greater detail below, output shafts (9032, 9052) are generally configured to communicate power to a predetermined operational function associated with multi-drive mechanism (9020). For instance, in examples where multi-drive mechanism (9020) is incorporated into drive systems (8620, 8720, 8820), one or both output shaft (9032, 9052) may be configured to communicate power to a given function of surgical instrument (110).

First power source (9030) is configured to selectively couple to a first drive gear (9036) via first output shaft (9032). In particular, a resilient member (9044) extends between first power source (9030) and first drive gear (9036). Resilient member (9044) is generally configured to resiliently bias first drive gear (9036) toward a decoupled configuration, while also permitting selective coupling of first drive gear (9036) to first output shaft (9032). In the present example, resilient member (9044) includes a coil spring, but may include resilient bands, torsion springs, leaf springs, and/or etc.

On an opposite side of first drive gear (9036), first drive gear (9036) is coupled to an actuator (9040) by a drive rod (9042) extending between actuator (9040) and first drive gear (9036). Actuator (9040) is generally configured to move first drive gear (9036) against the resilient bias of resilient member (9044) via drive rod (9042) to couple first drive gear (9036) to first output shaft (9032). Although actuator (9040) is shown schematically in the present example, it should be understood that actuator (9040) may take on a variety of forms. For instance, in some examples, actuator (9040) may include a rotary drive element, a solenoid, a pneumatic or hydraulic piston/ram, a lead screw mechanism, and/or etc.

Second power source (9050) is coupled to a second drive gear (9056) via second output shaft (9052). Second drive gear (9056) is configured to mesh with an intermediate gear (9058), which includes a drive output (9070) extending from an intermediate gear (9058). Although not shown, it should be understood that drive output (9070) may be coupled to a predetermined operational function. Thus, second power source (9050) may be configured to power a predetermined operational function via second drive gar (9056) and intermediate gear (9058).

FIGS. 147A and 147B show an exemplary use of multi-drive mechanism (9020). In use, multi-drive mechanism (9020) may shift from a single drive configuration to a multi-drive configuration to drive a predetermined operational function with second power source (9050) alone or in combination with first power source (9030). For instance, in configurations with multi-drive mechanism (9020) incorporated into drive systems (8620, 8720, 8820), multi-drive mechanism (9020) may be used to power a function of surgical instrument (110) using only second power source (9050) when multi-drive mechanism (9020) is in the single drive configuration. The same function of surgical instrument (110) may then be driven with both first power source (9030) and second power source (9050) when multi-drive mechanism (9020) is in the multi-drive configuration for increased mechanical advantage of the same function.

As best seen in FIG. 147A, the single drive configuration includes first drive gear (9036) disengaged from first output shaft (9032) via resilient feature (9044). As a result, first power source (9030) is unable to communicate rotary power to first drive gear (9036). Moreover, a resilient feature, also referred to as resilient member (9044) pushes first drive gear (9036) out of alignment with intermediate gear (9058) such that first drive gear (9036) is unable to communicate rotary power to drive output (9070) via intermediate gear (9058).

Also in the single drive configuration, second drive gear (9056) may be meshed with intermediate gear (9058). Rotary power may thus be communicated from second power source (9050) to intermediate gear (9058) and drive output (9070) via second output shaft (9052) and second drive gear (9056). Thus, in the single drive configuration, only second power source (9050) is configured to provide drive to drive output (9070).

As best seen in FIG. 147B, multi-drive mechanism (9020) may be transitioned from the single drive configuration to the multi-drive configuration using actuator (9040). Specifically, actuator (9040) may advance drive rod (9042), which may also advance first drive gear (9036) into engagement with first output shaft (9032). Once first drive gear (9036) is engaged with first output shaft (9032), first power source (9030) may communicate rotary power to first drive gear (9036) via first output shaft (9032).

Advancement of first drive gear (9036) also moves first drive gear (9036) into alignment with intermediate gear (9058). Upon alignment, first drive gear (9036) and intermediate gear (9058) are configured to mesh. Thus, first power source (9030) is configured to communicate power to intermediate gear (9058) and drive output (9070) via first output shaft (9032) and first drive gear (9036).

Second power source (9050), second output shaft (9052) and second drive gear (9056), meanwhile, remain in the same configuration described above with respect to the single drive configuration. Thus, in the multi-drive configuration, both first power source (9030) and second power source (9050) are configured to communicate power to drive output (9070) via intermediate gear (9058). As a result, the power output of drive output (9070) may increase by the sum of the power from first power source (9030) and the power from second power source (9050). In some examples, this may approximately double the mechanical advantage provided by drive output (9070).

XIV. Exemplary Shifting Mechanisms for Adjustable Mechanical Advantage

As noted above, in some examples surgical instrument (110) may be used with certain drive systems and or mechanisms similar to drive systems (8620, 8720, 8820) described above. In some examples, suitable drive mechanisms may include drive inputs configured to communicate power from robotic arm (42) to surgical instrument (110) to drive various functions of surgical instrument (110) such as rotation of shaft assembly (114), articulation of end effector (116), and/or actuation of end effector (116). In some examples, it may be desirable to modify the mechanical advantage provided to a given function during a procedure to enhance operational utility of surgical instrument (110). By way of example only, such examples may include certain shifting mechanisms configured to adjust the mechanical advantage of a given drive. While a variety of suitable shifting mechanisms are described below as including such features in specific configurations, it should be understood that in other examples such features may be combined in different configurations without departing from the various concepts described herein.

A. Exemplary Shifting Mechanism with Continuously Variable Belt Drive

FIG. 148 shows an exemplary shifting mechanism (9110) that may be readily incorporated into any one or more of drive systems (8620, 8720, 8820) described above. Shifting mechanism (9110) is generally configured to provide continuously variable adjustment of a rotary drive. For instance, in the case of incorporation with drive system (8620), shifting mechanism (9110) may be associated with any one or more of drive inputs (8632, 8634, 8652, 8672, 8674) to adjust the rotary motion of a given drive input (8632, 8634, 8652, 8672, 8674) to have a selected mechanical advantage, which may be used to ultimately drive a given function associated with the given drive input (8632, 8634, 8652, 8672, 8674).

As best seen in FIGS. 149-150, shifting mechanism (9110) includes a rotary drive assembly (9120), an adjustment assembly (9130) and a belt (9150). Rotary drive assembly (9120) includes an input shaft (9122), a first rotary drive element (9124) and a second rotary drive element (9126). Input shaft (9122) is coupled to first rotary drive element (9124) and/or second rotary drive element (9126) such that input shaft (9122) is configured to rotate both first rotary drive element (9124) and second rotary drive element (9126). Although not shown, it should be understood that input shaft (9122) may extend through first rotary drive element (9124) to second rotary drive element (9126) to communicate rotation of input shaft (9122) to second rotary drive element (9126). Furthermore, input shaft (9122) may include one or more keys, splines, or other features configured to communicate rotary motion from input shaft (9122) to first rotary drive element (9124) and second rotary drive element (9126).

First rotary drive element (9124) and second rotary drive element (9126) each define a generally conical shape. Optionally, in some examples, the conical shape of first rotary drive element (9124) and second rotary drive element (9126) may include a curvature such as the one shown in FIGS. 149-150. First rotary drive element (9124) is generally facing second rotary drive element (9126) such that the smaller diameter associated with each of first rotary drive element (9124) and second rotary drive element (9126) are proximate each other. Thus, first rotary drive element (9124) and second rotary drive element (9126) together may define a generally V-shaped or U-shaped cross-section.

Rotary drive assembly (9120) further includes a resilient feature (9128) disposed between first rotary drive element (9124) and second rotary drive element (9126). Resilient feature (9128) is generally configured to bias first rotary drive element (9124) and second rotary drive element (9126) toward each other. In the present example, resilient feature (9128) includes a coil spring. In other examples, resilient feature (9128) may include various alternative configurations such as resilient bands, leaf springs, disc springs, and/or etc.

Adjustment assembly (9130) is disposed between first rotary drive element (9124) and second rotary drive element (9126). Adjustment assembly (9130) is generally configured to engage first rotary drive element (9124) and second rotary drive element (9126) to selectively adjust the distance between first rotary drive element (9124) and second rotary drive element (9126). As will be described in greater detail below, this feature may be used to selectively adjust a mechanical advantage associated with shifting mechanism (9110).

Adjustment assembly (9130) includes a first plunger (9132) and a second plunger (9140). First plunger (9132) and second plunger (9140) may be disposed on opposing sides of first rotary drive element (9124) and second rotary drive element (9126). Together, first plunger (9132) and second plunger (9140) may be configured to engage first rotary drive element (9124) and second rotary drive element (9126) to apply a compressive force to first rotary drive element (9124) and second rotary drive element (9126), which may force first rotary drive element (9124) and second rotary drive element (9126) away from each other.

First plunger (9132) and second plunger (9140) each include a respective adjustment shaft (9134, 9142) and a respective biasing feature (9136, 9144). Each adjustment shaft (9134, 9142) is configured to control the relative position of a respective first plunger (9132) or second plunger (9140) relative to first rotary drive element (9124) and second rotary drive element (9126). Meanwhile each biasing feature (9136, 9144) is configured to provide a resilient bias forcing a respective first plunger (9132) or second plunger (9140) toward first rotary drive element (9124) and second rotary drive element (9126). Each biasing feature (9136, 9144) is optional and may be omitted in some examples. However, in examples having biasing features (9136, 9144), such features may be desirable to simply manipulation of each adjustment shaft (9134, 9142). For instance, in the present example, the relative position of each adjustment shaft (9134, 9142) may be set using only a pulling force due to the presence of biasing features (9136, 9144) rather than a combination of pulling and pushing forces.

Belt (9150) is looped around each of first rotary drive element (9124) and second rotary drive element (9126). Belt (9150) is generally configured to frictionally engage first rotary drive element (9124) and second rotary drive element (9126) to transfer rotatory motion of first rotary drive element (9124) and second rotary drive element (9126) to belt (9150). Although not shown, it should be understood that an opposite loop of belt (9150) may be in communication with a wheel, gear, shaft, or other features. Such features may be used to communicate movement of belt (9150) to other components for ultimate use in driving one or more functions of surgical instrument (940).

FIGS. 149 and 150 show an exemplary use of shifting mechanism (9110). In use, shifting mechanism (9110) generally functions as a continuously variable transmission to provide an output via belt (9150) having various mechanical advantages. The particular mechanical advantage of the output of belt (9150) is generally established by the position of first plunger (9132) and second plunger (9140) relative to first rotary drive element (9124) and second rotary drive element (9126).

As can be seen in FIG. 149, first plunger (9132) and second plunger (9140) may initially be positioned relative to first rotary drive element (9124) and second rotary drive element (9126) proximate an outer diameter defined by first rotary drive element (9124) and second rotary drive element (9126). First plunger (9132) and second plunger (9140) may be positioned as shown by pulling each respective adjustment shaft (9134, 9142) against the resilient bias of each respective biasing feature (9136, 9144) to move first plunger (9132, 9140) away from first rotary drive element (9124) and second rotary drive element (9126).

With first plunger (9132) and second plunger (9140) positioned proximate the outer diameter defined by first rotary drive element (9124) and second rotary drive element (9126), first rotary drive element (9124) and second rotary drive element (9126) may be driven towards each other via resilient feature (9128). As a result, first rotary drive element (9124) and second rotary drive element (9126) may be separated by a relatively small distance. Belt (9150), which may have a fixed width, may thus engage first rotary drive element (9124) and second rotary drive element (9126) at a relatively large diameter portion of each of first rotary drive element (9124) and second rotary drive element (9126). Belt (9150) may thus be driven by first rotary drive element (9124) and second rotary drive element (9126) using input shaft (9122) with a relatively high mechanical advantage. In other words, belt (9150) may have a greater force output when shifting mechanism (9110) is in the configuration shown in FIG. 149.

To adjust the mechanical advantage associated with belt (9150), first plunger (9132) and second plunger (9140) may be moved to adjust their position relative to first rotary drive element (9124) and second rotary drive element (9126). As can be seen in FIG. 150, movement of first plunger (9132) and second plunger (9140) toward first rotary drive element (9124) and second rotary drive element (9126) may force first rotary drive element (9124) and second rotary drive element (9126) away from each other against the resilient bias of resilient feature. As noted above, belt (9150) may have a fixed width such that separation of first rotary drive element (9124) and second rotary drive element (9126) may result in belt (9150) engaging first rotary drive element (9124) and second rotary drive element (9126) at a smaller diameter portion relative to the engagement shown in FIG. 149. Belt (9150) may thus be driven by first rotary drive element (9124) and second rotary drive element (9126) using input shaft (9122) with a relatively low mechanical advantage. In other words, belt (9150) may have a lower force output when shifting mechanism (9110) is in the configuration shown in FIG. 150.

Although the present use shows first plunger (9132) and second plunger (9140) in only two positions relative to first rotary drive element (9124) and second rotary drive element (9126), it should be understood that in other uses a plurality of other relative positions may be used. Specifically, first plunger (9132) and second plunger (9140) may be used at a variety of positions relative to first rotary drive element (9124) and second rotary drive element (9126). Varying positions may be desirable to provide fine adjustment of the particular mechanical advantage associated with belt (9150).

B. Exemplary Alternative Shifting Mechanism with Continuously Variable Belt Drive FIG. 151 shows an exemplary alternative shifting mechanism (9210) similar to shifting mechanism (9110) described above. For instance, as with shifting mechanism (9110) described above, shifting mechanism (9210) of the present example may be readily incorporated into any one or more of drive systems (8620, 8720, 8820) described above. Shifting mechanism (9210) is similarly generally configured to provide continuously variable adjustment of a rotary drive. For instance, in the case of incorporation with drive system (8620), shifting mechanism (9210) may be associated with any one or more of drive inputs (8632, 8634, 8652, 8672, 8674) to adjust the rotary motion of a given drive input (8632, 8634, 8652, 8672, 8674) to have a selected mechanical advantage, which may be used to ultimately drive a given function associated with the given drive input (8632, 8634, 8652, 8672, 8674).

Shifting mechanism (9210) includes an input assembly (9220), an output assembly (9240) and a belt (9260) extending between input assembly (9220) and output assembly (9240). Input assembly (9220) includes an input shaft (9222), an input sheave (9224) and a retainer (9230). Input shaft (9222) is generally configured to receive rotary input from, for example, any suitable rotary input used drive systems (8620, 8720, 8820) described above to rotate input sheave (9224) and retainer (9230) to drive movement of belt (9260).

Input sheave (9224) and retainer (9230) are coupled to input shaft (9222) such that input sheave (9224) and retainer (9230) may rotate with input shaft (9222). Input sheave (9224) and retainer (9230) each include a respective angled portion (9226, 9232) configured to engage belt (9260). Specifically, input sheave (9224) and retainer (9230) are disposed on input shaft (9222) with each angled portion (9226, 9232) facing the other angled portion (9232, 9226). In this configuration, angled portions (9226, 9232) together form a V-shaped or U-shaped profile angled outwardly from the axis of input shaft (9222). This profile formed by angled portions (9226, 9232) is generally configured to receive belt (9260).

One or more portions of input sheave (9224) may be generally configured to move angled portion (9226) along the longitudinal axis of input shaft (9222) while still permitting input sheave (9224) to rotate with input shaft (9222). Such movement of angled portion (9226) may be relative to angled portion (9232) of retainer (9230). In other words, retainer (9230) is generally configured to remain in a fixed position relative to the longitudinal axis of input shaft (9222).

It should be understood that a variety of structures may be used for movement of angled portion (9226). For instance, in some examples, movement of angled portion (9226) may be driven by oil or other fluids injected into input sheave (9234) for telescopic expansion of input sheave (9224). In other examples, motor drives, magnetic drives, lead screws, and/or solenoids may be used to drive movement of angled portion (9226) of input sheave (9224).

Output assembly (9240) includes an output shaft (9242), an output sheave (9244) and a retainer (9250). Output shaft (9242) is generally configured to communicate rotary motion transferred via belt (960) from input assembly (9220) to other portions of surgical instrument (940) to ultimately drive one or more functions of surgical instrument (940). In the present example, output shaft (9242) includes an output gear (9248), which may be configured to mesh with other components of surgical instrument (940) such as various gears described above in connection with drive systems (8620, 8720, 8820).

Output sheave (9244) and retainer (9250) are coupled to output shaft (9242) such that output sheave (9244) and retainer (9250) may rotate with output shaft (9242). Output sheave (9244) and retainer (9250) each include a respective angled portion (9246, 9252) configured to engage belt (9260). Specifically, output sheave (9244) and retainer (9250) are disposed on output shaft (9242) with each angled portion (9246, 9252) facing the other angled portion (9252, 9246). In this configuration, angled portions (9246, 9252) together form a V-shaped or U-shaped profile angled outwardly from the axis of output shaft (9242). This profile formed by angled portions (9246, 9252) is generally configured to receive belt (9260).

One or more portions of output sheave (9244) may be generally configured to move angled portion (9246) along the longitudinal axis of output shaft (9242) while still permitting output sheave (9244) to rotate with output shaft (9242). Such movement of angled portion (9246) may be relative to angled portion (9252) of retainer (9250). In other words, retainer (9250) is generally configured to remain in a fixed position relative to the longitudinal axis of output shaft (9242).

It should be understood that a variety of structures may be used for movement of angled portion (9246). For instance, in some examples, movement of angled portion (9246) may be driven by oil or other fluid injected into output sheave (9244) for telescopic expansion of output sheave (9244). In other examples, motor drives, magnetic drives, lead screws, and/or solenoids may be used to drive movement of angled portion (9246) of output sheave (9244).

FIGS. 151 and 152 show an exemplary use of shifting mechanism (9210). In use, shifting mechanism (9210) generally functions as a continuously variable transmission to provide an output via output gear (9248) having various mechanical advantages. The particular mechanical advantage of the output gear (9248) is generally established by the position of angled portion (9226) of input sheave (9224) relative to angled portion (9232) of retainer (9230) and the position of angled portion (9246) of output sheave (9244) relative to angled portion (9252) of retainer (9250).

As can be seen, both angled portion (9226) of input sheave (9224) and angled portion (9246) of output sheave (9244) are movable relative to each respective retainer (9230, 950). Such movement may change the profile defined between input sheave (9224) and retainer (9230), and between output sheave (9244) and retainer (9250). This change in profile, may change engagement of belt (9260) with either input sheave (9224) and retainer (9230), or output sheave (9244) and retainer (9250). For instance, movement of angled portion (9226) of input sheave (9224) closer to retainer (9230) may result in a narrowing of the profile defined between input sheave (9224) and retainer (9230). As a result, belt (9260) may engage input sheave (9224) and retainer (9230) at an increasing diameter portion of input sheave (9224) and retainer (9230). Similarly, movement of angled portion (9246) of output sheave (9244) closer to retainer (9250) may result in a narrowing of the profile defined between output sheave (9244) and retainer (9250). As a result, belt (9260) may engage output sheave (9244) and retainer (9250) at an increasing diameter portion of output sheave (9244) and retainer (9250).

Both input sheave (9224) and output sheave (9244) may be adjusted as described above during use to engage belt (9260) at different diameter positions relative to input sheave (9224) and/or output sheave (9244). As a result, shifting mechanism (9210) may be used to provide a variety of drive ratios for belt (9260) between input assembly (9220) and output assembly (9240). This may be desirable in use with surgical instrument (940) to drive one or more functions of surgical instrument (940) with different drive characteristics. For instance, during some procedures, shifting mechanism (9210) may be set to provide a relatively high mechanical advantage or relatively high force output at output gear (9248) for applications requiring greater actuation forces. In other procedures, shifting mechanism (9210) may be set to provide a relatively low mechanical advantage or relatively low force output at output gear (9248) for applications requiring less force and greater speed.

C. Exemplary Alternative Shifting Mechanism with Movable Arm

FIGS. 153 through 155 show an exemplary alternative shifting mechanism (9310) that may be readily incorporated into any one or more of drive systems (8620, 8720, 8820) described above in addition to, or in lieu of, shifting mechanisms (9110, 910) described above. For instance, in the case of incorporation with drive system (8620), shifting mechanism (9310) may be associated with any one or more of drive inputs (8632, 8634, 8652, 8672, 8674) to adjust the rotary motion of a given drive input (8632, 8634, 8652, 8672, 8674) to have a selected mechanical advantage, which may be used to ultimately drive a given function associated with the given drive input (8632, 8634, 8652, 8672, 8674).

Shifting mechanism (9310) includes a drive assembly (9320), a shift assembly (9340), and a reduction assembly (9370). Shifting mechanism (9310) is generally configured to use shift assembly (9340) to selectively shift between a direct drive configuration via drive assembly (9320) to a reduction drive configuration via reduction assembly (9370). As will be described in greater detail below, the direct drive configuration may be desirable for operation with relatively high speed at a relatively low torque. Meanwhile, the reduction drive configuration may be desirable for operation with relatively low speed at a relatively high torque. In one merely exemplary configuration, shifting mechanism (9310) may be incorporated into drive system (8620) for use with actuation drive module (8650) to selectively shift between high speed, low torque operation of end effector (116) to low speed, high torque operation of end effector (116).

Drive assembly (9320) includes an input shaft (9322) and an output shaft (9326). Input shaft (9322) is generally configured to couple with one or more motors to provide rotary power to shifting mechanism (9310). In merely one exemplary implementation, input shaft (9322) may be coupled to articulation drive input (8652) of actuation drive module (8650), or any other suitable drive input. Regardless, input shaft (9322) includes an input gear (9324) coupled thereto and configured to rotate with input shaft (9322). Input gear (9324) includes an engagement portion (9325) oriented towards output shaft (9326). As will be described in greater detail below, engagement portion (9325) is generally configured to engage a portion of shift assembly (9340) to transmit rotary motion from input gear (9324) to output shaft (9326) in some configurations.

Output shaft (9326) is coaxial with input shaft (9322). Although not shown, it should be understood that a portion of output shaft (9326) may be configured to communicate with other components of surgical instrument (110) to drive one or more operational functions thereof. For instance, in an implementation with actuation drive module (8650), output shaft (9326) may couple to actuation drive gear (8654) or other components associated therewith to drive actuation of end effector (116).

Output shaft (9326) defines a smooth portion (9328) and a keyed portion (9330). Smooth portion (9328) is configured to receive an idler gear (9332) such that idler gear (9332) may be independently rotatable relative to output shaft (9326). Keyed portion (9330) defines a spline, key, key channel or other rotational lock feature. As will be described in greater detail below, keyed portion (9330) is generally configured to engage a portion of shift assembly (9340) to transmit rotary motion from a portion of shift assembly (9340) to output shaft (9326).

Idler gear (9332) includes an engagement portion (9334) extending downwardly from a portion of idler gear (9332) toward input shaft (9322). As will be described in greater detail below, engagement portion (9334) is generally configured to engage a portion of shift assembly (9340) to transmit rotary motion from idler gear (9332) to output shaft (9326) via shift assembly (9340) in some configurations.

As best seen in FIGS. 154 and 155, shift assembly (9340) includes a shift arm (9342), a clutch (9350), and a shift shaft (9360). Shift arm (9342) includes a clutch receiver (9344) and a shift receiver (9346) on opposing ends of shift arm (9342). Clutch receiver (9344) defines a hollow cylindrical member configured to receive clutch (9350). Similarly, shift receiver (9346) defines a hollow cylindrical member configured to receive shift shaft (9360). Furthermore, the interior of shift receiver (9346) includes a cam protrusion (9348) extending into the hollow interior of shift receiver (9346). As will be described in greater detail below, cam protrusion (9348) is generally configured to engage a portion of shift shaft (9360) to drive movement of shift arm (9342) along shift shaft (9360).

Clutch (9350) includes an arm receiver (9352), a lower engagement portion (9354), an upper engagement portion (9356), and a keyed bore (9358). Arm receiver (9352) is configured to be received within clutch receiver (9344) of shift arm (9342). Thus, arm receiver (9352) defines a channel indentation within clutch (9350). This configuration of arm receiver (9352) defines a flange structure on opposing sides of clutch (9350) to hold clutch receiver (9344) of shift arm (9342) within arm receiver (9352). As will be described in greater detail below, this configuration of arm receiver (9352) and clutch receiver (9344) is configured to permit shift arm (9342) to drive movement of clutch (9350) relative to input shaft (9322) and output shaft (9326).

Lower engagement portion (9354) and upper engagement portion (9356) are both configured to engage portions of drive assembly (9320) to rotatably fix clutch (9350) relative to a given portion of drive assembly (9320). Specifically, lower engagement portion (9354) and upper engagement portion (9356) each include blocks, teeth or other engagement features configured to mate with certain counterpart components. As will be described in greater detail below, clutch (9350) may be moved by shift arm (9342) to drive engagement between either lower engagement portion (9354) or upper engagement portion (9356) with a corresponding engagement portion (9325, 9334) of drive assembly (9320).

Keyed bore (9358) extends through the center of clutch (9350). Specifically, keyed bore (9358) is configured to receive a portion of output shaft (9326) such that at least a portion of output shaft (9326) may extend through clutch (9350). Keyed bore (9358) is generally configured to engage keyed portion (9330) of output shaft (9326). As such, it should be understood that keyed bore (9358) may include features corresponding to keyed portion (9330) such as keys, keyways, spline channels, splines, and/or etch. Such engagement may be configured such that clutch (9350) may be rotationally locked relative to output shaft (9326). Thus, clutch (9350) may be configured to drive rotation of output shaft (9326). Meanwhile, clutch (9350) may also be configured to laterally slide relative to output shaft (9326). As will be described in greater detail below, this lateral sliding may be desirable to permit movement of clutch (9350) via shift arm (9342).

As best seen in FIG. 155, shift shaft (9360) is configured to be received within shift receiver (9346) of shift arm (9342). Shift shaft (9360) defines a cam profile (9362) indented into a portion of shift shaft (9360). The particular shape of cam profile (9362) is one that defines a low portion and a high portion with a sloped portion between the low portion and the high portion. As will be described in greater detail below, cam profile (9362) is generally configured to receive cam protrusion (9348) of shift arm (9342) to drive shift arm (9342) axially up or down along the length of shift arm (9342) by rotating shift shaft (9360). In other words, shift shaft (9360) is generally configured to convert rotation thereof into axial translation of shift arm (9342) via cam profile (9362).

Rotation of shift shaft (9360) may be controlled by a variety of mechanisms. For instance, in examples where shifting mechanism (9310) is incorporated into drive system (8620), shift shaft (9360) may be coupled to secondary rotation drive input (8674) to facilitate rotation of shift shaft (9360). In other examples, shift shaft (9360) may be coupled to any other suitable drive input to receive rotary motion from one or more motors associated with robotic arm (42). In still other examples, shift shaft (9360) may be coupled to a separate actuator for manual rotation via a rotation knob, lever, crank, push button, and/or etc.

Reduction assembly (9370) includes a reduction shaft (9372), a large reduction gear (9374) and a small reduction gear (9376). Large reduction gear (9374) and small reduction gear (9376) are both coupled to reduction shaft (9372) such that reduction shaft (9372), large reduction gear (9374), and small reduction gear (9376) are all configured to rotate together.

Large reduction gear (9374) is configured to mesh with input gear (9324). Meanwhile, small reduction gear (9376) is configured to mesh with idler gear (9332). As will be described in greater detail below, large reduction gear (9374) is configured to be rotated by input gear (9324), which may rotate small reduction gear (9376) via reduction shaft (9372) to ultimately rotate idler gear (9332). As will also be described in greater detail below, idler gear (9332) may idle in some configurations, but drive output shaft (9326) rotation in other configurations. Thus, reduction assembly (9370) may generally continuously rotate during use, but such rotation may be unused in some configurations.

FIGS. 156A and 156B show an exemplary use of shifting mechanism (9310). As can be seen, shifting mechanism (9310) may initially be in the direct drive configuration as shown in FIG. 156A. Shifting mechanism (9310) may then shift to the reduction drive configuration shown in FIG. 156B via rotation of shift shaft (9360).

In the direct drive configuration shown in FIG. 156A, shift shaft (9360) is rotated to drive shaft arm (9342) downwardly toward input gear (9324) via engagement between cam profile (9362) and cam protrusion (9348). With shift arm (9342) driven downwardly, lower engagement portion (9354) of clutch (9350) is driven into engagement with engagement portion (9325) of input gear (9324). As a result, input gear (9324) may drive rotation of clutch (9350). Clutch (9350) may then drive rotation of output shaft (9326). Thus, in the direct drive configuration, rotation of input shaft (9322) directly drives rotation of output shaft (9326) via clutch (9350).

In the present use, the direct drive configuration corresponds to a relatively high-speed drive with relatively low torque. In use with surgical instrument (110) this form of drive may be desirable for functions requiring low force. For instance, in use of shifting mechanism (9310) with surgical instrument (110) to drive actuation of end effector (116), it may be desirable to initially actuate end effector (116) with high speed and low torque for procedural steps where end effector (116) is prepared for use or for procedural steps where end effector (116) is being initially closed without manipulating tissue.

To shift shifting mechanism (9310) from the direct drive configuration to the reduction drive configuration, shift shaft (9360) may be rotated to drive movement of shift arm (9342) upwardly toward idler gear (9332). Specifically, engagement between cam profile (9362) and cam protrusion (9348) may convert rotation of shift shaft (9360) into axial translation of shift arm (9342). Movement of shift arm (9342) may then drive upper engagement portion (9356) of clutch (9350) into engagement with engagement portion (9334) of idler gear (9332).

Upon engagement between upper engagement portion (9356) of clutch (9350) and engagement portion (9334) of idler gear (9332), clutch (9350) and idler gear (9332) may be rotationally locked to each other such that rotation of idler gear (9332) may rotate clutch (9350). Input gear (9324) may then drive rotation of large reduction gear (9374), which may drive rotation of reduction shaft (9372) and small reduction gear (9376). Small reduction gear (9376) may then drive rotation of idler gear (9332). Idler gear (9332) may then rotate clutch (9350) due to engagement between upper engagement portion (9356) of clutch (9350) and engagement portion (9334) of idler gear (9332). Clutch (9350) may then rotate output shaft (9326) via keyed bore (9358) of clutch (9350) and keyed portion (9339) of output shaft (9326).

In the present use, the reduction drive configuration corresponds to a relatively low-speed drive with relatively high torque. In use with surgical instrument (110) this form of drive may be desirable for functions requiring high force. For instance, in use of shifting mechanism (9310) with surgical instrument (110) to drive actuation of end effector (116), it may be desirable to actuate end effector (116) with low speed and high torque for procedural steps where end effector (116) is used in connection with manipulating tissue such as clamping, cutting, and/or stapling.

D. Exemplary Alternative Shifting Mechanism with Planetary Gear

FIG. 157 shows an exemplary alternative shifting mechanism (9410) that may be readily incorporated into any one or more of drive systems (8620, 8720, 8820) described above in addition to, or in lieu of, shifting mechanisms (9110, 9210, 9310) described above. Shifting mechanism (9410) of the present example is generally configured to selectively drive two functions of surgical instrument (110) using a planetary gear driven by a single motor. For instance, in the case of incorporation with drive system (8620), shifting mechanism (9410) may be associated with any one of drive inputs (8632, 8634, 8652, 8672, 8674) to drive multiple functions of surgical instrument (110) with input from only one drive input (8632, 8634, 8652, 8672, 8674). In one merely exemplary implementation, shifting mechanism (9410) may receive input from first articulation drive input (8632), second articulation drive input (8634), or primary rotation drive input (8672) to selectively drive articulation of end effector (116) and rotation of shaft assembly (114) using only one of first articulation drive input (8632), second articulation drive input (8634), or primary rotation drive input (8672). Of course, in other examples, shifting mechanism (9410) may be used in combination with other drive inputs (8632, 8634, 8652, 8672, 8674) to drive other combinations of functions as will be apparent to those of ordinary skill in the art in view of the teachings herein.

Shifting mechanism (9410) includes a drive assembly (9420), a shift assembly (9440) and an output assembly (9470). As will bd described in greater detail below, drive assembly (9420) is generally configured to provide rotary input to shifting mechanism (9410) that may be diverted to two or more outputs of output assembly (9470) using shift assembly (9440). Shift assembly (9440) includes a motor (9422), an upper control gear (9426), and a lower control gear (9428). Motor (9422) of the present example may correspond to a motor in robotic arm (42). In the context of implementation with drive system (8620), motor (9422) may correspond to any of the motors associated with drive inputs (8632, 8634, 8652, 8672, 8674).

Upper control gear (9426) and lower control gear (9428) are positioned above motor (9422). Upper control gear (9426) and lower control gear (9428) are further in communication with motor (9422) such that motor (9422) may communicate rotary motion to upper control gear (9426) or lower control gear (9428), depending on the configuration of shifting mechanism (9410). As will be described in greater detail below, upper control gear (9426) and lower control gear (9428) are generally configured to be rotationally locked and unlocked by one or more portions of shift assembly (9440) to control communication of rotary motion to output assembly (9470).

As best seen in FIG. 158, the interior of upper control gear (9426) houses a planetary gear mechanism. Specifically, motor (9422) is in direct communication with a sun gear (9424) disposed at the central rotational axis of upper control gear (9426). Around sun gear (9424), a plurality of planet gears (9430) are arranged in a ring-shaped formation. Planet gears (9430) are rotatably fixed to lower control gear (9428). It should be understood that upper control gear (9426) and lower control gear (9428) are positioned coaxially relative to each other such that planet gears (9430) are configured to rotate about sun gear (9424) within the interior of upper control gear (9426).

A planet drive shaft (9432) is positioned above planet gears (9430). Specifically, planet gears (9430) are also rotatably fixed to planet drive shaft (9432). Thus, lower control gear (9428) and planet drive shaft (9432) are together configured to operate as a planet gear carrier, while upper control gear (9426) is configured to act as a planetary ring gear. It should be understood that reference to planet gears (9430) herein as being "rotatably fixed" refers planet gears (9430) being fixed in a given position relative to lower control gear (9428) and planet drive shaft (9432), yet also being free to rotate relative to lower control gear (9428) and planet drive shaft (9432) about a rotation axis defined by each respective planet gear (9430).

Shift assembly (9440) includes a cam shifter (9442), an upper lock arm (9444), and a lower lock arm (9448). Cam shifter (9442) is generally configured to rotate to selectively manipulate the position of lock arms (9444, 9448) relative to control gears (9426, 9428). Specifically, cam shifter (9442) includes a pair of cams (9443) extending outwardly from a cylindrical surface of cam shifter (9442). Each cam (9443) defines a protrusion that is positioned at a different position along the circumference of cam shifter (9442). Because of this different positioning of each cam (9443), cams (9443) may manipulate each lock arm (9444, 9448) at a different rotational position of cam shifter (9442).

Lock arms (9444, 9448) are generally configured to selectively lock rotation of a respective control gear (9426, 9428). Specifically, upper lock arm (9444) is associated with upper control gear (9428). Meanwhile, lower lock arm (9448) is associated with lower control gear (9428). Each lock arm (9444, 9448) includes a respective pivot (9446, 9450) such that each lock arm (9444, 9448) may be pivoted to engage one or more teeth disposed on an end of each lock arm (9444, 9448) with a respective control gear (9426, 9428).

Output assembly (9470) is disposed above drive assembly (9420) and is generally configured to receive rotary input from drive assembly (9420) and to communicate such rotary input to other portions of surgical instrument (110). Output assembly (9470) includes an upper output gear (9472), a lower output gear (9476), an upper drive gear (9480), and a lower drive gear (9482). Upper output gear (9472) is in communication with planet drive shaft (9432) such that planet drive shaft (9432) is configured to rotate upper output gear (9472). Meanwhile, lower output gear (9476) is integral, or otherwise in communication, with upper control gear (9426) such that upper control gear (9426) is configured to rotate lower output gear (9476).

Upper drive gear (9480) and lower drive gear (9482) are each configured to communicate with other portions of surgical instrument (110) to drive functions of surgical instrument (110). For instance, in some examples upper drive gear (9480) may be in communication with a function such as end effector (116) articulation, end effector (116) actuation, or shaft assembly (114) rotation. Meanwhile, lower drive gear (9482) may be in communication with another function such as shaft assembly (114) rotation, end effector (116) actuation, or end effector (116) articulation. Thus, it should be understood that upper drive gear (9480) and lower drive gear (9482) may be configured to drive different functions of surgical instrument (110) (or different aspects of a function such as pitch and yaw articulation of end effector (116)).

Upper drive gear (9480) is configured to communicate with upper output gear (9472) via an upper idler gear (9474) configured to mesh with both upper drive gear (9480) and upper output gear (9472). Similarly, lower drive gear (9482) is configured to communicate with lower output gear (9476) via a lower idler gear (9478) configured to mesh with both lower drive gear (9482) and lower output gear (9476). It should be understood that idler gears (9474, 9478) in the present example are merely optional and may be omitted in some examples. In other words, in some examples, drive gears (9480, 9482) may be configured to mesh directly with a respective output gear (9472, 9476).

In an exemplary use of shifting mechanism (9410) cam shifter (9442) may be rotated to alternate between unlocking rotation of upper control gear (9426) and lower control gear (9428). Depending on which of upper control gear (9426) and lower control gear (9428) is unlocked for rotation, either lower drive gear (9482) or upper drive gear (9480) may be driven by motor (9422).

In a first use with lower drive gear (9482) driven by motor (9422), cam shifter (9442) may be rotated to pivot lower lock arm (9448) about pivot (9450) to drive one or more teeth of lower lock arm (9448) into engagement with lower control gear (9428). In this configuration, rotation of lower control gear (9428) is locked, while rotation of upper control gear (9426) is unlocked.

With rotation of lower control gear (9428) locked, planet gears (9430) are also in a fixed position within upper control gear (9426), but still remain rotatable relative to the rotation axis of each planet gear (9430). Planet gears (9430) may then be rotated via motor (9422) by sun gear (9424). Rotation of planet gears (9430) may then rotate upper control gear (9426), which may include internal gearing to facilitate engagement between the interior of upper control gear (9426) and planet gears (9430).

Upon rotation of upper control gear (9426) output assembly (9470) may be driven using rotation of upper control gear (9426), which may rotate lower output gear (9476). Lower output gear (9476) may then rotate lower idler gear (9478), which may ultimately rotate lower drive gear (9482). As noted above, lower drive gear (9482) may then be used to drive various functions of surgical instrument such as rotation of shaft assembly (114), actuation of end effector (116), or articulation of end effector (116).

In a second use with upper drive gear (9480) driven by motor (9422), cam shifter (9442) may be rotated to pivot upper lock arm (9444) about pivot (9446) to drive one or more teeth of upper lock arm (9444) into engagement with upper control gear (9426). Cam shifter (9442) may also be rotated to pivot lower lock arm (9448) about pivot (9450) to drive one or more teeth of lower lock arm (9448) out of engagement with lower control gear (9428). In this configuration, rotation of upper control gear (9426) is locked, while rotation of lower control gear (9428) is unlocked.

With rotation of upper control gear (9426) locked, planet gears (9430) may be used to drive rotation of lower control gear (9428). Specifically, lower control gear (9428) is freely rotatable, so planet gears (9430) may rotate lower control gear (9428). Meanwhile, with upper control gear (9426), rotation of planet gears (9430) via sun gear (9424) drives planet gears (9430) around the interior of upper control gear (9426) with gearing of upper control gear (9426) acting similarly to a track or cylindrical rack for planet gears (9430) to travel along. Thus, motor (9422) may drive rotation of lower control gear (9428) via sun gear (9424) and planet gears (9430).

As noted above, planet drive shaft (9432) is also coupled to planet gears (9430). As such, planet gears (9430) may likewise drive rotation of planet drive shaft (9432). Upon rotation of planet drive shaft (9432), output assembly (9470) may be driven using rotation of planet drive shaft (9432). Specifically, planet drive shaft (9432) is coupled to upper output gear (9472) such that planet drive shaft (9432) may rotate upper output gear (9472). Upper output gear (9472) may then rotate upper idler gear (9474), which may ultimately rotate upper drive gear (9480). As noted above, upper drive gear (9480) may then be used to drive various functions of surgical instrument (110) such as articulation of end effector (116), actuation of end effector (116), or rotation of shaft assembly (114).

XV. Exemplary Surgical Instrument with Positive Jaw Opening Mechanism

In some examples, structures similar to end effector (116) described above may counter compressive forces or stick loads during procedures. Such forces result in challenges associated with opening structures similar to end effector (116) under some circumstances. Such challenges may be more apparent in end effectors including a spring or other resilient feature for opening. Thus, it may be desirable to incorporate various features into surgical instruments similar to surgical instrument (110) described above suitable for opening an end effector using a manually applied positive force rather than relying on a passive spring force. Although certain specific features are described below, it should be understood that such features may be combined in other examples. Additionally, certain features described below may be readily combined with other features described herein as will be apparent to those of ordinary skill in the art in view of the teachings herein.

FIGS. 159 and 160A show an exemplary alternative surgical instrument (9510) that may be readily used in connection with robotic surgical system (10) described above in lieu of surgical instrument (110). Surgical instrument (9510) of the present example is substantially similar to surgical instrument (110) described above. For instance, as with surgical instrument (110) described above, surgical instrument (9510) of the present example includes an instrument base (9512), a shaft assembly (9514) extending distally from instrument base (9512), and an end effector (9516) at a distal end of shaft assembly (9514). Instrument base (9512) of the present example is similar to instrument base (942) described above in that instrument base (9512) may include an attachment interface (not shown) configured to interface with and be driven by corresponding output couplers (not shown) of robotic arm (42). Instrument base (9512) also includes a drive system (9520) similar to drive system (120) described above.

Drive system (9520) may include a manual actuator (9525), which is shown in the form of a knob configured to be manually rotated. Manual actuator (9525) may engage other components of surgical instrument (9510) to serve as a "bailout" mechanism to obtain a desired movement in end effector (9516) without powered actuation of drive system (9520).

End effector (9516) of the present example is also similar to end effector (116) described above. For instance, like with end effector (116) described above, end effector (9516) of the present example is configured as a surgical stapler, which may also be referred to herein as an "endocutter," configured to clamp, cut, and staple tissue. As best seen in FIG. 160A, end effector (9516) includes opposing upper and lower jaws (9550, 9552) configured to move relative to one another between open and closed positions for clamping and releasing tissue.

One or both of upper and lower jaws (9550, 9522) may be configured to pivot and thereby actuate end effector (9516) between open and closed positions. Lower jaw (9552) includes a removable staple cartridge (9554), which may be substantially similar to staple cartridge (154) described above. In the illustrated example, lower jaw (9552) is pivotable relative to upper jaw (9550) to move between an open, unclamped position and a closed, clamped position.

End effector (9516) similarly includes a driving assembly (9564) that includes a pusher member (9566) that is operatively coupled with an actuation mechanism via a push rod (9568). Firing assembly (9558) may also include a wedge sled (not shown), and a knife member (not shown) to facilitate cutting and/or stapling of tissue.

Pusher member (9566) as including first and second flanges (9584, 9585). First flange (9584) is configured to be received in a longitudinal slot (9586) of upper jaw (9550) and second flange (9585) is configured to be received in a longitudinal slot (9587) of staple cartridge (9554) of lower jaw (9552). Similar to first and second flanges (184, 185) described above, first and second flanges (9584, 9585) are configured to move along longitudinal slots (9586, 9587) during actuation of pusher member (9566).

Drive system (9520) of the present example further includes an actuation capstan (9522) with a pair of actuation drive cables (9524, 9526) extending distally from actuation capstan (9522). Actuation capstan (9522) is generally configured for rotation by other components of drive system (9520). During rotation, actuation capstan (9522) is generally configured to lengthen or release one actuation drive cable (9524, 9526), while tensioning or pulling another actuation drive cable (9524, 9526), depending on the direction of rotation of actuation capstan (9522).

Actuation drive cables (9524, 9526) are generally configured to manipulate pusher member (9566) of end effector (9516) to actuate end effector (9516). Specifically, actuation drive cables (9524, 9526) include a retraction actuation drive cable (9524) and an advancement actuation drive cable (9526). Retraction actuation drive cable (9524) is configured to manipulate pusher member (9566) proximally, while advancement actuation drive cable (9526) is configured to manipulate pusher member (9566) distally. In some examples, retraction actuation drive cable (9524) may have a greater thickness or diameter relative to advancement actuation drive cable (9526) to promote proximal movement of pusher member (9566) during a bailout condition.

Although not shown, it should be understood that in some examples actuation drive cables (9524, 9526) may be in communication with other components such as pulleys, blocks, tackles, frames, shuttles and/or etc. disposed within shaft assembly (9514) to facilitate manipulation of pusher member (9566) via actuation drive cables (9524, 9526). Such other components may be in communication with push rod (9568) to transmit motion of actuation drive cables (9524, 9526) to pusher member (9566). In some examples, such other components associated with actuation drive cables (9524, 9526) may be configured in accordance with at least some of the teachings of Section XVI of the pending application entitled "Exemplary Bailout Mechanisms for Surgical Instrument" and Section XVII of the pending application entitled "Exemplary Alternative Manual Drivers.".

Unlike surgical instrument (110) described above, surgical instrument (9510) of the present example includes a manual jaw release mechanism (9530) associated with drive system (9520). Manual jaw release mechanism (9530) is generally configured to directly manipulate one or more of actuation drive cables (9524, 9526) to manipulate actuation of end effector (9516) without reliance on other components of drive system (9520).

Manual Jaw Release Mechanism (9530) includes an actuator (9532), an actuation rod (9536), and tension posts (9540). Actuator (9532) is disposed on the exterior of instrument base (9512) such that actuator (9532) is accessible to an operator for manual actuation. Actuator (9532) of the present example is configured as a pivot arm to be manually pivoted, pulled, or rotated by an operator. As such, actuator (9532) includes a pivot (9534) defining an axis about which actuator (9532) may pivot.

Actuation rod (9536) extends laterally from actuator (9532) toward retraction actuation drive cable (9524). Actuation rod (9536) includes a cable manipulator (9538) configured to engage retraction actuation drive cable (9524). Cable manipulator (9538) in the present example is in the form of a hook configured to bend around a portion of retraction actuation drive cable (9524). Although cable manipulator (9538) uses a hook form in the present example, it should be understood that in other examples, cable manipulator (9538) may take on a variety of forms such as a loop, a movable cam feature, a plate and rod configuration, and/or etc.

Actuator (9532) is coupled to actuation rod (9536) and is configured to drive lateral movement of actuation rod (9536) upon movement of actuator (9532). Specifically, tension posts (9540) are positioned proximate retraction actuation drive cable (9524). In this configuration, movement of actuation rod (9536) may be relative to tension posts (9540) to pull retraction actuation drive cable (9524) between tension posts (9540), thereby adding tension to retraction actuation drive cable (9524). As will be described in greater detail below, actuator (9532), actuation rod (9536), and tension posts (9540) may operate together to manipulate one or more of actuation drive cables (9524, 9526) independently of drive system (9520).

Unlike end effector (116) described above, end effector (9516) of the present example includes a positive jaw opening feature (9590) configured to receive input from pusher member (9566) to drive movement of upper jaw (9550) relative to lower jaw (9552). As best seen in FIG. 160A, positive jaw opening feature (9590) is formed by a proximal portion of upper jaw (9550) extending at an angle downwardly from an upper portion of upper jaw (9550) and into longitudinal slot (9586). Although positive jaw opening feature (9590) of the present example is shown as having a specific configuration, it should be understood that in other examples the configuration of positive jaw opening feature (9590) may vary. For instance, in some examples, the angle of extension of positive jaw opening feature (9590) may be smaller or lager. In other examples, positive jaw opening feature (9590) may have a convex or concave curved configuration. In still other examples, positive jaw opening feature (9590) may be in the form of a detent mechanism.

Regardless of the particular configuration of positive jaw opening feature (9590), positive jaw opening feature (9590) is generally configured to engage a portion of pusher member (9566) such as first flange (9584) during proximal translation of pusher member (9566). The position of positive jaw opening feature (9590) is proximate the proximal end of upper jaw (9550), which may also correspond to a hinge or pivot used for movement of upper jaw (9550) relative to low jaw (9552). Thus, engagement between positive jaw opening feature (9590) and pusher member (9566) may exert a force on upper jaw (9550), which may pivot upper jaw (9550) open relative to lower jaw (9552).

FIGS. 159, 160A and 160B show an exemplary use of manual jaw release mechanism (9530) and positive jaw opening feature (9590) to move upper jaw (9550) relative to lower jaw (9552). As can be seen, in FIG. 159, manual jaw release mechanism (9530) may be actuated by moving actuator (9532) from an initial disengaged position (phantom) to an engaged position (solid lines). This may include pivoting of actuator (9532), which may pull actuation rod (9536) laterally. Lateral movement of actuation rod (9536) may then pull retraction actuation drive cable (9524) laterally between tension posts (9540). This lateral pulling of retraction actuation drive cable (9524) may increase the tension on retraction actuation drive cable (9524). As will be described in greater detail below, this tension may be communicated through shaft assembly (9514) to pusher member (9566) of end effector (9516).

FIG. 160A shows the position of pusher member (9566) with actuator (9532) in the initial disengaged position. In this position, pusher member (9566) may be retracted within longitudinal slots (9586, 9587) and be proximate positive jaw opening feature (9590).

Upon movement of actuator (9532) to the engaged position, tension applied to retraction actuation drive cable (9524) may pull pusher member (9566) proximally as shown in FIG. 160B. Proximal movement of pusher member (9566) may then engage positive jaw opening feature (9590). As pusher member (9566) continues moving proximally, additional force may be exerted on positive jaw opening feature (9590), which may force upper jaw (9550) into the position shown in FIG. 160B.

FIGS. 161A and 161B show an exemplary alternative cable manipulator (9638) that may be used with manual jaw release mechanism (9530) described above in lieu of cable manipulator (9538). Cable manipulator (9638) is similar to cable manipulator (9538) described above in that cable manipulator (9638) is configured to manipulate one or more of actuation drive cables (9524, 9526) to increase tension in one or more of actuation drive cables (9524, 9526) by moving one or more of actuation drive cables (9524, 9526) out of plane.

Unlike cable manipulator (9538) described above, cable manipulator (9638) of the present example is generally configured as a cam mechanism rather than a hook. Moreover, cable manipulator (9638) of the present example is generally configured to manipulate both of retraction actuation drive cable (9524) and advancement actuation drive cable (9526) rather than only retraction actuation drive cable (9524).

Cable manipulator (9538) includes a drive member (9640), a drive arm (9642), and a cam block (9644). Drive member (9640) is configured to couple to actuation rod (9536) such that drive member (9640) is configured to be driven relative to actuation drive cables (9524, 9526). Drive member (9640) of the present example is in the form of a double L-pattern or a patter having block and cutout. Alternatively, drive member (9640) may be formed of a loop, cylinder, or other similar feature.

Drive arm (9642) extends from drive member (9640) to cam block (9644). Drive member (9640) includes a drive post (9643) configured to engage drive member (9640). Specifically, drive post (9643) is configured for receipt within a portion of drive member (9640) such that drive post (9643) may be moved laterally in both directions by drive member (9640), but still pivot or rotate within drive member (9640). Opposite drive post (9643), drive arm (9642) is rotatably coupled to cam block (9644).

Cam block (9644) defines a generally triangular body with drive arm (9642) coupled at one vertex, a first cam (9646) coupled at another vertex and a second cam (9648) coupled at another vertex. Cam block (9644) is generally configured to rotate between actuation drive cables (9524, 9526) to selectively engage first cam (9646) or second cam (9648) with a given actuation drive cable (9524, 9526). Specifically, first cam (9646) is configured to engage retraction actuation drive cable (9524), while second cam (9648) is configured to engage advancement actuation drive cable (9526). Although not shown, it should be understood that cam block (9644) may be rotatably secured to a grounding structure such as a post or rod configured to maintain the position of cam block (9644) within surgical instrument (9510), while permitting rotation of cam block (9644) relative to actuation drive cables (9524, 9526).

FIGS. 161A and 161B show an exemplary use of cable manipulator (9638). As best seen in FIG. 161A, drive member (9640) may initially be pulled laterally toward retraction actuation drive cable (9524). In use with manual jaw release mechanism (9530), this may correspond to actuator (9532) being moved to the engaged position. Alternatively, in some uses with manual jaw release mechanism (9530), actuator (9532) this may correspond to actuator (9532) being moved to the disengaged position.

As drive member (9640) moves, drive member (9640) may pull drive post (9643) of drive arm (9642) laterally in the same direction. This pulling motion of drive arm (9642) may pull one side of cam block (9644), thereby rotating cam block (9644) in the direction of drive arm (9642). Upon rotation of cam block (9644), second cam (9648) may be driven into contact with advancement actuation drive cable (9526) as first cam (9646) may be driven away from retraction actuation drive cable (9524). Thus, actuation drive cable (9526) may be driven out of plane, thereby increasing the tension applied to actuation drive cable (9526).

Next, drive member (9640) may be driven laterally in the opposite direction as shown in FIG. 161B. As drive member (9640) moves, drive member (9640) may push drive post (9642) of drive arm (9642) laterally towards actuation drive cable (9526). This pushing motion of drive arm (9642) may pull one side of cam block (9644), thereby rotating cam block (9644) in the direction of drive arm (9642). Upon rotation of cam block (9644), second cam (9648) may be driven way from advancement action drive cable (9526) as first cam (9646) may be driven into contact with retraction actuation cable (9524). Thus, retraction drive cable (9524) may be driven out of plane, thereby increasing the tension applied to retraction drive cable (9524).

XVI. Exemplary Bailout Mechanisms for Surgical Instrument

In some examples of drive system (120) of surgical instrument (110) described above, it may be desirable to include certain bailout features to provide manual drive of drive system (120). For instance, during the course of a surgical procedure, unexpected operational conditions may sometimes be encountered. When such conditions are encountered, it may be desirable to immediately terminate or pause the surgical procedure, for example after a distal firing stroke of surgical instrument (110) has initiated. To do so, it may be desirable to actuate one or more portions of surgical instrument (110) manually or without input from robotic surgical system (10). One merely exemplary bailout feature may be a drive to retract actuation assembly, shown as a driving assembly (164). This bailout feature may be desirable to return firing system components of surgical instrument (110) to a proximal, pre-fired position and enable jaws (150, 152) of end effector (116) to be opened to release the clamped tissue and subsequently withdraw end effector (116) from a patient. This particular bailout feature may be referred to as a manual bailout mechanism in some examples.

In such manual bailout mechanisms, manual drive features may be integrated into robotically controlled drive features. Such a configuration may be desirable to promote a compact and light weight design. However, such integration may lead to a more complex mechanism, which may require more force during manual drive. As a result, it may be desirable to incorporate certain features into such manual bailout mechanisms to promote ease of use during manual operation.

A. Exemplary Bailout Mechanism

FIG. 162 shows an exemplary bailout mechanism (10310) (also referred to as bailout assembly, opening mechanism, or opening assembly) that may be readily incorporated into drive system (120) of surgical instrument (110) described above. Bailout mechanism (10310) is generally configured to drive movement of jaws (150, 152) of end effector (116) between an open and closed configuration using either motor driven input or manual input. Bailout mechanism (10310) includes a motor input shaft (10312) to facilitate motor input and a manual drive wheel (10320) (also referred to as a knob, driver, or manual drive input) to facilitate manual input.

Motor input shaft (10312) extends proximally from attachment interface (118). Although not shown, a distal end of motor input shaft (10312) may include an input coupler similar to input couplers (130) described above. As with input couplers (130) described above, the input coupler may be configured to engage or otherwise communicate with a corresponding output coupler (not shown) of robotic arm (42) to rotate motor input shaft (10312).

A proximal end of motor input shaft (10312) includes an input gear (10314). Input gear (10314) is configured to mesh with a combination drive gear (10330). As will be described in greater detail below, input gear (10314) is generally configured to transmit rotary input provided by motor input shaft (10312) to other components of bailout mechanism (10310) to ultimately drive movement of jaws (150, 152) of end effector (116).

Manual drive wheel (10320) is generally configured for manual rotation by an operator. In the present example, manual drive wheel (10320) extends from the proximal end of bailout mechanism (10310) to permit actuation from the proximal end of surgical instrument (110). However, in other examples, manual drive wheel (10320) may have a variety of alternative positions relative to surgical instrument (110). The shape of manual drive wheel (10320) is generally cylindrical to promote grasping by an operator. To further promote gasping, manual drive wheel (10320) may include one or more grasping features such as grooves, knurling, ribs, and/or etc.

A manual drive gear (10322) extends distally from manual drive wheel (10320). As will be described in greater detail below, manual drive gear (10322) is generally configured to communicate a manual rotary input from manual drive wheel (10320) to other portions of bailout mechanism (10310) to ultimately drive movement of jaws (150, 152) of end effector (116). In some examples, manual drive gear (10322) may be integral with manual drive wheel (10320) such that any rotatory motion of manual drive wheel (10320) is communicated to manual drive gear (10322). In other examples, manual drive wheel (10320) and manual drive gear (10322) may be connected by an intermediate mechanism to modify communication of at least some rotary input of manual drive wheel (10320) to manual drive gear (10322). By way of example only, one suitable intermediate mechanism may be a ratcheting mechanism to permit drive of manual drive gear (10322) when manual drive wheel (10320) is rotated in one direction, but prevent drive of manual drive gear (10322) when manual drive wheel (10320) is rotated in another direction. Of course, various alternative suitable intermediate mechanisms may be used as will be appreciated by those of ordinary skill in the art in view of the teachings herein.

Manual drive gear (10322) is in communication with input gear (10314). Thus, manual drive gear (10322) is configured to transmit rotary motion to input gear (10314) from manual drive wheel (10320). Input gear (10314), in turn, is in communication with a combination drive gear (10330). Combination drive gear (10330) is configured to drive an integral bevel gear (10332), which communicates with a capstan gear (10334). Capstan gear (10334) defines a bevel complementary to the bevel of bevel gear (10332) to promote meshing of the two gears (10332, 10334). Capstan gear (10334) is in communication with a capstan (10336), which is configured to rotate with capstan gear (10334) to manipulate actuation cables (10340, 10342).

Capstan (10336) defines a shaft extending from capstan gear (10334) perpendicularly relative to a longitudinal axis defined by elongate shaft (114) of surgical instrument (110). Capstan (10336) is configured as a double capstan and defines two spool channels (10338, 10339) configured to receive actuation cables (10340, 10342) in a helical pattern. In particular, capstan (10336) defines a first spool channel (10338) having a first pitch and a second spool channel (10339) having a second pitch. In the present example, the first pitch and the second pitch are opposite of each other to promote an opposite threading for each actuation cable (10340, 10342). As a consequence, rotation of capstan (10336) in one direction may pull a portion of one actuation cable (10340, 10342) toward capstan (10336), while releasing a portion of another actuation cable (10342, 10340) to move away from capstan (10336).

Actuation cables (10340, 10342) extend distally away from capstan (10336) and into elongate shaft (114) of surgical instrument (110). In the present example, bailout mechanism (10310) includes a retraction actuation cable (10340) and an advancement actuation cable (10342). As will be described in greater detail below, retraction actuation cable (10340) and advancement actuation cable (10342) are together configured to manipulate structures within elongate shaft (114) to control movement of end effector (116) using rotation of capstan (10336) via motor input shaft (10312) or manual drive wheel (10320).

As best seen in FIGS. 163 and 164, bailout mechanism (10310) further includes a shuttle (10350), which may be disposed within elongate shaft (114) of surgical instrument (110). Shuttle (10350) is generally configured to translate within elongate shaft (114) to drive movement of end effector (116). In particular, shuttle (10350) includes an elongate frame (10352) having a manipulation end (10354) and a coupling end (10356). Manipulation end (10354) is in communication with push rod (168) to drive movement pusher member (166), which may be configured to manipulate lower jaw (152) relative to upper jaw (150). Thus, shuttle (10350) is configured to manipulate jaws (150, 152) by translating within elongate shaft (114) to push and pull push rod (168).

As noted above, movement of jaws (150, 152) may be controlled by actuation cables (10340, 10342). Thus, shuttle (10350) of the present example is configured to engage actuation cables (10340, 10342) to facilitate translation of shuttle (10350) within elongate shaft (114) via actuation cables (10340, 10342). Specifically, coupling end (10356) of shuttle (10350) is configured to couple to each end of actuation cable (10340, 10342). As best seen in FIGS. 163 and 164, coupling end (10356) includes a retraction receiver (10358) and an advancement receiver (10360). Retraction receiver (10358) is configured to receive retraction actuation cable (10340). Similarly, advancement receiver (10360) is configured to receive advancement actuation cable (10342).

Retraction receiver (10358) and advancement receiver (10360) are oriented in opposite directions to permit application of different force vectors to shuttle (10350). For instance, retraction receiver (10358) is oriented proximally to permit retraction actuation cable (10340) to pull shuttle distally (10350). Similarly, advancement receiver (10360) is oriented distally to permit advancement actuation cable (10342) to pull shuttle proximally with the assistance of other portions of shuttle (10350) described in greater detail below.

Bailout mechanism (10310) further includes a block (10370) disposed within elongate frame (10352) of shuttle (10350). Block (10370) includes a pully (10372) configured to receive advancement actuation cable (10342). Specifically, pully (10372) is configured to reverse the direction of advancement actuation cable (10342) such that advancement actuation cable (10342) may pass through coupling end (10356) of shuttle (10350), reverse at pully (10372), and then return to coupling end (10356) to couple to advancement receiver (10360). The configuration of pully (10372) and coupling end (10356) is generally desirable to permit advancement actuation cable (10342) to pull shuttle (10350) distally using tension provided by capstan (10336).

Block (10370) of the present example is not physically secured to shuttle (10350). In other words, shuttle (10350) may move relative to block (10370). Although not shown, it should be understood that block (10370) may be secured or otherwise mechanically grounded to elongate shaft (114). This configuration may be desirable to increase the mechanical advantage of advancement actuation cable (10342) and pully (10372). In other examples, block (10370) may be secured directly to shuttle (10350) to provide similar functionality without added mechanical advantage.

Returning to FIG. 162, in an exemplary use, bailout mechanism (10310) may receive input from either motor input shaft (10312) or manual drive wheel (10320). In both uses, this may result in turning of input gear (10314) either by motor input shaft (10312) directly or manual drive gear (10322).

Rotation of input gear (10314) by wither motor input shaft (10312) or manual drive gear (10322) may result in rotation of combination drive gear (10330). Rotation of combination drive gear (10330) rotates bevel gear (10332), which rotates capstan gear (10334). As a result of rotation of capstan gear (10334), capstan (10336) likewise rotates. One actuation cable (10340, 10342) will then be tensioned and another actuation cable (10342, 10340) will be relaxed, depending on the direction of rotation of capstan (10336).

As shown in FIGS. 163 and 164, translation of shuttle (10350) may be controlled by tensioning or relaxing a given actuation cable (10340, 10342). For instance, if capstan (10336) is rotated to tension retraction actuation cable (10340), retraction actuation cable (10340) will pull directly on coupling end (10356) of shuttle (10350) to translate shuttle (10350) proximally. This proximal translation of shuttle (10350) will pull pusher member (166) proximally and thereby open jaws (150, 152).

Alternatively, if capstan (10336) is rotated in an opposite direction to tension advancement actuation cable (10342), the tension on advancement actuation cable (10342) will be directed through pully (10372) and then to coupling end (10356) to pull shuttle (10350) distally. This distal translation of shuttle (10350) will push pusher member (166) distally and thereby close jaws (150, 152).

B. Exemplary Bailout Mechanism with Improved Retraction Feature

FIG. 165 shows an exemplary alternative bailout mechanism (10410) (also referred to as bailout assembly, opening mechanism, or opening assembly) that may be readily incorporated into drive system (120) of surgical instrument (110) described above. Bailout mechanism (10410) is substantially similar to bailout mechanism (10310) described above. For instance, like with bailout mechanism (10310) described above, bailout mechanism (10410) of the present example is generally configured to drive movement of jaws (150, 152) of end effector (116) between an open and closed configuration using either motor driven input or manual input. As such, bailout mechanism (10410) of the present example includes a motor input shaft (10412) and a manual drive wheel (10420) (also referred to as a knob, driver, or manual drive input) to facilitate manual input.

As with motor input shaft (10312) described above, motor input shaft (10412) of the present example extends proximally from attachment interface (118) and includes an input gear (10414) similar to input gear (10314) described above. Input gear (10414) is configured to mesh with a combination drive gear (10430), which may be used to drive other components of bailout mechanism (10410), as will be described in greater detail below.

Manual drive wheel (10420) is substantially similar to manual drive wheel (10320) described above in that manual drive wheel (10420) is generally configured for manual rotation by an operator. Thus, the shape of manual drive wheel (10420) is generally cylindrical to promote grasping by an operator. Also like manual drive wheel (10320) described above, manual drive wheel (10420) of the present example includes a manual drive gear (10422) extending distally therefrom.

Manual drive gear (10422) is in communication with input gear (10414). Thus, manual drive gear (10422) is configured to transmit rotary motion to input gear (10414) from manual drive wheel (10420). Input gear (10414), in turn, is in communication with a combination drive gear (10430). Combination drive gear (10430) is configured to drive an integral bevel gear (10432), which communicates with a capstan gear (10434). Capstan gear (10434) defines a bevel complementary to the bevel of bevel gear (10432) to promote meshing of the two gears (10332, 10434). Capstan gear (10434) is in communication with a capstan (10436), which is configured to rotate with capstan gear (10434) to manipulate actuation cables (10440, 10442).

Capstan (10436) of the present example is substantially similar to capstan (10436) described above. For instance, capstan (10436) defines a shaft extending from capstan gear (10434) perpendicularly relative to a longitudinal axis defined by elongate shaft (114) of surgical instrument (110). Capstan (10436) is configured as a double capstan and defines two spool channels (10438, 10439) configured to receive actuation cables (10440, 10442) in a helical pattern. As similarly described above, spool channels (10438, 10439) include a first spool channel (10438) having a first pitch and a second spool channel (10439) having a second pitch. The first pitch and the second pitch are opposite of each other to promote an opposite threading for each actuation cable (10440, 10442). As a consequence, rotation of capstan (10436) in one direction may pull a portion of one actuation cable (10440, 10442) toward capstan (10436), while releasing a portion of another actuation cable (10442, 10440) to move away from capstan (10436).

Actuation cables (10440, 10442) extend distally away from capstan (10436) and into elongate shaft (114) of surgical instrument (110). In the present example, bailout mechanism (10410) includes a retraction actuation cable (10440) and an advancement actuation cable (10442). As with retraction actuation cable (10340) and advancement actuation cable (10342) described above, retraction actuation cable (10440) and advancement actuation cable (10442) of the present example are together configured to manipulate structures within elongate shaft (114) to control movement of end effector (116) using rotation of capstan (10436) via motor input shaft (10412) or manual drive wheel (10420).

Unlike retraction actuation cable (10340) and advancement actuation cable (10342) described above, retraction actuation cable (10440) and advancement actuation cable (10442) of the present example define differing diameters or thicknesses. In particular, retraction actuation cable (10440) of the present example defines a diameter ($T_r$) that is greater than a diameter ($T_a$) defined by advancement actuation cable (10442). This configuration may be desirable in some circumstances to promote the physical integrity of bailout mechanism (10410). For instance, in some circumstances, a relatively large load may be applied to jaws (150, 152) of end effector (116) by tissue, bone, or other structures proximate end effector (116). Such a load may resist movement of jaws (150, 152) from a closed to open configuration. As a result, it may be beneficial for retraction actuation cable (10440) to withstand relatively high loads to move jaws (150, 152) from the closed configuration to the open configuration in such circumstances.

Although the present example promotes physical integrity of bailout mechanism (10410) using an increased diameter of retraction actuation cable (10440) relative to advancement actuation cable (10442) (e.g., $T_r > T_a$), such benefits may be achieved by varying other physical properties of actuation cables (10440, 10442). For instance, in some examples, retraction actuation cable (10440) may be of a different material relative to advancement action cable (10442) (e.g., INCONEL versus stainless steel). In other examples, actuation cables (10440, 10442) may be of the same material but of a different configuration. For instance, in some examples, both actuation cables (10440, 10442) may be braided, but retraction actuation cable (10440) may have a higher strength braid relative to advancement actuation cable (10442). In still other examples, various combinations of different physical properties may be used to promote physical integrity of bailout mechanism (10410). In addition, or in the alternative, retraction actuation cable (10440) may be independently manipulated in some examples such that retraction actuation cable (10440) is configured as an independent direct pull cable.

As best seen in FIG. 166, bailout mechanism (10410) further includes a shuttle (10450), which may be disposed within elongate shaft (114) of surgical instrument (110). Shuttle (10450) is substantially similar to shuttle (10350) described above. For instance, shuttle (10450) of the present example generally configured to translate within elongate shaft (114) to drive movement of end effector (116). As with shuttle (10350) described above, shuttle (10450) of the present example includes an elongate frame (10452) having a manipulation end (10454) and a coupling end (10456). Manipulation end (10454) is in communication with push rod (168) such that shuttle (10450) is configured to manipulate jaws (150, 152) by translating within elongate shaft (114) to push and pull push rod (168).

Coupling end (10456) of shuttle (10450) is configured to couple to each end of actuation cable (10440, 10442). As best seen in FIG. 167, coupling end (10456) includes a retraction receiver (10458) and an advancement receiver (10460). Retraction receiver (10458) is configured to receive retraction actuation cable (10440). Similarly, advancement receiver (10460) is configured to receive advancement actuation cable (10442). Although actuation cables (10440, 10442) of the present example couple to coupling end (10456) of shuttle (10450), it should be understood that in some examples, one or more of actuation cables (10440, 10442) may bypass shuttle (10450) entirely and coupled directly to pusher member (166). For instance, in some examples, retraction actuation cable (10440) may couple directly to pusher member (166) with retraction actuation cable (10440) being configured to directly pull pusher member (166).

Unlike coupling end (10356) described above, coupling end (10456) of the present example includes a release feature (10462) associated with advancement receiver (10460). Release feature (10462) of the present example is configured to couple advancement actuation cable (10442) to coupling end (10456) until a predetermined load is applied to advancement actuation cable (10442), at which point release feature (10462) is configured to release advancement actuation cable (10442). In other words, release feature (10462) is configured to operate as a mechanical fuse to release advancement actuation cable (10442) from coupling end (10456) upon the application of a load exceeding a predetermined threshold to advancement actuation cable (10442). This configuration may be desirable to promote ease of use for bailout mechanism (10410) during certain circumstances. For instance, when encountering some bailout conditions, relatively large force may be required to fully close jaws (150, 152). In such circumstances, advancement actuation cable (10442) may automatically release to prevent closure of jaws (150, 152) beyond certain predetermined force limits. Meanwhile, retraction actuation cable (10440) may remain attached to coupling end (10456) to permit proximal translation of shuttle (10450) for opening of jaws (150, 152), while preventing distal translation of shuttle (10450) for closure of jaws (150, 152).

Release feature (10462) of the present example includes a collar configured to release from advancement actuation cable (10442) upon application of a predetermined load. The collar may be crimped or swaged to an end of advancement actuation cable (10442) to promote fastening until the collar releases. Alternatively, some examples a portion of coupling end (10456) may be configured to release advancement actuation cable (10442). For instance, coupling end (10456) may include a lug or other feature configured to release upon application of a predetermined load. In such examples, the collar may remain coupled to advancement actuation cable (10442) upon release thereof.

Bailout mechanism (10410) further includes a block (10470) disposed within elongate frame (10452) of shuttle (10450). Block (10470) of the present example is substantially similar to block (10370) described above. For instance, like block (10370), block (10470) of the present example includes a pully (10472) configured to receive advancement actuation cable (10442) and reverse the direction of advancement actuation cable (10442). Also like block (10370) described above, block (10470) of the present example may move relative to shuttle (10450) and may be secured or otherwise mechanically grounded to elongate shaft (114). As noted above, this configuration may be desirable to increase the mechanical advantage of advancement actuation cable (10442) and pully (10472). In other examples, block (10470) may be secured directly to shuttle (10450) to provide similar functionality without added mechanical advantage.

It should be understood that block (10470) and pully (10472) in the present example is merely one example of a block and tackle mechanism that might be used to increase the mechanical advantage of either actuation cables (10440, 10442). Thus, even though the present example includes one block (10470) having one pully (10472), it should be understood that in other examples, multiple blocks (10470) with one pully (10472), multiple blocks (10470) with multiple pullies (10472), or one block (10470) with multiple pullies (10472) may be used to increase the force applied by either actuation cable (10440, 10442) or both. In merely one example, a similar block and tackle mechanism may be associated with retraction actuation cable (10440). Such a block and tackle may define multiple synchronized loops of retraction actuation cable (10440) to magnify the retraction force applied by retraction actuation cable (10440). Of course, various other suitable configurations of block and tackle mechanisms will be apparent to those of ordinary skill in the art in view of the teachings herein.

As shown in FIG. 168, in some examples, pusher member (166) may be coupled to push rod (168) using an axial strengthening feature (10490). Axial strengthen feature (10490) is generally configured to strengthen the interface between pusher member (166) and push rod (168) to resist separation between the two during relatively high axial loads (e.g., during proximal retraction of pusher member (166)). Axial strengthening feature (10490) may take on a variety of forms suitable to withstand relatively high axially loads. For instance, in the present example, axial strengthening feature (10490) include a mating keyed interface having a rounded key that may be received in a corresponding opening. In other examples, a threaded projection may be received in a threaded bore. In other examples, axial strengthening feature (10490) may include a coupler. In still other examples, pusher member (166) and push rod (168) may instead be welded to each other. Of course, axial strengthening feature (10490) of the present example is merely optional and may be omitted in some examples.

In use, bailout mechanism (10410) of the present example functions similarly to bailout mechanism (10310) described above. For instance, capstan (10436) may be rotated in a first direction by either motor input shaft (10412) or manual drive wheel (10420) to tension advancement actuation cable (10442) and simultaneously relax retraction actuation cable (10440) for advancement of shuttle (10450) distally and closure of jaws (150, 152). Similarly, capstan (10436) may be rotated in an opposite second direction by either motor input shaft (10412) or manual drive wheel (10420) to tension retraction actuation cable (10440) and simultaneously relax advancement actuation cable (10442) for retraction of shuttle (10450) proximally and opening of jaws (150, 152).

Unlike bailout mechanism (10310) described above, the present use of bailout mechanism (10410) may deviate upon an operator encountering unexpected operating conditions. For instance, in some circumstances external structures such as tissue, bone, other surgical instruments or equipment, and/or etc. may add additional forces to jaws (150, 152) either preventing complete closure or resisting opening of jaws (150, 152). In such circumstances, it may be beneficial to open jaws (150, 152) to move or reposition surgical instrument (110). As described above, jaws (150, 152) may be opened by retracting shuttle (10450) proximally via rotation of capstan (10436) to tension retraction actuation cable (10440). Due to the diameter ($T_r$) of retraction actuation cable (10440), retraction actuation cable (10440) may be used to apply additional force to shuttle (10450) and thus jaws (150, 152).

Also during use, excessive application of force to advancement actuation cable (10442) may result in release feature (10462) releasing advancement actuation cable (10442) from coupling end (10456) of shuttle (10450). As a result, distal translation of shuttle (10450) may be disabled, thereby permitting only proximal translation of shuttle (10450) via retraction actuation cable (10440). In addition, releasing of advancement actuation cable (10442) may release any tension applied to shuttle (10450) in the distal direction opposite the force applied by retraction actuation cable (10440), thereby reducing the force required for retraction actuation cable (10440) to translate shuttle (10450) proximally.

XVII. Exemplary Alternative Manual Drivers

In some circumstances, a bailout mechanism similar to bailout mechanisms (10310, 10410) described above may be operated manually by an operator using a manual input driver similar to manual drive wheels (10320, 10420) described above. However, in some circumstances, a limiting factor on operation of such bailout mechanisms may be the ability to apply force to the manual input driver. Additionally, in some circumstances, another limiting factor may be the direction of the application of force to the manual input driver. Thus, it may be desirable to incorporate features into such manual input drivers to increase a user's ability to apply force or to ensure the force is applied in a particular direction.

A. Exemplary Alternative Manual Drive Wheel with Arm

FIG. 169A shows an exemplary alternative manual drive wheel (10520) (also referred to as a knob, driver, or manual drive input), which may be readily incorporated into bailout mechanisms (10310, 10410) described above. Manual drive wheel (10520) is generally configured to enhance the ability of an operator to apply torque and/or power to manual drive wheel (10520), thereby enhancing the ability to drive bailout mechanisms (10310, 10410). Manual drive wheel (10520) is similar to manual drive wheels (10320, 10420) described above in that manual drive wheel (10520) defines a generally cylindrical shape suitable for grasping and may additionally include one or more gripping features to enhance an operators grip. Although not shown, it should be understood that manual drive wheel (10520) may be in communication with one or more gears similar to manual drive gears (10322, 10422) described above to transmit power from manual drive wheel (10520) to other components of bailout mechanisms (10310, 10410).

Unlike manual drive wheels (10320, 10420) described above, manual drive wheel (10520) of the present example includes an arm (10524) (alternatively referred to as a lever) configured to extend and retract relative to a portion of manual drive wheel (10520) to provide additional leverage for rotation of manual drive wheel (10520). In particular, arm (10524) is configured to pivot, flip or rotate from a retracted configuration shown in FIG. 169A to an extended configuration shown in FIG. 169B.

Arm (10524) in the present example defines a length approximately corresponding to the diameter of manual drive wheel (10520). Additionally, manual drive wheel (10520) defines a channel (10526) configured to receive arm (10524). Channel (10526) approximately corresponds to the thickness of arm (10524) to permit arm (10524) to be relatively flush with the top of manual drive wheel (10520) when arm (10524) is in the retracted configuration.

One side of arm (10524) may be coupled to a portion of manual drive wheel (10520) by a hinge, pivot shaft, living hinge, or other feature to promote pivoting, flipping or rotation of arm (10524) relative to a portion of manual drive wheel (10520). Meanwhile, an opposite end of arm (10524) remains free for manipulation by an operator. This permits arm (10524) to pivot about the coupling to increase the leverage provided by manual drive wheel (10520) by 2 times or more. Although arm (10524) of the present example is shown as using a pivoting, flipping or rotational action, it should be understood that other examples may include different configurations to provide extension of arm (10524). For instance, in some examples, channel (10526) may include a track or other feature to permit arm (10524) to slide laterally out relative to a portion of manual drive wheel (10520). Still other configurations for extension of arm (10524) will be apparent to those of ordinary skill in the art in view of the teachings herein.

To enhance grip of arm (10524) the exterior of arm (10524) may optionally include one or more grip features. Such grip features may take on a variety of forms such as indentations, protrusions, knurling, and/or etc. Additionally, in some examples such grip features may match grip features incorporated into the perimeter of the cylindrical portion of manual drive wheel (10520). In other examples, the grip features may be varied relative to those of manual drive wheel (10520).

In use, arm (10524) may initially be stowed in the retracted configuration as shown in FIG. 169A. In this configuration, manual drive wheel (10520) may be used similar to manual drive wheels (10320, 10420) described above. Specifically, an operator may grasp manual drive wheel (10520) and rotate manual drive wheel (10520) about an axis of rotation. Use of manual drive wheel (10520) while arm (10524) is in the retracted position may be desirable where limited force input is required or in circumstances where there is limited operational clearance between manual drive wheel (10520) and other medical components or equipment.

In some contexts, it may be desirable to exert additional force on manual drive wheel (10520). To assist with this, an operator may move arm (10524) from the retracted configuration shown in FIG. 169A to the extended configuration shown in FIG. 169B. In the present example, arm (10524) may be moved to the extended configuration by gasping the uncoupled end thereof and pivoting, flipping, or rotating arm (10524) to the position shown in FIG. 169B. In this position, arm extends from the cylindrical perimeter of manual drive wheel (10520) by about the diameter of manual drive wheel (10520). Thus, an operator may rotate manual drive wheel (10520) by applying a force to arm (10524). Because of the length of arm (10524), additional leverage is provided for increased torque.

Although not shown, in some examples, manual drive wheel (10520) may be in communication with a ratcheting mechanism. In such examples, manual drive wheel (10520) may be used either with arm (10524) in the retracted configuration or the extended configuration to move repeatedly through a desired range of motion. In use, this repeated motion provided by such a ratcheting mechanism may be desirable to make it easier for an operator to apply force to manual drive wheel (10520). This benefit may be especially present with arm (10524) in the extended configuration, as it may permit an operator to avoid adjusting grip on arm (10524) by not having to durn manual drive wheel (10520) through a complete rotation.

B. Exemplary Alternative Manual Drive Wheel with Instrument Retaining Feature

FIG. 170 shows an exemplary alternative manual drive wheel (10620) (alternatively referred to as a knob, driver, or manual drive input), which may be readily incorporated into bailout mechanisms (10310, 10410) described above. Manual drive wheel (10620) is generally configured to enhance the ability of an operator to apply torque and/or power to manual drive wheel (10620), thereby enhancing the ability to drive bailout mechanisms (10310, 10410). Manual drive wheel (10620) is similar to manual drive wheels (10320, 10420) described above in that manual drive wheel (10620) defines a generally cylindrical shape suitable for grasping and may additionally include one or more gripping features to enhance an operator's grip. Although not shown, it should be understood that manual drive wheel (10620) may be in communication with one or more gears similar to manual drive gears (10322, 10422) described above to transmit power from manual drive wheel (10620) to other components of bailout mechanisms (10310, 10410).

Unlike manual drive wheels (10320, 10420) described above, manual drive wheel (10620) of the present example includes an instrument retaining feature (10680). Instrument retaining feature (10680) is generally configured to promote application of force to manual drive wheel (10620) along a specific axis to promote engagement between surgical instrument (110) and robotic arm (42) at chassis (122) of surgical instrument (110). As best seen in FIGS. 171 and 172, instrument retaining feature (10680) includes a drive lock (10682), a resilient feature (10684), and a wheel lock (10686). Drive lock (10682) of the present example defines an irregular configuration similar to a castle nut. As will be described in greater detail below, the configuration of drive lock (10682) may be complementary to the configuration of wheel lock (10686) to promote releasable engagement between drive lock (10682) and wheel lock (10686). Although not shown, it should be understood that drive lock (10682) may be in communication with other components of bailout mechanisms (10310, 10410) to transmit rotary motion from manual drive wheel (10620) to other drive components of bailout mechanisms (10310, 10410).

Wheel lock (10686) is best seen in FIG. 172. As can be seen, wheel lock (10686) extends from an underside surface of manual drive wheel (10620). In this configuration, wheel lock (10686) is configured to selectively engage drive lock (10682) when manual drive wheel (10620) is coupled to the rest of surgical instrument (110). The particular configuration of wheel lock (10686) is complementary to the particular configuration of drive lock (10682). For instance, as noted above, drive lock (10682) includes a configuration similar to a castle nut. Thus, wheel lock (10686) of the present example likewise includes a configuration similar to a castle nut, but with an opposite pattern to promote mating engagement between drive lock (10682) and wheel lock (10686).

Although drive lock (10682) and wheel lock (10686) of the present example use a configuration similar to a castle nut, it should be understood that in other examples various alternative configurations may be used. For instance, the configuration used in the present example provides a paw or cam surface that may be used to selectively transfer rotary motion from wheel lock (10686) to drive lock (10682). Thus, any other suitable mating surface may be used as will be apparent to those of ordinary skill in the art in view of the teachings herein.

Returning to FIG. 171, resilient feature (10684) is disposed between drive lock (10682) and wheel lock (10686). Resilient feature (10684) is generally configured to bias wheel lock (10686) away from drive lock (10682) such that drive lock (10682) and wheel lock (10686) may not be matingly engaged unless a suitable force is applied to manual drive wheel (10620). Resilient feature (10684) of the present example is configured as a coil spring, although in other examples various alternative configurations may be used such as torsion springs, rubber or polymer cylinders, and/or etc.

In use, manual drive wheel (10620) may be initially in a disengaged configuration as shown in FIG. 170. In this configuration, resilient feature (10684) biases manual drive wheel (10620) proximally from surgical instrument (110) such that wheel lock (10686) is disengaged from drive lock (10682). With wheel lock (10686) disengaged from drive lock (10682), manual drive wheel (10620) may rotate freely without transmitting rotation to any other portion of bailout mechanism (10310, 10410).

To initiate drive of bailout mechanism (10310, 10410), a distal force may be applied to manual drive wheel (10620) as shown in FIG. 172. This force may overcome the force of resilient feature (10684) and drive manual drive wheel (10620) distally to engage wheel lock (10686) with drive lock (10682). Manual drive wheel (10620) may then be rotated. During rotation, rotation of manual drive wheel (10620) is communicated to other components of bailout mechanism (10310, 10410) via engagement between wheel lock (10686) and drive lock (10682).

As manual drive wheel (10620) is rotated, distal force sufficient to overcome the resilient bias of resilient feature (10684) may be maintained to maintain engagement between wheel lock (10686) and drive lock (10682). This distal force component may be desirable to force surgical instrument (110) distally toward robotic arm (42) to promote engagement between surgical instrument (110) and robotic arm (42). Without such a distal force component, an operator might apply excessive force to manual drive wheel (10620) leading to disengagement of surgical instrument (110) from robotic arm (42). Thus, manual drive wheel (10620) of the present example is desirable to prevent inadvertent disengagement between surgical instrument (110) and robotic arm (42).

XVIII. Exemplary Deflectable Firing Members for Surgical Staplers

In some instances, it may be desirable to provide a firing member (e.g., a push rod) for operatively coupling pusher member (166) with moveable member (128) to transmit proximal and/or distal motion therebetween during articulation of end effector (116) relative to a longitudinal axis defined by shaft assembly (114). It may also be desirable for such a firing member to be resistant to lateral/lateral misalignment during articulation of end effector (116) (e.g., via any suitable wrist architecture of end effector (116)), to thereby prevent the firing member from buckling. Each of the push rods (11310, 11410, 11510, 11610, 11710, 11810, 11910, 12010, 13110) described below may provide one or more of these functionalities. As used herein, the term "lateral" shall be understood to mean any direction that is laterally oriented relative to an axis; or that is otherwise non-parallel with the axis. The term "lateral" should not be read as being limited to directions that are only perpendicular to the axis. While a direction that is perpendicular to the axis may constitute a "lateral" direction, other directions that are obliquely oriented relative to the axis may also constitute "lateral" directions.

A. First Exemplary Deflectable Firing Member

FIGS. 173-175B show a distal portion of an exemplary push rod (11310) for use with surgical instrument (110) described above. Push rod (11310) is similar to push rod (168) described above except as otherwise described below. In this regard, push rod (11310) may operatively couple a pusher member (not shown), such as pusher member (166), with an actuation mechanism (not shown), such as moveable member (128), for transmitting proximal and/or distal motion between pusher member (166) and moveable member (128).

As shown in FIGS. 173-174, push rod (11310) includes a cylindrical tube (11312) extending distally from a proximal end (not shown) to a distal end (11314) along a longitudinal axis, such as the longitudinal axis defined by shaft assembly (114). In some versions, the proximal end of cylindrical tube (11312) may define an input surface for receiving forces from moveable member (128) and distal end (11314) of cylindrical tube (11312) may define an output surface for transmitting such forces to pusher member (166). Cylindrical tube (11312) may be formed of any suitable material, such as a metal or polymer-based material. Push rod (11310) also includes a lumen (11316) defined by an interior surface of cylindrical tube (11312). In some versions, lumen (11316) may be configured to slidably receive a pull rod (not shown), as described below in connection with FIGS. 181-183.

Push rod (11310) of the present version further includes a plurality of I-shaped slots (11320*a*, 11320*b*) each extending partially circumferentially about cylindrical tube (11312), and each including a pair of longitudinal slot end portions (11322) and an intermediate slot portion (11324) extending circumferentially therebetween and having longitudinally-opposed proximal and distal surfaces (11326, 11328). More particularly, slots (11320*a*, 11320*b*) are arranged in diametrically-opposed pairs spaced apart from each other at equal intervals along the length of tube (11312), such that a diametrically-opposed pair of bridges (11330) extend circumferentially between the respective slot end portions (11322) of each diametrically-opposed pair of slots (11320*a*, 11320*b*). In some versions, the portions of tube (11312) extending longitudinally between longitudinally-adjacent pairs of slots (11320*a*, 11320*b*) may be referred to as "segments." As described in greater detail below, slots (11320*a*, 11320*b*) may impart bending flexibility to push rod (11310), while bridges (11330) and/or surfaces (11326, 11328) may impart axial stiffness and/or lateral misalignment (e.g., skew) resistance to push rod (11310).

In the present version, slots (11320*a*, 11320*b*) are arranged in alternating pairs of diametrically-opposed slots (11320*a*) and diametrically-opposed slots (11320*b*), such that the pairs of diametrically-opposed slots (11320*a*) are each angularly offset from the pairs of diametrically-opposed slots (11320*b*), with intermediate slot portions (11324) of slots (11320*a*) extending circumferentially between respective laterally outer regions of tube (11312), and with intermediate slot portions (11324) of slots (11320*b*) extending circumferentially between respective laterally outer regions of tube (11312). In this manner, bridges (11330) defined between the respective slot end portions (11322) of each pair of diametrically-opposed slots (11320*a*) are positioned at such laterally outer regions of tube (11312), and bridges (11330) defined between the respective slot end portions (11322) of each pair of diametrically-opposed slots (11320*b*) are positioned at such laterally outer regions of tube (11312). In some versions, slots (11320*a*, 11320*b*) may each be laser cut into tube (11312). It will be appreciated that slots (11320*a*, 11320*b*) may each be formed in any other suitable manner.

Referring now to FIGS. 175A-175B, at least a distal portion of push rod (11310) is configured to transition between the natural state shown in FIGS. 173 and 174, at least one laterally deflected state (FIG. 175A), and at least one longitudinally compressed state (FIG. 175B). In some versions, push rod (11310) maybe resiliently biased toward the natural state, such as via bridges (11330).

As shown in FIG. 175A, at least the distal portion of push rod (11310) may be deflectable relative to the longitudinal axis of shaft assembly (114). In this regard, bridges (11330) may be sufficiently flexible to permit the distal portion of push rod (11310) to deflect laterally away from the longitudinal axis, while at least the intermediate slot portions (11324) of slots (11320*a*, 11320*b*) may provide relief space for the longitudinally-adjacent portions of tube (11312) to flex into during deflection of the distal portion, as indicated by arrow (A1) in FIG. 175A. While the distal portion of push rod (11310) is shown deflecting laterally outwardly (e.g., upwardly) from the longitudinal axis, it will be appreciated that the distal portion of push rod (11310) may deflect in any other lateral direction from the longitudinal axis. In this manner, push rod (11310) may conform to or otherwise accommodate articulation of end effector (116) relative to the longitudinal axis defined by shaft assembly (114) (e.g., via any suitable wrist architecture of end effector (116)).

As shown in FIG. 175B, at least the distal portion of push rod (11310) may also be compressible along the longitudinal axis of shaft assembly (114). In this regard, slots (11320*a*, 11320*b*) may permit proximal surfaces (11326) to be urged into engagement with the corresponding distal surfaces (11328), while bridges (11330) may be sufficiently rigid to inhibit engaged pairs of proximal and distal surfaces (11326, 11328) from skewing or otherwise shifting away from each other in a lateral direction during application of compressive axial loads thereto, as indicated by arrows (A2, A3) in FIG. 175B. In this manner, push rod (11310) may transmit compressive axial loads, such as for transmitting distal motion from moveable member (128) to pusher member (166) to advance pusher member (166) distally, via bridges (11330) and/or engaged pairs of proximal and distal surfaces (11326, 11328), while resisting lateral misalignment of proximal and distal surfaces (11326, 11328) via bridges (11330) to prevent push rod (11310) from buckling. In other words, push rod (11310) may have sufficient column strength to advance pusher member (166) distally, at least when push rod (11310) is in the compressed state. In some versions, push rod (11310) may also transmit tensile axial loads, such as for transmitting proximal motion from moveable member (128) to pusher member (166) to retract pusher member (166) proximally, via bridges (11330).

B. Second Exemplary Deflectable Firing Member

FIGS. 176-178B show a distal portion of another exemplary push rod (11410) for use with surgical instrument (110) described above. Push rod (11410) is similar to push rod (168) described above except as otherwise described below. In this regard, push rod (11410) may operatively couple a pusher member (not shown), such as pusher member (166), with an actuation mechanism (not shown), such as moveable member (128), for transmitting proximal and/or distal motion between pusher member (166) and moveable member (128).

As shown in FIGS. 176-177, push rod (11410) includes a cylindrical tube (11412) extending distally from a proximal end (not shown) to a distal end (11414) along a longitudinal axis, such as the longitudinal axis defined by shaft assembly (114). In some versions, the proximal end of cylindrical tube (11412) may define an input surface for receiving forces from moveable member (128) and distal end (11414) of cylindrical tube (11412) may define an output surface for transmitting such forces to pusher member (166). Cylindrical tube (11412) may be formed of any suitable material, such as a metal or polymer-based material. Push rod (11410) also includes a lumen (11416) defined by an interior surface of cylindrical tube (11412). In some versions, lumen (11416) may be configured to slidably receive a pull rod (not shown), as described below in connection with FIGS. 181-182.

Push rod (11410) of the present version further includes a plurality of linear slots (11420*a*, 11420*b*, 11420*c*) each extending partially circumferentially about cylindrical tube (11412), and each including a pair of ends (11422) and longitudinally-opposed proximal and distal surfaces (11426, 11428). More particularly, slots (11420*a*, 11420*b*, 11420*c*) are arranged in diametrically-opposed pairs spaced apart from each other at equal intervals along the length of tube (11412), such that a diametrically-opposed pair of bridges (11430) extend circumferentially between the respective slot ends (11422) of each diametrically-opposed pair of slots (11420*a*, 11420*b*, 11420*c*). In some versions, the portions of tube (11412) extending longitudinally between longitudinally-adjacent pairs of slots (11420*a*, 11420*b*, 11420*c*) may be referred to as "segments." As described in greater detail below, slots (11420*a*, 11420*b*, 11420*c*) may impart bending flexibility to push rod (11410), while bridges (11430) and/or surfaces (11426, 11428) may impart axial stiffness and/or lateral misalignment (e.g., skew) resistance to push rod (11410).

In the present version, slots (11420*a*, 11420*b*, 11420*c*) are arranged in alternating pairs of diametrically-opposed slots (11420*a*), radially obliquely-opposed slots (11420*b*), and diametrically-opposed slots (11420*c*), such that the pairs of diametrically-opposed slots (11420*a*) are each angularly offset from the pairs of radially obliquely-opposed slots (11420*b*), and further angularly offset from the pairs of diametrically-opposed slots (11420*c*), with slots (11420*a*) extending circumferentially between respective laterally outer regions of tube (11412), with slots (11420*b*) extending circumferentially between respective radially obliquely outer regions of tube (11412), and with slots (11420*c*) extending circumferentially between respective laterally outer regions of tube (11412). In this manner, bridges (11430) defined between the respective slot ends (11422) of each pair of diametrically-opposed slots (11420*a*) are positioned at such laterally outer regions of tube (11412), bridges (11430) defined between the respective slot ends (11422) of each pair of radially obliquely-opposed slots (11420*b*) are positioned at such radially obliquely outer regions of tube (11412), and bridges (11430) defined between the respective slot ends (11422) of each pair of diametrically-opposed slots (11420*c*) are positioned at such laterally outer regions of tube (11412). In some versions, slots (11420*a*, 11420*b*, 11420*c*) may each be laser cut into tube (11412). It will be appreciated that slots (11420*a*, 11420*b*, 11420*c*) may each be formed in any other suitable manner.

Referring now to FIGS. 178A-178B, at least a distal portion of push rod (11410) is configured to transition between the natural state shown in FIGS. 176 and 177, at least one laterally deflected state (FIG. 178A), and at least one longitudinally compressed state (FIG. 178B). In some versions, push rod (11410) may be resiliently biased toward the natural state, such as via bridges (11430).

As shown in FIG. 178A, at least the distal portion of push rod (11410) may be deflectable relative to the longitudinal axis of shaft assembly (114). In this regard, bridges (11430) may be sufficiently flexible to permit the distal portion of push rod (11410) to deflect laterally away from the longitudinal axis, while slots (11420*a*, 11420*b*, 11420*c*) may provide relief space for the longitudinally-adjacent portions of tube (11412) to flex into during deflection of the distal portion, as indicated by arrow (A4) in FIG. 178A. While the distal portion of push rod (11410) is shown deflecting laterally outwardly (e.g., upwardly) from the longitudinal axis, it will be appreciated that the distal portion of push rod (11410) may deflect outwardly in any other lateral direction from the longitudinal axis. In this manner, push rod (11410) may conform to or otherwise accommodate articulation of end effector (116) relative to the longitudinal axis defined by shaft assembly (114) (e.g., via any suitable wrist architecture of end effector (116)).

As shown in FIG. 178B, at least the distal portion of push rod (11410) may also be compressible along the longitudinal axis of shaft assembly (114). In this regard, slots (11420*a*, 11420*b*, 11420*c*) may permit proximal surfaces (11426) to be urged into engagement with the corresponding distal surfaces (11428), while bridges (11430) may be sufficiently rigid to inhibit engaged pairs of proximal and distal surfaces (11426, 11428) from skewing or otherwise shifting away from each other in a lateral direction during application of compressive axial loads thereto, as indicated by arrows (A5, A6) in FIG. 178B. In this manner, push rod (11410) may transmit compressive axial loads, such as for transmitting distal motion from moveable member (128) to pusher member (166) to advance pusher member (166) distally, via bridges (11430) and/or engaged pairs of proximal and distal surfaces (11426, 11428), while resisting lateral misalignment of proximal and distal surfaces (11426, 11428) via bridges (11430) to prevent push rod (11410) from buckling. In other words, push rod (11410) may have sufficient column strength to advance pusher member (166) distally, at least when push rod (11410) is in the compressed state. In some versions, push rod (11410) may also transmit tensile axial loads, such as for transmitting proximal motion from moveable member (128) to pusher member (166) to retract pusher member (166) proximally, via bridges (11430).

C. Third Exemplary Deflectable Firing Member

FIG. 179 shows a distal portion of another exemplary push rod (11510) for use with surgical instrument (110) described above. Push rod (11510) is similar to push rod (168) described above except as otherwise described below. In this regard, push rod (11510) may operatively couple a pusher member (not shown), such as pusher member (166), with an actuation mechanism (not shown), such as moveable member (128), for transmitting proximal and/or distal motion between pusher member (166) and moveable member (128).

As shown, push rod (11510) includes a cylindrical tube (11512) extending distally from a proximal end (not shown) to a distal end (11514) along a longitudinal axis, such as the longitudinal axis defined by shaft assembly (114). In some versions, the proximal end of cylindrical tube (11512) may define an input surface for receiving forces from moveable member (128) and distal end (11514) of cylindrical tube (11512) may define an output surface for transmitting such forces to pusher member (166). Cylindrical tube (11512) may be formed of any suitable material, such as a metal or polymer-based material. Push rod (11510) also includes a lumen (11516) defined by an interior surface of cylindrical tube (11512). In some versions, lumen (11516) may be configured to slidably receive a pull rod (not shown), as described below in connection with FIGS. 181-183.

Push rod (11510) of the present version further includes a plurality of I-shaped slots (11320*a*, 11320*b*) defining corresponding bridges (11330). Push rod (11510) further includes a plurality of step-shaped slots (11520) each extending partially longitudinally along cylindrical tube (11512), and each including a pair of slot ends (11522) and a plurality of linear slot portions (11524) extending longitudinally therebetween and angularly offset from each other. More particularly, slots (11520) are spaced apart from each other at equal intervals about the circumference of tube (11512), such that a step-shaped bridge (11530) extends circumferentially between each circumferentially-adjacent pair of slots (11520). In some versions, the portions of tube (11512) extending longitudinally between longitudinally-adjacent pairs of slots (11320*a*, 11320*b*) may be referred to as "segments." As described in greater detail below, slots (11320*a*, 11320*b*, 11520) may impart bending flexibility to push rod (11510), while bridges (11330, 11530) and/or surfaces (11326, 11328) may impart axial stiffness and/or lateral misalignment (e.g., skew) resistance to push rod (11510).

In the present version, slots (11320*a*, 11320*b*) are arranged in a manner similar to that described above in connection with FIGS. 173-175B, and are further divided into proximal and distal sets, with slots (11520) interposed between the proximal set of slots (11320*a*, 11320*b*) and the distal set of slots (11320*a*, 11320*b*). In some versions, slots (11320*a*, 11320*b*, 11520) may each be laser cut into tube (11512). It will be appreciated that slots (11320*a*, 11320*b*, 11520) may each be formed in any other suitable manner.

It will be appreciated that at least a distal portion of push rod (11510) is configured to transition between the natural state shown in FIG. 179, at least one laterally deflected state (not shown), and at least one longitudinally compressed state (not shown), in manners similar to those described above in connection with FIGS. 175A-175B and 178A-178B. In some versions, push rod (11510) may be resiliently biased toward the natural state, such as via bridges (11330, 11530).

For example, at least the distal portion of push rod (11510) may be deflectable relative to the longitudinal axis of shaft assembly (114). In this regard, bridges (11330, 11530) may be sufficiently flexible to permit the distal portion of push rod (11510) to deflect laterally outwardly from the longitudinal axis, while slots (11320*a*, 11320*b*, 11520) may provide relief space for the longitudinally-adjacent and/or circumferentially-adjacent portions of tube (11512) to flex into during deflection of the distal portion. In this manner, push rod (11510) may conform to or otherwise accommodate articulation of end effector (116) relative to the longitudinal axis defined by shaft assembly (114) (e.g., via any suitable wrist architecture of end effector (116)).

At least the distal portion of push rod (11510) may also be compressible along the longitudinal axis of shaft assembly (114). In this regard, slots (11320*a*, 11320*b*) may permit proximal surfaces (11326) to be urged into engagement with the corresponding distal surfaces (11328), while bridges (11330) may be sufficiently rigid to inhibit engaged pairs of proximal and distal surfaces (11326, 11328) from skewing or otherwise shifting away from each other in a lateral direction during application of compressive axial loads thereto. In this manner, push rod (11510) may transmit compressive axial loads, such as for transmitting distal motion from moveable member (128) to pusher member (166) to advance pusher member (166) distally, via bridges (11330, 11530) and/or engaged pairs of proximal and distal surfaces (11326, 11328), while resisting lateral misalignment of proximal and distal surfaces (11326, 11328) via bridges (11330) to prevent push rod (11510) from buckling. In other words, push rod (11510) may have sufficient column strength to advance pusher member (166) distally, at least when push rod (11510) is in the compressed state. In some versions, push rod (11510) may also transmit tensile axial loads, such as for transmitting proximal motion from moveable member (128) to pusher member (166) to retract pusher member (166) proximally, via bridges (11330, 11530).

D. Fourth Exemplary Deflectable Firing Member

FIG. 180 shows a distal portion of another exemplary push rod (11610) for use with surgical instrument (110) described above. Push rod (11610) is similar to push rod (168) described above except as otherwise described below. In this regard, push rod (11610) may operatively couple a pusher member (not shown), such as pusher member (166), with an actuation mechanism (not shown), such as moveable member (128), for transmitting proximal and/or distal motion between pusher member (166) and moveable member (128).

As shown, push rod (11610) includes a cylindrical tube (11612) extending distally from a proximal end (not shown) to a distal end (not shown) along a longitudinal axis, such as the longitudinal axis defined by shaft assembly (114). In some versions, the proximal end of cylindrical tube (11612) may define an input surface for receiving forces from moveable member (128) and the distal end of cylindrical tube (11612) may define an output surface for transmitting such forces to pusher member (166). Cylindrical tube (11612) may be formed of any suitable material, such as a metal or polymer-based material. Push rod (11610) may also include a lumen (not shown) defined by an interior surface of cylindrical tube (11612). In some versions, the lumen may be configured to slidably receive a pull rod (not shown), as described below in connection with FIGS. 181-183.

Push rod (11610) of the present version further includes a plurality of slots (11620*a*, 11620*b*) each extending partially circumferentially about cylindrical tube (11612), and each including a pair of generally hook-shaped slot end portions (11622) and a generally U-shaped intermediate slot portion (11624) extending circumferentially therebetween and having longitudinally-opposed proximal and distal surfaces (11626, 11628). More particularly, slots (11620*a*, 11620*b*) are arranged in diametrically-opposed pairs spaced apart from each other at equal intervals along the length of tube (11612), such that a diametrically-opposed pair of bridges (11630) extend circumferentially between the respective slot end portions (11622) of each diametrically-opposed pair of slots (11620*a*, 11620*b*). In some versions, the portions of tube (11612) extending longitudinally between longitudinally-adjacent pairs of slots (11620*a*, 11620*b*) may be referred to as "segments." As described in greater detail below, slots (11620*a*, 11620*b*) may impart bending flexibility to push rod (11610), while bridges (11630) and/or surfaces (11626, 11628) may impart axial stiffness and/or lateral misalignment (e.g., skew) resistance to push rod (11610).

In the present version, slots (11620*a*, 11620*b*) are arranged in alternating pairs of diametrically-opposed slots (11620*a*) and diametrically-opposed slots (11620*b*), such that the pairs of diametrically-opposed slots (11620*a*) are each angularly offset from the pairs of diametrically-opposed slots (11620*b*), with intermediate slot portions (11624) of slots (11620*a*) extending circumferentially between respective laterally outer regions of tube (11612), and with intermediate slot portions (11624) of slots (11620*b*) extending circumferentially between respective laterally outer regions of tube (11612). In this manner, bridges (11630) defined between the respective slot end portions (11622) of each pair of diametrically-opposed slots (11620*a*) are positioned at such laterally outer regions of tube (11612), and bridges (11630) defined between the respective slot end portions (11622) of each pair of diametrically-opposed slots (11620*b*) are positioned at such laterally outer regions of tube (11612). In some versions, slots (11620*a*, 11620*b*) may each be laser cut into tube (11612). It will be appreciated that slots (11620*a*, 11620*b*) may each be formed in any other suitable manner.

It will be appreciated that at least a distal portion of push rod (11610) is configured to transition between the natural state shown in FIG. 180, at least one laterally deflected state (not shown), and at least one longitudinally compressed state (not shown), in manners similar to those described above in connection with FIGS. 175A-175B and 178A-178B. In some versions, push rod (11610) may be resiliently biased toward the natural state, such as via bridges (11630).

For example, at least the distal portion of push rod (11610) may be deflectable relative to the longitudinal axis of shaft assembly (114). In this regard, bridges (11630) may be sufficiently flexible to permit the distal portion of push rod (11610) to deflect laterally away from the longitudinal axis, while slots (11620*a*, 11620*b*) may provide relief space for the longitudinally-adjacent portions of tube (11612) to flex into during deflection of the distal portion. In this manner, push rod (11610) may conform to or otherwise accommodate articulation of end effector (116) relative to the longitudinal axis defined by shaft assembly (114) (e.g., via any suitable wrist architecture of end effector (116)).

At least the distal portion of push rod (11610) may also be compressible along the longitudinal axis of shaft assembly (114). In this regard, slots (11620*a*, 11620*b*) may permit proximal surfaces (11626) to be urged into engagement with the corresponding distal surfaces (11628), while bridges (11630) may be sufficiently rigid to inhibit engaged pairs of proximal and distal surfaces (11626, 11628) from skewing or otherwise shifting away from each other in a lateral direction during application of compressive axial loads thereto. In this manner, push rod (11610) may transmit compressive axial loads, such as for transmitting distal motion from moveable member (128) to pusher member (166) to advance pusher member (166) distally, via bridges (11630) and/or engaged pairs of proximal and distal surfaces (11626, 11628), while resisting lateral misalignment of proximal and distal surfaces (11626, 11628) via bridges (11630) to prevent push rod (11610) from buckling. In other words, push rod (11610) may have sufficient column strength to advance pusher member (166) distally, at least when push rod (11610) is in the compressed state. In some versions, push rod (11610) may also transmit tensile axial loads, such as for transmitting proximal motion from moveable member (128) to pusher member (166) to retract pusher member (166) proximally, via bridges (11630).

E. Fifth Exemplary Deflectable Firing Member

FIGS. 181-183 show an actuation assembly (11700) including a pull rod (11702) and another exemplary push rod (11710) for use with surgical instrument (110) described above. Push rod (11710) is similar to push rod (168) described above except as otherwise described below. In this regard, push rod (11710) may operatively couple a pusher member (not shown), such as pusher member (166), with an actuation mechanism (not shown), such as moveable member (128), for transmitting distal motion between pusher member (166) and moveable member (128). Likewise, pull rod (11702) may operatively couple pusher member (166) with another actuation mechanism (not shown) for transmitting proximal motion between pusher member (166) and such another actuation mechanism.

As shown, push rod (11710) includes a cylindrical tube (11712) extending distally from a proximal end (11713) to a distal end (11714) along a longitudinal axis, such as the longitudinal axis defined by shaft assembly (114). In some versions, proximal end (11713) of cylindrical tube (11712) may define an input surface for receiving forces from moveable member (128) and distal end (11714) of cylindrical tube (11712) may define an output surface for transmitting such forces to pusher member (166). Cylindrical tube (11712) may be formed of any suitable material, such as a metal or polymer-based material. Push rod (11710) also includes a lumen (11716) defined by an interior surface of cylindrical tube (11712) for slidably receiving pull rod (11702).

Cylindrical tube (11712) of the present version further includes an intermediate flexible mesh portion (11720) having a plurality of strands (11722) that are combined in a matrix extending between proximal and distal rigid collar portions (11724, 11726) of cylindrical tube (11712). In some versions, intermediate mesh portion (11720) may have a smaller inner diameter than that of one or both collar portion(s) (11724, 11726). Intermediate mesh portion (11720) may have any suitable configuration, such as a webbed and/or coiled configuration. In some versions, strands (11722) may be 3D printed together to form intermediate mesh portion (11720). In other versions, strands (11722) may be individually formed as separate wires and knitted or woven together in a pattern or in a random association. Any number of suitable texture patterns may be used as would be apparent to a person having ordinary skill in the art in view of the teachings herein. Lasering and/or soldering techniques may be used to impart strands (11722) and/or intermediate mesh portion (11720) with a variety of different mechanical properties. It will be appreciated that strands (11722) and/or intermediate mesh portion (11720) may each be formed in any other suitable manner. As described in greater detail below, intermediate mesh portion (11720) including strands (11722) may impart bending flexibility and/or axial stiffness to push rod (11710).

As shown, pull rod (11702) includes a shaft in the form of a braided cable (11730) including a plurality of strands (11731) and extending distally from a proximal end (11732) to a distal aglet (11734) along a longitudinal axis, such as the longitudinal axis defined by shaft assembly (114). As described in greater detail below, braided cable (11730) may impart axial stiffness and/or lateral misalignment (e.g., skew) resistance to pull rod (11702), which may in turn impart lateral misalignment (e.g., skew) resistance to push rod (11710) via contact between an outer surface of pull rod (11702) and lumen (11716). In this regard, braided cable (11730) may have a stiffness greater than that of intermediate mesh portion (11720) and may have an outer diameter substantially equal to or slightly less than the inner diameter of at least intermediate mesh portion (11720) of push rod (11710) such that pull rod (11702) may be slidable longitudinally relative to push rod (11710) while providing radial support thereto. Braided cable (11730) may be formed of any suitable material, such as high strength steel. It will be appreciated that the shaft of pull rod (11702) may be provided in any other suitable form, such as a 3D printed and/or flexible rod.

It will be appreciated that push rod (11710) is configured to transition between the natural state shown in FIGS. 181-183, at least one laterally deflected state (not shown), and at least one longitudinally compressed state (not shown), in manners similar to those described above in connection with FIGS. 175A-175B and 178A-178B. Pull rod (11702) is also configured to transition between the natural state shown in FIGS. 181-182 and at least one laterally deflected state (not shown). In some versions, pull rod (11702) may be resiliently biased toward its natural state, such as via braided cable (11730), and push rod (11710) may likewise be resiliently biased toward its natural state, such as via strands (11722) and/or via the resilient biasing of pull rod (11702) toward its natural state.

For example, push rod (11710) and pull rod (11702) may each be deflectable relative to the longitudinal axis of shaft assembly (114). In this regard, strands (11722) may be sufficiently flexible to permit the distal portion of push rod (11710) to deflect laterally away from the longitudinal axis, while braided cable (11730) may be sufficiently flexible to permit the distal portion of pull rod (11702) to deflect laterally away from the longitudinal axis, such that push rod (11710) and pull rod (11702) may deflect laterally together. In this manner, push rod (11710) and pull rod (11702) may cooperatively conform to or otherwise accommodate articulation of end effector (116) relative to the longitudinal axis defined by shaft assembly (114) (e.g., via any suitable wrist architecture of end effector (116)).

At least the distal portion of push rod (11710) may also be compressible along the longitudinal axis of shaft assembly (114). In this regard, strands (11722) may be sufficiently flexible in the longitudinal direction to permit longitudinally-adjacent strands (11722) to be urged into engagement with each other, while braided cable (11730) may be sufficiently rigid in each radial direction to inhibit engaged pairs of strands (11722) from skewing or otherwise shifting away from each other in a radial direction during application of compressive axial loads thereto. In this manner, push rod (11710) may transmit compressive axial loads, such as for transmitting distal motion from moveable member (128) to pusher member (166) to advance pusher member (166) distally, via engaged pairs of strands (11722), while resisting lateral misalignment of strands (11722) via the radial support provided thereto by braided cable (11730) to prevent push rod (11710) from buckling. In other words, push rod (11710) may have sufficient column strength to advance pusher member (166) distally, at least when push rod (11710) is in the compressed state. In some versions, push rod (11710) may also transmit tensile axial loads, such as for transmitting proximal motion from moveable member (128) to pusher member (166) to retract pusher member (166) proximally, via strands (11722). In such cases, pull rod (11702) may be omitted, and strands (11722) may be sufficiently rigid in each radial direction to inhibit engaged pairs of strands (11722) from skewing or otherwise shifting away from each other in a radial direction during application of compressive axial loads thereto in the absence of braided cable (11730).

F. Sixth Exemplary Deflectable Firing Member

FIGS. 184A-185 show another exemplary push rod (11810) for use with surgical instrument (110) described above. Push rod (11810) is similar to push rod (168) described above except as otherwise described below. In this regard, push rod (11810) may operatively couple a pusher member (not shown), such as pusher member (166), with an actuation mechanism (not shown), such as moveable member (128), for transmitting proximal and/or distal motion between pusher member (166) and moveable member (128).

As shown in FIGS. 184A-184B, push rod (11810) includes a plurality of segments in the form of individual links (11812) flexibly stacked together in a columnar arrangement along a longitudinal axis, such as the longitudinal axis defined by shaft assembly (114). As best shown in FIG. 185, each link (11812) includes a generally cylindrical hub (11814), and further includes a generally conical proximal socket (11820) extending distally from a proximal end of hub (11814) and a generally conical distal nose (11822) extending distally from a distal end of hub (11814). Each socket (11820) is tapered and/or rounded radially inwardly toward a distal apex, and each nose (11822) is similarly tapered and/or rounded radially inwardly toward a distal apex such that the shape of each nose (11822) is generally complementary to that of each socket (11820). In this manner, the socket (11820) of a relatively distal link (11812) may matingly receive the nose (11822) of a longitudinally-adjacent, relatively proximal link (11812). In some versions, socket (11820) of the proximal-most link (11812) may define an input surface for receiving forces from moveable member (128) and nose (11822) of the distal-most link (11812) may define an output surface for transmitting such forces to pusher member (166). In the present version, each link (11812) further includes a central bore (not shown) extending between the apexes of the respective socket (11820) and nose (11822), the purposes of which are described below. Links (11812) may each be formed of any suitable material, such as a metal or polymer-based material. As described in greater detail below, sockets (11820) may each cooperate with the respective nose (11822) received therein to impart bending flexibility and/or axial stiffness to push rod (11810).

As shown, push rod (11810) further includes a central flexible shaft (11830) extending longitudinally through the central bores of the stacked plurality of links (11812). As described in greater detail below, flexible shaft (11830) may cooperate with the central bores of links (11812) to impart lateral misalignment (e.g., skew) resistance to push rod (11810). Push rod (11810) further includes first and second cables (11832, 11834), each wrapped helically about the stacked plurality of links (11812) and extending distally from a proximal annular ring (11840) to a distal annular ring (11842) positioned at corresponding ends of the stacked plurality of links (11812). In this regard, distal ring (11842) may be seated against a radially outer surface of nose (11822) of the distal-most link (11812) and proximal ring (11840) may be seated against the proximal end of the proximal-most link (11812), such that the stacked plurality of links (11812) is sandwiched between rings (11840, 11842). In some versions, one or both rings (11840, 11842) may be fixedly secured to the corresponding link (11812). As described in greater detail below, first and second cables (11832, 11834) may cooperate with links (11812) and rings (11840, 11842) to impart lateral misalignment (e.g., skew) resistance to push rod (11810).

In the present version, first cable (11832) is wrapped helically in a clockwise direction from a lateral lower region of proximal ring (11840) to a lateral lower region of distal ring (11842), and second cable (11834) is wrapped helically opposite first cable (11832) in a counterclockwise direction from a lateral upper region of distal ring (11842) to a lateral upper region of proximal ring (11840). Cables (11832, 11834) are each fixedly secured at their distal ends to distal ring (11842) and are each fixedly secured at their proximal ends to first and second caps (11844, 11846), respectively, which are each positioned proximally of proximal ring (11840), with intermittent portions of cables (11832, 11834) securely nested at periodic joints between longitudinally-adjacent pairs of links (11812) (e.g., between a radially outer surface of nose (11822) of the relatively proximal link (11812) of each pair and a proximal end of the relatively distal link (11812) of each pair). In this regard, cables (11832, 11834) each extend proximally through corresponding bores (not shown) in proximal ring (11840) to the respective cap (11844, 11846), which is resiliently biased proximally away from proximal ring (11840) by first and second compression springs (11850, 11852), respectively. It will be appreciated that caps (11844, 11846) may be resiliently biased proximally away from proximal ring (11840) by any other suitable biasing member. In any event, such biasing of caps (11844, 11846) may assist in maintaining the respective cables (11832, 11834) in tension by pulling cables (11832, 11834) proximally, as indicated by arrows (A7, A8) in FIG. 184A. In some versions, generally helical grooves (not shown) may be provided on links (11812) for receiving the respective cables (11832, 11834) to thereby hold or otherwise align the respective cables (11832, 11834) relative to links (11812).

With continuing reference to FIGS. 184A-184B, at least a distal portion of push rod (11810) is configured to transition between a natural state (FIG. 184A) and at least one laterally deflected state (FIG. 184B). In some versions, push rod (11810) may be resiliently biased toward the natural state, such as via flexible shaft (11830) and/or cables (11832, 11834).

As shown in FIG. 184B, at least the distal portion of push rod (11810) may be deflectable relative to the longitudinal axis of shaft assembly (114). In this regard, flexible shaft (11830) and/or cables (11832, 11834) may be sufficiently flexible to permit the distal portion of push rod (11810) to deflect laterally away from the longitudinal axis via pivotable engagement between noses (11822) and sockets (11820) of longitudinally-adjacent links (11812). While the distal portion of push rod (11810) is shown deflecting laterally outwardly (e.g., downwardly) from the longitudinal axis, it will be appreciated that the distal portion of push rod (11810) may deflect laterally from the longitudinal axis in any other direction. In this manner, push rod (11810) may conform to or otherwise accommodate articulation of end effector (116) relative to the longitudinal axis defined by shaft assembly (114) (e.g., via any suitable wrist architecture of end effector (116)). Cables (11832, 11834) may be maintained in tension as described above to inhibit engaged pairs of noses (11822) and sockets (11820) from skewing or otherwise shifting away from each other in a lateral direction during application of compressive axial loads thereto. Flexible shaft (11830) may also be sufficiently rigid to inhibit engaged pairs of noses (11822) and sockets (11820) from skewing or otherwise shifting away from each other in a lateral direction during application of compressive axial loads thereto. In this manner, push rod (11810) may transmit compressive axial loads, such as for transmitting distal motion from moveable member (128) to pusher member (166) to advance pusher member (166) distally, via engaged pairs of noses (11822) and sockets (11820), while resisting lateral misalignment of noses (11822) and sockets (11820) via cables (11832, 11834) and/or flexible shaft (11830) to prevent push rod (11810) from buckling. In other words, push rod (11810) may have sufficient column strength to advance pusher member (166) distally, even when push rod (11810) is in the deflected state. It will be appreciated that separate controls may be provided to apply additional tension to either cable (11832, 11834) based on the deflected state of push rod (11810) and/or the magnitude of the compressive axial loads. In some versions, push rod (11810) may also transmit tensile axial loads, such as for transmitting proximal motion from moveable member (128) to pusher member (166) to retract pusher member (166) proximally, via flexible shaft (11830) and/or cables (11832, 11834).

G. Seventh Exemplary Deflectable Firing Member

FIG. 186 shows a distal portion of another exemplary push rod (11910) for use with surgical instrument (110) described above. Push rod (11910) is similar to push rod (168) described above except as otherwise described below. In this regard, push rod (11910) may operatively couple a pusher member (not shown), such as pusher member (166), with an actuation mechanism (not shown), such as moveable member (128), for transmitting proximal and/or distal motion between pusher member (166) and moveable member (128).

As shown, push rod (11910) includes a plurality of segments in the form of individual links (11912) flexibly stacked together in a columnar arrangement along a longitudinal axis, such as the longitudinal axis defined by shaft assembly (114). Each link (11912) includes a generally spherical body (11914), such that a proximal rounded side of a relatively distal link (11912) may abut a distal rounded side of a longitudinally-adjacent, relatively proximal link (11912). In some versions, the proximal side of the proximal-most link (11912) may define an input surface for receiving forces from moveable member (128) and the distal side of the distal-most link (11912) may define an output surface for transmitting such forces to pusher member (166). In the present version, each link (11912) further includes a central bore (11924) extending between the proximal and distal sides, the purposes of which are described below. Links (11912) may each be formed of any suitable material, such as a metal or polymer-based material. As described in greater detail below, the rounded sides of longitudinally-adjacent links (11912) may cooperate with each other to impart bending flexibility to push rod (11910). Push rod (11910) further includes a central cable (11930) extending longitudinally through central bores (11924) of the stacked plurality of links (11912). As described in greater detail below, cable (11930) may cooperate with central bores (11924) of links (11912) to impart lateral misalignment (e.g., skew) resistance to push rod (11910).

It will be appreciated that at least a distal portion of push rod (11910) is configured to transition between the natural state shown in FIG. 186 and at least one laterally deflected state (not shown), in a manner similar to that described above in connection with FIGS. 184A-184B. In some versions, push rod (11910) maybe resiliently biased toward the natural state, such as via cable (11930).

For example, at least the distal portion of push rod (11910) may be deflectable relative to the longitudinal axis of shaft assembly (114). In this regard, cable (11930) may be sufficiently flexible to permit the distal portion of push rod (11910) to deflect laterally away from the longitudinal axis via engagement between the rounded sides of longitudinally-adjacent pairs of links (11912). In this manner, push rod (11910) may conform to or otherwise accommodate articulation of end effector (116) relative to the longitudinal axis defined by shaft assembly (114) (e.g., via any suitable wrist architecture of end effector (116)). Cable (11930) may be sufficiently rigid to inhibit engaged pairs of links (11912) from skewing or otherwise shifting away from each other in a lateral direction during application of compressive axial loads thereto. In this manner, push rod (11910) may transmit compressive axial loads, such as for transmitting distal motion from moveable member (128) to pusher member (166) to advance pusher member (166) distally, via engaged pairs of links (11912), while resisting lateral misalignment of links (11912) via cable (11930) to prevent push rod (11910) from buckling. In other words, push rod (11910) may have sufficient column strength to advance pusher member (166) distally, even when push rod (11910) is in the deflected state. In some versions, push rod (11910) may also transmit tensile axial loads, such as for transmitting proximal motion from moveable member (128) to pusher member (166) to retract pusher member (166) proximally, via cable (11930).

H. Eighth Exemplary Deflectable Firing Member

FIG. 187 shows a distal portion of another exemplary push rod (12010) for use with surgical instrument (110) described above. Push rod (12010) is similar to push rod (168) described above except as otherwise described below. In this regard, push rod (12010) may operatively couple a pusher member (not shown), such as pusher member (166), with an actuation mechanism (not shown), such as moveable member (128), for transmitting proximal and/or distal motion between pusher member (166) and moveable member (128).

As shown, push rod (12010) includes a plurality of segments in the form of individual links (12012) flexibly stacked together in a columnar arrangement along a longitudinal axis, such as the longitudinal axis defined by shaft assembly (114). Each link (12012) includes a generally conical hub (12014), and further includes a generally hemispherical proximal socket (12020) extending distally from a proximal end of hub (12014) and a generally hemispherical distal nose (12022) extending distally from a distal end of hub (12014). Each socket (12020) is rounded radially inwardly toward the proximal end of hub (12014), and each nose (12022) is similarly rounded radially inwardly toward the distal end of hub (12014) such that the shape of each nose (12022) is generally complementary to that of each socket (12020). In this manner, the socket (12020) of a relatively distal link (12012) may matingly receive the nose (12022) of a longitudinally-adjacent, relatively proximal link (12012). In the example shown, each socket (12020) of a relatively distal link (12012) also partially receives the hub (12014) of the longitudinally-adjacent, relatively proximal link (12012). In some versions, socket (12020) of the proximal-most link (12012) may define an input surface for receiving forces from moveable member (128) and nose (12022) of the distal-most link (12012) may define an output surface for transmitting such forces to pusher member (166). Links (12012) may each be formed of any suitable material, such as a metal or polymer-based material. As described in greater detail below, sockets (12020) may each cooperate with the respective nose (12022) received therein to impart bending flexibility and/or axial stiffness to push rod (12010), while sockets (12020) may each cooperate with the respective hub (12014) partially received therein to impart lateral misalignment (e.g., skew) resistance to push rod (12010).

It will be appreciated that at least a distal portion of push rod (12010) is configured to transition between the natural state shown in FIG. 187 and at least one laterally deflected state (not shown), in a manner similar to that described above in connection with FIGS. 184A-184B. In some versions, push rod (12010) may be malleable from the natural state toward the deflected state.

For example, at least the distal portion of push rod (12010) may be deflectable relative to the longitudinal axis of shaft assembly (114). In this regard, sockets (12020) may each be sufficiently wider than the portion of the respective hub (12014) received therein to permit the distal portion of push rod (12010) to deflect laterally away from the longitudinal axis via pivotable engagement between noses (12022) and sockets (12020) of longitudinally-adjacent pairs of links (12012). In this manner, push rod (12010) may conform to or otherwise accommodate articulation of end effector (116) relative to the longitudinal axis defined by shaft assembly (114) (e.g., via any suitable wrist architecture of end effector (116)). The portion the respective hub (12014) received within each socket (12020) may be sufficiently wide to inhibit engaged pairs of noses (12022) and sockets (12020) from skewing or otherwise shifting away from each other in a lateral direction during application of compressive axial loads thereto. In this manner, push rod (12010) may transmit compressive axial loads, such as for transmitting distal motion from moveable member (128) to pusher member (166) to advance pusher member (166) distally, via engaged pairs of noses (12022) and sockets (12020), while resisting lateral misalignment of links (12012) via cooperation between hubs (12014) and sockets (12020) to prevent push rod (12010) from buckling or jackknifing. In other words, push rod (12010) may have sufficient column strength to advance pusher member (166) distally, even when push rod (12010) is in the deflected state. In some versions, push rod (12010) may also transmit tensile axial loads, such as for transmitting proximal motion from moveable member (128) to pusher member (166) to retract pusher member (166) proximally, via engaged pairs of noses (12022) and sockets (12020).

XIX. Ninth Exemplary Deflectable Firing Member

FIGS. 188-189 show a driving assembly (13100) including a pusher member (13102) and another exemplary push rod (13110) for use with surgical instrument (110) described above. Driving assembly (13100) is similar to driving assembly (164) described above except as otherwise described below. In this regard, push rod (13110) may operatively couple pusher member (13102) with an actuation mechanism (not shown), such as moveable member (128), for transmitting distal motion between pusher member (13102) and moveable member (128).

As shown, push rod (13110) includes a plurality of segments in the form of individual links (13112) flexibly stacked together in a columnar arrangement along a longitudinal axis, such as the longitudinal axis defined by shaft assembly (114). Each link (13112) includes at least one proximal detent (not shown) and at least one distal pocket (not shown). In some versions, the shape of each detent is generally complementary to that of each pocket. In this manner, the pocket of a relatively proximal link (13112) may matingly receive the detent of a longitudinally-adjacent, relatively distal link (13112), while maintaining a slight separation therebetween. In some versions, links (13112) may each be 3D printed. As described in greater detail below, the pockets may each cooperate with the respective detent received therein to impart bending flexibility and/or axial stiffness to push rod (13110), while also cooperating with the respective detent to impart lateral misalignment (e.g., skew) resistance to push rod (13110). In the embodiment shown, push rod (13110) also includes a distal key (13150) extending distally from the distal-most link (13112) and having a generally truncated circular cross-sectional shape, the purpose of which is described below.

As shown, pusher member (13102) includes first and second flanges (184, 185) described above in connection with FIG. 8. Pusher member (13102) of the present version further includes a keyway (13152) having a generally truncated circular cross-sectional shape complementary to that of distal key (13150) of push rod (13110). In this manner, keyway (13152) may receive and frictionally engage distal key (13150) to thereby couple push rod (13110) to pusher member (13102) and, more particularly, to secure pusher member (13102) against rotation relative to push rod (13110) about the longitudinal axis of shaft assembly (114).

It will be appreciated that at least a distal portion of push rod (13110) is configured to transition between the natural state shown in FIG. 188, at least one laterally deflected state (not shown), and at least one longitudinally compressed state (not shown), in manners similar to those described above in connection with FIGS. 175A-175, 178A-178B, and 184A-184B. In some versions, push rod (13110) maybe resiliently biased toward the natural state.

For example, at least the distal portion of push rod (13110) may be deflectable relative to the longitudinal axis of shaft assembly (114). In this regard, the distal portion of push rod (13110) may be permitted to deflect laterally away from the longitudinal axis via pivotable engagement between detents and pockets of longitudinally-adjacent pairs of links (13112). For example, the detents may interact with the pockets to resist but not prevent pivoting between longitudinally-adjacent pairs of links (13112). In this manner, push rod (13110) may conform to or otherwise accommodate articulation of end effector (116) relative to the longitudinal axis defined by shaft assembly (114) (e.g., via any suitable wrist architecture of end effector (116)).

At least the distal portion of push rod (13110) may also be compressible along the longitudinal axis of shaft assembly (114). In this regard, the slight separation between detents and pockets of longitudinally-adjacent pairs of links (13112) may permit such detents and pockets of longitudinally-adjacent pairs of links (13112) to be urged into engagement with each other, while the detents may be sufficiently rigid to inhibit engaged pairs of detents and pockets from skewing or otherwise shifting away from each other in a lateral direction during application of compressive axial loads thereto. In this manner, push rod (13110) may transmit compressive axial loads, such as for transmitting distal motion from moveable member (128) to pusher member (13102) to advance pusher member (13102) distally, via engaged pairs of detents and pockets, while resisting lateral misalignment of engaged pairs of detents and pockets to prevent push rod (13110) from buckling. In other words, push rod (13110) may have sufficient column strength to advance pusher member (13102) distally, at least when push rod (13110) is in the compressed state. In some versions, push rod (13110) may also transmit tensile axial loads, such as for transmitting proximal motion from moveable member (128) to pusher member (13102) to retract pusher member (13102) proximally, via engaged pairs of detents and pockets.

XX. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of operating a robotically controlled surgical instrument that includes an end effector, a driving assembly, and a lockout, the method comprising: (a)inhibiting actuation of the driving assembly when the lockout is in a locked configuration in response to an unspent staple cartridge being absent from a first jaw of the end effector; (b) inserting the unspent staple cartridge into the first jaw of the end effector to switch the lockout to an unlocked configuration; and (c) actuating the driving assembly to pivot the first jaw, which includes the staple cartridge, toward a second jaw of the end effector to at least one of staple or cut tissue with the end effector when the lockout is in the unlocked configuration.

Example 2

The method of Example 1, further comprising transitioning the end effector between an articulated position and a non-articulated position using an articulation joint disposed between a shaft assembly and the end effector, wherein the lockout is disposed within or proximal to the articulation joint.

Example 3

The method of any one or more of the preceding Examples, wherein inhibiting actuation further comprises inhibiting actuation in the locked configuration deflecting a deflectable portion of the lockout along a lateral axis that extends transversely to a longitudinal axis of the driving assembly.

Example 4

The method of any one or more of the preceding Examples, further comprising biasing the lockout toward the locked configuration using a biasing element.

Example 5

The method of any one or more of the preceding Examples, wherein the lockout comprises a lever pivotably coupled to the end effector and a protrusion fixedly coupled to the driving assembly, wherein inhibiting actuation further comprises engaging the lever with the protrusion when the lockout is in the locked configuration to prevent distal translation of the driving assembly through the second jaw, wherein allowing actuation further comprises disengaging the protrusion from the lever when the lockout is in the unlocked configuration to permit distal translation of the driving assembly through the second jaw.

Example 6

The method of Example 5, wherein the lever is resiliently biased toward engagement with the protrusion.

Example 7

The method of any one or more of the preceding Examples, wherein the stapling assembly includes a wedge sled, wherein actuating the driving assembly includes: (a) moving the wedge sled relative to the one of the first jaw or the second jaw to drive movement of one or more staples using the driving assembly; and (b) releasably holding the wedge sled in a predetermined position within the stapling assembly while the stapling assembly is in a pre-fired configuration using a restriction feature.

Example 8

The method of any one or more of the preceding Examples, further comprising providing an electronic indication linked to a physical location of a drive member within the end effector as the drive member advances longitudinally through the end effector using a drive member visualization assembly.

Example 9

The method of any one or more of the preceding Examples, wherein the surgical instrument further comprises a bailout mechanism including a first elongate actuation element and a second elongate actuation element, the method further comprising selectively applying tension to the first elongate actuation element and the second elongate actuation element to move a pusher member, wherein the first elongate actuation element is stronger in tension than the second elongate actuation element.

Example 10

The method of any one or more of the preceding Examples, further comprising selectively advancing the driving assembly distally using a flexible firing member, the flexible firing member comprising: (i) a plurality of segments, (ii) at least one axial force transmission feature configured to transmit axial forces between the segments, and (iii) at least one lateral alignment feature configured to resist lateral misalignment of the segments.

Example 11

A method of operating a robotically controlled surgical instrument that includes an end effector, a motor, and a driving assembly, the method comprising: (a) distally advancing the driving assembly within the end effector; (b) measuring at least one of a firing force of the motor, a current of the motor, or a temperature of the motor; (c) making a determination that at least one of: (i) the measured firing force of the motor exceeds a predetermined force threshold, (ii) the measured current of the motor exceeds a predetermined current threshold, or (iii) the measured temperature of the motor exceeds a predetermined temperature threshold; and (d) in response to making the determination, reducing or stopping power to the motor.

Example 12

The method of Example 11, wherein reducing or stopping power to the motor is performed for a predetermined period of time in response to determining that the measured firing force exceeds the predetermined force threshold or the measured temperature exceeds the predetermined temperature threshold.

Example 13

The method of any one or more of Examples 11 through 12, wherein reducing or stopping power to the motor is terminated in response to identifying a difference between a measured change in temperature of the motor due to actuation of the driving assembly and an estimated change in temperature of the motor due to actuation of the driving assembly to deploy staples from a stapling assembly.

Example 14

The method of any one or more of Examples 11 through 13, further comprising modifying a motion profile by instructing the motor to provide an intermittent pulse of power or continuous power to alter performance of the end effector.

Example 15

The method of any one or more of Examples 11 through 14, further comprising repeatedly starting and stopping the motor until at least one of the measured firing force is less than a second force threshold or the measured temperature is less than a second temperature threshold.

Example 16

The method of any one or more of Examples 11 through 14, wherein the method further comprises, after reducing or stopping power to the motor, activating an algorithmic bumping mode, the algorithmic bumping mode comprising: (A) activating the motor to advance a firing member distally with a first plurality starting and stopping motions at a first rate and a first power level, and (B) activating the motor to retract the firing member proximally with a second plurality of starting and stopping motions at a second rate and a second power level, wherein the first rate is different than the second rate, wherein the first power level is different than the second power level.

Example 17

The method of Example 16, wherein the first rate and the first power level are based, at least partially, on how many cycles the firing member has been previously used.

Example 18

The method of any one or more of Examples 11 through 17, further comprising: (a) receiving a first signal at a processor from a first sensor assembly indicative of a first condition of a stapling assembly; (b) receiving a second signal at the processor from a second sensor assembly indicative of a second condition of the stapling assembly, and (c) selectively permitting or restricting a firing stroke based upon the first signal and the second signal using the processor.

Example 19

The method of Example 18, further comprising monitoring the first signal and the second signal independently, wherein selectively permitting or restricting the firing stroke further comprises restricting the firing stroke based upon either the first signal or the second signal indicating a negative condition of the stapling assembly.

Example 20

A method of operating a robotically controlled surgical instrument that includes an end effector having first and second jaws, a jaw closure assembly, and a firing assembly, the method comprising: (a) driving the jaw closure assembly to thereby pivot the first jaw toward the second jaw to a first closed position; (b) operatively disengaging the jaw closure assembly and operatively engaging the firing assembly; (c) distally advancing a firing member of the firing assembly, wherein the firing member is configured to one or both of drive a blade through tissue or drive a plurality of staples into the tissue; (d) detecting an initiation condition; (e) in response to detecting the initiation condition, operatively disengaging the firing assembly and operatively re-engaging the jaw closure assembly; (f) driving the jaw closure assembly to further pivot the first jaw toward the second jaw to a second closed position; (g) operatively disengaging the jaw closure assembly and operatively re-engaging the firing assembly; and (h) distally advancing the firing member further within the end effector.

XXI. Miscellaneous

Any one or more of the teachings, expressions, embodiments, examples, etc. described herein may be combined with any one or more of the teachings, expressions, embodiments, examples, etc. described in U.S. patent application Ser. No. 17/402,675, entitled "Multi-Threshold Motor Control Algorithm for Powered Surgical Stapler," filed on Aug. 16, 2021, issued as U.S. Pat. No. 11,992,209; U.S. patent application Ser. No. 17/402,677, entitled "Variable Response Motor Control Algorithm for Powered Surgical Stapler," filed on Aug. 16, 2021, issued as U.S. Pat. No. 11,944,297 on Apr. 2, 2024; U.S. patent application Ser. No. 17/402,679, entitled "Powered Surgical Stapler Having Independently Operable Closure and Firing Systems," filed on Aug. 16, 2021, published as U.S. Pub. No. 2023/0051756 on Feb. 16, 2023, issued as U.S. Pat. No. 11,779,332 on Oct. 10, 2023; U.S. patent application Ser. No. 17/402,695, entitled "Firing System Features for Surgical Stapler," filed on Aug. 16, 2021, issued as U.S. Pat. No. 12,213,668; U.S. patent application Ser. No. 17/402,701, entitled "Multiple-Sensor Firing Lockout Mechanism for Powered Surgical Stapler," filed on Aug. 16, 2021, issued as U.S. Pat. No. 11,992,210; U.S. patent application Ser. No. 17/402,703, entitled "Proximally Located Firing Lockout Mechanism for Surgical Stapler," filed on Aug. 16, 2021, issued as U.S. Pat. No. 11,957,336 on Apr. 16, 2024; U.S. patent application Ser. No. 17/402,720, entitled "Cartridge-Based Firing Lockout Mechanism for Surgical Stapler," filed on Aug. 16, 2021, issued as U.S. Pat. No. 12,011,164 on Jun. 18, 2024; U.S. patent application Ser. No. 17/402,732, entitled "Multi-position Restraining Member for Sled Movement," filed on Aug. 16, 2021, issued as U.S. Pat. No. 11,986,182 on May 21, 2024; U.S. patent application Ser. No. 17/402,738, entitled "Firing Member Tracking Feature for Surgical Stapler," filed on Aug. 16, 2021, issued as U.S. Pat. No. 12,171,428 on Dec. 24, 2024; U.S. patent application Ser. No. 17/402,744, entitled "Adjustable Power Transmission Mechanism for Powered Surgical Stapler," filed on Aug. 16, 2021, issued as U.S. Pat. No. 12,029,508 on Jul. 9, 2024; U.S. patent application Ser. No. 17/402,749, entitled "Firing Bailout System for Powered Surgical Stapler," filed on Aug. 16, 2021, issued as U.S. Pat. No. 12,089,842 on Sep. 17, 2024; and/or U.S. patent application Ser. No. 17/402,759, entitled "Deflectable Firing Member for Surgical Stapler," filed on Aug. 16, 2021, issued as U.S. Pat. No. 12,458,348 on Nov. 4, 2025. The disclosure of each of these applications is incorporated by reference herein in its.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler, comprising:
(a) an end effector comprising:
(i) a plurality of staples, and
(ii) a staple actuator moveable in a first direction from a start position to an end position to drive the plurality of staples into tissue;
(b) a motor operably coupled with the staple actuator; and
(c) a processor configured to operate the motor in each of:
(i) a first impact mode that includes fluctuating a power output of the motor at a first frequency between substantially no power output and a first power output to thereby advance the staple actuator discontinuously in the first direction toward the end position, and
(ii) a second impact mode that includes fluctuating a power output of the motor at a second frequency between substantially no power output and a second power output to thereby advance the staple actuator discontinuously in a second direction toward the start position,
wherein the processor is further configured to:
(i) activate the motor to advance the staple actuator through the end effector in the first direction,
(ii) while the staple actuator advances in the first direction, detect an initiation condition,
(iii) in response to detecting the initiation condition, activate an algorithmic bumping sequence that includes the first impact mode and the second impact mode, sequentially, and
(iv) in response to completing the algorithmic bumping sequence, activate the motor to advance the staple actuator in the first direction to the end position.

2. The surgical stapler of claim 1, wherein the second frequency of the second impact mode differs from the first frequency of the first impact mode.

3. The surgical stapler of claim 1, wherein the first direction comprises a first longitudinal direction and the second direction comprises a second longitudinal direction.

4. The surgical stapler of claim 3, wherein the first longitudinal direction comprises a distal direction and the second longitudinal direction comprises a proximal direction.

5. The surgical stapler of claim 1, wherein the second power output of the second impact mode differs from the first power output of the first impact mode.

6. The surgical stapler of claim 5, wherein the second power output of the second impact mode is greater than the first power output of the first impact mode.

7. The surgical stapler of claim 1, wherein at least one of the first power output or the second power output is based, at least partially, on a quantity of firing cycles completed by the staple actuator.

8. The surgical stapler of claim 1, wherein the initiation condition comprises a predetermined power input used by the motor to longitudinally advance the staple actuator.

9. The surgical stapler of claim 1, wherein the initiation condition comprises a predetermined rate of travel of the staple actuator.

10. The surgical stapler of claim 1, wherein the end effector further comprises a cutting edge configured to sever tissue, the cutting edge being actuatable by the staple actuator.

11. The surgical stapler of claim 1, wherein the end effector comprises a pair of jaws configured to cooperate to grasp tissue.

12. The surgical stapler of claim 1, further comprising a shaft extending proximally from the end effector.

13. A surgical instrument, comprising:
(a) an end effector including:
(i) a plurality of surgical fasteners, and
(ii) a surgical fastener actuator movable from a start position to an end position to drive the surgical fasteners into tissue;
(b) a motor operably coupled with the surgical fastener actuator; and
(c) a processor configured to:
(i) activate the motor to advance the surgical fastener actuator within the end effector from the start position toward the end position,
(ii) detect an initiation condition while advancing the surgical fastener actuator toward the end position,
(iii) in response to detecting the initiation condition, perform a sequence having a first sequence portion and a subsequent second sequence portion, each of the first and second sequence portions including fluctuating a power output of the motor at a predetermined frequency between substantially no power output and a predetermined power output to thereby advance the firing driver discontinuously in a predetermined direction, wherein the first and second sequence portions differ in at least the predetermined direction, and
(iv) after completing the sequence, activate the motor to advance the surgical fastener actuator to the end position.

14. The surgical instrument of claim 13, wherein the predetermined power output of the second sequence portion differs from the predetermined power output of the first sequence portion.

15. The surgical instrument of claim 13, wherein each of the first and second sequence portions includes fluctuating the power output of the motor as a step function.

16. The surgical instrument of claim 13, wherein the predetermined direction of the first sequence portion includes a first longitudinal direction, and the predetermined direction of the second sequence portion includes a second longitudinal direction opposed the first longitudinal direction.

17. The surgical instrument of claim 16, wherein the first and second sequence portions further differ in the predetermined frequency and the predetermined power output.

* * * * *